US010898567B2

(12) United States Patent
Krebber et al.

(10) Patent No.: US 10,898,567 B2
(45) Date of Patent: Jan. 26, 2021

(54) SYNTHETIC LONG PEPTIDES (SLP) FOR THERAPEUTIC VACCINATION AGAINST HEPATITIS B VIRUS INFECTION

(71) Applicant: ISA Pharmaceuticals B.V., Leiden (NL)

(72) Inventors: Wilhelmus Johannes Theodorus Alexander Krebber, Leiden (NL); Johan Herman Kessler, Leiden (NL); Cornelis Joseph Maria Melief, Haarlem (NL); Kitty Michelle Corinne Kwappenberg, Leiden (NL)

(73) Assignee: ISA PHARMACEUTICALS B.V., Leiden (NL)

( * ) Notice: Subject to any disclaimer, the term of this patent is extended or adjusted under 35 U.S.C. 154(b) by 0 days.

(21) Appl. No.: 16/458,894

(22) Filed: Jul. 1, 2019

(65) Prior Publication Data
US 2019/0314494 A1 Oct. 17, 2019

Related U.S. Application Data

(62) Division of application No. 15/315,526, filed as application No. PCT/NL2015/050390 on Jun. 1, 2015.

(30) Foreign Application Priority Data

Jun. 2, 2014 (EP) .................... 14170733

(51) Int. Cl.
*A61K 39/29* (2006.01)
*A61K 39/12* (2006.01)
*C07K 14/005* (2006.01)
*A61K 38/00* (2006.01)
*A61K 39/00* (2006.01)

(52) U.S. Cl.
CPC ............ *A61K 39/292* (2013.01); *A61K 39/12* (2013.01); *C07K 14/005* (2013.01); *A61K 38/00* (2013.01); *A61K 2039/53* (2013.01); *A61K 2039/572* (2013.01); *C12N 2730/10134* (2013.01)

(58) Field of Classification Search
None
See application file for complete search history.

(56) References Cited

U.S. PATENT DOCUMENTS 6,607,727 B1 * 8/2003 Chisari .................. A61K 39/29
424/227.1
6,964,769 B2 * 11/2005 Sebbel ................ A61K 39/385
424/189.1
2009/0311283 A1 12/2009 Sette et al.
2010/0068228 A1 3/2010 Sette et al.
2012/0149120 A1 6/2012 Lee et al.

FOREIGN PATENT DOCUMENTS

WO WO-2006/034545 A1 4/2006
WO WO-2006/097285 A1 9/2006
WO WO-2010/017209 A2 2/2010

OTHER PUBLICATIONS

Vaudin et al. Journal of genetic virology, 1988, vol. 69, p. 1383-1389.*
Mahanty et al. (BMC Immunology, 2015, p. 1-5).*
"Hepatitis B", World Health Organization, Jul. 2013, obtained from the Internet, URL: https://web.archive.org/web/20130715020541/http://www.who.int/mediacentre/factsheets/fs204/en.
Ganem et al., "Hepatis B virus infection—natural history and clinical consequences", The New England Journal of Medicine, 2004, vol. 350, pp. 1118-1129.
Grimm et al., "Hepatitis B virus: from immunobiologyto immunotherapy", Clinical Science, 2013, vol. 124, pp. 77-85.
Huang et al., "Hepatitis B virus infections, its sequelae, and prevention by vaccination", Current Opinion in Immunology, 2011, vol. 23. pp. 237-243.
International Search Report issued in International Patent Application No. PCT/NL2015/050390 dated Aug. 3, 2015.
Lok, "Chronic Hepatitis N", The New England Journal of Medicine, May 30, 2002, vol. 346, No. 22, pp. 1681-1684.
Mahanty et al. "Immunogenicity of infectious pathogens and vaccine antigens." BMC immunology 16.1 (2015): 31.
Michel et al., "Therapeutic vaccines and immune-based therapies for the treatment of chronic hepatitis B: perspectives and challenges", Journal of Hepatology, 2011, vol. 54, pp. 1286-1296.
Pol et al. "Efficacy and limitations of a specific immunotherapy in chronic hepatitis B", Journal of Hepatology, 2001, vol. 34, pp. 917-921.
Rehermann et al., "Immunology of Hepatitis B virus and Hepatitis C virus infection", Nature Reviews—Immunology, Mar. 2005, vol. 5, pp. 215-229.
Thimme et al., "CD8 T cells mediate viral clearance and disease pathogenesis during acute Hepatitis B virus infection", Journal of Virology, Jan. 2003, vol. 77, No. 1, pp. 68-76.
Vaudin et al. "The complete nucleotide sequence of the genome of a hepatitis B virus isolated from a naturally infected chimpanzee." Journal of General Virology 69.6 (1988): 1383-1389.
Zaaijer et al., "Substitution rate of the hepatitis B virus surface gene", Journal of Viral Hepatitis, vol. 15, No. 4, 2008, pp. 289-245.
Zoulim et al., "Management of treatment failure in chronic hepatitis B", Journal of Hepatology, 2012, pp. S112-S122.

* cited by examiner

*Primary Examiner* — Agnieszka Boesen
(74) *Attorney, Agent, or Firm* — Foley & Lardner LLP

(57) ABSTRACT

The present invention relates to the fields of medicine and immunology. In particular, it relates to novel peptides that may be used in the treatment and/or prevention of a Hepatitis B viral infection and/or an Hepatitis B related disease or condition.

19 Claims, 6 Drawing Sheets
Specification includes a Sequence Listing.

Fig. 1a

SLP no.1, HBV Polymerase aa 1 – 30 (SEQ ID NO: 51)

| # | aa | pos | mark | value |
|---|---|---|---|---|
| 1 | M | 1 | + | 1.08 |
| 2 | P | 2 | | 0.09 |
| 3 | L | 3 | | 0.99 |
| 4 | S | 4 | | 0.27 |
| 5 | Y | 5 | + | 1.87 |
| 6 | Q | 6 | | 0.88 |
| 7 | H | 7 | | 0.70 |
| 8 | F | 8 | + | 1.42 |
| 9 | R | 9 | | 1.83 |
| 10 | K | 10 | | 1.21 |
| 11 | L | 11 | + | 1.89 |
| 12 | L | 12 | | 1.82 |
| 13 | L | 13 | | 1.71 |
| 14 | L | 14 | | 1.85 |
| 15 | D | 15 | | 0.80 |
| 16 | D | 16 | | 0.57 |
| 17 | G | 17 | | 0.07 |
| 18 | T | 18 | | 0.12 |
| 19 | E | 19 | | 0.52 |
| 20 | A | 20 | | 1.41 |
| 21 | G | 21 | | 0.62 |
| 22 | P | 22 | | 0.06 |
| 23 | L | 23 | | 0.79 |
| 24 | E | 24 | | 0.44 |
| 25 | E | 25 | | 0.97 |
| 26 | E | 26 | | 0.33 |
| 27 | L | 27 | | 1.36 |
| 28 | P | 28 | | 0.07 |
| 29 | R | 29 | | 0.94 |
| 30 | L | 30 | | 1.77 |

SLP no.10, HBV Polymerase aa 419 – 456 (SEQ ID NO: 60)

| # | aa | pos | mark | value |
|---|---|---|---|---|
| 1 | N | 419 | | 0.83 |
| 2 | L | 420 | + | 1.42 |
| 3 | L | 421 | | 1.64 |
| 4 | S | 422 | | 0.84 |
| 5 | S | 423 | | 0.60 |
| 6 | N | 424 | | 0.13 |
| 7 | L | 425 | + | 1.79 |
| 8 | S | 426 | | 0.30 |
| 9 | W | 427 | | 1.77 |
| 10 | L | 428 | + | 1.54 |
| 11 | S | 429 | | 0.55 |
| 12 | L | 430 | + | 1.74 |
| 13 | D | 431 | | 0.11 |
| 14 | V | 432 | + | 1.41 |
| 15 | S | 433 | | 0.37 |
| 16 | A | 434 | | 1.33 |
| 17 | A | 435 | | 0.74 |
| 18 | F | 436 | | 1.90 |
| 19 | Y | 437 | + | 1.81 |
| 20 | H | 438 | | 0.61 |
| 21 | L | 439 | + | 1.79 |
| 22 | P | 440 | | 0.16 |
| 23 | L | 441 | | 1.00 |
| 24 | H | 442 | | 0.25 |
| 25 | P | 443 | | 0.27 |
| 26 | A | 444 | | 0.89 |
| 27 | A | 445 | | 0.62 |
| 28 | M | 446 | + | 1.63 |
| 29 | P | 447 | | 0.32 |
| 30 | H | 448 | | 0.52 |
| 31 | L | 449 | + | 1.61 |
| 32 | L | 450 | + | 1.81 |
| 33 | L | 451 | | 0.84 |
| 34 | G | 452 | | 0.32 |
| 35 | S | 453 | | 0.77 |
| 36 | S | 454 | | 0.26 |
| 37 | G | 455 | | 0.11 |
| 38 | L | 456 | | 1.81 |

SLP no.13, HBV Polymerase aa 481 – 514 (SEQ ID NO: 63)

| # | aa | pos | mark | value |
|---|---|---|---|---|
| 1 | H | 481 | | 0.31 |
| 2 | D | 482 | | 0.87 |
| 3 | S | 483 | | 0.13 |
| 4 | C | 484 | | 0.18 |
| 5 | S | 485 | | 0.30 |
| 6 | R | 486 | | 1.12 |
| 7 | Q | 487 | | 0.56 |
| 8 | L | 488 | + | 1.49 |
| 9 | Y | 489 | | 0.96 |
| 10 | V | 490 | + | 1.20 |
| 11 | S | 491 | | 0.58 |
| 12 | M | 492 | + | 1.59 |
| 13 | M | 493 | | 1.55 |
| 14 | L | 494 | + | 1.55 |
| 15 | Y | 495 | | 1.34 |
| 16 | Y | 496 | + | 1.80 |
| 17 | K | 497 | | 1.07 |
| 18 | T | 498 | | 0.21 |
| 19 | G | 499 | | 1.86 |
| 20 | G | 500 | | 0.13 |
| 21 | W | 501 | + | 1.93 |
| 22 | K | 502 | | 0.71 |
| 23 | L | 503 | + | 1.95 |
| 24 | H | 504 | | 0.88 |
| 25 | L | 505 | + | 1.71 |
| 26 | Y | 506 | + | 1.90 |
| 27 | S | 507 | | 0.29 |
| 28 | H | 508 | | 0.84 |
| 29 | P | 509 | | 0.08 |
| 30 | L | 510 | | 0.99 |
| 31 | V | 511 | | 0.55 |
| 32 | L | 512 | + | 1.95 |
| 33 | G | 513 | | 0.48 |
| 34 | F | 514 | | 1.62 |

Fig. 1b

SLP no.14, HBV Polymerase aa 524 - 559 (SEQ ID NO: 64)

| # | aa | AA | +/- | Value |
|---|----|----|-----|-------|
| 1 | 524 | S |  | 0,42 |
| 2 | 525 | P |  | 0,57 |
| 3 | 526 | F |  | 0,96 |
| 4 | 527 | L |  | 0,99 |
| 5 | 528 | L | + | 1,72 |
| 6 | 529 | A | + | 1,51 |
| 7 | 530 | Q |  | 1,00 |
| 8 | 531 | F | + | 1,59 |
| 9 | 532 | T |  | 0,30 |
| 10 | 533 | S |  | 0,76 |
| 11 | 534 | A |  | 0,92 |
| 12 | 535 | L |  | 0,94 |
| 13 | 536 | C |  | 0,65 |
| 14 | 537 | S |  | 0,41 |
| 15 | 538 | V | + | 1,40 |
| 16 | 539 | V | + | 1,34 |
| 17 | 540 | R | + | 1,19 |
| 18 | 541 | R | + | 1,69 |
| 19 | 542 | A |  | 0,50 |
| 20 | 543 | F | + | 1,06 |
| 21 | 544 | P |  | 0,13 |
| 22 | 545 | H |  | 0,14 |
| 23 | 546 | C |  | 0,21 |
| 24 | 547 | L | + | 1,96 |
| 25 | 548 | A | + | 1,06 |
| 26 | 549 | F | + | 1,82 |
| 27 | 550 | S |  | 0,25 |
| 28 | 551 | Y | + | 1,93 |
| 29 | 552 | M |  | 2,02 |
| 30 | 553 | D |  | 0,88 |
| 31 | 554 | D |  | 0,76 |
| 32 | 555 | V |  | 0,60 |
| 33 | 556 | V |  | 0,34 |
| 34 | 557 | L | + | 1,21 |
| 35 | 558 | G |  | 0,31 |
| 36 | 559 | A |  | 1,49 |

SLP no.18, HBV Polymerase aa 653 - 691 (SEQ ID NO: 68)

| # | aa | AA | +/- | Value |
|---|----|----|-----|-------|
| 1 | 653 | Y | + | 1,69 |
| 2 | 654 | P |  | 0,20 |
| 3 | 655 | A |  | 0,11 |
| 4 | 656 | L |  | 0,95 |
| 5 | 657 | M | + | 1,18 |
| 6 | 658 | P |  | 0,13 |
| 7 | 659 | L |  | 1,00 |
| 8 | 660 | Y | + | 1,81 |
| 9 | 661 | A | + | 1,43 |
| 10 | 662 | C |  | 0,21 |
| 11 | 663 | I |  | 1,19 |
| 12 | 664 | Q |  | 0,20 |
| 13 | 665 | K | + | 1,41 |
| 14 | 666 | K |  | 1,01 |
| 15 | 667 | Q |  | 1,04 |
| 16 | 668 | A |  | 0,96 |
| 17 | 669 | F |  | 1,07 |
| 18 | 670 | T |  | 0,07 |
| 19 | 671 | F | + | 1,58 |
| 20 | 672 | S |  | 0,78 |
| 21 | 673 | P |  | 0,16 |
| 22 | 674 | T |  | 0,07 |
| 23 | 675 | Y | + | 1,81 |
| 24 | 676 | K |  | 1,78 |
| 25 | 677 | A | + | 1,62 |
| 26 | 678 | F |  | 0,94 |
| 27 | 679 | L |  | 0,51 |
| 28 | 680 | S |  | 0,71 |
| 29 | 681 | K | + | 1,52 |
| 30 | 682 | Q |  | 0,56 |
| 31 | 683 | Y |  | 1,56 |
| 32 | 684 | M | + | 1,51 |
| 33 | 685 | N |  | 0,39 |
| 34 | 686 | L | + | 1,83 |
| 35 | 687 | Y | + | 1,58 |
| 36 | 688 | P |  | 0,10 |
| 37 | 689 | V |  | 0,93 |
| 38 | 690 | A |  | 1,25 |
| 39 | 691 | R |  | 1,78 |

SLP no.21, HBV Polymerase aa 754 - 791 (SEQ ID NO: 71)

| # | aa | AA | +/- | Value |
|---|----|----|-----|-------|
| 1 | 754 | V |  | 0,55 |
| 2 | 755 | L | + | 1,83 |
| 3 | 756 | S |  | 0,42 |
| 4 | 757 | R | + | 1,59 |
| 5 | 758 | K |  | 0,82 |
| 6 | 759 | Y | + | 1,71 |
| 7 | 760 | T |  | 0,92 |
| 8 | 761 | S |  | 0,13 |
| 9 | 762 | F | + | 1,77 |
| 10 | 763 | P |  | 0,18 |
| 11 | 764 | W |  | 0,99 |
| 12 | 765 | L |  | 1,24 |
| 13 | 766 | L | + | 1,92 |
| 14 | 767 | G |  | 0,64 |
| 15 | 768 | C |  | 0,66 |
| 16 | 769 | T |  | 0,19 |
| 17 | 770 | A | + | 1,76 |
| 18 | 771 | N |  | 0,39 |
| 19 | 772 | W | + | 1,72 |
| 20 | 773 | I |  | 0,22 |
| 21 | 774 | L | + | 1,41 |
| 22 | 775 | R | + | 1,01 |
| 23 | 776 | G |  | 0,55 |
| 24 | 777 | T |  | 0,80 |
| 25 | 778 | S |  | 0,39 |
| 26 | 779 | F | + | 1,20 |
| 27 | 780 | V |  | 1,19 |
| 28 | 781 | Y | + | 1,69 |
| 29 | 782 | V | + | 1,67 |
| 30 | 783 | P |  | 0,23 |
| 31 | 784 | S |  | 0,55 |
| 32 | 785 | A | + | 1,35 |
| 33 | 786 | L | + | 1,57 |
| 34 | 787 | N |  | 0,25 |
| 35 | 788 | P |  | 0,38 |
| 36 | 789 | A |  | 0,68 |
| 37 | 790 | D |  | 0,18 |
| 38 | 791 | D |  | 0,43 |

Fig. 1c

SLP no. 24, HBV Core aa 107 – 141 (SEQ ID NO: 74)

| # | Pos | AA | + | Value |
|---|---|---|---|---|
| 1 | 107 | D | | 0.70 |
| 2 | 108 | P | | 0.06 |
| 3 | 109 | A | | 0.07 |
| 4 | 110 | S | | 0.21 |
| 5 | 111 | R | + | 1.05 |
| 6 | 112 | D | | 0.48 |
| 7 | 113 | L | + | 1.11 |
| 8 | 114 | V | | 0.89 |
| 9 | 115 | V | + | 1.38 |
| 10 | 116 | N | | 0.55 |
| 11 | 117 | Y | + | 1.68 |
| 12 | 118 | V | + | 1.72 |
| 13 | 119 | N | | 0.72 |
| 14 | 120 | T | | 0.70 |
| 15 | 121 | N | | 0.40 |
| 16 | 122 | V | | 1.04 |
| 17 | 123 | G | | 0.09 |
| 18 | 124 | L | | 1.89 |
| 19 | 125 | K | | 0.33 |
| 20 | 126 | I | | 1.53 |
| 21 | 127 | R | + | 1.11 |
| 22 | 128 | Q | | 0.32 |
| 23 | 129 | L | + | 1.67 |
| 24 | 130 | L | + | 1.23 |
| 25 | 131 | W | | 1.66 |
| 26 | 132 | F | + | 1.02 |
| 27 | 133 | H | | 0.49 |
| 28 | 134 | I | + | 1.69 |
| 29 | 135 | S | | 0.55 |
| 30 | 136 | C | | 0.82 |
| 31 | 137 | L | | 1.95 |
| 32 | 138 | T | | 0.32 |
| 33 | 139 | F | | 1.49 |
| 34 | 140 | G | | 0.23 |
| 35 | 141 | R | | 1.41 |

SLP no. 25, HBV Core aa 136 – 169 (SEQ ID NO: 75)

| # | Pos | AA | + | Value |
|---|---|---|---|---|
| 1 | 136 | C | | 0.82 |
| 2 | 137 | L | | 1.95 |
| 3 | 138 | T | | 0.32 |
| 4 | 139 | F | + | 1.49 |
| 5 | 140 | G | | 0.23 |
| 6 | 141 | R | | 1.41 |
| 7 | 142 | E | | 0.81 |
| 8 | 143 | T | | 0.33 |
| 9 | 144 | V | | 1.38 |
| 10 | 145 | L | + | 1.87 |
| 11 | 146 | E | | 0.93 |
| 12 | 147 | Y | + | 1.68 |
| 13 | 148 | L | + | 1.23 |
| 14 | 149 | V | | 1.23 |
| 15 | 150 | S | | 0.57 |
| 16 | 151 | F | + | 1.50 |
| 17 | 152 | G | | 0.48 |
| 18 | 153 | V | + | 1.80 |
| 19 | 154 | W | + | 1.34 |
| 20 | 155 | I | | 1.63 |
| 21 | 156 | R | + | 1.61 |
| 22 | 157 | T | | 0.42 |
| 23 | 158 | P | | 0.28 |
| 24 | 159 | P | | 0.12 |
| 25 | 160 | A | | 0.99 |
| 26 | 161 | Y | | 1.46 |
| 27 | 162 | R | | 0.95 |
| 28 | 163 | P | | 0.52 |
| 29 | 164 | P | | 0.08 |
| 30 | 165 | N | | 0.09 |
| 31 | 166 | A | | 1.01 |
| 32 | 167 | P | | 0.15 |
| 33 | 168 | I | | 1.00 |
| 34 | 169 | L | | 1.90 |

SLP no. 26, HBV consensus seq X protein aa 36 – 68 (SEQ ID NO: 76)

| # | Pos | AA | + | Value |
|---|---|---|---|---|
| 1 | 36 | A | | 1.55 |
| 2 | 37 | L | + | 1.14 |
| 3 | 38 | P | | 0.14 |
| 4 | 39 | S | | 0.07 |
| 5 | 40 | P | | 0.42 |
| 6 | 41 | P | | 0.06 |
| 7 | 42 | S | | 0.12 |
| 8 | 43 | S | | 0.27 |
| 9 | 44 | A | | 0.97 |
| 10 | 45 | V | + | 1.49 |
| 11 | 46 | P | | 0.25 |
| 12 | 47 | P | | 1.05 |
| 13 | 48 | D | | 0.42 |
| 14 | 49 | H | | 0.79 |
| 15 | 50 | G | | 0.78 |
| 16 | 51 | A | | 1.30 |
| 17 | 52 | H | | 0.24 |
| 18 | 53 | L | + | 1.87 |
| 19 | 54 | S | | 0.20 |
| 20 | 55 | L | + | 1.93 |
| 21 | 56 | R | | 0.63 |
| 22 | 57 | G | | 0.23 |
| 23 | 58 | L | + | 1.33 |
| 24 | 59 | P | | 0.05 |
| 25 | 60 | V | | 1.05 |
| 26 | 61 | C | | 0.87 |
| 27 | 62 | F | + | 1.65 |
| 28 | 63 | F | + | 1.48 |
| 29 | 64 | S | | 0.26 |
| 30 | 65 | S | | 0.59 |
| 31 | 66 | A | | 0.95 |
| 32 | 67 | G | | 0.11 |
| 33 | 68 | P | | 0.08 |

Fig. 1d

SLP no.27. HBV consensus seq X protein aa 61 – 95 (SEQ ID NO: 77)

| # | aa | pos | +/− | value |
|---|----|-----|-----|-------|
| 1 | C* | 61 |   | 0,87 |
| 2 | A | 62 | + | 1,65 |
| 3 | F | 63 | + | 1,48 |
| 4 | S | 64 |   | 0,26 |
| 5 | S | 65 |   | 0,59 |
| 6 | A | 66 |   | 0,95 |
| 7 | G | 67 |   | 0,11 |
| 8 | P | 68 |   | 0,08 |
| 9 | C | 69 |   | 0,07 |
| 10 | A | 70 |   | 0,45 |
| 11 | L | 71 | + | 1,74 |
| 12 | R | 72 |   | 1,24 |
| 13 | F | 73 | + | 1,58 |
| 14 | T | 74 |   | 0,40 |
| 15 | S | 75 |   | 0,80 |
| 16 | A | 76 |   | 0,99 |
| 17 | R | 77 |   | 1,06 |
| 18 | R | 78 | + | 1,59 |
| 19 | M | 79 | + | 1,80 |
| 20 | E | 80 |   | 0,97 |
| 21 | T | 81 |   | 0,61 |
| 22 | T | 82 |   | 0,40 |
| 23 | V | 83 | + | 1,51 |
| 24 | N | 84 |   | 0,84 |
| 25 | A | 85 | + | 1,44 |
| 26 | H | 86 |   | 0,74 |
| 27 | Q | 87 |   | 0,30 |
| 28 | I | 88 |   | 0,68 |
| 29 | L | 89 |   | 0,67 |
| 30 | P | 90 |   | 0,13 |
| 31 | K | 91 |   | 0,39 |
| 32 | V | 92 |   | 1,32 |
| 33 | L | 93 | + | 1,59 |
| 34 | H | 94 |   | 0,83 |
| 35 | K | 95 |   | 1,60 |

SYNTHETIC LONG PEPTIDES (SLP) FOR THERAPEUTIC VACCINATION AGAINST HEPATITIS B VIRUS INFECTION

CROSS-REFERENCE TO RELATED APPLICATIONS

This application is a divisional of U.S. patent application Ser. No. 15/315,526, filed Dec. 1, 2016, published Aug. 31, 2017 as US 2017/0246293 A1, which is a National Phase of International Patent Application No. PCT/NL2015/050390, filed Jun. 1, 2015, published on Dec. 10, 2015 as WO 2015/187009 A1, which claims priority to European Patent Application No. 14170733.1, filed Jun. 2, 2014. The contents of these applications are herein incorporated by reference in their entirety.

SEQUENCE LISTING

The instant application contains a Sequence Listing which has been submitted in ASCII format via EFS-WEB and is hereby incorporated by reference in its entirety. Said ASCII copy, created on May 8, 2017, is named 069818_2180SequenceListing.txt and is 412 KB.

FIELD OF THE INVENTION

The present invention relates to the fields of medicine and immunology. In particular, it relates to novel peptides that may be used in the treatment and/or prevention of a Hepatitis B viral infection and/or an Hepatitis B related disease or condition.

BACKGROUND OF THE INVENTION

Chronic infection with the hepatitis B virus (HBV) is a major global health problem. HBV is the prototype member of the Hepadnaviridae family, which have a strong preference for infecting liver cells (Ganem et al, 2004). Despite the availability since three decades of an efficacious preventive vaccine for the protection against hepatitis B, an estimated two billion people have nevertheless been infected with HBV and more than 240 million currently have chronic (long-term) hepatitis B infection, with a geographical predominance in regions outside Western Europe and North America (World Health Organization, July 2013).

Transmission of the virus between people occurs by direct blood-to-blood contact or via semen or vaginal fluid of an infected person. In endemic areas, the infection occurs characteristically by perinatal transmission from mother to child. Thus, although HBV is not transmitted casually, the virus—via similar modes of entry as human immunodeficiency virus (HIV) but being at least 50 times more infectious—can be easily transmitted by perinatal, percutaneous or sexual exposure. Frequent person-to-person contact with infected individuals accordingly poses a serious risk to groups like health workers.

Infection with HBV can develop as an acute viral hepatitis, an illness that begins with general ill-health, loss of appetite, nausea, vomiting, body aches, mild fever, and dark urine, and then progresses to development of jaundice. The illness lasts for a few weeks and then gradually improves in most affected adults. A few people may have more severe liver disease (fulminant hepatic failure), and may die as a result. The infection may be entirely asymptomatic and may go unrecognized. Chronic infection with hepatitis B virus either may be asymptomatic or may be associated with a chronic inflammation of the liver (chronic hepatitis), leading to cirrhosis over a period of many years. This type of infection dramatically increases the incidence of hepatocellular carcinoma (liver cancer), also with a latency of many years.

Treatment of chronically HBV-infected individuals with antiviral drugs such as nucleoside/nucleotide analogues (e.g. Entecavir and Tenofovir) or interferon (IFN)α efficiently decreases serum viral loads. However, antiviral therapy rarely leads to a sustained virological response and drug resistance occurs (Zoulim et al., 2012). Moreover, the great majority of HBV carriers remains untreated.

Approximately 15-40% of chronic HBV carriers will develop clinically significant liver diseases in their lifetime with a high risk of death from liver cirrhosis and associated liver failure or hepatocellular carcinoma (HCC) (Lok, 2002; and Huang et al., 2011). Yearly up to one million people die worldwide due to the acute or chronic consequences of hepatitis B (Michel et al, 2001; Grimm et al, 2013). Due to the failure of antiviral drugs to eradicate infection, and consequently the need for long-term if not lifelong antiviral therapy with its drawbacks such as toxic side-effects and high costs, there is an urgent need for novel therapeutic approaches (Grimm et al., 2013).

The present invention is meant to enable efficacious therapeutic vaccination against chronic HBV infection. Therapeutic vaccination constitutes a promising strategy to treat chronic hepatitis B (Michel et al., 2011).

Next to the humoral immune response against HBV, which is predominantly involved in the protection against HBV infection by the current prophylactic vaccines (Lok, 2002), the cellular immune response is unequivocally involved in the natural resistance against HBV infection.

Perinatal transmission of HBV from mothers to neonates and infections during the first years of life result in persistent infection in more than 90% of children. By contrast, infection during adulthood clears spontaneously in more than 90% of cases and results in lifelong protective immunity (Rehermann et al., 2005).

In acute, self-limited hepatitis B virus infection, vigorous polyclonal and multispecific CD8$^+$ cytotoxic T cell (CTL) and CD4$^+$ T-helper (Th) cell responses to many HBV antigens are readily demonstrable in the peripheral blood (Michel et al., 2011).

These T cell responses are crucial in HBV clearance and control. Experiments in HBV-infected chimpanzees have shown the essential role of HBV-specific CD8$^+$ T cells as effector cells in this process (Thimme et al., 2003). In contrast to the response in patients with resolved HBV infections, in patients with chronic hepatitis B the T cell responses are usually very weak, focused on only a few epitopes and functionally impaired (Michel et al., 2011). The goal of therapeutic vaccination is to install vigorous and robust multivalent CTL and T-helper cell responses directed to many HBV antigens, thereby pursuing viral clearance, hepatitis control and cure.

Despite the fact that great progress has been made in understanding the etiology and epidemiology of the disease, there is still a need for an effective therapeutic HBV vaccine.

DETAILED DESCRIPTION OF THE INVENTION

The inventors identified a selection of HBV antigens to be used for efficacious therapeutic vaccination. Based on HLA class I and class II binding capacities of HBV protein-derived peptides and analysis of the generation of these HLA class I binding peptides by cleavages made by the proteasome, the most immunogenic regions, covering a very high percentage of all possible T cell epitopes in the global hepatitis B patient population, have been uncovered in the HBV polymerase protein, core protein, X protein and large surface protein. These regions contain high numbers of T cell epitopes and when administered to the hepatitis B patient—either as chemically synthesized long peptide or via genetic approaches—such a vaccination is envisioned to induce a vigorous T cell response, resolving the HBV infection.

The use of relatively short peptides is highly preferred for medical purposes as these can be efficiently synthesized in vitro, which is not possible or uneconomical for native proteins larger than approximately 100, i.e. 95, 96, 97, 98, 99, 100, 101, 102, 103, 104, 105 amino acids. Chemical synthesis of peptides is routine practice and various suitable methods are known to the skilled person. Chemical synthesis of peptides also overcomes the problems associated with recombinant production of intact proteins, which is difficult to standardize and requires extensive purification and quality control measures. Peptides with a length that exceeds the length of human leukocyte antigen (HLA) class I and class II epitopes (e.g. having a length as indicated below herein) are particularly advantageous for use as vaccine component because they are large enough to be taken up by professional antigen presenting cells (APC), in particular Dendritic cell (DC), as explained in WO02/070006, and processed in the DC before cell surface presentation of the contained HLA class I-presented and HLA class II-presented epitopes takes place. Therefore, the disadvantageous induction of T cell tolerance by the systemic presentation of minimal HLA class I-presented epitopes on non-antigen presenting cells (as shown in Toes et al., 1996a, and Toes et al., 1996b), is prevented by the application of peptides exceeding the length of human leukocyte antigen (HLA) class I and class II epitopes (as shown in Zwaveling et al., 2002).

The present invention relates to novel peptides of about 15 to about 100 amino acids in length, also denominated herein as long peptides, that each exceed the length of human leukocyte antigen (HLA) class I and class II presented epitopes and that induce a combined $CD4^+$ and $CD8^+$ T cell response that is therapeutically successful and inducing cure in a high percentage of patients. Preferably, the long peptides of the invention are synthetic peptides, denominated herein as synthetic long peptides (SLPs). As compared to vaccination with the peptides of the present invention, therapeutic vaccination with full length HBV proteins is likely to be less potent (Rosalia et al., 2013). From the viewpoint of manufacture and administration of peptides to patients, immunization with the complete set of overlapping long peptides or SLPs spanning the full length HBV polymerase, HBV core protein, HBV X protein and HBV large surface protein is not feasible. To narrow the number of peptides in a vaccine, it is needed to incorporate the most immunogenic SLPs that are recognized by the highest percentage of patients. The present invention provides for peptides and peptide vaccines to meet this need. Using a stepwise sophisticated selection procedure based on bioinformatics analyses that are experimentally underpinned, the long peptide and/or SLP sequences with the highest coverage of HLA class I-restricted cytotoxic T lymphocyte epitopes and HLA class II-restricted T helper epitopes were identified. The selections as described herein identify the long peptide and/or SLP sequences that incorporate HBV-derived T cell epitopes that are presented on all predominantly expressed HLA class I and class II alleles. By covering the vast majority of worldwide expressed HLA haplotypes (Bui et al., 2006), the long peptide and/or SLP vaccine composition can be used in all HBV infected individuals. The present invention describes the identification and selection of HBV-derived long peptides, preferably SLPs, that are highly immunogenic and capable of inducing a potent combined HBV-directed $CD4^+$ T helper and $CD8^+$ cytotoxic T cell response, when administered as a vaccine composition to patients. Such highly immunogenic long peptides from HBV have not been disclosed in the prior art. The HBV-derived long peptides of the invention were identified based on a putative immunogenicity score developed and validated by the inventors and as disclosed herein. The putative immunogenicity is quantified herein using the T cell Regional Immunogenicity Assessment (TRIA) score. The TRIA score is based on the cumulative Class I-BCI score of said peptide, which is indicative for their immunogenic CTL activating capacity, and the cumulative Class II-B score of said peptide, which is indicative for their immunogenic Th-cell activating capacity. Calculation of the cumulative Class I-BCI score and the cumulative Class II-B score is described in detail herein in the Examples section. The TRIA score is calculated as the sum of the cumulative Class I-BCI score and the cumulative Class II-B score. A strong correlation was found between this TRIA score and the T cell responses found in PBMC of HBV-immune donors. Therefore, the TRIA score enables the selection of optimal immunogenic long peptides.

In a first aspect, the present invention provides a peptide derived from an HBV protein. Preferably the peptide of the invention comprises or consists of a peptide selected from the group consisting of SEQ ID NO: 51-79, 1142-1145 and 1468-1471, more preferably the peptide of the invention comprises or consist of a peptide selected from the group consisting of SEQ ID NO: 51, 55, 60, 63, 64, 68, 71, 74, 75, 76, 77, 1142 and 1469, more preferably selected from the group consisting of SEQ ID NO: 51, 55, 60, 63, 64, 68, 71, 74, 75, 77, 1142 and 1469, even more preferably selected from the group consisting of SEQ ID NO: 55, 60, 63, 64, 68, 71, 74, 75, 76, 77 and 1469, even more preferably selected from the group consisting of SEQ ID NO: 55, 60, 63, 64, 68, 71, 74, 75, 77 and 1469, even more preferably selected from the group consisting of SEQ ID NO: 60, 63, 71, 74, 75 and 1469, most preferably selected from the group of SEQ ID NO: 75, 1469 and 63. Further preferred is a peptide of the invention that comprises or consists of a peptide selected from the group consisting of SEQ ID NO: 51, 60, 63, 64, 68, 71, 74-77. Also preferred is a peptide of the invention that comprises or consists of a peptide selected from the group consisting of SEQ ID NO: 63, 71 and 75. Preferably, the peptide of the invention comprises at least about 70 predicted T-cell epitopes. More preferably, the peptide of the invention comprises at least about 70 predicted T-cell epitopes and at least about 3 proteasomal cleavage sites. Preferably, the peptide if the invention comprises at least about 70 predicted HLA class I-restricted $CD8^+$ cytotoxic T-cell epitopes, at least about 1 predicted HLA class II-restricted $CD4^+$ T-helper epitope. More preferably, the peptide if the invention comprises at least about 70 predicted HLA class I-restricted $CD8^+$ cytotoxic T-cell epitopes, at least about 1 predicted HLA class II-restricted $CD4^+$ T-helper epitope and at least about 3 proteasomal cleavage sites. HLA class I-restricted $CD8^+$ cytotoxic T-cell epitope is also denominated herein as CTL epitope and HLA class II-restricted $CD4^+$ T-helper epitope is also denominated herein as Th-cell epitope. Preferably, the peptide of the invention comprises at least about 70 predicted CTL epitopes, at least about 15 predicted Th-cell epitopes. More preferably, the peptide of the invention comprises at least about 70 predicted CTL epitopes, at least about 15 predicted Th-cell epitopes and at least about 3 proteasomal cleavage sites. Preferably, the peptide of the invention comprises at least about 95 predicted CTL epitopes, at least about 25 predicted Th-cell epitopes. More preferably, the peptide of the invention comprises at least about 95 predicted CTL epitopes, at least about 25 predicted Th-cell epitopes and at least about 3 proteasomal cleavage sites. Preferably, the peptide of the invention comprises at least about 125 predicted CTL epitopes, at least about 50 predicted Th-cell epitopes. More preferably, a peptide of the invention comprises at least about 125 predicted CTL epitopes, at least about 50 predicted Th-cell epitopes and at least about 3 proteasomal cleavage sites. Preferably, a peptide of the invention has a TRIA score of at least about 6300, at least about 8000, at least about 9000, at least about 10000, or preferably at least about 14000.

A peptide of the invention can advantageously be used in the prevention and/or treatment of an HBV related disease or condition in a subject, preferably a mammal, more preferably a human. Preferably, the peptide of the invention comprises or consists of an amino acid sequence, preferably a contiguous amino acid sequence, of any of the proteins selected from the group consisting of HBV protein polymerase, HBV core protein, HBV X-protein and HBV large surface protein. Preferably, said peptide comprises or consists of a peptide selected from the group consisting of SEQ ID NO: 51-79, 1142-1145 and 1468-1471. A peptide of this group is characterized in that it has a TRIA score of at least 6300, indicating the high immunogenic capacity for CD4+ and CD8+ T cell activation. Furthermore, a peptide of this group is characterized in that it comprises at least 70 predicted HLA class I-restricted $CD8^+$ cytotoxic T-cell epitopes, at least 1 predicted HLA class II-restricted $CD4^+$ T-helper epitope. Preferably, a peptide of this group comprises at least 3 proteasomal cleavage sites.

More preferably, the peptide of the invention comprises or consists of a peptide selected from the group consisting of SEQ ID NO: 51-53, 55-57, 60-66, 68-78, 1142-1145 and 1468-1471. A peptide of this group is characterized in that it has a TRIA score of at least 8000.

More preferably, the peptide of the invention comprises or consists of a peptide selected from the group consisting of SEQ ID NO: 51-53, 55-57, 60-66, 68, 69, 71-79, 1142-1145 and 1468-1471. A peptide of this group is characterized in that it comprises at least 70 predicted CTL epitopes, at least 15 predicted Th-cell epitopes. Preferably, a peptide of this group comprises at least 3 proteasomal cleavage sites. Preferably, the peptide of the invention comprises or consists of a peptide selected from the group consisting of SEQ ID NO: 51-53, 55, 57, 60, 63, 64, 66, 68, 71, 72, 74-78, 1142, 1145, 1468-1471.

More preferably, the peptide of the invention comprises or consists of a peptide selected from the group consisting of SEQ ID NO: 53, 55-57, 60-66, 68, 69, 71, 73-78, 1142-1145, 1468-1471. A peptide of this group is characterized in that it has a TRIA score of at least 9000.

Even more preferably, the peptide of the invention is a peptide that comprises or consists of a peptide selected from the group consisting of SEQ ID NO: 55-57, 60-65, 68, 69, 71, 74, 75, 77, 78, 1142-1145, 1468, 1469 and 1471. A peptide of this group is characterized in that it has a TRIA score of at least 10000.

Even more preferably, the peptide of the invention comprises or consists of a peptide selected from the group consisting of SEQ ID NO: 52, 53, 55, 57, 60, 61, 63, 64, 68, 69, 71, 72, 75, 77, 78, 1142-1145, 1468, 1469 and 1471. A peptide of this group is characterized in that it comprises at least 95 predicted CTL epitopes, at least 25 predicted Th-cell epitopes. Preferably, a peptide of this group comprises at least 3 proteasomal cleavage sites. Preferably, the peptide of the invention comprises or consists of a peptide selected from the group consisting of SEQ ID NO: 55, 60, 63, 64, 68, 71, 75, 77, 1142, 1469.

Most preferably, the peptide of the invention comprises or consists of a peptide selected from the group consisting of SEQ ID NO: 63, 75, 1143-1145, 1468 and 1469. A peptide of this group is characterized in that it has a TRIA score of at least 14000. Furthermore, a peptide of this group is characterized in that it comprises at least 125 predicted CTL epitopes, at least 50 predicted Th-cell epitopes. Preferably, a peptide of this group comprises at least 3 proteasomal cleavage sites.

A "T-cell epitope" is defined herein as a linear fragment of a polypeptide antigen, which is recognized and bound by a T-cell receptor, preferably a human T-cell receptor, after being made accessible to a T-cell receptor by intracellular proteolytic processing of the polypeptide antigen and subsequent presentation by an HLA class I or HLA class II molecule on the cell surface of an antigen-presenting cell. A "predicted T-cell epitope" is to be understood herein as a linear fragment of a polypeptide antigen for which liberation from the source protein or peptide by proteolytic cleavage and T-cell receptor recognition and/or binding has been predicted using bioinformatics analyses based on algorithms that predict HLA class I and II peptide binding and C-terminal generation by the proteasome of all possible HLA class I binding peptides (with a length of a HLA class I ligand; 8-12 aa) contained in the HBV proteins. A "confirmed T-cell epitope" is to be understood herein as a linear fragment of a polypeptide antigen for which liberation from the source protein or source polypeptide by proteolytic cleavage and T-cell receptor recognition and/or binding, and more preferably $CD4^+$ or $CD8^+$ T cell activation capability, have been established experimentally as disclosed herein. A "linear fragment" is understood herein to be a contiguous amino acid sequence of a polypeptide antigen, said polypeptide antigen preferably being an HBV protein, more preferably a protein selected from the group consisting of HBV protein polymerase, HBV core protein, HBV X-protein and HBV large surface protein. An identical linear fragment of a polypeptide antigen showing binding affinity to a second or further type of HLA class I or HLA class II molecule is to be understood herein as a second or further T-cell epitope. In other words, a specific linear fragment of a polypeptide antigen being capable to bind to two types of HLA molecules is understood herein to be two separate or distinct T-cell epitopes, and is scored twice within the cumulative BCI Class I- and/or Class II-B score. A T-cell epitope typically comprises or consists of at least 8 amino acids and up to 20 or (exceptionally) even more amino acids. A T-cell epitope can be an HLA class I-restricted $CD8^+$ cytotoxic T cell (CTL) epitope or an HLA class II-restricted $CD4^+$ T-helper (Th–)cell epitope. HLA class I restricted epitopes (also referred to as CTL epitopes) are typically presented via the classical proteasome dependent HLA class I processing route, whereas HLA class-II molecules are typically loaded with linear fragments in the late endosomal compartment. Preferably, a peptide according to the invention comprises T-cell epitopes that are selected from the group consisting of SEQ ID NO: 80-276, 278-314, 316-429, 432-483, 486-545, 548-636, 638-1140, and 1146-1466 (see Tables 4-7). A preferred peptide according to the invention comprises at least 70, 71, 72, 73, 74, 75, 79, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225 or from about 230 to about 233 predicted T-cell epitopes from HBV core protein, HBV polymerase, HBV X protein and/or HBV large surface protein. A more preferred peptide according to the invention comprises at least 95, 96, 97, 98, 100, 105, 110, 115, 120, 125, 130, 135, 140, 145, 150, 155, 160, 165, 170, 175, 180, 185, 190, 195, 200, 205, 210, 215, 220, 225 or from about 230 to about 233 predicted T-cell epitopes from HBV core protein, HBV polymerase, HBV X protein and/or HBV large surface protein. An even more preferred peptide according to the invention comprises at least 70, 71, 72, 73, 74, 75, 79, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225 or from about 230 to about 233 predicted T-cell epitopes selected from the group consisting of SEQ ID NO: 80-276, 278-314, 316-429, 432-483, 486-545, 548-636, 638-1140, and 1146-1466. An even more preferred peptide according to the invention comprises at least 95, 96, 97, 98, 100, 105, 110, 115, 120, 125, 130, 135, 140, 145, 150, 155, 160, 165, 170, 175, 180, 185, 190, 195, 200, 205, 210, 215, 220, 225 or from about 230 to about 233 predicted T-cell epitopes selected from the group consisting of SEQ ID NO: 80-276, 278-314, 316-429, 432-483, 486-545, 548-636, 638-1140, and 1146-1466. Preferably, the predicted T-cell epitopes of the present invention are confirmed experimentally as disclosed herein. A preferred peptide according to the invention comprises at least 1, 2, 3, 4, 5, 6, 7, 8, 9, 10, 11, 12, 13, 14, 15, 16, 17, 18, 19, 20, 25, 30, 35, 40, 45, 50, 55, 60, 65 or 70 confirmed T-cell epitopes from HBV core protein, HBV polymerase, HBV X protein and/or HBV large surface protein. A more preferred peptide according to the invention comprises at least 20, 21, 22, 23, 24, 25, 26, 27, 28, 29, 30, 35, 40, 45, 50, 55, 60, 65, 70, 75, 80, 85, 90 or 95 confirmed T-cell epitopes from HBV core protein, HBV polymerase, HBV X protein and/or HBV large surface protein. An even more preferred peptide according to the invention comprises at least 1, 2, 3, 4, 5, 6, 7, 8, 9, 10, 11, 12, 13, 14, 15, 16, 17, 18, 19, 20, 25, 30, 35, 40, 45, 50, 55, 60, 65 or 70 confirmed T-cell epitopes selected from the group consisting of SEQ ID NO: 80-276, 278-314, 316-429, 432-483, 486-545, 548-636, 638-1140, and 1146-1466. An even more preferred peptide according to the invention comprises at least 20, 21, 22, 23, 24, 25, 26, 27, 28, 29, 30, 35, 40, 45, 50, 55, 60, 65, 70, 75, 80, 85, 90 or 95 confirmed T-cell epitopes selected from the group consisting of SEQ ID NO: 80-276, 278-314, 316-429, 432-483, 486-545, 548-636, 638-1140, and 1146-1466.

A "proteasomal cleavage site" is understood herein as a site in a protein or polypeptide that is cleaved by the proteasome, preferably a human proteasome/proteasome naturally present in a human cell. A specific proteasomal cleavage site liberating the C-terminus of the epitope is preferably present exactly after the C-terminus of the epitope amino acid sequence, in order to allow the epitope's C-terminal residue to be liberated from the larger peptide and to be presented by the HLA class I molecule. The first important event that defines an HLA class I-restricted CD8$^+$ cytotoxic T-cell (CTL) epitope is the release of the epitope (or the epitope-precursor) from its flanking protein regions through enzymatic cleavage by cytosolic peptidases. The multicatalytic proteasome is the primary enzyme complex required for the generation of the exact C-terminus of the vast majority of CTL epitopes (Rock et al., 2004). Proteasomes are multicatalytic enzyme complexes abundantly present intracellularly and are considered responsible for the generation of the C terminus of the vast majority of CTL epitopes (Craiu et al, 1997; Stoltze et al., 1998; Mo et al., 1999). The generation of the amino-terminus of a CTL epitope, on the other hand, is much more flexible because several amino-terminal exo-peptidases (like ERAP1, puromycin sensitive aminopeptidase, bleomycin hydrolase and others) reside in the cytosol and endoplasmic reticulum and these trimming enzymes have the capacity to shorten an N-terminal elongated epitope-precursor to its precise length. In contrast, C-terminal trimming has not been reported. Therefore the identification of the proteasome-mediated cleavage sites in a protein or in a polypeptide, like a peptide of the invention, can be used as an important identifier of almost every CTL epitope, because the proteasomal cleavages determine and enable C-terminal epitope generation (Kessler et al., 2001; Kessler and Melief, 2007). The assessment of proteasomal cleavage sites in the HBV core protein, HBV polymerase, HBV X protein and/or HBV large surface protein identifies the C-termini of intracellularly produced HBV peptide fragments, specifically for HLA class I presented peptide fragments. Length requirements are much less strict for loading of HLA class II with peptide fragments. Therefore, precise enzymatic generation of the HLA class II binding peptide fragment is not needed. These T-cell epitope requirements have been used in the present invention to localize and design long peptides derived from the full length sequences of an HBV protein which comprises preferred CD8$^+$ cytotoxic T cell (CTL) and CD4$^+$ T-helper (Th-)cell epitopes and/or combinations thereof and are thus highly immunogenic and therefore suitable peptides for synthesis and (therapeutic) vaccination purposes.

Proteasome mediated proteolytic cleavages can be predicted in silico using a prediction algorithm. Cleavage as performed by the proteasome can be verified in a proteasome mediated cleavage assay as disclosed herein, which measures the C-terminal liberation of the epitope from its flanking regions (Kessler et al., 2001; Kessler and Melief, 2007). A cell free proteasome cleavage assay identifying and quantitatively measuring the amino acid (aa) positions and the abundancy of cleavages by the proteasome in a polypeptide can be used to determine which peptides are generated from the source protein (or source polypeptide), thereby establishing the peptide pool available for epitope generation. The cell free proteasome cleavage assay involves the co-incubation of a polypeptide (preferably having a length of 28-40 aa, more preferably having a length of 30-39 aa) with a preparation of purified proteasomes in an appropriate buffer solution. Two main forms of proteasomes exist, the immunoproteasomes, which are mainly expressed in professional antigen presenting cells, like e.g. Dendritic Cells, and the constitutive proteasomes, which are expressed mainly in other cell types. These types contain variant catalytic subunits with slightly different catalytic activity. Although most epitopes are liberated by both types of proteasomes, sometimes differential epitope generation occurs dependent on proteasome type (Morel et al., 2000; Chapiro et al., 2006). Accordingly, proteasome-mediated cleavage assays may be performed separately with these two proteasome types. Preferably, a constitutive 20S-proteasome or immune 20S-proteasome is used as disclosed herein. The reaction mixture comprising the peptides to be cleaved and either of the two proteasome types (purified proteasome preparations) is incubated at 37° C. and samples are drawn at 1 h, 3 h, 6 h and 24 h time points as detailed in the Examples herein. Subsequently, generated peptide cleavage fragments and the remaining source polypeptide are identified and quantified by mass spectrometry (Kessler et al., 2001). This assay reveals both the positions in the polypeptide (and thus in the source protein) where the proteasome cleaves and the cleavage efficiency (abundancy) at these positions. A cleavage site can be confirmed by detection of fragments containing as COOH terminus the residue NH2-terminal from the cleavage site together with the (possible) complementary fragment(s), as calculated from the intensities of the fragment peaks in the mass spectra (preferably present for >1%, more preferably present for ≥7%, at 24 h incubation), in both the digestion with constitutive proteasomes and the digestion with immunoproteasomes. Preferably, a peptide of the invention comprises at least 1, 2, 3, 4, 5, 6, 7, 8, 9, 10, 11, 12, 13, 14, 15, 16, 17, 18, 19, 20 or more, preferably at least 3, proteasomal cleavage site as defined herein. More preferably, a peptide of the invention comprises at least 1, 2, 3, 4, 5, 6, 7, 8, 9, 10, 11, 12, 13, 14, 15, 16, 17, 18, 19, 20 or more, preferably at least 3, proteasomal cleavage site as assessed and verified in a proteasomal cleavage assay as described above.

As indicated above, examples of T-cell epitopes are HLA class I-restricted CD8$^+$ cytotoxic T cell (CTL) epitopes and HLA class II-restricted CD4$^+$ T-helper (Th–)cell epitopes. A "CTL epitope" is understood herein as a linear fragment of a polypeptide antigen that is liberated from the source protein by proteasome mediated proteolytic cleavage and subsequently presented by an HLA class I molecule on the cell surface of an antigen presenting cell (APC), preferably a human antigen presenting cell. A "predicted CTL epitope" is understood herein as a linear fragment of a polypeptide antigen for which liberation from its source protein by proteolytic cleavages and HLA class I molecule binding have been predicted using bioinformatics analyses based on algorithms that predict HLA class I peptide binding and C-terminal generation by the proteasome of all HLA class I binding short peptides (with a length of a CTL epitope: 8-12 aa) contained in the HBV proteins. Preferably, a predicted CTL epitope of the present invention is confirmed experimentally as disclosed herein. A CTL epitope of the invention is preferably capable of activating a CD8$^+$ T cell response. A "confirmed CTL epitope" is understood herein as a linear fragment of a polypeptide antigen for which liberation by proteolytic cleavages and HLA class I molecule binding, more preferably CD8$^+$ T cell activation, have been established experimentally as disclosed herein. A CTL epitope of the invention is preferably capable of activating a CD8$^+$ T cell response. A CTL epitope typically comprises at least 8 up to 12, or exceptionally up to 13 or 14 amino acids. Preferably a CTL epitope consists of 8-14 amino acids, i.e. has a length of at least 8 up to 14 amino acids.

A CTL epitope is defined by two important intracellular events being (i) proteasome mediated proteolytic cleavage and (ii) binding to an HLA class I molecule, which takes place in the endoplasmic reticulum (ER). The stronger a linear peptide fragment binds and the slower the off-rate, the more likely that this linear peptide fragment will become a cell surface presented immunogenic CTL epitope (Van der Burg et al., 1996). Analysis of proteasome mediated proteolytic cleavages can be performed as indicated above. Preferably, specific binding to an HLA class I molecule is predicted using an in silico prediction algorithm and established by using an HLA class I peptide binding assay as known by the person skilled in the art (Kessler and Melief, 2007; Kessler et al., 2003). Preferably, the HLA class I-restricted epitope in a long peptide according to the invention is predicted to be generated at its C-terminus by the proteasome and preferably has a predicted high affinity binding capacity for the HLA class I molecule using an assay as described in van der Burg et al., 1995 and Kessler et al., 2003; e.g. $IC_{50}$≤about 5 µM may be considered high affinity binding, about 5 µM<$IC_{50}$≤about 15 µM may be considered intermediate affinity binding, about 15 µM<$IC_{50}$≤100 µM may be considered low affinity binding and $IC_{50}$>about 100 µM may be considered as no binding. To measure class I binding affinity of a peptide or fragments thereof, various HLA class I binding assays are available. The assays can be divided into cell-free assays (using soluble HLA) versus cellular assays (using HLA class I molecules on the cell surface), and competitive assays (resulting in semi-quantitative data) versus assays that do not use a labeled reference peptide and are therefore quantitative (Kessler and Melief, 2007; Viatte et al., 2006). The assays have in common that the HLA class I peptide binding affinity is reliably assessed.

The actual presentation of a CTL epitope on the cell surface, i.e. the net result of both proteasomal cleavage, possible other proteolytic events like N-terminal trimming, and binding and presentation by an HLA class I molecule, which events together define a CTL epitope as indicated above, can be demonstrated by a biochemical approach or by a functional approach using cytotoxic T cells with a T-cell receptor specific for the epitope and HLA class I molecule (geno)type, as known by the person skilled in the art (Kessler and Melief, 2007).

The biochemical approach involves the biochemical purification of HLA-epitope complexes from cells expressing the HBV antigen of the invention together with the presenting HLA class I molecule (geno)type, followed by the mass spectrometric search for the epitope in the eluted HLA class I-bound CTL receptor ligands as known by the person skilled in the art (Schirle et al., 2000; Schirle et al., 2001).

The functional approach involves a CTL line or clone that is specifically recognizing the HLA-epitope, which is used as a tool to demonstrate the natural processing and actual presentation of the epitope by HLA class I molecules. In this methodology, using a CTL induction assay as known in the art, either the synthetically generated minimal (i.e. exact length) epitope or the peptide sequence of interest encompassing the epitope, for instance a peptide, long peptides and/or SLP as defined herein, is used to stimulate and select HLA-epitope-specific cytotoxic T cells. To that end, briefly, a multivalent CD8$^+$ T cell population, or a multivalent mixed CD8$^+$ and CD4$^+$ T cell population, is stimulated with autologous target cells of which the HLA class I molecules on the cell surface are either exogenously loaded with the precise synthetic epitope or endogenously loaded with intracellularly generated CTL epitopes derived from the exogenously loaded long peptide of the invention after its uptake by the antigen presenting target cells. In case the autologous target cells are loaded with a peptide, e.g. the synthetic long peptide of the invention, or fragments thereof, encompassing the epitope, the epitope is generated after cellular uptake of the peptide and its intracellular processing by the proteasome together with other N-terminal trimming peptidases. Subsequently, using a T cell recognition assay, the HLA-epitope-specific CTL is used to demonstrate the intracellular generation and natural presentation of the epitope of the invention by HLA class I molecules on the surface of HBV-infected cells. Specific recognition of an HLA class I restricted epitope by a CTL demonstrates the cell surface expression of the epitope and reveals its immunogenicity, i.e. the presence of epitope-specific T cells in the (T-cell receptor) repertoire of a selected donor. Preferably, the CD8$^+$ T cell activating capability has been demonstrated ex vivo and/or in vivo, in T cells from human healthy control individuals or even more preferably in T cells from a human patient with an HBV related disease or condition and/or from a healthy control. The activation is preferably assessed ex vivo or in vivo, more preferably in a human patient with an HBV related disease. A CTL epitope for which liberation by proteolytic cleavage and HLA class I molecules presentation, or preferably CD8+ T cell activating capability, has been demonstrated experimentally is denominated herein as a confirmed CTL epitope.

A peptide of the invention preferably comprises at least 70, 71, 72, 73, 74, 75, 79, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230 and to up to 233 predicted CTL epitopes as defined herein. Preferably, a peptide of the invention comprises at least 70, 71, 72, 73, 74, 75, 79, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230 and to up to 233 predicted CTL epitopes as defined herein. Preferably, a peptide according to the invention comprises at least 70, 71, 72, 73, 74, 75, 79, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230 and to up to 233 predicted CTL epitopes from the HBV core protein, HBV polymerase, HBV X protein and/or HBV large surface protein. More preferably a peptide according to the invention comprises at least 70, 71, 72, 73, 74, 75, 79, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230 and to up to 233 predicted CTL epitopes from the HBV core protein, HBV polymerase, HBV X protein or HBV large surface protein. Even more preferably, a peptide according to the invention comprises or consists of a contiguous amino acid sequence of any of the proteins selected from the group consisting of HBV core protein, HBV polymerase, HBV X protein and HBV large surface protein, wherein said contiguous amino acid sequence comprises at least 70, 71, 72, 73, 74, 75, 79, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230 and to up to 233 predicted CTL epitopes. Preferably, a peptide according to the invention comprises at least 70, 71, 72, 73, 74, 75, 79, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230 and to up to 233 CTL predicted epitopes selected from the group consisting of SEQ ID NO: 80-276, 278-314, 316-429, 432-483, 486-545, 548-636, 638-685; 846-923, 959-1090, and 1146-1395 (see Tables 4a, 5a, 6a and 7a). Even more preferably, a peptide of the invention preferably comprises at least 1, 2, 3, 4, 5, 6, 7, 8, 9, 10, 15, 20, 25, 30, 40, 50, 60, 70, or preferably at least 95 confirmed CTL epitopes as defined herein and verified using a biochemical or functional assay as described above. Most preferred is a peptide of the invention that comprises at least 1, 2, 3, 4, 5, 6, 7, 8, 9, 10, 11, 12, 13, 14, 15, 16, 17, 18, 19, 20, 25, 30, 35, 40, 45, 50, 55, 60, 65 or 70 or preferably at least 20, 21, 22, 23, 24, 25, 26, 27, 28, 29, 30, 35, 40, 45, 50, 55, 60, 65, 70, 75, 80, 85, 90 or 95 confirmed CTL epitopes as defined herein and verified using a functional assay as described above. Preferably, a peptide of the invention comprises at least 1, 2, 3, 4, 5, 6, 7, 8, 9, 10, 11, 12, 13, 14, 15, 16, 17, 18, 19, 20, 25, 30, 35, 40, 45, 50, 55, 60, 65 or 70 or preferably at least 20, 21, 22, 23, 24, 25, 26, 27, 28, 29, 30, 35, 40, 45, 50, 55, 60, 65, 70, 75, 80, 85, 90 or 95 confirmed CTL epitopes selected from the group consisting of SEQ ID NO: 80-276, 278-314, 316-429, 432-483, 486-545, 548-636, 638-685; 846-923, 959-1090, and 1146-1395.

A "Th-cell epitope" is understood herein to be a linear peptide fragment that is recognized by an HLA class II molecule. A "predicted Th-cell epitope" is understood herein as a linear fragment of a polypeptide antigen for which HLA class II molecule recognition has been predicted using sophisticated bioinformatics analyses that are experimentally underpinned. Preferably, a predicted Th-cell epitope of the present invention is confirmed experimentally as disclosed herein. A Th-cell epitope of the invention is preferably capable of inducing a CD4+ T cell response. A "confirmed Th-cell epitope" is understood herein as a linear fragment of a polypeptide antigen for which HLA class II molecule recognition has been established experimentally as known by the person skilled in the art and further detailed herein.

An HLA class II-restricted CD4+ T-helper cell (Th-cell) epitope typically comprises 15 up to 20, or exceptionally even more, amino acids. Preferably, an HLA class II-restricted T-helper cell epitope comprises or 10-20 or 10-15 amino acids. Specific recognition of a predicted HBV-derived Th-cell epitope can be tested and/or verified in a Th-cell induction assay. To this end the peptide or fragment thereof, long peptide and/or SLP sequence of interest comprising the predicted Th-cell epitope is exogenously loaded on the surface of target cells and subsequently these peptide-loaded target cells are co-incubated with a multivalent autologous T helper cell population. After several rounds of stimulation, epitope-specific T helper cells can be selected and can be back-tested for the recognition of the T helper cell epitope contained in the peptide or SLP thereby proving its natural cell surface presentation. Preferably, an HLA class II-restricted CD4+ T-helper cell epitope comprised in a peptide according to the invention is capable of inducing or activating a CD4+ T-helper cell in a human patient with an HBV related disease or condition. The induction or activation is preferably assessed ex vivo or in vivo, more preferably in a human patient with an HBV related disease. Most preferably, the HLA class II-restricted epitope is capable of activating a CD4+ T-helper memory and/or CD4+ T-helper effector response, i.e. activation of a CD45RO-positive CD4+ T-helper cell. This will lead, by virtue of the 'license to kill' signal through CD40-triggering of DC (Lanzavecchia, 1998) to a more robust CD8+ effector and memory cytotoxic T cell response. In another setting the activated CD4+ T-helper cells may activate non-HLA restricted killer cells of the immune system. A Th-cell epitope for which recognition by an HLA class II molecule, or preferably CD4+ activating capability, has been demonstrated experimentally is denominated herein as a confirmed Th-cell epitope.

Preferably, a peptide according to the invention comprises at least one predicted Th-cell epitope from HBV core protein, HBV polymerase, HBV X protein and/or HBV large surface protein. Preferably, a peptide of the invention comprises at least 1, 2, 3, 4, 5, 6, 8, 7, 8, 9, 10 or preferably at least 15 predicted Th-cell epitope(s) as defined herein. Preferably, a peptide according to the invention comprises at least 1, 2, 3, 4, 5, 6, 8, 7, 8, 9, 10, or preferably at least 15 predicted Th-cell epitope(s) from the HBV core protein, HBV polymerase, HBV X protein and/or HBV large surface protein. Even more preferably, a peptide according to the invention comprises or consists of a contiguous amino acid sequence of any of the proteins selected from the group consisting of HBV core protein, HBV polymerase, HBV X protein and HBV large surface protein, wherein said contiguous amino acid sequence comprises at least 1, 2, 3, 4, 5, 6, 8, 7, 8, 9, 10, or preferably at least 15 predicted Th-cell epitope(s). Preferably, a peptide according to the invention comprises at least 1, 2, 3, 4, 5, 6, 8, 7, 8, 9, 10, or preferably at least 15 predicted Th-cell epitope(s) selected from the group consisting of SEQ ID NO: 686-845; 924-958, 1091-1140, and 1396-1466 (see Tables 4b, 5b, 6b, and 7b). More preferably, a peptide of the invention comprises at least 1, 2, 3, 4, 5, 6, 8, 7, 8, 9, 10, or preferably at least 15 confirmed Th-cell epitope(s) as defined herein. Even more preferably, a peptide of the invention comprises at least 1, 2, 3, 4, 5, 6, 8, 7, 8, 9, 10, or preferably at least 15 confirmed Th-cell epitope(s) as defined herein and verified using an T helper cell induction assay as described above. Preferably, a peptide of the invention comprises at least 1, 2, 3, 4, 5, 6, 8, 7, 8, 9, 10, or preferably at least 15 confirmed Th-cell epitope selected from the group consisting of SEQ ID NO: 686-845; 924-958, 1091-1140, and 1396-1466.

Preferably, a peptide according to the invention comprises both at least 70 predicted CTL epitopes and at least one predicted Th-cell epitope from the HBV core protein, HBV polymerase, HBV X protein and/or HBV large surface protein. More preferably, a peptide according to the invention is a peptide derived from the HBV core protein, HBV polymerase, HBV X protein and/or HBV large surface protein, preferably is a fragment of the HBV core protein, HBV polymerase, HBV X protein and/or HBV large surface protein, that comprises at least 70 predicted CTL epitopes, at least one predicted Th-cell epitope and at least 3 proteasomal cleavage sites. The presence of at least 3 proteasomal cleavage sites, at least 70 predicted CTL epitopes and at least 1 Th epitope within a single peptide according to the invention, being a continuous amino acids fragment of an antigen protein of interest, has been observed to be particularly advantageous due to synergy between the Th response and the CTL response in mounting and maintaining an effective CD8+ cytotoxic T cell response. Several published studies have demonstrated that CD4+ T-helper cells upon interaction with HLA class II epitope presenting dendritic cells (DC) upregulate CD40 ligand. The interaction of the Th-cell by its CD40 ligand with the CD40 molecule on the DC leads to activation of the DC. Activated DCs display upregulated costimulatory molecules and secrete CTL-promoting cytokines. This allows both a more robust CD8+ CTL response induced by such an activated DC that presents HLA class I restricted epitopes and a much more robust CTL memory response (Ridge et al., 1998; Schoenberger et al., 1998; Sun et al., 2004). The need for CD40 expression on DC for robust CD8+ CTL responses following vaccination with synthetic long peptides (length of 35 aa.) has been demonstrated in Zwaveling et al. (2002).

Accordingly, a preferred peptide according to the invention comprises at least 70 predicted CTL epitopes and at least one predicted Th-cell epitope; preferably at least 70 predicted CTL epitopes selected from the group consisting of SEQ ID NO: 80-276, 278-314, 316-429, 432-483, 486-545, 548-636, 638-685; 846-923, 959-1090, and 1146-1395 and at least one predicted Th-cell epitope selected from the group consisting of SEQ ID NO: 686-845; 924-958, 1091-1140, and 1396-1466. A more preferred peptide according to the invention comprises at least 70 predicted CTL epitopes and at least 15 predicted Th-cell epitopes; preferably at least 70 predicted CTL epitopes selected from the group consisting of SEQ ID NO: 80-276, 278-314, 316-429, 432-483, 486-545, 548-636, 638-685; 846-923, 959-1090, and 1146-1395 and at least 15 predicted Th-cell epitopes selected from the group consisting of SEQ ID NO: 686-845; 924-95, 1091-1140, and 1396-1466. More preferably, a peptide according to the invention comprises at least 71, 72, 73, 74, 75, 80, 85, 90, 95, 100, 105, 110, 115, 120, 125, 130, 135, 140, 145, 150, 155, 160, 165, 170 up to 175 predicted CTL epitopes selected from the group consisting of SEQ ID NO: 80-276, 278-314, 316-429, 432-483, 486-545, 548-636, 638-685; 846-923, 959-1090, and 1146-1395 and at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95 up to 96 predicted Th-cell epitopes selected from the group consisting of SEQ ID NO: 686-845; 924-958, 1091-1140, and 1396-1466. Even more preferably, a peptide according to the invention comprises at least 95, 100, 105, 110, 115, 120, 125, 130, 135, 140, 145, 150, 155, 160, 165, 170 up to 175 predicted CTL epitopes selected from the group consisting of SEQ ID NO: 80-276, 278-314, 316-429, 432-483, 486-545, 548-636, 638-685; 846-923, 959-1090, and 1146-1395 and at least 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95 up to 96 predicted Th-cell epitopes selected from the group consisting of SEQ ID NO: 686-845; 924-958, 1091-1140, and 1396-1466. Preferably, a peptide according to the invention comprises at least 95 predicted CTL epitopes as defined herein and at least 25 predicted Th-cell epitopes as defined herein.

More preferably, a preferred peptide according to the invention comprises at least 5 confirmed CTL epitopes and at least one confirmed Th-cell epitope; preferably at least 5 confirmed CTL epitopes selected from the group consisting of SEQ ID NO: 80-276, 278-314, 316-429, 432-483, 486-545, 548-636, 638-685; 846-923, 959-1090, and 1146-1395 and at least one confirmed Th-cell epitope selected from the group consisting of SEQ ID NO: 686-845; 924-958, 1091-1140, and 1396-1466. A more preferred peptide according to the invention comprises at least 15 confirmed CTL epitopes and at least one confirmed Th-cell epitope; preferably at least 15 confirmed CTL epitopes selected from the group consisting of SEQ ID NO: 80-276, 278-314, 316-429, 432-483, 486-545, 548-636, 638-685; 846-923, 959-1090, and 1146-1395 and at least one confirmed Th-cell epitope selected from the group consisting of SEQ ID NO: 686-845; 924-95, 1091-1140, and 1396-1466. More preferably, a peptide according to the invention comprises at least 1, 2, 3, 4, 5, 6, 7, 8, 9, 10, 11, 12, 13, 14, 15, 16, 17, 18, 19, 20, 25, 30, 35, 40, 45, 50, 55, 60, 65 or 70 confirmed CTL epitopes selected from the group consisting of SEQ ID NO: 80-276, 278-314, 316-429, 432-483, 486-545, 548-636, 638-685; 846-923, 959-1090, and 1146-1395 and at least 1, 2, 3, 4, 5, 6, 7, 8, 9, 10, 11, 12, 13, 14, 15, 16, 17, 18, 19, 20 confirmed Th-cell epitopes selected from the group consisting of SEQ ID NO: 686-845; 924-958, 1091-1140, and 1396-1466. Even more preferably, a peptide according to the invention comprises at least 20, 21, 22, 23, 24, 25, 26, 27, 28, 29, 30, 35, 40, 45, 50, 55, 60, 65, 70, 75, 80, 85, 90 or 95 confirmed CTL epitopes selected from the group consisting of SEQ ID NO: 80-276, 278-314, 316-429, 432-483, 486-545, 548-636, 638-685; 846-923, 959-1090, and 1146-1395 and at least 1, 2, 3, 4, 5, 6, 7, 8, 9, 10, 11, 12, 13, 14, 15, 16, 17, 18, 19, 20 confirmed Th-cell epitopes selected from the group consisting of SEQ ID NO: 686-845; 924-958, 1091-1140, and 1396-1466. Preferably, a peptide according to the invention comprises at least 15 confirmed CTL epitopes as defined herein and at least 5 confirmed Th-cell epitopes as defined herein.

The HLA class I epitopes in the peptides according to the invention are preferably capable of being presented on HLA molecules being encoded by HLA alleles that are predominant in the population of human subjects to be treated. Preferred HLA class I epitopes in peptides according to the invention are epitopes capable of binding to: HLA-A0101; HLA-A0201; HLA-A0206; HLA-A0301; HLA-A1101; HLA-A2301; HLA-A2402; HLA-A2501; HLA-A2601; HLA-A2902; HLA-A3001; HLA-A3002; HLA-A3101; HLA-A3201; HLA-A3303; HLA-A6801; HLA-A6802; HLA-A7401; HLA-B0702; HLA-B0801; HLA-B1301; HLA-B1302; HLA-B1402; HLA-B1501; HLA-B1502; HLA-B1525; HLA-B1801; HLA-B2702; HLA-B2705; HLA-B3501; HLA-B3503; HLA-B3701; HLA-B3801; HLA-B3901; HLA-B4001; HLA-B4002; HLA-B4402; HLA-B4403; HLA-B4601; HLA-B4801; HLA-B4901; HLA-B5001; HLA-B5101; HLA-B5201; HLA-B5301; HLA-B5501; HLA-B5601; HLA-B5701; HLA-B5801 and HLA-B5802. In a preferred embodiment, a peptide of the invention, covers at least 10%, 20%, 30%, 40%, 50%, 60%, 70%, 80%, 90%, or 100% of the HLA class I molecules that are encoded by HLA alleles predominant in the population of human subjects to be treated, wherein "Cover an HLA class I molecule" is understood herein as comprising a CTL epitope that shows binding affinity, preferably intermediate binding affinity, more preferably high binding affinity to said HLA class I molecule. Preferably, a peptide of the invention covers at least 10%, 20%, 30%, 40%, 50%, 60%, 70%, 80%, 90%, or 100% of group of HLA class I molecules consisting of: HLA-A0101; HLA-A0201; HLA-A0206; HLA-A0301; HLA-A1101; HLA-A2301; HLA-A2402; HLA-A2501; HLA-A2601; HLA-A2902; HLA-A3001; HLA-A3002; HLA-A3101; HLA-A3201; HLA-A3303; HLA-A6801; HLA-A6802; HLA-A7401; HLA-B0702; HLA-B0801; HLA-B1301; HLA-B1302; HLA-B1402; HLA-B1501; HLA-B1502; HLA-B1525; HLA-B1801; HLA-B2702; HLA-B2705; HLA-B3501; HLA-B3503; HLA-B3701; HLA-B3801; HLA-B3901; HLA-B4001; HLA-B4002; HLA-B4402; HLA-B4403; HLA-B4601; HLA-B4801; HLA-B4901; HLA-B5001; HLA-B5101; HLA-B5201; HLA-B5301; HLA-B5501; HLA-B5601; HLA-B5701; HLA-B5801 and HLA-B5802.

The HBV genome (SEQ ID NO: 3; see Table 1) consists of a partially double-stranded circular DNA molecule having four overlapping open reading frames (ORFs) that are responsible for the transcription and expression of seven different hepatitis B proteins through the use of multiple in-frame start codons. The HBV proteins are the core protein and the e antigen (HBeAg) encoded by the C gene, the HBV polymerase encoded by the P gene, the viral surface proteins (small (S), middle (M), and large (L)) encoded by the S gene, and X protein encoded by the X gene. There is an outer shell (or envelope) composed of several proteins known collectively as HBs or surface Proteins. This outer shell is frequently referred to as the surface coat. The outer surface coat surrounds an inner protein shell, composed of HBc protein. This inner shell is referred to as the core particle or capsid. Finally the core particle surrounds the viral DNA and the enzyme DNA polymerase.

The HBV core protein is the major component of the viral nucleocapsid. The amino acid sequences of the HBV polymerase, HBV core protein, HBV X protein and HBV large surface protein are represented by SEQ ID NO: 1, 4, 45 and 1141 respectively (see Table 1).

A preferred amino acid sequence of a human HBV polymerase protein is a sequence having at least 70%, 75%, 80%, 85%, 90%, 91%, 92%, 93%, 94%, 95%, 96%, 97%, 98%, 99%, 100% identity with the sequence depicted in SEQ ID NO: 1; a preferred coding sequence is a sequence having at least about 70%, 75%, 80%, 85%, 90%, 91%, 92%, 93%, 94%, 95%, 96%, 97%, 98%, 99%, 100% identity with the sequence depicted in SEQ ID NO: 2. A preferred amino acid sequence of an HBV core protein is a sequence having at least about 70%, 75%, 80%, 85%, 90%, 91%, 92%, 93%, 94%, 95%, 96%, 97%, 98%, 99%, 100% identity with the sequence depicted in SEQ ID NO: 4; a preferred coding sequence is a sequence having at least about 70%, 75%, 80%, 85%, 90%, 91%, 92%, 93%, 94%, 95%, 96%, 97%, 98%, 99%, 100% identity with the sequence depicted in SEQ ID NO: 5. A preferred amino acid sequence of an HBV large surface protein is a sequence having at least about 70%, 75%, 80%, 85%, 90%, 91%, 92%, 93%, 94%, 95%, 96%, 97%, 98%, 99%, 100% identity with the sequence depicted in SEQ ID NO: 1141, a preferred coding sequence is a sequence having at least 70%, 75%, 80%, 85%, 90%, 91%, 92%, 93%, 94%, 95%, 96%, 97%, 98%, 99%, 100% identity with the sequence depicted in SEQ ID NO: 1467.

The full length consensus amino acid sequence of the X protein was obtained by deducing the optimal sequence from the 39 published and reviewed full length (154 amino acid) HBV X protein amino acid sequences in the UniProt database (at: www.uniprot.org). These 39 sequences were first aligned and subsequently for each aa position the most frequently occurring aa was selected for that position in the consensus sequence. The 39 sequences with the following entries were included in the analysis: P69713; P03165; P0C686; P69714; Q8JMY5; Q69604; Q05499; O91531; Q9PX75; P20976; P20975; P20977; P24026; Q9PXA2; Q67923; P0C685; P0C678; O93195; Q9E6S8; P12936; Q91C38; Q913A9; Q8JMY3; Q8JN06; Q8JMZ5; Q69607; Q91B15; Q80IU5; Q4R1S9; Q4R1S1; Q9YZR6; P0C687; Q9QMI3; P0C681; Q80IU8; Q99HR6; P17102; Q67877; and Q69027 (see Table 2). A preferred consensus amino acid sequence of a human HBV X protein is a sequence having at least about 70%, 75%, 80%, 85%, 90%, 91%, 92%, 93%, 94%, 95%, 96%, 97%, 98%, 99%, 100% identity with the sequence depicted in SEQ ID NO: 45. The consensus amino acid sequence may be encoded by any coding sequence known or designed; the person skilled in the art knows how to design a coding sequence from a known amino acid sequence; such coding sequence may be a codon-optimized sequence. The terms "HBV X protein" and "consensus HBV X protein" are used interchangeably herein.

Percentage of identity is herein determined by calculating the ratio of the number of identical nucleotides/amino acids in the sequence divided by the length of the total nucleotides/amino acids of said sequence, minus the lengths of any gaps. Identity with a given SEQ ID NO means identity based on the full length of said sequence (i.e. over its whole length or as a whole).

Within the context of the present invention, "a peptide derived from an HBV protein" means that the peptide comprises at least 15 and at most 100 consecutive amino acids originating from the HBV core protein, HBV polymerase, HBV X consensus protein and/or HBV large surface protein. In other words, "a peptide derived from the HBV polymerase protein" comprises at most 100 consecutive amino acids of SEQ ID NO: 1, "a peptide derived from the HBV core protein" comprises at most 100 consecutive amino acids of SEQ ID NO: 4, "a peptide derived from the HBV X consensus protein" comprises at most 100 consecutive amino acids of SEQ ID NO: 45, and "a peptide derived from the HBV large surface protein" comprises at most 100 consecutive amino acids of SEQ ID NO: 1141. Preferably, "a peptide derived from the HBV polymerase protein" consists of at most 100 consecutive amino acids of SEQ ID NO: 1, "a peptide derived from the HBV core protein" consists of at most 100 consecutive amino acids of SEQ ID NO: 4, "a peptide derived from the HBV X consensus protein" consists of at most 100 consecutive amino acids of SEQ ID NO: 45, and "a peptide derived from the HBV large surface protein" consists of at most 100 consecutive amino acids of SEQ ID NO: 1141. Therefore, by definition, a peptide according to the invention is distinct from a full length HBV core protein, HBV polymerase, HBV X protein and/or HBV large surface protein, as these full length proteins are all longer than 100 amino acids. Preferably, the peptide of the present invention is from about 15 to about 100 amino acids in length. More preferably the length of the peptide is from 15 up to 100 length indicated herein as the length of the peptide is 15-100 amino acids, or preferably the length of the peptide is 15-95 amino acids, or 15-90 amino acids, or 15-85 amino acids, or 15-70 amino acids, or 15-65 amino acids, or 15-60 amino acids, or 15-55 amino acids, or 15-50 amino acids, even more preferably 15-45 amino acids, even more preferably, 15-40 amino acids, even more preferably 17-39, even more preferably 19-43 amino acids, even more preferably 22-40 amino acids, even more preferably 28-40 and even more preferably 30-39 amino acids. Within the context of the present invention "a peptide which comprises at most 100 amino acids derived from an HBV protein" preferably means that the number of consecutive amino acids originating from an HBV protein, preferably being a protein selected from the group consisting of HBV core protein, HBV polymerase, HBV X consensus protein and HBV large surface protein and present in a peptide as defined herein, is 100, 99, 98, 97, 96, 95, 94, 93, 92, 91, 90, 89, 88, 87, 86, 85, 84, 83, 82, 81, 80, 79, 78, 77, 76, 75, 74, 73, 72, 71, 70, 69, 68, 67, 66, 65, 64, 63, 62, 61, 60, 59, 58, 57, 56, 55, 54, 53, 52, 51, 50, 49, 48, 47, 46, 45, 44, 43, 42, 41, 40, 39, 38, 37, 36, 35, 34, 33, 32, 31, or 30 amino acids or less. Within the context of the present invention "a peptide which comprises at least 15 amino acids derived from an HBV protein" preferably means that the number of consecutive amino acids originating from a protein selected from the group consisting of HBV core protein, HBV polymerase, HBV X consensus protein and HBV large surface protein and present in a peptide as defined herein, is at least 15, 16, 17, 18, 19, 20, 21, 22, 23, 24, 25, 26, 27, 28, 29, 30, 31, 32, 33, 34, 35, 36, 37, 38, 39, 40, 41, 42, 43, 44 or 45 amino acids. Within the context of the present invention "a peptide which comprises 15-100 amino acids derived from an HBV protein" preferably means that the number of consecutive amino acids originating from a protein selected from the group consisting of HBV core protein, HBV polymerase, HBV X consensus protein and HBV large surface protein and present in a peptide as defined herein, is at least 15, 16, 17, 18, 19, 20, 21, 22, 23, 24, 25, 26, 27, 28, 29, 30, 31, 32, 33, 34, 35, 36, 37, 38, 39, 40, 41, 42, 43, 44 or 45 amino acids and no more than 100, 99, 98, 97, 96, 95, 94, 93, 92, 91, 90, 89, 88, 87, 86, 85, 84, 83, 82, 81, 80, 79, 78, 77, 76, 75, 74, 73, 72, 71, 70, 69, 68, 67, 66, 65, 64, 63, 62, 61, 60, 59, 58, 57, 56, 55, 54, 53, 52, 51, 50, 49, 48, 47, 46, 45, 44, 43, 42, 41, 40, 39, 38, 37, 36, 35, 34, 33, 32, 31, or 30 amino acids. Within the context of the present invention "a peptide which comprises 15-100 amino acids derived from an HBV protein" preferably means that the number of consecutive amino acids originating from a protein selected from the group consisting of SEQ ID NO: 1, 4, 45 and 1141 and present in a peptide as defined herein, is at least 15, 16, 17, 18, 19, 20, 21, 22, 23, 24, 25, 26, 27, 28, 29, 30, 31, 32, 33, 34, 35, 36, 37, 38, 39, 40, 41, 42, 43, 44 or 45 amino acids and no more than about 100, 99, 98, 97, 96, 95, 94, 93, 92, 91, 90, 89, 88, 87, 86, 85, 84, 83, 82, 81, 80, 79, 78, 77, 76, 75, 74, 73, 72, 71, 70, 69, 68, 67, 66, 65, 64, 63, 62, 61, 60, 59, 58, 57, 56, 55, 54, 53, 52, 51, 50, 49, 48, 47, 46, 45, 44, 43, 42, 41, 40, 39, 38, 37, 36, 35, 34, 33, 32, 31, or 30 amino acids. More preferably, the length of the contiguous amino acid sequence from HBV core protein, HBV polymerase, HBV X protein and/or HBV large surface protein comprised within the peptide is 15-100 amino acids, or preferably 15-95 amino acids, or 15-90 amino acids, or 15-85 amino acids, or 15-70 amino acids, or 15-65 amino acids, or 15-60 amino acids, or 15-55 amino acids, or 15-50 amino acids, even more preferably 15-45 amino acids, even more preferably, 15-40 amino acids, even more preferably 17-39, even more preferably 19-43 amino acids, even more preferably 22-40 amino acids, even more preferably 28-40 and even more preferably 30-39 amino acids. Even more preferably, the length of the contiguous amino acid sequence from the sequences selected from the group consisting of SEQ ID NO: 1, 4, 45 and 1141 comprised within the peptide is 15-100 amino acids, or preferably 15-95 amino acids, or 15-90 amino acids, or 15-85 amino acids, or 15-70 amino acids, or 15-65 amino acids, or 15-60 amino acids, or 15-55 amino acids, or 15-50 amino acids, even more preferably 15-45 amino acids, even more preferably, 15-40 amino acids, even more preferably 17-39, even more preferably 19-43 amino acids, even more preferably 22-40 amino acids, even more preferably 28-40 and even more preferably 30-39 amino acids. A peptide according to the invention may comprise additional amino acids than the ones originating from an HBV core protein, HBV polymerase, HBV X protein and/or HBV large surface protein or may entirely be made of or consist of an amino acid sequence originating from a protein selected from the group consisting of HBV core protein, HBV polymerase, HBV X protein and/or HBV large surface protein. A peptide according to the invention may comprise several parts of non-contiguous amino acid sequences from an HBV core protein, HBV polymerase, HBV X protein and/or HBV large surface protein, wherein it is to be understood that said peptide has a length, a TRIA score and/or amount and type of T cell epitopes as defined herein.

According to one embodiment, a peptide according to the invention consists of any of the contiguous amino acid sequence from HBV core protein, HBV polymerase, HBV X protein and/or HBV large surface protein as defined herein and indicated by its representing SEQ ID NO, whereby it is understood that no amino acids are appended to either end of the said peptide.

According to another embodiment, the peptide according to the invention comprises any of the contiguous amino acid sequences from HBV core protein, HBV polymerase, HBV X protein and/or HBV large surface protein as defined herein and indicated by its representing SEQ ID NO and further may comprise a modified amino acid and/or a covalently linked functional group such as a fluorinated group, a human toll-like receptor ligand and/or agonist, an oligonucleotide conjugate, PSA, a sugar chains or glycan, a pam3cys and/or derivative thereof, preferably a pam3cys lipopeptide or variant or derivative thereof, preferably such as described in WO2013051936A1, CpG oligodeoxynucleotides (CpG-ODNs), Cyclic dinucleotides (CDNs), 2-aminoisobutyric acid (Abu), Muramyl dipeptide (MDP), a DC pulse cassette, a tetanus toxin derived peptide.

In an embodiment, the peptide of the invention comprises or consists of a non-naturally occurring sequence as a result of the synthesis of non-natural lengths or as a result of comprising additional amino acids not originating from an HBV core protein, HBV polymerase, HBV X protein and/or HBV large surface protein or as a result of comprising non-contiguous amino acid sequences from an HBV core protein, HBV polymerase, HBV X protein and/or HBV large surface protein, and/or as a result of comprising a modified amino acid and/or a non-naturally occurring amino acid and/or a covalently linked functional group such as a fluorinated group, a fluorcarbon group, a human toll-like receptor ligand and/or agonist, an oligonucleotide conjugate, PSA, a sugar chains or glycan, a pam3cys and/or derivative thereof preferably such as described in WO2013051936A1, CpG oligodeoxynucleotides (CpG-ODNs), Cyclic dinucleotides (CDNs), a DC pulse cassette, a tetanus toxin derived peptide, a human HMGB1 derived peptide; either within the peptide or appended to the peptide, as indicated above. The peptide of the invention may comprise 2-aminoisobutyric acid (Abu, an isostereomer of cysteine). A cysteine of the peptide of the invention may be replaced by Abu. Encompassed within the present invention is a peptide of SEQ ID NO: 77, wherein the N-terminal cysteine has been replaced by Abu.

Preferably, a peptide of the invention is an isolated peptide, wherein "isolated" does not reflect the extent to which the peptide is purified, but indicates that the peptide has been removed from its natural milieu (i.e., that has been subject to human manupilation), and may be a recombinantly produced peptide or a synthetically produced peptide.

Preferably, the invention relates to a peptide that can be effectively used in the prevention, partial clearance and/or treatment or full clearance of a HBV related disease or condition in a subject, preferably as detectable by:

an activation or an induction of the immune system and/or an increase in HBV specific activated CD4$^+$ and/or CD8$^+$ T-cells in peripheral blood or an increase of the cytokines produced by these T-cells after at least one week of treatment; and/or an inhibition of proliferation of HBV infection or a detectable decrease of HBV infected cells or a decrease in cell viability of HBV infected cells; and/or an induction or increased induction of HBV infected cell death; and/or an inhibition or prevention of the increase of HBV infected cells.

In all embodiments of the present invention, a subject is preferably a mammal, more preferably a human. A subject may be an animal model, preferably a non-human mammalian model with humanized HLA class I and class II molecules, or a mammalian, preferably human, organ, such as a liver.

In all embodiments of the present invention, the term "HBV related disease or condition" is preferably defined as acute HBV infection, chronic HBV infection and other conditions where the hepatitis virus is found in the blood or body fluids containing blood of a subject, such as liver cirrhosis and liver cancer, or optionally of an asymptomatic subject that is characterized by the presence of the virus in the body of said subject.

In the context of the invention, a patient may survive and may be considered as being disease free as a consequence of treatment according to the invention. Alternatively, the disease or condition may have been stopped or regressed (i.e. cleared or partially cleared infection). A significant increase of HBV-specific activated CD4$^+$ or CD8$^+$ cells in peripheral blood at least one week after vaccination is preferably at least a 5%, 10%, 20%, 30% increase or more. An inhibition of the proliferation of HBV infected cells is preferably at least 5%, 10%, 15%, 20%, 25%, 30%, 35%, 40%, 45%, 50%, 55%, 60%, 65%, 70%, 75% inhibition or more. An induction of HBV infected cell death may be at least 1%, 2%, 3%, 4%, 5%, 6%, 7%, 8%, 9%, 10%, 15%, 20%, 25%, or more. HBV infection may be inhibited at least 5%, 10%, 20%, 30%, 40%, 50%, 55%, 60%, 65%, 70% or 75% induction, or more. HBV infected cells may be reduced by at least 5%, 10%, 15%, 20%, 25%, 30%, 35%, 40%, 45%, 50%, 55%, 60%, 65%, 70%, 75%, 80%, 85%, 90%, 95%, 98% or 100%.

In each embodiment, within this or further aspects disclosed herein, wherein the effect of a peptide according to the invention, a composition according to the invention, a polynucleotide according to the invention, a viral vector comprising a polynucleotide according to the invention and/or a cell according to the invention and/or a cell obtained or obtainable by a method according to the invention, is quantified, the assay may be carried out by comparison to a subject not treated or to the same subject before treatment.

Acute and chronic HBV infection can be treated using the present invention. A peptide according to the invention comprising epitopes which are to be presented to T-cell receptors of CD8$^+$ cytotoxic T cells and/or CD4$^+$ T-helper cells preferably fulfill a number of structural requirements as defined herein. In vitro and ex vivo T cell experiments are preferably used to confirm the capability of peptides according to the invention to induce substantial CD4$^+$ T-helper and CD8$^+$ cytotoxic T cell responses. The peptides of the present invention thereby provide a marked improvement in the selection of relatively short peptides that may be chemically synthesized, comprising the most potent and most widely applicable HLA class I and/or class II presented T cell epitopes derived from HBV.

In an embodiment, a peptide is distinct from a contiguous sequence of amino acids of HBV core protein, HBV polymerase, HBV X protein and/or HBV large surface protein.

A peptide according to the invention comprising a T-cell epitope from HBV core protein, HBV polymerase, HBV X protein and/or HBV large surface protein, may be modified by deletion or substitution of one or more amino acids, by extension at the N- and/or C-terminus with additional amino acids or functional groups, which may improve bio-availability, targeting to T-cells, or comprise or release immune modulating substances that provide adjuvant or (co) stimulatory functions. The optional additional amino acids at the N- and/or C-terminus are preferably not present in the corresponding positions in the native amino acid sequence of HBV core protein, HBV polymerase, HBV X protein and/or HBV large surface protein.

A peptide according to the invention comprising a T-cell epitope is obtainable by chemical synthesis and subsequent purification according to methods well-known in the art. (see e.g. Atherton et al., 1989; Barany et al., 1979; Fields et al., 1997). A peptide according to the invention is preferably soluble in physiologically acceptable watery solutions (e.g. PBS) comprising no more than 35, 20, 10, 5 or 0% DMSO. In such a solution the peptide according to the invention is preferably soluble at a concentration of at least 0.5, 1, 2, 4, or 8 mg peptide per ml. More preferably, a mixture of more than one different peptide according to the invention is soluble at a concentration of at least 0.5, 1, 2, 4, or 8 mg peptide per ml in such solutions.

The peptides according to the invention may be easily synthesized and are large enough to be taken up by professional antigen presenting cells, in particular dendritic cells (DC), processed by the proteasome and/or the endosomal/lysosomal degradation and antigen processing system and preferably have sufficient length to contain at least 1, 5, 10, 15, 20, 25, 30, 35, 40, 45, 50, 55, 60, 65, 70, 73, 75, 80, 85, 90, 95, 100, 105, 110, 115, 120, 125, 130, 135, 140, 145, 150, 155, 160, 165, 170 to preferably up to 175 CTL epitopes and/or at least 1, 5, 10, 15, 20, 25, 30, 35, 40, 45, 50, 55, 60, 65, 70, 75, 80, 85, 90, 95 to preferably up to 96 Th-cell epitopes as defined herein. Optionally, a peptide according to the invention may comprise N- or C-terminal extensions, which may be amino acids, modified amino acids or other functional groups that may for instance enhance bio-availability, cellular uptake, processing and/or solubility.

Preferably, a peptide according to the invention is a peptide comprising a peptide with an amino acid sequence selected from the group consisting of:
  a fragment of 15 to 30 amino acids of SEQ ID NO: 51, preferably contiguous amino acids,
  a fragment of 15 to 35 amino acids of SEQ ID NO: 52, preferably contiguous amino acids,
  a fragment of 15 to 33 amino acids of SEQ ID NO: 53, preferably contiguous amino acids,
  a fragment of 15 to 33 amino acids of SEQ ID NO: 54, preferably contiguous amino acids,
  a fragment of 15 to 39 amino acids of SEQ ID NO: 55, preferably contiguous amino acids,
  a fragment of 15 to 35 amino acids of SEQ ID NO: 56, preferably contiguous amino acids,
  a fragment of 15 to 34 amino acids of SEQ ID NO: 57, preferably contiguous amino acids,
  a fragment of 15 to 32 amino acids of SEQ ID NO: 58, preferably contiguous amino acids,
  a fragment of 15 to 33 amino acids of SEQ ID NO: 59, preferably contiguous amino acids,
  a fragment of 15 to 38 amino acids of SEQ ID NO: 60, preferably contiguous amino acids,
  a fragment of 15 to 38 amino acids of SEQ ID NO: 61, preferably contiguous amino acids,
  a fragment of 15 to 33 amino acids of SEQ ID NO: 62, preferably contiguous amino acids,
  a fragment of 15 to 34 amino acids of SEQ ID NO: 63, preferably contiguous amino acids,
  a fragment of 15 to 36 amino acids of SEQ ID NO: 64, preferably contiguous amino acids,
  a fragment of 15 to 34 amino acids of SEQ ID NO: 65, preferably contiguous amino acids,
  a fragment of 15 to 34 amino acids of SEQ ID NO: 66, preferably contiguous amino acids,
  a fragment of 15 to 34 amino acids of SEQ ID NO: 67, preferably contiguous amino acids,
  a fragment of 15 to 39 amino acids of SEQ ID NO: 68, preferably contiguous amino acids,
  a fragment of 15 to 35 amino acids of SEQ ID NO: 69, preferably contiguous amino acids,
  a fragment of 15 to 32 amino acids of SEQ ID NO: 70, preferably contiguous amino acids,
  a fragment of 15 to 38 amino acids of SEQ ID NO: 71, preferably contiguous amino acids,
  a fragment of 15 to 36 amino acids of SEQ ID NO: 72, preferably contiguous amino acids,
  a fragment of 15 to 36 amino acids of SEQ ID NO: 73, preferably contiguous amino acids,
  a fragment of 15 to 35 amino acids of SEQ ID NO: 74, preferably contiguous amino acids,
  a fragment of 15 to 34 amino acids of SEQ ID NO: 75, preferably contiguous amino acids,
  a fragment of 15 to 33 amino acids of SEQ ID NO: 76, preferably contiguous amino acids,
  a fragment of 15 to 35 amino acids of SEQ ID NO: 77, preferably contiguous amino acids,
  a fragment of 15 to 35 amino acids of SEQ ID NO: 78, preferably contiguous amino acids,
  a fragment of 15 to 34 amino acids of SEQ ID NO: 79, preferably contiguous amino acids,
  a fragment of 15 to 34 amino acids of SEQ ID NO: 1142, preferably contiguous amino acids,
  a fragment of 15 to 34 amino acids of SEQ ID NO: 1143, preferably contiguous amino acids,
  a fragment of 15 to 34 amino acids of SEQ ID NO: 1144, preferably contiguous amino acids,
  a fragment of 15 to 36 amino acids of SEQ ID NO: 1145, preferably contiguous amino acids,
  a fragment of 15 to 32 amino acids of SEQ ID NO: 1468, preferably contiguous amino acids,
  a fragment of 15 to 31 amino acids of SEQ ID NO: 1469, preferably contiguous amino acids,
  a fragment of 15 to 30 amino acids of SEQ ID NO: 1470, preferably contiguous amino acids,
  a fragment of 15 to 31 amino acids of SEQ ID NO: 1471, preferably contiguous amino acids, and;
  wherein the length of the preferably contiguous amino acid sequence is preferably at least 15, 16, 17, 18, 19, 20, 21, 22, 23, 24, 25, 26, 27, 28, 29, 30, 31, 32 or 33 amino acids and/or preferably no more than 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15 amino acids, most preferably a length of 30-39 amino acids.

In a second aspect, the invention provides a polynucleotide encoding a peptide according to the invention, preferably a peptide as defined herein above. A polynucleotide may be any polynucleotide comprising e.g. RNA, DNA, and/or cDNA; a polynucleotide may be single stranded or double stranded and may comprise nucleotide analogues and/or nucleotide equivalents such as a peptide nucleic acid (PNA) and a morpholino nucleotide analogue. A polynucleotide may be codon optimized for a host of choice to facilitate expression of the encoded subject matter.

The polynucleotide according to the invention does not encode a wild-type full length HBV core protein, HBV polymerase, HBV X protein and/or HBV large surface protein, but rather encode a peptide according to the invention as such, or flanked by amino acid sequence that are not contiguous with a wild-type HBV core protein, HBV polymerase, HBV X protein and/or HBV large surface protein. Such flanking amino acids may be from proteins other than a wild-type HBV and/or they may be from other locations within a wild-type HBV core protein, HBV polymerase, HBV X protein and/or HBV large surface protein that are not contiguous with the peptide they flank. Preferably, the polynucleotide encodes two or more peptides according to the invention arranged as beads-on-string, whereby the peptides according to the invention (the beads) are linked directly together and/or are linked through linker sequences that are from proteins other than a wild-type HBV core protein, HBV polymerase, HBV X protein and/or HBV large surface protein, and/or from other locations within a wild-type HBV core protein, HBV polymerase, HBV X protein and/or HBV large surface protein, that are not contiguous with the peptide they flank. The amino acid sequences flanking or linking the peptides may comprise proteolytic cleavage sites. A polynucleotide according to the invention may be applied to deliver a peptide according to the invention in various ways. A polynucleotide according to the invention may e.g. be used in the production of recombinant protein or peptide in a suitable host cell (e.g. a bacterial host cell such as *E. coli*, a suitable yeast host cell such as *S. cerevisiae*, a suitable filamentous fungal such as an *Aspergillus* or mammalian host cell) from which the recombinant protein or peptide may be purified. Alternatively the polynucleotide may be operably linked to expression regulatory sequences (promoters and the like) and incorporated in an expression construct for human cells. Such (autologous) cells may be transfected or transduced ex vivo to be (re)-administered to a subject in need thereof. Alternatively such expression construct according to the invention may be incorporated into a suitable gene therapy vector. Viral vectors (based on a defective virus) are more efficient agents for gene transfer as compared to non-viral agents. Suitable viral expression constructs include e.g. vectors that are based on adenovirus, adeno-associated virus (AAV), retroviruses or modified vaccinia Ankara (MVA). The polynucleotide according to the invention may also be operably linked to a sequence encoding and adjuvant such as a Toll-like receptor (TLR) ligand, a NOD ligand, or a RIG-I ligand.

In a third aspect, the present invention provides a cell comprising the polynucleotide according to the second aspect of the invention. Such cell can be used for e.g. production of a peptide according to the invention or for medical purposes such as prevention and/or treatment of an HBV related disease as defined elsewhere herein. Said cell may be any host cell. For the specific applications such as described here above, the selection of the host cell may be made according to such use. The host cell may be a prokaryote or may be a eukaryote. A preferred prokaryote cell is *E. coli*. When the cell is a eukaryote, the cell preferably is a mammalian, insect, plant, fungal, or algal cell. Preferred mammalian cells include e.g. Chinese hamster ovary (CHO) cells, COS cells, 293 cells, PerC6 cells, and antigen presenting cells such as dendritic cells. Preferred insect cells include e.g. Sf9 and Sf21 cells and derivatives thereof. Preferred fungal cells include *Candida, Hansenula, Kluyveromyces, Pichia, Saccharomyces, Schizosaccharomyces, Yarrowia* and filamentous fungal cells. Most preferably, the eukaryotic cell is a human antigen presenting cell, preferably a dendritic cell.

Methods to introduce a polynucleotide into a cell are known to the person skilled in the art. When expression of the polynucleotide is desired, the person skilled in the art knows how to achieve such; the polynucleotide may e.g. be provided with proper control sequences such as a promoter and terminator sequence and may be inserted into a proper vector such as a plasmid or a method described in the second aspect of the invention may be used.

The present invention also provides for an antigen presenting cell such as a dendritic cell as defined earlier herein that has been contacted and/or loaded with a peptide according to the invention, preferably a peptide according to the first aspect of the present invention. Such preferably autologous dendritic cell may be used for immune therapeutic treatment of a subject in need thereof. Such dendritic cell can be isolated from the subject, loaded with at least one peptide according to the invention and used for treatment.

In a fourth aspect, the present invention provides a method for the preparation of an HBV specific T-cell, said method comprising contacting a T-cell with an antigen presenting cell expressing a polynucleotide according to the invention and/or contacting a T-cell with an antigen presenting cell loaded with a peptide according to the invention; and, optionally, culturing said T-cell. The T-cell is preferably a $CD8^+$ cytotoxic T-cell or a $CD4^+$ T-helper cell.

Contacting a cell with a polynucleotide may be performed using any method known to the person skilled in the art, preferably a polynucleotide according to the invention is introduced into the antigen presenting cell (APC), preferably a dendritic cell, using transfection. Before contacting, the polynucleotide according to the invention may be provided with proper control sequences, or be comprised into a proper vector such as described elsewhere herein.

Contacting a T-cell with a peptide according to the invention can be performed by any method known to the person skilled in the art. Preferably, a peptide or an epitope comprised in a peptide is presented to the $CD8^+$ cytotoxic T-cell or $CD4^+$ T-helper cell by an HLA class I or an HLA class II molecule on the surface of an antigen presenting cell, preferably a dendritic cell. The person skilled in the art knows how to load an antigen presenting cell with a peptide.

Culturing said T-cell may be performed using any method known by the person skilled in the art. Maintaining a T-cell under conditions to keep the cell alive is herein also to be construed to be culturing.

Preferably, the T-cell according to this aspect of the invention is contacted with a peptide according to the invention as defined in the first aspect of the invention.

In a fifth aspect, the present invention provides a T-cell obtainable by the method depicted in the fourth aspect of the present invention. Preferably, such T-cell is a T-cell that is obtained by the method according to the fourth aspect of the invention. The T-cell is preferably a $CD8^+$ cytotoxic T-cell or a $CD4^+$ T-helper cell.

Preferably, the T-cell according to this aspect of the invention has been contacted with a peptide according to the invention as defined in the first aspect of the invention.

In a sixth aspect, the present invention provides a composition useful for the prevention and/or treatment of an HBV related disease or related condition, comprising a peptide according to the invention and/or a polynucleotide according to the invention and/or a cell, preferably a T-cell, according to the invention and/or a cell, preferably a T-cell, obtained by the method according to the fourth aspect of the invention and a pharmaceutically acceptable carrier.

When comprising a peptide according to the invention, the composition according to the invention preferably comprises at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32 and up to 33 different peptides according to the invention. Preferably, a composition according to the invention comprises a peptide according to the invention as defined in the first aspect of the invention. In a preferred embodiment, a composition of the invention comprises a combination of peptides wherein said combination of peptides covers at least 70%, 80%, 90%, 92%, 94%, 95%, 96%, 97%, 98%, 99% or 100% of the HLA class I molecules that are encoded by HLA alleles predominant in the population of human subjects to be treated as defined herein above.

When comprising a polynucleotide according to the present invention, the composition according to the invention preferably comprises at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32 and up to 33 different polynucleotides according to the invention. Preferably, a composition according to the invention comprises a polynucleotide according to the invention as defined in the second aspect of the invention.

When comprising a cell according to the invention, the composition according to the invention preferably comprises at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32 and up to 33 different cells, preferably T-cells that have been contacted with a peptide according to the invention. Preferably, said T-cells have been contacted with a peptide according to the invention as defined in the first aspect of the invention. The T-cell is preferably a CD8$^+$ cytotoxic T-cell or a CD4$^+$ T-helper cell.

In a preferred embodiment, the composition of the invention comprises at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32 and up to 33 different peptides of the peptides consisting of or comprising of a peptide selected from the group consisting of SEQ ID NO: 51-79, 1142-1145 and 1468-1471, more preferably selected from the group consisting of SEQ ID NO: 51, 55, 60, 63, 64, 68, 71, 74, 75, 76, 77, 1142 and 1469, more preferably selected from the group consisting of SEQ ID NO: 51, 55, 60, 63, 64, 68, 71, 74, 75, 77, 1142 and 1469, even more preferably selected from the group consisting of SEQ ID NO: 55, 60, 63, 64, 68, 71, 74, 75, 76, 77 and 1469, even more preferably selected from the group consisting of SEQ ID NO: 55, 60, 63, 64, 68, 71, 74, 75, 77 and 1469, even more preferably selected from the group consisting of SEQ ID NO: 60, 63, 71, 74, 75 and 1469, most preferably selected from the group of SEQ ID NO: 75, 1469 and 63. Further preferred is a composition that comprises at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32 and up to 33 different peptides of the peptides consisting of or comprising of a peptide selected from the group consisting of SEQ ID NO: 51, 60, 63, 64, 68, 71, 74-77, more preferably selected from the group consisting of SEQ ID NO: 63, 71 and 75.

In a preferred embodiment, the composition of the invention comprises at least a peptide that comprises or consists of a peptide of SEQ ID NO: 63 and peptide that comprises or consists of a peptide of SEQ ID NO: 1143.

Also preferred is a composition that comprises at least a peptide that comprises or consists of a peptide of SEQ ID NO: 63 and peptide that comprises or consists of a peptide of SEQ ID NO: 75.

Also preferred is a composition that comprises at least a peptide that comprises or consists of a peptide of SEQ ID NO: 1143 and peptide that comprises or consists of a peptide of SEQ ID NO: 75.

Also preferred is a composition that comprises at least a peptide that comprises or consists of a peptide of SEQ ID NO: 71 and peptide that comprises or consists of a peptide of SEQ ID NO: 75.

Also preferred is a composition that comprises at least a peptide that comprises or consists of a peptide of SEQ ID NO: 71 and peptide that comprises or consists of a peptide of SEQ ID NO: 63.

Also preferred is a composition that comprises at least a peptide that comprises or consists of a peptide of SEQ ID NO: 1144 and peptide that comprises or consists of a peptide of SEQ ID NO: 63.

Also preferred is a composition that comprises at least a peptide that comprises or consists of a peptide of SEQ ID NO: 1144 and peptide that comprises or consists of a peptide of SEQ ID NO: 75.

Also preferred is a composition that comprises at least a peptide that comprises or consists of a peptide of SEQ ID NO: 1144 and peptide that comprises or consists of a peptide of SEQ ID NO: 1143.

Also preferred is a composition that comprises at least a peptide that comprises or consists of a peptide of SEQ ID NO: 63, a peptide that comprises or consists of a peptide of SEQ ID NO: 1143, and a peptide that comprises or consists of a peptide of SEQ ID NO: 75.

Also preferred is a composition that comprises at least a peptide that comprises or consists of a peptide of SEQ ID NO: 63, a peptide that comprises or consists of a peptide of SEQ ID NO: 1143, a peptide that comprises or consists of a peptide of SEQ ID NO: 75, and a peptide that comprises or consists of a peptide of SEQ ID NO: 1144.

Also preferred is a composition that comprises at least a peptide that comprises or consists of a peptide of SEQ ID NO: 75, and a peptide that comprises or consists of a peptide of SEQ ID NO: 1469. Also preferred is a composition that comprises at least a peptide that comprises or consists of a peptide of SEQ ID NO: 63, and a peptide that comprises or consists of a peptide of SEQ ID NO: 1469.

Also preferred is a composition that comprises at least a peptide that comprises or consists of a peptide of SEQ ID NO: 75, a peptide that comprises or consists of a peptide of SEQ ID NO: 1469, and a peptide that comprises or consists of a peptide of SEQ ID NO: 63. Preferably, said composition further comprising a peptide that comprises or consists of a peptide of SEQ ID NO: 60 and/or that comprises or consists of a peptide of SEQ ID NO: 71, and/or that comprises or consists of a peptide of SEQ ID NO: 74.

A preferred composition of the invention comprises a peptide that consists of or comprises a peptide of SEQ ID NO: 75, a peptide that consists of or comprises a peptide of SEQ ID NO: 63, and a peptide that consists of or comprises a peptide of SEQ ID NO: 1469

A preferred composition of the invention comprises a peptide that consists of or comprises a peptide of SEQ ID NO: 75, a peptide that consists of or comprises a peptide of SEQ ID NO: 63, and a peptide that consists of or comprises a peptide of SEQ ID NO:
71.

A pharmaceutically acceptable carrier can be any such carrier known to the person skilled in the art, e.g. buffered aqueous solutions at physiological ionic strength and/or osmolarity (such as e.g. PBS).

Preferably, a composition according to the present invention further comprises at least one adjuvant. Such adjuvant may be any adjuvant known to the person skilled in the art. Preferred adjuvants are defined later herein.

A preferred use of a peptide, polynucleotide, composition, cell and/or T-cell according to the invention or a T-cell obtainable or obtained by a method according to the invention is the use as a medicament. A specific preferred use of a peptide, polynucleotide, composition, cell and/or T-cell according to the invention or a T-cell obtainable or obtained by a method according to the invention is for the treatment and/or prevention of an HBV related disease or condition. Accordingly, the invention provides for the use of a peptide, polynucleotide, composition, cell and/or T-cell according to the invention or a T-cell obtainable or obtained by a method according to the invention for the manufacturing of a medicament for the treatment and/or prevention of an HBV related disease.

The invention further provides a method for the prevention and/or treatment of an HBV related disease or condition comprising administering to a subject an effective amount of a peptide, polynucleotide, composition, cell or T-cell according to the invention and/or a T-cell obtainable or obtained by a method according to the invention.

Formulation of medicaments, ways of administration and the use of pharmaceutically acceptable excipients are known and customary in the art and for instance described in Remington; The Science and Practice of Pharmacy, 21$^{st}$ Edition 2005, University of Sciences in Philadelphia. Pharmaceutical compositions and medicaments according to the invention are preferably formulated to be suitable for intravenous or subcutaneous, or intramuscular administration, although other administration routes can be envisaged, such as mucosal administration or intradermal and/or intracutaneous administration, e.g. by injection. Intradermal administration is preferred herein. Advantages and/or preferred embodiments that are specifically associated with intradermal administration are later on defined in a separate section entitled "intradermal administration".

It is furthermore encompassed by the present invention that the administration of a peptide, a polynucleotide, a composition and/or a cell according to the invention and/or a cell obtainable or obtained by a method according to the invention with an appropriate pharmaceutical excipient such as an adjuvant and/or a carrier may be carried out as a single administration. Alternatively, the administration may be repeated if needed and/or distinct peptides, polynucleotides, compositions and/or cells according to the invention and/or cells obtainable or obtained by a method according to the invention with appropriate pharmaceutical excipients such as adjuvants and/or carriers, may be sequentially administered.

The peptide, polynucleotide, composition and/or cell according to the invention and/or cell obtainable or obtained by a method according to the invention (also referred to as medicaments according to the invention) may preferably comprise at least one immune response stimulating compound or adjuvant. Advantageously the medicaments according to the invention may additionally comprise one or more synthetic adjuvants. Such adjuvant may be admixed to the medicament according to the invention or may be administered separately to the subject, mammal or human, to be treated. Particularly preferred are those adjuvants that are known to act via the Toll-like receptors and/or via a RIG-I (Retinoic acid-Inducible Gene-1) protein and/or via an endothelin receptor. Immune modifying compounds that are capable of activation of the innate immune system can be activated particularly well via Toll like receptors (TLRs), including TLRs 1-10. Compounds capable of activating TLR receptors and modifications and derivatives thereof are well documented in the art. TLR1 may be activated by bacterial lipoproteins and acetylated forms thereof, TLR2 may in addition be activated by Gram positive bacterial glycolipids, LPS, LPA, LTA, fimbriae, outer membrane proteins, heat shock proteins from bacteria or from the host, and Mycobacterial lipoarabinomannans. TLR3 may be activated by dsRNA, in particular of viral origin, or by the chemical compound poly(I:C). TLR4 may be activated by Gram negative LPS, LTA, Heat shock proteins from the host or from bacterial origin, viral coat or envelope proteins, taxol or derivatives thereof, hyaluronan containing oligosaccharides and fibronectins. TLR5 may be activated with bacterial flagellae or flagellin. TLR6 may be activated by mycobacterial lipoproteins and group B *Streptococcus* heat labile soluble factor (GB S-F) or *Staphylococcus* modulins. TLR7 may be activated by imidazoquinolines, such as imiquimod, resiquimod and derivatives imiquimod or resiquimod. TLR9 may be activated by unmethylated CpG DNA or chromatin—IgG complexes. In particular TLR3, TLR7 and TLR9 play an important role in mediating an innate immune response against viral infections, and compounds capable of activating these receptors are particularly preferred for use in the methods of treatment and in the compositions or medicaments according to the invention. Particularly preferred adjuvants comprise, but are not limited to, synthetically produced compounds comprising dsRNA, poly(I:C), unmethylated CpG DNA which trigger TLR3 and TLR9 receptors, IC31, a TLR 9 agonist, IMSA-VAC, a TLR 4 agonist, Montanide ISA-51, Montanide ISA 720 (an adjuvant produced by Seppic 7, France). RIG-I protein is known to be activated by dsRNA just like TLR3 (Kato et al, 2005). A particularly preferred TLR ligand is a pam3cys and/or derivative thereof, preferably a pam3cys lipopeptide or variant or derivative thereof, preferably such as described in WO2013051936A1. Further preferred adjuvants are Cyclic dinucleotides (CDNs), Muramyl dipeptide (MDP) and poly-ICLC. In a preferred embodiment, the adjuvants of the invention are non-naturally occurring adjuvants such as the pam3cys lipopeptide derivative as described in WO2013051936A1, Poly-ICLC, imidazoquinoline such as imiquimod, resiquimod or derivatives thereof, CpG oligodeoxynucleotides (CpG-ODNs) having a non-naturally occurring sequence, and peptide-based adjuvants, such as muramyl dipeptide (MDP) or tetanus toxoid peptide, comprising non-naturally occurring amino acids.

In another preferred embodiment, the synthetic adjuvant compounds are physically linked to the peptides of the invention. Physical linkage of adjuvants and costimulatory compounds or functional groups to the HLA class I and HLA class II epitope comprising peptides provides an enhanced immune response by improved targeting to antigen-presenting cells, in particular dendritic cells, that internalize, metabolize and display antigen and by simultaneously stimulating such cells to up-regulate expression of a variety of co-stimulatory molecules, thereby becoming efficient T cell response inducing and enhancing cells. Another preferred immune modifying compound is an inhibitor of an endothelin receptor such as BQ-788 (Buckanovich R J et al., 2008; Ishikawa K, 1994). BQ-788 is N-cis-2,6-dimethylpiperidinocarbonyl-L-gamma-methylleucyl-D-1-methoxycarbonyltryptophanyl-D-norleucine. However any derivative of BQ-788 or modified BQ-788 compound is also encompassed within the scope of this invention. Another preferred immune response stimulating compound or adjuvant is Interferon alpha (IFNα), more preferably pegylated Interferon alpha, which may be admixed to the medicament according to the invention, or may be administered separately to the subject as an immuno-modulatory agent. It is to be construed herein that when an immune response stimulating compound is admixed to the medicament according to the invention, it is depicted as an adjuvant; when administered separately, it is depicted as an immuno-modulatory agent, or an immuno-modulator, which terms are used herein interchangeably. Furthermore, the use of antigen presenting cell (co)stimulatory molecules, as set out in WO99/61065 and in WO03/084999, in combination with the peptides and compositions of the invention is preferred. In particular the use of 4-1BB and/or CD40 ligands, agonistic antibodies, OX40 ligands, CD27 ligands or functional fragments and derivatives thereof, as well as synthetic compounds with similar agonistic activity are preferably administered separately or combined with the peptides of the invention to subjects to be treated in order to further stimulate the mounting of an optimal immune response in the subject.

In addition, a preferred embodiment comprises delivery of the medicaments according to the invention, with or without additional immune stimulants such as TLR ligands and/or anti CD40/anti-4-1BB/anti-OX-40 or anti-CD27 antibodies in a slow release vehicle such as mineral oil (e.g. Montanide ISA 51) or PLGA. Alternatively, the medicament according to the invention may be delivered intradermally, e.g. by injection, with or without immune stimulants (adjuvants and/or immuno-modulators). Preferably, for intradermal delivery the medicaments according to the invention are administered in a composition consisting of the medicaments and one or more immunologically inert pharmaceutically acceptable carriers, e.g. buffered aqueous solutions at physiological ionic strength and/or osmolarity (such as e.g. PBS).

In a preferred embodiment, a medicament according to the invention as defined herein is formulated to be suitable for intradermal administration or application. Intradermal is known to the skilled person. In the context of the invention, intradermal is synonymous with intradermal and is distinct from subcutaneous. A most superficial application of a substance is epicutaneous (on the skin), then would come an intradermal application (in or into the skin), then a subcutaneous application (in the tissues just under the skin), then an intramuscular application (into the body of the muscle). An intradermal application is usually given by injection. An intradermal injection of a substance can be done to test a possible reaction, allergy and/or cellular immunity to it, but can also be performed to elicit a specific antibody or T cell immune response. A subcutaneous application is usually also given by injection: a needle is injected in the tissues under the skin.

The advantage of intradermal administration is that the formulation procedure can be simplified and be made more robust. Furthermore, intradermal vaccine delivery has been repeatedly shown to allow significant dose sparing for eliciting vaccine-induced antibody or T cell responses when compared to conventional administration methods such as intramuscular and subcutaneous administration. This effect is attributed to the relatively dense network of immune cells present in the skin. This was also shown with the HPV16 synthetic long peptides in a human study published by Van der Burg et al. (2007). In this study it was shown that intradermal injection of pools of HPV16 synthetic long peptides is safe and results in the migration of HPV16-specific T cells into the skin as well as in an increase in the number of HPV16-specific T cells circulating in the blood.

In an embodiment, a medicament according to the invention does not comprise any adjuvant such as Montanide ISA-51, and specifically Montanide ISA-51. This means that the formulation of the medicament is more simple: an oil-water based emulsion is preferably also not present in a medicament according to the invention. Accordingly, a medicament according to the invention preferably does not comprise an adjuvant such as Montanide ISA-51 and specifically Montanide ISA-51 and/or does not comprise an oil-in-water based emulsion; more preferably a medicament according to the invention comprises neither of these to adjuvant and even more preferably comprises no adjuvant at all. Therefore, in an embodiment, the medicament according to the invention is a, preferably buffered, aqueous solution, preferably at physiological ionic strength and/or osmolality, such as e.g. PBS (Phosphate Buffer Saline) or water for injection (WFI), comprising or consisting of one or more medicaments as defined earlier herein. The skilled person knows how to prepare such a solution.

A medicament according to the invention has another advantage, which is that by intradermally administering low amounts of a medicament, preferably a peptide as earlier herein defined, an immunogenic effect may still be achieved. The amount of each peptide used is preferably ranged from 1 and 1000 μg, more preferably from 5 and 500 μg, even more preferably from 10 and 100 μg.

In an embodiment, the medicament according to the invention comprises a peptide as earlier defined herein and at least one adjuvant, said adjuvant being not formulated in an oil-in water based emulsion and/or not being of an oil-in-water emulsion type as earlier defined herein. This type of medicament according to the invention may be administered as a single administration. Alternatively, the administration of a peptide as earlier herein defined and/or an adjuvant may be repeated if needed and/or distinct peptides and/or distinct adjuvants may be sequentially administered. It is further encompassed by the present invention that a peptide according to the invention is administered intradermally whereas an adjuvant as defined herein is sequentially administered. The adjuvant may be intradermally administered. However any other way of administration may be used for the adjuvant. Intradermal administration of a peptide may be attractive since typically and depending on the disease, the injection of the vaccine is realized at or as close by as possible to the site of the disease resulting in the local activation of the disease draining lymph node, resulting in a stronger local activation of the immune system. A preferred immune response stimulating compound (immuno-modulator) or adjuvant for intradermal administration is Interferon alpha (IFNα), more preferably pegylated Interferon alpha, which may be admixed to the medicament according to the invention, or may be administered separately, for example by subcutaneous injection to the subject. When administered separately the Interferon alpha is preferably also administered subcutaneously and is preferably administered at a dose of 1 microgram/kilogram of body weight within 10 cm proximity to the site where the medicament according to the invention is administered, such described in Zeestraten et al, 2013.

Another typical advantage of the medicaments according to the invention is that relatively low amounts of peptides may be used, in one single shot, in a simple formulation and without any adjuvant known to give undesired side-effects as Montanide ISA-51.

The medicament for intradermal administration may be any medicament according to the invention as defined herein. A medicament according to the invention used for subcutaneous administration may be the same as the one used for intradermal administration and may thus be any medicament according to the invention as defined herein. The skilled person knows how to formulate a medicament suited for subcutaneous administration.

Preferably, a medicament according to the invention for subcutaneous administration comprises a peptide as already herein defined in combination with an adjuvant. Preferred adjuvants or immune modulators have already been mentioned herein. Other preferred adjuvants are of the type of an oil-in water emulsions such as incomplete Freund's adjuvant or IFA, Montanide ISA-51 or Montanide ISA 720 (Seppic France). In a further preferred embodiment, a medicament according to the invention suited for subcutaneous administration comprises one or more peptides according to the invention, an adjuvant or immune modulator as earlier defined herein and an inert pharmaceutically acceptable carrier and/or excipients all as earlier defined herein. Formulation of medicaments, and the use of pharmaceutically acceptable excipients are known and customary in the art and for instance described in Remington; The Science and Practice of Pharmacy, 21$^{st}$ Edition 2005, University of Sciences in Philadelphia. A preferred immune response stimulating compound or adjuvant for subcutaneous administration is Interferon alpha (IFNα), more preferably pegylated Interferon alpha, which may be admixed to the medicament according to the invention, or may be administered separately to the subject. When administered separately, the Interferon alpha is preferably also administered subcutaneously and is preferably administered at a dose of 1 microgram/kilogram of body weight within 10 cm proximity to the site where the medicament according to the invention is administered, such described in Zeestraten et al., 2013.

In an embodiment, the medicament according to the invention suited for intradermal administration may be simultaneously administered with a medicament according to the invention suited for subcutaneous administration. Alternatively, both medicaments may be sequentially intradermally and subsequently subcutaneously administered or vice versa (first subcutaneous administration followed by intradermal administration). In this embodiment as in the earlier described embodiment dedicated to the intradermal administration, the intradermal and/or subcutaneous administration of a medicament according to the invention, preferably a peptide according to the invention, and/or of an adjuvant may be repeated if needed and/or of distinct medicament, preferably peptides and/or of distinct adjuvants may be sequentially intradermally and/or subcutaneously administered. It is further encompassed by the present invention that a medicament according to the invention, preferably a peptide is administered intradermally and/or subcutaneously whereas an adjuvant as defined herein is sequentially administered as immune-modulator. The adjuvant or immune-modulator may be intradermally and/or subcutaneously administered. However any other way of administration may be used for the adjuvant or immune-modulator.

We expect the combination of an intradermal and a subcutaneous administration of a medicament according to the invention is advantageous. DC in the epidermis are clearly different from DC in the dermis and in the subcutis. The intracutaneous (intradermal) immunization will cause antigen processing and activation of epidermal DC (Langerin-positive Langerhans cells) that through their dendritic network are in close contact with the keratinocytes. This will also optimally activate inflammatory pathways in the interactions between Langerhans cell and keratinocytes, followed by trafficking of antigen loaded and activated Langerhans cell to the skin-draining lymph nodes. The subcutaneous administration will activate other DC subsets, that will also become loaded with antigen and travel independently to the skin-draining lymph nodes. Conceivably, the use of a medicament which may be administered both intradermally and subcutaneously may lead to a synergistic stimulation of T-cells in these draining nodes by the different DC sub sets.

A medicament according to the present invention and the methods of treatment described herein using a medicament according to the invention may advantageously be combined with other medicaments and methods of treatment. As such, a medicament according to the invention or a method of treatment according to the invention may be combined with e.g. therapy, and/or antibody therapy against an HBV related disease or may be combined with e.g. immunotherapy and/or antibody therapy against another than HBV related disease, or may be combined with immunotherapy against another antigen than HBV to treat an HBV related disease.

In this document and in its claims, the verb "to comprise" and its conjugations is used in its non-limiting sense to mean that items following the word are included, but items not specifically mentioned are not excluded. In addition, reference to an element by the indefinite article "a" or "an" does not exclude the possibility that more than one of the element is present, unless the context clearly requires that there be one and only one of the elements. The indefinite article "a" or "an" thus usually means "at least one". The word "about" or "approximately" when used in association with a numerical value (e.g. about 10) preferably means that the value may be the given value (of 10) more or less 0.1% of the value.

The sequence information as provided herein should not be so narrowly construed as to require inclusion of erroneously identified bases. The skilled person is capable of identifying such erroneously identified bases and knows how to correct for such errors. In case of sequence errors, the sequence of the HBV core, HBV polymerase and HBV large surface protein polypeptides obtainable by expression of the gene present in SEQ ID NO: 5, 2 and 1467 containing the respective nucleic acid sequence coding for the polypeptides should prevail.

All patent and literature references cited in the present specification are hereby incorporated by reference in their entirety.

Unless stated otherwise, the practice of the invention will employ standard conventional methods of molecular biology, virology, microbiology or biochemistry. Such techniques are described in Sambrook et al. (1989) Molecular Cloning, A Laboratory Manual (2$^{nd}$ edition), Cold Spring Harbor Laboratory, Cold Spring Harbor Laboratory Press; in Sambrook and Russell (2001) *Molecular Cloning: A Laboratory Manual*, Third Edition, Cold Spring Harbor Laboratory Press, NY; in Volumes 1 and 2 of Ausubel et al. (1994) *Current Protocols in Molecular Biology, Current Protocols*, USA; and in Volumes I and II of Brown (1998) *Molecular Biology LabFax*, Second Edition, Academic Press (UK); *Oligonucleotide Synthesis* (N. Gait editor); *Nucleic Acid Hybridization* (Hames and Higgins, eds.).

BRIEF DESCRIPTION OF THE DRAWINGS

FIGS. 1A-1D: Proteasome-mediated cleavage pattern of long vaccine peptides as predicted in silico and observed in experimental in vitro digestions. For each SLP, the observed cleavage sites are indicated by arrows (major and minor cleavage sites are indicated by bold and thin arrows, respectively, as further detailed herein). Further, for each of the ten SLPs tested in the digestion experiments (SLP1, SLP10 and SLP21 in FIG. 1A; SLP14, SLP18 and SLP21 in FIG. 1B; SLP24, SLP25 and SLP26 in FIG. 1C; and SLP 27 in FIG. 1D), the predicted C-score is indicated in the first row, the confirmed predicted cleavage sites are indicated in the second row (indicated as '+'), the amino acid position within the source protein is indicated in the third row, the respective amino acids in the sequence are indicated in the fourth row, and the amino acid number within the SLP is indicated in the fifth row. For SLP27, C* indicates the cysteine replacement by Abu.

FIG. 2: Overview of responding naïve donors after T cell induction with HBV-derived long peptides. Combined data of IFNγ production as measured by ELISA ('ELISA'); hatched box SI (Stimulation Index)>1.5, and T cell proliferation ('Prolif') as measured by 3H thymidine incorporation; hatched box SI>1.5. N.t.: not tested FIG. 3: Overview of responding HBV-immune donors after stimulation with HBV-derived long peptides. Data represent IFNγ-ELISpot results, with hatched boxes indicating a positive response with SI (Stimulation Index)>3, white boxes SI<3.

Figure 4:
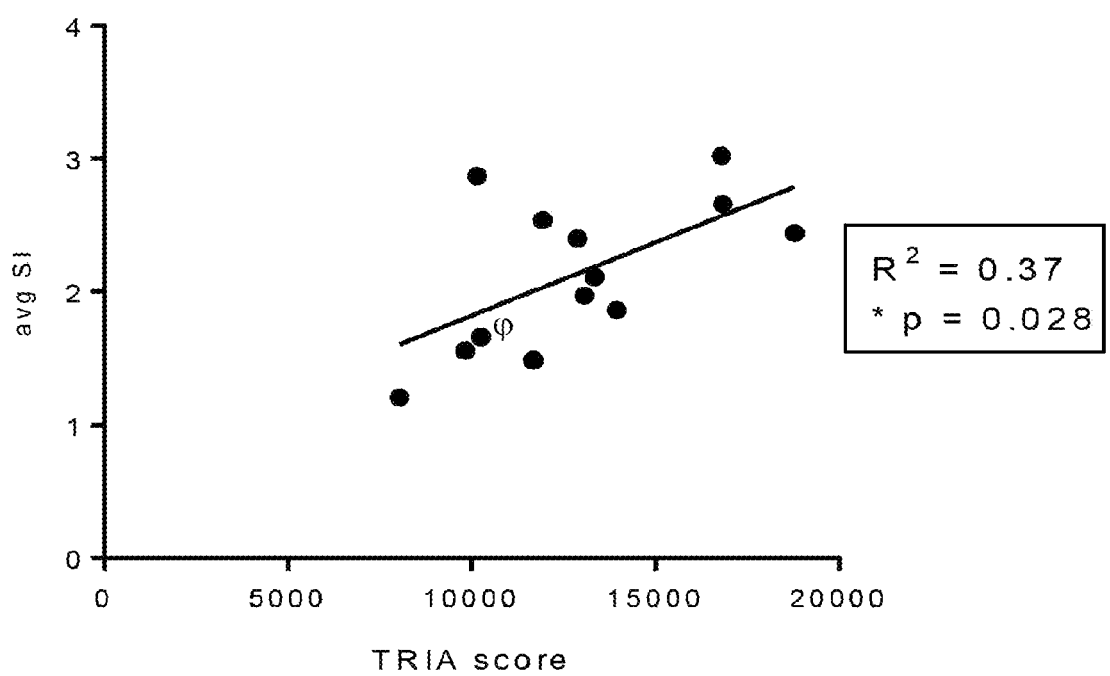
FIG. 4: The average Stimulation Index (SI) for each peptide, as measured in an IFNγ ELISpot assay, plotted against the predicted TRIA score of the corresponding peptide. Abu-SLP27 is indicated (φ).

The invention is further explained in the following examples. These examples do not limit the scope of the invention, but merely serve to clarify the invention.

EXAMPLES

Introduction

In the current invention, we developed an optimal T cell inducing vaccine composition consisting of synthetic long peptides to treat chronically HBV-infected patients. A selection of 37 long peptides (Table 3; sequences ranging from 30 to 39 amino acids) was made encompassing the regions of the HBV Polymerase, Core protein, Surface Antigen and X-protein with the highest putative T cell immunity inducing capacity. To this end first putative HLA class I restricted cytotoxic T cell (CTL) epitopes and putative HLA class II restricted T helper epitopes were identified in these proteins using algorithms that predict HLA class I and II peptide binding and C-terminal generation by the proteasome of all HLA class I binding short peptides (with a length of a CTL epitope; 8-12 aa) contained in the HBV proteins. Numerical values were assigned to all putative CTL epitopes and T helper epitopes reflecting their immunogenicity quality. The quality of any CTL epitope was assessed using the so-called Class I-BCI score (Class I-Binding-Cleavage-Immunogenicity score), incorporating the combination of the HLA class I binding capacity of the epitope in conjunction with the likelihood of its C-terminal liberation from the source protein by the proteasome. Putative T helper epitopes were assessed using the so-called Class II-B score (Class II-Binding score) reflecting their binding capacity and thus predicted immunogenic quality. The combined cumulative value, i.e. the sum of the cumulative Class I-BCI score and the cumulative Class II-B score, was calculated for all possible long peptides, reflecting the cumulative quantity and quality of all CTL epitopes and T helper epitopes, and is expressed in the T cell Regional Immunogenicity Assessment (TRIA) score. Accordingly, the TRIA score enabled the assessment of the total T cell immunogenicity of any possible long peptide (length 30-39 aa) in the HBV proteins. The 37 HBV-derived long peptides with the highest TRIA scores were selected.

Next, we assessed whether naïve donors and donors that have cleared an HBV infection in the past are able to respond to one or more of a subset of 13 long peptides with varying TRIA scores selected from the broad set of 37 long peptides.

PBMC were obtained from buffy coats of twelve healthy donors, six of which were HBV-naïve and six others had cleared an HBV-infection in the past. Using long-term T cell induction assays, we found responses against 12 out of 13 peptides in naïve donors (eleven of which induced responses in multiple donors), confirming the ability of these SLPs to induce T cell responses in a great majority of individuals that had not encountered the antigens before. The strength of T cell responses found in PBMC of HBV-immune donors against these 13 long vaccine peptides correlated with their predicted strength of overall T cell immunogenicity, as expressed in their TRIA scores, validating the predictive value of the TRIA score for selecting immunogenic peptides. Thus the TRIA score is a reliable criterion for the selection of optimal immunogenic long peptides, invigorating us to select the long peptides with the highest TRIA scores into our HBV SLP-based vaccine.

Material and Methods

Peptide Synthesis

Peptides were synthesized using solid phase Fmoc/tBu chemistry on a PTI Prelude peptide synthesizer and purified on a Gilson preparative HPLC system to >95% purity. The identity and purity of the peptides were confirmed with UPLC-MS on a Waters Acquity UPLC/TQD system.

Prediction of CTL and T Helper Cell Immunity Inducing Capacity in Selected HBV-Derived SLPs by Net-Based Algorithm The putative CTL immunity inducing capacity per SLP was predicted by calculating the cumulative Class I-BCI score per SLP. As detailed below, the cumulative BCI score is based on the Class I-B score, which is a measure for HLA class I peptide binding, and the C-score, which is a measure for proteosomal epitope liberation.

The putative T helper cell immunity inducing capacity per SLP was predicted by calculating the cumulative Class II-B score per SLP. As detailed below, the cumulative Class II-B score is based on the Class II-B score, which is a measure for HLA class II peptide binding.

The total putative immunity inducing capacity per SLP was predicted by summation of the cumulative Class I-BCI score and the cumulative Class II-B score, which value is denominated herein as the TRIA score.

Class I-B Score

Peptide binding to 50 HLA class I molecules (see text) of HBV polymerase-derived peptides, HBV Core protein-derived peptides, HBV Surface Antigen-derived peptides and HBV X protein-derived peptides was assessed in silico using a proprietary algorithm. The upper $1.5^{th}$ percentile of the predicted binding peptides to each HLA class I molecule was selected. The 'Class I-Binding score (Class I-B score)' is derived from the ranking of the predicted binding affinity of the peptides. Briefly, the ranking was first reversed and subsequently normalized to 100, so that the peptide predicted to bind best has a score of 100. Example: five peptides were selected (5 within the $1.5^{th}$ percentile). Peptides were first assigned the 'reverse ranking score' 5 to 1 (5 for the best binding peptide). Subsequently, each reverse ranking score is normalized to the number of peptides within the upper $1.5^{th}$ percentile, so that the best binder scores 100. To that end, the ranking score for each peptide is multiplied with 100/5 (=20). The best binder then obtains a Class I-B score: 5×20=100, the second best binder has a Class I-B score of 4×20=80, etc. In general, the ranking score is multiplied with 100/n (n=number of peptide within the $1.5^{th}$ percentile). As a consequence, the best predicted binder (to a certain HLA class I molecule) always scores 100, irrespective of the precise number of peptides within the $1.5^{th}$ percentile that are selected.

C-Score

C-terminal generation by the proteasome of the upper $1.5^{th}$ percentile of predicted high affinity binding peptides of HBV polymerase, HBV Core protein, HBV Surface Antigen and HBV X-protein (for each HLA class I molecule) was assessed using two proprietary algorithms, which predict the likelihood of a proteasomal cleavage after a certain amino acid position in HBV polymerase, HBV Core protein, HBV Surface Antigen and HBV X-protein, respectively, and can score between 0 and 1, where a higher value represents a higher likelihood of cleavage after the amino acid. The value 0.5 may be used as an arbitrary threshold value: >0.5 the cleavage is likely to occur, and <0.5 the cleavage is likely to not occur. Accordingly, a value close to 1 indicates a high likelihood of cleavage after the specific residue. Because great differences between the predictions by both different algorithms occur, we developed the Cleavage score (C-score) that takes into account the prediction results of both proprietary algorithms. The C-score is the summation of the separate scores by both methods. Therefore, the C-score for each position in HBV polymerase is maximally (close to) 2, and minimally (close to) 0, where close to 2 reflects a very high likelihood by BOTH methods that the cleavage after the residue will be produced by the proteasome, and a C-score close to 1 is considered as an indifferent tendency for cleavage by the proteasome (as predicted on average by both network methods).

Class I-BCI Score

To incorporate in one quantitative measure both the Class I-B score and the C-score, which are the measures indicative for the likelihood that a peptide will bind with high affinity to HLA class I molecules and will be C-terminally produced, the Class I-Binding-Cleavage-Immunogenicity (Class I-BCI) score was developed. The Class I-BCI score is the Class I-B score multiplied by the C-score. As such the Class I-BCI can attain a maximal value of 200 (100×2) (arbitrary units).

Cumulative Class I-BCI Score

The cumulative Class I-BCI score for each long peptide according to the invention was used as (one of two) selection criterion to identify the peptides of the invention. The cumulative Class I-BCI score is a quantitative reflection of both the total number of $CD8^+$ cytotoxic T cell epitopes that are contained in a long peptide according to the invention and their predicted quality, in terms of binding capacity and likelihood of intracellular generation by the proteasome, and is as such indicative for the $CD8^+$ cytotoxic T cell-inducing power of each peptide according to the invention (its $CD8^+$ T cell immunogenicity). A relatively high cumulative Class I-BCI score of a peptide according to the invention indicates a high $CD8^+$ T cell immunogenicity.

Class II-B Score

Peptide binding to 13 prevalent HLA class II molecules of HBV polymerase-derived peptides, HBV Core protein-derived peptides, HBV Surface Antigen-derived peptides and HBV X protein-derived peptides was assessed in silico using a proprietary algorithm. The 'Class II-Binding score' (Class II-B score) is derived from the ranking of the predicted binding affinity of the peptides. Briefly, the ranking was first reversed and subsequently normalized to 100, so that the peptide predicted to bind best has a score of 100. To reduce the number of peptides in the list, all length variants of peptides predicted to bind to a particular HLA class II molecule with a lower predicted binding (lower Class II-B score) are discarded in the list.

Cumulative Class II-B Score

The cumulative Class II-B score for each long peptide according to the invention was used as the second selection criterion to identify the peptides of the invention. The cumulative Class II-B score is a quantitative reflection of both the total number of $CD4^+$ T-helper cell epitopes that are contained in a long peptide according to the invention and their predicted quality, in terms of binding capacity, and is as such indicative for the $CD4^+$ T cell-inducing power of each peptide according to the invention (its $CD4^+$ T cell immunogenicity). A relatively high cumulative Class II-B score of a peptide according to the invention indicates a high $CD4^+$ T cell immunogenicity T Cell Regional Immunogenicity Assessment (TRIA) Score The TRIA score for a particular peptide of the invention (SLP) is the sum of cumulative Class I-BCI score and the cumulative Class II-B score of that particular long peptide of the invention (SLP).

Proteasomal Digestion

Dithiotreitol (DTT; Sigma-Aldrich) was freshly dissolved in UPLC-grade water and added to a 2× concentrated proteasome digestion buffer (60 mM Trizma-base; pH 7.5; Sigma-Aldrich, 20 mM KCl; Sigma-Aldrich, 10 mM $MgCl_2$; Sigma-Aldrich, 10 mM NaCl; Sigma-Aldrich) to an end concentration DTT of 2 mM. Then, 130 µl UPLC-grade water was added to 3 reaction vials, along with 150 µl of the 2× concentrated proteasome digestion buffer containing 2 mM DTT, and 10 µl of the peptide to be tested (stock concentration 300 nmol/ml). After vortexing the vials, 10 µl of water was added to vial 1 (mock control digest), 1 µg (10 µl) of constitutive 20S-proteasome (stock 0.1 mg/ml; Enzo Life Sciences) to vial 2, and 1 µg (10 µl) of immune 20S-proteasome (stock 0.1 mg/ml; Enzo Life Sciences) to vial 3. A 50 µl sample for T=0 was taken directly after vortexing and 4 µl of Formic acid (Sigma-Aldrich) was added to stop the reaction. The reaction vials were vortexed and incubated at 37° C. Samples of 50 µl were collected after 1 h, 3 h, 6 h and 24 h incubation. The reactions were stopped with 4 µl Formic acid, and all samples were stored at 20° C.

Mass Spectrometry Analysis of Digested Fragments

A Q-TOF1 mass spectrometer (Waters) equipped with an online nanoelectrospray interface with an approximate flow rate of 250 nl/min was used for electrospray ionization-mass spectrometry. Peptide-digestion samples were trapped on a precolumn (MCA-300-05-C18; Dionex) and were eluted with a steep gradient of 70-90% buffer B over 10 min (buffer A, water, acetonitrile and formic acid, 95:3:1 (vol/vol/vol); buffer B, water, acetonitrile and formic acid, 10:90:1 (vol/vol/vol)). Mass spectra were recorded from a mass of 50-2000 daltons. In tandem mass spectrometry mode, ions were selected with a window of 3 daltons. The collision gas was argon ($4\times10^{-5}$ mbar), and the collision voltage was ~30 V. For peptide digestion by purified constitutive proteasome and immunoproteasome, peaks in the mass spectra were searched in source substrate peptides with BioLynx software (Waters) and the abundance of a specific digestion fragment was assessed quantitatively as its percentage of the total summed intensities, including undigested substrate.

Cells

Peripheral blood mononuclear cells (PBMC) from healthy donors were isolated by centrifugation over a Ficoll gradient. To generate dendritic cells (DCs), approximately $50*10^6$ PBMC were brought to a concentration of $3*10^6$ cells/ml complete medium (IMDM, Lonza, supplemented with 8% HS, Seralab; penicillin/streptomycin, Lonza; L-glutamin, Lonza) and seeded 3 ml/well in a 6-wells plate (Corning). After incubation for 1.5 hours at 37° C., non-adherent cells were washed away in three washing steps using complete medium (day 0). The adherent cells were cultured for three days at 37° C. in 2 ml/well of complete medium containing 800 U/ml GM-CSF and 500 U/ml IL-4 (Peprotech). On day 3, 1 ml of complete medium containing 2400 U/ml GM-C SF and 1500 U/ml IL-4 was added to each well and cultured for another three days at 37° C.

Induction of T Cells

On day 6, long peptides distributed over 3 pools were added to monocyte-derived DCs of naïve donors at a 3 nmol/ml concentration and incubated overnight at 37° C. Pool 1 comprises SLP 26 (SEQ ID NO: 76), SLP 24 (SEQ ID NO: 74), SLP 1 (SEQ ID NO: 51) and SLP 30 (SEQ ID NO: 1142); Pool 2 comprises Abu-SLP 27 (SEQ ID NO: 77, wherein the cysteine on amino acid position 1 is replaced by Abu), SLP 25 (SEQ ID NO: 75), SLP 10 (SEQ ID NO: 60) and SLP 34 (SEQ ID NO: 1469); and Pool 3 comprises SLP 5 (SEQ ID NO: 55), SLP 13 (SEQ ID NO: 63), SLP 14 (SEQ ID NO: 64) and SLP 21 (SEQ ID NO: 21). On day 7, the cells were washed twice with complete medium to remove peptides. DC and autologous PBMC were co-cultured in a 1:10 ratio for 10 days at 37° C. in the presence of 10 ng/ml IL-7 and 100 pg/ml IL-12p70. The T cell lines generated by this process were checked every 2-3 days and split when necessary.

Restimulation of T Cell Lines

Three days after T cell induction (day 10), a second batch of autologous DC was differentiated and loaded with peptide pools as described above. On day 10 after initiation of the T cell line (day 17), the peptide-loaded DC were washed twice with complete medium and added to the T cells in a 1:10 (DC:T cell) ratio in the presence of 10 ng/ml IL-7 and 100 pg/ml IL-12p70. The cells were co-cultured for 7 days. On day 17, also a new batch of DC was differentiated and loaded with peptide pools as described above. For this second restimulation, starting on day 24, DC and T cells were co-cultured in a 1:10 ratio. Two days after restimulation, 30 IU/ml IL-2 (Peprotech) and 5 ng/ml IL-15 (Peprotech) were added to the culture medium. A third restimulation, starting on day 31, was performed identically to the second restimulation.

T Cell Proliferation and IFNγ Production

To measure T cell activation and proliferation, autologous DC were loaded for 6 hours with each of the 13 HBV-derived peptides separately on day 23, 30 and 37 of the T cell induction protocol described above. The DCs were washed and 5,000 peptide-loaded DC were co-cultured with 50,000 T cells for 48 hours. Then, supernatant was collected for ELISA (IFNγ ELISA, Diaclone) and culture medium containing $^3$H thymidine was added to all wells. Radioactive $^3$H thymidine is incorporated in the DNA of newly formed (proliferated) cells, which is measured after 16 hours of incubation on a MicroBeta liquid scintillation counter (Wallac/Perkin Elmer).

IFNγ-ELISpot

To detect antigen-specific IFNγ-producing human T cells, the PBMC were first pre-stimulated with 3 nmol/ml of the indicated peptide for 72 hours at 37° C. During this stimulation, ELISpot PVDF plates (Mabtech) were coated with 5 ug/ml anti-human IFNγ mAb 1-D1K coating antibody (Mabtech) in PBS and incubated overnight at 4° C. After stimulation of the PBMC, the coating antibody was aspirated from the plate, and washed 4 times with PBS. To block aspecific binding, 100 µl of IMDM containing 8% FCS was added to all wells and incubated at 37° C. for 1 hour. In the meantime, stimulated PBMC were harvested, centrifuged, resuspended in X-vivo 15 medium (Lonza) and counted. All PBMC samples were brought to a concentration of $1.5*10^6$ cells/ml in X-vivo 15 medium. The medium in the wells of the PVDF plate was aspirated and 100 µl of each PBMC sample was added to the plate in quadruplicates. The plates were incubated at 37° C. overnight. The next day, the supernatant was discarded and plates are washed 6 times with PBS/Tween20 0.05%. The biotinylated anti-human IFNγ mAb 7-B6-1 (Mabtech) was added to all wells (100 µl/well) at a 0.3 µg/ml concentration in PBS with 1% FBS, and incubated for 2 hours at RT. Next, plates were washed 6 times using PBS/Tween20 0.05% and 1 µg/ml Extravidin-Alkaline phosphatase (ALP) (Sigma-Aldrich) was added to all wells (100 µl/well) in PBS with 1% FBS. The plates were incubated for 1 hour at RT. ALP substrate solution BCIP/NBT-plus (Mabtech) was prepared and 100 µl/well was added to all wells after the plates were washed 4 times with PBS/Tween20 0.05%. To terminate the colorimetric reaction (after 1-20 minutes), tap water was used to wash the plates extensively. After drying, the formed spots were measured on a Biosys Bioreader 5000.

Results

Selection of Long Peptides Based on HLA Class I Peptide Binding Prediction and Predicted C-Terminal Generation of all Possible CD8$^+$ T Cell Epitopes Contained in the Long Peptides A high quality CD8$^+$ T cell epitope is defined as a peptide that possesses both a predicted high affinity for the HLA class I molecule to which it binds and is also predicted to be generated at its C-terminus by a proteolytic cleavage of the proteasome. Peptides according to the present invention were selected in HBV protein regions that contain optimally high numbers of high quality CD8$^+$ and CD4$^+$ T cell epitopes. To this end, first the HLA class I binding and C-terminal generation of all possible CD8$^+$ T cell epitopes was assessed using a proprietary HLA class I peptide binding algorithm and two proprietary algorithms predicting the cleavages by the proteasome. Subsequently, we devised a single quantitative measure, the so-called binding-cleavage-immunogenicity (BCI) Class I-score, that for each short peptide (8-13 amino acids) incorporates both its predicted binding affinity for the HLA class I molecule to which it binds and the likelihood that the peptide is generated by the proteasome in the cells. The Class I-BCI score is calculated from (1) the binding Class I-score (Class I-B score), which is derived from the results of the in silico prediction of HLA class I peptide binding using the aforementioned algorithm, and (2) the cleavage score (C-score), which is derived from the results of the in silico prediction of the proteasome-mediated C-terminal generation of the peptide by the proteasome using the aforementioned algorithms. Tables 4a, 5a, 6a, and 7a present the Class I-BCI score for all possible CD8$^+$ T cell epitopes of these Polymerase, Core protein, Surface Antigen or X-protein derived SLPs, respectively, together with the cumulative BCI Class I score. Tables 4b, 5b, 6b and 7b present the Class II-B score for all possible CD4$^+$ T cell epitopes of these Polymerase, Core protein, Surface Antigen or X-protein derived SLPs, respectively, together with the cumulative Class II-B score. Together the cumulative Class I-BCI score (for CTL epitopes) and the cumulative B Class II-score (for T helper epitopes) resulted in one quantitative value, the so-called Total Regional Immunogenicity Assessment (TRIA) score, reflecting the overall T cell immunogenicity of a long vaccine peptide (Table 3). Based on the highest TRIA scores, 37 SLPs derived from HBV Polymerase, Core protein, Surface Antigen or X-protein were selected for further evaluation (Table 3). From these, to validate the predictive power of the TRIA score, we chose a representative set of 13 SLPs, which included SLP with relatively low and high TRIA scores, for in vitro immunogenicity assessment. These 13 peptides were divided over three peptide pools for T cell induction assays, as described (see below).

Peptide Fragment Analysis after Proteasomal Digestion of SLPs Reveals High Accuracy of in Silico Predictions An important component of the identification of putative CTL epitopes is the prediction of their C-terminal generation by a proteasome-mediated cleavage. To validate the reliability of this prediction, proteasomal digestion patterns were experimentally assessed for all but 3 of the 13 functionally tested long vaccine peptides (three long peptides were not being cleaved due to technical reasons).

Digestion experiments were performed separately with 20S constitutive proteasomes and 20S immuno proteasome preparations. The combined analysis of cleavages produced by both types of proteasomes allows the assessment of the C-terminal generation of CTL epitopes that are expressed both on the surface of antigen presenting cells (mainly dendritic cells), containing immunoproteasomes, and on the surface of cancer cells, especially from solid tumors, which mainly express constitutive proteasomes. For vaccination purposes these epitopes are preferred because vaccination with such epitopes will allow the induction of CTL by vaccination and the subsequent eradication of cancer cells by these CTL after recognition of the epitopes on the surface of cancer cells.

As indicated in FIG. 1, 10 long peptides of the invention (length 30-39 aa) were co-incubated in an appropriate buffer with the proteasome preparations at 37° C. for 0, 1, 3, 6 and 24 h. After incubation for the indicated interval reactions were stopped and digestion mixtures, containing the digestion fragments, were measured by mass spectrometry as described herein. The mass spectra were (semi-quantitatively) analyzed to assess the position and abundance of the cleavage sites. The results of 24 h digestion are shown in FIG. 1.

The observed cleavage sites observed after 24 h incubation are indicated with arrows. Only cleavage sites that were observed in both the digestion with constitutive proteasomes and the digestion with immunoproteasomes are shown. Major cleavage sites and minor cleavages sites at 24 h digestion are depicted with bold and thin arrows, respectively, according to the following classification:

Major cleavage site: fragments containing as COOH terminus the residue $NH_2$-terminal from the cleavage site together with the (possible) complementary fragment(s) are present for ≥7% at 24 h incubation, as calculated from the intensities of the fragment peaks in the mass spectra.

Minor cleavage site: fragments containing as COOH terminus the residue $NH_2$-terminal from the cleavage site together with the (possible) complementary fragment(s) are present for <7% at 24 h incubation. Cleavage sites with a cumulative fragment abundance of <1% are not shown.

FIG. 1 also indicates the C-score of proteasomal cleavage prediction. This score indicates the likelihood of cleavage C-terminal of the residue directly under the C-score. If the C-score>1 the cleavage site is considered predicted to be cleaved by both the constitutive proteasome and the immunoproteasome. As described herein, the C-score is a summation of the predictions by two in silico algorithms separately predicting the proteasome-mediated cleavages by constitutive proteasomes and the cleavages by immunoproteasomes. Each separate prediction can attain a maximal value of 1. Accordingly, the maximal value of the C-score is 2. C-scores>1 are together counted as the total number of predicted cleavage sites (the C-terminus of the long substrate peptide is not taken into account, because cleavage after this residue cannot be tested).

FIG. 1 further indicates the confirmed cleavages (indicated by '+'), which are those predicted cleavage sites (C-score>1) that are confirmed to be cleaved after 24 h in the proteasome-mediated digestion assay.

As indicated by FIG. 1, for SLP1 36% (4/11), for SLP10 71% (10/14), for SLP13 62% (10/16), for SLP14 100% (13/13), for SLP18 65% (13/20), for SLP21 87% (14/16), for SLP24 62% (10/16), for SLP25 57% (8/14), for SLP26 72% (8/11), and for SLP27 75% (9/12) of the predicted cleavage sites have been confirmed here.

Figures 2, 3:
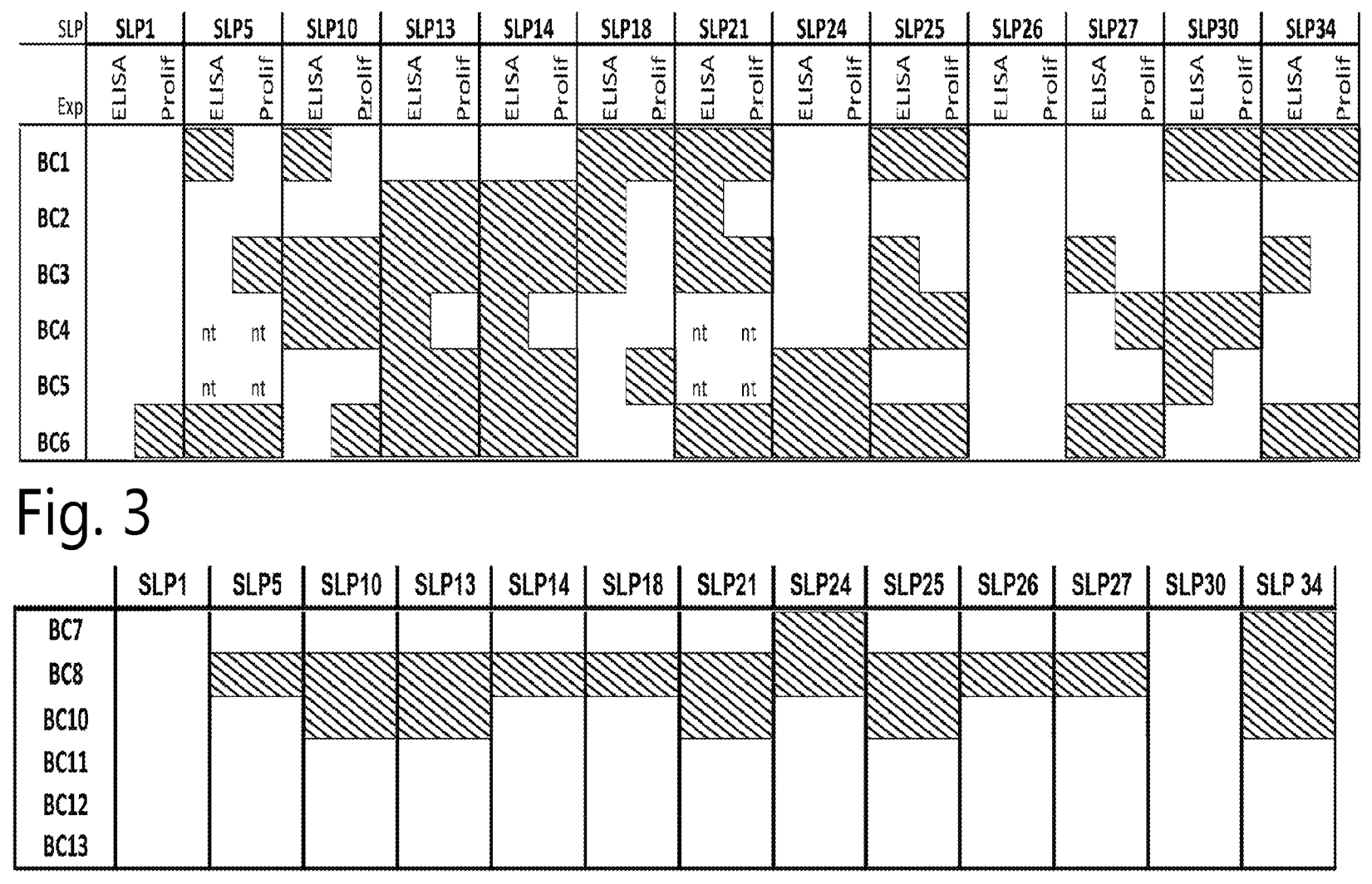

Induction of T Cell Responses Against 12 Out of 13 Selected Peptides in a Naïve Population To assess whether the 13 selected peptides are able to induce a T cell response in naïve donors, PBMC were isolated from buffy coats derived from six healthy donors that had not experienced an HBV-infection. These PBMC were restimulated with either of the 3 peptide pools to obtain T cell lines, that were subsequently stimulated with the selected 13 peptides. The production of IFNγ and T cell proliferation ($^3$H thymidine incorporation) were measured as a read-out for T cell activation. Results are shown in FIG. 2, indicating the percentage of donors showing a positive T cell response with a stimulation index (SI) of 1.5 or higher. The SI is calculated by dividing the measured sample value by the value of non-stimulated control cells. Induced responses in naïve donors were detected against 12 of the 13 pre-selected peptides, while 11 pre-selected peptides induced a response in multiple naïve donors.

Strength of Pre-Existing T Cell Responses in HBV-Immune Donors Correlates with TRIA Score Subjects that have gone through an HBV infection and successfully cleared it, possess circulating memory T cells specific for HBV. To assess the relevance of the selected vaccine peptides for the clearance of a naturally occurring HBV infection, we tested the presence of T cell responses against the 13 selected HBV peptides in PBMC derived from six HBV-immune donors. After isolation of the PBMC, cells were stimulated with each of the 13 peptides and an IFNγ-ELISpot was performed to detect T cell responses. PBMC samples from 3 out of 6 tested donors showed a positive IFNγ response against one or more of the 13 peptides (SI>3). Responses were observed against 11 (SLP 5, 10, 13, 14, 18, 21, 24, 25, 26, 27 and 34, represented by SEQ ID NO: 55, 60, 63, 64, 68, 71, 74, 75, 76, 77 and 1469, respectively) out of the 13 peptides, 6 of which induced responses in multiple donors (SLP 10, 13, 21, 24, 25 and 34, represented by SEQ ID NO: 60, 63, 71, 74, 75 and 1469, respectively). The results are summarized in FIG. 3, indicating the donors showing a positive IFNγ$^+$ T cell response against a peptide. For each SLP tested, the average SI of the IFNγ-responses was calculated; 1.21 for SLP1, 2.11 for SLP5, 2.40 for SLP10, 2.44 for SLP13, 1.97 for SLP14, 1.86 for SLP18, 2.87 for SLP21, 2.54 for SLP24, 2.66 for SLP25, 1.56 for SLP26, 1.66 for Abu-SLP27, 1.49 for SLP30 and 3.02 for SLP34. Importantly, when the average SI of the IFNγ-responses to each peptide is plotted against the corresponding TRIA score, we see a significant correlation (FIG. 4), both while including ($R^2$=0.37, p=0.028; see FIG. 4) the results of Abu-SLP27 and while excluding ($R^2$=0.34, p=0.048; not shown) the results of Abu-SLP27. This validates the use of the TRIA score for the selection of immunogenic peptides.

Discussion

The experimental results presented herein validate, and therefore support, the selection and underscore the immunological relevance of the HBV-derived long vaccine peptides of the present invention. These long vaccine peptides encompass the HBV protein regions with the highest number of high quality HLA class I and HLA class II binding epitopes in an outbred population. A preferred combination of the vaccine peptides will be incorporated in a novel HBV SLP vaccine composition to treat chronically HBV-infected patients. Using algorithms to predict the peptide binding affinity of short peptides (8-12 aa) for all prevalent HLA class I molecules and the likelihood of the C-terminal generation of these short peptides by cleavage by the proteasome, in combination with the identification of the putative T helper epitopes, we identified highly immunogenic regions from which the optimal 37 long vaccine peptides were selected.

To enable proper selection of long vaccine peptides in the present invention, a quantitative measure was developed, the TRIA score. Without such a quantitative measure attributed to all possible long HBV peptides, a proper selection of the optimal long peptides is not possible. The TRIA score is a quantitative representation of the quality and quantity of all putative HLA class I restricted $CD8^+$ cytotoxic T cell epitopes and HLA class II restricted $CD4^+$ T helper epitopes contained in a long peptide. The TRIA score was calculated for all possible HBV peptides with a length of 30-39 aa, which is the optimal peptide length for vaccination purposes, enabling the rational selection of a set of highly immunogenic long vaccine peptides.

For further testing and validation of the immunological relevance, we selected a set of 13 SLP with varying TRIA scores. First, we experimentally digested these SLP using either constitutive proteasome or immunoproteasome. The generated fragments showed a clear overlap with the predicted C-terminal cleavage sites, expressed in the BCI score.

Thereafter, T cell assays were performed using PBMC from both naïve and HBV-immune donors. Nearly all 13 selected SLPs were able to induce T cell responses in PBMC derived from naïve healthy donors, which proves that the selected SLP set has the potential to induce responses by the T cell repertoire that had not been stimulated before. Within the same set of vaccine peptides, a strong correlation was observed between the TRIA score of a certain vaccine peptide and the strength of the IFNγ-response in HBV-immune donors, indicating that the TRIA score is a predictive value for in vivo immunogenicity and thus functionality of the vaccine peptides.

TABLE 1

Protein and DNA sequences of HBV polymerase, HBV core and HBV large surface proteins.

| SEQ ID NO: | SEQ type | Gene / Gene product | Sequence |
|---|---|---|---|
| 1 | Protein | HBV Polymerase | MPLSYQHFRKLLLLDDGTEAGPLEEELPRLADADLHRRVAE DLNLGNLNVSIPWTHKVGNFTGLYSSTVPIFNPEWQTPSFP KIHLQEDIINRCQQFVGPLTVNEKRRLKLIMPARFYPTHTK YLPLDKGIKPYYPDQVVNHYFQTRHYLHTLWKAGILYKRET TRSASFCGSPYSWEQELQHGRLVIKTSQRHGDESFCSQSSG ILSRSSVGPCIRSQLKQSRLGLQPRQGRLASSQPSRSGSIR AKAHPSTRRYFGVEPSGSGHIDHSVNNSSSCLHQSAVRKAA YSHLSTSKRQSSSGHAVEFHCLPPNSAGSQSQGSVSSCWWL QFRNSKPCSEYCLSHLVNLREDWGPCDEHGEHHIRIPRTPA RVTGGVFLVDKNPHNTAESRLVVDFSQFSRGISRVSWPKFA VPNLQSLTNLLSSNLSWLSLDVSAAFYHIPLHPAAMPHLLI GSSGLSRYVARLSSNSRINNNQYGTMQNLHDSCSRQLYVSL MLLYKTYGWKLHLYSHPIVLGFRKIPMGVGLSPFLLAQFTS AICSVVRRAFPHCLAFSYMDDVVLGAKSVQHRESLYTAVTN FLLSLGTHLNPNKTKRWGYSLNFMGYIIGSWGTLPQDHIVQ KIKHCFRKLPVNRPIDWKVCQRIVGLLGFAAPFTQCGYPAL MPLYACIQAKQAFTFSPTYKAFLSKQYMNLYPVARQRPGLC QVFADATPTGWGLAIGHQRMRGTFVAPLPIHTAELLAACFA RSRSGAKLIGTDNSVVLSRKYTSFPWLLGCTANWILRGTSF VYVPSALNPADDPSRGRLGLSRPLLRLPFQPTTGRTSLYAV SPSVPSHLPVRVHFASPLHVAWRPP |
| 2 | CDS | HBV Polymerase | See sequence listing |
| 3 | Genomic | HBV genome | See sequence listing |
| 4 | Protein | HBV Core | MQLFHLCLIISCTCPTVQASKLCLGWLWGMDIDPYKEFGAT VELLSFLPSDFFPSVRDLLDTASALYREALESPEHCSPHHT ALRQAILCWGELMTLATWVGNNLEDPASRDLVVNYVNTNVG LKIRQLLWFHISCLTFGRETVLEYLVSFGVWIRTPPAYRPP NAPILSTLPETTVVRRRDRGRSPRRRTPSPRRRRSPSPRRR RSQSRESQC |
| 5 | CDS | HBV Core | See sequence listing |
| 1141 | Protein | HBV large surface protein | MGGWSSKPRKGMGTNLSVPNPLGFFPDHQLDPAFGANSNNP DWDFNPVKDDWPAANQVGVGAFGPRLTPPHGGILGWSPQAQ GILTTVSTIPPPASTNRQSGRQPTPISPPLRDSHPQAMQWN STAFHQTLQDPRVRGLYLPAGGSSSGTVNPAPNIASHISSI SARTGDPVTNMENITSGFLGPLLVLQAGFFLLTRILTIPQS LDSWWTSLNFLGGSPVCLGQNSQSPTSNHSPTSCPPICPGY RWMCLRRFITFLFILLLCLIFLLVLLDYQGMLPVCPLIPGS TTTSTGPCKTCTTPAQGNSMFPSCCCTKPTDGNCTCIPIPS SWAFAKYLWEWASVRFSWLSLLVPFVQWFVGLSPTVWLSAI WMMWYWGPSLYSIVSPFIPLLPIFFCLWVYI |

TABLE 2

Different HBV X protein variants and the deduced consensus protein sequence.

| SEQ ID NO. | UniProt ENTRY | HBV genotype source | Number of mismatches as compared to consensus sequence | X protein sequence |
|---|---|---|---|---|
| 6 | Q91C38 | Hepatitis B virus genotype A1 subtype adw2 (isolate South Africa/84/2001)(HBV-A) | 12 | see sequence listing |
| 7 | O91531 | Hepatitis B virus genotype A2 (isolate Japan/11D11HCCW/1998)(HBV-A) | 9 | see sequence listing |
| 8 | P69714 | Hepatitis B virus genotype A2 subtype adw (isolate Japan/Nishioka/1983)(HBV-A) | 8 | see sequence listing |
| 9 | P17102 | Hepatitis B virus genotype A2 subtype adw2 (isolate Germany/991/1990)(HBV-A) | 7 | see sequence listing |
| 10 | P69713 | Hepatitis B virus genotype A2 subtype adw2 (strain Rutter 1979)(HBV-A) | 7 | see sequence listing |
| 11 | Q4R1S1 | Hepatitis B virus genotype A3 (isolate Cameroon/CMR711/1994)(HBV-A) | 16 | see sequence listing |
| 12 | Q4R1S9 | Hepatitis B virus genotype A3 (isolate Cameroon/CMR983/1994)(HBV-A) | 15 | see sequence listing |
| 13 | P0C678 | Hepatitis B virus genotype B1 (isolate Japan/Ry30/2002)(HBV-B) | II | see sequence listing |
| 14 | Q9PX75 | Hepatitis B virus genotype B1 (isolate Japan/Yamagata-2/1998)(HBV-B) | 12 | see sequence listing |
| 15 | P20976 | Hepatitis B virus genotype B1 subtype adw (isolate Japan/pJDW233/1988)(HBV-B) | 8 | see sequence listing |
| 16 | P20975 | Hepatitis B virus genotype B2 (isolate Indonesia/pIDW420/1988)(HBV-B) | 10 | see sequence listing |
| 17 | Q9PXA2 | Hepatitis B virus genotype B2 (isolate Vietnam/16091/1992)(HBV-B) | 15 | see sequence listing |
| 18 | P0C685 | Hepatitis B virus genotype B2 (isolate Vietnam/9873/1997)(HBV-B) | 11 | see sequence listing |
| 19 | Q67923 | Hepatitis B virus genotype B2 subtype adw (isolate China/patient4/1996)(HBV-B) | 11 | see sequence listing |
| 20 | P20977 | Hepatitis B virus genotype B/C subtype adw (isolate Okinawa/pODW282/1998)(HBV-B) | 12 | see sequence listing |
| 21 | Q9E6S8 | Hepatitis B virus genotype C (isolate Vietnam/3270/2000)(HBV-C) | 6 | see sequence listing |
| 22 | P0C686 | Hepatitis B virus genotype C subtype adr (isolate Japan/Nishioka/1983)(HBV-C) | 9 | see sequence listing |
| 23 | P12936 | Hepatitis B virus genotype C subtype adr (strain Japan/adr4/1983)(HBV-C) | 8 | see sequence listing |
| 24 | Q9YZR6 | Hepatitis B virus genotype C subtype ar (isolate Japan/S-207/1988)(HBV-C) | 10 | see sequence listing |
| 25 | Q69027 | Hepatitis B virus genotype C subtype ayr (isolate Human/Japan/Okamoto/-)(HBV-C) | 8 | see sequence listing |
| 26 | P0C687 | Hepatitis B virus genotype C subtype ayw (isolate Australia/AustRC/1992)(HBV-C) | 14 | see sequence listing |
| 27 | Q913A9 | Hepatitis B virus genotype C subtype ayw (isolate China/Tibet127/2002)(HBV-C) | 5 | see sequence listing |
| 28 | P24026 | Hepatitis B virus genotype D (isolate France/alpha1/1989)(HBV-D) | 12 | see sequence listing |
| 29 | O93195 | Hepatitis B virus genotype D (isolate Germany/1-91/1991)(HBV-D) | 14 | see sequence listing |

TABLE 2-continued

Different HBV X protein variants and the deduced consensus protein sequence.

| SEQ ID NO. | UniProt ENTRY | HBV genotype source | Number of mismatches as compared to consensus sequence | X protein sequence |
|---|---|---|---|---|
| 30 | P0C681 | Hepatitis B virus genotype D subtype ayw (isolate Australia/AustKW/1991)(HBV-D) | 9 | see sequence listing |
| 31 | P03165 | Hepatitis B virus genotype D subtype ayw (isolate France/Tiollais/1979)(HBV-D) | 7 | see sequence listing |
| 32 | Q67877 | Hepatitis B virus genotype D subtype ayw (isolate Italy/C1/1992)(HBV-D) | 8 | see sequence listing |
| 33 | Q9QMI3 | Hepatitis B virus genotype D subtype ayw (isolate Japan/JYW796/1988)(HBV-D) | 9 | see sequence listing |
| 34 | Q80IU8 | Hepatitis B virus genotype E (isolate Cote d'Ivoire/ABI-129/2003)(HBV-E) | 11 | see sequence listing |
| 35 | Q80IU5 | Hepatitis B virus genotype E (isolate Cote d'Ivoire/ABI-212/2003)(HBV-E) | 7 | see sequence listing |
| 36 | Q69604 | Hepatitis B virus genotype E subtype ayw4 (isolate Kou)(HBV-E) | 8 | see sequence listing |
| 37 | Q8JMY3 | Hepatitis B virus genotype F1 subtype adw4 (isolate El Salvador/1116Sal/1997)(HBV-F) | 20 | see sequence listing |
| 38 | Q99HR6 | Hepatitis B virus genotype F2 (isolate Argentina/sal6/2000)(HBV-F) | 19 | see sequence listing |
| 39 | Q05499 | Hepatitis B virus genotype F2 (isolate Brazil/w4B)(HBV-F) | 21 | see sequence listing |
| 40 | Q69607 | Hepatitis B virus genotype F2 subtype adw4q (isolate Senegal/9203)(HBV-F) | 21 | see sequence listing |
| 41 | Q9IBI5 | Hepatitis B virus genotype G (isolate IG29227/2000)(HBV-G) | 31 | see sequence listing |
| 42 | Q8JMY5 | Hepatitis B virus genotype H (isolate United States/LAS2523/2002)(HBV-H) | 22 | see sequence listing |
| 43 | Q8JN06 | Hepatitis B virus genotype H subtype adw4 (isolate Nicaragua/1853Nic/1997)(HBV-H) | 22 | see sequence listing |
| 44 | Q8JMZ5 | Hepatitis B virus genotype H subtype adw4 (isolate Nicaragua/2928Nic/1997)(HBV-H) | 22 | see sequence listing |
| 45 | — | Consensus aa sequence | — | MAARLCCQLDPARDVLCLRPV GAESRGRPLSGPLGALPSPSP SAVPADHGAHLSRGLPVCAF SSAGPCALRFTSARRMETTVN AHQILPKVLHKRTLGLSAMST TDLEAYFKDCVFKDWEELGEE IRLKVFVLGGCRHKLVCSPAP CNFFTSA |

TABLE 3

Synthetic long peptide (SLP) sequences.

| SEQ ID NO: | SLP# | Cumulative Class I-BCI[A] | Cumulative Class II-B score[B] | TRIA score[C] | Source | Sequence |
|---|---|---|---|---|---|---|
| 51 | SLP1 | 7264 | 780 | 8044 | HBV Polymerase aa 1 - 30 | MPLSYQHFRKLLLLDDGTEAGPLEEELPRL |
| 52 | SLP2 | 6943 | 1323 | 8266 | HBV Polymerase aa 52 - 86 | IPWTHKVGNFTGLYSSTVPIFNPEWQTPSFPKIHL |

TABLE 3-continued

Synthetic long peptide (SLP) sequences.

| SEQ ID NO: | SLP# | Cumulative Class I-BCI[A] | Cumulative Class II-B score[B] | TRIA score[C] | Source | Sequence |
|---|---|---|---|---|---|---|
| 53 | SLP3 | 6469 | 3070 | 9539 | HBV Polymerase aa 103 - 135 | VNEKRRLKLIMPARFYPTHTKYLPLDKGIKPYY |
| 54 | SLP4 | 6169 | 143 | 6312 | HBV Polymerase aa 118 - 150 | YPTHTKYLPLDKGIKPYYPDQVVNHYFQTRHYL |
| 55 | SLP5 | 11815 | 1519 | 13334 | HBV Polymerase aa 139 - 177 | VVNHYFQTRHYLHTLWKAGILYKRETTRSASFCGSPYSW |
| 56 | SLP6 | 10432 | 928 | 11360 | HBV Polymerase aa 143 - 177 | YFQTRHYLHTLWKAGILYKRETTRSASFCGSPYSW |
| 57 | SLP7 | 10325 | 1817 | 12142 | HBV Polymerase aa 137- 170 | DQVVNHYFQTRHYLHTLWKAGILYKRETTRSASF |
| 58 | SLP8 | 7246 | 3 | 7249 | HBV Polymerase aa 316 - 347 | SQSQGSVSSCWWLQFRNSKPCSEYCLSHLVNL |
| 59 | SLP9 | 6722 | 527 | 7249 | HBV Polymerase aa 385 - 417 | TAESRLVVDFSQFSRGISRVSWPKFAVPNLQSL |
| 60 | SLP10 | 11926 | 943 | 12869 | HBV Polymerase aa 419 - 456 | NLLSSNLSWLSLDVSAAFYHIPLHPAAMPHLLIGSSGL |
| 61 | SLP11 | 12384 | 1058 | 13442 | HBV Polymerase aa 422 - 459 | SSNLSWLSLDVSAAFYHIPLHPAAMPHLLIGSSGLSRY |
| 62 | SLP12 | 12198 | 426 | 12624 | HBV Polymerase aa 427 - 459 | WLSLDVSAAFYHIPLHPAAMPHLLIGSSGLSRY |
| 63 | SLP13 | 15733 | 3046 | 18779 | HBV Polymerase aa 481 - 514 | HDSCSRQLYVSLMLLYKTYGWKLHLYSHPIVLGF |
| 64 | SLP14 | 12015 | 1042 | 13057 | HBV Polymerase aa 524 - 559 | SPFLLAQFTSAICSVVRRAFPHCLAFSYMDDVVLGA |
| 65 | SLP15 | 11658 | 783 | 12441 | HBV Polymerase aa 526 - 559 | FLLAQFTSAICSVVRRAFPHCLAFSYMDDVVLGA |
| 66 | SLP16 | 8255 | 1482 | 9737 | HBV Polymerase aa 565 - 598 | RESLYTAVTNFLLSLGIHLNPNKTKRWGYSLNFM |
| 67 | SLP17 | 6396 | 223 | 6619 | HBV Polymerase aa 584 - 617 | NPNKTKRWGYSLNFMGYIIGSWGTLPQDHIVQKI |
| 68 | SLP18 | 12576 | 1365 | 13941 | HBV Polymerase aa 653 - 691 | YPALMPLYACIQAKQAFTFSPTYKAFLSKQYMNLYPVAR |
| 69 | SLP19 | 10420 | 1181 | 11601 | HBV Polymerase aa 657 - 691 | MPLYACIQAKQAFTFSPTYKAFLSKQYMNLYPVAR |
| 70 | SLP20 | 7869 | 244 | 8113 | HBV Polymerase aa 715 - 746 | QRMRGTFVAPLPIHTAELLAACFARSRSGAKL |
| 71 | SLP21 | 8555 | 1591 | 10146 | HBV Polymerase aa 754 - 791 | VLSRKYTSFPWLLGCTANWILRGTSFVYVPSALNPADD |
| 72 | SLP22 | 6817 | 1709 | 8526 | HBV Polymerase aa 757 - 792 | RKYTSFPWLLGCTANWILRGTSFVYVPSALNPADDP |
| 73 | SLP23 | 8553 | 903 | 9456 | HBV Polymerase aa 754 - 789 | VLSRKYTSFPWLLGCTANWILRGTSFVYVPSALNPA |
| 74 | SLP24 | 7277 | 4649 | 11926 | HBV Core aa 107 - 141 | DPASRDLVVNYVNTNVGLKIRQLLWFHISCLTFGR |
| 75 | SLP25 | 11331 | 5493 | 16824 | HBV Core aa 136 - 169 | CLTFGRETVLEYLVSFGVWIRTPPAYRPPNAPIL |
| 76 | SLP26 | 5422 | 4414 | 9836 | HBV consensus seq X protein aa 36 - 68 | ALPSPSPSAVPADHGAHLSRGLPVCAFSSAGP |
| 77 | SLP27 | 6468 | 3788 | 10256 | HBV consensus seq X protein aa 61 - 95 | CAFSSAGPCALRFTSARRMETTVNAHQILPKVLHK |
| 78 | SLP28 | 7354 | 3170 | 10524 | HBV consensus seq X protein aa 86 -120 | HQILPKVLHKRTLGLSAMSTTDLEAYFKDCVFKDW |
| 79 | SLP29 | 5862 | 1024 | 6886 | HBV consensus seq X protein aa 108 - 141 | LEAYFKDCVFKDWEELGEEIRLKVFVLGGCRHKL |
| 1142 | SLP30 | 6882 | 4798 | 11680 | HBV large surface protein aa 175 - 210 | MENITSGFLGPLLVLQAGFFLLTRILTIPQSLDSWW |
| 1143 | SLP31 | 10214 | 7238 | 17452 | HBV large surface protein aa 239 - 274 | CPPICPGYRWMCLRRFIIFLFILLLCLIFLLVLLDY |
| 1144 | SLP32 | 14976 | 1815 | 16791 | HBV large surface protein aa 323 - 358 | CIPIPSSWAFAKYLWEWASVRFSWLSLLVPFVQWFV |
| 1468 | SLP33 | 13107 | 1815 | 14922 | HBV large surface protein aa 327 - 358 | PSSWAFAKYLWEWASVRFSWLSLLVPFVQWFV |
| 1469 | SLP34 | 12851 | 1815 | 14666 | HBV large surface protein aa 328 -358 | SSWAFAKYLWEWASVRFSWLSLLVPFVQWFV |

TABLE 3-continued

Synthetic long peptide (SLP) sequences.

| SEQ ID NO: | SLP# | Cumulative Class I-BCI[A] | Cumulative Class II-B score[B] | TRIA score[C] | Source | Sequence |
|---|---|---|---|---|---|---|
| 1145 | SLP35 | 9736 | 4425 | 14161 | HBV large surface protein aa 365 - 400 | WLSAIWMMWYWGPSLYSIVSPFIPLLPIFFCLWVYI |
| 1470 | SLP36 | 5389 | 4035 | 9424 | HBV large surface protein aa 371 - 400 | MMWYWGPSLYSIVSPFIPLLPIFFCLWVYI |
| 1471 | SLP37 | 6880 | 4160 | 11040 | HBV large surface protein aa 370 - 400 | WMMWYWGPSLYSIVSPFIPLLPIFFCLWVYI |

[A] Cumulative Class I-BCI score: See Material and Methods (Examples section).
[B] Cumulative Class II-B score: See Material and Methods (Examples section).
[C] TRIA score is the sum of the Cumulative Class I-BCI score and the Cumulative Class II-B score.

TABLE 4a

Predicted HLA class I-restricted CD8+ cytotoxic T cell epitopes contained in SLP sequences from HBV polymerase protein.

HLA class I binding peptides in SLP sequences derived from HBV Polymerase protein

| Start | End | Length | Sequence[A] | SEQ ID NO: | HLA class I molecule | Class I-B score[B] | C-score[C] | Class I-BCI score[D] | SLP# | SLP Start | SLP End |
|---|---|---|---|---|---|---|---|---|---|---|---|
| 1 | 8 | 8 | MPLSYQHF | 80 | A*6802 | 9 | 1.42 | 13 | 1 | 1 | 30 |
| 1 | 8 | 8 | MPLSYQHF | 80 | B*0801 | 20 | 1.42 | 29 | 1 | 1 | 30 |
| 1 | 8 | 8 | MPLSYQHF | 80 | B*1402 | 62 | 1.42 | 88 | 1 | 1 | 30 |
| 1 | 8 | 8 | MPLSYQHF | 80 | B*1502 | 13 | 1.42 | 18 | 1 | 1 | 30 |
| 1 | 8 | 8 | MPLSYQHF | 80 | B*1801 | 57 | 1.42 | 81 | 1 | 1 | 30 |
| 1 | 8 | 8 | MPLSYQHF | 80 | B*3503 | 96 | 1.42 | 136 | 1 | 1 | 30 |
| 1 | 8 | 8 | MPLSYQHF | 80 | B*5101 | 77 | 1.42 | 109 | 1 | 1 | 30 |
| 1 | 8 | 8 | MPLSYQHF | 80 | B*5301 | 92 | 1.42 | 130 | 1 | 1 | 30 |
| 1 | 8 | 8 | MPLSYQHF | 80 | B*5501 | 26 | 1.42 | 36 | 1 | 1 | 30 |
| 1 | 8 | 8 | MPLSYQHF | 80 | B*5601 | 23 | 1.42 | 33 | 1 | 1 | 30 |
| 1 | 9 | 9 | MPLSYQHFR | 81 | A*3101 | 77 | 1.83 | 142 | 1 | 1 | 30 |
| 1 | 9 | 9 | MPLSYQHFR | 81 | A*3303 | 77 | 1.83 | 142 | 1 | 1 | 30 |
| 1 | 9 | 9 | MPLSYQHFR | 81 | A*6801 | 78 | 1.83 | 143 | 1 | 1 | 30 |
| 1 | 9 | 9 | MPLSYQHFR | 81 | B*5101 | 22 | 1.83 | 40 | 1 | 1 | 30 |
| 2 | 9 | 8 | PLSYQHFR | 82 | A*3101 | 22 | 1.83 | 39 | 1 | 1 | 30 |
| 2 | 9 | 8 | PLSYQHFR | 82 | A*3303 | 45 | 1.83 | 83 | 1 | 1 | 30 |
| 2 | 9 | 8 | PLSYQHFR | 82 | A*7401 | 28 | 1.83 | 51 | 1 | 1 | 30 |
| 1 | 10 | 10 | MPLSYQHFRK | 83 | B*3501 | 41 | 1.21 | 50 | 1 | 1 | 30 |
| 3 | 10 | 8 | LSYQHFRK | 84 | A*0301 | 90 | 1.21 | 110 | 1 | 1 | 30 |
| 3 | 10 | 8 | LSYQHFRK | 84 | A*1101 | 89 | 1.21 | 108 | 1 | 1 | 30 |
| 3 | 10 | 8 | LSYQHFRK | 84 | A*3001 | 43 | 1.21 | 53 | 1 | 1 | 30 |
| 3 | 10 | 8 | LSYQHFRK | 84 | A*7401 | 45 | 1.21 | 55 | 1 | 1 | 30 |

TABLE 4a-continued

Predicted HLA class I-restricted CD8+ cytotoxic T cell epitopes contained in SLP sequences from HBV polymerase protein.

HLA class I binding peptides in SLP sequences derived from HBV Polymerase protein

| Start | End | Length | Sequence$^A$ | SEQ ID NO: | HLA class I molecule | Class I-B score$^B$ | C-score$^C$ | Class I-BCI score$^D$ | Peptide of invention (SLP) SLP# | SLP Start | SLP End |
|---|---|---|---|---|---|---|---|---|---|---|---|
| 1 | 11 | 11 | MPLSYQHFRKL | 85 | B*0702 | 87 | 1.89 | 165 | 1 | 1 | 30 |
| 1 | 11 | 11 | MPLSYQHFRKL | 85 | B*0801 | 97 | 1.89 | 183 | 1 | 1 | 30 |
| 1 | 11 | 11 | MPLSYQHFRKL | 85 | B*1402 | 96 | 1.89 | 182 | 1 | 1 | 30 |
| 1 | 11 | 11 | MPLSYQHFRKL | 85 | B*3501 | 45 | 1.89 | 86 | 1 | 1 | 30 |
| 1 | 11 | 11 | MPLSYQHFRKL | 85 | B*3503 | 86 | 1.89 | 164 | 1 | 1 | 30 |
| 1 | 11 | 11 | MPLSYQHFRKL | 85 | B*3901 | 58 | 1.89 | 111 | 1 | 1 | 30 |
| 1 | 11 | 11 | MPLSYQHFRKL | 85 | B*5101 | 90 | 1.89 | 170 | 1 | 1 | 30 |
| 1 | 11 | 11 | MPLSYQHFRKL | 85 | B*5301 | 66 | 1.89 | 124 | 1 | 1 | 30 |
| 1 | 11 | 11 | MPLSYQHFRKL | 85 | B*5501 | 79 | 1.89 | 150 | 1 | 1 | 30 |
| 1 | 11 | 11 | MPLSYQHFRKL | 85 | B*5601 | 62 | 1.89 | 117 | 1 | 1 | 30 |
| 3 | 11 | 9 | LSYQHFRKL | 86 | B*5201 | 45 | 1.89 | 85 | 1 | 1 | 30 |
| 4 | 11 | 8 | SYQHFRKL | 87 | A*2301 | 57 | 1.89 | 108 | 1 | 1 | 30 |
| 4 | 11 | 8 | SYQHFRKL | 87 | A*2402 | 65 | 1.89 | 123 | 1 | 1 | 30 |
| 3 | 12 | 10 | LSYQHFRKLL | 88 | B*5201 | 37 | 1.82 | 68 | 1 | 1 | 30 |
| 4 | 12 | 9 | SYQHFRKLL | 89 | A*2402 | 26 | 1.82 | 48 | 1 | 1 | 30 |
| 5 | 12 | 8 | YQHFRKLL | 90 | B*0801 | 66 | 1.82 | 120 | 1 | 1 | 30 |
| 5 | 12 | 8 | YQHFRKLL | 90 | B*1402 | 54 | 1.82 | 98 | 1 | 1 | 30 |
| 5 | 12 | 8 | YQHFRKLL | 90 | B*3901 | 78 | 1.82 | 142 | 1 | 1 | 30 |
| 5 | 12 | 8 | YQHFRKLL | 90 | B*4801 | 71 | 1.82 | 130 | 1 | 1 | 30 |
| 3 | 13 | 11 | LSYQHFRKLLL | 91 | B*0801 | 59 | 1.71 | 101 | 1 | 1 | 30 |
| 3 | 13 | 11 | LSYQHFRKLLL | 91 | B*5201 | 65 | 1.71 | 111 | 1 | 1 | 30 |
| 3 | 13 | 11 | LSYQHFRKLLL | 91 | B*5701 | 11 | 1.71 | 18 | 1 | 1 | 30 |
| 4 | 13 | 10 | SYQHFRKLLL | 92 | A*2301 | 28 | 1.71 | 47 | 1 | 1 | 30 |
| 4 | 13 | 10 | SYQHFRKLLL | 92 | A*2402 | 33 | 1.71 | 57 | 1 | 1 | 30 |
| 5 | 13 | 9 | YQHFRKLLL | 93 | B*0801 | 31 | 1.71 | 52 | 1 | 1 | 30 |
| 5 | 13 | 9 | YQHFRKLLL | 93 | B*1402 | 61 | 1.71 | 104 | 1 | 1 | 30 |
| 5 | 13 | 9 | YQHFRKLLL | 93 | B*3901 | 64 | 1.71 | 109 | 1 | 1 | 30 |
| 5 | 13 | 9 | YQHFRKLLL | 93 | B*4801 | 98 | 1.71 | 168 | 1 | 1 | 30 |
| 6 | 13 | 8 | QHFRKLLL | 94 | B*1402 | 80 | 1.71 | 136 | 1 | 1 | 30 |
| 6 | 13 | 8 | QHFRKLLL | 94 | B*3801 | 55 | 1.71 | 94 | 1 | 1 | 30 |
| 6 | 13 | 8 | QHFRKLLL | 94 | B*3901 | 77 | 1.71 | 131 | 1 | 1 | 30 |
| 4 | 14 | 11 | SYQHFRKLLLL | 95 | A*2301 | 76 | 1.85 | 140 | 1 | 1 | 30 |
| 4 | 14 | 11 | SYQHFRKLLLL | 95 | A*2402 | 82 | 1.85 | 152 | 1 | 1 | 30 |
| 5 | 14 | 10 | YQHFRKLLLL | 96 | A*0201 | 36 | 1.85 | 67 | 1 | 1 | 30 |

TABLE 4a-continued

Predicted HLA class I-restricted CD8⁺ cytotoxic T cell epitopes contained in SLP sequences from HBV polymerase protein.

HLA class I binding peptides in SLP sequences derived from HBV Polymerase protein

| Start | End | Length | Sequence [A] | SEQ ID NO: | HLA class I molecule | Class I-B score [B] | C-score [C] | Class I-BCI score [D] | Peptide of invention (SLP) | | |
|---|---|---|---|---|---|---|---|---|---|---|---|
| | | | | | | | | | SLP# | SLP Start | SLP End |
| 5 | 14 | 10 | YQHFRKLLLL | 96 | B*1402 | 53 | 1.85 | 97 | 1 | 1 | 30 |
| 5 | 14 | 10 | YQHFRKLLLL | 96 | B*3901 | 70 | 1.85 | 130 | 1 | 1 | 30 |
| 5 | 14 | 10 | YQHFRKLLLL | 96 | B*4801 | 85 | 1.85 | 156 | 1 | 1 | 30 |
| 6 | 14 | 9 | QHFRKLLLL | 97 | B*1402 | 60 | 1.85 | 110 | 1 | 1 | 30 |
| 6 | 14 | 9 | QHFRKLLLL | 97 | B*3801 | 84 | 1.85 | 155 | 1 | 1 | 30 |
| 7 | 14 | 8 | HFRKLLLL | 98 | B*0801 | 75 | 1.85 | 138 | 1 | 1 | 30 |
| 5 | 15 | 11 | YQHFRKLLLLD | 99 | B*2705 | 94 | 0.80 | 75 | 1 | 1 | 30 |
| 6 | 16 | 11 | QHFRKLLLLDD | 100 | B*2705 | 18 | 0.57 | 10 | 1 | 1 | 30 |
| 8 | 18 | 11 | FRKLLLLDDGT | 101 | B*2705 | 51 | 0.12 | 6 | 1 | 1 | 30 |
| 12 | 20 | 9 | LLLDDGTEA | 102 | A*0201 | 24 | 1.41 | 34 | 1 | 1 | 30 |
| 13 | 23 | 11 | LLDDGTEAGPL | 103 | A*0206 | 33 | 0.79 | 26 | 1 | 1 | 30 |
| 18 | 27 | 10 | TEAGPLEEEL | 104 | B*1301 | 70 | 1.36 | 96 | 1 | 1 | 30 |
| 18 | 27 | 10 | TEAGPLEEEL | 104 | B*3701 | 10 | 1.36 | 13 | 1 | 1 | 30 |
| 18 | 27 | 10 | TEAGPLEEEL | 104 | B*3801 | 35 | 1.36 | 47 | 1 | 1 | 30 |
| 18 | 27 | 10 | TEAGPLEEEL | 104 | B*4002 | 60 | 1.36 | 82 | 1 | 1 | 30 |
| 23 | 30 | 8 | LEEELPRL | 105 | B*0702 | 75 | 1.77 | 133 | 1 | 1 | 30 |
| 23 | 30 | 8 | LEEELPRL | 105 | B*1301 | 69 | 1.77 | 122 | 1 | 1 | 30 |
| 23 | 30 | 8 | LEEELPRL | 105 | B*3701 | 52 | 1.77 | 93 | 1 | 1 | 30 |
| 23 | 30 | 8 | LEEELPRL | 105 | B*3801 | 33 | 1.77 | 58 | 1 | 1 | 30 |
| 23 | 30 | 8 | LEEELPRL | 105 | B*4001 | 74 | 1.77 | 131 | 1 | 1 | 30 |
| | | | | | Cumulative BCI Class I score [E]: | | | 7264 | | | |
| 52 | 61 | 10 | IPWTHKVGNF | 106 | B*1402 | 43 | 1.19 | 52 | 2 | 52 | 86 |
| 52 | 61 | 10 | IPWTHKVGNF | 106 | B*3501 | 47 | 1.19 | 55 | 2 | 52 | 86 |
| 52 | 61 | 10 | IPWTHKVGNF | 106 | B*3503 | 64 | 1.19 | 76 | 2 | 52 | 86 |
| 52 | 61 | 10 | IPWTHKVGNF | 106 | B*5301 | 41 | 1.19 | 49 | 2 | 52 | 86 |
| 52 | 61 | 10 | IPWTHKVGNF | 106 | B*5501 | 41 | 1.19 | 48 | 2 | 52 | 86 |
| 54 | 61 | 8 | WTHKVGNF | 107 | A*2501 | 84 | 1.19 | 100 | 2 | 52 | 86 |
| 54 | 61 | 8 | WTHKVGNF | 107 | A*2601 | 82 | 1.19 | 98 | 2 | 52 | 86 |
| 54 | 61 | 8 | WTHKVGNF | 107 | B*4601 | 44 | 1.19 | 53 | 2 | 52 | 86 |
| 54 | 61 | 8 | WTHKVGNF | 107 | B*5802 | 10 | 1.19 | 12 | 2 | 52 | 86 |
| 52 | 62 | 11 | IPWTHKVGNFT | 108 | B*5501 | 50 | 0.50 | 25 | 2 | 52 | 86 |
| 52 | 62 | 11 | IPWTHKVGNFT | 108 | B*5601 | 60 | 0.50 | 30 | 2 | 52 | 86 |
| 54 | 64 | 11 | WTHKVGNFTGL | 109 | A*2501 | 80 | 1.66 | 132 | 2 | 52 | 86 |
| 54 | 64 | 11 | WTHKVGNFTGL | 109 | A*2601 | 64 | 1.66 | 107 | 2 | 52 | 86 |
| 56 | 64 | 9 | HKVGNFTGL | 110 | B*1402 | 23 | 1.66 | 39 | 2 | 52 | 86 |

TABLE 4a-continued

Predicted HLA class I-restricted CD8+ cytotoxic T cell epitopes contained in SLP sequences from HBV polymerase protein.

HLA class I binding peptides in SLP sequences derived from HBV Polymerase protein

| Start | End | Length | Sequence [A] | SEQ ID NO: | HLA class I molecule | Class I-B score [B] | C-score [C] | Class I-BCI score [D] | SLP# | SLP Start | SLP End |
|---|---|---|---|---|---|---|---|---|---|---|---|
| 56 | 64 | 9 | HKVGNFTGL | 110 | B*3901 | 35 | 1.66 | 58 | 2 | 52 | 86 |
| 57 | 64 | 8 | KVGNFTGL | 111 | A*3201 | 32 | 1.66 | 53 | 2 | 52 | 86 |
| 55 | 65 | 11 | THKVGNFTGLY | 112 | A*3002 | 28 | 1.39 | 39 | 2 | 52 | 86 |
| 56 | 65 | 10 | HKVGNFTGLY | 113 | A*2601 | 23 | 1.39 | 32 | 2 | 52 | 86 |
| 56 | 65 | 10 | HKVGNFTGLY | 113 | A*2902 | 21 | 1.39 | 29 | 2 | 52 | 86 |
| 56 | 65 | 10 | HKVGNFTGLY | 113 | A*3002 | 80 | 1.39 | 111 | 2 | 52 | 86 |
| 57 | 65 | 9 | KVGNFTGLY | 114 | A*0101 | 34 | 1.39 | 47 | 2 | 52 | 86 |
| 57 | 65 | 9 | KVGNFTGLY | 114 | A*0301 | 39 | 1.39 | 55 | 2 | 52 | 86 |
| 57 | 65 | 9 | KVGNFTGLY | 114 | A*2902 | 79 | 1.39 | 110 | 2 | 52 | 86 |
| 57 | 65 | 9 | KVGNFTGLY | 114 | A*3002 | 100 | 1.39 | 139 | 2 | 52 | 86 |
| 58 | 65 | 8 | VGNFTGLY | 115 | A*0101 | 49 | 1.39 | 68 | 2 | 52 | 86 |
| 58 | 65 | 8 | VGNFTGLY | 115 | A*2902 | 62 | 1.39 | 86 | 2 | 52 | 86 |
| 58 | 65 | 8 | VGNFTGLY | 115 | A*3002 | 93 | 1.39 | 129 | 2 | 52 | 86 |
| 61 | 71 | 11 | FTGLYSSTVPI | 116 | A*2501 | 24 | 1.12 | 27 | 2 | 52 | 86 |
| 61 | 71 | 11 | FTGLYSSTVPI | 116 | A*3201 | 30 | 1.12 | 34 | 2 | 52 | 86 |
| 61 | 71 | 11 | FTGLYSSTVPI | 116 | A*6802 | 31 | 1.12 | 35 | 2 | 52 | 86 |
| 61 | 71 | 11 | FTGLYSSTVPI | 116 | B*5101 | 15 | 1.12 | 17 | 2 | 52 | 86 |
| 61 | 71 | 11 | FTGLYSSTVPI | 116 | B*5201 | 24 | 1.12 | 26 | 2 | 52 | 86 |
| 62 | 71 | 10 | TGLYSSTVPI | 117 | B*5201 | 33 | 1.12 | 37 | 2 | 52 | 86 |
| 63 | 71 | 9 | GLYSSTVPI | 118 | A*0201 | 69 | 1.12 | 77 | 2 | 52 | 86 |
| 63 | 71 | 9 | GLYSSTVPI | 118 | A*3201 | 88 | 1.12 | 99 | 2 | 52 | 86 |
| 63 | 71 | 9 | GLYSSTVPI | 118 | B*1525 | 42 | 1.12 | 48 | 2 | 52 | 86 |
| 63 | 71 | 9 | GLYSSTVPI | 118 | B*5201 | 35 | 1.12 | 40 | 2 | 52 | 86 |
| 64 | 71 | 8 | LYSSTVPI | 119 | A*2301 | 66 | 1.12 | 73 | 2 | 52 | 86 |
| 64 | 71 | 8 | LYSSTVPI | 119 | A*2402 | 81 | 1.12 | 91 | 2 | 52 | 86 |
| 63 | 72 | 10 | GLYSSTVPIF | 120 | A*2402 | 44 | 1.40 | 61 | 2 | 52 | 86 |
| 63 | 72 | 10 | GLYSSTVPIF | 120 | A*3001 | 74 | 1.40 | 104 | 2 | 52 | 86 |
| 63 | 72 | 10 | GLYSSTVPIF | 120 | B*1501 | 95 | 1.40 | 133 | 2 | 52 | 86 |
| 63 | 72 | 10 | GLYSSTVPIF | 120 | B*1502 | 80 | 1.40 | 112 | 2 | 52 | 86 |
| 63 | 72 | 10 | GLYSSTVPIF | 120 | B*1525 | 92 | 1.40 | 128 | 2 | 52 | 86 |
| 64 | 72 | 9 | LYSSTVPIF | 121 | A*2301 | 79 | 1.40 | 111 | 2 | 52 | 86 |
| 64 | 72 | 9 | LYSSTVPIF | 121 | A*2402 | 98 | 1.40 | 138 | 2 | 52 | 86 |
| 65 | 72 | 8 | YSSTVPIF | 122 | A*0101 | 26 | 1.40 | 37 | 2 | 52 | 86 |
| 65 | 72 | 8 | YSSTVPIF | 122 | B*4601 | 85 | 1.40 | 119 | 2 | 52 | 86 |
| 65 | 72 | 8 | YSSTVPIF | 122 | B*5301 | 59 | 1.40 | 83 | 2 | 52 | 86 |

TABLE 4a-continued

Predicted HLA class I-restricted CD8+ cytotoxic T cell epitopes contained in SLP sequences from HBV polymerase protein.

HLA class I binding peptides in SLP sequences derived from HBV Polymerase protein

| Start | End | Length | Sequence[A] | SEQ ID NO: | HLA class I molecule | Class I-B score[B] | C-score[C] | Class I-BCI score[D] | Peptide of invention (SLP) SLP# | SLP Start | SLP End |
|---|---|---|---|---|---|---|---|---|---|---|---|
| 65 | 72 | 8 | YSSTVPIF | 122 | B*5701 | 56 | 1.40 | 79 | 2 | 52 | 86 |
| 65 | 72 | 8 | YSSTVPIF | 122 | B*5801 | 80 | 1.40 | 112 | 2 | 52 | 86 |
| 65 | 72 | 8 | YSSTVPIF | 122 | B*5802 | 77 | 1.40 | 108 | 2 | 52 | 86 |
| 65 | 74 | 10 | YSSTVPIFNP | 123 | B*5701 | 98 | 0.65 | 64 | 2 | 52 | 86 |
| 65 | 74 | 10 | YSSTVPIFNP | 123 | B*5801 | 85 | 0.65 | 55 | 2 | 52 | 86 |
| 66 | 76 | 11 | SSTVPIFNPEW | 124 | B*5701 | 100 | 1.48 | 148 | 2 | 52 | 86 |
| 66 | 76 | 11 | SSTVPIFNPEW | 124 | B*5801 | 97 | 1.48 | 143 | 2 | 52 | 86 |
| 66 | 76 | 11 | SSTVPIFNPEW | 124 | B*5802 | 93 | 1.48 | 137 | 2 | 52 | 86 |
| 67 | 76 | 10 | STVPIFNPEW | 125 | B*4402 | 19 | 1.48 | 28 | 2 | 52 | 86 |
| 67 | 76 | 10 | STVPIFNPEW | 125 | B*4403 | 64 | 1.48 | 95 | 2 | 52 | 86 |
| 67 | 76 | 10 | STVPIFNPEW | 125 | B*5802 | 91 | 1.48 | 135 | 2 | 52 | 86 |
| 69 | 76 | 8 | VPIFNPEW | 126 | B*3503 | 5 | 1.48 | 8 | 2 | 52 | 86 |
| 69 | 76 | 8 | VPIFNPEW | 126 | B*5101 | 32 | 1.48 | 47 | 2 | 52 | 86 |
| 69 | 76 | 8 | VPIFNPEW | 126 | B*5301 | 90 | 1.48 | 133 | 2 | 52 | 86 |
| 70 | 79 | 10 | PIFNPEWQTP | 127 | A*3201 | 36 | 0.51 | 19 | 2 | 52 | 86 |
| 71 | 81 | 11 | IFNPEWQTPSF | 128 | A*2301 | 95 | 1.19 | 112 | 2 | 52 | 86 |
| 71 | 81 | 11 | IFNPEWQTPSF | 128 | A*2402 | 79 | 1.19 | 94 | 2 | 52 | 86 |
| 73 | 81 | 9 | NPEWQTPSF | 129 | B*0702 | 55 | 1.19 | 65 | 2 | 52 | 86 |
| 73 | 81 | 9 | NPEWQTPSF | 129 | B*3501 | 92 | 1.19 | 109 | 2 | 52 | 86 |
| 73 | 81 | 9 | NPEWQTPSF | 129 | B*3503 | 62 | 1.19 | 74 | 2 | 52 | 86 |
| 73 | 81 | 9 | NPEWQTPSF | 129 | B*5301 | 84 | 1.19 | 99 | 2 | 52 | 86 |
| 74 | 81 | 8 | PEWQTPSF | 130 | B*1801 | 71 | 1.19 | 85 | 2 | 52 | 86 |
| 74 | 81 | 8 | PEWQTPSF | 130 | B*4402 | 62 | 1.19 | 73 | 2 | 52 | 86 |
| 74 | 81 | 8 | PEWQTPSF | 130 | B*4403 | 72 | 1.19 | 85 | 2 | 52 | 86 |
| 76 | 83 | 8 | WQTPSFPK | 131 | A*1101 | 7 | 0.81 | 5 | 2 | 52 | 86 |
| 74 | 84 | 11 | PEWQTPSFPKI | 132 | B*1301 | 82 | 1.32 | 108 | 2 | 52 | 86 |
| 74 | 84 | 11 | PEWQTPSFPKI | 132 | B*1302 | 15 | 1.32 | 20 | 2 | 52 | 86 |
| 74 | 84 | 11 | PEWQTPSFPKI | 132 | B*4001 | 4 | 1.32 | 6 | 2 | 52 | 86 |
| 74 | 84 | 11 | PEWQTPSFPKI | 132 | B*4402 | 31 | 1.32 | 41 | 2 | 52 | 86 |
| 74 | 84 | 11 | PEWQTPSFPKI | 132 | B*4403 | 36 | 1.32 | 48 | 2 | 52 | 86 |
| 74 | 84 | 11 | PEWQTPSFPKI | 132 | B*4901 | 78 | 1.32 | 103 | 2 | 52 | 86 |
| 76 | 84 | 9 | WQTPSFPKI | 133 | A*0206 | 67 | 1.32 | 88 | 2 | 52 | 86 |
| 76 | 84 | 9 | WQTPSFPKI | 133 | B*1301 | 99 | 1.32 | 130 | 2 | 52 | 86 |
| 76 | 84 | 9 | WQTPSFPKI | 133 | B*1302 | 51 | 1.32 | 67 | 2 | 52 | 86 |

TABLE 4a-continued

Predicted HLA class I-restricted CD8+ cytotoxic T cell epitopes contained in SLP sequences from HBV polymerase protein.

HLA class I binding peptides in SLP sequences derived from HBV Polymerase protein

| Start | End | Length | Sequence [A] | SEQ ID NO: | H

TABLE 4a-continued

Predicted HLA class I-restricted CD8+ cytotoxic T cell epitopes contained in SLP sequences from HBV polymerase prot TABLE 4a-continued Predicted HLA class I-restricted CD8+ cytotoxic T cell epitopes contained in SLP sequences from HBV polymerase protein.

HLA class I binding peptides in SLP sequences derived from HBV Polymerase protein

| Start | End | Length | Sequence[A] | SEQ ID NO: | HLA class I molecule | Class I-B score[B] | C-score[C] | Class I-BCI score[D] | Peptide of invention (SLP) | | |
|---|---|---|---|---|---|---|---|---|---|---|---|
| | | | | | | | | | SLP# | SLP Start | SLP End |
| 113 | 123 | 11 | MPARFYPTHTK | 158 | B*5501 | 49 | 1.38 | 67 | 3 | 103 | 135 |
| 113 | 123 | 11 | MPARFYPTHTK | 158 | B*5601 | 54 | 1.38 | 74 | 3 | 103 | 135 |
| 115 | 123 | 9 | ARFYPTHTK | 159 | B*2705 | 87 | 1.38 | 119 | 3 | 103 | 135 |
| 116 | 123 | 8 | RFYPTHTK | 160 | A*0301 | 84 | 1.38 | 115 | 3 | 103 | 135 |
| 116 | 123 | 8 | RFYPTHTK | 160 | A*3001 | 79 | 1.38 | 109 | 3 | 103 | 135 |
| 116 | 123 | 8 | RFYPTHTK | 160 | A*3101 | 76 | 1.38 | 105 | 3 | 103 | 135 |
| 116 | 123 | 8 | RFYPTHTK | 160 | A*7401 | 57 | 1.38 | 79 | 3 | 103 | 135 |
| 115 | 124 | 10 | ARFYPTHTKY | 161 | A*2902 | 6 | 1.50 | 10 | 3 | 103 | 135 |
| 115 | 124 | 10 | ARFYPTHTKY | 161 | B*2702 | 61 | 1.50 | 92 | 3 | 103 | 135 |
| 115 | 124 | 10 | ARFYPTHTKY | 161 | B*2705 | 55 | 1.50 | 83 | 3 | 103 | 135 |
| 116 | 124 | 9 | RFYPTHTKY | 162 | A*2902 | 92 | 1.50 | 138 | 3 | 103 | 135 |
| 116 | 124 | 9 | RFYPTHTKY | 162 | A*3002 | 1 | 1.50 | 2 | 3 | 103 | 135 |
| 117 | 124 | 8 | FYPTHTKY | 163 | B*3501 | 51 | 1.50 | 76 | 3 | 103 | 135 |
| 115 | 125 | 11 | ARFYPTHTKYL | 164 | B*2702 | 67 | 1.93 | 130 | 3 | 103 | 135 |
| 115 | 125 | 11 | ARFYPTHTKYL | 164 | B*2705 | 34 | 1.93 | 66 | 3 | 103 | 135 |
| 116 | 125 | 10 | RFYPTHTKYL | 165 | B*4801 | 4 | 1.93 | 7 | 3 | 103 | 135 |
| 117 | 125 | 9 | FYPTHTKYL | 166 | A*2402 | 39 | 1.93 | 74 | 3 | 103 | 135 |
| 118 | 125 | 8 | YPTHTKYL | 167 | B*1402 | 42 | 1.93 | 82 | 3 | 103 | 135 |
| 118 | 125 | 8 | YPTHTKYL | 167 | B*3501 | 17 | 1.93 | 33 | 3 | 103 | 135 |
| 118 | 125 | 8 | YPTHTKYL | 167 | B*3503 | 78 | 1.93 | 151 | 3 | 103 | 135 |
| 118 | 125 | 8 | YPTHTKYL | 167 | B*5101 | 43 | 1.93 | 83 | 3 | 103 | 135 |
| 118 | 125 | 8 | YPTHTKYL | 167 | B*5301 | 51 | 1.93 | 98 | 3 | 103 | 135 |
| 118 | 125 | 8 | YPTHTKYL | 167 | B*5501 | 31 | 1.93 | 60 | 3 | 103 | 135 |
| 117 | 126 | 10 | FYPTHTKYLP | 168 | A*2402 | 54 | 0.14 | 7 | 3 | 103 | 135 |
| 118 | 126 | 9 | YPTHTKYLP | 169 | B*5301 | 2 | 0.14 | 0 | 3 | 103 | 135 |
| 117 | 127 | 11 | FYPTHTKYLPL | 170 | A*2301 | 52 | 0.94 | 49 | 3 | 103 | 135 |
| 117 | 127 | 11 | FYPTHTKYLPL | 170 | A*2402 | 56 | 0.94 | 53 | 3 | 103 | 135 |
| 118 | 127 | 10 | YPTHTKYLPL | 171 | B*0702 | 65 | 0.94 | 61 | 3 | 103 | 135 |
| 118 | 127 | 10 | YPTHTKYLPL | 171 | B*1402 | 100 | 0.94 | 94 | 3 | 103 | 135 |
| 118 | 127 | 10 | YPTHTKYLPL | 171 | B*3501 | 75 | 0.94 | 70 | 3 | 103 | 135 |
| 118 | 127 | 10 | YPTHTKYLPL | 171 | B*3503 | 100 | 0.94 | 94 | 3 | 103 | 135 |
| 118 | 127 | 10 | YPTHTKYLPL | 171 | B*3901 | 96 | 0.94 | 90 | 3 | 103 | 135 |
| 118 | 127 | 10 | YPTHTKYLPL | 171 | B*5101 | 83 | 0.94 | 78 | 3 | 103 | 135 |
| 118 | 127 | 10 | YPTHTKYLPL | 171 | B*5301 | 82 | 0.94 | 77 | 3 | 103 | 135 |

TABLE 4a-continued

Predicted HLA class I-restricted CD8+ cytotoxic T cell epitopes contained in SLP sequences from HBV polymerase protein.

HLA class I binding peptides in SLP sequences derived from HBV Polymerase protein

| Start | End | Length | Sequence[A] | SEQ ID NO: | HLA class I molecule | Class I-B score[B] | C-score[C] | Class I-BCI score[D] | SLP# | SLP Start | SLP End |
|---|---|---|---|---|---|---|---|---|---|---|---|
| 118 | 127 | 10 | YPTHTKYLPL | 171 | B*5501 | 87 | 0.94 | 82 | 3 | 103 | 135 |
| 118 | 127 | 10 | YPTHTKYLPL | 171 | B*5601 | 67 | 0.94 | 63 | 3 | 103 | 135 |
| 120 | 127 | 8 | THTKYLPL | 172 | B*1402 | 95 | 0.94 | 89 | 3 | 103 | 135 |
| 120 | 127 | 8 | THTKYLPL | 172 | B*3801 | 80 | 0.94 | 75 | 3 | 103 | 135 |
| 119 | 128 | 10 | PTHTKYLPLD | 173 | A*3001 | 46 | 0.71 | 33 | 3 | 103 | 135 |
| 121 | 129 | 9 | HTKYLPLDK | 174 | A*0301 | 18 | 0.41 | 7 | 3 | 103 | 135 |
| 121 | 129 | 9 | HTKYLPLDK | 174 | A*3001 | 90 | 0.41 | 37 | 3 | 103 | 135 |
| 123 | 131 | 9 | KYLPLDKGI | 175 | A*2301 | 34 | 1.23 | 43 | 3 | 103 | 135 |
| 123 | 131 | 9 | KYLPLDKGI | 175 | A*2402 | 21 | 1.23 | 26 | 3 | 103 | 135 |
| 125 | 132 | 8 | LPLDKGIK | 176 | B*3501 | 56 | 0.80 | 45 | 3 | 103 | 135 |
| 125 | 134 | 10 | LPLDKGIKPY | 177 | B*3501 | 87 | 1.08 | 94 | 3 | 103 | 135 |
| 125 | 134 | 10 | LPLDKGIKPY | 177 | B*3503 | 36 | 1.08 | 39 | 3 | 103 | 135 |
| 125 | 134 | 10 | LPLDKGIKPY | 177 | B*5301 | 39 | 1.08 | 43 | 3 | 103 | 135 |
| 125 | 134 | 10 | LPLDKGIKPY | 177 | B*5501 | 13 | 1.08 | 14 | 3 | 103 | 135 |
| 126 | 134 | 9 | PLDKGIKPY | 178 | A*0101 | 25 | 1.08 | 27 | 3 | 103 | 135 |
| 127 | 134 | 8 | LDKGIKPY | 179 | B*3501 | 9 | 1.08 | 10 | 3 | 103 | 135 |
| 125 | 135 | 11 | LPLDKGIKPYY | 180 | B*3501 | 77 | 1.16 | 90 | 3 | 103 | 135 |
| 125 | 135 | 11 | LPLDKGIKPYY | 180 | B*5301 | 57 | 1.16 | 67 | 3 | 103 | 135 |
| 126 | 135 | 10 | PLDKGIKPYY | 181 | A*0101 | 55 | 1.16 | 64 | 3 | 103 | 135 |
| 126 | 135 | 10 | PLDKGIKPYY | 181 | A*2902 | 3 | 1.16 | 4 | 3 | 103 | 135 |
| | | | | | Cumulative Class I-BCI score: | | | 6469 | | | |
| 118 | 127 | 10 | YPTHTKYLPL | 171 | B*0702 | 65 | 0.94 | 61 | 4 | 118 | 150 |
| 118 | 127 | 10 | YPTHTKYLPL | 171 | B*1402 | 100 | 0.94 | 94 | 4 | 118 | 150 |
| 118 | 127 | 10 | YPTHTKYLPL | 171 | B*3501 | 75 | 0.94 | 70 | 4 | 118 | 150 |
| 118 | 127 | 10 | YPTHTKYLPL | 171 | B*3503 | 100 | 0.94 | 94 | 4 | 118 | 150 |
| 118 | 127 | 10 | YPTHTKYLPL | 171 | B*3901 | 96 | 0.94 | 90 | 4 | 118 | 150 |
| 118 | 127 | 10 | YPTHTKYLPL | 171 | B*5101 | 83 | 0.94 | 78 | 4 | 118 | 150 |
| 118 | 127 | 10 | YPTHTKYLPL | 171 | B*5301 | 82 | 0.94 | 77 | 4 | 118 | 150 |
| 118 | 127 | 10 | YPTHTKYLPL | 171 | B*5501 | 87 | 0.94 | 82 | 4 | 118 | 150 |
| 118 | 127 | 10 | YPTHTKYLPL | 171 | B*5601 | 67 | 0.94 | 63 | 4 | 118 | 150 |
| 120 | 127 | 8 | THTKYLPL | 172 | B*1402 | 95 | 0.94 | 89 | 4 | 118 | 150 |
| 120 | 127 | 8 | THTKYLPL | 172 | B*3801 | 80 | 0.94 | 75 | 4 | 118 | 150 |
| 119 | 128 | 10 | PTHTKYLPLD | 173 | A*3001 | 46 | 0.71 | 33 | 4 | 118 | 150 |
| 121 | 129 | 9 | HTKYLPLDK | 174 | A*0301 | 18 | 0.41 | 7 | 4 | 118 | 150 |
| 121 | 129 | 9 | HTKYLPLDK | 174 | A*3001 | 90 | 0.41 | 37 | 4 | 118 | 150 |

TABLE 4a-continued

Predicted HLA class I-restricted CD8+ cytotoxic T cell epitopes contained in SLP sequences from HBV polymerase protein.

HLA class I binding peptides in SLP sequences derived from HBV Polymerase protein

| Start | End | Length | Sequence [A] | SEQ ID NO: | HLA class I molecule | Class I-B score [B] | C-score [C] | Class I-BCI score [D] | SLP# | Peptide of invention (SLP) SLP Start | SLP End |
|---|---|---|---|---|---|---|---|---|---|---|---|
| 123 | 131 | 9 | KYLPLDKGI | 175 | A*2301 | 34 | 1.23 | 43 | 4 | 118 | 150 |
| 123 | 131 | 9 | KYLPLDKGI | 175 | A*2402 | 21 | 1.23 | 26 | 4 | 118 | 150 |
| 125 | 132 | 8 | LPLDKGIK | 176 | B*3501 | 56 | 0.80 | 45 | 4 | 118 | 150 |
| 125 | 134 | 10 | LPLDKGIKPY | 177 | B*3501 | 87 | 1.08 | 94 | 4 | 118 | 150 |
| 125 | 134 | 10 | LPLDKGIKPY | 177 | B*3503 | 36 | 1.08 | 39 | 4 | 118 | 150 |
| 125 | 134 | 10 | LPLDKGIKPY | 177 | B*5301 | 39 | 1.08 | 43 | 4 | 118 | 150 |
| 125 | 134 | 10 | LPLDKGIKPY | 177 | B*5501 | 13 | 1.08 | 14 | 4 | 118 | 150 |
| 126 | 134 | 9 | PLDKGIKPY | 178 | A*0101 | 25 | 1.08 | 27 | 4 | 118 | 150 |
| 127 | 134 | 8 | LDKGIKPY | 179 | B*3501 | 9 | 1.08 | 10 | 4 | 118 | 150 |
| 125 | 135 | 11 | LPLDKGIKPYY | 180 | B*3501 | 77 | 1.16 | 90 | 4 | 118 | 150 |
| 125 | 135 | 11 | LPLDKGIKPYY | 180 | B*5301 | 57 | 1.16 | 67 | 4 | 118 | 150 |
| 126 | 135 | 10 | PLDKGIKPYY | 181 | A*0101 | 55 | 1.16 | 64 | 4 | 118 | 150 |
| 126 | 135 | 10 | PLDKGIKPYY | 181 | A*2902 | 3 | 1.16 | 4 | 4 | 118 | 150 |
| 132 | 139 | 8 | KPYYPDQV | 182 | B*5101 | 65 | 1.05 | 68 | 4 | 118 | 150 |
| 132 | 139 | 8 | KPYYPDQV | 182 | B*5501 | 64 | 1.05 | 67 | 4 | 118 | 150 |
| 132 | 139 | 8 | KPYYPDQV | 182 | B*5601 | 59 | 1.05 | 62 | 4 | 118 | 150 |
| 132 | 140 | 9 | KPYYPDQVV | 183 | B*0702 | 36 | 1.80 | 65 | 4 | 118 | 150 |
| 132 | 140 | 9 | KPYYPDQVV | 183 | B*5101 | 70 | 1.80 | 126 | 4 | 118 | 150 |
| 132 | 140 | 9 | KPYYPDQVV | 183 | B*5501 | 86 | 1.80 | 155 | 4 | 118 | 150 |
| 132 | 140 | 9 | KPYYPDQVV | 183 | B*5601 | 65 | 1.80 | 118 | 4 | 118 | 150 |
| 135 | 142 | 8 | YPDQVVNH | 184 | B*3501 | 89 | 1.63 | 146 | 4 | 118 | 150 |
| 134 | 143 | 10 | YYPDQVVNHY | 185 | A*0101 | 23 | 1.33 | 30 | 4 | 118 | 150 |
| 134 | 143 | 10 | YYPDQVVNHY | 185 | A*2402 | 25 | 1.33 | 33 | 4 | 118 | 150 |
| 134 | 143 | 10 | YYPDQVVNHY | 185 | A*2902 | 65 | 1.33 | 87 | 4 | 118 | 150 |
| 134 | 143 | 10 | YYPDQVVNHY | 185 | A*3002 | 25 | 1.33 | 34 | 4 | 118 | 150 |
| 135 | 143 | 9 | YPDQVVNHY | 186 | A*0101 | 62 | 1.33 | 83 | 4 | 118 | 150 |
| 135 | 143 | 9 | YPDQVVNHY | 186 | B*3501 | 83 | 1.33 | 110 | 4 | 118 | 150 |
| 135 | 143 | 9 | YPDQVVNHY | 186 | B*3503 | 55 | 1.33 | 74 | 4 | 118 | 150 |
| 135 | 143 | 9 | YPDQVVNHY | 186 | B*5301 | 44 | 1.33 | 59 | 4 | 118 | 150 |
| 136 | 143 | 8 | PDQVVNHY | 187 | B*3501 | 4 | 1.33 | 5 | 4 | 118 | 150 |
| 134 | 144 | 11 | YYPDQVVNHYF | 188 | A*2301 | 100 | 1.77 | 177 | 4 | 118 | 150 |
| 135 | 144 | 10 | YPDQVVNHYF | 189 | B*3501 | 100 | 1.77 | 177 | 4 | 118 | 150 |
| 135 | 144 | 10 | YPDQVVNHYF | 189 | B*3503 | 95 | 1.77 | 168 | 4 | 118 | 150 |
| 135 | 144 | 10 | YPDQVVNHYF | 189 | B*5301 | 100 | 1.77 | 177 | 4 | 118 | 150 |
| 137 | 144 | 8 | DQVVNHYF | 190 | B*1801 | 52 | 1.77 | 93 | 4 | 118 | 150 |

TABLE 4a-continued

Predicted HLA class I-restricted CD8+ cytotoxic T cell epitopes contained in SLP sequences from HBV polymerase protein.

HLA class I binding peptides in SLP sequences derived from HBV Polymerase protein

| Start | End | Length | Sequence[A] | SEQ ID NO: | HLA class I molecule | Class I-B score[B] | C-score[C] | Class I-BCI score[D] | SLP# | Peptide of invention (SLP) SLP Start | SLP End |
|---|---|---|---|---|---|---|---|---|---|---|---|
| 137 | 147 | 11 | DQVVNHYFQTR | 191 | A*3303 | 21 | 1.63 | 34 | 4 | 118 | 150 |
| 138 | 147 | 10 | QVVNHYFQTR | 192 | A*3101 | 1 | 1.63 | 2 | 4 | 118 | 150 |
| 138 | 147 | 10 | QVVNHYFQTR | 192 | A*3303 | 86 | 1.63 | 140 | 4 | 118 | 150 |
| 138 | 147 | 10 | QVVNHYFQTR | 192 | A*6801 | 68 | 1.63 | 110 | 4 | 118 | 150 |
| 138 | 147 | 10 | QVVNHYFQTR | 192 | A*7401 | 17 | 1.63 | 28 | 4 | 118 | 150 |
| 139 | 147 | 9 | VVNHYFQTR | 193 | A*3101 | 87 | 1.63 | 143 | 4 | 118 | 150 |
| 139 | 147 | 9 | VVNHYFQTR | 193 | A*3303 | 73 | 1.63 | 120 | 4 | 118 | 150 |
| 139 | 147 | 9 | VVNHYFQTR | 193 | A*7401 | 72 | 1.63 | 117 | 4 | 118 | 150 |
| 139 | 149 | 11 | VVNHYFQTRHY | 194 | A*0101 | 42 | 1.90 | 79 | 4 | 118 | 150 |
| 139 | 149 | 11 | VVNHYFQTRHY | 194 | A*2902 | 70 | 1.90 | 133 | 4 | 118 | 150 |
| 139 | 149 | 11 | VVNHYFQTRHY | 194 | A*3002 | 90 | 1.90 | 172 | 4 | 118 | 150 |
| 139 | 149 | 11 | VVNHYFQTRHY | 194 | B*1501 | 50 | 1.90 | 95 | 4 | 118 | 150 |
| 139 | 149 | 11 | VVNHYFQTRHY | 194 | B*1502 | 44 | 1.90 | 85 | 4 | 118 | 150 |
| 141 | 149 | 9 | NHYFQTRHY | 195 | B*3801 | 16 | 1.90 | 31 | 4 | 118 | 150 |
| 142 | 149 | 8 | HYFQTRHY | 196 | A*2902 | 25 | 1.90 | 48 | 4 | 118 | 150 |
| 142 | 149 | 8 | HYFQTRHY | 196 | A*3002 | 44 | 1.90 | 83 | 4 | 118 | 150 |
| 141 | 150 | 10 | NHYFQTRHYL | 197 | B*1402 | 94 | 1.93 | 181 | 4 | 118 | 150 |
| 141 | 150 | 10 | NHYFQTRHYL | 197 | B*3801 | 53 | 1.93 | 102 | 4 | 118 | 150 |
| 141 | 150 | 10 | NHYFQTRHYL | 197 | B*3901 | 88 | 1.93 | 170 | 4 | 118 | 150 |
| 142 | 150 | 9 | HYFQTRHYL | 198 | A*2301 | 69 | 1.93 | 133 | 4 | 118 | 150 |
| 142 | 150 | 9 | HYFQTRHYL | 198 | B*1402 | 34 | 1.93 | 66 | 4 | 118 | 150 |
| 142 | 150 | 9 | HYFQTRHYL | 198 | B*3901 | 3 | 1.93 | 5 | 4 | 118 | 150 |
| 143 | 150 | 8 | YFQTRHYL | 199 | A*2301 | 74 | 1.93 | 143 | 4 | 118 | 150 |
| 143 | 150 | 8 | YFQTRHYL | 199 | A*2402 | 74 | 1.93 | 142 | 4 | 118 | 150 |
| 143 | 150 | 8 | YFQTRHYL | 199 | B*0801 | 93 | 1.93 | 180 | 4 | 118 | 150 |
| | | | | | Cumulative Class I-BCI score: | | | 6169 | | | |
| 139 | 149 | 11 | VVNHYFQTRHY | 194 | A*0101 | 42 | 1.90 | 79 | 5 | 139 | 177 |
| 139 | 149 | 11 | VVNHYFQTRHY | 194 | A*2902 | 70 | 1.90 | 133 | 5 | 139 | 177 |
| 139 | 149 | 11 | VVNHYFQTRHY | 194 | A*3002 | 90 | 1.90 | 172 | 5 | 139 | 177 |
| 139 | 149 | 11 | VVNHYFQTRHY | 194 | B*1501 | 50 | 1.90 | 95 | 5 | 139 | 177 |
| 139 | 149 | 11 | VVNHYFQTRHY | 194 | B*1502 | 44 | 1.90 | 85 | 5 | 139 | 177 |
| 141 | 149 | 9 | NHYFQTRHY | 195 | B*3801 | 16 | 1.90 | 31 | 5 | 139 | 177 |
| 142 | 149 | 8 | HYFQTRHY | 196 | A*2902 | 25 | 1.90 | 48 | 5 | 139 | 177 |
| 142 | 149 | 8 | HYFQTRHY | 196 | A*3002 | 44 | 1.90 | 83 | 5 | 139 | 177 |
| 141 | 150 | 10 | NHYFQTRHYL | 197 | B*1402 | 94 | 1.93 | 181 | 5 | 139 | 177 |

TABLE 4a-continued

Predicted HLA class I-restricted CD8+ cytotoxic T cell epitopes contained in SLP sequences from HBV polymerase protein.

HLA class I binding peptides in SLP sequences derived from HBV Polymerase protein

| Start | End | Length | Sequence[A] | SEQ ID NO: | HLA class I molecule | Class I-B score[B] | C-score[C] | Class I-BCI score[D] | Peptide of invention (SLP) | | |
|---|---|---|---|---|---|---|---|---|---|---|---|
| | | | | | | | | | SLP# | SLP Start | SLP End |
| 141 | 150 | 10 | NHYFQTRHYL | 197 | B*3801 | 53 | 1.93 | 102 | 5 | 139 | 177 |
| 141 | 150 | 10 | NHYFQTRHYL | 197 | B*3901 | 88 | 1.93 | 170 | 5 | 139 | 177 |
| 142 | 150 | 9 | HYFQTRHYL | 198 | A*2301 | 69 | 1.93 | 133 | 5 | 139 | 177 |
| 142 | 150 | 9 | HYFQTRHYL | 198 | B*1402 | 34 | 1.93 | 66 | 5 | 139 | 177 |
| 142 | 150 | 9 | HYFQTRHYL | 198 | B*3901 | 3 | 1.93 | 5 | 5 | 139 | 177 |
| 143 | 150 | 8 | YFQTRHYL | 199 | A*2301 | 74 | 1.93 | 143 | 5 | 139 | 177 |
| 143 | 150 | 8 | YFQTRHYL | 199 | A*2402 | 74 | 1.93 | 142 | 5 | 139 | 177 |
| 143 | 150 | 8 | YFQTRHYL | 199 | B*0801 | 93 | 1.93 | 180 | 5 | 139 | 177 |
| 142 | 151 | 10 | HYFQTRHYLH | 200 | A*2301 | 33 | 0.39 | 13 | 5 | 139 | 177 |
| 142 | 151 | 10 | HYFQTRHYLH | 200 | A*2402 | 49 | 0.39 | 19 | 5 | 139 | 177 |
| 142 | 151 | 10 | HYFQTRHYLH | 200 | A*2902 | 16 | 0.39 | 6 | 5 | 139 | 177 |
| 143 | 151 | 9 | YFQTRHYLH | 201 | A*2902 | 57 | 0.39 | 22 | 5 | 139 | 177 |
| 143 | 153 | 11 | YFQTRHYLHTL | 202 | A*2301 | 98 | 1.22 | 120 | 5 | 139 | 177 |
| 143 | 153 | 11 | YFQTRHYLHTL | 202 | A*2402 | 100 | 1.22 | 122 | 5 | 139 | 177 |
| 143 | 153 | 11 | YFQTRHYLHTL | 202 | B*0801 | 100 | 1.22 | 122 | 5 | 139 | 177 |
| 144 | 153 | 10 | FQTRhYLHTL | 203 | A*0201 | 27 | 1.22 | 33 | 5 | 139 | 177 |
| 144 | 153 | 10 | FQTRHYLHTL | 203 | B*1301 | 63 | 1.22 | 77 | 5 | 139 | 177 |
| 144 | 153 | 10 | FQTRHYLHTL | 203 | B*1402 | 52 | 1.22 | 63 | 5 | 139 | 177 |
| 144 | 153 | 10 | FQTRHYLHTL | 203 | B*3701 | 62 | 1.22 | 75 | 5 | 139 | 177 |
| 144 | 153 | 10 | FQTRHYLHTL | 203 | B*3801 | 71 | 1.22 | 87 | 5 | 139 | 177 |
| 144 | 153 | 10 | FQTRHYLHTL | 203 | B*3901 | 94 | 1.22 | 114 | 5 | 139 | 177 |
| 144 | 153 | 10 | FQTRHYLHTL | 203 | B*4801 | 81 | 1.22 | 98 | 5 | 139 | 177 |
| 145 | 153 | 9 | QTRHYLHTL | 204 | A*2501 | 65 | 1.22 | 79 | 5 | 139 | 177 |
| 146 | 153 | 8 | TRHYLHTL | 205 | B*1402 | 72 | 1.22 | 87 | 5 | 139 | 177 |
| 146 | 153 | 8 | TRHYLHTL | 205 | B*2702 | 60 | 1.22 | 73 | 5 | 139 | 177 |
| 146 | 153 | 8 | TRHYLHTL | 205 | B*2705 | 70 | 1.22 | 85 | 5 | 139 | 177 |
| 144 | 154 | 11 | FQTRHYLHTLW | 206 | B*1301 | 68 | 1.50 | 101 | 5 | 139 | 177 |
| 144 | 154 | 11 | FQTRHYLHTLW | 206 | B*2702 | 37 | 1.50 | 56 | 5 | 139 | 177 |
| 145 | 154 | 10 | QTRHYLHTLW | 207 | B*4402 | 35 | 1.50 | 52 | 5 | 139 | 177 |
| 145 | 154 | 10 | QTRHYLHTLW | 207 | B*5802 | 70 | 1.50 | 104 | 5 | 139 | 177 |
| 146 | 154 | 9 | TRHYLHTLW | 208 | B*2702 | 76 | 1.50 | 114 | 5 | 139 | 177 |
| 147 | 154 | 8 | RHYLHTLW | 209 | A*2301 | 47 | 1.50 | 70 | 5 | 139 | 177 |
| 147 | 154 | 8 | RHYLHTLW | 209 | A*2402 | 35 | 1.50 | 52 | 5 | 139 | 177 |
| 147 | 154 | 8 | RHYLHTLW | 209 | B*2702 | 99 | 1.50 | 148 | 5 | 139 | 177 |

TABLE 4a-continued

Predicted HLA class I-restricted CD8+ cytotoxic T cell epitopes contained in SLP sequences from HBV polymerase protein.

HLA class I binding peptides in SLP sequences derived from HBV Polymerase protein

| Start | End | Length | Sequence[A] | SEQ ID NO: | HLA class I molecule | Class I-B score[B] | C-score[C] | Class I-BCI score[D] | SLP# | Peptide of invention (SLP) SLP Start | SLP End |
|---|---|---|---|---|---|---|---|---|---|---|---|
| 147 | 154 | 8 | RHYLHTLW | 209 | B*3801 | 98 | 1.50 | 147 | 5 | 139 | 177 |
| 147 | 154 | 8 | RHYLHTLW | 209 | B*5701 | 35 | 1.50 | 52 | 5 | 139 | 177 |
| 147 | 154 | 8 | RHYLHTLW | 209 | B*5801 | 22 | 1.50 | 33 | 5 | 139 | 177 |
| 147 | 154 | 8 | RHYLHTLW | 209 | B*5802 | 26 | 1.50 | 39 | 5 | 139 | 177 |
| 145 | 155 | 11 | QTRHYLHTLWK | 210 | A*0301 | 54 | 0.72 | 39 | 5 | 139 | 177 |
| 145 | 155 | 11 | QTRHYLHTLWK | 210 | A*1101 | 35 | 0.72 | 25 | 5 | 139 | 177 |
| 145 | 155 | 11 | QTRHYLHTLWK | 210 | A*3001 | 96 | 0.72 | 69 | 5 | 139 | 177 |
| 146 | 155 | 10 | TRHYLHTLWK | 211 | B*2705 | 36 | 0.72 | 26 | 5 | 139 | 177 |
| 147 | 155 | 9 | RHYLHTLWK | 212 | A*0301 | 70 | 0.72 | 51 | 5 | 139 | 177 |
| 147 | 155 | 9 | RHYLHTLWK | 212 | B*2702 | 7 | 0.72 | 5 | 5 | 139 | 177 |
| 148 | 155 | 8 | HYLHTLWK | 213 | A*3101 | 29 | 0.72 | 21 | 5 | 139 | 177 |
| 146 | 156 | 11 | TRHYLHTLWKA | 214 | B*2705 | 58 | 1.23 | 72 | 5 | 139 | 177 |
| 148 | 156 | 9 | HYLHTLWKA | 215 | A*2301 | 31 | 1.23 | 38 | 5 | 139 | 177 |
| 147 | 157 | 11 | RHYLHTLWKAG | 216 | B*2705 | 6 | 0.73 | 4 | 5 | 139 | 177 |
| 148 | 157 | 10 | HYLHTLWKAG | 217 | A*3201 | 74 | 0.73 | 54 | 5 | 139 | 177 |
| 148 | 158 | 11 | HYLHTLWKAGI | 218 | A*2301 | 93 | 0.63 | 59 | 5 | 139 | 177 |
| 148 | 158 | 11 | HYLHTLWKAGI | 218 | A*2402 | 95 | 0.63 | 60 | 5 | 139 | 177 |
| 149 | 158 | 10 | YLHTLWKAGI | 219 | A*0201 | 7 | 0.63 | 4 | 5 | 139 | 177 |
| 151 | 158 | 8 | HTLWKAGI | 220 | A*3201 | 62 | 0.63 | 39 | 5 | 139 | 177 |
| 149 | 159 | 11 | YLHTLWKAGIL | 221 | B*0801 | 88 | 0.85 | 75 | 5 | 139 | 177 |
| 149 | 159 | 11 | YLHTLWKAGIL | 221 | B*3901 | 22 | 0.85 | 19 | 5 | 139 | 177 |
| 150 | 159 | 10 | LHTLWKAGIL | 222 | B*0801 | 69 | 0.85 | 59 | 5 | 139 | 177 |
| 150 | 159 | 10 | LHTLWKAGIL | 222 | B*3801 | 51 | 0.85 | 43 | 5 | 139 | 177 |
| 150 | 159 | 10 | LHTLWKAGIL | 222 | B*3901 | 34 | 0.85 | 29 | 5 | 139 | 177 |
| 151 | 159 | 9 | HTLWKAGIL | 223 | B*5802 | 1 | 0.85 | 1 | 5 | 139 | 177 |
| 151 | 160 | 10 | HTLWKAGILY | 224 | A*0101 | 72 | 1.87 | 134 | 5 | 139 | 177 |
| 151 | 160 | 10 | HTLWKAGILY | 224 | A*0301 | 7 | 1.87 | 12 | 5 | 139 | 177 |
| 151 | 160 | 10 | HTLWKAGILY | 224 | A*2501 | 47 | 1.87 | 88 | 5 | 139 | 177 |
| 151 | 160 | 10 | HTLWKAGILY | 224 | A*2601 | 67 | 1.87 | 125 | 5 | 139 | 177 |
| 151 | 160 | 10 | HTLWKAGILY | 224 | A*2902 | 2 | 1.87 | 3 | 5 | 139 | 177 |
| 151 | 160 | 10 | HTLWKAGILY | 224 | A*3002 | 49 | 1.87 | 92 | 5 | 139 | 177 |
| 152 | 160 | 9 | TLWKAGILY | 225 | A*0301 | 36 | 1.87 | 67 | 5 | 139 | 177 |
| 152 | 160 | 9 | TLWKAGILY | 225 | A*2902 | 78 | 1.87 | 145 | 5 | 139 | 177 |
| 152 | 160 | 9 | TLWKAGILY | 225 | A*3002 | 4 | 1.87 | 8 | 5 | 139 | 177 |
| 153 | 160 | 8 | LWKAGILY | 226 | A*2902 | 56 | 1.87 | 104 | 5 | 139 | 177 |

TABLE 4a-continued

Predicted HLA class I-restricted CD8+ cytotoxic T cell epitopes contained in SLP sequences from HBV polymerase protein.

HLA class I binding peptides in SLP sequences derived from HBV Polymerase protein

| Start | End | Length | Sequence[A] | SEQ ID NO: | HLA class I molecule | Class I-B score[B] | C-score[C] | Class I-BCI score[D] | Peptide of invention (SLP) | | |
|---|---|---|---|---|---|---|---|---|---|---|---|
| | | | | | | | | | SLP# | SLP Start | SLP End |
| 153 | 160 | 8 | LWKAGILY | 226 | A*3002 | 85 | 1.87 | 158 | 5 | 139 | 177 |
| 153 | 160 | 8 | LWKAGILY | 226 | B*3501 | 8 | 1.87 | 15 | 5 | 139 | 177 |
| 151 | 161 | 11 | HTLWKAGILYK | 227 | A*0301 | 89 | 1.41 | 125 | 5 | 139 | 177 |
| 151 | 161 | 11 | HTLWKAGILYK | 227 | A*1101 | 100 | 1.41 | 141 | 5 | 139 | 177 |
| 151 | 161 | 11 | HTLWKAGILYK | 227 | A*3001 | 78 | 1.41 | 110 | 5 | 139 | 177 |
| 151 | 161 | 11 | HTLWKAGILYK | 227 | A*3101 | 46 | 1.41 | 64 | 5 | 139 | 177 |
| 151 | 161 | 11 | HTLWKAGILYK | 227 | A*3303 | 25 | 1.41 | 36 | 5 | 139 | 177 |
| 151 | 161 | 11 | HTLWKAGILYK | 227 | A*6801 | 75 | 1.41 | 106 | 5 | 139 | 177 |
| 151 | 161 | 11 | HTLWKAGILYK | 227 | A*7401 | 83 | 1.41 | 117 | 5 | 139 | 177 |
| 152 | 161 | 10 | TLWKAGILYK | 228 | A*0301 | 87 | 1.41 | 122 | 5 | 139 | 177 |
| 152 | 161 | 10 | TLWKAGILYK | 228 | A*1101 | 59 | 1.41 | 83 | 5 | 139 | 177 |
| 152 | 161 | 10 | TLWKAGILYK | 228 | A*7401 | 71 | 1.41 | 100 | 5 | 139 | 177 |
| 153 | 161 | 9 | LWKAGILYK | 229 | A*3001 | 57 | 1.41 | 80 | 5 | 139 | 177 |
| 152 | 162 | 11 | TLWKAGILYKR | 230 | A*3101 | 61 | 1.49 | 91 | 5 | 139 | 177 |
| 152 | 162 | 11 | TLWKAGILYKR | 230 | A*3303 | 72 | 1.49 | 107 | 5 | 139 | 177 |
| 152 | 162 | 11 | TLWKAGILYKR | 230 | A*7401 | 82 | 1.49 | 122 | 5 | 139 | 177 |
| 153 | 162 | 10 | LWKAGILYKR | 231 | A*3101 | 86 | 1.49 | 128 | 5 | 139 | 177 |
| 153 | 162 | 10 | LWKAGILYKR | 231 | A*3303 | 59 | 1.49 | 88 | 5 | 139 | 177 |
| 155 | 162 | 8 | KAGILYKR | 232 | A*3101 | 67 | 1.49 | 100 | 5 | 139 | 177 |
| 155 | 162 | 8 | KAGILYKR | 232 | A*7401 | 27 | 1.49 | 40 | 5 | 139 | 177 |
| 158 | 166 | 9 | ILYKRETTR | 233 | A*0301 | 66 | 1.75 | 115 | 5 | 139 | 177 |
| 158 | 166 | 9 | ILYKRETTR | 233 | A*3101 | 23 | 1.75 | 40 | 5 | 139 | 177 |
| 158 | 166 | 9 | ILYKRETTR | 233 | A*3303 | 51 | 1.75 | 89 | 5 | 139 | 177 |
| 158 | 166 | 9 | ILYKRETTR | 233 | A*7401 | 90 | 1.75 | 158 | 5 | 139 | 177 |
| 158 | 168 | 11 | ILYKRETTRSA | 234 | B*0801 | 56 | 1.80 | 100 | 5 | 139 | 177 |
| 160 | 170 | 11 | YKRETTRSASF | 235 | B*0702 | 17 | 1.82 | 32 | 5 | 139 | 177 |
| 160 | 170 | 11 | YKRETTRSASF | 235 | B*0801 | 81 | 1.82 | 148 | 5 | 139 | 177 |
| 160 | 170 | 11 | YKRETTRSASF | 235 | B*1402 | 68 | 1.82 | 123 | 5 | 139 | 177 |
| 160 | 170 | 11 | YKRETTRSASF | 235 | B*1501 | 53 | 1.82 | 97 | 5 | 139 | 177 |
| 160 | 170 | 11 | YKRETTRSASF | 235 | B*1502 | 65 | 1.82 | 118 | 5 | 139 | 177 |
| 160 | 170 | 11 | YKRETTRSASF | 235 | B*1525 | 46 | 1.82 | 83 | 5 | 139 | 177 |
| 161 | 170 | 10 | KRETTRSASF | 236 | B*2702 | 53 | 1.82 | 97 | 5 | 139 | 177 |
| 162 | 170 | 9 | RETTRSASF | 237 | B*4001 | 57 | 1.82 | 103 | 5 | 139 | 177 |
| 162 | 170 | 9 | RETTRSASF | 237 | B*4402 | 88 | 1.82 | 161 | 5 | 139 | 177 |

TABLE 4a-continued

Predicted HLA class I-restricted CD8+ cytotoxic T cell epitopes contained in SLP sequences from HBV polymerase protein.

HLA class I binding peptides in SLP sequences derived from HBV Polymerase protein

| Start | End | Length | Sequence [A] | SEQ ID NO: | HLA class I molecule | Class I-B score [B] | C-score [C] | Class I-BCI score [D] | SLP# | Peptide of invention (SLP) SLP Start | SLP End |
|---|---|---|---|---|---|---|---|---|---|---|---|
| 162 | 170 | 9 | RETTRSASF | 237 | B*4403 | 60 | 1.82 | 109 | 5 | 139 | 177 |
| 162 | 170 | 9 | RETTRSASF | 237 | B*5001 | 44 | 1.82 | 80 | 5 | 139 | 177 |
| 163 | 170 | 8 | ETTRSASF | 238 | A*2501 | 100 | 1.82 | 182 | 5 | 139 | 177 |
| 163 | 170 | 8 | ETTRSASF | 238 | A*2601 | 100 | 1.82 | 182 | 5 | 139 | 177 |
| 166 | 175 | 10 | RSASFCGSPY | 239 | A*0101 | 79 | 1.16 | 92 | 5 | 139 | 177 |
| 166 | 175 | 10 | RSASFCGSPY | 239 | A*2501 | 45 | 1.16 | 52 | 5 | 139 | 177 |
| 166 | 175 | 10 | RSASFCGSPY | 239 | B*1501 | 94 | 1.16 | 108 | 5 | 139 | 177 |
| 166 | 175 | 10 | RSASFCGSPY | 239 | B*1502 | 78 | 1.16 | 90 | 5 | 139 | 177 |
| 166 | 175 | 10 | RSASFCGSPY | 239 | B*1525 | 80 | 1.16 | 92 | 5 | 139 | 177 |
| 166 | 175 | 10 | RSASFCGSPY | 239 | B*4403 | 32 | 1.16 | 37 | 5 | 139 | 177 |
| 166 | 175 | 10 | RSASFCGSPY | 239 | B*4601 | 84 | 1.16 | 97 | 5 | 139 | 177 |
| 166 | 175 | 10 | RSASFCGSPY | 239 | B*5802 | 68 | 1.16 | 79 | 5 | 139 | 177 |
| 167 | 175 | 9 | SASFCGSPY | 240 | A*3002 | 79 | 1.16 | 91 | 5 | 139 | 177 |
| 167 | 175 | 9 | SASFCGSPY | 240 | B*3501 | 81 | 1.16 | 94 | 5 | 139 | 177 |
| 168 | 175 | 8 | ASFCGSPY | 241 | A*1101 | 70 | 1.16 | 80 | 5 | 139 | 177 |
| 168 | 175 | 8 | ASFCGSPY | 241 | A*2902 | 54 | 1.16 | 62 | 5 | 139 | 177 |
| 168 | 175 | 8 | ASFCGSPY | 241 | B*5701 | 44 | 1.16 | 51 | 5 | 139 | 177 |
| 167 | 176 | 10 | SASFCGSPYS | 242 | A*3001 | 8 | 0.16 | 1 | 5 | 139 | 177 |
| 167 | 176 | 10 | SASFCGSPYS | 242 | B*5701 | 76 | 0.16 | 12 | 5 | 139 | 177 |
| 167 | 176 | 10 | SASFCGSPYS | 242 | B*5801 | 76 | 0.16 | 12 | 5 | 139 | 177 |
| 168 | 176 | 9 | ASFCGSPYS | 243 | B*5802 | 19 | 0.16 | 3 | 5 | 139 | 177 |
| 167 | 177 | 11 | SASFCGSPYSW | 244 | B*5301 | 79 | 1.90 | 150 | 5 | 139 | 177 |
| 167 | 177 | 11 | SASFCGSPYSW | 244 | B*5701 | 94 | 1.90 | 179 | 5 | 139 | 177 |
| 167 | 177 | 11 | SASFCGSPYSW | 244 | B*5801 | 100 | 1.90 | 190 | 5 | 139 | 177 |
| 167 | 177 | 11 | SASFCGSPYSW | 244 | B*5802 | 100 | 1.90 | 190 | 5 | 139 | 177 |
| 168 | 177 | 10 | ASFCGSPYSW | 245 | B*4402 | 69 | 1.90 | 132 | 5 | 139 | 177 |
| 168 | 177 | 10 | ASFCGSPYSW | 245 | B*4403 | 28 | 1.90 | 53 | 5 | 139 | 177 |
| 168 | 177 | 10 | ASFCGSPYSW | 245 | B*5802 | 99 | 1.90 | 188 | 5 | 139 | 177 |
| 169 | 177 | 9 | SFCGSPYSW | 246 | A*2301 | 26 | 1.90 | 49 | 5 | 139 | 177 |
| | | | | | Cumulative BCI Class I score: | | | 11815 | | | |
| 143 | 150 | 8 | YFQTRHYL | 199 | A*2301 | 74 | 1.93 | 143 | 6 | 143 | 177 |
| 143 | 150 | 8 | YFQTRHYL | 199 | A*2402 | 74 | 1.93 | 142 | 6 | 143 | 177 |
| 143 | 150 | 8 | YFQTRHYL | 199 | B*0801 | 93 | 1.93 | 180 | 6 | 143 | 177 |
| 142 | 151 | 10 | HYFQTRHYLH | 200 | A*2301 | 33 | 0.39 | 13 | 6 | 143 | 177 |
| 142 | 151 | 10 | HYFQTRHYLH | 200 | A*2402 | 49 | 0.39 | 19 | 6 | 143 | 177 |

TABLE 4a-continued

Predicted HLA class I-restricted CD8+ cytotoxic T cell epitopes contained in SLP sequences from HBV polymerase prot TABLE 4a-continued Predicted HLA class I-restricted CD8+ cytotoxic T cell epitopes contained in SLP sequences from HBV polymerase prot TABLE 4a-continued Predicted HLA class I-restricted CD8+ cytotoxic T cell epitopes contained in SLP sequences from HBV polymerase protein.

HLA class I binding peptides in SLP sequences derived from HBV Polymerase protein

| | | | | SEQ ID NO: | HLA class I molecule | Class I-B score[B] | C-score[C] | Class I-BCI score[D] | Peptide of invention (SLP) | | |
|---|---|---|---|---|---|---|---|---|---|---|---|
| Start | End | Length | Sequence[A] | | | | | | SLP# | SLP Start | SLP End |
| 152 | 161 | 10 | TLWKAGILYK | 228 | A*1101 | 59 | 1.41 | 83 | 6 | 143 | 177 |
| 152 | 161 | 10 | TLWKAGILYK | 228 | A*7401 | 71 | 1.41 | 100 | 6 | 143 | 177 |
| 153 | 161 | 9 | LWKAGILYK | 229 | A*3001 | 57 | 1.41 | 80 | 6 | 143 | 177 |
| 152 | 162 | 11 | TLWKAGILYKR | 230 | A*3101 | 61 | 1.49 | 91 | 6 | 143 | 177 |
| 152 | 162 | 11 | TLWKAGILYKR | 230 | A*3303 | 72 | 1.49 | 107 | 6 | 143 | 177 |
| 152 | 162 | 11 | TLWKAGILYKR | 230 | A*7401 | 82 | 1.49 | 122 | 6 | 143 | 177 |
| 153 | 162 | 10 | LWKAGILYKR | 231 | A*3101 | 86 | 1.49 | 128 | 6 | 143 | 177 |
| 153 | 162 | 10 | LWKAGILYKR | 231 | A*3303 | 59 | 1.49 | 88 | 6 | 143 | 177 |
| 155 | 162 | 8 | KAGILYKR | 232 | A*3101 | 67 | 1.49 | 100 | 6 | 143 | 177 |
| 155 | 162 | 8 | KAGILYKR | 232 | A*7401 | 27 | 1.49 | 40 | 6 | 143 | 177 |
| 158 | 166 | 9 | ILYKRETTR | 233 | A*0301 | 66 | 1.75 | 115 | 6 | 143 | 177 |
| 158 | 166 | 9 | ILYKRETTR | 233 | A*3101 | 23 | 1.75 | 40 | 6 | 143 | 177 |
| 158 | 166 | 9 | ILYKRETTR | 233 | A*3303 | 51 | 1.75 | 89 | 6 | 143 | 177 |
| 158 | 166 | 9 | ILYKRETTR | 233 | A*7401 | 90 | 1.75 | 158 | 6 | 143 | 177 |
| 158 | 168 | 11 | ILYKRETTRSA | 234 | B*0801 | 56 | 1.80 | 100 | 6 | 143 | 177 |
| 160 | 170 | 11 | YKRETTRSASF | 235 | B*0702 | 17 | 1.82 | 32 | 6 | 143 | 177 |
| 160 | 170 | 11 | YKRETTRSASF | 235 | B*0801 | 81 | 1.82 | 148 | 6 | 143 | 177 |
| 160 | 170 | 11 | YKRETTRSASF | 235 | B*1402 | 68 | 1.82 | 123 | 6 | 143 | 177 |
| 160 | 170 | 11 | YKRETTRSASF | 235 | B*1501 | 53 | 1.82 | 97 | 6 | 143 | 177 |
| 160 | 170 | 11 | YKRETTRSASF | 235 | B*1502 | 65 | 1.82 | 118 | 6 | 143 | 177 |
| 160 | 170 | 11 | YKRETTRSASF | 235 | B*1525 | 46 | 1.82 | 83 | 6 | 143 | 177 |
| 161 | 170 | 10 | KRETTRSASF | 236 | B*2702 | 53 | 1.82 | 97 | 6 | 143 | 177 |
| 162 | 170 | 9 | RETTRSASF | 237 | B*4001 | 57 | 1.82 | 103 | 6 | 143 | 177 |
| 162 | 170 | 9 | RETTRSASF | 237 | B*4402 | 88 | 1.82 | 161 | 6 | 143 | 177 |
| 162 | 170 | 9 | RETTRSASF | 237 | B*4403 | 60 | 1.82 | 109 | 6 | 143 | 177 |
| 162 | 170 | 9 | RETTRSASF | 237 | B*5001 | 44 | 1.82 | 80 | 6 | 143 | 177 |
| 163 | 170 | 8 | ETTRSASF | 238 | A*2501 | 100 | 1.82 | 182 | 6 | 143 | 177 |
| 163 | 170 | 8 | ETTRSASF | 238 | A*2601 | 100 | 1.82 | 182 | 6 | 143 | 177 |
| 166 | 175 | 10 | RSASFCGSPY | 239 | A*0101 | 79 | 1.16 | 92 | 6 | 143 | 177 |
| 166 | 175 | 10 | RSASFCGSPY | 239 | A*2501 | 45 | 1.16 | 52 | 6 | 143 | 177 |
| 166 | 175 | 10 | RSASFCGSPY | 239 | B*1501 | 94 | 1.16 | 108 | 6 | 143 | 177 |
| 166 | 175 | 10 | RSASFCGSPY | 239 | B*1502 | 78 | 1.16 | 90 | 6 | 143 | 177 |
| 166 | 175 | 10 | RSASFCGSPY | 239 | B*1525 | 80 | 1.16 | 92 | 6 | 143 | 177 |
| 166 | 175 | 10 | RSASFCGSPY | 239 | B*4403 | 32 | 1.16 | 37 | 6 | 143 | 177 |
| 166 | 175 | 10 | RSASFCGSPY | 239 | B*4601 | 84 | 1.16 | 97 | 6 | 143 | 177 |

TABLE 4a-continued

Predicted HLA class I-restricted CD8+ cytotoxic T cell epitopes contained in SLP sequences from HBV polymerase protein.

HLA class I binding peptides in SLP sequences derived from HBV Polymerase protein

| Start | End | Length | Sequence[A] | SEQ ID NO: | HLA class I molecule | Class I-B score[B] | C-score[C] | Class I-BCI score[D] | SLP# | Peptide of invention (SLP) SLP Start | SLP End |
|---|---|---|---|---|---|---|---|---|---|---|---|
| 166 | 175 | 10 | RSASFCGSPY | 239 | B*5802 | 68 | 1.16 | 79 | 6 | 143 | 177 |
| 167 | 175 | 9 | SASFCGSPY | 240 | A*3002 | 79 | 1.16 | 91 | 6 | 143 | 177 |
| 167 | 175 | 9 | SASFCGSPY | 240 | B*3501 | 81 | 1.16 | 94 | 6 | 143 | 177 |
| 168 | 175 | 8 | ASFCGSPY | 241 | A*1101 | 70 | 1.16 | 80 | 6 | 143 | 177 |
| 168 | 175 | 8 | ASFCGSPY | 241 | A*2902 | 54 | 1.16 | 62 | 6 | 143 | 177 |
| 168 | 175 | 8 | ASFCGSPY | 241 | B*5701 | 44 | 1.16 | 51 | 6 | 143 | 177 |
| 167 | 176 | 10 | SASFCGSPYS | 242 | A*3001 | 8 | 0.16 | 1 | 6 | 143 | 177 |
| 167 | 176 | 10 | SASFCGSPYS | 242 | B*5701 | 76 | 0.16 | 12 | 6 | 143 | 177 |
| 167 | 176 | 10 | SASFCGSPYS | 242 | B*5801 | 76 | 0.16 | 12 | 6 | 143 | 177 |
| 168 | 176 | 9 | ASFCGSPYS | 243 | B*5802 | 19 | 0.16 | 3 | 6 | 143 | 177 |
| 167 | 177 | 11 | SASFCGSPYSW | 244 | B*5301 | 79 | 1.90 | 150 | 6 | 143 | 177 |
| 167 | 177 | 11 | SASFCGSPYSW | 244 | B*5701 | 94 | 1.90 | 179 | 6 | 143 | 177 |
| 167 | 177 | 11 | SASFCGSPYSW | 244 | B*5801 | 100 | 1.90 | 190 | 6 | 143 | 177 |
| 167 | 177 | 11 | SASFCGSPYSW | 244 | B*5802 | 100 | 1.90 | 190 | 6 | 143 | 177 |
| 168 | 177 | 10 | ASFCGSPYSW | 245 | B*4402 | 69 | 1.90 | 132 | 6 | 143 | 177 |
| 168 | 177 | 10 | ASFCGSPYSW | 245 | B*4403 | 28 | 1.90 | 53 | 6 | 143 | 177 |
| 168 | 177 | 10 | ASFCGSPYSW | 245 | B*5802 | 99 | 1.90 | 188 | 6 | 143 | 177 |
| 169 | 177 | 9 | SFCGSPYSW | 246 | A*2301 | 26 | 1.90 | 49 | 6 | 143 | 177 |
| | | | | | Cumulative Class I-BCI score: | | | 10432 | | | |
| 137 | 147 | 11 | DQVVNHYFQTR | 191 | A*3303 | 21 | 1.63 | 34 | 7 | 137 | 170 |
| 138 | 147 | 10 | QVVNHYFQTR | 192 | A*3101 | 1 | 1.63 | 2 | 7 | 137 | 170 |
| 138 | 147 | 10 | QVVNHYFQTR | 192 | A*3303 | 86 | 1.63 | 140 | 7 | 137 | 170 |
| 138 | 147 | 10 | QVVNHYFQTR | 192 | A*6801 | 68 | 1.63 | 110 | 7 | 137 | 170 |
| 138 | 147 | 10 | QVVNHYFQTR | 192 | A*7401 | 17 | 1.63 | 28 | 7 | 137 | 170 |
| 139 | 147 | 9 | VVNHYFQTR | 193 | A*3101 | 87 | 1.63 | 143 | 7 | 137 | 170 |
| 139 | 147 | 9 | VVNHYFQTR | 193 | A*3303 | 73 | 1.63 | 120 | 7 | 137 | 170 |
| 139 | 147 | 9 | VVNHYFQTR | 193 | A*7401 | 72 | 1.63 | 117 | 7 | 137 | 170 |
| 139 | 149 | 11 | VVNHYFQTRHY | 194 | A*0101 | 42 | 1.90 | 79 | 7 | 137 | 170 |
| 139 | 149 | 11 | VVNHYFQTRHY | 194 | A*2902 | 70 | 1.90 | 133 | 7 | 137 | 170 |
| 139 | 149 | 11 | VVNHYFQTRHY | 194 | A*3002 | 90 | 1.90 | 172 | 7 | 137 | 170 |
| 139 | 149 | 11 | VVNHYFQTRHY | 194 | B*1501 | 50 | 1.90 | 95 | 7 | 137 | 170 |
| 139 | 149 | 11 | VVNHYFQTRHY | 194 | B*1502 | 44 | 1.90 | 85 | 7 | 137 | 170 |
| 141 | 149 | 9 | NHYFQTRHY | 195 | B*3801 | 16 | 1.90 | 31 | 7 | 137 | 170 |
| 142 | 149 | 8 | HYFQTRHY | 196 | A*2902 | 25 | 1.90 | 48 | 7 | 137 | 170 |
| 142 | 149 | 8 | HYFQTRHY | 196 | A*3002 | 44 | 1.90 | 83 | 7 | 137 | 170 |

TABLE 4a-continued

Predicted HLA class I-restricted CD8+ cytotoxic T cell epitopes contained in SLP sequences from HBV polymerase protein.

HLA class I binding peptides in SLP sequences derived from HBV Polymerase protein

| Start | End | Length | Sequence [A] | SEQ ID NO: | HLA class I molecule | Class I-B score[B] | C-score[C] | Class I-BCI score[D] | Peptide of invention (SLP) | | |
|---|---|---|---|---|---|---|---|---|---|---|---|
| | | | | | | | | | SLP# | SLP Start | SLP End |
| 141 | 150 | 10 | NHYFQTRHYL | 197 | B*1402 | 94 | 1.93 | 181 | 7 | 137 | 170 |
| 141 | 150 | 10 | NHYFQTRHYL | 197 | B*3801 | 53 | 1.93 | 102 | 7 | 137 | 170 |
| 141 | 150 | 10 | NHYFQTRHYL | 197 | B*3901 | 88 | 1.93 | 170 | 7 | 137 | 170 |
| 142 | 150 | 9 | HYFQTRHYL | 198 | A*2301 | 69 | 1.93 | 133 | 7 | 137 | 170 |
| 142 | 150 | 9 | HYFQTRHYL | 198 | B*1402 | 34 | 1.93 | 66 | 7 | 137 | 170 |
| 142 | 150 | 9 | HYFQTRHYL | 198 | B*3901 | 3 | 1.93 | 5 | 7 | 137 | 170 |
| 143 | 150 | 8 | YFQTRHYL | 199 | A*2301 | 74 | 1.93 | 143 | 7 | 137 | 170 |
| 143 | 150 | 8 | YFQTRHYL | 199 | A*2402 | 74 | 1.93 | 142 | 7 | 137 | 170 |
| 143 | 150 | 8 | YFQTRHYL | 199 | B*0801 | 93 | 1.93 | 180 | 7 | 137 | 170 |
| 142 | 151 | 10 | HYFQTRHYLH | 200 | A*2301 | 33 | 0.39 | 13 | 7 | 137 | 170 |
| 142 | 151 | 10 | HYFQTRHYLH | 200 | A*2402 | 49 | 0.39 | 19 | 7 | 137 | 170 |
| 142 | 151 | 10 | HYFQTRHYLH | 200 | A*2902 | 16 | 0.39 | 6 | 7 | 137 | 170 |
| 143 | 151 | 9 | YFQTRHYLH | 201 | A*2902 | 57 | 0.39 | 22 | 7 | 137 | 170 |
| 143 | 153 | 11 | YFQTRHYLHTL | 202 | A*2301 | 98 | 1.22 | 120 | 7 | 137 | 170 |
| 143 | 153 | 11 | YFQTRHYLHTL | 202 | A*2402 | 100 | 1.22 | 122 | 7 | 137 | 170 |
| 143 | 153 | 11 | YFQTRHYLHTL | 202 | B*0801 | 100 | 1.22 | 122 | 7 | 137 | 170 |
| 144 | 153 | 10 | FQTRhYLHTL | 203 | A*0201 | 27 | 1.22 | 33 | 7 | 137 | 170 |
| 144 | 153 | 10 | FQTRHYLHTL | 203 | B*1301 | 63 | 1.22 | 77 | 7 | 137 | 170 |
| 144 | 153 | 10 | FQTRHYLHTL | 203 | B*1402 | 52 | 1.22 | 63 | 7 | 137 | 170 |
| 144 | 153 | 10 | FQTRHYLHTL | 203 | B*3701 | 62 | 1.22 | 75 | 7 | 137 | 170 |
| 144 | 153 | 10 | FQTRHYLHTL | 203 | B*3801 | 71 | 1.22 | 87 | 7 | 137 | 170 |
| 144 | 153 | 10 | FQTRHYLHTL | 203 | B*3901 | 94 | 1.22 | 114 | 7 | 137 | 170 |
| 144 | 153 | 10 | FQTRHYLHTL | 203 | B*4801 | 81 | 1.22 | 98 | 7 | 137 | 170 |
| 145 | 153 | 9 | QTRHYLHTL | 204 | A*2501 | 65 | 1.22 | 79 | 7 | 137 | 170 |
| 146 | 153 | 8 | TRHYLHTL | 205 | B*1402 | 72 | 1.22 | 87 | 7 | 137 | 170 |
| 146 | 153 | 8 | TRHYLHTL | 205 | B*2702 | 60 | 1.22 | 73 | 7 | 137 | 170 |
| 146 | 153 | 8 | TRHYLHTL | 205 | B*2705 | 70 | 1.22 | 85 | 7 | 137 | 170 |
| 144 | 154 | 11 | FQTRHYLHTLW | 206 | B*1301 | 68 | 1.50 | 101 | 7 | 137 | 170 |
| 144 | 154 | 11 | FQTRHYLHTLW | 206 | B*2702 | 37 | 1.50 | 56 | 7 | 137 | 170 |
| 145 | 154 | 10 | QTRHYLHTLW | 207 | B*4402 | 35 | 1.50 | 52 | 7 | 137 | 170 |
| 145 | 154 | 10 | QTRHYLHTLW | 207 | B*5802 | 70 | 1.50 | 104 | 7 | 137 | 170 |
| 146 | 154 | 9 | TRHYLHTLW | 208 | B*2702 | 76 | 1.50 | 114 | 7 | 137 | 170 |
| 147 | 154 | 8 | RHYLHTLW | 209 | A*2301 | 47 | 1.50 | 70 | 7 | 137 | 170 |
| 147 | 154 | 8 | RHYLHTLW | 209 | A*2402 | 35 | 1.50 | 52 | 7 | 137 | 170 |

TABLE 4a-continued

Predicted HLA class I-restricted CD8+ cytotoxic T cell epitopes contained in SLP sequences from HBV polymerase protein.

HLA class I binding peptides in SLP sequences derived from HBV Polymerase protein

| Start | End | Length | Sequence [A] | SEQ ID NO: | HLA class I molecule | Class I-B score [B] | C-score [C] | Class I-BCI score [D] | SLP# | SLP Start | SLP End |
|---|---|---|---|---|---|---|---|---|---|---|---|
| 147 | 154 | 8 | RHYLHTLW | 209 | B*2702 | 99 | 1.50 | 148 | 7 | 137 | 170 |
| 147 | 154 | 8 | RHYLHTLW | 209 | B*3801 | 98 | 1.50 | 147 | 7 | 137 | 170 |
| 147 | 154 | 8 | RHYLHTLW | 209 | B*5701 | 35 | 1.50 | 52 | 7 | 137 | 170 |
| 147 | 154 | 8 | RHYLHTLW | 209 | B*5801 | 22 | 1.50 | 33 | 7 | 137 | 170 |
| 147 | 154 | 8 | RHYLHTLW | 209 | B*5802 | 26 | 1.50 | 39 | 7 | 137 | 170 |
| 145 | 155 | 11 | QTRHYLHTLWK | 210 | A*0301 | 54 | 0.72 | 39 | 7 | 137 | 170 |
| 145 | 155 | 11 | QTRHYLHTLWK | 210 | A*1101 | 35 | 0.72 | 25 | 7 | 137 | 170 |
| 145 | 155 | 11 | QTRHYLHTLWK | 210 | A*3001 | 96 | 0.72 | 69 | 7 | 137 | 170 |
| 146 | 155 | 10 | TRHYLHTLWK | 211 | B*2705 | 36 | 0.72 | 26 | 7 | 137 | 170 |
| 147 | 155 | 9 | RHYLHTLWK | 212 | A*0301 | 70 | 0.72 | 51 | 7 | 137 | 170 |
| 147 | 155 | 9 | RHYLHTLWK | 212 | B*2702 | 7 | 0.72 | 5 | 7 | 137 | 170 |
| 148 | 155 | 8 | HYLHTLWK | 213 | A*3101 | 29 | 0.72 | 21 | 7 | 137 | 170 |
| 146 | 156 | 11 | TRHYLHTLWKA | 214 | B*2705 | 58 | 1.23 | 72 | 7 | 137 | 170 |
| 148 | 156 | 9 | HYLHTLWKA | 215 | A*2301 | 31 | 1.23 | 38 | 7 | 137 | 170 |
| 147 | 157 | 11 | RHYLHTLWKAG | 216 | B*2705 | 6 | 0.73 | 4 | 7 | 137 | 170 |
| 148 | 157 | 10 | HYLHTLWKAG | 217 | A*3201 | 74 | 0.73 | 54 | 7 | 137 | 170 |
| 148 | 158 | 11 | HYLHTLWKAGI | 218 | A*2301 | 93 | 0.63 | 59 | 7 | 137 | 170 |
| 148 | 158 | 11 | HYLHTLWKAGI | 218 | A*2402 | 95 | 0.63 | 60 | 7 | 137 | 170 |
| 149 | 158 | 10 | YLHTLWKAGI | 219 | A*0201 | 7 | 0.63 | 4 | 7 | 137 | 170 |
| 151 | 158 | 8 | HTLWKAGI | 220 | A*3201 | 62 | 0.63 | 39 | 7 | 137 | 170 |
| 149 | 159 | 11 | YLHTLWKAGIL | 221 | B*0801 | 88 | 0.85 | 75 | 7 | 137 | 170 |
| 149 | 159 | 11 | YLHTLWKAGIL | 221 | B*3901 | 22 | 0.85 | 19 | 7 | 137 | 170 |
| 150 | 159 | 10 | LHTLWKAGIL | 222 | B*0801 | 69 | 0.85 | 59 | 7 | 137 | 170 |
| 150 | 159 | 10 | LHTLWKAGIL | 222 | B*3801 | 51 | 0.85 | 43 | 7 | 137 | 170 |
| 150 | 159 | 10 | LHTLWKAGIL | 222 | B*3901 | 34 | 0.85 | 29 | 7 | 137 | 170 |
| 151 | 159 | 9 | HTLWKAGIL | 223 | B*5802 | 1 | 0.85 | 1 | 7 | 137 | 170 |
| 151 | 160 | 10 | HTLWKAGILY | 224 | A*0101 | 72 | 1.87 | 134 | 7 | 137 | 170 |
| 151 | 160 | 10 | HTLWKAGILY | 224 | A*0301 | 7 | 1.87 | 12 | 7 | 137 | 170 |
| 151 | 160 | 10 | HTLWKAGILY | 224 | A*2501 | 47 | 1.87 | 88 | 7 | 137 | 170 |
| 151 | 160 | 10 | HTLWKAGILY | 224 | A*2601 | 67 | 1.87 | 125 | 7 | 137 | 170 |
| 151 | 160 | 10 | HTLWKAGILY | 224 | A*2902 | 2 | 1.87 | 3 | 7 | 137 | 170 |
| 151 | 160 | 10 | HTLWKAGILY | 224 | A*3002 | 49 | 1.87 | 92 | 7 | 137 | 170 |
| 152 | 160 | 9 | TLWKAGILY | 225 | A*0301 | 36 | 1.87 | 67 | 7 | 137 | 170 |
| 152 | 160 | 9 | TLWKAGILY | 225 | A*2902 | 78 | 1.87 | 145 | 7 | 137 | 170 |
| 152 | 160 | 9 | TLWKAGILY | 225 | A*3002 | 4 | 1.87 | 8 | 7 | 137 | 170 |

TABLE 4a-continued

Predicted HLA class I-restricted CD8+ cytotoxic T cell epitopes contained in SLP sequences from HBV polymerase protein.

HLA class I binding peptides in SLP sequences derived from HBV Polymerase protein

| | | | | SEQ ID NO: | HLA class I molecule | Class I-B score[B] | C-score[C] | Class I-BCI score[D] | Peptide of invention (SLP) | | |
|---|---|---|---|---|---|---|---|---|---|---|---|
| Start | End | Length | Sequence[A] | | | | | | SLP# | SLP Start | SLP End |
| 153 | 160 | 8 | LWKAGILY | 226 | A*2902 | 56 | 1.87 | 104 | 7 | 137 | 170 |
| 153 | 160 | 8 | LWKAGILY | 226 | A*3002 | 85 | 1.87 | 158 | 7 | 137 | 170 |
| 153 | 160 | 8 | LWKAGILY | 226 | B*3501 | 8 | 1.87 | 15 | 7 | 137 | 170 |
| 151 | 161 | 11 | HTLWKAGILYK | 227 | A*0301 | 89 | 1.41 | 125 | 7 | 137 | 170 |
| 151 | 161 | 11 | HTLWKAGILYK | 227 | A*1101 | 100 | 1.41 | 141 | 7 | 137 | 170 |
| 151 | 161 | 11 | HTLWKAGILYK | 227 | A*3001 | 78 | 1.41 | 110 | 7 | 137 | 170 |
| 151 | 161 | 11 | HTLWKAGILYK | 227 | A*3101 | 46 | 1.41 | 64 | 7 | 137 | 170 |
| 151 | 161 | 11 | HTLWKAGILYK | 227 | A*3303 | 25 | 1.41 | 36 | 7 | 137 | 170 |
| 151 | 161 | 11 | HTLWKAGILYK | 227 | A*6801 | 75 | 1.41 | 106 | 7 | 137 | 170 |
| 151 | 161 | 11 | HTLWKAGILYK | 227 | A*7401 | 83 | 1.41 | 117 | 7 | 137 | 170 |
| 152 | 161 | 10 | TLWKAGILYK | 228 | A*0301 | 87 | 1.41 | 122 | 7 | 137 | 170 |
| 152 | 161 | 10 | TLWKAGILYK | 228 | A*1101 | 59 | 1.41 | 83 | 7 | 137 | 170 |
| 152 | 161 | 10 | TLWKAGILYK | 228 | A*7401 | 71 | 1.41 | 100 | 7 | 137 | 170 |
| 153 | 161 | 9 | LWKAGILYK | 229 | A*3001 | 57 | 1.41 | 80 | 7 | 137 | 170 |
| 152 | 162 | 11 | TLWKAGILYKR | 230 | A*3101 | 61 | 1.49 | 91 | 7 | 137 | 170 |
| 152 | 162 | 11 | TLWKAGILYKR | 230 | A*3303 | 72 | 1.49 | 107 | 7 | 137 | 170 |
| 152 | 162 | 11 | TLWKAGILYKR | 230 | A*7401 | 82 | 1.49 | 122 | 7 | 137 | 170 |
| 153 | 162 | 10 | LWKAGILYKR | 231 | A*3101 | 86 | 1.49 | 128 | 7 | 137 | 170 |
| 153 | 162 | 10 | LWKAGILYKR | 231 | A*3303 | 59 | 1.49 | 88 | 7 | 137 | 170 |
| 155 | 162 | 8 | KAGILYKR | 232 | A*3101 | 67 | 1.49 | 100 | 7 | 137 | 170 |
| 155 | 162 | 8 | KAGILYKR | 232 | A*7401 | 27 | 1.49 | 40 | 7 | 137 | 170 |
| 158 | 166 | 9 | ILYKRETTR | 233 | A*0301 | 66 | 1.75 | 115 | 7 | 137 | 170 |
| 158 | 166 | 9 | ILYKRETTR | 233 | A*3101 | 23 | 1.75 | 40 | 7 | 137 | 170 |
| 158 | 166 | 9 | ILYKRETTR | 233 | A*3303 | 51 | 1.75 | 89 | 7 | 137 | 170 |
| 158 | 166 | 9 | ILYKRETTR | 233 | A*7401 | 90 | 1.75 | 158 | 7 | 137 | 170 |
| 158 | 168 | 11 | ILYKRETTRSA | 234 | B*0801 | 56 | 1.80 | 100 | 7 | 137 | 170 |
| 160 | 170 | 11 | YKRETTRSASF | 235 | B*0702 | 17 | 1.82 | 32 | 7 | 137 | 170 |
| 160 | 170 | 11 | YKRETTRSASF | 235 | B*0801 | 81 | 1.82 | 148 | 7 | 137 | 170 |
| 160 | 170 | 11 | YKRETTRSASF | 235 | B*1402 | 68 | 1.82 | 123 | 7 | 137 | 170 |
| 160 | 170 | 11 | YKRETTRSASF | 235 | B*1501 | 53 | 1.82 | 97 | 7 | 137 | 170 |
| 160 | 170 | 11 | YKRETTRSASF | 235 | B*1502 | 65 | 1.82 | 118 | 7 | 137 | 170 |
| 160 | 170 | 11 | YKRETTRSASF | 235 | B*1525 | 46 | 1.82 | 83 | 7 | 137 | 170 |
| 161 | 170 | 10 | KRETTRSASF | 236 | B*2702 | 53 | 1.82 | 97 | 7 | 137 | 170 |
| 162 | 170 | 9 | RETTRSASF | 237 | B*4001 | 57 | 1.82 | 103 | 7 | 137 | 170 |

TABLE 4a-continued

Predicted HLA class I-restricted CD8⁺ cytotoxic T cell epitopes contained in SLP sequences from HBV polymerase protein.

HLA class I binding peptides in SLP sequences derived from HBV Polymerase protein

| Start | End | Length | Sequence [A] | SEQ ID NO: | HLA class I molecule | Class I-B score [B] | C-score [C] | Class I-BCI score [D] | SLP# | SLP Start | SLP End |
|---|---|---|---|---|---|---|---|---|---|---|---|
| 162 | 170 | 9 | RETTRSASF | 237 | B*4402 | 88 | 1.82 | 161 | 7 | 137 | 170 |
| 162 | 170 | 9 | RETTRSASF | 237 | B*4403 | 60 | 1.82 | 109 | 7 | 137 | 170 |
| 162 | 170 | 9 | RETTRSASF | 237 | B*5001 | 44 | 1.82 | 80 | 7 | 137 | 170 |
| 163 | 170 | 8 | ETTRSASF | 238 | A*2501 | 100 | 1.82 | 182 | 7 | 137 | 170 |
| 163 | 170 | 8 | ETTRSASF | 238 | A*2601 | 100 | 1.82 | 182 | 7 | 137 | 170 |
| | | | | | Cumulative Class I-BCI score: | | | 10325 | | | |
| 316 | 326 | 11 | SQSQGSVSSCW | 247 | B*4402 | 46 | 1.49 | 69 | 8 | 316 | 347 |
| 316 | 326 | 11 | SQSQGSVSSCW | 247 | B*4403 | 24 | 1.49 | 36 | 8 | 316 | 347 |
| 317 | 326 | 10 | QSQGSVSSCW | 248 | B*4402 | 54 | 1.49 | 80 | 8 | 316 | 347 |
| 317 | 326 | 10 | QSQGSVSSCW | 248 | B*5802 | 64 | 1.49 | 95 | 8 | 316 | 347 |
| 319 | 326 | 8 | QGSYSSCW | 249 | B*5801 | 15 | 1.49 | 23 | 8 | 316 | 347 |
| 317 | 327 | 11 | QSQGSVSSCWW | 250 | B*5701 | 79 | 1.02 | 80 | 8 | 316 | 347 |
| 317 | 327 | 11 | QSQGSVSSCWW | 250 | B*5801 | 88 | 1.02 | 90 | 8 | 316 | 347 |
| 317 | 327 | 11 | QSQGSVSSCWW | 250 | B*5802 | 75 | 1.02 | 77 | 8 | 316 | 347 |
| 319 | 327 | 9 | QGSYSSCWW | 251 | B*5701 | 38 | 1.02 | 39 | 8 | 316 | 347 |
| 319 | 327 | 9 | QGSYSSCWW | 251 | B*5801 | 10 | 1.02 | 10 | 8 | 316 | 347 |
| 320 | 327 | 8 | GSYSSCWW | 252 | B*5701 | 92 | 1.02 | 94 | 8 | 316 | 347 |
| 320 | 327 | 8 | GSYSSCWW | 252 | B*5801 | 95 | 1.02 | 97 | 8 | 316 | 347 |
| 320 | 327 | 8 | GSYSSCWW | 252 | B*5802 | 84 | 1.02 | 86 | 8 | 316 | 347 |
| 318 | 328 | 11 | SQGSVSSCWWL | 253 | B*4801 | 37 | 1.77 | 65 | 8 | 316 | 347 |
| 320 | 329 | 10 | GSVSSCWWLQ | 254 | A*3201 | 21 | 0.81 | 17 | 8 | 316 | 347 |
| 320 | 330 | 11 | GSVSSCWWLQF | 255 | B*1525 | 22 | 1.91 | 42 | 8 | 316 | 347 |
| 320 | 330 | 11 | GSVSSCWWLQF | 255 | B*5701 | 74 | 1.91 | 142 | 8 | 316 | 347 |
| 320 | 330 | 11 | GSVSSCWWLQF | 255 | B*5802 | 65 | 1.91 | 125 | 8 | 316 | 347 |
| 321 | 330 | 10 | SVSSCWWLQF | 256 | A*2601 | 31 | 1.91 | 59 | 8 | 316 | 347 |
| 321 | 330 | 10 | SVSSCWWLQF | 256 | A*3201 | 58 | 1.91 | 110 | 8 | 316 | 347 |
| 322 | 330 | 9 | VSSCWWLQF | 257 | A*0101 | 53 | 1.91 | 101 | 8 | 316 | 347 |
| 322 | 330 | 9 | VSSCWWLQF | 257 | A*2402 | 23 | 1.91 | 44 | 8 | 316 | 347 |
| 322 | 330 | 9 | VSSCWWLQF | 257 | B*4601 | 21 | 1.91 | 41 | 8 | 316 | 347 |
| 322 | 330 | 9 | VSSCWWLQF | 257 | B*5701 | 58 | 1.91 | 110 | 8 | 316 | 347 |
| 322 | 330 | 9 | VSSCWWLQF | 257 | B*5801 | 73 | 1.91 | 139 | 8 | 316 | 347 |
| 323 | 330 | 8 | SSCWWLQF | 258 | A*2301 | 21 | 1.91 | 40 | 8 | 316 | 347 |
| 323 | 330 | 8 | SSCWWLQF | 258 | A*3201 | 42 | 1.91 | 81 | 8 | 316 | 347 |
| 323 | 330 | 8 | SSCWWLQF | 258 | B*5801 | 59 | 1.91 | 113 | 8 | 316 | 347 |
| 321 | 331 | 11 | SVSSCWWLQFR | 259 | A*1101 | 65 | 0.81 | 53 | 8 | 316 | 347 |

TABLE 4a-continued

Predicted HLA class I-restricted CD8⁺ cytotoxic T cell epitopes contained in SLP sequences from HBV polymerase protein.

HLA class I binding peptides in SLP sequences derived from HBV Polymerase protein

| Start | End | Length | Sequence [A] | SEQ ID NO: | HLA class I molecule | Class I-B score[B] | C-score[C] | Class I-BCI score[D] | Peptide of invention (SLP) | | |
|---|---|---|---|---|---|---|---|---|---|---|---|
| | | | | | | | | | SLP# | SLP Start | SLP End |
| 321 | 331 | 11 | SVSSCWWLQFR | 259 | A*3303 | 100 | 0.81 | 81 | 8 | 316 | 347 |
| 321 | 331 | 11 | SVSSCWWLQFR | 259 | A*6801 | 96 | 0.81 | 78 | 8 | 316 | 347 |
| 321 | 331 | 11 | SVSSCWWLQFR | 259 | A*7401 | 98 | 0.81 | 79 | 8 | 316 | 347 |
| 322 | 331 | 10 | VSSCWWLQFR | 260 | A*3101 | 95 | 0.81 | 77 | 8 | 316 | 347 |
| 322 | 331 | 10 | VSSCWWLQFR | 260 | A*3303 | 56 | 0.81 | 46 | 8 | 316 | 347 |
| 322 | 331 | 10 | VSSCWWLQFR | 260 | B*5701 | 30 | 0.81 | 25 | 8 | 316 | 347 |
| 322 | 331 | 10 | VSSCWWLQFR | 260 | B*5801 | 42 | 0.81 | 34 | 8 | 316 | 347 |
| 323 | 331 | 9 | SSCWWLQFR | 261 | A*1101 | 41 | 0.81 | 34 | 8 | 316 | 347 |
| 323 | 331 | 9 | SSCWWLQFR | 261 | A*3101 | 94 | 0.81 | 76 | 8 | 316 | 347 |
| 323 | 331 | 9 | SSCWWLQFR | 261 | A*3303 | 85 | 0.81 | 69 | 8 | 316 | 347 |
| 323 | 331 | 9 | SSCWWLQFR | 261 | A*7401 | 87 | 0.81 | 70 | 8 | 316 | 347 |
| 324 | 331 | 8 | SCWWLQFR | 262 | A*3303 | 44 | 0.81 | 36 | 8 | 316 | 347 |
| 327 | 334 | 8 | WLQFRNSK | 263 | A*0301 | 20 | 0.52 | 10 | 8 | 316 | 347 |
| 328 | 335 | 8 | LQFRNSKP | 264 | A*0206 | 21 | 0.10 | 2 | 8 | 316 | 347 |
| 327 | 336 | 10 | WLQFrNSKPC | 265 | A*0201 | 18 | 0.14 | 3 | 8 | 316 | 347 |
| 328 | 337 | 10 | LQFRNSKPCS | 266 | A*3001 | 99 | 0.26 | 26 | 8 | 316 | 347 |
| 329 | 339 | 11 | QFRNSKPCSEY | 267 | A*3002 | 10 | 1.63 | 16 | 8 | 316 | 347 |
| 331 | 339 | 9 | RNSKPCSEY | 268 | A*3002 | 8 | 1.63 | 14 | 8 | 316 | 347 |
| 332 | 339 | 8 | NSKPCSEY | 269 | A*3002 | 20 | 1.63 | 32 | 8 | 316 | 347 |
| 336 | 343 | 8 | CSEYCLSH | 270 | A*0101 | 40 | 0.58 | 23 | 8 | 316 | 347 |
| 337 | 344 | 8 | SEYCLSHL | 271 | B*1301 | 97 | 1.01 | 98 | 8 | 316 | 347 |
| 337 | 344 | 8 | SEYCLSHL | 271 | B*1302 | 37 | 1.01 | 37 | 8 | 316 | 347 |
| 337 | 344 | 8 | SEYCLSHL | 271 | B*1801 | 67 | 1.01 | 67 | 8 | 316 | 347 |
| 337 | 344 | 8 | SEYCLSHL | 271 | B*3701 | 100 | 1.01 | 101 | 8 | 316 | 347 |
| 337 | 344 | 8 | SEYCLSHL | 271 | B*3801 | 96 | 1.01 | 97 | 8 | 316 | 347 |
| 337 | 344 | 8 | SEYCLSHL | 271 | B*4001 | 100 | 1.01 | 101 | 8 | 316 | 347 |
| 337 | 344 | 8 | SEYCLSHL | 271 | B*4002 | 100 | 1.01 | 101 | 8 | 316 | 347 |
| 337 | 344 | 8 | SEYCLSHL | 271 | B*4402 | 85 | 1.01 | 85 | 8 | 316 | 347 |
| 337 | 344 | 8 | SEYCLSHL | 271 | B*4403 | 88 | 1.01 | 89 | 8 | 316 | 347 |
| 337 | 344 | 8 | SEYCLSHL | 271 | B*4801 | 46 | 1.01 | 47 | 8 | 316 | 347 |
| 337 | 344 | 8 | SEYCLSHL | 271 | B*4901 | 96 | 1.01 | 97 | 8 | 316 | 347 |
| 337 | 344 | 8 | SEYCLSHL | 271 | B*5001 | 96 | 1.01 | 97 | 8 | 316 | 347 |
| 337 | 344 | 8 | SEYCLSHL | 271 | B*5201 | 57 | 1.01 | 57 | 8 | 316 | 347 |
| 335 | 345 | 11 | PCSEYCLSHLV | 272 | A*0201 | 40 | 1.78 | 71 | 8 | 316 | 347 |
| 337 | 345 | 9 | SEYCLSHLV | 273 | B*1301 | 94 | 1.78 | 168 | 8 | 316 | 347 |

TABLE 4a-continued

Predicted HLA class I-restricted CD8+ cytotoxic T cell epitopes contained in SLP sequences from HBV polymerase protein.

HLA class I binding peptides in SLP sequences derived from HBV Polymerase protein

| Start | End | Length | Sequence[A] | SEQ ID NO: | HLA class I molecule | Class I-B score[B] | C-score[C] | Class I-BCI score[D] | SLP# | Peptide of invention (SLP) SLP Start | SLP End |
|---|---|---|---|---|---|---|---|---|---|---|---|
| 337 | 345 | 9 | SEYCLSHLV | 273 | B*1302 | 48 | 1.78 | 85 | 8 | 316 | 347 |
| 337 | 345 | 9 | SEYCLSHLV | 273 | B*1801 | 29 | 1.78 | 51 | 8 | 316 | 347 |
| 337 | 345 | 9 | SEYCLSHLV | 273 | B*4001 | 65 | 1.78 | 116 | 8 | 316 | 347 |
| 337 | 345 | 9 | SEYCLSHLV | 273 | B*4002 | 70 | 1.78 | 125 | 8 | 316 | 347 |
| 337 | 345 | 9 | SEYCLSHLV | 273 | B*4402 | 77 | 1.78 | 137 | 8 | 316 | 347 |
| 337 | 345 | 9 | SEYCLSHLV | 273 | B*4403 | 80 | 1.78 | 142 | 8 | 316 | 347 |
| 337 | 345 | 9 | SEYCLSHLV | 273 | B*4901 | 100 | 1.78 | 178 | 8 | 316 | 347 |
| 337 | 345 | 9 | SEYCLSHLV | 273 | B*5001 | 100 | 1.78 | 178 | 8 | 316 | 347 |
| 337 | 345 | 9 | SEYCLSHLV | 273 | B*5201 | 71 | 1.78 | 126 | 8 | 316 | 347 |
| 337 | 346 | 10 | SEYCLSHLVN | 274 | B*4001 | 39 | 0.24 | 10 | 8 | 316 | 347 |
| 337 | 346 | 10 | SEYCLSHLVN | 274 | B*4403 | 76 | 0.24 | 18 | 8 | 316 | 347 |
| 337 | 346 | 10 | SEYCLSHLVN | 274 | B*5001 | 24 | 0.24 | 6 | 8 | 316 | 347 |
| 337 | 347 | 11 | SEYCLSHLVNL | 275 | B*1301 | 100 | 1.66 | 166 | 8 | 316 | 347 |
| 337 | 347 | 11 | SEYCLSHLVNL | 275 | B*1302 | 45 | 1.66 | 75 | 8 | 316 | 347 |
| 337 | 347 | 11 | SEYCLSHLVNL | 275 | B*1801 | 86 | 1.66 | 142 | 8 | 316 | 347 |
| 337 | 347 | 11 | SEYCLSHLVNL | 275 | B*3701 | 95 | 1.66 | 158 | 8 | 316 | 347 |
| 337 | 347 | 11 | SEYCLSHLVNL | 275 | B*3801 | 94 | 1.66 | 156 | 8 | 316 | 347 |
| 337 | 347 | 11 | SEYCLSHLVNL | 275 | B*4001 | 96 | 1.66 | 158 | 8 | 316 | 347 |
| 337 | 347 | 11 | SEYCLSHLVNL | 275 | B*4002 | 95 | 1.66 | 157 | 8 | 316 | 347 |
| 337 | 347 | 11 | SEYCLSHLVNL | 275 | B*4402 | 81 | 1.66 | 134 | 8 | 316 | 347 |
| 337 | 347 | 11 | SEYCLSHLVNL | 275 | B*4403 | 84 | 1.66 | 139 | 8 | 316 | 347 |
| 337 | 347 | 11 | SEYCLSHLVNL | 275 | B*4901 | 91 | 1.66 | 151 | 8 | 316 | 347 |
| 337 | 347 | 11 | SEYCLSHLVNL | 275 | B*5001 | 92 | 1.66 | 152 | 8 | 316 | 347 |
| 337 | 347 | 11 | SEYCLSHLVNL | 275 | B*5201 | 63 | 1.66 | 104 | 8 | 316 | 347 |
| 338 | 347 | 10 | EYCLSHLVNL | 276 | A*2301 | 48 | 1.66 | 80 | 8 | 316 | 347 |
| | | | | | Cumulative Class I-BCI score: | | | 7246 | | | |
| 386 | 394 | 9 | AESRLVVDF | 278 | B*1801 | 10 | 1.80 | 17 | 9 | 385 | 417 |
| 386 | 394 | 9 | AESRLVVDF | 278 | B*4001 | 48 | 1.80 | 86 | 9 | 385 | 417 |
| 386 | 394 | 9 | AESRLVVDF | 278 | B*4002 | 50 | 1.80 | 90 | 9 | 385 | 417 |
| 386 | 394 | 9 | AESRLVVDF | 278 | B*4402 | 100 | 1.80 | 180 | 9 | 385 | 417 |
| 386 | 394 | 9 | AESRLVVDF | 278 | B*4403 | 100 | 1.80 | 180 | 9 | 385 | 417 |
| 386 | 394 | 9 | AESRLVVDF | 278 | B*4901 | 43 | 1.80 | 78 | 9 | 385 | 417 |
| 386 | 394 | 9 | AESRLVVDF | 278 | B*5001 | 36 | 1.80 | 65 | 9 | 385 | 417 |
| 386 | 396 | 11 | AESRLVVDFSQ | 279 | B*4402 | 15 | 0.65 | 10 | 9 | 385 | 417 |
| 386 | 396 | 11 | AESRLVVDFSQ | 279 | B*4403 | 8 | 0.65 | 5 | 9 | 385 | 417 |

TABLE 4a-continued

Predicted HLA class I-restricted CD8+ cytotoxic T cell epitopes contained in SLP sequences from HBV polymerase protein.

HLA class I binding peptides in SLP sequences derived from HBV Polymerase protein

| Start | End | Length | Sequence [A] | SEQ ID NO: | HLA class I molecule | Class I-B score[B] | C-score[C] | Class I-BCI score[D] | Peptide of invention (SLP) | | |
|---|---|---|---|---|---|---|---|---|---|---|---|
| | | | | | | | | | SLP# | SLP Start | SLP End |
| 387 | 397 | 11 | ESRLVVDFSQF | 280 | A*2501 | 49 | 1.86 | 91 | 9 | 385 | 417 |
| 387 | 397 | 11 | ESRLVVDFSQF | 280 | A*2601 | 5 | 1.86 | 10 | 9 | 385 | 417 |
| 388 | 397 | 10 | SRLVVDFSQF | 281 | B*2702 | 92 | 1.86 | 170 | 9 | 385 | 417 |
| 389 | 397 | 9 | RLVVDFSQF | 282 | A*2301 | 43 | 1.86 | 80 | 9 | 385 | 417 |
| 389 | 397 | 9 | RLVVDFSQF | 282 | B*1501 | 70 | 1.86 | 131 | 9 | 385 | 417 |
| 389 | 397 | 9 | RLVVDFSQF | 282 | B*1525 | 78 | 1.86 | 145 | 9 | 385 | 417 |
| 390 | 397 | 8 | LVVDFSQF | 283 | A*2501 | 59 | 1.86 | 110 | 9 | 385 | 417 |
| 390 | 397 | 8 | LVVDFSQF | 283 | A*2601 | 79 | 1.86 | 148 | 9 | 385 | 417 |
| 390 | 397 | 8 | LVVDFSQF | 283 | B*1501 | 59 | 1.86 | 110 | 9 | 385 | 417 |
| 390 | 397 | 8 | LVVDFSQF | 283 | B*1502 | 72 | 1.86 | 134 | 9 | 385 | 417 |
| 390 | 397 | 8 | LVVDFSQF | 283 | B*1525 | 56 | 1.86 | 104 | 9 | 385 | 417 |
| 390 | 397 | 8 | LVVDFSQF | 283 | B*4601 | 57 | 1.86 | 107 | 9 | 385 | 417 |
| 389 | 399 | 11 | RLVVDFSQFSR | 284 | A*0301 | 15 | 1.78 | 26 | 9 | 385 | 417 |
| 389 | 399 | 11 | RLVVDFSQFSR | 284 | A*3101 | 81 | 1.78 | 144 | 9 | 385 | 417 |
| 389 | 399 | 11 | RLVVDFSQFSR | 284 | A*7401 | 96 | 1.78 | 172 | 9 | 385 | 417 |
| 390 | 399 | 10 | LVVDFSQFSR | 285 | A*3101 | 89 | 1.78 | 158 | 9 | 385 | 417 |
| 390 | 399 | 10 | LVVDFSQFSR | 285 | A*3201 | 6 | 1.78 | 11 | 9 | 385 | 417 |
| 390 | 399 | 10 | LVVDFSQFSR | 285 | A*3303 | 83 | 1.78 | 148 | 9 | 385 | 417 |
| 390 | 399 | 10 | LVVDFSQFSR | 285 | A*6801 | 88 | 1.78 | 157 | 9 | 385 | 417 |
| 390 | 399 | 10 | LVVDFSQFSR | 285 | A*7401 | 70 | 1.78 | 124 | 9 | 385 | 417 |
| 391 | 399 | 9 | VVDFSQFSR | 286 | A*1101 | 11 | 1.78 | 19 | 9 | 385 | 417 |
| 391 | 399 | 9 | VVDFSQFSR | 286 | A*3303 | 18 | 1.78 | 33 | 9 | 385 | 417 |
| 391 | 399 | 9 | VVDFSQFSR | 286 | A*7401 | 79 | 1.78 | 141 | 9 | 385 | 417 |
| 390 | 400 | 11 | LVVDFSQFSRG | 287 | A*6802 | 6 | 0.16 | 1 | 9 | 385 | 417 |
| 392 | 401 | 10 | VDFSQFSRGI | 288 | B*1301 | 76 | 1.23 | 93 | 9 | 385 | 417 |
| 392 | 401 | 10 | VDFSQFSRGI | 288 | B*1302 | 44 | 1.23 | 54 | 9 | 385 | 417 |
| 392 | 401 | 10 | VDFSQFSRGI | 288 | B*5201 | 88 | 1.23 | 108 | 9 | 385 | 417 |
| 393 | 403 | 11 | DFSQFSRGISR | 289 | A*3303 | 55 | 0.77 | 42 | 9 | 385 | 417 |
| 394 | 403 | 10 | FSQFSRGISR | 290 | A*3101 | 14 | 0.77 | 11 | 9 | 385 | 417 |
| 394 | 403 | 10 | FSQFSRGISR | 290 | A*3303 | 11 | 0.77 | 9 | 9 | 385 | 417 |
| 394 | 403 | 10 | FSQFSRGISR | 290 | A*6801 | 60 | 0.77 | 46 | 9 | 385 | 417 |
| 395 | 403 | 9 | SQFSRGISR | 291 | A*1101 | 13 | 0.77 | 10 | 9 | 385 | 417 |
| 395 | 403 | 9 | SQFSRGISR | 291 | A*3101 | 62 | 0.77 | 48 | 9 | 385 | 417 |
| 395 | 403 | 9 | SQFSRGISR | 291 | A*3303 | 70 | 0.77 | 54 | 9 | 385 | 417 |

TABLE 4a-continued

Predicted HLA class I-restricted CD8+ cytotoxic T cell epitopes contained in SLP sequences from HBV polymerase protein.

HLA class I binding peptides in SLP sequences derived from HBV Polymerase protein

| | | | | | | | | | Peptide of invention (SLP) | | |
|---|---|---|---|---|---|---|---|---|---|---|---|
| Start | End | Length | Sequence $^A$ | SEQ ID NO: | HLA class I molecule | Class I-B score $^B$ | C-score $^C$ | Class I-BCI score $^D$ | SLP# | SLP Start | SLP End |
| 395 | 403 | 9 | SQFSRGISR | 291 | A*7401 | 95 | 0.77 | 73 | 9 | 385 | 417 |
| 396 | 403 | 8 | QFSRGISR | 292 | A*3303 | 48 | 0.77 | 37 | 9 | 385 | 417 |
| 395 | 404 | 10 | SQFSrGISRV | 293 | A*0201 | 45 | 1.90 | 85 | 9 | 385 | 417 |
| 395 | 404 | 10 | SQFSRGISRV | 293 | B*1302 | 23 | 1.90 | 43 | 9 | 385 | 417 |
| 395 | 404 | 10 | SQFSRGISRV | 293 | B*1402 | 4 | 1.90 | 8 | 9 | 385 | 417 |
| 395 | 404 | 10 | SQFSRGISRV | 293 | B*3901 | 27 | 1.90 | 52 | 9 | 385 | 417 |
| 395 | 404 | 10 | SQFSRGISRV | 293 | B*4801 | 35 | 1.90 | 66 | 9 | 385 | 417 |
| 395 | 404 | 10 | SQFSRGISRV | 293 | B*5201 | 69 | 1.90 | 130 | 9 | 385 | 417 |
| 398 | 405 | 8 | SRGISRVS | 294 | B*2705 | 12 | 0.22 | 3 | 9 | 385 | 417 |
| 397 | 406 | 10 | FSRGISRVSW | 295 | B*4601 | 38 | 1.40 | 53 | 9 | 385 | 417 |
| 397 | 406 | 10 | FSRGISRVSW | 295 | B*5301 | 15 | 1.40 | 21 | 9 | 385 | 417 |
| 397 | 406 | 10 | FSRGISRVSW | 295 | B*5802 | 87 | 1.40 | 122 | 9 | 385 | 417 |
| 398 | 406 | 9 | SRGISRVSW | 296 | B*2702 | 65 | 1.40 | 91 | 9 | 385 | 417 |
| 399 | 406 | 8 | RGISRVSW | 297 | B*2702 | 28 | 1.40 | 39 | 9 | 385 | 417 |
| 399 | 406 | 8 | RGISRVSW | 297 | B*5701 | 73 | 1.40 | 102 | 9 | 385 | 417 |
| 399 | 406 | 8 | RGISRVSW | 297 | B*5801 | 68 | 1.40 | 95 | 9 | 385 | 417 |
| 399 | 406 | 8 | RGISRVSW | 297 | B*5802 | 74 | 1.40 | 103 | 9 | 385 | 417 |
| 400 | 408 | 9 | GISRVSWPK | 298 | A*0301 | 62 | 0.98 | 61 | 9 | 385 | 417 |
| 400 | 408 | 9 | GISRVSWPK | 298 | A*1101 | 93 | 0.98 | 91 | 9 | 385 | 417 |
| 400 | 408 | 9 | GISRVSWPK | 298 | A*7401 | 40 | 0.98 | 39 | 9 | 385 | 417 |
| 401 | 408 | 8 | ISRVSWPK | 299 | A*0301 | 13 | 0.98 | 13 | 9 | 385 | 417 |
| 401 | 408 | 8 | ISRVSWPK | 299 | A*1101 | 30 | 0.98 | 30 | 9 | 385 | 417 |
| 401 | 408 | 8 | ISRVSWPK | 299 | A*3001 | 95 | 0.98 | 92 | 9 | 385 | 417 |
| 399 | 409 | 11 | RGISRVSWPKF | 300 | A*2301 | 7 | 1.38 | 10 | 9 | 385 | 417 |
| 399 | 409 | 11 | RGISRVSWPKF | 300 | B*5802 | 7 | 1.38 | 10 | 9 | 385 | 417 |
| 400 | 409 | 10 | GISRVSWPKF | 301 | A*3001 | 55 | 1.38 | 77 | 9 | 385 | 417 |
| 400 | 409 | 10 | GISRVSWPKF | 301 | A*3201 | 98 | 1.38 | 136 | 9 | 385 | 417 |
| 401 | 409 | 9 | ISRVSWPKF | 302 | B*5701 | 88 | 1.38 | 122 | 9 | 385 | 417 |
| 402 | 409 | 8 | SRVSWPKF | 303 | B*2702 | 90 | 1.38 | 125 | 9 | 385 | 417 |
| 402 | 409 | 8 | SRVSWPKF | 303 | B*2705 | 57 | 1.38 | 78 | 9 | 385 | 417 |
| 403 | 410 | 8 | RVSWPKFA | 304 | A*3001 | 16 | 0.84 | 14 | 9 | 385 | 417 |
| 401 | 411 | 11 | ISRVSWPKFAV | 305 | A*3001 | 70 | 1.60 | 111 | 9 | 385 | 417 |
| 402 | 411 | 10 | SRVSWPKFAV | 306 | B*3901 | 6 | 1.60 | 10 | 9 | 385 | 417 |
| 403 | 411 | 9 | RVSWPKFAV | 307 | A*6802 | 4 | 1.60 | 7 | 9 | 385 | 417 |
| 403 | 411 | 9 | RVSWPKFAV | 307 | B*0702 | 6 | 1.60 | 9 | 9 | 385 | 417 |

TABLE 4a-continued

Predicted HLA class I-restricted CD8+ cytotoxic T cell epitopes contained in SLP sequences from HBV polymerase protein.

HLA class I binding peptides in SLP sequences derived from HBV Polymerase protein

| Start | End | Length | Sequence[A] | SEQ ID NO: | HLA class I molecule | Class I-B score[B] | C-score[C] | Class I-BCI score[D] | SLP# | SLP Start | SLP End |
|---|---|---|---|---|---|---|---|---|---|---|---|
| 404 | 411 | 8 | VSWPKFAV | 308 | B*5201 | 41 | 1.60 | 66 | 9 | 385 | 417 |
| 405 | 412 | 8 | SWPKFAVP | 309 | A*0206 | 100 | 0.48 | 48 | 9 | 385 | 417 |
| 404 | 414 | 11 | VSWPKFAVPNL | 310 | B*5201 | 16 | 1.63 | 26 | 9 | 385 | 417 |
| 404 | 414 | 11 | VSWPKFAVPNL | 310 | B*5701 | 18 | 1.63 | 30 | 9 | 385 | 417 |
| 405 | 414 | 10 | SWPKFAVPNL | 311 | A*2301 | 78 | 1.63 | 127 | 9 | 385 | 417 |
| 405 | 414 | 10 | SWPKFAVPNL | 311 | A*2402 | 75 | 1.63 | 123 | 9 | 385 | 417 |
| 406 | 414 | 9 | WPKFAVPNL | 312 | B*1402 | 21 | 1.63 | 35 | 9 | 385 | 417 |
| 406 | 414 | 9 | WPKFAVPNL | 312 | B*3503 | 18 | 1.63 | 29 | 9 | 385 | 417 |
| 409 | 417 | 9 | FAVPNLQSL | 313 | A*0206 | 54 | 1.89 | 102 | 9 | 385 | 417 |
| 409 | 417 | 9 | FAVPNLQSL | 313 | B*3503 | 46 | 1.89 | 87 | 9 | 385 | 417 |
| 409 | 417 | 9 | FAVPNLQSL | 313 | B*4601 | 95 | 1.89 | 180 | 9 | 385 | 417 |
| 410 | 417 | 8 | AVPNLQSL | 314 | B*0702 | 29 | 1.89 | 55 | 9 | 385 | 417 |
| | | | | | Cumulative BCI Class I score: | | | 6722 | | | |
| 420 | 427 | 8 | LLSSNLSW | 316 | B*5301 | 20 | 1.77 | 35 | 10 | 419 | 456 |
| 420 | 427 | 8 | LLSSNLSW | 316 | B*5701 | 48 | 1.77 | 86 | 10 | 419 | 456 |
| 420 | 427 | 8 | LLSSNLSW | 316 | B*5801 | 66 | 1.77 | 117 | 10 | 419 | 456 |
| 420 | 427 | 8 | LLSSNLSW | 316 | B*5802 | 30 | 1.77 | 54 | 10 | 419 | 456 |
| 419 | 428 | 10 | NLLSsNLSWL | 317 | A*0201 | 100 | 1.54 | 154 | 10 | 419 | 456 |
| 420 | 428 | 9 | LLSSNLSWL | 318 | A*0201 | 86 | 1.54 | 133 | 10 | 419 | 456 |
| 421 | 428 | 8 | LSSNLSWL | 319 | B*0702 | 78 | 1.54 | 121 | 10 | 419 | 456 |
| 421 | 429 | 9 | LSSNLSWLS | 320 | A*0101 | 30 | 0.55 | 16 | 10 | 419 | 456 |
| 420 | 430 | 11 | LLSSNLSWLSL | 321 | B*0801 | 8 | 1.74 | 15 | 10 | 419 | 456 |
| 421 | 430 | 10 | LSSNLSWLSL | 322 | A*3201 | 47 | 1.74 | 82 | 10 | 419 | 456 |
| 421 | 430 | 10 | LSSNLSWLSL | 322 | B*5701 | 27 | 1.74 | 48 | 10 | 419 | 456 |
| 421 | 430 | 10 | LSSNLSWLSL | 322 | B*5801 | 3 | 1.74 | 6 | 10 | 419 | 456 |
| 421 | 430 | 10 | LSSNLSWLSL | 322 | B*5802 | 29 | 1.74 | 50 | 10 | 419 | 456 |
| 422 | 431 | 10 | SSNLSWLSLD | 323 | A*3001 | 22 | 0.11 | 2 | 10 | 419 | 456 |
| 422 | 432 | 11 | SSNLSWLSLDV | 324 | A*0201 | 38 | 1.41 | 53 | 10 | 419 | 456 |
| 424 | 432 | 9 | NLSWLSLDV | 325 | A*0201 | 29 | 1.41 | 41 | 10 | 419 | 456 |
| 425 | 432 | 8 | LSWLSLDV | 326 | A*0206 | 4 | 1.41 | 6 | 10 | 419 | 456 |
| 425 | 432 | 8 | LSWLSLDV | 326 | B*1302 | 1 | 1.41 | 2 | 10 | 419 | 456 |
| 425 | 432 | 8 | LSWLSLDV | 326 | B*5201 | 55 | 1.41 | 77 | 10 | 419 | 456 |
| 425 | 435 | 11 | LSWLSLDVSAA | 327 | B*5601 | 9 | 0.74 | 7 | 10 | 419 | 456 |
| 427 | 435 | 9 | WLSLDVSAA | 328 | A*0201 | 14 | 0.74 | 10 | 10 | 419 | 456 |
| 426 | 436 | 11 | SWLSLDVSAAF | 329 | A*2301 | 91 | 1.90 | 174 | 10 | 419 | 456 |

TABLE 4a-continued

Predicted HLA class I-restricted CD8+ cytotoxic T cell epitopes contained in SLP sequences from HBV polymerase protein.

HLA class I binding peptides in SLP sequences derived from HBV Polymerase protein

| Start | End | Length | Sequence[A] | SEQ ID NO: | HLA class I molecule | Class I-B score[B] | C-score[C] | Class I-BCI score[D] | Peptide of invention (SLP) | | |
|---|---|---|---|---|---|---|---|---|---|---|---|
| | | | | | | | | | SLP# | SLP Start | SLP End |
| 426 | 436 | 11 | SWLSLDVSAAF | 329 | A*2402 | 93 | 1.90 | 177 | 10 | 419 | 456 |
| 426 | 436 | 11 | SWLSLDVSAAF | 329 | A*2902 | 32 | 1.90 | 60 | 10 | 419 | 456 |
| 426 | 436 | 11 | SWLSLDVSAAF | 329 | B*1801 | 38 | 1.90 | 72 | 10 | 419 | 456 |
| 427 | 436 | 10 | WLSLDVSAAF | 330 | B*1501 | 72 | 1.90 | 137 | 10 | 419 | 456 |
| 427 | 436 | 10 | WLSLDVSAAF | 330 | B*1502 | 89 | 1.90 | 169 | 10 | 419 | 456 |
| 427 | 436 | 10 | WLSLDVSAAF | 330 | B*1525 | 54 | 1.90 | 103 | 10 | 419 | 456 |
| 428 | 436 | 9 | LSLDVSAAF | 331 | B*1501 | 73 | 1.90 | 140 | 10 | 419 | 456 |
| 428 | 436 | 9 | LSLDVSAAF | 331 | B*1525 | 76 | 1.90 | 145 | 10 | 419 | 456 |
| 428 | 436 | 9 | LSLDVSAAF | 331 | B*3501 | 69 | 1.90 | 132 | 10 | 419 | 456 |
| 428 | 436 | 9 | LSLDVSAAF | 331 | B*3503 | 51 | 1.90 | 98 | 10 | 419 | 456 |
| 428 | 436 | 9 | LSLDVSAAF | 331 | B*4601 | 75 | 1.90 | 144 | 10 | 419 | 456 |
| 428 | 436 | 9 | LSLDVSAAF | 331 | B*5801 | 63 | 1.90 | 119 | 10 | 419 | 456 |
| 427 | 437 | 11 | WLSLDVSAAFY | 332 | A*0101 | 74 | 1.81 | 133 | 10 | 419 | 456 |
| 427 | 437 | 11 | WLSLDVSAAFY | 332 | A*2601 | 38 | 1.81 | 69 | 10 | 419 | 456 |
| 427 | 437 | 11 | WLSLDVSAAFY | 332 | A*2902 | 75 | 1.81 | 135 | 10 | 419 | 456 |
| 427 | 437 | 11 | WLSLDVSAAFY | 332 | B*1502 | 22 | 1.81 | 40 | 10 | 419 | 456 |
| 428 | 437 | 10 | LSLDVSAAFY | 333 | A*0101 | 100 | 1.81 | 181 | 10 | 419 | 456 |
| 428 | 437 | 10 | LSLDVSAAFY | 333 | A*2902 | 83 | 1.81 | 149 | 10 | 419 | 456 |
| 428 | 437 | 10 | LSLDVSAAFY | 333 | A*3002 | 99 | 1.81 | 178 | 10 | 419 | 456 |
| 428 | 437 | 10 | LSLDVSAAFY | 333 | B*1501 | 22 | 1.81 | 40 | 10 | 419 | 456 |
| 428 | 437 | 10 | LSLDVSAAFY | 333 | B*4601 | 69 | 1.81 | 124 | 10 | 419 | 456 |
| 428 | 437 | 10 | LSLDVSAAFY | 333 | B*5802 | 57 | 1.81 | 102 | 10 | 419 | 456 |
| 429 | 437 | 9 | SLDVSAAFY | 334 | A*0101 | 85 | 1.81 | 153 | 10 | 419 | 456 |
| 429 | 437 | 9 | SLDVSAAFY | 334 | A*3002 | 59 | 1.81 | 107 | 10 | 419 | 456 |
| 430 | 437 | 8 | LDVSAAFY | 335 | B*3501 | 31 | 1.81 | 55 | 10 | 419 | 456 |
| 430 | 439 | 10 | LDVSAAFYHI | 336 | B*1301 | 96 | 1.79 | 171 | 10 | 419 | 456 |
| 430 | 439 | 10 | LDVSAAFYHI | 336 | B*1302 | 49 | 1.79 | 88 | 10 | 419 | 456 |
| 430 | 439 | 10 | LDVSAAFYHI | 336 | B*3701 | 57 | 1.79 | 102 | 10 | 419 | 456 |
| 430 | 439 | 10 | LDVSAAFYHI | 336 | B*4901 | 57 | 1.79 | 101 | 10 | 419 | 456 |
| 430 | 439 | 10 | LDVSAAFYHI | 336 | B*5201 | 98 | 1.79 | 175 | 10 | 419 | 456 |
| 431 | 439 | 9 | DVSAAFYHI | 337 | A*6802 | 46 | 1.79 | 81 | 10 | 419 | 456 |
| 432 | 439 | 8 | VSAAFYHI | 338 | A*3201 | 18 | 1.79 | 32 | 10 | 419 | 456 |
| 432 | 439 | 8 | VSAAFYHI | 338 | B*1302 | 28 | 1.79 | 50 | 10 | 419 | 456 |
| 432 | 439 | 8 | VSAAFYHI | 338 | B*5101 | 8 | 1.79 | 15 | 10 | 419 | 456 |

TABLE 4a-continued

Predicted HLA class I-restricted CD8+ cytotoxic T cell epitopes contained in SLP sequences from HBV polymerase protein.

HLA class I binding peptides in SLP sequences derived from HBV Polymerase protein

| Start | End | Length | Sequence[A] | SEQ ID NO: | HLA class I molecule | Class I-B score[B] | C-score[C] | Class I-BCI score[D] | SLP# | Peptide of invention (SLP) SLP Start | SLP End |
|---|---|---|---|---|---|---|---|---|---|---|---|
| 432 | 439 | 8 | VSAAFYHI | 338 | B*5201 | 96 | 1.79 | 172 | 10 | 419 | 456 |
| 432 | 439 | 8 | VSAAFYHI | 338 | B*5701 | 65 | 1.79 | 116 | 10 | 419 | 456 |
| 432 | 439 | 8 | VSAAFYHI | 338 | B*5801 | 64 | 1.79 | 115 | 10 | 419 | 456 |
| 432 | 439 | 8 | VSAAFYHI | 338 | B*5802 | 49 | 1.79 | 88 | 10 | 419 | 456 |
| 431 | 441 | 11 | DVSAAFYHIPL | 339 | A*2501 | 33 | 1.00 | 33 | 10 | 419 | 456 |
| 431 | 441 | 11 | DVSAAFYHIPL | 339 | A*2601 | 51 | 1.00 | 51 | 10 | 419 | 456 |
| 432 | 441 | 10 | VSAAFYHIPL | 340 | A*6802 | 35 | 1.00 | 35 | 10 | 419 | 456 |
| 432 | 441 | 10 | VSAAFYHIPL | 340 | B*5802 | 14 | 1.00 | 15 | 10 | 419 | 456 |
| 433 | 441 | 9 | SAAFYHIPL | 341 | B*1402 | 79 | 1.00 | 79 | 10 | 419 | 456 |
| 433 | 441 | 9 | SAAFYHIPL | 341 | B*3503 | 34 | 1.00 | 34 | 10 | 419 | 456 |
| 434 | 441 | 8 | AAFYHIPL | 342 | B*0801 | 64 | 1.00 | 65 | 10 | 419 | 456 |
| 434 | 441 | 8 | AAFYHIPL | 342 | B*1402 | 57 | 1.00 | 57 | 10 | 419 | 456 |
| 434 | 441 | 8 | AAFYHIPL | 342 | B*3801 | 6 | 1.00 | 6 | 10 | 419 | 456 |
| 434 | 441 | 8 | AAFYHIPL | 342 | B*3901 | 32 | 1.00 | 33 | 10 | 419 | 456 |
| 434 | 441 | 8 | AAFYHIPL | 342 | B*4801 | 63 | 1.00 | 64 | 10 | 419 | 456 |
| 433 | 442 | 10 | SAAFYHIPLH | 343 | A*3001 | 83 | 0.25 | 20 | 10 | 419 | 456 |
| 434 | 444 | 11 | AAFYHIPLHPA | 344 | A*3001 | 11 | 0.89 | 10 | 10 | 419 | 456 |
| 434 | 444 | 11 | AAFYHIPLHPA | 344 | B*5501 | 20 | 0.89 | 18 | 10 | 419 | 456 |
| 434 | 444 | 11 | AAFYHIPLHPA | 344 | B*5601 | 21 | 0.89 | 18 | 10 | 419 | 456 |
| 437 | 444 | 8 | YHIPLHPA | 345 | B*1402 | 19 | 0.89 | 17 | 10 | 419 | 456 |
| 437 | 444 | 8 | YHIPLHPA | 345 | B*3901 | 87 | 0.89 | 78 | 10 | 419 | 456 |
| 437 | 445 | 9 | YHIPLHPAA | 346 | B*1402 | 18 | 0.62 | 11 | 10 | 419 | 456 |
| 436 | 446 | 11 | FYHIPLHPAAM | 347 | A*2402 | 19 | 1.63 | 31 | 10 | 419 | 456 |
| 437 | 446 | 10 | YHIPLHPAAM | 348 | B*1402 | 99 | 1.63 | 161 | 10 | 419 | 456 |
| 437 | 446 | 10 | YHIPLHPAAM | 348 | B*3503 | 74 | 1.63 | 121 | 10 | 419 | 456 |
| 437 | 446 | 10 | YHIPLHPAAM | 348 | B*3801 | 86 | 1.63 | 140 | 10 | 419 | 456 |
| 437 | 446 | 10 | YHIPLHPAAM | 348 | B*3901 | 100 | 1.63 | 163 | 10 | 419 | 456 |
| 438 | 446 | 9 | HIPLHPAAM | 349 | A*2501 | 73 | 1.63 | 120 | 10 | 419 | 456 |
| 438 | 446 | 9 | HIPLHPAAM | 349 | B*1402 | 3 | 1.63 | 5 | 10 | 419 | 456 |
| 439 | 446 | 8 | IPLHPAAM | 350 | B*1402 | 86 | 1.63 | 140 | 10 | 419 | 456 |
| 439 | 446 | 8 | IPLHPAAM | 350 | B*3503 | 93 | 1.63 | 152 | 10 | 419 | 456 |
| 439 | 446 | 8 | IPLHPAAM | 350 | B*5101 | 55 | 1.63 | 90 | 10 | 419 | 456 |
| 439 | 446 | 8 | IPLHPAAM | 350 | B*5301 | 64 | 1.63 | 104 | 10 | 419 | 456 |
| 439 | 446 | 8 | IPLHPAAM | 350 | B*5501 | 85 | 1.63 | 138 | 10 | 419 | 456 |
| 439 | 446 | 8 | IPLHPAAM | 350 | B*5601 | 73 | 1.63 | 119 | 10 | 419 | 456 |

TABLE 4a-continued

Predicted HLA class I-restricted CD8+ cytotoxic T cell epitopes contained in SLP sequences from HBV polymerase protein.

HLA class I binding peptides in SLP sequences derived from HBV Polymerase protein

| Start | End | Length | Sequence $^A$ | SEQ ID NO: | HLA class I molecule | Class I-B score $^B$ | C-score $^C$ | Class I-BCI score $^D$ | SLP# | Peptide of invention (SLP) SLP Start | SLP End |
|---|---|---|---|---|---|---|---|---|---|---|---|
| 439 | 449 | 11 | IPLHPAAMPHL | 351 | B*0702 | 58 | 1.61 | 93 | 10 | 419 | 456 |
| 439 | 449 | 11 | IPLHPAAMPHL | 351 | B*1402 | 31 | 1.61 | 50 | 10 | 419 | 456 |
| 439 | 449 | 11 | IPLHPAAMPHL | 351 | B*3503 | 32 | 1.61 | 52 | 10 | 419 | 456 |
| 439 | 449 | 11 | IPLHPAAMPHL | 351 | B*5101 | 53 | 1.61 | 86 | 10 | 419 | 456 |
| 439 | 449 | 11 | IPLHPAAMPHL | 351 | B*5501 | 38 | 1.61 | 62 | 10 | 419 | 456 |
| 441 | 449 | 9 | LHPAAMPHL | 352 | B*3801 | 76 | 1.61 | 121 | 10 | 419 | 456 |
| 442 | 449 | 8 | HPAAMPHL | 353 | B*1402 | 85 | 1.61 | 136 | 10 | 419 | 456 |
| 442 | 449 | 8 | HPAAMPHL | 353 | B*3503 | 73 | 1.61 | 117 | 10 | 419 | 456 |
| 442 | 449 | 8 | HPAAMPHL | 353 | B*3901 | 53 | 1.61 | 85 | 10 | 419 | 456 |
| 442 | 449 | 8 | HPAAMPHL | 353 | B*5101 | 48 | 1.61 | 78 | 10 | 419 | 456 |
| 442 | 449 | 8 | HPAAMPHL | 353 | B*5301 | 38 | 1.61 | 61 | 10 | 419 | 456 |
| 442 | 449 | 8 | HPAAMPHL | 353 | B*5501 | 55 | 1.61 | 88 | 10 | 419 | 456 |
| 442 | 449 | 8 | HPAAMPHL | 353 | B*5601 | 29 | 1.61 | 47 | 10 | 419 | 456 |
| 441 | 450 | 10 | LHPAAMPHLL | 354 | B*3801 | 67 | 1.81 | 122 | 10 | 419 | 456 |
| 442 | 450 | 9 | HPAAMPHLL | 355 | B*0702 | 70 | 1.81 | 126 | 10 | 419 | 456 |
| 442 | 450 | 9 | HPAAMPHLL | 355 | B*1402 | 93 | 1.81 | 168 | 10 | 419 | 456 |
| 442 | 450 | 9 | HPAAMPHLL | 355 | B*3501 | 29 | 1.81 | 53 | 10 | 419 | 456 |
| 442 | 450 | 9 | HPAAMPHLL | 355 | B*3503 | 85 | 1.81 | 154 | 10 | 419 | 456 |
| 442 | 450 | 9 | HPAAMPHLL | 355 | B*3901 | 97 | 1.81 | 176 | 10 | 419 | 456 |
| 442 | 450 | 9 | HPAAMPHLL | 355 | B*5301 | 33 | 1.81 | 59 | 10 | 419 | 456 |
| 442 | 450 | 9 | HPAAMPHLL | 355 | B*5501 | 72 | 1.81 | 130 | 10 | 419 | 456 |
| 442 | 450 | 9 | HPAAMPHLL | 355 | B*5601 | 58 | 1.81 | 104 | 10 | 419 | 456 |
| 441 | 451 | 11 | LHPAAMPHLLI | 356 | B*3801 | 61 | 0.84 | 51 | 10 | 419 | 456 |
| 442 | 451 | 10 | HPAAMPHLLI | 357 | B*1402 | 71 | 0.84 | 59 | 10 | 419 | 456 |
| 442 | 451 | 10 | HPAAMPHLLI | 357 | B*3503 | 72 | 0.84 | 60 | 10 | 419 | 456 |
| 442 | 451 | 10 | HPAAMPHLLI | 357 | B*3901 | 38 | 0.84 | 31 | 10 | 419 | 456 |
| 442 | 451 | 10 | HPAAMPHLLI | 357 | B*5201 | 61 | 0.84 | 51 | 10 | 419 | 456 |
| 442 | 451 | 10 | HPAAMPHLLI | 357 | B*5301 | 36 | 0.84 | 30 | 10 | 419 | 456 |
| 442 | 451 | 10 | HPAAMPHLLI | 357 | B*5501 | 84 | 0.84 | 70 | 10 | 419 | 456 |
| 442 | 451 | 10 | HPAAMPHLLI | 357 | B*5601 | 90 | 0.84 | 75 | 10 | 419 | 456 |
| 444 | 451 | 8 | AAMPHLLI | 358 | A*3201 | 59 | 0.84 | 49 | 10 | 419 | 456 |
| 444 | 451 | 8 | AAMPHLLI | 358 | B*1302 | 35 | 0.84 | 29 | 10 | 419 | 456 |
| 444 | 451 | 8 | AAMPHLLI | 358 | B*5101 | 47 | 0.84 | 39 | 10 | 419 | 456 |
| 444 | 451 | 8 | AAMPHLLI | 358 | B*5201 | 94 | 0.84 | 79 | 10 | 419 | 456 |

TABLE 4a-continued

Predicted HLA class I-restricted CD8⁺ cytotoxic T cell epitopes contained in SLP sequences from HBV polymerase protein.

HLA class I binding peptides in SLP sequences derived from HBV Polymerase protein

| Start | End | Length | Sequence [A] | SEQ ID NO: | HLA class I molecule | Class I-B score [B] | C-score [C] | Class I-BCI score [D] | SLP# | Peptide of invention (SLP) SLP Start | SLP End |
|---|---|---|---|---|---|---|---|---|---|---|---|
| 444 | 451 | 8 | AAMPHLLI | 358 | B*5801 | 37 | 0.84 | 31 | 10 | 419 | 456 |
| 442 | 452 | 11 | HPAAMPHLLIG | 359 | A*0201 | 51 | 0.32 | 16 | 10 | 419 | 456 |
| 442 | 452 | 11 | HPAAMPHLLIG | 359 | A*0206 | 38 | 0.32 | 12 | 10 | 419 | 456 |
| 446 | 453 | 8 | MPHLLIGS | 360 | A*6802 | 16 | 0.77 | 12 | 10 | 419 | 456 |
| 446 | 453 | 8 | MPHLLIGS | 360 | B*5601 | 28 | 0.77 | 22 | 10 | 419 | 456 |
| 446 | 454 | 9 | MPHLLIGSS | 361 | B*5501 | 37 | 0.26 | 10 | 10 | 419 | 456 |
| 446 | 454 | 9 | MPHLLIGSS | 361 | B*5601 | 41 | 0.26 | 11 | 10 | 419 | 456 |
| 446 | 455 | 10 | MPHLLIGSSG | 362 | B*0702 | 35 | 0.11 | 4 | 10 | 419 | 456 |
| 446 | 455 | 10 | MPHLLIGSSG | 362 | B*3501 | 40 | 0.11 | 4 | 10 | 419 | 456 |
| 446 | 455 | 10 | MPHLLIGSSG | 362 | B*5501 | 3 | 0.11 | 0 | 10 | 419 | 456 |
| 446 | 455 | 10 | MPHLLIGSSG | 362 | B*5601 | 18 | 0.11 | 2 | 10 | 419 | 456 |
| 446 | 456 | 11 | MPHLLIGSSGL | 363 | B*0702 | 93 | 1.81 | 168 | 10 | 419 | 456 |
| 446 | 456 | 11 | MPHLLIGSSGL | 363 | B*0801 | 44 | 1.81 | 80 | 10 | 419 | 456 |
| 446 | 456 | 11 | MPHLLIGSSGL | 363 | B*1402 | 92 | 1.81 | 167 | 10 | 419 | 456 |
| 446 | 456 | 11 | MPHLLIGSSGL | 363 | B*3501 | 27 | 1.81 | 48 | 10 | 419 | 456 |
| 446 | 456 | 11 | MPHLLIGSSGL | 363 | B*3503 | 70 | 1.81 | 127 | 10 | 419 | 456 |
| 446 | 456 | 11 | MPHLLIGSSGL | 363 | B*3901 | 62 | 1.81 | 113 | 10 | 419 | 456 |
| 446 | 456 | 11 | MPHLLIGSSGL | 363 | B*5101 | 40 | 1.81 | 73 | 10 | 419 | 456 |
| 446 | 456 | 11 | MPHLLIGSSGL | 363 | B*5301 | 18 | 1.81 | 33 | 10 | 419 | 456 |
| 446 | 456 | 11 | MPHLLIGSSGL | 363 | B*5501 | 71 | 1.81 | 129 | 10 | 419 | 456 |
| 446 | 456 | 11 | MPHLLIGSSGL | 363 | B*5601 | 53 | 1.81 | 95 | 10 | 419 | 456 |
| 448 | 456 | 9 | HLLIGSSGL | 364 | B*1502 | 83 | 1.81 | 151 | 10 | 419 | 456 |
| 449 | 456 | 8 | LLIGSSGL | 365 | B*0702 | 77 | 1.81 | 139 | 10 | 419 | 456 |
| | | | | | Cumulative BCI Class Iscore: | | | 11926 | | | |
| 422 | 432 | 11 | SSNLSWLSLDV | 324 | A*0201 | 38 | 1.41 | 53 | 11 | 422 | 459 |
| 424 | 432 | 9 | NLSWLSLDV | 325 | A*0201 | 29 | 1.41 | 41 | 11 | 422 | 459 |
| 425 | 432 | 8 | LSWLSLDV | 326 | A*0206 | 4 | 1.41 | 6 | 11 | 422 | 459 |
| 425 | 432 | 8 | LSWLSLDV | 326 | B*1302 | 1 | 1.41 | 2 | 11 | 422 | 459 |
| 425 | 432 | 8 | LSWLSLDV | 326 | B*5201 | 55 | 1.41 | 77 | 11 | 422 | 459 |
| 425 | 435 | 11 | LSWLSLDVSAA | 327 | B*5601 | 9 | 0.74 | 7 | 11 | 422 | 459 |
| 427 | 435 | 9 | WLSLDVSAA | 328 | A*0201 | 14 | 0.74 | 10 | 11 | 422 | 459 |
| 426 | 436 | 11 | SWLSLDVSAAF | 329 | A*2301 | 91 | 1.90 | 174 | 11 | 422 | 459 |
| 426 | 436 | 11 | SWLSLDVSAAF | 329 | A*2402 | 93 | 1.90 | 177 | 11 | 422 | 459 |
| 426 | 436 | 11 | SWLSLDVSAAF | 329 | A*2902 | 32 | 1.90 | 60 | 11 | 422 | 459 |
| 426 | 436 | 11 | SWLSLDVSAAF | 329 | B*1801 | 38 | 1.90 | 72 | 11 | 422 | 459 |

TABLE 4a-continued

Predicted HLA class I-restricted CD8+ cytotoxic T cell epitopes contained in SLP sequences from HBV polymerase protein.

HLA class I binding peptides in SLP sequences derived from HBV Polymerase protein

| Start | End | Length | Sequence [A] | SEQ ID NO: | HLA class I molecule | Class I-B score[B] | C-score[C] | Class I-BCI score[D] | SLP# | Peptide of invention (SLP) SLP Start | SLP End |
|---|---|---|---|---|---|---|---|---|---|---|---|
| 427 | 436 | 10 | WLSLDVSAAF | 330 | B*1501 | 72 | 1.90 | 137 | 11 | 422 | 459 |
| 427 | 436 | 10 | WLSLDVSAAF | 330 | B*1502 | 89 | 1.90 | 169 | 11 | 422 | 459 |
| 427 | 436 | 10 | WLSLDVSAAF | 330 | B*1525 | 54 | 1.90 | 103 | 11 | 422 | 459 |
| 428 | 436 | 9 | LSLDVSAAF | 331 | B*1501 | 73 | 1.90 | 140 | 11 | 422 | 459 |
| 428 | 436 | 9 | LSLDVSAAF | 331 | B*1525 | 76 | 1.90 | 145 | 11 | 422 | 459 |
| 428 | 436 | 9 | LSLDVSAAF | 331 | B*3501 | 69 | 1.90 | 132 | 11 | 422 | 459 |
| 428 | 436 | 9 | LSLDVSAAF | 331 | B*3503 | 51 | 1.90 | 98 | 11 | 422 | 459 |
| 428 | 436 | 9 | LSLDVSAAF | 331 | B*4601 | 75 | 1.90 | 144 | 11 | 422 | 459 |
| 428 | 436 | 9 | LSLDVSAAF | 331 | B*5801 | 63 | 1.90 | 119 | 11 | 422 | 459 |
| 427 | 437 | 11 | WLSLDVSAAFY | 332 | A*0101 | 74 | 1.81 | 133 | 11 | 422 | 459 |
| 427 | 437 | 11 | WLSLDVSAAFY | 332 | A*2601 | 38 | 1.81 | 69 | 11 | 422 | 459 |
| 427 | 437 | 11 | WLSLDVSAAFY | 332 | A*2902 | 75 | 1.81 | 135 | 11 | 422 | 459 |
| 427 | 437 | 11 | WLSLDVSAAFY | 332 | B*1502 | 22 | 1.81 | 40 | 11 | 422 | 459 |
| 428 | 437 | 10 | LSLDVSAAFY | 333 | A*0101 | 100 | 1.81 | 181 | 11 | 422 | 459 |
| 428 | 437 | 10 | LSLDVSAAFY | 333 | A*2902 | 83 | 1.81 | 149 | 11 | 422 | 459 |
| 428 | 437 | 10 | LSLDVSAAFY | 333 | A*3002 | 99 | 1.81 | 178 | 11 | 422 | 459 |
| 428 | 437 | 10 | LSLDVSAAFY | 333 | B*1501 | 22 | 1.81 | 40 | 11 | 422 | 459 |
| 428 | 437 | 10 | LSLDVSAAFY | 333 | B*4601 | 69 | 1.81 | 124 | 11 | 422 | 459 |
| 428 | 437 | 10 | LSLDVSAAFY | 333 | B*5802 | 57 | 1.81 | 102 | 11 | 422 | 459 |
| 429 | 437 | 9 | SLDVSAAFY | 334 | A*0101 | 85 | 1.81 | 153 | 11 | 422 | 459 |
| 429 | 437 | 9 | SLDVSAAFY | 334 | A*3002 | 59 | 1.81 | 107 | 11 | 422 | 459 |
| 430 | 437 | 8 | LDVSAAFY | 335 | B*3501 | 31 | 1.81 | 55 | 11 | 422 | 459 |
| 430 | 439 | 10 | LDVSAAFYHI | 336 | B*1301 | 96 | 1.79 | 171 | 11 | 422 | 459 |
| 430 | 439 | 10 | LDVSAAFYHI | 336 | B*1302 | 49 | 1.79 | 88 | 11 | 422 | 459 |
| 430 | 439 | 10 | LDVSAAFYHI | 336 | B*3701 | 57 | 1.79 | 102 | 11 | 422 | 459 |
| 430 | 439 | 10 | LDVSAAFYHI | 336 | B*4901 | 57 | 1.79 | 101 | 11 | 422 | 459 |
| 430 | 439 | 10 | LDVSAAFYHI | 336 | B*5201 | 98 | 1.79 | 175 | 11 | 422 | 459 |
| 431 | 439 | 9 | DVSAAFYHI | 337 | A*6802 | 46 | 1.79 | 81 | 11 | 422 | 459 |
| 432 | 439 | 8 | VSAAFYHI | 338 | A*3201 | 18 | 1.79 | 32 | 11 | 422 | 459 |
| 432 | 439 | 8 | VSAAFYHI | 338 | B*1302 | 28 | 1.79 | 50 | 11 | 422 | 459 |
| 432 | 439 | 8 | VSAAFYHI | 338 | B*5101 | 8 | 1.79 | 15 | 11 | 422 | 459 |
| 432 | 439 | 8 | VSAAFYHI | 338 | B*5201 | 96 | 1.79 | 172 | 11 | 422 | 459 |
| 432 | 439 | 8 | VSAAFYHI | 338 | B*5701 | 65 | 1.79 | 116 | 11 | 422 | 459 |
| 432 | 439 | 8 | VSAAFYHI | 338 | B*5801 | 64 | 1.79 | 115 | 11 | 422 | 459 |
| 432 | 439 | 8 | VSAAFYHI | 338 | B*5802 | 49 | 1.79 | 88 | 11 | 422 | 459 |

TABLE 4a-continued

Predicted HLA class I-restricted CD8+ cytotoxic T cell epitopes contained in SLP sequences from HBV polymerase protein.

HLA class I binding peptides in SLP sequences derived from HBV Polymerase protein

| Start | End | Length | Sequence[A] | SEQ ID NO: | HLA class I molecule | Class I-B score[B] | C-score[C] | Class I-BCI score[D] | SLP# | SLP Start | SLP End |
|---|---|---|---|---|---|---|---|---|---|---|---|
| 431 | 441 | 11 | DVSAAFYHIPL | 339 | A*2501 | 33 | 1.00 | 33 | 11 | 422 | 459 |
| 431 | 441 | 11 | DVSAAFYHIPL | 339 | A*2601 | 51 | 1.00 | 51 | 11 | 422 | 459 |
| 432 | 441 | 10 | VSAAFYHIPL | 340 | A*6802 | 35 | 1.00 | 35 | 11 | 422 | 459 |
| 432 | 441 | 10 | VSAAFYHIPL | 340 | B*5802 | 14 | 1.00 | 15 | 11 | 422 | 459 |
| 433 | 441 | 9 | SAAFYHIPL | 341 | B*1402 | 79 | 1.00 | 79 | 11 | 422 | 459 |
| 433 | 441 | 9 | SAAFYHIPL | 341 | B*3503 | 34 | 1.00 | 34 | 11 | 422 | 459 |
| 434 | 441 | 8 | AAFYHIPL | 342 | B*0801 | 64 | 1.00 | 65 | 11 | 422 | 459 |
| 434 | 441 | 8 | AAFYHIPL | 342 | B*1402 | 57 | 1.00 | 57 | 11 | 422 | 459 |
| 434 | 441 | 8 | AAFYHIPL | 342 | B*3801 | 6 | 1.00 | 6 | 11 | 422 | 459 |
| 434 | 441 | 8 | AAFYHIPL | 342 | B*3901 | 32 | 1.00 | 33 | 11 | 422 | 459 |
| 434 | 441 | 8 | AAFYHIPL | 342 | B*4801 | 63 | 1.00 | 64 | 11 | 422 | 459 |
| 433 | 442 | 10 | SAAFYHIPLH | 343 | A*3001 | 83 | 0.25 | 20 | 11 | 422 | 459 |
| 434 | 444 | 11 | AAFYHIPLHPA | 344 | A*3001 | 11 | 0.89 | 10 | 11 | 422 | 459 |
| 434 | 444 | 11 | AAFYHIPLHPA | 344 | B*5501 | 20 | 0.89 | 18 | 11 | 422 | 459 |
| 434 | 444 | 11 | AAFYHIPLHPA | 344 | B*5601 | 21 | 0.89 | 18 | 11 | 422 | 459 |
| 437 | 444 | 8 | YHIPLHPA | 345 | B*1402 | 19 | 0.89 | 17 | 11 | 422 | 459 |
| 437 | 444 | 8 | YHIPLHPA | 345 | B*3901 | 87 | 0.89 | 78 | 11 | 422 | 459 |
| 437 | 445 | 9 | YHIPLHPAA | 346 | B*1402 | 18 | 0.62 | 11 | 11 | 422 | 459 |
| 436 | 446 | 11 | FYHIPLHPAAM | 347 | A*2402 | 19 | 1.63 | 31 | 11 | 422 | 459 |
| 437 | 446 | 10 | YHIPLHPAAM | 348 | B*1402 | 99 | 1.63 | 161 | 11 | 422 | 459 |
| 437 | 446 | 10 | YHIPLHPAAM | 348 | B*3503 | 74 | 1.63 | 121 | 11 | 422 | 459 |
| 437 | 446 | 10 | YHIPLHPAAM | 348 | B*3801 | 86 | 1.63 | 140 | 11 | 422 | 459 |
| 437 | 446 | 10 | YHIPLHPAAM | 348 | B*3901 | 100 | 1.63 | 163 | 11 | 422 | 459 |
| 438 | 446 | 9 | HIPLHPAAM | 349 | A*2501 | 73 | 1.63 | 120 | 11 | 422 | 459 |
| 438 | 446 | 9 | HIPLHPAAM | 349 | B*1402 | 3 | 1.63 | 5 | 11 | 422 | 459 |
| 439 | 446 | 8 | IPLHPAAM | 350 | B*1402 | 86 | 1.63 | 140 | 11 | 422 | 459 |
| 439 | 446 | 8 | IPLHPAAM | 350 | B*3503 | 93 | 1.63 | 152 | 11 | 422 | 459 |
| 439 | 446 | 8 | IPLHPAAM | 350 | B*5101 | 55 | 1.63 | 90 | 11 | 422 | 459 |
| 439 | 446 | 8 | IPLHPAAM | 350 | B*5301 | 64 | 1.63 | 104 | 11 | 422 | 459 |
| 439 | 446 | 8 | IPLHPAAM | 350 | B*5501 | 85 | 1.63 | 138 | 11 | 422 | 459 |
| 439 | 446 | 8 | IPLHPAAM | 350 | B*5601 | 73 | 1.63 | 119 | 11 | 422 | 459 |
| 439 | 449 | 11 | IPLHPAAMPHL | 351 | B*0702 | 58 | 1.61 | 93 | 11 | 422 | 459 |
| 439 | 449 | 11 | IPLHPAAMPHL | 351 | B*1402 | 31 | 1.61 | 50 | 11 | 422 | 459 |
| 439 | 449 | 11 | IPLHPAAMPHL | 351 | B*3503 | 32 | 1.61 | 52 | 11 | 422 | 459 |

TABLE 4a-continued

Predicted HLA class I-restricted CD8+ cytotoxic T cell epitopes contained in SLP sequences from HBV polymerase protein.

HLA class I binding peptides in SLP sequences derived from HBV Polymerase protein

| Start | End | Length | Sequence[A] | SEQ ID NO: | HLA class I molecule | Class I-B score[B] | C-score[C] | Class I-BCI score[D] | SLP# | SLP Start | SLP End |
|---|---|---|---|---|---|---|---|---|---|---|---|
| 439 | 449 | 11 | IPLHPAAMPHL | 351 | B*5101 | 53 | 1.61 | 86 | 11 | 422 | 459 |
| 439 | 449 | 11 | IPLHPAAMPHL | 351 | B*5501 | 38 | 1.61 | 62 | 11 | 422 | 459 |
| 441 | 449 | 9 | LHPAAMPHL | 352 | B*3801 | 76 | 1.61 | 121 | 11 | 422 | 459 |
| 442 | 449 | 8 | HPAAMPHL | 353 | B*1402 | 85 | 1.61 | 136 | 11 | 422 | 459 |
| 442 | 449 | 8 | HPAAMPHL | 353 | B*3503 | 73 | 1.61 | 117 | 11 | 422 | 459 |
| 442 | 449 | 8 | HPAAMPHL | 353 | B*3901 | 53 | 1.61 | 85 | 11 | 422 | 459 |
| 442 | 449 | 8 | HPAAMPHL | 353 | B*5101 | 48 | 1.61 | 78 | 11 | 422 | 459 |
| 442 | 449 | 8 | HPAAMPHL | 353 | B*5301 | 38 | 1.61 | 61 | 11 | 422 | 459 |
| 442 | 449 | 8 | HPAAMPHL | 353 | B*5501 | 55 | 1.61 | 88 | 11 | 422 | 459 |
| 442 | 449 | 8 | HPAAMPHL | 353 | B*5601 | 29 | 1.61 | 47 | 11 | 422 | 459 |
| 441 | 450 | 10 | LHPAAMPHLL | 354 | B*3801 | 67 | 1.81 | 122 | 11 | 422 | 459 |
| 442 | 450 | 9 | HPAAMPHLL | 355 | B*0702 | 70 | 1.81 | 126 | 11 | 422 | 459 |
| 442 | 450 | 9 | HPAAMPHLL | 355 | B*1402 | 93 | 1.81 | 168 | 11 | 422 | 459 |
| 442 | 450 | 9 | HPAAMPHLL | 355 | B*3501 | 29 | 1.81 | 53 | 11 | 422 | 459 |
| 442 | 450 | 9 | HPAAMPHLL | 355 | B*3503 | 85 | 1.81 | 154 | 11 | 422 | 459 |
| 442 | 450 | 9 | HPAAMPHLL | 355 | B*3901 | 97 | 1.81 | 176 | 11 | 422 | 459 |
| 442 | 450 | 9 | HPAAMPHLL | 355 | B*5301 | 33 | 1.81 | 59 | 11 | 422 | 459 |
| 442 | 450 | 9 | HPAAMPHLL | 355 | B*5501 | 72 | 1.81 | 130 | 11 | 422 | 459 |
| 442 | 450 | 9 | HPAAMPHLL | 355 | B*5601 | 58 | 1.81 | 104 | 11 | 422 | 459 |
| 441 | 451 | 11 | LHPAAMPHLLI | 356 | B*3801 | 61 | 0.84 | 51 | 11 | 422 | 459 |
| 442 | 451 | 10 | HPAAMPHLLI | 357 | B*1402 | 71 | 0.84 | 59 | 11 | 422 | 459 |
| 442 | 451 | 10 | HPAAMPHLLI | 357 | B*3503 | 72 | 0.84 | 60 | 11 | 422 | 459 |
| 442 | 451 | 10 | HPAAMPHLLI | 357 | B*3901 | 38 | 0.84 | 31 | 11 | 422 | 459 |
| 442 | 451 | 10 | HPAAMPHLLI | 357 | B*5201 | 61 | 0.84 | 51 | 11 | 422 | 459 |
| 442 | 451 | 10 | HPAAMPHLLI | 357 | B*5301 | 36 | 0.84 | 30 | 11 | 422 | 459 |
| 442 | 451 | 10 | HPAAMPHLLI | 357 | B*5501 | 84 | 0.84 | 70 | 11 | 422 | 459 |
| 442 | 451 | 10 | HPAAMPHLLI | 357 | B*5601 | 90 | 0.84 | 75 | 11 | 422 | 459 |
| 444 | 451 | 8 | AAMPHLLI | 358 | A*3201 | 59 | 0.84 | 49 | 11 | 422 | 459 |
| 444 | 451 | 8 | AAMPHLLI | 358 | B*1302 | 35 | 0.84 | 29 | 11 | 422 | 459 |
| 444 | 451 | 8 | AAMPHLLI | 358 | B*5101 | 47 | 0.84 | 39 | 11 | 422 | 459 |
| 444 | 451 | 8 | AAMPHLLI | 358 | B*5201 | 94 | 0.84 | 79 | 11 | 422 | 459 |
| 444 | 451 | 8 | AAMPHLLI | 358 | B*5801 | 37 | 0.84 | 31 | 11 | 422 | 459 |
| 442 | 452 | 11 | HPAAMPHLLIG | 359 | A*0201 | 51 | 0.32 | 16 | 11 | 422 | 459 |
| 442 | 452 | 11 | HPAAMPHLLIG | 359 | A*0206 | 38 | 0.32 | 12 | 11 | 422 | 459 |
| 446 | 453 | 8 | MPHLLIGS | 360 | A*6802 | 16 | 0.77 | 12 | 11 | 422 | 459 |

TABLE 4a-continued

Predicted HLA class I-restricted CD8+ cytotoxic T cell epitopes contained in SLP sequences from HBV polymerase protein.

HLA class I binding peptides in SLP sequences derived from HBV Polymerase protein

| Start | End | Length | Sequence [A] | SEQ ID NO: | HLA class I molecule | Class I-B score[B] | C-score[C] | Class I-BCI score[D] | SLP# | Peptide of invention (SLP) SLP Start | SLP End |
|---|---|---|---|---|---|---|---|---|---|---|---|
| 446 | 453 | 8 | MPHLLIGS | 360 | B*5601 | 28 | 0.77 | 22 | 11 | 422 | 459 |
| 446 | 454 | 9 | MPHLLIGSS | 361 | B*5501 | 37 | 0.26 | 10 | 11 | 422 | 459 |
| 446 | 454 | 9 | MPHLLIGSS | 361 | B*5601 | 41 | 0.26 | 11 | 11 | 422 | 459 |
| 446 | 455 | 10 | MPHLLIGSSG | 362 | B*0702 | 35 | 0.11 | 4 | 11 | 422 | 459 |
| 446 | 455 | 10 | MPHLLIGSSG | 362 | B*3501 | 40 | 0.11 | 4 | 11 | 422 | 459 |
| 446 | 455 | 10 | MPHLLIGSSG | 362 | B*5501 | 3 | 0.11 | 0 | 11 | 422 | 459 |
| 446 | 455 | 10 | MPHLLIGSSG | 362 | B*5601 | 18 | 0.11 | 2 | 11 | 422 | 459 |
| 446 | 456 | 11 | MPHLLIGSSGL | 363 | B*0702 | 93 | 1.81 | 168 | 11 | 422 | 459 |
| 446 | 456 | 11 | MPHLLIGSSGL | 363 | B*0801 | 44 | 1.81 | 80 | 11 | 422 | 459 |
| 446 | 456 | 11 | MPHLLIGSSGL | 363 | B*1402 | 92 | 1.81 | 167 | 11 | 422 | 459 |
| 446 | 456 | 11 | MPHLLIGSSGL | 363 | B*3501 | 27 | 1.81 | 48 | 11 | 422 | 459 |
| 446 | 456 | 11 | MPHLLIGSSGL | 363 | B*3503 | 70 | 1.81 | 127 | 11 | 422 | 459 |
| 446 | 456 | 11 | MPHLLIGSSGL | 363 | B*3901 | 62 | 1.81 | 113 | 11 | 422 | 459 |
| 446 | 456 | 11 | MPHLLIGSSGL | 363 | B*5101 | 40 | 1.81 | 73 | 11 | 422 | 459 |
| 446 | 456 | 11 | MPHLLIGSSGL | 363 | B*5301 | 18 | 1.81 | 33 | 11 | 422 | 459 |
| 446 | 456 | 11 | MPHLLIGSSGL | 363 | B*5501 | 71 | 1.81 | 129 | 11 | 422 | 459 |
| 446 | 456 | 11 | MPHLLIGSSGL | 363 | B*5601 | 53 | 1.81 | 95 | 11 | 422 | 459 |
| 448 | 456 | 9 | HLLIGSSGL | 364 | B*1502 | 83 | 1.81 | 151 | 11 | 422 | 459 |
| 449 | 456 | 8 | LLIGSSGL | 365 | B*0702 | 77 | 1.81 | 139 | 11 | 422 | 459 |
| 448 | 458 | 11 | HLLIGSSGLSR | 366 | A*0301 | 11 | 1.14 | 13 | 11 | 422 | 459 |
| 448 | 458 | 11 | HLLIGSSGLSR | 366 | A*3101 | 19 | 1.14 | 22 | 11 | 422 | 459 |
| 448 | 458 | 11 | HLLIGSSGLSR | 366 | A*3303 | 17 | 1.14 | 19 | 11 | 422 | 459 |
| 448 | 458 | 11 | HLLIGSSGLSR | 366 | A*7401 | 62 | 1.14 | 71 | 11 | 422 | 459 |
| 449 | 458 | 10 | LLIGSSGLSR | 367 | A*7401 | 6 | 1.14 | 7 | 11 | 422 | 459 |
| 449 | 459 | 11 | LLIGSSGLSRY | 368 | A*2501 | 57 | 1.50 | 85 | 11 | 422 | 459 |
| 449 | 459 | 11 | LLIGSSGLSRY | 368 | A*2601 | 77 | 1.50 | 115 | 11 | 422 | 459 |
| 449 | 459 | 11 | LLIGSSGLSRY | 368 | A*2902 | 89 | 1.50 | 133 | 11 | 422 | 459 |
| 449 | 459 | 11 | LLIGSSGLSRY | 368 | A*3002 | 66 | 1.50 | 99 | 11 | 422 | 459 |
| 449 | 459 | 11 | LLIGSSGLSRY | 368 | B*1501 | 81 | 1.50 | 122 | 11 | 422 | 459 |
| 449 | 459 | 11 | LLIGSSGLSRY | 368 | B*1502 | 57 | 1.50 | 86 | 11 | 422 | 459 |
| 449 | 459 | 11 | LLIGSSGLSRY | 368 | B*1525 | 41 | 1.50 | 61 | 11 | 422 | 459 |
| 449 | 459 | 11 | LLIGSSGLSRY | 368 | B*4601 | 28 | 1.50 | 42 | 11 | 422 | 459 |
| 450 | 459 | 10 | LIGSSGLSRY | 369 | A*0101 | 45 | 1.50 | 68 | 11 | 422 | 459 |
| 450 | 459 | 10 | LIGSSGLSRY | 369 | A*3002 | 35 | 1.50 | 53 | 11 | 422 | 459 |

TABLE 4a-continued

Predicted HLA class I-restricted CD8+ cytotoxic T cell epitopes contained in SLP sequences from HBV polymerase protein.

HLA class I binding peptides in SLP sequences derived from HBV Polymerase protein

| Start | End | Length | Sequence [A] | SEQ ID NO: | HLA class I molecule | Class I-B score[B] | C-score[C] | Class I-BCI score[D] | Peptide of invention (SLP) | | |
|---|---|---|---|---|---|---|---|---|---|---|---|
| | | | | | | | | | SLP# | SLP Start | SLP End |
| 451 | 459 | 9 | IGSSGLSRY | 370 | A*3002 | 94 | 1.50 | 141 | 11 | 422 | 459 |
| 452 | 459 | 8 | GSSGLSRY | 371 | A*0101 | 83 | 1.50 | 124 | 11 | 422 | 459 |
| 452 | 459 | 8 | GSSGLSRY | 371 | A*3002 | 77 | 1.50 | 116 | 11 | 422 | 459 |
| | | | | | Cumulative Class I-BCI score: | | | 12384 | | | |
| 427 | 435 | 9 | WLSLDVSAA | 328 | A*0201 | 14 | 0.74 | 10 | 12 | 427 | 459 |
| 426 | 436 | 11 | SWLSLDVSAAF | 329 | A*2301 | 91 | 1.90 | 174 | 12 | 427 | 459 |
| 426 | 436 | 11 | SWLSLDVSAAF | 329 | A*2402 | 93 | 1.90 | 177 | 12 | 427 | 459 |
| 426 | 436 | 11 | SWLSLDVSAAF | 329 | A*2902 | 32 | 1.90 | 60 | 12 | 427 | 459 |
| 426 | 436 | 11 | SWLSLDVSAAF | 329 | B*1801 | 38 | 1.90 | 72 | 12 | 427 | 459 |
| 427 | 436 | 10 | WLSLDVSAAF | 330 | B*1501 | 72 | 1.90 | 137 | 12 | 427 | 459 |
| 427 | 436 | 10 | WLSLDVSAAF | 330 | B*1502 | 89 | 1.90 | 169 | 12 | 427 | 459 |
| 427 | 436 | 10 | WLSLDVSAAF | 330 | B*1525 | 54 | 1.90 | 103 | 12 | 427 | 459 |
| 428 | 436 | 9 | LSLDVSAAF | 331 | B*1501 | 73 | 1.90 | 140 | 12 | 427 | 459 |
| 428 | 436 | 9 | LSLDVSAAF | 331 | B*1525 | 76 | 1.90 | 145 | 12 | 427 | 459 |
| 428 | 436 | 9 | LSLDVSAAF | 331 | B*3501 | 69 | 1.90 | 132 | 12 | 427 | 459 |
| 428 | 436 | 9 | LSLDVSAAF | 331 | B*3503 | 51 | 1.90 | 98 | 12 | 427 | 459 |
| 428 | 436 | 9 | LSLDVSAAF | 331 | B*4601 | 75 | 1.90 | 144 | 12 | 427 | 459 |
| 428 | 436 | 9 | LSLDVSAAF | 331 | B*5801 | 63 | 1.90 | 119 | 12 | 427 | 459 |
| 427 | 437 | 11 | WLSLDVSAAFY | 332 | A*0101 | 74 | 1.81 | 133 | 12 | 427 | 459 |
| 427 | 437 | 11 | WLSLDVSAAFY | 332 | A*2601 | 38 | 1.81 | 69 | 12 | 427 | 459 |
| 427 | 437 | 11 | WLSLDVSAAFY | 332 | A*2902 | 75 | 1.81 | 135 | 12 | 427 | 459 |
| 427 | 437 | 11 | WLSLDVSAAFY | 332 | B*1502 | 22 | 1.81 | 40 | 12 | 427 | 459 |
| 428 | 437 | 10 | LSLDVSAAFY | 333 | A*0101 | 100 | 1.81 | 181 | 12 | 427 | 459 |
| 428 | 437 | 10 | LSLDVSAAFY | 333 | A*2902 | 83 | 1.81 | 149 | 12 | 427 | 459 |
| 428 | 437 | 10 | LSLDVSAAFY | 333 | A*3002 | 99 | 1.81 | 178 | 12 | 427 | 459 |
| 428 | 437 | 10 | LSLDVSAAFY | 333 | B*1501 | 22 | 1.81 | 40 | 12 | 427 | 459 |
| 428 | 437 | 10 | LSLDVSAAFY | 333 | B*4601 | 69 | 1.81 | 124 | 12 | 427 | 459 |
| 428 | 437 | 10 | LSLDVSAAFY | 333 | B*5802 | 57 | 1.81 | 102 | 12 | 427 | 459 |
| 429 | 437 | 9 | SLDVSAAFY | 334 | A*0101 | 85 | 1.81 | 153 | 12 | 427 | 459 |
| 429 | 437 | 9 | SLDVSAAFY | 334 | A*3002 | 59 | 1.81 | 107 | 12 | 427 | 459 |
| 430 | 437 | 8 | LDVSAAFY | 335 | B*3501 | 31 | 1.81 | 55 | 12 | 427 | 459 |
| 430 | 439 | 10 | LDVSAAFYHI | 336 | B*1301 | 96 | 1.79 | 171 | 12 | 427 | 459 |
| 430 | 439 | 10 | LDVSAAFYHI | 336 | B*1302 | 49 | 1.79 | 88 | 12 | 427 | 459 |
| 430 | 439 | 10 | LDVSAAFYHI | 336 | B*3701 | 57 | 1.79 | 102 | 12 | 427 | 459 |
| 430 | 439 | 10 | LDVSAAFYHI | 336 | B*4901 | 57 | 1.79 | 101 | 12 | 427 | 459 |

TABLE 4a-continued

Predicted HLA class I-restricted CD8+ cytotoxic T cell epitopes contained in SLP sequences from HBV polymerase protein.

HLA class I binding peptides in SLP sequences derived from HBV Polymerase protein

| Start | End | Length | Sequence[A] | SEQ ID NO: | HLA class I molecule | Class I-B score[B] | C-score[C] | Class I-BCI score[D] | SLP# | Peptide of invention (SLP) SLP Start | SLP End |
|---|---|---|---|---|---|---|---|---|---|---|---|
| 430 | 439 | 10 | LDVSAAFYHI | 336 | B*5201 | 98 | 1.79 | 175 | 12 | 427 | 459 |
| 431 | 439 | 9 | DVSAAFYHI | 337 | A*6802 | 46 | 1.79 | 81 | 12 | 427 | 459 |
| 432 | 439 | 8 | VSAAFYHI | 338 | A*3201 | 18 | 1.79 | 32 | 12 | 427 | 459 |
| 432 | 439 | 8 | VSAAFYHI | 338 | B*1302 | 28 | 1.79 | 50 | 12 | 427 | 459 |
| 432 | 439 | 8 | VSAAFYHI | 338 | B*5101 | 8 | 1.79 | 15 | 12 | 427 | 459 |
| 432 | 439 | 8 | VSAAFYHI | 338 | B*5201 | 96 | 1.79 | 172 | 12 | 427 | 459 |
| 432 | 439 | 8 | VSAAFYHI | 338 | B*5701 | 65 | 1.79 | 116 | 12 | 427 | 459 |
| 432 | 439 | 8 | VSAAFYHI | 338 | B*5801 | 64 | 1.79 | 115 | 12 | 427 | 459 |
| 432 | 439 | 8 | VSAAFYHI | 338 | B*5802 | 49 | 1.79 | 88 | 12 | 427 | 459 |
| 431 | 441 | 11 | DVSAAFYHIPL | 339 | A*2501 | 33 | 1.00 | 33 | 12 | 427 | 459 |
| 431 | 441 | 11 | DVSAAFYHIPL | 339 | A*2601 | 51 | 1.00 | 51 | 12 | 427 | 459 |
| 432 | 441 | 10 | VSAAFYHIPL | 340 | A*6802 | 35 | 1.00 | 35 | 12 | 427 | 459 |
| 432 | 441 | 10 | VSAAFYHIPL | 340 | B*5802 | 14 | 1.00 | 15 | 12 | 427 | 459 |
| 433 | 441 | 9 | SAAFYHIPL | 341 | B*1402 | 79 | 1.00 | 79 | 12 | 427 | 459 |
| 433 | 441 | 9 | SAAFYHIPL | 341 | B*3503 | 34 | 1.00 | 34 | 12 | 427 | 459 |
| 434 | 441 | 8 | AAFYHIPL | 342 | B*0801 | 64 | 1.00 | 65 | 12 | 427 | 459 |
| 434 | 441 | 8 | AAFYHIPL | 342 | B*1402 | 57 | 1.00 | 57 | 12 | 427 | 459 |
| 434 | 441 | 8 | AAFYHIPL | 342 | B*3801 | 6 | 1.00 | 6 | 12 | 427 | 459 |
| 434 | 441 | 8 | AAFYHIPL | 342 | B*3901 | 32 | 1.00 | 33 | 12 | 427 | 459 |
| 434 | 441 | 8 | AAFYHIPL | 342 | B*4801 | 63 | 1.00 | 64 | 12 | 427 | 459 |
| 433 | 442 | 10 | SAAFYHIPLH | 343 | A*3001 | 83 | 0.25 | 20 | 12 | 427 | 459 |
| 434 | 444 | 11 | AAFYHIPLHPA | 344 | A*3001 | 11 | 0.89 | 10 | 12 | 427 | 459 |
| 434 | 444 | 11 | AAFYHIPLHPA | 344 | B*5501 | 20 | 0.89 | 18 | 12 | 427 | 459 |
| 434 | 444 | 11 | AAFYHIPLHPA | 344 | B*5601 | 21 | 0.89 | 18 | 12 | 427 | 459 |
| 437 | 444 | 8 | YHIPLHPA | 345 | B*1402 | 19 | 0.89 | 17 | 12 | 427 | 459 |
| 437 | 444 | 8 | YHIPLHPA | 345 | B*3901 | 87 | 0.89 | 78 | 12 | 427 | 459 |
| 437 | 445 | 9 | YHIPLHPAA | 346 | B*1402 | 18 | 0.62 | 11 | 12 | 427 | 459 |
| 436 | 446 | 11 | FYHIPLHPAAM | 347 | A*2402 | 19 | 1.63 | 31 | 12 | 427 | 459 |
| 437 | 446 | 10 | YHIPLHPAAM | 348 | B*1402 | 99 | 1.63 | 161 | 12 | 427 | 459 |
| 437 | 446 | 10 | YHIPLHPAAM | 348 | B*3503 | 74 | 1.63 | 121 | 12 | 427 | 459 |
| 437 | 446 | 10 | YHIPLHPAAM | 348 | B*3801 | 86 | 1.63 | 140 | 12 | 427 | 459 |
| 437 | 446 | 10 | YHIPLHPAAM | 348 | B*3901 | 100 | 1.63 | 163 | 12 | 427 | 459 |
| 438 | 446 | 9 | HIPLHPAAM | 349 | A*2501 | 73 | 1.63 | 120 | 12 | 427 | 459 |
| 438 | 446 | 9 | HIPLHPAAM | 349 | B*1402 | 3 | 1.63 | 5 | 12 | 427 | 459 |
| 439 | 446 | 8 | IPLHPAAM | 350 | B*1402 | 86 | 1.63 | 140 | 12 | 427 | 459 |

TABLE 4a-continued

Predicted HLA class I-restricted CD8+ cytotoxic T cell epitopes contained in SLP sequences from HBV polymerase protein.

HLA class I binding peptides in SLP sequences derived from HBV Polymerase protein

| Start | End | Length | Sequence[A] | SEQ ID NO: | HLA class I molecule | Class I-B score[B] | C-score[C] | Class I-BCI score[D] | Peptide of invention (SLP) | | |
|---|---|---|---|---|---|---|---|---|---|---|---|
| | | | | | | | | | SLP# | SLP Start | SLP End |
| 439 | 446 | 8 | IPLHPAAM | 350 | B*3503 | 93 | 1.63 | 152 | 12 | 427 | 459 |
| 439 | 446 | 8 | IPLHPAAM | 350 | B*5101 | 55 | 1.63 | 90 | 12 | 427 | 459 |
| 439 | 446 | 8 | IPLHPAAM | 350 | B*5301 | 64 | 1.63 | 104 | 12 | 427 | 459 |
| 439 | 446 | 8 | IPLHPAAM | 350 | B*5501 | 85 | 1.63 | 138 | 12 | 427 | 459 |
| 439 | 446 | 8 | IPLHPAAM | 350 | B*5601 | 73 | 1.63 | 119 | 12 | 427 | 459 |
| 439 | 449 | 11 | IPLHPAAMPHL | 351 | B*0702 | 58 | 1.61 | 93 | 12 | 427 | 459 |
| 439 | 449 | 11 | IPLHPAAMPHL | 351 | B*1402 | 31 | 1.61 | 50 | 12 | 427 | 459 |
| 439 | 449 | 11 | IPLHPAAMPHL | 351 | B*3503 | 32 | 1.61 | 52 | 12 | 427 | 459 |
| 439 | 449 | 11 | IPLHPAAMPHL | 351 | B*5101 | 53 | 1.61 | 86 | 12 | 427 | 459 |
| 439 | 449 | 11 | IPLHPAAMPHL | 351 | B*5501 | 38 | 1.61 | 62 | 12 | 427 | 459 |
| 441 | 449 | 9 | LHPAAMPHL | 352 | B*3801 | 76 | 1.61 | 121 | 12 | 427 | 459 |
| 442 | 449 | 8 | HPAAMPHL | 353 | B*1402 | 85 | 1.61 | 136 | 12 | 427 | 459 |
| 442 | 449 | 8 | HPAAMPHL | 353 | B*3503 | 73 | 1.61 | 117 | 12 | 427 | 459 |
| 442 | 449 | 8 | HPAAMPHL | 353 | B*3901 | 53 | 1.61 | 85 | 12 | 427 | 459 |
| 442 | 449 | 8 | HPAAMPHL | 353 | B*5101 | 48 | 1.61 | 78 | 12 | 427 | 459 |
| 442 | 449 | 8 | HPAAMPHL | 353 | B*5301 | 38 | 1.61 | 61 | 12 | 427 | 459 |
| 442 | 449 | 8 | HPAAMPHL | 353 | B*5501 | 55 | 1.61 | 88 | 12 | 427 | 459 |
| 442 | 449 | 8 | HPAAMPHL | 353 | B*5601 | 29 | 1.61 | 47 | 12 | 427 | 459 |
| 441 | 450 | 10 | LHPAAMPHLL | 354 | B*3801 | 67 | 1.81 | 122 | 12 | 427 | 459 |
| 442 | 450 | 9 | HPAAMPHLL | 355 | B*0702 | 70 | 1.81 | 126 | 12 | 427 | 459 |
| 442 | 450 | 9 | HPAAMPHLL | 355 | B*1402 | 93 | 1.81 | 168 | 12 | 427 | 459 |
| 442 | 450 | 9 | HPAAMPHLL | 355 | B*3501 | 29 | 1.81 | 53 | 12 | 427 | 459 |
| 442 | 450 | 9 | HPAAMPHLL | 355 | B*3503 | 85 | 1.81 | 154 | 12 | 427 | 459 |
| 442 | 450 | 9 | HPAAMPHLL | 355 | B*3901 | 97 | 1.81 | 176 | 12 | 427 | 459 |
| 442 | 450 | 9 | HPAAMPHLL | 355 | B*5301 | 33 | 1.81 | 59 | 12 | 427 | 459 |
| 442 | 450 | 9 | HPAAMPHLL | 355 | B*5501 | 72 | 1.81 | 130 | 12 | 427 | 459 |
| 442 | 450 | 9 | HPAAMPHLL | 355 | B*5601 | 58 | 1.81 | 104 | 12 | 427 | 459 |
| 441 | 451 | 11 | LHPAAMPHLLI | 356 | B*3801 | 61 | 0.84 | 51 | 12 | 427 | 459 |
| 442 | 451 | 10 | HPAAMPHLLI | 357 | B*1402 | 71 | 0.84 | 59 | 12 | 427 | 459 |
| 442 | 451 | 10 | HPAAMPHLLI | 357 | B*3503 | 72 | 0.84 | 60 | 12 | 427 | 459 |
| 442 | 451 | 10 | HPAAMPHLLI | 357 | B*3901 | 38 | 0.84 | 31 | 12 | 427 | 459 |
| 442 | 451 | 10 | HPAAMPHLLI | 357 | B*5201 | 61 | 0.84 | 51 | 12 | 427 | 459 |
| 442 | 451 | 10 | HPAAMPHLLI | 357 | B*5301 | 36 | 0.84 | 30 | 12 | 427 | 459 |
| 442 | 451 | 10 | HPAAMPHLLI | 357 | B*5501 | 84 | 0.84 | 70 | 12 | 427 | 459 |

TABLE 4a-continued

Predicted HLA class I-restricted CD8+ cytotoxic T cell epitopes contained in SLP sequences from HBV polymerase protein.

HLA class I binding peptides in SLP sequences derived from HBV Polymerase protein

| Start | End | Length | Sequence[A] | SEQ ID NO: | HLA class I molecule | Class I-B score[B] | C-score[C] | Class I-BCI score[D] | Peptide of invention (SLP) | | |
|---|---|---|---|---|---|---|---|---|---|---|---|
| | | | | | | | | | SLP# | SLP Start | SLP End |
| 442 | 451 | 10 | HPAAMPHLLI | 357 | B*5601 | 90 | 0.84 | 75 | 12 | 427 | 459 |
| 444 | 451 | 8 | AAMPHLLI | 358 | A*3201 | 59 | 0.84 | 49 | 12 | 427 | 459 |
| 444 | 451 | 8 | AAMPHLLI | 358 | B*1302 | 35 | 0.84 | 29 | 12 | 427 | 459 |
| 444 | 451 | 8 | AAMPHLLI | 358 | B*5101 | 47 | 0.84 | 39 | 12 | 427 | 459 |
| 444 | 451 | 8 | AAMPHLLI | 358 | B*5201 | 94 | 0.84 | 79 | 12 | 427 | 459 |
| 444 | 451 | 8 | AAMPHLLI | 358 | B*5801 | 37 | 0.84 | 31 | 12 | 427 | 459 |
| 442 | 452 | 11 | HPAAMPHLLIG | 359 | A*0201 | 51 | 0.32 | 16 | 12 | 427 | 459 |
| 442 | 452 | 11 | HPAAMPHLLIG | 359 | A*0206 | 38 | 0.32 | 12 | 12 | 427 | 459 |
| 446 | 453 | 8 | MPHLLIGS | 360 | A*6802 | 16 | 0.77 | 12 | 12 | 427 | 459 |
| 446 | 453 | 8 | MPHLLIGS | 360 | B*5601 | 28 | 0.77 | 22 | 12 | 427 | 459 |
| 446 | 454 | 9 | MPHLLIGSS | 361 | B*5501 | 37 | 0.26 | 10 | 12 | 427 | 459 |
| 446 | 454 | 9 | MPHLLIGSS | 361 | B*5601 | 41 | 0.23 | 11 | 12 | 427 | 459 |
| 446 | 455 | 10 | MPHLLIGSSG | 362 | B*0702 | 35 | 0.11 | 4 | 12 | 427 | 459 |
| 446 | 455 | 10 | MPHLLIGSSG | 362 | B*3501 | 40 | 0.11 | 4 | 12 | 427 | 459 |
| 446 | 455 | 10 | MPHLLIGSSG | 362 | B*5501 | 3 | 0.11 | 0 | 12 | 427 | 459 |
| 446 | 455 | 10 | MPHLLIGSSG | 362 | B*5601 | 18 | 0.11 | 2 | 12 | 427 | 459 |
| 446 | 456 | 11 | MPHLLIGSSGL | 363 | B*0702 | 93 | 1.81 | 168 | 12 | 427 | 459 |
| 446 | 456 | 11 | MPHLLIGSSGL | 363 | B*0801 | 44 | 1.81 | 80 | 12 | 427 | 459 |
| 446 | 456 | 11 | MPHLLIGSSGL | 363 | B*1402 | 92 | 1.81 | 167 | 12 | 427 | 459 |
| 446 | 456 | 11 | MPHLLIGSSGL | 363 | B*3501 | 27 | 1.81 | 48 | 12 | 427 | 459 |
| 446 | 456 | 11 | MPHLLIGSSGL | 363 | B*3503 | 70 | 1.81 | 127 | 12 | 427 | 459 |
| 446 | 456 | 11 | MPHLLIGSSGL | 363 | B*3901 | 62 | 1.81 | 113 | 12 | 427 | 459 |
| 446 | 456 | 11 | MPHLLIGSSGL | 363 | B*5101 | 40 | 1.81 | 73 | 12 | 427 | 459 |
| 446 | 456 | 11 | MPHLLIGSSGL | 363 | B*5301 | 18 | 1.81 | 33 | 12 | 427 | 459 |
| 446 | 456 | 11 | MPHLLIGSSGL | 363 | B*5501 | 71 | 1.81 | 129 | 12 | 427 | 459 |
| 446 | 456 | 11 | MPHLLIGSSGL | 363 | B*5601 | 53 | 1.81 | 95 | 12 | 427 | 459 |
| 448 | 456 | 9 | HLLIGSSGL | 364 | B*1502 | 83 | 1.81 | 151 | 12 | 427 | 459 |
| 449 | 456 | 8 | LLIGSSGL | 365 | B*0702 | 77 | 1.81 | 139 | 12 | 427 | 459 |
| 448 | 458 | 11 | HLLIGSSGLSR | 366 | A*0301 | 11 | 1.14 | 13 | 12 | 427 | 459 |
| 448 | 458 | 11 | HLLIGSSGLSR | 366 | A*3101 | 19 | 1.14 | 22 | 12 | 427 | 459 |
| 448 | 458 | 11 | HLLIGSSGLSR | 366 | A*3303 | 17 | 1.14 | 19 | 12 | 427 | 459 |
| 448 | 458 | 11 | HLLIGSSGLSR | 366 | A*7401 | 62 | 1.14 | 71 | 12 | 427 | 459 |
| 449 | 458 | 10 | LLIGSSGLSR | 367 | A*7401 | 6 | 1.14 | 7 | 12 | 427 | 459 |
| 449 | 459 | 11 | LLIGSSGLSRY | 368 | A*2501 | 57 | 1.50 | 85 | 12 | 427 | 459 |
| 449 | 459 | 11 | LLIGSSGLSRY | 368 | A*2601 | 77 | 1.50 | 115 | 12 | 427 | 459 |

TABLE 4a-continued

Predicted HLA class I-restricted CD8+ cytotoxic T cell epitopes contained in SLP sequences from HBV polymerase protein.

HLA class I binding peptides in SLP sequences derived from HBV Polymerase protein

| Start | End | Length | Sequence[A] | SEQ ID NO: | HLA class I molecule | Class I-B score[B] | C-score[C] | Class I-BCI score[D] | SLP# | Peptide of invention (SLP) SLP Start | SLP End |
|---|---|---|---|---|---|---|---|---|---|---|---|
| 449 | 459 | 11 | LLIGSSGLSRY | 368 | A*2902 | 89 | 1.50 | 133 | 12 | 427 | 459 |
| 449 | 459 | 11 | LLIGSSGLSRY | 368 | A*3002 | 66 | 1.50 | 99 | 12 | 427 | 459 |
| 449 | 459 | 11 | LLIGSSGLSRY | 368 | B*1501 | 81 | 1.50 | 122 | 12 | 427 | 459 |
| 449 | 459 | 11 | LLIGSSGLSRY | 368 | B*1502 | 57 | 1.50 | 86 | 12 | 427 | 459 |
| 449 | 459 | 11 | LLIGSSGLSRY | 368 | B*1525 | 41 | 1.50 | 61 | 12 | 427 | 459 |
| 449 | 459 | 11 | LLIGSSGLSRY | 368 | B*4601 | 28 | 1.50 | 42 | 12 | 427 | 459 |
| 450 | 459 | 10 | LIGSSGLSRY | 369 | A*0101 | 45 | 1.50 | 68 | 12 | 427 | 459 |
| 450 | 459 | 10 | LIGSSGLSRY | 369 | A*3002 | 35 | 1.50 | 53 | 12 | 427 | 459 |
| 451 | 459 | 9 | IGSSGLSRY | 370 | A*3002 | 94 | 1.50 | 141 | 12 | 427 | 459 |
| 452 | 459 | 8 | GSSGLSRY | 371 | A*0101 | 83 | 1.50 | 124 | 12 | 427 | 459 |
| 452 | 459 | 8 | GSSGLSRY | 371 | A*3002 | 77 | 1.50 | 116 | 12 | 427 | 459 |
|  |  |  |  |  | Cumulative Class I-BCI score: |  |  | 12198 |  |  |  |
| 485 | 492 | 8 | SRQLYVSL | 372 | B*1402 | 84 | 1.59 | 134 | 13 | 481 | 514 |
| 485 | 492 | 8 | SRQLYVSL | 372 | B*2702 | 89 | 1.59 | 142 | 13 | 481 | 514 |
| 485 | 492 | 8 | SRQLYVSL | 372 | B*3901 | 86 | 1.59 | 137 | 13 | 481 | 514 |
| 485 | 492 | 8 | SRQLYVSL | 372 | B*4801 | 2 | 1.59 | 3 | 13 | 481 | 514 |
| 484 | 493 | 10 | CSRQLYVSLM | 373 | B*4601 | 43 | 1.55 | 66 | 13 | 481 | 514 |
| 485 | 493 | 9 | SRQLYVSLM | 374 | B*2702 | 88 | 1.55 | 137 | 13 | 481 | 514 |
| 485 | 493 | 9 | SRQLYVSLM | 374 | B*2705 | 85 | 1.55 | 132 | 13 | 481 | 514 |
| 486 | 493 | 8 | RQLYVSLM | 375 | A*3201 | 53 | 1.55 | 82 | 13 | 481 | 514 |
| 486 | 493 | 8 | RQLYVSLM | 375 | B*1301 | 85 | 1.55 | 131 | 13 | 481 | 514 |
| 486 | 493 | 8 | RQLYVSLM | 375 | B*1302 | 13 | 1.55 | 20 | 13 | 481 | 514 |
| 486 | 493 | 8 | RQLYVSLM | 375 | B*1402 | 15 | 1.55 | 24 | 13 | 481 | 514 |
| 486 | 493 | 8 | RQLYVSLM | 375 | B*1501 | 48 | 1.55 | 75 | 13 | 481 | 514 |
| 486 | 493 | 8 | RQLYVSLM | 375 | B*1525 | 75 | 1.55 | 116 | 13 | 481 | 514 |
| 486 | 493 | 8 | RQLYVSLM | 375 | B*2702 | 73 | 1.55 | 114 | 13 | 481 | 514 |
| 486 | 493 | 8 | RQLYVSLM | 375 | B*3901 | 51 | 1.55 | 79 | 13 | 481 | 514 |
| 486 | 493 | 8 | RQLYVSLM | 375 | B*4801 | 94 | 1.55 | 146 | 13 | 481 | 514 |
| 485 | 494 | 10 | SRQLYVSLML | 376 | B*1402 | 49 | 1.55 | 77 | 13 | 481 | 514 |
| 485 | 494 | 10 | SRQLYVSLML | 376 | B*2702 | 87 | 1.55 | 135 | 13 | 481 | 514 |
| 485 | 494 | 10 | SRQLYVSLML | 376 | B*2705 | 88 | 1.55 | 137 | 13 | 481 | 514 |
| 485 | 494 | 10 | SRQLYVSLML | 376 | B*3901 | 52 | 1.55 | 81 | 13 | 481 | 514 |
| 486 | 494 | 9 | RQLYVSLML | 377 | A*0206 | 19 | 1.55 | 29 | 13 | 481 | 514 |
| 486 | 494 | 9 | RQLYVSLML | 377 | A*3201 | 79 | 1.55 | 122 | 13 | 481 | 514 |
| 486 | 494 | 9 | RQLYVSLML | 377 | B*1301 | 80 | 1.55 | 125 | 13 | 481 | 514 |

TABLE 4a-continued

Predicted HLA class I-restricted CD8+ cytotoxic T cell epitopes contained in SLP sequences from HBV polymerase protein.

HLA class I binding peptides in SLP sequences derived from HBV Polymerase protein

| Start | End | Length | Sequence[A] | SEQ ID NO: | HLA class I molecule | Class I-B score[B] | C-score[C] | Class I-BCI score[D] | SLP# | Peptide of invention (SLP) SLP Start | SLP End |
|---|---|---|---|---|---|---|---|---|---|---|---|
| 486 | 494 | 9 | RQLYVSLML | 377 | B*1302 | 21 | 1.55 | 33 | 13 | 481 | 514 |
| 486 | 494 | 9 | RQLYVSLML | 377 | B*2702 | 72 | 1.55 | 112 | 13 | 481 | 514 |
| 486 | 494 | 9 | RQLYVSLML | 377 | B*2705 | 52 | 1.55 | 81 | 13 | 481 | 514 |
| 486 | 494 | 9 | RQLYVSLML | 377 | B*4001 | 52 | 1.55 | 81 | 13 | 481 | 514 |
| 486 | 494 | 9 | RQLYVSLML | 377 | B*4801 | 96 | 1.55 | 149 | 13 | 481 | 514 |
| 487 | 494 | 8 | QLYVSLML | 378 | A*0201 | 58 | 1.55 | 90 | 13 | 481 | 514 |
| 485 | 495 | 11 | SRQLYVSLMLL | 379 | B*1402 | 16 | 1.34 | 22 | 13 | 481 | 514 |
| 485 | 495 | 11 | SRQLYVSLMLL | 379 | B*2702 | 98 | 1.34 | 131 | 13 | 481 | 514 |
| 485 | 495 | 11 | SRQLYVSLMLL | 379 | B*2705 | 25 | 1.34 | 34 | 13 | 481 | 514 |
| 486 | 495 | 10 | RQLYVSLMLL | 380 | A*0206 | 48 | 1.34 | 64 | 13 | 481 | 514 |
| 486 | 495 | 10 | RQLYVSLMLL | 380 | B*1301 | 87 | 1.34 | 117 | 13 | 481 | 514 |
| 486 | 495 | 10 | RQLYVSLMLL | 380 | B*1302 | 34 | 1.34 | 45 | 13 | 481 | 514 |
| 486 | 495 | 10 | RQLYVSLMLL | 380 | B*2702 | 86 | 1.34 | 115 | 13 | 481 | 514 |
| 486 | 495 | 10 | RQLYVSLMLL | 380 | B*3801 | 10 | 1.34 | 14 | 13 | 481 | 514 |
| 486 | 495 | 10 | RQLYVSLMLL | 380 | B*3901 | 43 | 1.34 | 57 | 13 | 481 | 514 |
| 486 | 495 | 10 | RQLYVSLMLL | 380 | B*4801 | 100 | 1.34 | 134 | 13 | 481 | 514 |
| 488 | 495 | 8 | LYVSLMLL | 381 | A*2301 | 72 | 1.34 | 97 | 13 | 481 | 514 |
| 488 | 495 | 8 | LYVSLMLL | 381 | A*2402 | 72 | 1.34 | 96 | 13 | 481 | 514 |
| 488 | 495 | 8 | LYVSLMLL | 381 | B*0702 | 91 | 1.34 | 122 | 13 | 481 | 514 |
| 486 | 496 | 11 | RQLYVSLMLLY | 382 | A*0301 | 61 | 1.80 | 109 | 13 | 481 | 514 |
| 486 | 496 | 11 | RQLYVSLMLLY | 382 | B*1501 | 47 | 1.80 | 84 | 13 | 481 | 514 |
| 486 | 496 | 11 | RQLYVSLMLLY | 382 | B*1525 | 68 | 1.80 | 122 | 13 | 481 | 514 |
| 486 | 496 | 11 | RQLYVSLMLLY | 382 | B*2702 | 84 | 1.80 | 152 | 13 | 481 | 514 |
| 486 | 496 | 11 | RQLYVSLMLLY | 382 | B*2705 | 76 | 1.80 | 137 | 13 | 481 | 514 |
| 487 | 496 | 10 | QLYVSLMLLY | 383 | B*4403 | 44 | 1.80 | 79 | 13 | 481 | 514 |
| 488 | 496 | 9 | LYVSLMLLY | 384 | A*2902 | 98 | 1.80 | 177 | 13 | 481 | 514 |
| 489 | 496 | 8 | YVSLMLLY | 385 | A*0101 | 94 | 1.80 | 170 | 13 | 481 | 514 |
| 489 | 496 | 8 | YVSLMLLY | 385 | A*2501 | 90 | 1.80 | 162 | 13 | 481 | 514 |
| 489 | 496 | 8 | YVSLMLLY | 385 | A*2601 | 97 | 1.80 | 176 | 13 | 481 | 514 |
| 489 | 496 | 8 | YVSLMLLY | 385 | A*3002 | 87 | 1.80 | 157 | 13 | 481 | 514 |
| 489 | 496 | 8 | YVSLMLLY | 385 | B*3501 | 88 | 1.80 | 159 | 13 | 481 | 514 |
| 489 | 496 | 8 | YVSLMLLY | 385 | B*4601 | 56 | 1.80 | 100 | 13 | 481 | 514 |
| 487 | 497 | 11 | QLYVSLMLLYK | 386 | A*1101 | 85 | 1.07 | 91 | 13 | 481 | 514 |
| 487 | 497 | 11 | QLYVSLMLLYK | 386 | A*7401 | 61 | 1.07 | 65 | 13 | 481 | 514 |

TABLE 4a-continued

Predicted HLA class I-restricted CD8⁺ cytotoxic T cell epitopes contained in SLP sequences from HBV polymerase protein.

HLA class I binding peptides in SLP sequences derived from HBV Polymerase protein

| Start | End | Length | Sequence $^A$ | SEQ ID NO: | HLA class I molecule | Class I-B score$^B$ | C-score$^C$ | Class I-BCI score$^D$ | SLP# | Peptide of invention (SLP) SLP Start | SLP End |
|---|---|---|---|---|---|---|---|---|---|---|---|
| 488 | 497 | 10 | LYVSLMLLYK | 387 | A*0301 | 25 | 1.07 | 26 | 13 | 481 | 514 |
| 489 | 497 | 9 | YVSLMLLYK | 388 | A*0301 | 67 | 1.07 | 72 | 13 | 481 | 514 |
| 489 | 497 | 9 | YVSLMLLYK | 388 | A*1101 | 91 | 1.07 | 98 | 13 | 481 | 514 |
| 489 | 497 | 9 | YVSLMLLYK | 388 | A*6801 | 66 | 1.07 | 71 | 13 | 481 | 514 |
| 489 | 497 | 9 | YVSLMLLYK | 388 | A*7401 | 12 | 1.07 | 13 | 13 | 481 | 514 |
| 490 | 497 | 8 | VSLMLLYK | 389 | A*0301 | 80 | 1.07 | 86 | 13 | 481 | 514 |
| 490 | 497 | 8 | VSLMLLYK | 389 | A*1101 | 98 | 1.07 | 105 | 13 | 481 | 514 |
| 490 | 497 | 8 | VSLMLLYK | 389 | A*7401 | 35 | 1.07 | 38 | 13 | 481 | 514 |
| 489 | 499 | 11 | YVSLMLLYKTY | 390 | A*0101 | 81 | 1.86 | 151 | 13 | 481 | 514 |
| 489 | 499 | 11 | YVSLMLLYKTY | 390 | A*2501 | 55 | 1.86 | 102 | 13 | 481 | 514 |
| 489 | 499 | 11 | YVSLMLLYKTY | 390 | A*2601 | 74 | 1.86 | 138 | 13 | 481 | 514 |
| 489 | 499 | 11 | YVSLMLLYKTY | 390 | A*2902 | 86 | 1.86 | 159 | 13 | 481 | 514 |
| 489 | 499 | 11 | YVSLMLLYKTY | 390 | A*3002 | 42 | 1.86 | 78 | 13 | 481 | 514 |
| 489 | 499 | 11 | YVSLMLLYKTY | 390 | B*1502 | 31 | 1.86 | 58 | 13 | 481 | 514 |
| 489 | 499 | 11 | YVSLMLLYKTY | 390 | B*4601 | 13 | 1.86 | 24 | 13 | 481 | 514 |
| 490 | 499 | 10 | VSLMLLYKTY | 391 | A*0101 | 75 | 1.86 | 140 | 13 | 481 | 514 |
| 490 | 499 | 10 | VSLMLLYKTY | 391 | A*3002 | 48 | 1.86 | 89 | 13 | 481 | 514 |
| 490 | 499 | 10 | VSLMLLYKTY | 391 | B*5802 | 38 | 1.86 | 70 | 13 | 481 | 514 |
| 492 | 499 | 8 | LMLLYKTY | 392 | A*2902 | 52 | 1.86 | 97 | 13 | 481 | 514 |
| 492 | 499 | 8 | LMLLYKTY | 392 | B*1525 | 19 | 1.86 | 35 | 13 | 481 | 514 |
| 492 | 499 | 8 | LMLLYKTY | 392 | B*3501 | 57 | 1.86 | 106 | 13 | 481 | 514 |
| 491 | 500 | 10 | SLMLLYKTYG | 393 | A*0201 | 9 | 0.13 | 1 | 13 | 481 | 514 |
| 491 | 501 | 11 | SLMLLYKTYGW | 394 | A*3201 | 68 | 1.93 | 132 | 13 | 481 | 514 |
| 492 | 501 | 10 | LMLLYKTYGW | 395 | A*2301 | 17 | 1.93 | 33 | 13 | 481 | 514 |
| 492 | 501 | 10 | LMLLYKTYGW | 395 | B*5301 | 28 | 1.93 | 54 | 13 | 481 | 514 |
| 492 | 501 | 10 | LMLLYKTYGW | 395 | B*5802 | 36 | 1.93 | 70 | 13 | 481 | 514 |
| 493 | 501 | 9 | MLLYKTYGW | 396 | A*3201 | 92 | 1.93 | 179 | 13 | 481 | 514 |
| 493 | 501 | 9 | MLLYKTYGW | 396 | B*5701 | 36 | 1.93 | 70 | 13 | 481 | 514 |
| 493 | 501 | 9 | MLLYKTYGW | 396 | B*5801 | 31 | 1.93 | 59 | 13 | 481 | 514 |
| 494 | 501 | 8 | LLYKTYGW | 397 | A*3201 | 50 | 1.93 | 97 | 13 | 481 | 514 |
| 494 | 501 | 8 | LLYKTYGW | 397 | B*5701 | 47 | 1.93 | 91 | 13 | 481 | 514 |
| 494 | 501 | 8 | LLYKTYGW | 397 | B*5801 | 53 | 1.93 | 102 | 13 | 481 | 514 |
| 494 | 501 | 8 | LLYKTYGW | 397 | B*5802 | 6 | 1.93 | 11 | 13 | 481 | 514 |
| 492 | 502 | 11 | LMLLYKTYGWK | 398 | A*0206 | 15 | 0.71 | 10 | 13 | 481 | 514 |
| 492 | 502 | 11 | LMLLYKTYGWK | 398 | A*0301 | 79 | 0.71 | 56 | 13 | 481 | 514 |

TABLE 4a-continued

Predicted HLA class I-restricted CD8+ cytotoxic T cell epitopes contained in SLP sequences from HBV polymerase protein.

HLA class I binding peptides in SLP sequences derived from HBV Polymerase protein

| Start | End | Length | Sequence [A] | SEQ ID NO: | HLA class I molecule | Class I-B score[B] | C-score[C] | Class I-BCI score[D] | SLP# | Peptide of invention (SLP) S TABLE 4a-continued Predicted HLA class I-restricted CD8+ cytotoxic T cell epitopes contained in SLP sequences from HBV polymerase protein.

HLA class I binding peptides in SLP sequences derived from HBV Polymerase protein

| Start | End | Length | Sequence [A] | SEQ ID NO: | HLA class I molecule | Class I-B score[B] | C-score[C] | Class I-BCI score[D] | Peptide of invention (SLP) | | |
|---|---|---|---|---|---|---|---|---|---|---|---|
| | | | | | | | | | SLP# | SLP Start | SLP End |
| 498 | 506 | 9 | TYGWKLHLY | 414 | A*2402 | 37 | 1.90 | 70 | 13 | 481 | 514 |
| 498 | 506 | 9 | TYGWKLHLY | 414 | A*2902 | 90 | 1.90 | 172 | 13 | 481 | 514 |
| 498 | 506 | 9 | TYGWKLHLY | 414 | A*3002 | 70 | 1.90 | 134 | 13 | 481 | 514 |
| 499 | 506 | 8 | YGWKLHLY | 415 | A*2902 | 97 | 1.90 | 184 | 13 | 481 | 514 |
| 499 | 506 | 8 | YGWKLHLY | 415 | A*3002 | 76 | 1.90 | 145 | 13 | 481 | 514 |
| 499 | 506 | 8 | YGWKLHLY | 415 | B*3501 | 55 | 1.90 | 104 | 13 | 481 | 514 |
| 500 | 510 | 11 | GWKLHLYSHPI | 416 | B*0801 | 32 | 0.99 | 32 | 13 | 481 | 514 |
| 501 | 510 | 10 | WKLHLYSHPI | 417 | B*1301 | 54 | 0.99 | 53 | 13 | 481 | 514 |
| 501 | 510 | 10 | WKLHLYSHPI | 417 | B*1302 | 27 | 0.99 | 27 | 13 | 481 | 514 |
| 501 | 510 | 10 | WKLHLYSHPI | 417 | B*3701 | 43 | 0.99 | 42 | 13 | 481 | 514 |
| 501 | 510 | 10 | WKLHLYSHPI | 417 | B*3901 | 69 | 0.99 | 68 | 13 | 481 | 514 |
| 501 | 510 | 10 | WKLHLYSHPI | 417 | B*5201 | 78 | 0.99 | 78 | 13 | 481 | 514 |
| 502 | 510 | 9 | KLHLYSHPI | 418 | A*0201 | 49 | 0.99 | 48 | 13 | 481 | 514 |
| 502 | 510 | 9 | KLHLYSHPI | 418 | A*3201 | 77 | 0.99 | 77 | 13 | 481 | 514 |
| 503 | 510 | 8 | LHLYSHPI | 419 | B*1402 | 78 | 0.99 | 77 | 13 | 481 | 514 |
| 503 | 510 | 8 | LHLYSHPI | 419 | B*2702 | 10 | 0.99 | 10 | 13 | 481 | 514 |
| 503 | 510 | 8 | LHLYSHPI | 419 | B*3801 | 92 | 0.99 | 91 | 13 | 481 | 514 |
| 503 | 510 | 8 | LHLYSHPI | 419 | B*5101 | 52 | 0.99 | 51 | 13 | 481 | 514 |
| 503 | 510 | 8 | LHLYSHPI | 419 | B*5201 | 84 | 0.99 | 84 | 13 | 481 | 514 |
| 502 | 511 | 10 | KLHLYSHPIV | 420 | A*0201 | 13 | 0.55 | 7 | 13 | 481 | 514 |
| 502 | 511 | 10 | KLHLYSHPIV | 420 | A*3001 | 98 | 0.55 | 54 | 13 | 481 | 514 |
| 503 | 511 | 9 | LHLYSHPIV | 421 | B*5101 | 3 | 0.55 | 2 | 13 | 481 | 514 |
| 504 | 511 | 8 | HLYSHPIV | 422 | A*0201 | 56 | 0.55 | 30 | 13 | 481 | 514 |
| 504 | 511 | 8 | HLYSHPIV | 422 | B*0801 | 25 | 0.55 | 14 | 13 | 481 | 514 |
| 502 | 512 | 11 | KLHLYSHPIVL | 423 | A*3201 | 41 | 1.95 | 80 | 13 | 481 | 514 |
| 502 | 512 | 11 | KLHLYSHPIVL | 423 | B*0801 | 27 | 1.95 | 53 | 13 | 481 | 514 |
| 502 | 512 | 11 | KLHLYSHPIVL | 423 | B*4801 | 56 | 1.95 | 109 | 13 | 481 | 514 |
| 503 | 512 | 10 | LHLYSHPIVL | 424 | B*1402 | 91 | 1.95 | 177 | 13 | 481 | 514 |
| 503 | 512 | 10 | LHLYSHPIVL | 424 | B*3801 | 78 | 1.95 | 151 | 13 | 481 | 514 |
| 503 | 512 | 10 | LHLYSHPIVL | 424 | B*3901 | 83 | 1.95 | 162 | 13 | 481 | 514 |
| 504 | 512 | 9 | HLYSHPIVL | 425 | A*0201 | 18 | 1.95 | 35 | 13 | 481 | 514 |
| 504 | 512 | 9 | HLYSHPIVL | 425 | B*1402 | 83 | 1.95 | 162 | 13 | 481 | 514 |
| 504 | 512 | 9 | HLYSHPIVL | 425 | B*1502 | 24 | 1.95 | 47 | 13 | 481 | 514 |
| 504 | 512 | 9 | HLYSHPIVL | 425 | B*3901 | 91 | 1.95 | 177 | 13 | 481 | 514 |
| 505 | 512 | 8 | LYSHPIVL | 426 | A*2301 | 22 | 1.95 | 44 | 13 | 481 | 514 |

TABLE 4a-continued

Predicted HLA class I-restricted CD8+ cytotoxic T cell epitopes contained in SLP sequences from HBV polymerase protein.

HLA class I binding peptides in SLP sequences derived from HBV Polymerase protein

| Start | End | Length | Sequence[A] | SEQ ID NO: | HLA class I molecule | Class I-B score[B] | C-score[C] | Class I-BCI score[D] | SLP# | SLP Start | SLP End |
|---|---|---|---|---|---|---|---|---|---|---|---|
| 505 | 512 | 8 | LYSHPIVL | 426 | A*2402 | 46 | 1.95 | 89 | 13 | 481 | 514 |
| 504 | 514 | 11 | HLYSHPIVLGF | 427 | A*2501 | 43 | 1.62 | 69 | 13 | 481 | 514 |
| 504 | 514 | 11 | HLYSHPIVLGF | 427 | A*2601 | 10 | 1.62 | 17 | 13 | 481 | 514 |
| 504 | 514 | 11 | HLYSHPIVLGF | 427 | A*3201 | 100 | 1.62 | 162 | 13 | 481 | 514 |
| 504 | 514 | 11 | HLYSHPIVLGF | 427 | B*1402 | 30 | 1.62 | 49 | 13 | 481 | 514 |
| 504 | 514 | 11 | HLYSHPIVLGF | 427 | B*1501 | 80 | 1.62 | 129 | 13 | 481 | 514 |
| 504 | 514 | 11 | HLYSHPIVLGF | 427 | B*1502 | 96 | 1.62 | 156 | 13 | 481 | 514 |
| 504 | 514 | 11 | HLYSHPIVLGF | 427 | B*1525 | 90 | 1.62 | 145 | 13 | 481 | 514 |
| 505 | 514 | 10 | LYSHPIVLGF | 428 | A*2301 | 84 | 1.62 | 136 | 13 | 481 | 514 |
| 505 | 514 | 10 | LYSHPIVLGF | 428 | A*2402 | 86 | 1.62 | 139 | 13 | 481 | 514 |
| 505 | 514 | 10 | LYSHPIVLGF | 428 | A*2902 | 76 | 1.62 | 123 | 13 | 481 | 514 |
| 506 | 514 | 9 | YSHPIVLGF | 429 | B*4601 | 64 | 1.62 | 103 | 13 | 481 | 514 |
| 506 | 514 | 9 | YSHPIVLGF | 429 | B*5801 | 71 | 1.62 | 115 | 13 | 481 | 514 |
| 506 | 514 | 9 | YSHPIVLGF | 429 | B*5802 | 59 | 1.62 | 96 | 13 | 481 | 514 |
| | | | | | Cumulative BCI Class Iscore: | | | 15733 | | | |
| 524 | 531 | 8 | SPFLLAQF | 432 | B*1402 | 67 | 1.59 | 106 | 14 | 524 | 559 |
| 524 | 531 | 8 | SPFLLAQF | 432 | B*1502 | 6 | 1.59 | 9 | 14 | 524 | 559 |
| 524 | 531 | 8 | SPFLLAQF | 432 | B*3503 | 61 | 1.59 | 97 | 14 | 524 | 559 |
| 524 | 531 | 8 | SPFLLAQF | 432 | B*5301 | 72 | 1.59 | 115 | 14 | 524 | 559 |
| 524 | 532 | 9 | SPFLLAQFT | 433 | B*5601 | 17 | 0.30 | 5 | 14 | 524 | 559 |
| 524 | 533 | 10 | SPFLLAQFTS | 434 | A*3201 | 5 | 0.76 | 3 | 14 | 524 | 559 |
| 524 | 533 | 10 | SPFLLAQFTS | 434 | B*3501 | 1 | 0.76 | 1 | 14 | 524 | 559 |
| 524 | 533 | 10 | SPFLLAQFTS | 434 | B*5601 | 27 | 0.76 | 21 | 14 | 524 | 559 |
| 526 | 533 | 8 | FLLAQFTS | 435 | A*0201 | 42 | 0.76 | 32 | 14 | 524 | 559 |
| 524 | 534 | 11 | SPFLLAQFTSA | 436 | B*0702 | 46 | 0.92 | 43 | 14 | 524 | 559 |
| 524 | 534 | 11 | SPFLLAQFTSA | 436 | B*3503 | 3 | 0.92 | 2 | 14 | 524 | 559 |
| 524 | 534 | 11 | SPFLLAQFTSA | 436 | B*5101 | 25 | 0.92 | 23 | 14 | 524 | 559 |
| 524 | 534 | 11 | SPFLLAQFTSA | 436 | B*5501 | 98 | 0.92 | 90 | 14 | 524 | 559 |
| 524 | 534 | 11 | SPFLLAQFTSA | 436 | B*5601 | 95 | 0.92 | 88 | 14 | 524 | 559 |
| 526 | 534 | 9 | FLLAQFTSA | 437 | A*0201 | 84 | 0.92 | 78 | 14 | 524 | 559 |
| 526 | 534 | 9 | FLLAQFTSA | 437 | A*0206 | 98 | 0.92 | 91 | 14 | 524 | 559 |
| 526 | 534 | 9 | FLLAQFTSA | 437 | B*0801 | 78 | 0.92 | 72 | 14 | 524 | 559 |
| 526 | 535 | 10 | FLLAQFTSAI | 438 | A*0201 | 76 | 0.94 | 71 | 14 | 524 | 559 |
| 526 | 535 | 10 | FLLAQFTSAI | 438 | A*0206 | 79 | 0.94 | 75 | 14 | 524 | 559 |
| 526 | 535 | 10 | FLLAQFTSAI | 438 | B*1302 | 11 | 0.94 | 11 | 14 | 524 | 559 |

TABLE 4a-continued

Predicted HLA class I-restricted CD8+ cytotoxic T cell epitopes contained in SLP sequences from HBV polymerase prot TABLE 4a-continued Predicted HLA class I-restricted CD8+ cytotoxic T cell epitopes contained in SLP sequences from HBV polymerase protein.

HLA

TABLE 4a-continued

Predicted HLA class I-restricted CD8+ cytotoxic T cell epitopes contained in SLP sequences from HBV polymerase protein.

HLA class I binding peptides in SLP sequences derived from HBV Polymerase protein

| Start | End | Length | Sequence[A] | SEQ ID NO: | HLA class I molecule | Class I-B score[B] | C-score[C] | Class I-BCI score[D] | Peptide of invention (SLP) SLP# | SLP Start | SLP End |
|---|---|---|---|---|---|---|---|---|---|---|---|
| 538 | 545 | 8 | VVRRAFPH | 458 | A*3001 | 10 | 0.14 | 1 | 14 | 524 | 559 |
| 537 | 546 | 10 | SVVRRAFPHC | 459 | A*3001 | 28 | 0.21 | 6 | 14 | 524 | 559 |
| 537 | 547 | 11 | SVVRRAFPHCL | 460 | B*0801 | 71 | 1.96 | 140 | 14 | 524 | 559 |
| 539 | 547 | 9 | VRRAFPHCL | 461 | B*1402 | 28 | 1.96 | 56 | 14 | 524 | 559 |
| 539 | 547 | 9 | VRRAFPHCL | 461 | B*2702 | 51 | 1.96 | 99 | 14 | 524 | 559 |
| 539 | 547 | 9 | VRRAFPHCL | 461 | B*2705 | 3 | 1.96 | 6 | 14 | 524 | 559 |
| 540 | 547 | 8 | RRAFPHCL | 462 | B*1402 | 47 | 1.96 | 93 | 14 | 524 | 559 |
| 540 | 547 | 8 | RRAFPHCL | 462 | B*2702 | 96 | 1.96 | 189 | 14 | 524 | 559 |
| 540 | 547 | 8 | RRAFPHCL | 462 | B*2705 | 93 | 1.96 | 182 | 14 | 524 | 559 |
| 540 | 547 | 8 | RRAFPHCL | 462 | B*3901 | 9 | 1.96 | 18 | 14 | 524 | 559 |
| 540 | 547 | 8 | RRAFPHCL | 462 | B*4801 | 6 | 1.96 | 11 | 14 | 524 | 559 |
| 538 | 548 | 11 | VVRRAFPHCLA | 463 | A*3001 | 86 | 1.06 | 91 | 14 | 524 | 559 |
| 540 | 548 | 9 | RRAFPHCLA | 464 | B*2702 | 45 | 1.06 | 47 | 14 | 524 | 559 |
| 540 | 548 | 9 | RRAFPHCLA | 464 | B*2705 | 39 | 1.06 | 41 | 14 | 524 | 559 |
| 541 | 548 | 8 | RAFPHCLA | 465 | A*3001 | 68 | 1.06 | 72 | 14 | 524 | 559 |
| 540 | 549 | 10 | RRAFPHCLAF | 466 | B*2702 | 95 | 1.82 | 173 | 14 | 524 | 559 |
| 540 | 549 | 10 | RRAFPHCLAF | 466 | B*2705 | 91 | 1.82 | 165 | 14 | 524 | 559 |
| 541 | 549 | 9 | RAFPHCLAF | 467 | A*3201 | 73 | 1.82 | 132 | 14 | 524 | 559 |
| 541 | 549 | 9 | RAFPHCLAF | 467 | B*1301 | 79 | 1.82 | 143 | 14 | 524 | 559 |
| 541 | 549 | 9 | RAFPHCLAF | 467 | B*1402 | 66 | 1.82 | 119 | 14 | 524 | 559 |
| 541 | 549 | 9 | RAFPHCLAF | 467 | B*1501 | 84 | 1.82 | 153 | 14 | 524 | 559 |
| 541 | 549 | 9 | RAFPHCLAF | 467 | B*3501 | 68 | 1.82 | 124 | 14 | 524 | 559 |
| 541 | 549 | 9 | RAFPHCLAF | 467 | B*4601 | 97 | 1.82 | 176 | 14 | 524 | 559 |
| 541 | 549 | 9 | RAFPHCLAF | 467 | B*5201 | 75 | 1.82 | 135 | 14 | 524 | 559 |
| 541 | 549 | 9 | RAFPHCLAF | 467 | B*5701 | 59 | 1.82 | 107 | 14 | 524 | 559 |
| 541 | 549 | 9 | RAFPHCLAF | 467 | B*5801 | 81 | 1.82 | 148 | 14 | 524 | 559 |
| 542 | 549 | 8 | AFPHCLAF | 468 | A*2301 | 71 | 1.82 | 128 | 14 | 524 | 559 |
| 542 | 549 | 8 | AFPHCLAF | 468 | A*2402 | 70 | 1.82 | 128 | 14 | 524 | 559 |
| 543 | 550 | 8 | FPHCLAFS | 469 | B*3501 | 67 | 0.25 | 17 | 14 | 524 | 559 |
| 543 | 550 | 8 | FPHCLAFS | 469 | B*5501 | 17 | 0.25 | 4 | 14 | 524 | 559 |
| 543 | 550 | 8 | FPHCLAFS | 469 | B*5601 | 56 | 0.25 | 14 | 14 | 524 | 559 |
| 541 | 551 | 11 | RAFPHCLAFSY | 470 | A*0301 | 77 | 1.93 | 149 | 14 | 524 | 559 |
| 541 | 551 | 11 | RAFPHCLAFSY | 470 | A*3201 | 94 | 1.93 | 182 | 14 | 524 | 559 |
| 541 | 551 | 11 | RAFPHCLAFSY | 470 | B*1301 | 66 | 1.93 | 128 | 14 | 524 | 559 |

TABLE 4a-continued

Predicted HLA class I-restricted CD8+ cytotoxic T cell epitopes contained in SLP sequences from HBV polymerase protein.

HLA class I binding peptides in SLP sequences derived from HBV Polymerase protein

| Start | End | Length | Sequence[A] | SEQ ID NO: | HLA class I molecule | Class I-B score[B] | C-score[C] | Class I-BCI score[D] | SLP# | SLP Start | SLP End |
|---|---|---|---|---|---|---|---|---|---|---|---|
| 541 | 551 | 11 | RAFPHCLAFSY | 470 | B*1501 | 91 | 1.93 | 175 | 14 | 524 | 559 |
| 541 | 551 | 11 | RAFPHCLAFSY | 470 | B*1502 | 93 | 1.93 | 179 | 14 | 524 | 559 |
| 541 | 551 | 11 | RAFPHCLAFSY | 470 | B*1525 | 95 | 1.93 | 183 | 14 | 524 | 559 |
| 541 | 551 | 11 | RAFPHCLAFSY | 470 | B*5701 | 89 | 1.93 | 173 | 14 | 524 | 559 |
| 541 | 551 | 11 | RAFPHCLAFSY | 470 | B*5802 | 86 | 1.93 | 165 | 14 | 524 | 559 |
| 542 | 551 | 10 | AFPHCLAFSY | 471 | A*2902 | 94 | 1.93 | 181 | 14 | 524 | 559 |
| 543 | 551 | 9 | FPHCLAFSY | 472 | B*3501 | 97 | 1.93 | 188 | 14 | 524 | 559 |
| 543 | 551 | 9 | FPHCLAFSY | 472 | B*3503 | 91 | 1.93 | 175 | 14 | 524 | 559 |
| 543 | 551 | 9 | FPHCLAFSY | 472 | B*5301 | 98 | 1.93 | 190 | 14 | 524 | 559 |
| 543 | 551 | 9 | FPHCLAFSY | 472 | B*5501 | 83 | 1.93 | 160 | 14 | 524 | 559 |
| 542 | 552 | 11 | AFPHCLAFSYM | 473 | A*2402 | 4 | 1.02 | 4 | 14 | 524 | 559 |
| 543 | 552 | 10 | FPHCLAFSYM | 474 | B*0702 | 64 | 1.02 | 65 | 14 | 524 | 559 |
| 543 | 552 | 10 | FPHCLAFSYM | 474 | B*1402 | 90 | 1.02 | 92 | 14 | 524 | 559 |
| 543 | 552 | 10 | FPHCLAFSYM | 474 | B*3501 | 96 | 1.02 | 98 | 14 | 524 | 559 |
| 543 | 552 | 10 | FPHCLAFSYM | 474 | B*3503 | 99 | 1.02 | 100 | 14 | 524 | 559 |
| 543 | 552 | 10 | FPHCLAFSYM | 474 | B*3901 | 68 | 1.02 | 69 | 14 | 524 | 559 |
| 543 | 552 | 10 | FPHCLAFSYM | 474 | B*5101 | 98 | 1.02 | 100 | 14 | 524 | 559 |
| 543 | 552 | 10 | FPHCLAFSYM | 474 | B*5301 | 97 | 1.02 | 98 | 14 | 524 | 559 |
| 543 | 552 | 10 | FPHCLAFSYM | 474 | B*5501 | 97 | 1.02 | 98 | 14 | 524 | 559 |
| 543 | 552 | 10 | FPHCLAFSYM | 474 | B*5601 | 87 | 1.02 | 89 | 14 | 524 | 559 |
| 545 | 555 | 11 | HCLAFSYMDDV | 475 | A*0201 | 73 | 0.60 | 44 | 14 | 524 | 559 |
| 547 | 555 | 9 | LAFSYMDDV | 476 | B*5101 | 20 | 0.60 | 12 | 14 | 524 | 559 |
| 547 | 556 | 10 | LAFSYMDDVV | 477 | B*5201 | 51 | 0.34 | 17 | 14 | 524 | 559 |
| 549 | 556 | 8 | FSYMDDVV | 478 | B*4601 | 34 | 0.34 | 12 | 14 | 524 | 559 |
| 549 | 556 | 8 | FSYMDDVV | 478 | B*5101 | 23 | 0.34 | 8 | 14 | 524 | 559 |
| 549 | 556 | 8 | FSYMDDVV | 478 | B*5201 | 39 | 0.34 | 13 | 14 | 524 | 559 |
| 547 | 557 | 11 | LAFSYMDDVVL | 479 | B*3503 | 11 | 1.21 | 13 | 14 | 524 | 559 |
| 547 | 557 | 11 | LAFSYMDDVVL | 479 | B*3801 | 29 | 1.21 | 35 | 14 | 524 | 559 |
| 547 | 557 | 11 | LAFSYMDDVVL | 479 | B*3901 | 19 | 1.21 | 24 | 14 | 524 | 559 |
| 547 | 557 | 11 | LAFSYMDDVVL | 479 | B*4801 | 23 | 1.21 | 28 | 14 | 524 | 559 |
| 549 | 557 | 9 | FSYMDDVVL | 480 | B*3901 | 25 | 1.21 | 30 | 14 | 524 | 559 |
| 549 | 557 | 9 | FSYMDDVVL | 480 | B*4601 | 62 | 1.21 | 76 | 14 | 524 | 559 |
| 550 | 557 | 8 | SYMDDVVL | 481 | A*2301 | 38 | 1.21 | 46 | 14 | 524 | 559 |
| 550 | 557 | 8 | SYMDDVVL | 481 | A*2402 | 47 | 1.21 | 57 | 14 | 524 | 559 |
| 551 | 559 | 9 | YMDDVVLGA | 482 | A*0101 | 66 | 1.49 | 98 | 14 | 524 | 559 |

TABLE 4a-continued

Predicted HLA class I-restricted CD8+ cytotoxic T cell epitopes contained in SLP sequences from HBV polymerase protein.

HLA class I binding peptides in SLP sequences derived from HBV Polymerase protein

| | | | | SEQ ID | HLA class I | Class I-B | | Class I-BCI | Peptide of invention (SLP) | | |
|---|---|---|---|---|---|---|---|---|---|---|---|
| Start | End | Length | Sequence[A] | NO: | molecule | score[B] | C-score[C] | score[D] | SLP# | SLP Start | SLP End |
| 551 | 559 | 9 | YMDDVVLGA | 482 | A*0201 | 100 | 1.49 | 149 | 14 | 524 | 559 |
| 551 | 559 | 9 | YMDDVVLGA | 482 | A*0206 | 71 | 1.49 | 105 | 14 | 524 | 559 |
| 552 | 559 | 8 | MDDVVLGA | 483 | A*6802 | 34 | 1.49 | 50 | 14 | 524 | 559 |
| | | | | | Cumulative Class I-BCI score: | | | 12015 | | | |
| 526 | 533 | 8 | FLLAQFTS | 435 | A*0201 | 42 | 0.76 | 32 | 15 | 526 | 559 |
| 524 | 534 | 11 | SPFLLAQFTSA | 436 | B*0702 | 46 | 0.92 | 43 | 15 | 526 | 559 |
| 524 | 534 | 11 | SPFLLAQFTSA | 436 | B*3503 | 3 | 0.92 | 2 | 15 | 526 | 559 |
| 524 | 534 | 11 | SPFLLAQFTSA | 436 | B*5101 | 25 | 0.92 | 23 | 15 | 526 | 559 |
| 524 | 534 | 11 | SPFLLAQFTSA | 436 | B*5501 | 98 | 0.92 | 90 | 15 | 526 | 559 |
| 524 | 534 | 11 | SPFLLAQFTSA | 436 | B*5601 | 95 | 0.92 | 88 | 15 | 526 | 559 |
| 526 | 534 | 9 | FLLAQFTSA | 437 | A*0201 | 84 | 0.92 | 78 | 15 | 526 | 559 |
| 526 | 534 | 9 | FLLAQFTSA | 437 | A*0206 | 98 | 0.92 | 91 | 15 | 526 | 559 |
| 526 | 534 | 9 | FLLAQFTSA | 437 | B*0801 | 78 | 0.92 | 72 | 15 | 526 | 559 |
| 526 | 535 | 10 | FLLAQFTSAI | 438 | A*0201 | 76 | 0.94 | 71 | 15 | 526 | 559 |
| 526 | 535 | 10 | FLLAQFTSAI | 438 | A*0206 | 79 | 0.94 | 75 | 15 | 526 | 559 |
| 526 | 535 | 10 | FLLAQFTSAI | 438 | B*1302 | 11 | 0.94 | 11 | 15 | 526 | 559 |
| 526 | 535 | 10 | FLLAQFTSAI | 438 | B*3801 | 47 | 0.94 | 44 | 15 | 526 | 559 |
| 526 | 535 | 10 | FLLAQFTSAI | 438 | B*4601 | 11 | 0.94 | 11 | 15 | 526 | 559 |
| 526 | 535 | 10 | FLLAQFTSAI | 438 | B*5201 | 14 | 0.94 | 13 | 15 | 526 | 559 |
| 527 | 535 | 9 | LLAQFTSAI | 439 | A*3201 | 3 | 0.94 | 3 | 15 | 526 | 559 |
| 527 | 535 | 9 | LLAQFTSAI | 439 | B*1525 | 17 | 0.94 | 16 | 15 | 526 | 559 |
| 527 | 535 | 9 | LLAQFTSAI | 439 | B*5501 | 19 | 0.94 | 18 | 15 | 526 | 559 |
| 528 | 535 | 8 | LAQFTSAI | 440 | B*5101 | 62 | 0.94 | 58 | 15 | 526 | 559 |
| 528 | 535 | 8 | LAQFTSAI | 440 | B*5201 | 76 | 0.94 | 72 | 15 | 526 | 559 |
| 528 | 535 | 8 | LAQFTSAI | 440 | B*5301 | 5 | 0.94 | 5 | 15 | 526 | 559 |
| 527 | 537 | 11 | LLAQFTSAICS | 441 | A*6802 | 22 | 0.41 | 9 | 15 | 526 | 559 |
| 528 | 538 | 11 | LAQFTSAICSV | 442 | B*5101 | 13 | 1.40 | 19 | 15 | 526 | 559 |
| 528 | 538 | 11 | LAQFTSAICSV | 442 | B*5201 | 12 | 1.40 | 16 | 15 | 526 | 559 |
| 529 | 538 | 10 | AQFTSAICSV | 443 | A*0201 | 55 | 1.40 | 77 | 15 | 526 | 559 |
| 529 | 538 | 10 | AQFTSAICSV | 443 | A*0206 | 85 | 1.40 | 119 | 15 | 526 | 559 |
| 529 | 538 | 10 | AQFTSAICSV | 443 | B*1301 | 83 | 1.40 | 116 | 15 | 526 | 559 |
| 529 | 538 | 10 | AQFTSAICSV | 443 | B*1302 | 46 | 1.40 | 65 | 15 | 526 | 559 |
| 529 | 538 | 10 | AQFTSAICSV | 443 | B*3701 | 14 | 1.40 | 20 | 15 | 526 | 559 |
| 529 | 538 | 10 | AQFTSAICSV | 443 | B*3901 | 10 | 1.40 | 15 | 15 | 526 | 559 |
| 529 | 538 | 10 | AQFTSAICSV | 443 | B*4801 | 77 | 1.40 | 108 | 15 | 526 | 559 |

TABLE 4a-continued

Predicted HLA class I-restricted CD8+ cytotoxic T cell epitopes contained in SLP sequences from HBV polymerase protein.

HLA class I binding peptides in SLP sequences derived from HBV Polymerase protein

| Start | End | Length | Sequence [A] | SEQ ID NO: | HLA class I molecule | Class I-B score[B] | C-score[C] | Class I-BCI score[D] | Peptide of invention (SLP) SLP# | SLP Start | SLP End |
|---|---|---|---|---|---|---|---|---|---|---|---|
| 529 | 538 | 10 | AQFTSAICSV | 443 | B*4901 | 30 | 1.40 | 43 | 15 | 526 | 559 |
| 529 | 538 | 10 | AQFTSAICSV | 443 | B*5001 | 64 | 1.40 | 90 | 15 | 526 | 559 |
| 529 | 538 | 10 | AQFTSAICSV | 443 | B*5201 | 82 | 1.40 | 115 | 15 | 526 | 559 |
| 531 | 538 | 8 | FTSAICSV | 444 | A*2501 | 82 | 1.40 | 114 | 15 | 526 | 559 |
| 531 | 538 | 8 | FTSAICSV | 444 | A*2601 | 49 | 1.40 | 68 | 15 | 526 | 559 |
| 529 | 539 | 11 | AQFTSAICSVV | 445 | B*1301 | 75 | 1.34 | 100 | 15 | 526 | 559 |
| 529 | 539 | 11 | AQFTSAICSVV | 445 | B*1302 | 41 | 1.34 | 55 | 15 | 526 | 559 |
| 529 | 539 | 11 | AQFTSAICSVV | 445 | B*4002 | 20 | 1.34 | 27 | 15 | 526 | 559 |
| 529 | 539 | 11 | AQFTSAICSVV | 445 | B*4801 | 62 | 1.34 | 83 | 15 | 526 | 559 |
| 529 | 539 | 11 | AQFTSAICSVV | 445 | B*4901 | 26 | 1.34 | 35 | 15 | 526 | 559 |
| 529 | 539 | 11 | AQFTSAICSVV | 445 | B*5001 | 60 | 1.34 | 81 | 15 | 526 | 559 |
| 529 | 539 | 11 | AQFTSAICSVV | 445 | B*5201 | 53 | 1.34 | 71 | 15 | 526 | 559 |
| 531 | 539 | 9 | FTSAICSVV | 446 | A*6802 | 49 | 1.34 | 65 | 15 | 526 | 559 |
| 531 | 539 | 9 | FTSAICSVV | 446 | B*4601 | 31 | 1.34 | 42 | 15 | 526 | 559 |
| 531 | 539 | 9 | FTSAICSVV | 446 | B*5201 | 2 | 1.34 | 3 | 15 | 526 | 559 |
| 531 | 539 | 9 | FTSAICSVV | 446 | B*5601 | 4 | 1.34 | 5 | 15 | 526 | 559 |
| 530 | 540 | 11 | QFTSAICSVVR | 447 | A*3303 | 30 | 1.19 | 35 | 15 | 526 | 559 |
| 531 | 540 | 10 | FTSAICSVVR | 448 | A*3101 | 38 | 1.19 | 45 | 15 | 526 | 559 |
| 531 | 540 | 10 | FTSAICSVVR | 448 | A*3303 | 92 | 1.19 | 109 | 15 | 526 | 559 |
| 531 | 540 | 10 | FTSAICSVVR | 448 | A*6801 | 100 | 1.19 | 119 | 15 | 526 | 559 |
| 531 | 540 | 10 | FTSAICSVVR | 448 | A*7401 | 68 | 1.19 | 81 | 15 | 526 | 559 |
| 531 | 540 | 10 | FTSAICSVVR | 448 | B*5701 | 23 | 1.19 | 27 | 15 | 526 | 559 |
| 532 | 540 | 9 | TSAICSVVR | 449 | A*6801 | 82 | 1.19 | 98 | 15 | 526 | 559 |
| 533 | 540 | 8 | SAICSVVR | 450 | A*3101 | 11 | 1.19 | 14 | 15 | 526 | 559 |
| 533 | 540 | 8 | SAICSVVR | 450 | A*3303 | 39 | 1.19 | 47 | 15 | 526 | 559 |
| 533 | 540 | 8 | SAICSVVR | 450 | A*6801 | 81 | 1.19 | 96 | 15 | 526 | 559 |
| 531 | 541 | 11 | FTSAICSVVRR | 451 | A*1101 | 2 | 1.69 | 4 | 15 | 526 | 559 |
| 531 | 541 | 11 | FTSAICSVVRR | 451 | A*3101 | 32 | 1.69 | 54 | 15 | 526 | 559 |
| 531 | 541 | 11 | FTSAICSVVRR | 451 | A*3303 | 96 | 1.69 | 162 | 15 | 526 | 559 |
| 531 | 541 | 11 | FTSAICSVVRR | 451 | A*7401 | 77 | 1.69 | 130 | 15 | 526 | 559 |
| 532 | 541 | 10 | TSAICSVVRR | 452 | A*3101 | 37 | 1.69 | 62 | 15 | 526 | 559 |
| 532 | 541 | 10 | TSAICSVVRR | 452 | A*6801 | 99 | 1.69 | 167 | 15 | 526 | 559 |
| 533 | 541 | 9 | SAICSVVRR | 453 | A*3101 | 6 | 1.69 | 11 | 15 | 526 | 559 |
| 533 | 541 | 9 | SAICSVVRR | 453 | A*3303 | 63 | 1.69 | 107 | 15 | 526 | 559 |

TABLE 4a-continued

Predicted HLA class I-restricted CD8+ cytotoxic T cell epitopes contained in SLP sequences from HBV polymerase protein.

HLA class I binding peptides in SLP sequences derived from HBV Polymerase protein

| Start | End | Length | Sequence[A] | SEQ ID NO: | HLA class I molecule | Class I-B score[B] | C-score[C] | Class I-BCI score[D] | Peptide of invention (SLP) | | |
|---|---|---|---|---|---|---|---|---|---|---|---|
| | | | | | | | | | SLP# | SLP Start | SLP TABLE 4a-continued Predicted HLA class I-restricted CD8+ cytotoxic T cell epitopes contained in SLP sequences from HBV polymerase protein.

HLA class I binding peptides in SLP sequences derived from HBV Polymerase protein

| Start | End | Length | Sequence[A] | SEQ ID NO: | HLA class I molecule | Class I-B score[B] | C-score[C] | Class I-BCI score[D] | Peptide of invention (SLP) | | |
|---|---|---|---|---|---|---|---|---|---|---|---|
| | | | | | | | | | SLP# | SLP Start | SLP End |
| 541 | 549 | 9 | RAFPHCLAF | 467 | B*1402 | 66 | 1.82 | 119 | 15 | 526 | 559 |
| 541 | 549 | 9 | RAFPHCLAF | 467 | B*1501 | 84 | 1.82 | 153 | 15 | 526 | 559 |
| 541 | 549 | 9 | RAFPHCLAF | 467 | B*3501 | 68 | 1.82 | 124 | 15 | 526 | 559 |
| 541 | 549 | 9 | RAFPHCLAF | 467 | B*4601 | 97 | 1.82 | 176 | 15 | 526 | 559 |
| 541 | 549 | 9 | RAFPHCLAF | 467 | B*5201 | 75 | 1.82 | 135 | 15 | 526 | 559 |
| 541 | 549 | 9 | RAFPHCLAF | 467 | B*5701 | 59 | 1.82 | 107 | 15 | 526 | 559 |
| 541 | 549 | 9 | RAFPHCLAF | 467 | B*5801 | 81 | 1.82 | 148 | 15 | 526 | 559 |
| 542 | 549 | 8 | AFPHCLAF | 468 | A*2301 | 71 | 1.82 | 128 | 15 | 526 | 559 |
| 542 | 549 | 8 | AFPHCLAF | 468 | A*2402 | 70 | 1.82 | 128 | 15 | 526 | 559 |
| 543 | 550 | 8 | FPHCLAFS | 469 | B*3501 | 67 | 0.25 | 17 | 15 | 526 | 559 |
| 543 | 550 | 8 | FPHCLAFS | 469 | B*5501 | 17 | 0.25 | 4 | 15 | 526 | 559 |
| 543 | 550 | 8 | FPHCLAFS | 469 | B*5601 | 56 | 0.25 | 14 | 15 | 526 | 559 |
| 541 | 551 | 11 | RAFPHCLAFSY | 470 | A*0301 | 77 | 1.93 | 149 | 15 | 526 | 559 |
| 541 | 551 | 11 | RAFPHCLAFSY | 470 | A*3201 | 94 | 1.93 | 182 | 15 | 526 | 559 |
| 541 | 551 | 11 | RAFPHCLAFSY | 470 | B*1301 | 66 | 1.93 | 128 | 15 | 526 | 559 |
| 541 | 551 | 11 | RAFPHCLAFSY | 470 | B*1501 | 91 | 1.93 | 175 | 15 | 526 | 559 |
| 541 | 551 | 11 | RAFPHCLAFSY | 470 | B*1502 | 93 | 1.93 | 179 | 15 | 526 | 559 |
| 541 | 551 | 11 | RAFPHCLAFSY | 470 | B*1525 | 95 | 1.93 | 183 | 15 | 526 | 559 |
| 541 | 551 | 11 | RAFPHCLAFSY | 470 | B*5701 | 89 | 1.93 | 173 | 15 | 526 | 559 |
| 541 | 551 | 11 | RAFPHCLAFSY | 470 | B*5802 | 86 | 1.93 | 165 | 15 | 526 | 559 |
| 542 | 551 | 10 | AFPHCLAFSY | 471 | A*2902 | 94 | 1.93 | 181 | 15 | 526 | 559 |
| 543 | 551 | 9 | FPHCLAFSY | 472 | B*3501 | 97 | 1.93 | 188 | 15 | 526 | 559 |
| 543 | 551 | 9 | FPHCLAFSY | 472 | B*3503 | 91 | 1.93 | 175 | 15 | 526 | 559 |
| 543 | 551 | 9 | FPHCLAFSY | 472 | B*5301 | 98 | 1.93 | 190 | 15 | 526 | 559 |
| 543 | 551 | 9 | FPHCLAFSY | 472 | B*5501 | 83 | 1.93 | 160 | 15 | 526 | 559 |
| 542 | 552 | 11 | AFPHCLAFSYM | 473 | A*2402 | 4 | 1.02 | 4 | 15 | 526 | 559 |
| 543 | 552 | 10 | FPHCLAFSYM | 474 | B*0702 | 64 | 1.02 | 65 | 15 | 526 | 559 |
| 543 | 552 | 10 | FPHCLAFSYM | 474 | B*1402 | 90 | 1.02 | 92 | 15 | 526 | 559 |
| 543 | 552 | 10 | FPHCLAFSYM | 474 | B*3501 | 96 | 1.02 | 98 | 15 | 526 | 559 |
| 543 | 552 | 10 | FPHCLAFSYM | 474 | B*3503 | 99 | 1.02 | 100 | 15 | 526 | 559 |
| 543 | 552 | 10 | FPHCLAFSYM | 474 | B*3901 | 68 | 1.02 | 69 | 15 | 526 | 559 |
| 543 | 552 | 10 | FPHCLAFSYM | 474 | B*5101 | 98 | 1.02 | 100 | 15 | 526 | 559 |
| 543 | 552 | 10 | FPHCLAFSYM | 474 | B*5301 | 97 | 1.02 | 98 | 15 | 526 | 559 |
| 543 | 552 | 10 | FPHCLAFSYM | 474 | B*5501 | 97 | 1.02 | 98 | 15 | 526 | 559 |

TABLE 4a-continued

Predicted HLA class I-restricted CD8[+] cytotoxic T cell epitopes contained in SLP sequences from HBV polymerase protein.

HLA class I binding peptides in SLP sequences derived from HBV Polymerase protein

| Start | End | Length | Sequence[A] | SEQ ID NO: | HLA class I molecule | Class I-B score[B] | C-score[C] | Class I-BCI score[D] | SLP# | Peptide of invention (SLP) SLP Start | SLP End |
|---|---|---|---|---|---|---|---|---|---|---|---|
| 543 | 552 | 10 | FPHCLAFSYM | 474 | B*5601 | 87 | 1.02 | 89 | 15 | 526 | 559 |
| 545 | 555 | 11 | HCLAFSYMDDV | 475 | A*0201 | 73 | 0.60 | 44 | 15 | 526 | 559 |
| 547 | 555 | 9 | LAFSYMDDV | 476 | B*5101 | 20 | 0.60 | 12 | 15 | 526 | 559 |
| 547 | 556 | 10 | LAFSYMDDVV | 477 | B*5201 | 51 | 0.34 | 17 | 15 | 526 | 559 |
| 549 | 556 | 8 | FSYMDDVV | 478 | B*4601 | 34 | 0.34 | 12 | 15 | 526 | 559 |
| 549 | 556 | 8 | FSYMDDVV | 478 | B*5101 | 23 | 0.34 | 8 | 15 | 526 | 559 |
| 549 | 556 | 8 | FSYMDDVV | 478 | B*5201 | 39 | 0.34 | 13 | 15 | 526 | 559 |
| 547 | 557 | 11 | LAFSYMDDVVL | 479 | B*3503 | 11 | 1.21 | 13 | 15 | 526 | 559 |
| 547 | 557 | 11 | LAFSYMDDVVL | 479 | B*3801 | 29 | 1.21 | 35 | 15 | 526 | 559 |
| 547 | 557 | 11 | LAFSYMDDVVL | 479 | B*3901 | 19 | 1.21 | 24 | 15 | 526 | 559 |
| 547 | 557 | 11 | LAFSYMDDVVL | 479 | B*4801 | 23 | 1.21 | 28 | 15 | 526 | 559 |
| 549 | 557 | 9 | FSYMDDVVL | 480 | B*3901 | 25 | 1.21 | 30 | 15 | 526 | 559 |
| 549 | 557 | 9 | FSYMDDVVL | 480 | B*4601 | 62 | 1.21 | 76 | 15 | 526 | 559 |
| 550 | 557 | 8 | SYMDDVVL | 481 | A*2301 | 38 | 1.21 | 46 | 15 | 526 | 559 |
| 550 | 557 | 8 | SYMDDVVL | 481 | A*2402 | 47 | 1.21 | 57 | 15 | 526 | 559 |
| 551 | 559 | 9 | YMDDVVLGA | 482 | A*0101 | 66 | 1.49 | 98 | 15 | 526 | 559 |
| 551 | 559 | 9 | YMDDVVLGA | 482 | A*0201 | 100 | 1.49 | 149 | 15 | 526 | 559 |
| 551 | 559 | 9 | YMDDVVLGA | 482 | A*0206 | 71 | 1.49 | 105 | 15 | 526 | 559 |
| 552 | 559 | 8 | MDDVVLGA | 483 | A*6802 | 34 | 1.49 | 50 | 15 | 526 | 559 |
| | | | | | Cumulative Class I-BCI score: | | | 11658 | | | |
| 565 | 572 | 8 | RESLYTAV | 486 | B*1301 | 93 | 1.67 | 155 | 16 | 565 | 598 |
| 565 | 572 | 8 | RESLYTAV | 486 | B*1302 | 31 | 1.67 | 52 | 16 | 565 | 598 |
| 565 | 572 | 8 | RESLYTAV | 486 | B*3701 | 81 | 1.67 | 135 | 16 | 565 | 598 |
| 565 | 572 | 8 | RESLYTAV | 486 | B*4001 | 91 | 1.67 | 153 | 16 | 565 | 598 |
| 565 | 572 | 8 | RESLYTAV | 486 | B*4002 | 90 | 1.67 | 151 | 16 | 565 | 598 |
| 565 | 572 | 8 | RESLYTAV | 486 | B*4402 | 65 | 1.67 | 109 | 16 | 565 | 598 |
| 565 | 572 | 8 | RESLYTAV | 486 | B*4403 | 52 | 1.67 | 87 | 16 | 565 | 598 |
| 565 | 572 | 8 | RESLYTAV | 486 | B*4801 | 44 | 1.67 | 74 | 16 | 565 | 598 |
| 565 | 572 | 8 | RESLYTAV | 486 | B*4901 | 87 | 1.67 | 145 | 16 | 565 | 598 |
| 565 | 572 | 8 | RESLYTAV | 486 | B*5001 | 88 | 1.67 | 147 | 16 | 565 | 598 |
| 565 | 573 | 9 | RESLYTAVT | 487 | B*4002 | 40 | 1.11 | 45 | 16 | 565 | 598 |
| 565 | 573 | 9 | RESLYTAVT | 487 | B*5001 | 56 | 1.11 | 62 | 16 | 565 | 598 |
| 565 | 574 | 10 | RESLYTAVTN | 488 | B*4002 | 35 | 0.69 | 24 | 16 | 565 | 598 |
| 565 | 575 | 11 | RESLYTAVTNF | 489 | B*1301 | 73 | 1.85 | 136 | 16 | 565 | 598 |
| 565 | 575 | 11 | RESLYTAVTNF | 489 | B*1801 | 81 | 1.85 | 150 | 16 | 565 | 598 |

TABLE 4a-continued

Predicted HLA class I-restricted CD8+ cytotoxic T cell epitopes contained in SLP sequences from HBV polymerase protein.

HLA class I binding peptides in SLP sequences derived from HBV Polymerase protein

| | | | | | | Class | | Class | Peptide of invention (SLP) | | |
| | | | | SEQ ID | HLA class I | I-B | | I-BCI | | | |
| Start | End | Length | Sequence[A] | NO: | molecule | score[B] | C-score[C] | score[D] | SLP# | SLP Start | SLP End |
|---|---|---|---|---|---|---|---|---|---|---|---|
| 565 | 575 | 11 | RESLYTAVTNF | 489 | B*4001 | 78 | 1.85 | 145 | 16 | 565 | 598 |
| 565 | 575 | 11 | RESLYTAVTNF | 489 | B*4002 | 75 | 1.85 | 139 | 16 | 565 | 598 |
| 565 | 575 | 11 | RESLYTAVTNF | 489 | B*4402 | 96 | 1.85 | 178 | 16 | 565 | 598 |
| 565 | 575 | 11 | RESLYTAVTNF | 489 | B*4403 | 92 | 1.85 | 170 | 16 | 565 | 598 |
| 565 | 575 | 11 | RESLYTAVTNF | 489 | B*4901 | 70 | 1.85 | 129 | 16 | 565 | 598 |
| 565 | 575 | 11 | RESLYTAVTNF | 489 | B*5001 | 68 | 1.85 | 126 | 16 | 565 | 598 |
| 566 | 575 | 10 | ESLYTAVTNF | 490 | A*2601 | 95 | 1.85 | 176 | 16 | 565 | 598 |
| 567 | 575 | 9 | SLYTAVTNF | 491 | B*1501 | 64 | 1.85 | 119 | 16 | 565 | 598 |
| 567 | 575 | 9 | SLYTAVTNF | 491 | B*1525 | 86 | 1.85 | 160 | 16 | 565 | 598 |
| 568 | 575 | 8 | LYTAVTNF | 492 | A*2301 | 90 | 1.85 | 166 | 16 | 565 | 598 |
| 568 | 575 | 8 | LYTAVTNF | 492 | A*2402 | 91 | 1.85 | 169 | 16 | 565 | 598 |
| 567 | 576 | 10 | SLYTAVTNFL | 493 | A*0201 | 64 | 1.69 | 109 | 16 | 565 | 598 |
| 568 | 576 | 9 | LYTAVTNFL | 494 | A*2301 | 16 | 1.69 | 26 | 16 | 565 | 598 |
| 568 | 576 | 9 | LYTAVTNFL | 494 | A*2402 | 53 | 1.69 | 89 | 16 | 565 | 598 |
| 569 | 576 | 8 | YTAVTNFL | 495 | A*0101 | 2 | 1.69 | 3 | 16 | 565 | 598 |
| 569 | 576 | 8 | YTAVTNFL | 495 | A*2501 | 71 | 1.69 | 121 | 16 | 565 | 598 |
| 569 | 576 | 8 | YTAVTNFL | 495 | A*2601 | 59 | 1.69 | 100 | 16 | 565 | 598 |
| 569 | 576 | 8 | YTAVTNFL | 495 | B*4601 | 80 | 1.69 | 136 | 16 | 565 | 598 |
| 567 | 577 | 11 | SLYTAVTNFLL | 496 | A*3201 | 48 | 1.86 | 90 | 16 | 565 | 598 |
| 568 | 577 | 10 | LYTAVTNFLL | 497 | A*2301 | 60 | 1.86 | 112 | 16 | 565 | 598 |
| 568 | 577 | 10 | LYTAVTNFLL | 497 | A*2402 | 67 | 1.86 | 124 | 16 | 565 | 598 |
| 568 | 577 | 10 | LYTAVTNFLL | 497 | B*3801 | 8 | 1.86 | 15 | 16 | 565 | 598 |
| 569 | 577 | 9 | YTAVTNFLL | 498 | A*0101 | 70 | 1.86 | 130 | 16 | 565 | 598 |
| 569 | 577 | 9 | YTAVTNFLL | 498 | A*6802 | 28 | 1.86 | 52 | 16 | 565 | 598 |
| 569 | 577 | 9 | YTAVTNFLL | 498 | B*5801 | 41 | 1.86 | 75 | 16 | 565 | 598 |
| 569 | 579 | 11 | YTAVTNFLLSL | 499 | A*0101 | 58 | 1.91 | 112 | 16 | 565 | 598 |
| 569 | 579 | 11 | YTAVTNFLLSL | 499 | A*2501 | 69 | 1.91 | 132 | 16 | 565 | 598 |
| 569 | 579 | 11 | YTAVTNFLLSL | 499 | A*2601 | 56 | 1.91 | 108 | 16 | 565 | 598 |
| 569 | 579 | 11 | YTAVTNFLLSL | 499 | B*3801 | 43 | 1.91 | 82 | 16 | 565 | 598 |
| 569 | 579 | 11 | YTAVTNFLLSL | 499 | B*4601 | 89 | 1.91 | 169 | 16 | 565 | 598 |
| 569 | 579 | 11 | YTAVTNFLLSL | 499 | B*5801 | 14 | 1.91 | 26 | 16 | 565 | 598 |
| 572 | 579 | 8 | VTNFLLSL | 500 | A*3201 | 26 | 1.91 | 49 | 16 | 565 | 598 |
| 572 | 579 | 8 | VTNFLLSL | 500 | B*0702 | 23 | 1.91 | 44 | 16 | 565 | 598 |
| 571 | 581 | 11 | AVTNFLLSLGI | 501 | A*3201 | 9 | 1.49 | 14 | 16 | 565 | 598 |
| 573 | 581 | 9 | TNFLLSLGI | 502 | B*5201 | 31 | 1.49 | 47 | 16 | 565 | 598 |

TABLE 4a-continued

Predicted HLA class I-restricted CD8+ cytotoxic T cell epitopes contained in SLP sequences from HBV polymerase protein.

HLA class I binding peptides in SLP sequences derived from HBV Polymerase protein

| Start | End | Length | Sequence[A] | SEQ ID NO: | HLA class I molecule | Class I-B score[B] | C-score[C] | Class I-BCI score[D] | Peptide of invention (SLP) SLP# | SLP Start | SLP End |
|---|---|---|---|---|---|---|---|---|---|---|---|
| 575 | 583 | 9 | FLLSLGIHL | 503 | A*0201 | 82 | 1.27 | 104 | 16 | 565 | 598 |
| 575 | 583 | 9 | FLLSLGIHL | 503 | A*0206 | 46 | 1.27 | 58 | 16 | 565 | 598 |
| 576 | 583 | 8 | LLSLGIHL | 504 | B*0702 | 90 | 1.27 | 114 | 16 | 565 | 598 |
| 578 | 585 | 8 | SLGIHLNP | 505 | A*0201 | 98 | 0.14 | 14 | 16 | 565 | 598 |
| 576 | 586 | 11 | LLSLGIHLNPN | 506 | A*0206 | 75 | 0.09 | 7 | 16 | 565 | 598 |
| 577 | 587 | 11 | LSLGIHLNPNK | 507 | A*0301 | 10 | 0.12 | 1 | 16 | 565 | 598 |
| 577 | 587 | 11 | LSLGIHLNPNK | 507 | A*1101 | 50 | 0.12 | 6 | 16 | 565 | 598 |
| 578 | 587 | 10 | SLGIHLNPNK | 508 | A*0301 | 30 | 0.12 | 3 | 16 | 565 | 598 |
| 578 | 587 | 10 | SLGIHLNPNK | 508 | A*1101 | 24 | 0.12 | 3 | 16 | 565 | 598 |
| 580 | 587 | 8 | GIHLNPNK | 509 | A*0301 | 26 | 0.12 | 3 | 16 | 565 | 598 |
| 580 | 587 | 8 | GIHLNPNK | 509 | A*1101 | 17 | 0.12 | 2 | 16 | 565 | 598 |
| 582 | 589 | 8 | HLNPNKTK | 510 | A*0301 | 51 | 1.61 | 82 | 16 | 565 | 598 |
| 582 | 590 | 9 | HLNPNKTKR | 511 | A*3101 | 85 | 1.52 | 129 | 16 | 565 | 598 |
| 582 | 590 | 9 | HLNPNKTKR | 511 | A*3303 | 54 | 1.52 | 81 | 16 | 565 | 598 |
| 582 | 590 | 9 | HLNPNKTKR | 511 | A*7401 | 20 | 1.52 | 30 | 16 | 565 | 598 |
| 584 | 591 | 8 | NPNKTKRW | 512 | B*5301 | 46 | 1.80 | 83 | 16 | 565 | 598 |
| 585 | 594 | 10 | PNKTKRWGYS | 513 | A*3201 | 55 | 0.53 | 29 | 16 | 565 | 598 |
| 587 | 594 | 8 | KTKRWGYS | 514 | A*3001 | 67 | 0.53 | 36 | 16 | 565 | 598 |
| 586 | 595 | 10 | NKTKRWGYSL | 515 | B*1402 | 46 | 1.81 | 84 | 16 | 565 | 598 |
| 587 | 595 | 9 | KTKRWGYSL | 516 | A*3001 | 64 | 1.81 | 116 | 16 | 565 | 598 |
| 587 | 595 | 9 | KTKRWGYSL | 516 | A*3201 | 85 | 1.81 | 154 | 16 | 565 | 598 |
| 587 | 595 | 9 | KTKRWGYSL | 516 | B*5701 | 50 | 1.81 | 91 | 16 | 565 | 598 |
| 587 | 595 | 9 | KTKRWGYSL | 516 | B*5802 | 52 | 1.81 | 94 | 16 | 565 | 598 |
| 588 | 595 | 8 | TKRWGYSL | 517 | B*1402 | 56 | 1.81 | 101 | 16 | 565 | 598 |
| 589 | 596 | 8 | KRWGYSLN | 518 | B*2702 | 42 | 0.19 | 8 | 16 | 565 | 598 |
| 589 | 596 | 8 | KRWGYSLN | 518 | B*2705 | 75 | 0.19 | 14 | 16 | 565 | 598 |
| 587 | 597 | 11 | KTKRWGYSLNF | 519 | A*2402 | 2 | 1.95 | 3 | 16 | 565 | 598 |
| 587 | 597 | 11 | KTKRWGYSLNF | 519 | A*3001 | 41 | 1.95 | 80 | 16 | 565 | 598 |
| 587 | 597 | 11 | KTKRWGYSLNF | 519 | A*3002 | 41 | 1.95 | 80 | 16 | 565 | 598 |
| 587 | 597 | 11 | KTKRWGYSLNF | 519 | A*3201 | 91 | 1.95 | 177 | 16 | 565 | 598 |
| 587 | 597 | 11 | KTKRWGYSLNF | 519 | B*5701 | 77 | 1.95 | 150 | 16 | 565 | 598 |
| 587 | 597 | 11 | KTKRWGYSLNF | 519 | B*5801 | 44 | 1.95 | 86 | 16 | 565 | 598 |
| 587 | 597 | 11 | KTKRWGYSLNF | 519 | B*5802 | 81 | 1.95 | 158 | 16 | 565 | 598 |
| 589 | 597 | 9 | KRWGYSLNF | 520 | A*3201 | 12 | 1.95 | 24 | 16 | 565 | 598 |

TABLE 4a-continued

Predicted HLA class I-restricted CD8+ cytotoxic T cell epitopes contained in SLP sequences from HBV polymerase protein.

HLA class I binding peptides in SLP sequences derived from HBV Polymerase protein

| Start | End | Length | Sequence $^A$ | SEQ ID NO: | H

TABLE 4a-continued

Predicted HLA class I-restricted CD8+ cytotoxic T cell epitopes contained in SLP sequences from HBV polymerase protein.

HLA class I binding peptides in SLP sequences derived from HBV Polymerase protein

| Start | End | Length | Sequence[A] | SEQ ID NO: | HLA class I molecule | Class I-B score[B] | C-score[C] | Class I-BCI score[D] | Peptide of invention (SLP) | | |
|---|---|---|---|---|---|---|---|---|---|---|---|
| | | | | | | | | | SLP# | SLP Start | SLP End |
| 589 | 599 | 11 | KRWGYSLNFMG | 524 | B*2702 | 57 | 0.64 | 36 | 17 | 584 | 617 |
| 589 | 599 | 11 | KRWGYSLNFMG | 524 | B*2705 | 24 | 0.64 | 15 | 17 | 584 | 617 |
| 590 | 600 | 11 | RWGYSLNFMGY | 525 | A*3002 | 82 | 1.89 | 155 | 17 | 584 | 617 |
| 592 | 600 | 9 | GYSLNFMGY | 526 | A*2902 | 73 | 1.89 | 138 | 17 | 584 | 617 |
| 593 | 600 | 8 | YSLNFMGY | 527 | A*0101 | 87 | 1.89 | 164 | 17 | 584 | 617 |
| 593 | 600 | 8 | YSLNFMGY | 527 | A*2501 | 88 | 1.89 | 166 | 17 | 584 | 617 |
| 593 | 600 | 8 | YSLNFMGY | 527 | A*2601 | 87 | 1.89 | 165 | 17 | 584 | 617 |
| 593 | 600 | 8 | YSLNFMGY | 527 | A*2902 | 100 | 1.89 | 189 | 17 | 584 | 617 |
| 593 | 600 | 8 | YSLNFMGY | 527 | A*3002 | 86 | 1.89 | 163 | 17 | 584 | 617 |
| 593 | 600 | 8 | YSLNFMGY | 527 | B*1501 | 42 | 1.89 | 80 | 17 | 584 | 617 |
| 593 | 600 | 8 | YSLNFMGY | 527 | B*1502 | 48 | 1.89 | 91 | 17 | 584 | 617 |
| 593 | 600 | 8 | YSLNFMGY | 527 | B*1525 | 37 | 1.89 | 71 | 17 | 584 | 617 |
| 593 | 600 | 8 | YSLNFMGY | 527 | B*4601 | 79 | 1.89 | 149 | 17 | 584 | 617 |
| 593 | 600 | 8 | YSLNFMGY | 527 | B*5801 | 27 | 1.89 | 51 | 17 | 584 | 617 |
| 593 | 600 | 8 | YSLNFMGY | 527 | B*5802 | 25 | 1.89 | 47 | 17 | 584 | 617 |
| 591 | 601 | 11 | WGYSLNFMGYI | 528 | B*1302 | 25 | 0.91 | 23 | 17 | 584 | 617 |
| 591 | 601 | 11 | WGYSLNFMGYI | 528 | B*5201 | 67 | 0.91 | 60 | 17 | 584 | 617 |
| 593 | 601 | 9 | YSLNFMGYI | 529 | A*2501 | 76 | 0.91 | 68 | 17 | 584 | 617 |
| 593 | 601 | 9 | YSLNFMGYI | 529 | B*4601 | 30 | 0.91 | 27 | 17 | 584 | 617 |
| 593 | 601 | 9 | YSLNFMGYI | 529 | B*5201 | 49 | 0.91 | 44 | 17 | 584 | 617 |
| 593 | 601 | 9 | YSLNFMGYI | 529 | B*5802 | 78 | 0.91 | 71 | 17 | 584 | 617 |
| 594 | 601 | 8 | SLNFMGYI | 530 | A*3201 | 39 | 0.91 | 36 | 17 | 584 | 617 |
| 592 | 602 | 11 | GYSLNFMGYII | 531 | A*2301 | 62 | 0.67 | 42 | 17 | 584 | 617 |
| 592 | 602 | 11 | GYSLNFMGYII | 531 | A*2402 | 68 | 0.67 | 46 | 17 | 584 | 617 |
| 593 | 602 | 10 | YSLNFMGYII | 532 | A*0206 | 52 | 0.67 | 35 | 17 | 584 | 617 |
| 593 | 602 | 10 | YSLNFMGYII | 532 | B*1301 | 62 | 0.67 | 42 | 17 | 584 | 617 |
| 593 | 602 | 10 | YSLNFMGYII | 532 | B*1302 | 39 | 0.67 | 27 | 17 | 584 | 617 |
| 593 | 602 | 10 | YSLNFMGYII | 532 | B*3801 | 20 | 0.67 | 14 | 17 | 584 | 617 |
| 593 | 602 | 10 | YSLNFMGYII | 532 | B*5201 | 92 | 0.67 | 62 | 17 | 584 | 617 |
| 593 | 602 | 10 | YSLNFMGYII | 532 | B*5802 | 4 | 0.67 | 3 | 17 | 584 | 617 |
| 594 | 602 | 9 | SLNFmGyII | 533 | A*3201 | 71 | 0.67 | 48 | 17 | 584 | 617 |
| 595 | 602 | 8 | LNFMGYII | 534 | B*1302 | 30 | 0.67 | 20 | 17 | 584 | 617 |
| 595 | 602 | 8 | LNFMGYII | 534 | B*5101 | 7 | 0.67 | 4 | 17 | 584 | 617 |
| 595 | 602 | 8 | LNFMGYII | 534 | B*5201 | 90 | 0.67 | 61 | 17 | 584 | 617 |
| 597 | 604 | 8 | FMGYIIGS | 535 | A*0201 | 36 | 0.52 | 19 | 17 | 584 | 617 |

TABLE 4a-continued

Predicted HLA class I-restricted CD8+ cytotoxic T cell epitopes contained in SLP sequences from HBV polymerase protein.

HLA class I binding peptides in SLP sequences derived from HBV Polymerase protein

| Start | End | Length | Sequence[A] | SEQ ID NO: | HLA class I molecule | Class I-B score[B] | C-score[C] | Class I-BCI score[D] | SLP# | SLP Start | SLP End |
|---|---|---|---|---|---|---|---|---|---|---|---|
| 595 | 605 | 11 | LNFMGYIIGSW | 536 | B*5701 | 5 | 1.77 | 8 | 17 | 584 | 617 |
| 596 | 605 | 10 | NFMGYIIGSW | 537 | A*2301 | 50 | 1.77 | 88 | 17 | 584 | 617 |
| 596 | 605 | 10 | NFMGYIIGSW | 537 | B*4402 | 50 | 1.77 | 88 | 17 | 584 | 617 |
| 597 | 605 | 9 | FMGYIIGSW | 538 | B*4601 | 52 | 1.77 | 93 | 17 | 584 | 617 |
| 598 | 605 | 8 | MGYIIGSW | 539 | A*6802 | 25 | 1.77 | 44 | 17 | 584 | 617 |
| 598 | 605 | 8 | MGYIIGSW | 539 | B*5201 | 29 | 1.77 | 52 | 17 | 584 | 617 |
| 598 | 605 | 8 | MGYIIGSW | 539 | B*5301 | 56 | 1.77 | 99 | 17 | 584 | 617 |
| 598 | 605 | 8 | MGYIIGSW | 539 | B*5701 | 85 | 1.77 | 150 | 17 | 584 | 617 |
| 598 | 605 | 8 | MGYIIGSW | 539 | B*5801 | 78 | 1.77 | 138 | 17 | 584 | 617 |
| 598 | 605 | 8 | MGYIIGSW | 539 | B*5802 | 80 | 1.77 | 141 | 17 | 584 | 617 |
| 598 | 608 | 11 | MGYIIGSWGTL | 540 | B*1402 | 33 | 1.71 | 57 | 17 | 584 | 617 |
| 599 | 608 | 10 | GYIIGSWGTL | 541 | A*3201 | 83 | 1.71 | 142 | 17 | 584 | 617 |
| 600 | 608 | 9 | YIIGSWGTL | 542 | A*0206 | 2 | 1.71 | 4 | 17 | 584 | 617 |
| 600 | 608 | 9 | YIIGSWGTL | 542 | A*2501 | 92 | 1.71 | 157 | 17 | 584 | 617 |
| 600 | 608 | 9 | YIIGSWGTL | 542 | A*2601 | 28 | 1.71 | 48 | 17 | 584 | 617 |
| 600 | 608 | 9 | YIIGSWGTL | 542 | B*1502 | 67 | 1.71 | 114 | 17 | 584 | 617 |
| 607 | 614 | 8 | TLPQDHIV | 543 | A*0201 | 4 | 0.56 | 2 | 17 | 584 | 617 |
| 606 | 616 | 11 | GTLPQDHIVQK | 544 | A*0301 | 8 | 1.05 | 9 | 17 | 584 | 617 |
| 606 | 616 | 11 | GTLPQDHIVQK | 544 | A*1101 | 63 | 1.05 | 66 | 17 | 584 | 617 |
| 608 | 617 | 10 | LPQDHIVQKI | 545 | B*5101 | 82 | 1.83 | 150 | 17 | 584 | 617 |
| 608 | 617 | 10 | LPQDHIVQKI | 545 | B*5301 | 26 | 1.83 | 48 | 17 | 584 | 617 |
| | | | | | Cumulative BCI Class Iscore: | | | 6396 | | | |
| 653 | 660 | 8 | YPALMPLY | 548 | A*0101 | 36 | 1.81 | 65 | 18 | 653 | 691 |
| 653 | 660 | 8 | YPALMPLY | 548 | A*2601 | 21 | 1.81 | 37 | 18 | 653 | 691 |
| 653 | 660 | 8 | YPALMPLY | 548 | A*2902 | 41 | 1.81 | 75 | 18 | 653 | 691 |
| 653 | 660 | 8 | YPALMPLY | 548 | B*3501 | 95 | 1.81 | 171 | 18 | 653 | 691 |
| 653 | 660 | 8 | YPALMPLY | 548 | B*3503 | 84 | 1.81 | 151 | 18 | 653 | 691 |
| 653 | 660 | 8 | YPALMPLY | 548 | B*5101 | 38 | 1.81 | 69 | 18 | 653 | 691 |
| 653 | 660 | 8 | YPALMPLY | 548 | B*5301 | 89 | 1.81 | 160 | 18 | 653 | 691 |
| 653 | 660 | 8 | YPALMPLY | 548 | B*5501 | 28 | 1.81 | 50 | 18 | 653 | 691 |
| 653 | 660 | 8 | YPALMPLY | 548 | B*5601 | 37 | 1.81 | 67 | 18 | 653 | 691 |
| 652 | 661 | 10 | GYPALMPLYA | 549 | A*2402 | 40 | 1.43 | 58 | 18 | 653 | 691 |
| 653 | 661 | 9 | YPALMPLYA | 550 | B*0702 | 9 | 1.43 | 12 | 18 | 653 | 691 |
| 653 | 661 | 9 | YPALMPLYA | 550 | B*3503 | 59 | 1.43 | 85 | 18 | 653 | 691 |
| 653 | 661 | 9 | YPALMPLYA | 550 | B*5101 | 27 | 1.43 | 38 | 18 | 653 | 691 |

TABLE 4a-continued

Predicted HLA class I-restricted CD8+ cytotoxic T cell epitopes contained in SLP sequences from HBV polymerase protein.

HLA class I binding peptides in SLP sequences derived from HBV Polymerase protein

| Start | End | Length | Sequence $^A$ | SEQ ID NO: | HLA class I molecule | Class I-B score $^B$ | C-score $^C$ | Class I-BCI score $^D$ | SLP# | Peptide of invention (SLP) SLP Start | SLP End |
|---|---|---|---|---|---|---|---|---|---|---|---|
| 653 | 661 | 9 | YPALMPLYA | 550 | B*5501 | 94 | 1.43 | 135 | 18 | 653 | 691 |
| 653 | 661 | 9 | YPALMPLYA | 550 | B*5601 | 100 | 1.43 | 143 | 18 | 653 | 691 |
| 653 | 662 | 10 | YPALMPLYAC | 551 | B*0702 | 4 | 0.21 | 1 | 18 | 653 | 691 |
| 653 | 662 | 10 | YPALMPLYAC | 551 | B*3501 | 72 | 0.21 | 15 | 18 | 653 | 691 |
| 653 | 662 | 10 | YPALMPLYAC | 551 | B*3503 | 69 | 0.21 | 14 | 18 | 653 | 691 |
| 653 | 662 | 10 | YPALMPLYAC | 551 | B*5301 | 54 | 0.21 | 11 | 18 | 653 | 691 |
| 653 | 662 | 10 | YPALMPLYAC | 551 | B*5501 | 70 | 0.21 | 15 | 18 | 653 | 691 |
| 653 | 662 | 10 | YPALMPLYAC | 551 | B*5601 | 86 | 0.21 | 18 | 18 | 653 | 691 |
| 655 | 662 | 8 | ALMPLYAC | 552 | A*0201 | 11 | 0.21 | 2 | 18 | 653 | 691 |
| 653 | 663 | 11 | YPALMPLYACI | 553 | B*0702 | 54 | 1.19 | 64 | 18 | 653 | 691 |
| 653 | 663 | 11 | YPALMPLYACI | 553 | B*1402 | 40 | 1.19 | 48 | 18 | 653 | 691 |
| 653 | 663 | 11 | YPALMPLYACI | 553 | B*3501 | 33 | 1.19 | 40 | 18 | 653 | 691 |
| 653 | 663 | 11 | YPALMPLYACI | 553 | B*3503 | 82 | 1.19 | 98 | 18 | 653 | 691 |
| 653 | 663 | 11 | YPALMPLYACI | 553 | B*5101 | 100 | 1.19 | 119 | 18 | 653 | 691 |
| 653 | 663 | 11 | YPALMPLYACI | 553 | B*5201 | 27 | 1.19 | 33 | 18 | 653 | 691 |
| 653 | 663 | 11 | YPALMPLYACI | 553 | B*5301 | 87 | 1.19 | 104 | 18 | 653 | 691 |
| 653 | 663 | 11 | YPALMPLYACI | 553 | B*5501 | 69 | 1.19 | 82 | 18 | 653 | 691 |
| 653 | 663 | 11 | YPALMPLYACI | 553 | B*5601 | 77 | 1.19 | 92 | 18 | 653 | 691 |
| 655 | 663 | 9 | ALMPLYACI | 554 | A*0201 | 67 | 1.19 | 80 | 18 | 653 | 691 |
| 657 | 664 | 8 | MPLYACIQ | 555 | B*5501 | 12 | 0.20 | 2 | 18 | 653 | 691 |
| 657 | 664 | 8 | MPLYACIQ | 555 | B*5601 | 8 | 0.20 | 2 | 18 | 653 | 691 |
| 657 | 665 | 9 | MPLYACIQA | 556 | B*3501 | 44 | 1.41 | 62 | 18 | 653 | 691 |
| 657 | 665 | 9 | MPLYACIQA | 556 | B*3503 | 49 | 1.41 | 68 | 18 | 653 | 691 |
| 657 | 665 | 9 | MPLYACIQA | 556 | B*5101 | 80 | 1.41 | 112 | 18 | 653 | 691 |
| 657 | 665 | 9 | MPLYACIQA | 556 | B*5501 | 93 | 1.41 | 131 | 18 | 653 | 691 |
| 657 | 665 | 9 | MPLYACIQA | 556 | B*5601 | 99 | 1.41 | 139 | 18 | 653 | 691 |
| 657 | 666 | 10 | MPLYACIQAK | 557 | B*3501 | 43 | 1.01 | 43 | 18 | 653 | 691 |
| 657 | 666 | 10 | MPLYACIQAK | 557 | B*5601 | 3 | 1.01 | 3 | 18 | 653 | 691 |
| 658 | 666 | 9 | PLYACIQAK | 558 | A*0301 | 74 | 1.01 | 75 | 18 | 653 | 691 |
| 659 | 669 | 11 | LYACIQAKQAF | 559 | A*2301 | 86 | 1.07 | 92 | 18 | 653 | 691 |
| 659 | 669 | 11 | LYACIQAKQAF | 559 | A*2402 | 88 | 1.07 | 94 | 18 | 653 | 691 |
| 660 | 669 | 10 | YACIQAKQAF | 560 | B*1502 | 26 | 1.07 | 28 | 18 | 653 | 691 |
| 663 | 671 | 9 | IQAKQAFTF | 561 | A*2402 | 84 | 1.58 | 133 | 18 | 653 | 691 |
| 663 | 671 | 9 | IQAKQAFTF | 561 | B*1301 | 61 | 1.58 | 96 | 18 | 653 | 691 |

TABLE 4a-continued

Predicted HLA class I-restricted CD8+ cytotoxic T cell epitopes contained in SLP sequences from HBV polymerase protein.

HLA class I binding peptides in SLP sequences derived from HBV Polymerase protein

| Start | End | Length | Sequence[A] | SEQ ID NO: | HLA class I molecule | Class I-B score[B] | C-score[C] | Class I-BCI score[D] | SLP# | SLP Start | SLP End |
|---|---|---|---|---|---|---|---|---|---|---|---|
| 663 | 671 | 9 | IQAKQAFTF | 561 | B*1501 | 63 | 1.58 | 99 | 18 | 653 | 691 |
| 663 | 671 | 9 | IQAKQAFTF | 561 | B*1525 | 71 | 1.58 | 112 | 18 | 653 | 691 |
| 664 | 671 | 8 | QAKQAFTF | 562 | B*1501 | 8 | 1.58 | 12 | 18 | 653 | 691 |
| 664 | 671 | 8 | QAKQAFTF | 562 | B*1502 | 37 | 1.58 | 59 | 18 | 653 | 691 |
| 664 | 671 | 8 | QAKQAFTF | 562 | B*1525 | 14 | 1.58 | 21 | 18 | 653 | 691 |
| 664 | 671 | 8 | QAKQAFTF | 562 | B*5802 | 3 | 1.58 | 5 | 18 | 653 | 691 |
| 666 | 675 | 10 | KQAFTFSPTY | 563 | A*2902 | 27 | 1.81 | 49 | 18 | 653 | 691 |
| 666 | 675 | 10 | KQAFTFSPTY | 563 | A*3002 | 30 | 1.81 | 53 | 18 | 653 | 691 |
| 666 | 675 | 10 | KQAFTFSPTY | 563 | B*1501 | 89 | 1.81 | 161 | 18 | 653 | 691 |
| 666 | 675 | 10 | KQAFTFSPTY | 563 | B*1502 | 63 | 1.81 | 114 | 18 | 653 | 691 |
| 666 | 675 | 10 | KQAFTFSPTY | 563 | B*1525 | 85 | 1.81 | 153 | 18 | 653 | 691 |
| 666 | 675 | 10 | KQAFTFSPTY | 563 | B*5001 | 32 | 1.81 | 58 | 18 | 653 | 691 |
| 667 | 675 | 9 | QAFTFSPTY | 564 | A*2902 | 46 | 1.81 | 83 | 18 | 653 | 691 |
| 667 | 675 | 9 | QAFTFSPTY | 564 | A*3002 | 58 | 1.81 | 104 | 18 | 653 | 691 |
| 667 | 675 | 9 | QAFTFSPTY | 564 | B*1525 | 66 | 1.81 | 119 | 18 | 653 | 691 |
| 667 | 675 | 9 | QAFTFSPTY | 564 | B*3501 | 73 | 1.81 | 133 | 18 | 653 | 691 |
| 667 | 675 | 9 | QAFTFSPTY | 564 | B*5701 | 12 | 1.81 | 22 | 18 | 653 | 691 |
| 668 | 675 | 8 | AFTFSPTY | 565 | A*2902 | 60 | 1.81 | 109 | 18 | 653 | 691 |
| 668 | 675 | 8 | AFTFSPTY | 565 | A*3002 | 56 | 1.81 | 102 | 18 | 653 | 691 |
| 666 | 676 | 11 | KQAFTFSPTYK | 566 | A*0301 | 100 | 1.78 | 178 | 18 | 653 | 691 |
| 666 | 676 | 11 | KQAFTFSPTYK | 566 | A*1101 | 83 | 1.78 | 147 | 18 | 653 | 691 |
| 666 | 676 | 11 | KQAFTFSPTYK | 566 | A*3001 | 49 | 1.78 | 87 | 18 | 653 | 691 |
| 666 | 676 | 11 | KQAFTFSPTYK | 566 | A*7401 | 60 | 1.78 | 106 | 18 | 653 | 691 |
| 667 | 676 | 10 | QAFTFSPTYK | 567 | A*0301 | 64 | 1.78 | 114 | 18 | 653 | 691 |
| 667 | 676 | 10 | QAFTFSPTYK | 567 | A*1101 | 78 | 1.78 | 139 | 18 | 653 | 691 |
| 667 | 676 | 10 | QAFTFSPTYK | 567 | A*6801 | 91 | 1.78 | 162 | 18 | 653 | 691 |
| 667 | 676 | 10 | QAFTFSPTYK | 567 | A*7401 | 59 | 1.78 | 104 | 18 | 653 | 691 |
| 669 | 676 | 8 | FTFSPTYK | 568 | A*0301 | 98 | 1.78 | 175 | 18 | 653 | 691 |
| 669 | 676 | 8 | FTFSPTYK | 568 | A*1101 | 96 | 1.78 | 170 | 18 | 653 | 691 |
| 669 | 676 | 8 | FTFSPTYK | 568 | A*3101 | 25 | 1.78 | 45 | 18 | 653 | 691 |
| 669 | 676 | 8 | FTFSPTYK | 568 | A*3303 | 69 | 1.78 | 123 | 18 | 653 | 691 |
| 669 | 676 | 8 | FTFSPTYK | 568 | A*7401 | 99 | 1.78 | 176 | 18 | 653 | 691 |
| 669 | 677 | 9 | FTFSPTYKA | 569 | A*0201 | 2 | 1.62 | 4 | 18 | 653 | 691 |
| 669 | 677 | 9 | FTFSPTYKA | 569 | A*6802 | 47 | 1.62 | 76 | 18 | 653 | 691 |
| 669 | 677 | 9 | FTFSPTYKA | 569 | B*5601 | 36 | 1.62 | 58 | 18 | 653 | 691 |

TABLE 4a-continued

Predicted HLA class I-restricted CD8+ cytotoxic T cell epitopes contained in SLP sequences from HBV polymerase protein.

HLA class I binding peptides in SLP sequences derived from HBV Polymerase protein

| Start | End | Length | Sequence [A] | SEQ ID NO: | HLA class I molecule | Class I-B score[B] | C-score[C] | Class I-BCI score[D] | SLP# | Peptide of invention (SLP) SLP Start | SLP End |
|---|---|---|---|---|---|---|---|---|---|---|---|
| 668 | 678 | 11 | AFTFSPTYKAF | 570 | A*2402 | 14 | 0.94 | 13 | 18 | 653 | 691 |
| 669 | 678 | 10 | FTFSPTYKAF | 571 | A*0101 | 64 | 0.94 | 60 | 18 | 653 | 691 |
| 669 | 678 | 10 | FTFSPTYKAF | 571 | A*2501 | 96 | 0.94 | 90 | 18 | 653 | 691 |
| 669 | 678 | 10 | FTFSPTYKAF | 571 | A*2601 | 92 | 0.94 | 87 | 18 | 653 | 691 |
| 669 | 678 | 10 | FTFSPTYKAF | 571 | B*1501 | 88 | 0.94 | 82 | 18 | 653 | 691 |
| 669 | 678 | 10 | FTFSPTYKAF | 571 | B*1502 | 100 | 0.94 | 94 | 18 | 653 | 691 |
| 669 | 678 | 10 | FTFSPTYKAF | 571 | B*1525 | 83 | 0.94 | 78 | 18 | 653 | 691 |
| 669 | 678 | 10 | FTFSPTYKAF | 571 | B*3501 | 36 | 0.94 | 34 | 18 | 653 | 691 |
| 669 | 678 | 10 | FTFSPTYKAF | 571 | B*3503 | 43 | 0.94 | 41 | 18 | 653 | 691 |
| 669 | 678 | 10 | FTFSPTYKAF | 571 | B*4601 | 98 | 0.94 | 92 | 18 | 653 | 691 |
| 669 | 678 | 10 | FTFSPTYKAF | 571 | B*5802 | 48 | 0.94 | 45 | 18 | 653 | 691 |
| 670 | 678 | 9 | TFSPTYKAF | 572 | A*2301 | 83 | 0.94 | 78 | 18 | 653 | 691 |
| 670 | 678 | 9 | TFSPTYKAF | 572 | A*2402 | 42 | 0.94 | 39 | 18 | 653 | 691 |
| 669 | 679 | 11 | FTFSPTYKAFL | 573 | A*2501 | 61 | 0.51 | 32 | 18 | 653 | 691 |
| 669 | 679 | 11 | FTFSPTYKAFL | 573 | A*2601 | 46 | 0.51 | 24 | 18 | 653 | 691 |
| 669 | 679 | 11 | FTFSPTYKAFL | 573 | B*4601 | 61 | 0.51 | 31 | 18 | 653 | 691 |
| 672 | 679 | 8 | SPTYKAFL | 574 | B*0801 | 39 | 0.51 | 20 | 18 | 653 | 691 |
| 672 | 679 | 8 | SPTYKAFL | 574 | B*3503 | 15 | 0.51 | 8 | 18 | 653 | 691 |
| 672 | 679 | 8 | SPTYKAFL | 574 | B*5501 | 1 | 0.51 | 1 | 18 | 653 | 691 |
| 673 | 681 | 9 | PTYKAFLSK | 575 | A*0301 | 72 | 1.52 | 110 | 18 | 653 | 691 |
| 673 | 681 | 9 | PTYKAFLSK | 575 | A*1101 | 61 | 1.52 | 92 | 18 | 653 | 691 |
| 674 | 681 | 8 | TYKAFLSK | 576 | A*3001 | 77 | 1.52 | 117 | 18 | 653 | 691 |
| 674 | 681 | 8 | TYKAFLSK | 576 | A*3101 | 18 | 1.52 | 27 | 18 | 653 | 691 |
| 673 | 683 | 11 | PTYKAFLSKQY | 577 | A*0101 | 47 | 1.56 | 73 | 18 | 653 | 691 |
| 673 | 683 | 11 | PTYKAFLSKQY | 577 | A*2902 | 8 | 1.56 | 12 | 18 | 653 | 691 |
| 673 | 683 | 11 | PTYKAFLSKQY | 577 | A*3002 | 27 | 1.56 | 42 | 18 | 653 | 691 |
| 674 | 683 | 10 | TYKAFLSKQY | 578 | A*2902 | 67 | 1.56 | 104 | 18 | 653 | 691 |
| 674 | 683 | 10 | TYKAFLSKQY | 578 | A*3002 | 21 | 1.56 | 33 | 18 | 653 | 691 |
| 676 | 683 | 8 | KAFLSKQY | 579 | A*3002 | 51 | 1.56 | 79 | 18 | 653 | 691 |
| 676 | 683 | 8 | KAFLSKQY | 579 | B*1501 | 25 | 1.56 | 39 | 18 | 653 | 691 |
| 676 | 683 | 8 | KAFLSKQY | 579 | B*1502 | 11 | 1.56 | 17 | 18 | 653 | 691 |
| 676 | 683 | 8 | KAFLSKQY | 579 | B*1525 | 61 | 1.56 | 95 | 18 | 653 | 691 |
| 676 | 683 | 8 | KAFLSKQY | 579 | B*5701 | 71 | 1.56 | 111 | 18 | 653 | 691 |
| 676 | 683 | 8 | KAFLSKQY | 579 | B*5801 | 51 | 1.56 | 79 | 18 | 653 | 691 |

TABLE 4a-continued

Predicted HLA class I-restricted CD8+ cytotoxic T cell epitopes contained in SLP sequences from HBV polymerase protein.

HLA class I binding peptides in SLP sequences derived from HBV Polymerase protein

| Start | End | Length | Sequence[A] | SEQ ID NO: | HLA class I molecule | Class I-B score[B] | C-score[C] | Class I-BCI score[D] | SLP# | Peptide of invention (SLP) SLP Start | SLP End |
|---|---|---|---|---|---|---|---|---|---|---|---|
| 676 | 683 | 8 | KAFLSKQY | 579 | B*5802 | 62 | 1.56 | 97 | 18 | 653 | 691 |
| 676 | 684 | 9 | KAFLSKQYM | 580 | B*5701 | 82 | 1.51 | 124 | 18 | 653 | 691 |
| 676 | 684 | 9 | KAFLSKQYM | 580 | B*5801 | 46 | 1.51 | 69 | 18 | 653 | 691 |
| 676 | 685 | 10 | KAFLSKQYMN | 581 | A*3001 | 63 | 1.51 | 24 | 18 | 653 | 691 |
| 676 | 686 | 11 | KAFLSKQYMNL | 582 | A*3001 | 48 | 1.83 | 88 | 18 | 653 | 691 |
| 676 | 686 | 11 | KAFLSKQYMNL | 582 | A*3201 | 24 | 1.83 | 44 | 18 | 653 | 691 |
| 676 | 686 | 11 | KAFLSKQYMNL | 582 | B*4801 | 13 | 1.83 | 25 | 18 | 653 | 691 |
| 676 | 686 | 11 | KAFLSKQYMNL | 582 | B*5701 | 62 | 1.83 | 114 | 18 | 653 | 691 |
| 676 | 686 | 11 | KAFLSKQYMNL | 582 | B*5801 | 19 | 1.83 | 34 | 18 | 653 | 691 |
| 676 | 686 | 11 | KAFLSKQYMNL | 582 | B*5802 | 23 | 1.83 | 43 | 18 | 653 | 691 |
| 678 | 686 | 9 | FLSKQYMNL | 583 | A*0201 | 33 | 1.83 | 61 | 18 | 653 | 691 |
| 677 | 687 | 11 | AFLSKQYMNLY | 584 | A*2902 | 84 | 1.58 | 133 | 18 | 653 | 691 |
| 677 | 687 | 11 | AFLSKQYMNLY | 584 | A*3002 | 55 | 1.58 | 87 | 18 | 653 | 691 |
| 678 | 687 | 10 | FLSKQYMNLY | 585 | A*0101 | 98 | 1.58 | 155 | 18 | 653 | 691 |
| 678 | 687 | 10 | FLSKQYMNLY | 585 | A*2501 | 67 | 1.58 | 106 | 18 | 653 | 691 |
| 678 | 687 | 10 | FLSKQYMNLY | 585 | A*3002 | 34 | 1.58 | 53 | 18 | 653 | 691 |
| 678 | 687 | 10 | FLSKQYMNLY | 585 | B*1501 | 23 | 1.58 | 37 | 18 | 653 | 691 |
| 678 | 687 | 10 | FLSKQYMNLY | 585 | B*1502 | 35 | 1.58 | 56 | 18 | 653 | 691 |
| 678 | 687 | 10 | FLSKQYMNLY | 585 | B*4601 | 18 | 1.58 | 28 | 18 | 653 | 691 |
| 679 | 687 | 9 | LSKQYMNLY | 586 | A*0101 | 96 | 1.58 | 152 | 18 | 653 | 691 |
| 679 | 687 | 9 | LSKQYMNLY | 586 | A*3002 | 69 | 1.58 | 109 | 18 | 653 | 691 |
| 679 | 687 | 9 | LSKQYMNLY | 586 | B*1501 | 27 | 1.58 | 42 | 18 | 653 | 691 |
| 680 | 687 | 8 | SKQYMNLY | 587 | B*3501 | 21 | 1.59 | 34 | 18 | 653 | 691 |
| 679 | 689 | 11 | LSKQYMNLYPV | 588 | B*0801 | 37 | 0.93 | 35 | 18 | 653 | 691 |
| 681 | 689 | 9 | KQYMNLYPV | 589 | A*0201 | 89 | 0.93 | 83 | 18 | 653 | 691 |
| 681 | 689 | 9 | KQYMNLYPV | 589 | A*0206 | 96 | 0.93 | 89 | 18 | 653 | 691 |
| 681 | 689 | 9 | KQYMNLYPV | 589 | A*3201 | 44 | 0.93 | 41 | 18 | 653 | 691 |
| 681 | 689 | 9 | KQYMNLYPV | 589 | B*1301 | 72 | 0.93 | 67 | 18 | 653 | 691 |
| 681 | 689 | 9 | KQYMNLYPV | 589 | B*1302 | 38 | 0.93 | 35 | 18 | 653 | 691 |
| 681 | 689 | 9 | KQYMNLYPV | 589 | B*1525 | 29 | 0.93 | 27 | 18 | 653 | 691 |
| 681 | 689 | 9 | KQYMNLYPV | 589 | B*2702 | 48 | 0.93 | 45 | 18 | 653 | 691 |
| 681 | 689 | 9 | KQYMNLYPV | 589 | B*4801 | 88 | 0.93 | 82 | 18 | 653 | 691 |
| 681 | 689 | 9 | KQYMNLYPV | 589 | B*5001 | 48 | 0.93 | 45 | 18 | 653 | 691 |
| 681 | 689 | 9 | KQYMNLYPV | 589 | B*5201 | 73 | 0.93 | 67 | 18 | 653 | 691 |
| 682 | 689 | 8 | QYMNLYPV | 590 | A*2301 | 59 | 0.93 | 54 | 18 | 653 | 691 |

TABLE 4a-continued

Predicted HLA class I-restricted CD8[+] cytotoxic T cell epitopes contained in SLP sequences from HBV polymerase protein.

HLA class I binding peptides in SLP sequences derived from HBV Polymerase protein

| Start | End | Length | Sequence[A] | SEQ ID NO: | HLA class I molecule | Class I-B score[B] | C-score[C] | Class I-BCI score[D] | Peptide of invention (SLP) | | |
|---|---|---|---|---|---|---|---|---|---|---|---|
| | | | | | | | | | SLP# | SLP Start | SLP End |
| 682 | 689 | 8 | QYMNLYPV | 590 | A*2402 | 61 | 0.93 | 57 | 18 | 653 | 691 |
| 681 | 690 | 10 | KQYMNLYPVA | 591 | B*1302 | 3 | 1.25 | 4 | 18 | 653 | 691 |
| 681 | 690 | 10 | KQYMNLYPVA | 591 | B*4801 | 42 | 1.25 | 53 | 18 | 653 | 691 |
| 681 | 690 | 10 | KQYMNLYPVA | 591 | B*5001 | 16 | 1.25 | 20 | 18 | 653 | 691 |
| 681 | 691 | 11 | KQYMNLYPVAR | 592 | A*0301 | 49 | 1.78 | 88 | 18 | 653 | 691 |
| 681 | 691 | 11 | KQYMNLYPVAR | 592 | A*3101 | 100 | 1.78 | 178 | 18 | 653 | 691 |
| 681 | 691 | 11 | KQYMNLYPVAR | 592 | A*3201 | 23 | 1.78 | 40 | 18 | 653 | 691 |
| 681 | 691 | 11 | KQYMNLYPVAR | 592 | A*7401 | 100 | 1.78 | 178 | 18 | 653 | 691 |
| 682 | 691 | 10 | QYMNLYPVAR | 593 | A*3101 | 84 | 1.78 | 149 | 18 | 653 | 691 |
| 682 | 691 | 10 | QYMNLYPVAR | 593 | A*3303 | 90 | 1.78 | 160 | 18 | 653 | 691 |
| 683 | 691 | 9 | YMNLYPVAR | 594 | A*3101 | 78 | 1.78 | 140 | 18 | 653 | 691 |
| 683 | 691 | 9 | YMNLYPVAR | 594 | A*3303 | 89 | 1.78 | 158 | 18 | 653 | 691 |
| 683 | 691 | 9 | YMNLYPVAR | 594 | A*7401 | 94 | 1.78 | 167 | 18 | 653 | 691 |
| 684 | 691 | 8 | MNLYPVAR | 595 | A*3101 | 16 | 1.78 | 29 | 18 | 653 | 691 |
| 684 | 691 | 8 | MNLYPVAR | 595 | A*3303 | 75 | 1.78 | 133 | 18 | 653 | 691 |
| | | | | | Cumulative Class I-BCI score: | | | 12576 | | | |
| 657 | 665 | 9 | MPLYACIQA | 556 | B*3501 | 44 | 1.41 | 62 | 19 | 657 | 691 |
| 657 | 665 | 9 | MPLYACIQA | 556 | B*3503 | 49 | 1.41 | 68 | 19 | 657 | 691 |
| 657 | 665 | 9 | MPLYACIQA | 556 | B*5101 | 80 | 1.41 | 112 | 19 | 657 | 691 |
| 657 | 665 | 9 | MPLYACIQA | 556 | B*5501 | 93 | 1.41 | 131 | 19 | 657 | 691 |
| 657 | 665 | 9 | MPLYACIQA | 556 | B*5601 | 99 | 1.41 | 139 | 19 | 657 | 691 |
| 657 | 666 | 10 | MPLYACIQAK | 557 | B*3501 | 43 | 1.01 | 43 | 19 | 657 | 691 |
| 657 | 666 | 10 | MPLYACIQAK | 557 | B*5601 | 3 | 1.01 | 3 | 19 | 657 | 691 |
| 658 | 666 | 9 | PLYACIQAK | 558 | A*0301 | 74 | 1.01 | 75 | 19 | 657 | 691 |
| 659 | 669 | 11 | LYACIQAKQAF | 559 | A*2301 | 86 | 1.07 | 92 | 19 | 657 | 691 |
| 659 | 669 | 11 | LYACIQAKQAF | 559 | A*2402 | 88 | 1.07 | 94 | 19 | 657 | 691 |
| 660 | 669 | 10 | YACIQAKQAF | 560 | B*1502 | 26 | 1.07 | 28 | 19 | 657 | 691 |
| 663 | 671 | 9 | IQAKQAFTF | 561 | A*2402 | 84 | 1.58 | 133 | 19 | 657 | 691 |
| 663 | 671 | 9 | IQAKQAFTF | 561 | B*1301 | 61 | 1.58 | 96 | 19 | 657 | 691 |
| 663 | 671 | 9 | IQAKQAFTF | 561 | B*1501 | 63 | 1.58 | 99 | 19 | 657 | 691 |
| 663 | 671 | 9 | IQAKQAFTF | 561 | B*1525 | 71 | 1.58 | 112 | 19 | 657 | 691 |
| 664 | 671 | 8 | QAKQAFTF | 562 | B*1501 | 8 | 1.58 | 12 | 19 | 657 | 691 |
| 664 | 671 | 8 | QAKQAFTF | 562 | B*1502 | 37 | 1.58 | 59 | 19 | 657 | 691 |
| 664 | 671 | 8 | QAKQAFTF | 562 | B*1525 | 14 | 1.58 | 21 | 19 | 657 | 691 |
| 664 | 671 | 8 | QAKQAFTF | 562 | B*5802 | 3 | 1.58 | 5 | 19 | 657 | 691 |

TABLE 4a-continued

Predicted HLA class I-restricted CD8+ cytotoxic T cell epitopes contained in SLP sequences from HBV polymerase protein.

HLA class I binding peptides in SLP sequences derived from HBV Polymerase protein

| Start | End | Length | Sequence[A] | SEQ ID NO: | HLA class I

TABLE 4a-continued

Predicted HLA class I-restricted CD8+ cytotoxic T cell epitopes contained in SLP sequences from HBV polymerase protein.

HLA class I binding peptides in SLP sequences derived from HBV Polymerase protein

| Start | End | Length | Sequence[A] | SEQ ID NO: | HLA class I molecule | Class I-B score[B] | C-score[C] | Class I-BCI score[D] | SLP# | Peptide of invention (SLP) SLP Start | SLP End |
|---|---|---|---|---|---|---|---|---|---|---|---|
| 669 | 678 | 10 | FTFSPTYKAF | 571 | B*1502 | 100 | 0.94 | 94 | 19 | 657 | 691 |
| 669 | 678 | 10 | FTFSPTYKAF | 571 | B*1525 | 83 | 0.94 | 78 | 19 | 657 | 691 |
| 669 | 678 | 10 | FTFSPTYKAF | 571 | B*3501 | 36 | 0.94 | 34 | 19 | 657 | 691 |
| 669 | 678 | 10 | FTFSPTYKAF | 571 | B*3503 | 43 | 0.94 | 41 | 19 | 657 | 691 |
| 669 | 678 | 10 | FTFSPTYKAF | 571 | B*4601 | 98 | 0.94 | 92 | 19 | 657 | 691 |
| 669 | 678 | 10 | FTFSPTYKAF | 571 | B*5802 | 48 | 0.94 | 45 | 19 | 657 | 691 |
| 670 | 678 | 9 | TFSPTYKAF | 572 | A*2301 | 83 | 0.94 | 78 | 19 | 657 | 691 |
| 670 | 678 | 9 | TFSPTYKAF | 572 | A*2402 | 42 | 0.94 | 39 | 19 | 657 | 691 |
| 669 | 679 | 11 | FTFSPTYKAFL | 573 | A*2501 | 61 | 0.51 | 32 | 19 | 657 | 691 |
| 669 | 679 | 11 | FTFSPTYKAFL | 573 | A*2601 | 46 | 0.51 | 24 | 19 | 657 | 691 |
| 669 | 679 | 11 | FTFSPTYKAFL | 573 | B*4601 | 61 | 0.51 | 31 | 19 | 657 | 691 |
| 672 | 679 | 8 | SPTYKAFL | 574 | B*0801 | 39 | 0.51 | 20 | 19 | 657 | 691 |
| 672 | 679 | 8 | SPTYKAFL | 574 | B*3503 | 15 | 0.51 | 8 | 19 | 657 | 691 |
| 672 | 679 | 8 | SPTYKAFL | 574 | B*5501 | 1 | 0.51 | 1 | 19 | 657 | 691 |
| 673 | 681 | 9 | PTYKAFLSK | 575 | A*0301 | 72 | 1.52 | 110 | 19 | 657 | 691 |
| 673 | 681 | 9 | PTYKAFLSK | 575 | A*1101 | 61 | 1.52 | 92 | 19 | 657 | 691 |
| 674 | 681 | 8 | TYKAFLSK | 576 | A*3001 | 77 | 1.52 | 117 | 19 | 657 | 691 |
| 674 | 681 | 8 | TYKAFLSK | 576 | A*3101 | 18 | 1.52 | 27 | 19 | 657 | 691 |
| 673 | 683 | 11 | PTYKAFLSKQY | 577 | A*0101 | 47 | 1.56 | 73 | 19 | 657 | 691 |
| 673 | 683 | 11 | PTYKAFLSKQY | 577 | A*2902 | 8 | 1.56 | 12 | 19 | 657 | 691 |
| 673 | 683 | 11 | PTYKAFLSKQY | 577 | A*3002 | 27 | 1.56 | 42 | 19 | 657 | 691 |
| 674 | 683 | 10 | TYKAFLSKQY | 578 | A*2902 | 67 | 1.56 | 104 | 19 | 657 | 691 |
| 674 | 683 | 10 | TYKAFLSKQY | 578 | A*3002 | 21 | 1.56 | 33 | 19 | 657 | 691 |
| 676 | 683 | 8 | KAFLSKQY | 579 | A*3002 | 51 | 1.56 | 79 | 19 | 657 | 691 |
| 676 | 683 | 8 | KAFLSKQY | 579 | B*1501 | 25 | 1.56 | 39 | 19 | 657 | 691 |
| 676 | 683 | 8 | KAFLSKQY | 579 | B*1502 | 11 | 1.56 | 17 | 19 | 657 | 691 |
| 676 | 683 | 8 | KAFLSKQY | 579 | B*1525 | 61 | 1.56 | 95 | 19 | 657 | 691 |
| 676 | 683 | 8 | KAFLSKQY | 579 | B*5701 | 71 | 1.56 | 111 | 19 | 657 | 691 |
| 676 | 683 | 8 | KAFLSKQY | 579 | B*5801 | 51 | 1.56 | 79 | 19 | 657 | 691 |
| 676 | 683 | 8 | KAFLSKQY | 579 | B*5802 | 62 | 1.56 | 97 | 19 | 657 | 691 |
| 676 | 684 | 9 | KAFLSKQYM | 580 | B*5701 | 82 | 1.51 | 124 | 19 | 657 | 691 |
| 676 | 684 | 9 | KAFLSKQYM | 580 | B*5801 | 46 | 1.51 | 69 | 19 | 657 | 691 |
| 676 | 685 | 10 | KAFLSKQYMN | 581 | A*3001 | 63 | 1.51 | 24 | 19 | 657 | 691 |
| 676 | 686 | 11 | KAFLSKQYMNL | 582 | A*3001 | 48 | 1.83 | 88 | 19 | 657 | 691 |
| 676 | 686 | 11 | KAFLSKQYMNL | 582 | A*3201 | 24 | 1.83 | 44 | 19 | 657 | 691 |

TABLE 4a-continued

Predicted HLA class I-restricted CD8+ cytotoxic T cell epitopes contained in SLP sequences from HBV polymerase protein.

HLA class I binding peptides in SLP sequences derived from HBV Polymerase protein

| Start | End | Length | Sequence [A] | SEQ ID NO: | HLA class I molecule | Class I-B score[B] | C-score[C] | Class I-BCI score[D] | SLP# | SLP Start | SLP End |
|---|---|---|---|---|---|---|---|---|---|---|---|
| 676 | 686 | 11 | KAFLSKQYMNL | 582 | B*4801 | 13 | 1.83 | 25 | 19 | 657 | 691 |
| 676 | 686 | 11 | KAFLSKQYMNL | 582 | B*5701 | 62 | 1.83 | 114 | 19 | 657 | 691 |
| 676 | 686 | 11 | KAFLSKQYMNL | 582 | B*5801 | 19 | 1.83 | 34 | 19 | 657 | 691 |
| 676 | 686 | 11 | KAFLSKQYMNL | 582 | B*5802 | 23 | 1.83 | 43 | 19 | 657 | 691 |
| 678 | 686 | 9 | FLSKQYMNL | 583 | A*0201 | 33 | 1.83 | 61 | 19 | 657 | 691 |
| 677 | 687 | 11 | AFLSKQYMNLY | 584 | A*2902 | 84 | 1.58 | 133 | 19 | 657 | 691 |
| 677 | 687 | 11 | AFLSKQYMNLY | 584 | A*3002 | 55 | 1.58 | 87 | 19 | 657 | 691 |
| 678 | 687 | 10 | FLSKQYMNLY | 585 | A*0101 | 98 | 1.58 | 155 | 19 | 657 | 691 |
| 678 | 687 | 10 | FLSKQYMNLY | 585 | A*2501 | 67 | 1.58 | 106 | 19 | 657 | 691 |
| 678 | 687 | 10 | FLSKQYMNLY | 585 | A*3002 | 34 | 1.58 | 53 | 19 | 657 | 691 |
| 678 | 687 | 10 | FLSKQYMNLY | 585 | B*1501 | 23 | 1.58 | 37 | 19 | 657 | 691 |
| 678 | 687 | 10 | FLSKQYMNLY | 585 | B*1502 | 35 | 1.58 | 56 | 19 | 657 | 691 |
| 678 | 687 | 10 | FLSKQYMNLY | 585 | B*4601 | 18 | 1.58 | 28 | 19 | 657 | 691 |
| 679 | 687 | 9 | LSKQYMNLY | 586 | A*0101 | 96 | 1.58 | 152 | 19 | 657 | 691 |
| 679 | 687 | 9 | LSKQYMNLY | 586 | A*3002 | 69 | 1.58 | 109 | 19 | 657 | 691 |
| 679 | 687 | 9 | LSKQYMNLY | 586 | B*1501 | 27 | 1.58 | 42 | 19 | 657 | 691 |
| 680 | 687 | 8 | SKQYMNLY | 587 | B*3501 | 21 | 1.58 | 34 | 19 | 657 | 691 |
| 679 | 689 | 11 | LSKQYMNLYPV | 588 | B*0801 | 37 | 0.93 | 35 | 19 | 657 | 691 |
| 681 | 689 | 9 | KQYMNLYPV | 589 | A*0201 | 89 | 0.93 | 83 | 19 | 657 | 691 |
| 681 | 689 | 9 | KQYMNLYPV | 589 | A*0206 | 96 | 0.93 | 89 | 19 | 657 | 691 |
| 681 | 689 | 9 | KQYMNLYPV | 589 | A*3201 | 44 | 0.93 | 41 | 19 | 657 | 691 |
| 681 | 689 | 9 | KQYMNLYPV | 589 | B*1301 | 72 | 0.93 | 67 | 19 | 657 | 691 |
| 681 | 689 | 9 | KQYMNLYPV | 589 | B*1302 | 38 | 0.93 | 35 | 19 | 657 | 691 |
| 681 | 689 | 9 | KQYMNLYPV | 589 | B*1525 | 29 | 0.93 | 27 | 19 | 657 | 691 |
| 681 | 689 | 9 | KQYMNLYPV | 589 | B*2702 | 48 | 0.93 | 45 | 19 | 657 | 691 |
| 681 | 689 | 9 | KQYMNLYPV | 589 | B*4801 | 88 | 0.93 | 82 | 19 | 657 | 691 |
| 681 | 689 | 9 | KQYMNLYPV | 589 | B*5001 | 48 | 0.93 | 45 | 19 | 657 | 691 |
| 681 | 689 | 9 | KQYMNLYPV | 589 | B*5201 | 73 | 0.93 | 67 | 19 | 657 | 691 |
| 682 | 689 | 8 | QYMNLYPV | 590 | A*2301 | 59 | 0.93 | 54 | 19 | 657 | 691 |
| 682 | 689 | 8 | QYMNLYPV | 590 | A*2402 | 61 | 0.93 | 57 | 19 | 657 | 691 |
| 681 | 690 | 10 | KQYMNLYPVA | 591 | B*1302 | 3 | 1.25 | 4 | 19 | 657 | 691 |
| 681 | 690 | 10 | KQYMNLYPVA | 591 | B*4801 | 42 | 1.25 | 53 | 19 | 657 | 691 |
| 681 | 690 | 10 | KQYMNLYPVA | 591 | B*5001 | 16 | 1.25 | 20 | 19 | 657 | 691 |
| 681 | 691 | 11 | KQYMNLYPVAR | 592 | A*0301 | 49 | 1.78 | 88 | 19 | 657 | 691 |

TABLE 4a-continued

Predicted HLA class I-restricted CD8+ cytotoxic T cell epitopes contained in SLP sequences from HBV polymerase protein.

HLA class I binding peptides in SLP sequences derived from HBV Polymerase protein

| Start | End | Length | Sequence[A] | SEQ ID NO: | HLA class I molecule | Class I-B score[B] | C-score[C] | Class I-BCI score[D] | SLP# | Peptide of invention (SLP) SLP Start | SLP End |
|---|---|---|---|---|---|---|---|---|---|---|---|
| 681 | 691 | 11 | KQYMNLYPVAR | 592 | A*3101 | 100 | 1.78 | 178 | 19 | 657 | 691 |
| 681 | 691 | 11 | KQYMNLYPVAR | 592 | A*3201 | 23 | 1.78 | 40 | 19 | 657 | 691 |
| 681 | 691 | 11 | KQYMNLYPVAR | 592 | A*7401 | 100 | 1.78 | 178 | 19 | 657 | 691 |
| 682 | 691 | 10 | QYMNLYPVAR | 593 | A*3101 | 84 | 1.78 | 149 | 19 | 657 | 691 |
| 682 | 691 | 10 | QYMNLYPVAR | 593 | A*3303 | 90 | 1.78 | 160 | 19 | 657 | 691 |
| 683 | 691 | 9 | YMNLYPVAR | 594 | A*3101 | 78 | 1.78 | 140 | 19 | 657 | 691 |
| 683 | 691 | 9 | YMNLYPVAR | 594 | A*3303 | 89 | 1.78 | 158 | 19 | 657 | 691 |
| 683 | 691 | 9 | YMNLYPVAR | 594 | A*7401 | 94 | 1.78 | 167 | 19 | 657 | 691 |
| 684 | 691 | 8 | MNLYPVAR | 595 | A*3101 | 16 | 1.78 | 29 | 19 | 657 | 691 |
| 684 | 691 | 8 | MNLYPVAR | 595 | A*3303 | 75 | 1.78 | 133 | 19 | 657 | 691 |
| | | | | | Cumulative Class I-BCI score: | | | 10420 | | | |
| 716 | 723 | 8 | RMRGTFVA | 596 | A*3001 | 92 | 1.41 | 130 | 20 | 715 | 746 |
| 716 | 724 | 9 | RMRGTFVAP | 597 | A*3001 | 7 | 0.12 | 1 | 20 | 715 | 746 |
| 717 | 724 | 8 | MRGTFVAP | 598 | A*0206 | 94 | 0.12 | 11 | 20 | 715 | 746 |
| 715 | 725 | 11 | QRMRGTFVAPL | 599 | B*1402 | 89 | 0.99 | 88 | 20 | 715 | 746 |
| 715 | 725 | 11 | QRMRGTFVAPL | 599 | B*2702 | 83 | 0.99 | 82 | 20 | 715 | 746 |
| 715 | 725 | 11 | QRMRGTFVAPL | 599 | B*3801 | 57 | 0.99 | 57 | 20 | 715 | 746 |
| 715 | 725 | 11 | QRMRGTFVAPL | 599 | B*3901 | 99 | 0.99 | 98 | 20 | 715 | 746 |
| 715 | 725 | 11 | QRMRGTFVAPL | 599 | B*4801 | 29 | 0.99 | 29 | 20 | 715 | 746 |
| 716 | 725 | 10 | RMRGTFVAPL | 600 | B*0801 | 76 | 0.99 | 76 | 20 | 715 | 746 |
| 716 | 725 | 10 | RMRGTFVAPL | 600 | B*1402 | 65 | 0.99 | 64 | 20 | 715 | 746 |
| 716 | 725 | 10 | RMRGTFVAPL | 600 | B*1501 | 67 | 0.99 | 67 | 20 | 715 | 746 |
| 716 | 725 | 10 | RMRGTFVAPL | 600 | B*1525 | 47 | 0.99 | 47 | 20 | 715 | 746 |
| 716 | 725 | 10 | RMRGTFVAPL | 600 | B*4801 | 90 | 0.99 | 90 | 20 | 715 | 746 |
| 717 | 725 | 9 | MRGTFVAPL | 601 | B*1402 | 88 | 0.99 | 87 | 20 | 715 | 746 |
| 717 | 725 | 9 | MRGTFVAPL | 601 | B*2702 | 71 | 0.99 | 70 | 20 | 715 | 746 |
| 717 | 725 | 9 | MRGTFVAPL | 601 | B*3901 | 81 | 0.99 | 80 | 20 | 715 | 746 |
| 716 | 726 | 11 | RMRGTFVAPLP | 602 | A*3001 | 37 | 0.08 | 3 | 20 | 715 | 746 |
| 718 | 726 | 9 | RGTFVAPLP | 603 | B*5802 | 45 | 0.08 | 4 | 20 | 715 | 746 |
| 717 | 727 | 11 | MRGTFVAPLPI | 604 | B*1402 | 70 | 0.98 | 68 | 20 | 715 | 746 |
| 717 | 727 | 11 | MRGTFVAPLPI | 604 | B*2702 | 82 | 0.98 | 80 | 20 | 715 | 746 |
| 717 | 727 | 11 | MRGTFVAPLPI | 604 | B*3801 | 37 | 0.98 | 36 | 20 | 715 | 746 |
| 717 | 727 | 11 | MRGTFVAPLPI | 604 | B*3901 | 49 | 0.98 | 48 | 20 | 715 | 746 |
| 717 | 727 | 11 | MRGTFVAPLPI | 604 | B*5201 | 18 | 0.98 | 17 | 20 | 715 | 746 |
| 719 | 727 | 9 | GTFVAPLPI | 605 | A*3201 | 70 | 0.98 | 68 | 20 | 715 | 746 |

TABLE 4a-continued

Predicted HLA class I-restricted CD8+ cytotoxic T cell epitopes contained in SLP sequences from HBV polymerase protein.

HLA class I binding peptides in SLP sequences derived from HBV Polymerase protein

| Start | End | Length | Sequence [A] | SEQ ID NO: | HLA class I molecule | Class I-B score [B] | C-score [C] | Class I-BCI score [D] | Peptide of invention (SLP) | | |
|---|---|---|---|---|---|---|---|---|---|---|---|
| | | | | | | | | | SLP# | SLP Start | SLP End |
| 719 | 727 | 9 | GTFVAPLPI | 605 | B*5201 | 59 | 0.98 | 58 | 20 | 715 | 746 |
| 720 | 727 | 8 | TFVAPLPI | 606 | A*2301 | 19 | 0.98 | 19 | 20 | 715 | 746 |
| 720 | 727 | 8 | TFVAPLPI | 606 | A*2402 | 12 | 0.98 | 12 | 20 | 715 | 746 |
| 719 | 728 | 10 | GTFVAPLPIH | 607 | A*3001 | 97 | 0.37 | 36 | 20 | 715 | 746 |
| 721 | 730 | 10 | FVAPLPIHTA | 608 | A*0206 | 58 | 1.82 | 106 | 20 | 715 | 746 |
| 721 | 730 | 10 | FVAPLPIHTA | 608 | B*5601 | 51 | 1.82 | 94 | 20 | 715 | 746 |
| 723 | 730 | 8 | APLPIHTA | 609 | B*5501 | 67 | 1.82 | 123 | 20 | 715 | 746 |
| 723 | 730 | 8 | APLPIHTA | 609 | B*5601 | 76 | 1.82 | 138 | 20 | 715 | 746 |
| 723 | 732 | 10 | APLPIHTAEL | 610 | B*0702 | 67 | 1.48 | 99 | 20 | 715 | 746 |
| 723 | 732 | 10 | APLPIHTAEL | 610 | B*1402 | 69 | 1.48 | 102 | 20 | 715 | 746 |
| 723 | 732 | 10 | APLPIHTAEL | 610 | B*3503 | 66 | 1.48 | 98 | 20 | 715 | 746 |
| 723 | 732 | 10 | APLPIHTAEL | 610 | B*5501 | 53 | 1.48 | 79 | 20 | 715 | 746 |
| 723 | 732 | 10 | APLPIHTAEL | 610 | B*5601 | 44 | 1.48 | 65 | 20 | 715 | 746 |
| 725 | 732 | 8 | LPIHTAEL | 611 | B*1402 | 76 | 1.48 | 112 | 20 | 715 | 746 |
| 725 | 732 | 8 | LPIHTAEL | 611 | B*3503 | 89 | 1.48 | 132 | 20 | 715 | 746 |
| 725 | 732 | 8 | LPIHTAEL | 611 | B*3901 | 48 | 1.48 | 71 | 20 | 715 | 746 |
| 725 | 732 | 8 | LPIHTAEL | 611 | B*5101 | 88 | 1.48 | 131 | 20 | 715 | 746 |
| 725 | 732 | 8 | LPIHTAEL | 611 | B*5301 | 77 | 1.48 | 114 | 20 | 715 | 746 |
| 725 | 732 | 8 | LPIHTAEL | 611 | B*5501 | 74 | 1.48 | 110 | 20 | 715 | 746 |
| 725 | 732 | 8 | LPIHTAEL | 611 | B*5601 | 71 | 1.48 | 104 | 20 | 715 | 746 |
| 723 | 733 | 11 | APLPIHTAELL | 612 | B*0702 | 33 | 1.70 | 57 | 20 | 715 | 746 |
| 723 | 733 | 11 | APLPIHTAELL | 612 | B*1402 | 39 | 1.70 | 67 | 20 | 715 | 746 |
| 725 | 733 | 9 | LPIHTAELL | 613 | B*0702 | 1 | 1.70 | 2 | 20 | 715 | 746 |
| 725 | 733 | 9 | LPIHTAELL | 613 | B*1402 | 38 | 1.70 | 65 | 20 | 715 | 746 |
| 725 | 733 | 9 | LPIHTAELL | 613 | B*3503 | 57 | 1.70 | 97 | 20 | 715 | 746 |
| 725 | 733 | 9 | LPIHTAELL | 613 | B*5101 | 78 | 1.70 | 133 | 20 | 715 | 746 |
| 725 | 733 | 9 | LPIHTAELL | 613 | B*5301 | 61 | 1.70 | 103 | 20 | 715 | 746 |
| 725 | 733 | 9 | LPIHTAELL | 613 | B*5501 | 10 | 1.70 | 18 | 20 | 715 | 746 |
| 725 | 733 | 9 | LPIHTAELL | 613 | B*5601 | 26 | 1.70 | 44 | 20 | 715 | 746 |
| 725 | 734 | 10 | LPIHTAELLA | 614 | B*3503 | 42 | 1.12 | 47 | 20 | 715 | 746 |
| 725 | 734 | 10 | LPIHTAELLA | 614 | B*5501 | 81 | 1.12 | 91 | 20 | 715 | 746 |
| 725 | 734 | 10 | LPIHTAELLA | 614 | B*5601 | 92 | 1.12 | 103 | 20 | 715 | 746 |
| 725 | 735 | 11 | LPIHTAELLAA | 615 | B*0702 | 45 | 1.10 | 49 | 20 | 715 | 746 |
| 725 | 735 | 11 | LPIHTAELLAA | 615 | B*3501 | 76 | 1.10 | 84 | 20 | 715 | 746 |
| 725 | 735 | 11 | LPIHTAELLAA | 615 | B*3503 | 65 | 1.10 | 71 | 20 | 715 | 746 |

TABLE 4a-continued

Predicted HLA class I-restricted CD8+ cytotoxic T cell epitopes contained in SLP sequences from HBV polymerase protein.

HLA class I binding peptides in SLP sequences derived from HBV Polymerase protein

| Start | End | Length | Sequence[A] | SEQ ID NO: | HLA class I molecule | Class I-B score[B] | C-score[C] | Class I-BCI score[D] | SLP# | SLP Start | SLP End |
|---|---|---|---|---|---|---|---|---|---|---|---|
| 725 | 735 | 11 | LPIHTAELLAA | 615 | B*5101 | 45 | 1.10 | 49 | 20 | 715 | 746 |
| 725 | 735 | 11 | LPIHTAELLAA | 615 | B*5501 | 92 | 1.10 | 101 | 20 | 715 | 746 |
| 725 | 735 | 11 | LPIHTAELLAA | 615 | B*5601 | 97 | 1.10 | 107 | 20 | 715 | 746 |
| 728 | 735 | 8 | HTAELLAA | 616 | A*2501 | 31 | 1.10 | 34 | 20 | 715 | 746 |
| 728 | 735 | 8 | HTAELLAA | 616 | A*2601 | 72 | 1.10 | 79 | 20 | 715 | 746 |
| 728 | 735 | 8 | HTAELLAA | 616 | B*5501 | 9 | 1.10 | 10 | 20 | 715 | 746 |
| 728 | 735 | 8 | HTAELLAA | 616 | B*5601 | 32 | 1.10 | 35 | 20 | 715 | 746 |
| 728 | 736 | 9 | HTAELLAAC | 617 | A*2501 | 86 | 0.20 | 18 | 20 | 715 | 746 |
| 728 | 736 | 9 | HTAELLAAC | 617 | A*2601 | 54 | 0.20 | 11 | 20 | 715 | 746 |
| 728 | 737 | 10 | HTAELLAACF | 618 | A*0101 | 32 | 1.63 | 52 | 20 | 715 | 746 |
| 728 | 737 | 10 | HTAELLAACF | 618 | A*2501 | 94 | 1.63 | 153 | 20 | 715 | 746 |
| 728 | 737 | 10 | HTAELLAACF | 618 | A*2601 | 85 | 1.63 | 138 | 20 | 715 | 746 |
| 728 | 737 | 10 | HTAELLAACF | 618 | B*1502 | 43 | 1.63 | 69 | 20 | 715 | 746 |
| 728 | 737 | 10 | HTAELLAACF | 618 | B*4601 | 72 | 1.63 | 117 | 20 | 715 | 746 |
| 728 | 737 | 10 | HTAELLAACF | 618 | B*5802 | 42 | 1.63 | 68 | 20 | 715 | 746 |
| 730 | 737 | 8 | AELLAACF | 619 | B*1301 | 65 | 1.63 | 105 | 20 | 715 | 746 |
| 730 | 737 | 8 | AELLAACF | 619 | B*1801 | 76 | 1.63 | 124 | 20 | 715 | 746 |
| 730 | 737 | 8 | AELLAACF | 619 | B*4001 | 70 | 1.63 | 113 | 20 | 715 | 746 |
| 730 | 737 | 8 | AELLAACF | 619 | B*4002 | 65 | 1.63 | 106 | 20 | 715 | 746 |
| 730 | 737 | 8 | AELLAACF | 619 | B*4403 | 96 | 1.63 | 156 | 20 | 715 | 746 |
| 730 | 737 | 8 | AELLAACF | 619 | B*4901 | 52 | 1.63 | 85 | 20 | 715 | 746 |
| 730 | 737 | 8 | AELLAACF | 619 | B*5001 | 40 | 1.63 | 65 | 20 | 715 | 746 |
| 728 | 738 | 11 | HTAELLAACFA | 620 | A*2601 | 36 | 0.81 | 29 | 20 | 715 | 746 |
| 730 | 738 | 9 | AELLAACFA | 621 | B*1301 | 59 | 0.81 | 48 | 20 | 715 | 746 |
| 730 | 738 | 9 | AELLAACFA | 621 | B*1302 | 10 | 0.81 | 8 | 20 | 715 | 746 |
| 730 | 738 | 9 | AELLAACFA | 621 | B*3701 | 29 | 0.81 | 23 | 20 | 715 | 746 |
| 730 | 738 | 9 | AELLAACFA | 621 | B*4002 | 85 | 0.81 | 69 | 20 | 715 | 746 |
| 730 | 738 | 9 | AELLAACFA | 621 | B*4402 | 73 | 0.81 | 59 | 20 | 715 | 746 |
| 730 | 738 | 9 | AELLAACFA | 621 | B*4403 | 68 | 0.81 | 55 | 20 | 715 | 746 |
| 730 | 738 | 9 | AELLAACFA | 621 | B*4901 | 65 | 0.81 | 53 | 20 | 715 | 746 |
| 730 | 738 | 9 | AELLAACFA | 621 | B*5001 | 72 | 0.81 | 59 | 20 | 715 | 746 |
| 729 | 739 | 11 | TAELLAACFAR | 622 | A*6801 | 54 | 1.51 | 82 | 20 | 715 | 746 |
| 730 | 739 | 10 | AELLAACFAR | 623 | B*4002 | 45 | 1.51 | 68 | 20 | 715 | 746 |
| 731 | 739 | 9 | ELLAACFAR | 624 | A*3303 | 80 | 1.51 | 121 | 20 | 715 | 746 |

TABLE 4a-continued

Predicted HLA class I-restricted CD8+ cytotoxic T cell epitopes contained in SLP sequences from HBV polymerase protein.

HLA class I binding peptides in SLP sequences derived from HBV Polymerase protein

| Start | End | Length | Sequence[A] | SEQ ID NO: | HLA class I molecule | Class I-B score[B] | C-score[C] | Class I-BCI score[D] | SLP# | SLP Start | SLP End |
|---|---|---|---|---|---|---|---|---|---|---|---|
| 731 | 739 | 9 | ELLAACFAR | 624 | A*6801 | 71 | 1.51 | 107 | 20 | 715 | 746 |
| 731 | 739 | 9 | ELLAACFAR | 624 | A*7401 | 18 | 1.51 | 28 | 20 | 715 | 746 |
| 732 | 739 | 8 | LLAACFAR | 625 | A*3101 | 24 | 1.51 | 36 | 20 | 715 | 746 |
| 732 | 739 | 8 | LLAACFAR | 625 | A*3303 | 66 | 1.51 | 100 | 20 | 715 | 746 |
| 732 | 739 | 8 | LLAACFAR | 625 | A*6801 | 57 | 1.51 | 87 | 20 | 715 | 746 |
| 732 | 739 | 8 | LLAACFAR | 625 | A*7401 | 93 | 1.51 | 140 | 20 | 715 | 746 |
| 730 | 740 | 11 | AELLAACFARS | 626 | B*4402 | 12 | 0.24 | 3 | 20 | 715 | 746 |
| 730 | 740 | 11 | AELLAACFARS | 626 | B*4403 | 4 | 0.24 | 1 | 20 | 715 | 746 |
| 733 | 740 | 8 | LAACFARS | 627 | A*0206 | 13 | 0.24 | 3 | 20 | 715 | 746 |
| 731 | 741 | 11 | ELLAACFARSR | 628 | A*3303 | 37 | 1.17 | 43 | 20 | 715 | 746 |
| 732 | 741 | 10 | LLAACFARSR | 629 | A*3101 | 58 | 1.17 | 68 | 20 | 715 | 746 |
| 732 | 741 | 10 | LLAACFARSR | 629 | A*3303 | 6 | 1.17 | 7 | 20 | 715 | 746 |
| 732 | 741 | 10 | LLAACFARSR | 629 | A*7401 | 66 | 1.17 | 77 | 20 | 715 | 746 |
| 733 | 741 | 9 | LAACFARSR | 630 | A*3303 | 28 | 1.17 | 33 | 20 | 715 | 746 |
| 733 | 741 | 9 | LAACFARSR | 630 | A*6801 | 56 | 1.17 | 66 | 20 | 715 | 746 |
| 734 | 741 | 8 | AACFARSR | 631 | A*3101 | 15 | 1.17 | 18 | 20 | 715 | 746 |
| 737 | 744 | 8 | FARSRSGA | 632 | B*0801 | 85 | 0.75 | 63 | 20 | 715 | 746 |
| 737 | 744 | 8 | FARSRSGA | 632 | B*5501 | 59 | 0.75 | 44 | 20 | 715 | 746 |
| 737 | 744 | 8 | FARSRSGA | 632 | B*5601 | 1 | 0.75 | 1 | 20 | 715 | 746 |
| 737 | 745 | 9 | FARSRSGAK | 633 | A*3001 | 39 | 0.48 | 19 | 20 | 715 | 746 |
| 737 | 745 | 9 | FARSRSGAK | 633 | B*5501 | 16 | 0.48 | 8 | 20 | 715 | 746 |
| 737 | 746 | 10 | FARSRSGAKL | 634 | B*1402 | 25 | 1.60 | 41 | 20 | 715 | 746 |
| 737 | 746 | 10 | FARSRSGAKL | 634 | B*4601 | 3 | 1.60 | 5 | 20 | 715 | 746 |
| 737 | 746 | 10 | FARSRSGAKL | 634 | B*5501 | 15 | 1.60 | 24 | 20 | 715 | 746 |
| 738 | 746 | 9 | ARSRSGAKL | 635 | B*2702 | 12 | 1.60 | 19 | 20 | 715 | 746 |
| 739 | 746 | 8 | RSRSGAKL | 636 | A*3001 | 76 | 1.60 | 122 | 20 | 715 | 746 |
| | | | | | Cumulative BCI Class Iscore: | | | 7869 | | | |
| 754 | 762 | 9 | VLSRKYTSF | 638 | B*0801 | 68 | 1.77 | 120 | 21 | 754 | 791 |
| 754 | 762 | 9 | VLSRKYTSF | 638 | B*1501 | 17 | 1.77 | 30 | 21 | 754 | 791 |
| 755 | 762 | 8 | LSRKYTSF | 639 | B*0801 | 61 | 1.77 | 108 | 21 | 754 | 791 |
| 755 | 762 | 8 | LSRKYTSF | 639 | B*1501 | 98 | 1.77 | 174 | 21 | 754 | 791 |
| 755 | 762 | 8 | LSRKYTSF | 639 | B*1502 | 85 | 1.77 | 150 | 21 | 754 | 791 |
| 755 | 762 | 8 | LSRKYTSF | 639 | B*1525 | 81 | 1.77 | 144 | 21 | 754 | 791 |
| 755 | 762 | 8 | LSRKYTSF | 639 | B*4601 | 59 | 1.77 | 104 | 21 | 754 | 791 |
| 755 | 762 | 8 | LSRKYTSF | 639 | B*5701 | 61 | 1.77 | 107 | 21 | 754 | 791 |

TABLE 4a-continued

Predicted HLA class I-restricted CD8+ cytotoxic T cell epitopes contained in SLP sequences from HBV polymerase protein.

HLA class I binding peptides in SLP sequences derived from HBV Polymerase protein

| Start | End | Length | Sequence[A] | SEQ ID NO: | HLA class I molecule | Class I-B score[B] | C-score[C] | Class I-BCI score[D] | SLP# | SLP Start | SLP End |
|---|---|---|---|---|---|---|---|---|---|---|---|
| 755 | 762 | 8 | LSRKYTSF | 639 | B*5802 | 46 | 1.77 | 82 | 21 | 754 | 791 |
| 754 | 764 | 11 | VLSRKYTSFPW | 640 | A*3201 | 17 | 0.99 | 16 | 21 | 754 | 791 |
| 754 | 764 | 11 | VLSRKYTSFPW | 640 | B*5701 | 55 | 0.99 | 54 | 21 | 754 | 791 |
| 754 | 764 | 11 | VLSRKYTSFPW | 640 | B*5801 | 56 | 0.99 | 55 | 21 | 754 | 791 |
| 754 | 764 | 11 | VLSRKYTSFPW | 640 | B*5802 | 22 | 0.99 | 21 | 21 | 754 | 791 |
| 755 | 764 | 10 | LSRKYTSFPW | 641 | B*1525 | 10 | 0.99 | 10 | 21 | 754 | 791 |
| 755 | 764 | 10 | LSRKYTSFPW | 641 | B*5802 | 96 | 0.99 | 94 | 21 | 754 | 791 |
| 756 | 764 | 9 | SRKYTSFPW | 642 | B*2702 | 81 | 0.99 | 80 | 21 | 754 | 791 |
| 757 | 764 | 8 | RKYTSFPW | 643 | B*1301 | 52 | 0.99 | 51 | 21 | 754 | 791 |
| 757 | 764 | 8 | RKYTSFPW | 643 | B*2702 | 94 | 0.99 | 93 | 21 | 754 | 791 |
| 757 | 764 | 8 | RKYTSFPW | 643 | B*4402 | 4 | 0.99 | 4 | 21 | 754 | 791 |
| 757 | 764 | 8 | RKYTSFPW | 643 | B*4403 | 12 | 0.99 | 12 | 21 | 754 | 791 |
| 757 | 764 | 8 | RKYTSFPW | 643 | B*5701 | 3 | 0.99 | 3 | 21 | 754 | 791 |
| 757 | 764 | 8 | RKYTSFPW | 643 | B*5802 | 12 | 0.99 | 11 | 21 | 754 | 791 |
| 755 | 765 | 11 | LSRKYTSFPWL | 644 | A*3001 | 36 | 1.24 | 45 | 21 | 754 | 791 |
| 755 | 765 | 11 | LSRKYTSFPWL | 644 | B*0801 | 36 | 1.24 | 44 | 21 | 754 | 791 |
| 756 | 765 | 10 | SRKYTSFPWL | 645 | A*3001 | 21 | 1.24 | 26 | 21 | 754 | 791 |
| 756 | 765 | 10 | SRKYTSFPWL | 645 | B*1402 | 24 | 1.24 | 30 | 21 | 754 | 791 |
| 756 | 765 | 10 | SRKYTSFPWL | 645 | B*2702 | 46 | 1.24 | 57 | 21 | 754 | 791 |
| 756 | 765 | 10 | SRKYTSFPWL | 645 | B*2705 | 10 | 1.24 | 13 | 21 | 754 | 791 |
| 757 | 765 | 9 | RKYTSFPWL | 646 | B*1402 | 8 | 1.24 | 10 | 21 | 754 | 791 |
| 757 | 765 | 9 | RKYTSFPWL | 646 | B*2702 | 4 | 1.24 | 4 | 21 | 754 | 791 |
| 757 | 765 | 9 | RKYTSFPWL | 646 | B*4801 | 87 | 1.24 | 108 | 21 | 754 | 791 |
| 758 | 765 | 8 | KYTSFPWL | 647 | A*2301 | 81 | 1.24 | 101 | 21 | 754 | 791 |
| 758 | 765 | 8 | KYTSFPWL | 647 | A*2402 | 77 | 1.24 | 96 | 21 | 754 | 791 |
| 756 | 766 | 11 | SRKYTSFPWLL | 648 | B*1402 | 64 | 1.92 | 122 | 21 | 754 | 791 |
| 756 | 766 | 11 | SRKYTSFPWLL | 648 | B*2702 | 80 | 1.92 | 152 | 21 | 754 | 791 |
| 756 | 766 | 11 | SRKYTSFPWLL | 648 | B*3901 | 26 | 1.92 | 50 | 21 | 754 | 791 |
| 757 | 766 | 10 | RKYTSFPWLL | 649 | B*1302 | 8 | 1.92 | 16 | 21 | 754 | 791 |
| 757 | 766 | 10 | RKYTSFPWLL | 649 | B*1402 | 63 | 1.92 | 120 | 21 | 754 | 791 |
| 757 | 766 | 10 | RKYTSFPWLL | 649 | B*2702 | 70 | 1.92 | 134 | 21 | 754 | 791 |
| 757 | 766 | 10 | RKYTSFPWLL | 649 | B*3901 | 17 | 1.92 | 32 | 21 | 754 | 791 |
| 757 | 766 | 10 | RKYTSFPWLL | 649 | B*4801 | 75 | 1.92 | 144 | 21 | 754 | 791 |
| 758 | 766 | 9 | KYTSFPWLL | 650 | A*2301 | 97 | 1.92 | 185 | 21 | 754 | 791 |
| 758 | 766 | 9 | KYTSFPWLL | 600 | A*2402 | 96 | 1.92 | 185 | 21 | 754 | 791 |

TABLE 4a-continued

Predicted HLA class I-restricted CD8+ cytotoxic T cell epitopes contained in SLP sequences from HBV polymerase protein.

HLA class I binding peptides in SLP sequences derived from HBV Polymerase protein

| Start | End | Length | Sequence [A] | SEQ ID NO: | HLA class I molecule | Class I-B score[B] | C-score[C] | Class I-BCI score[D] | Peptide of invention (SLP) | | |
|---|---|---|---|---|---|---|---|---|---|---|---|
| | | | | | | | | | SLP# | SLP Start | SLP End |
| 759 | 766 | 8 | YTSFPWLL | 651 | A*0101 | 57 | 1.92 | 108 | 21 | 754 | 791 |
| 759 | 766 | 8 | YTSFPWLL | 651 | A*2601 | 18 | 1.92 | 34 | 21 | 754 | 791 |
| 759 | 766 | 8 | YTSFPWLL | 651 | B*5801 | 5 | 1.92 | 10 | 21 | 754 | 791 |
| 757 | 767 | 11 | RKYTSFPWLLG | 652 | B*2705 | 48 | 0.64 | 31 | 21 | 754 | 791 |
| 758 | 767 | 10 | KYTSFPWLLG | 653 | A*3201 | 11 | 0.64 | 7 | 21 | 754 | 791 |
| 759 | 767 | 9 | YTSFPWLLG | 654 | A*0101 | 9 | 0.64 | 6 | 21 | 754 | 791 |
| 762 | 769 | 8 | FPWLLGCT | 655 | B*3501 | 65 | 0.19 | 13 | 21 | 754 | 791 |
| 762 | 769 | 8 | FPWLLGCT | 655 | B*3503 | 8 | 0.19 | 2 | 21 | 754 | 791 |
| 762 | 769 | 8 | FPWLLGCT | 655 | B*5101 | 35 | 0.19 | 7 | 21 | 754 | 791 |
| 762 | 769 | 8 | FPWLLGCT | 655 | B*5501 | 66 | 0.19 | 13 | 21 | 754 | 791 |
| 762 | 769 | 8 | FPWLLGCT | 655 | B*5601 | 85 | 0.19 | 16 | 21 | 754 | 791 |
| 762 | 770 | 9 | FPWLLGCTA | 656 | B*1402 | 14 | 1.76 | 25 | 21 | 754 | 791 |
| 762 | 770 | 9 | FPWLLGCTA | 656 | B*3501 | 39 | 1.76 | 68 | 21 | 754 | 791 |
| 762 | 770 | 9 | FPWLLGCTA | 656 | B*3503 | 88 | 1.76 | 155 | 21 | 754 | 791 |
| 762 | 770 | 9 | FPWLLGCTA | 656 | B*5101 | 33 | 1.76 | 59 | 21 | 754 | 791 |
| 762 | 771 | 10 | FPWLLGCTAN | 657 | B*0702 | 7 | 0.39 | 3 | 21 | 754 | 791 |
| 762 | 771 | 10 | FPWLLGCTAN | 657 | B*3501 | 79 | 0.39 | 31 | 21 | 754 | 791 |
| 762 | 771 | 10 | FPWLLGCTAN | 657 | B*3503 | 24 | 0.39 | 9 | 21 | 754 | 791 |
| 762 | 771 | 10 | FPWLLGCTAN | 657 | B*5101 | 57 | 0.39 | 22 | 21 | 754 | 791 |
| 762 | 771 | 10 | FPWLLGCTAN | 657 | B*5301 | 52 | 0.39 | 20 | 21 | 754 | 791 |
| 762 | 771 | 10 | FPWLLGCTAN | 657 | B*5501 | 52 | 0.39 | 20 | 21 | 754 | 791 |
| 762 | 771 | 10 | FPWLLGCTAN | 657 | B*5601 | 69 | 0.39 | 27 | 21 | 754 | 791 |
| 762 | 772 | 11 | FPWLLGCTANW | 658 | B*1402 | 55 | 1.72 | 94 | 21 | 754 | 791 |
| 762 | 772 | 11 | FPWLLGCTANW | 658 | B*1801 | 48 | 1.72 | 82 | 21 | 754 | 791 |
| 762 | 772 | 11 | FPWLLGCTANW | 658 | B*3501 | 93 | 1.72 | 161 | 21 | 754 | 791 |
| 762 | 772 | 11 | FPWLLGCTANW | 658 | B*3503 | 81 | 1.72 | 140 | 21 | 754 | 791 |
| 762 | 772 | 11 | FPWLLGCTANW | 658 | B*3801 | 63 | 1.72 | 109 | 21 | 754 | 791 |
| 762 | 772 | 11 | FPWLLGCTANW | 658 | B*5101 | 87 | 1.72 | 149 | 21 | 754 | 791 |
| 762 | 772 | 11 | FPWLLGCTANW | 658 | B*5501 | 8 | 1.72 | 14 | 21 | 754 | 791 |
| 762 | 772 | 11 | FPWLLGCTANW | 658 | B*5601 | 50 | 1.72 | 86 | 21 | 754 | 791 |
| 763 | 772 | 10 | PWLLGCTANW | 659 | A*2301 | 67 | 1.72 | 116 | 21 | 754 | 791 |
| 763 | 772 | 10 | PWLLGCTANW | 659 | A*2402 | 32 | 1.72 | 54 | 21 | 754 | 791 |
| 764 | 772 | 9 | WLLGCTANW | 660 | B*5701 | 26 | 1.72 | 44 | 21 | 754 | 791 |
| 764 | 773 | 10 | WLLGcTANWI | 661 | A*0201 | 91 | 0.22 | 20 | 21 | 754 | 791 |

TABLE 4a-continued

Predicted HLA class I-restricted CD8⁺ cytotoxic T cell epitopes contained in SLP sequences from HBV polymerase protein.

HLA class I binding peptides in SLP sequences derived from HBV Polymerase protein

| Start | End | Length | Sequence[A] | SEQ ID NO: | HLA class I molecule | Class I-B score[B] | C-score[C] | Class I-BCI score[D] | SLP# | Peptide of invention (SLP) SLP Start | SLP End |
|---|---|---|---|---|---|---|---|---|---|---|---|
| 765 | 773 | 9 | LLGCTANWI | 662 | A*0201 | 71 | 0.22 | 15 | 21 | 754 | 791 |
| 764 | 774 | 11 | WLLGCTANWIL | 663 | B*3801 | 18 | 1.41 | 26 | 21 | 754 | 791 |
| 764 | 774 | 11 | WLLGCTANWIL | 663 | B*3901 | 74 | 1.41 | 104 | 21 | 754 | 791 |
| 764 | 774 | 11 | WLLGCTANWIL | 663 | B*4801 | 40 | 1.41 | 57 | 21 | 754 | 791 |
| 765 | 774 | 10 | LLGCtANWIL | 664 | A*0201 | 64 | 1.41 | 90 | 21 | 754 | 791 |
| 765 | 775 | 11 | LLGCTANWILR | 665 | A*7401 | 30 | 1.01 | 31 | 21 | 754 | 791 |
| 766 | 775 | 10 | LGCTANWILR | 666 | A*3201 | 33 | 1.01 | 34 | 21 | 754 | 791 |
| 768 | 775 | 8 | CTANWILR | 667 | A*1101 | 72 | 1.01 | 72 | 21 | 754 | 791 |
| 768 | 775 | 8 | CTANWILR | 667 | A*3101 | 53 | 1.01 | 54 | 21 | 754 | 791 |
| 768 | 775 | 8 | CTANWILR | 667 | A*3303 | 79 | 1.01 | 80 | 21 | 754 | 791 |
| 768 | 775 | 8 | CTANWILR | 667 | A*6801 | 94 | 1.01 | 95 | 21 | 754 | 791 |
| 768 | 775 | 8 | CTANWILR | 667 | A*7401 | 74 | 1.01 | 75 | 21 | 754 | 791 |
| 769 | 779 | 11 | TANWILRGTSF | 668 | B*1502 | 33 | 1.20 | 40 | 21 | 754 | 791 |
| 769 | 779 | 11 | TANWILRGTSF | 668 | B*3501 | 11 | 1.20 | 13 | 21 | 754 | 791 |
| 769 | 779 | 11 | TANWILRGTSF | 668 | B*4601 | 25 | 1.20 | 29 | 21 | 754 | 791 |
| 769 | 779 | 11 | TANWILRGTSF | 668 | B*5802 | 20 | 1.20 | 24 | 21 | 754 | 791 |
| 770 | 779 | 10 | ANWILRGTSF | 669 | B*4402 | 8 | 1.20 | 9 | 21 | 754 | 791 |
| 771 | 779 | 9 | NWILRGTSF | 670 | A*2301 | 2 | 1.20 | 2 | 21 | 754 | 791 |
| 771 | 779 | 9 | NWILRGTSF | 670 | A*2402 | 30 | 1.20 | 36 | 21 | 754 | 791 |
| 772 | 779 | 8 | WILRGTSF | 671 | B*0801 | 7 | 1.20 | 8 | 21 | 754 | 791 |
| 772 | 779 | 8 | WILRGTSF | 671 | B*1501 | 52 | 1.20 | 62 | 21 | 754 | 791 |
| 772 | 779 | 8 | WILRGTSF | 671 | B*1502 | 81 | 1.20 | 97 | 21 | 754 | 791 |
| 772 | 779 | 8 | WILRGTSF | 671 | B*1525 | 63 | 1.20 | 75 | 21 | 754 | 791 |
| 772 | 779 | 8 | WILRGTSF | 671 | B*4601 | 39 | 1.20 | 47 | 21 | 754 | 791 |
| 772 | 780 | 9 | WILRGTSFV | 672 | A*0201 | 100 | 1.19 | 119 | 21 | 754 | 791 |
| 772 | 780 | 9 | WILRGTSFV | 672 | A*0206 | 69 | 1.19 | 82 | 21 | 754 | 791 |
| 771 | 781 | 11 | NWILRGTSFVY | 673 | A*2902 | 51 | 1.69 | 86 | 21 | 754 | 791 |
| 771 | 781 | 11 | NWILRGTSFVY | 673 | B*1801 | 24 | 1.69 | 40 | 21 | 754 | 791 |
| 772 | 781 | 10 | WILRGTSFVY | 674 | B*1502 | 59 | 1.69 | 100 | 21 | 754 | 791 |
| 772 | 781 | 10 | WILRGTSFVY | 674 | B*1525 | 8 | 1.69 | 14 | 21 | 754 | 791 |
| 772 | 781 | 10 | WILRGTSFVY | 674 | B*4601 | 2 | 1.69 | 3 | 21 | 754 | 791 |
| 773 | 781 | 9 | ILRGTSFVY | 675 | A*0301 | 23 | 1.69 | 39 | 21 | 754 | 791 |
| 773 | 781 | 9 | ILRGTSFVY | 675 | A*2902 | 63 | 1.69 | 108 | 21 | 754 | 791 |
| 773 | 781 | 9 | ILRGTSFVY | 675 | A*3002 | 72 | 1.69 | 122 | 21 | 754 | 791 |
| 773 | 781 | 9 | ILRGTSFVY | 675 | B*1501 | 83 | 1.69 | 140 | 21 | 754 | 791 |

TABLE 4a-continued

Predicted HLA class I-restricted CD8+ cytotoxic T cell epitopes contained in SLP sequences from HBV polymerase protein.

HLA class I binding peptides in SLP sequences derived from HBV Polymerase protein

| | | | | | | Class | | Class | Peptide of invention (SLP) | | |
| | | | | SEQ | HLA class I | I-B | | I-BCI | | | |
| Start | End | Length | Sequence[A] | ID NO: | molecule | score[B] | C-score[C] | score[D] | SLP# | SLP Start | SLP End |
|---|---|---|---|---|---|---|---|---|---|---|---|
| 773 | 781 | 9 | ILRGTSFVY | 675 | B*1525 | 69 | 1.69 | 118 | 21 | 754 | 791 |
| 774 | 781 | 8 | LRGTSFVY | 676 | B*2702 | 23 | 1.69 | 39 | 21 | 754 | 791 |
| 774 | 781 | 8 | LRGTSFVY | 676 | B*2705 | 37 | 1.69 | 63 | 21 | 754 | 791 |
| 773 | 782 | 10 | ILRGTSFVYV | 677 | A*0201 | 71 | 1.67 | 119 | 21 | 754 | 791 |
| 776 | 785 | 10 | GTSFVYVPSA | 678 | A*3001 | 73 | 1.35 | 98 | 21 | 754 | 791 |
| 776 | 785 | 10 | GTSFVYVPSA | 678 | B*5701 | 45 | 1.35 | 61 | 21 | 754 | 791 |
| 778 | 786 | 9 | SFVYVPSAL | 679 | B*1402 | 7 | 1.57 | 11 | 21 | 754 | 791 |
| 779 | 786 | 8 | FVYVPSAL | 680 | A*2501 | 27 | 1.57 | 42 | 21 | 754 | 791 |
| 779 | 786 | 8 | FVYVPSAL | 600 | B*0801 | 5 | 1.57 | 8 | 21 | 754 | 791 |
| 779 | 786 | 8 | FVYVPSAL | 680 | B*1402 | 75 | 1.57 | 118 | 21 | 754 | 791 |
| 779 | 786 | 8 | FVYVPSAL | 680 | B*1502 | 54 | 1.57 | 85 | 21 | 754 | 791 |
| 779 | 786 | 8 | FVYVPSAL | 680 | B*3503 | 41 | 1.57 | 64 | 21 | 754 | 791 |
| 779 | 786 | 8 | FVYVPSAL | 680 | B*3801 | 41 | 1.57 | 64 | 21 | 754 | 791 |
| 779 | 786 | 8 | FVYVPSAL | 680 | B*3901 | 73 | 1.57 | 114 | 21 | 754 | 791 |
| 779 | 786 | 8 | FVYVPSAL | 680 | B*4601 | 77 | 1.57 | 121 | 21 | 754 | 791 |
| 779 | 786 | 8 | FVYVPSAL | 680 | B*5501 | 45 | 1.57 | 71 | 21 | 754 | 791 |
| 779 | 786 | 8 | FVYVPSAL | 680 | B*5601 | 24 | 1.57 | 38 | 21 | 754 | 791 |
| 781 | 788 | 8 | YVPSALNP | 681 | A*0206 | 73 | 0.38 | 27 | 21 | 754 | 791 |
| 779 | 789 | 11 | FVYVPSALNPA | 682 | A*6802 | 15 | 0.68 | 10 | 21 | 754 | 791 |
| 779 | 789 | 11 | FVYVPSALNPA | 682 | B*4601 | 67 | 0.68 | 46 | 21 | 754 | 791 |
| 779 | 789 | 11 | FVYVPSALNPA | 682 | B*5501 | 65 | 0.68 | 44 | 21 | 754 | 791 |
| 779 | 789 | 11 | FVYVPSALNPA | 682 | B*5601 | 74 | 0.68 | 51 | 21 | 754 | 791 |
| 781 | 789 | 9 | YVPSALNPA | 683 | A*0206 | 42 | 0.68 | 28 | 21 | 754 | 791 |
| 782 | 789 | 8 | VPSALNPA | 684 | B*0702 | 22 | 0.68 | 15 | 21 | 754 | 791 |
| 782 | 789 | 8 | VPSALNPA | 684 | B*3503 | 1 | 0.68 | 1 | 21 | 754 | 791 |
| 782 | 789 | 8 | VPSALNPA | 684 | B*5101 | 5 | 0.68 | 3 | 21 | 754 | 791 |
| 782 | 789 | 8 | VPSALNPA | 684 | B*5501 | 80 | 0.68 | 55 | 21 | 754 | 791 |
| 782 | 789 | 8 | VPSALNPA | 684 | B*5601 | 91 | 0.68 | 62 | 21 | 754 | 791 |
| 781 | 790 | 10 | YVPSALNPAD | 685 | A*3001 | 14 | 0.18 | 3 | 21 | 754 | 791 |
| | | | | | Cumulative Class I-BCI score: | | | 8555 | | | |
| 757 | 765 | 9 | RKYTSFPWL | 646 | B*1402 | 8 | 1.24 | 10 | 22 | 757 | 792 |
| 757 | 765 | 9 | RKYTSFPWL | 646 | B*2702 | 4 | 1.24 | 4 | 22 | 757 | 792 |
| 757 | 765 | 9 | RKYTSFPWL | 646 | B*4801 | 87 | 1.24 | 108 | 22 | 757 | 792 |
| 758 | 765 | 8 | KYTSFPWL | 647 | A*2301 | 81 | 1.24 | 101 | 22 | 757 | 792 |
| 758 | 765 | 8 | KYTSFPWL | 647 | A*2402 | 77 | 1.24 | 96 | 22 | 757 | 792 |

TABLE 4a-continued

Predicted HLA class I-restricted CD8+ cytotoxic T cell epitopes contained in SLP sequences from HBV polymerase protein.

HLA class I binding peptides in SLP sequences derived from HBV Polymerase protein

| Start | End | Length | Sequence[A] | SEQ ID NO: | HLA class I molecule | Class I-B score[B] | C-score[C] | Class I-BCI score[D] | SLP# | Peptide of invention (SLP) SLP Start | SLP End |
|---|---|---|---|---|---|---|---|---|---|---|---|
| 756 | 766 | 11 | SRKYTSFPWLL | 648 | B*1402 | 64 | 1.92 | 122 | 22 | 757 | 792 |
| 756 | 766 | 11 | SRKYTSFPWLL | 648 | B*2702 | 80 | 1.92 | 152 | 22 | 757 | 792 |
| 756 | 766 | 11 | SRKYTSFPWLL | 648 | B*3901 | 26 | 1.92 | 50 | 22 | 757 | 792 |
| 757 | 766 | 10 | RKYTSFPWLL | 649 | B*1302 | 8 | 1.92 | 16 | 22 | 757 | 792 |
| 757 | 766 | 10 | RKYTSFPWLL | 649 | B*1402 | 63 | 1.92 | 120 | 22 | 757 | 792 |
| 757 | 766 | 10 | RKYTSFPWLL | 649 | B*2702 | 70 | 1.92 | 134 | 22 | 757 | 792 |
| 757 | 766 | 10 | RKYTSFPWLL | 649 | B*3901 | 17 | 1.92 | 32 | 22 | 757 | 792 |
| 757 | 766 | 10 | RKYTSFPWLL | 649 | B*4801 | 75 | 1.92 | 144 | 22 | 757 | 792 |
| 758 | 766 | 9 | KYTSFPWLL | 650 | A*2301 | 97 | 1.92 | 185 | 22 | 757 | 792 |
| 758 | 766 | 9 | KYTSFPWLL | 650 | A*2402 | 96 | 1.92 | 185 | 22 | 757 | 792 |
| 759 | 766 | 8 | YTSFPWLL | 651 | A*0101 | 57 | 1.92 | 108 | 22 | 757 | 792 |
| 759 | 766 | 8 | YTSFPWLL | 651 | A*2601 | 18 | 1.92 | 34 | 22 | 757 | 792 |
| 759 | 766 | 8 | YTSFPWLL | 651 | B*5801 | 5 | 1.92 | 10 | 22 | 757 | 792 |
| 757 | 767 | 11 | RKYTSFPWLLG | 652 | B*2705 | 48 | 0.64 | 31 | 22 | 757 | 792 |
| 758 | 767 | 10 | KYTSFPWLLG | 653 | A*3201 | 11 | 0.64 | 7 | 22 | 757 | 792 |
| 759 | 767 | 9 | YTSFPWLLG | 654 | A*0101 | 9 | 0.64 | 6 | 22 | 757 | 792 |
| 762 | 769 | 8 | FPWLLGCT | 655 | B*3501 | 65 | 0.19 | 13 | 22 | 757 | 792 |
| 762 | 769 | 8 | FPWLLGCT | 655 | B*3503 | 8 | 0.19 | 2 | 22 | 757 | 792 |
| 762 | 769 | 8 | FPWLLGCT | 655 | B*5101 | 35 | 0.19 | 7 | 22 | 757 | 792 |
| 762 | 769 | 8 | FPWLLGCT | 655 | B*5501 | 66 | 0.19 | 13 | 22 | 757 | 792 |
| 762 | 769 | 8 | FPWLLGCT | 655 | B*5601 | 85 | 0.19 | 16 | 22 | 757 | 792 |
| 762 | 770 | 9 | FPWLLGCTA | 656 | B*1402 | 14 | 1.76 | 25 | 22 | 757 | 792 |
| 762 | 770 | 9 | FPWLLGCTA | 656 | B*3501 | 39 | 1.76 | 68 | 22 | 757 | 792 |
| 762 | 770 | 9 | FPWLLGCTA | 656 | B*3503 | 88 | 1.76 | 155 | 22 | 757 | 792 |
| 762 | 770 | 9 | FPWLLGCTA | 656 | B*5101 | 33 | 1.76 | 59 | 22 | 757 | 792 |
| 762 | 771 | 10 | FPWLLGCTAN | 657 | B*0702 | 7 | 0.39 | 3 | 22 | 757 | 792 |
| 762 | 771 | 10 | FPWLLGCTAN | 657 | B*3501 | 79 | 0.39 | 31 | 22 | 757 | 792 |
| 762 | 771 | 10 | FPWLLGCTAN | 657 | B*3503 | 24 | 0.39 | 9 | 22 | 757 | 792 |
| 762 | 771 | 10 | FPWLLGCTAN | 657 | B*5101 | 57 | 0.39 | 22 | 22 | 757 | 792 |
| 762 | 771 | 10 | FPWLLGCTAN | 657 | B*5301 | 52 | 0.39 | 20 | 22 | 757 | 792 |
| 762 | 771 | 10 | FPWLLGCTAN | 657 | B*5501 | 52 | 0.39 | 20 | 22 | 757 | 792 |
| 762 | 771 | 10 | FPWLLGCTAN | 657 | B*5601 | 69 | 0.39 | 27 | 22 | 757 | 792 |
| 762 | 772 | 11 | FPWLLGCTANW | 658 | B*1402 | 55 | 1.72 | 94 | 22 | 757 | 792 |
| 762 | 772 | 11 | FPWLLGCTANW | 658 | B*1801 | 48 | 1.72 | 82 | 22 | 757 | 792 |

TABLE 4a-continued

Predicted HLA class I-restricted CD8+ cytotoxic T cell epitopes contained in SLP sequences from HBV polymerase protein.

HLA class I binding peptides in SLP sequences derived from HBV Polymerase protein

| Start | End | Length | Sequence[A] | SEQ ID NO: | HLA class I molecule | Class I-B score[B] | C-score[C] | Class I-BCI score[D] | SLP# | Peptide of invention (SLP) SLP Start | SLP End |
|---|---|---|---|---|---|---|---|---|---|---|---|
| 762 | 772 | 11 | FPWLLGCTANW | 658 | B*3501 | 93 | 1.72 | 161 | 22 | 757 | 792 |
| 762 | 772 | 11 | FPWLLGCTANW | 658 | B*3503 | 81 | 1.72 | 140 | 22 | 757 | 792 |
| 762 | 772 | 11 | FPWLLGCTANW | 658 | B*3801 | 63 | 1.72 | 109 | 22 | 757 | 792 |
| 762 | 772 | 11 | FPWLLGCTANW | 658 | B*5101 | 87 | 1.72 | 149 | 22 | 757 | 792 |
| 762 | 772 | 11 | FPWLLGCTANW | 658 | B*5501 | 8 | 1.72 | 14 | 22 | 757 | 792 |
| 762 | 772 | 11 | FPWLLGCTANW | 658 | B*5601 | 50 | 1.72 | 86 | 22 | 757 | 792 |
| 763 | 772 | 10 | PWLLGCTANW | 659 | A*2301 | 67 | 1.72 | 116 | 22 | 757 | 792 |
| 763 | 772 | 10 | PWLLGCTANW | 659 | A*2402 | 32 | 1.72 | 54 | 22 | 757 | 792 |
| 764 | 772 | 9 | WLLGCTANW | 660 | B*5701 | 26 | 1.72 | 44 | 22 | 757 | 792 |
| 764 | 773 | 10 | WLLGcTANWI | 661 | A*0201 | 91 | 0.22 | 20 | 22 | 757 | 792 |
| 765 | 773 | 9 | LLGCTANWI | 662 | A*0201 | 71 | 0.22 | 15 | 22 | 757 | 792 |
| 764 | 774 | 11 | WLLGCTANWIL | 663 | B*3801 | 18 | 1.41 | 26 | 22 | 757 | 792 |
| 764 | 774 | 11 | WLLGCTANWIL | 663 | B*3901 | 74 | 1.41 | 104 | 22 | 757 | 792 |
| 764 | 774 | 11 | WLLGCTANWIL | 663 | B*4801 | 40 | 1.41 | 57 | 22 | 757 | 792 |
| 765 | 774 | 10 | LLGCtANWIL | 664 | A*0201 | 64 | 1.41 | 90 | 22 | 757 | 792 |
| 765 | 775 | 11 | LLGCTANWILR | 665 | A*7401 | 30 | 1.01 | 31 | 22 | 757 | 792 |
| 766 | 775 | 10 | LGCTANWILR | 666 | A*3201 | 33 | 1.01 | 34 | 22 | 757 | 792 |
| 768 | 775 | 8 | CTANWILR | 667 | A*1101 | 72 | 1.01 | 72 | 22 | 757 | 792 |
| 768 | 775 | 8 | CTANWILR | 667 | A*3101 | 53 | 1.01 | 54 | 22 | 757 | 792 |
| 768 | 775 | 8 | CTANWILR | 667 | A*3303 | 79 | 1.01 | 80 | 22 | 757 | 792 |
| 768 | 775 | 8 | CTANWILR | 667 | A*6801 | 94 | 1.01 | 95 | 22 | 757 | 792 |
| 768 | 775 | 8 | CTANWILR | 667 | A*7401 | 74 | 1.01 | 75 | 22 | 757 | 792 |
| 769 | 779 | 11 | TANWILRGTSF | 668 | B*1502 | 33 | 1.20 | 40 | 22 | 757 | 792 |
| 769 | 779 | 11 | TANWILRGTSF | 668 | B*3501 | 11 | 1.20 | 13 | 22 | 757 | 792 |
| 769 | 779 | 11 | TANWILRGTSF | 668 | B*4601 | 25 | 1.20 | 29 | 22 | 757 | 792 |
| 769 | 779 | 11 | TANWILRGTSF | 668 | B*5802 | 20 | 1.20 | 24 | 22 | 757 | 792 |
| 770 | 779 | 10 | ANWILRGTSF | 669 | B*4402 | 8 | 1.20 | 9 | 22 | 757 | 792 |
| 771 | 779 | 9 | NWILRGTSF | 670 | A*2301 | 2 | 1.20 | 2 | 22 | 757 | 792 |
| 771 | 779 | 9 | NWILRGTSF | 670 | A*2402 | 30 | 1.20 | 36 | 22 | 757 | 792 |
| 772 | 779 | 8 | WILRGTSF | 671 | B*0801 | 7 | 1.20 | 8 | 22 | 757 | 792 |
| 772 | 779 | 8 | WILRGTSF | 671 | B*1501 | 52 | 1.20 | 62 | 22 | 757 | 792 |
| 772 | 779 | 8 | WILRGTSF | 671 | B*1502 | 81 | 1.20 | 97 | 22 | 757 | 792 |
| 772 | 779 | 8 | WILRGTSF | 671 | B*1525 | 63 | 1.20 | 75 | 22 | 757 | 792 |
| 772 | 779 | 8 | WILRGTSF | 671 | B*4601 | 39 | 1.20 | 47 | 22 | 757 | 792 |
| 772 | 780 | 9 | WILRGTSFV | 672 | A*0201 | 100 | 1.19 | 119 | 22 | 757 | 792 |

TABLE 4a-continued

Predicted HLA class I-restricted CD8⁺ cytotoxic T cell epitopes contained in SLP sequences from HBV polymerase protein.

HLA class I binding peptides in SLP sequences derived from HBV Polymerase protein

| Start | End | Length | Sequence [A] | SEQ ID NO: | HLA class I molecule | Class I-B score[B] | C-score[C] | Class I-BCI score[D] | Peptide of invention (SLP) | | |
|---|---|---|---|---|---|---|---|---|---|---|---|
| | | | | | | | | | SLP# | S TABLE 4a-continued Predicted HLA class I-restricted CD8+ cytotoxic T cell epitopes contained in SLP sequences from HBV polymerase protein.

HLA class I binding peptides in SLP sequences derived from HBV Polymerase protein

| | | | | | | Class | | Class | Peptide of invention (SLP) | | |
| | | | | SEQ | HLA class I | I-B | | I-BCI | | | |
| Start | End | Length | Sequence [A] | ID NO: | molecule | score[B] | C-score[C] | score[D] | SLP# | SLP Start | SLP End |
|---|---|---|---|---|---|---|---|---|---|---|---|
| 782 | 789 | 8 | VPSALNPA | 684 | B*3503 | 1 | 0.68 | 1 | 22 | 757 | 792 |
| 782 | 789 | 8 | VPSALNPA | 684 | B*5101 | 5 | 0.68 | 3 | 22 | 757 | 792 |
| 782 | 789 | 8 | VPSALNPA | 684 | B*5501 | 80 | 0.68 | 55 | 22 | 757 | 792 |
| 782 | 789 | 8 | VPSALNPA | 684 | B*5601 | 91 | 0.68 | 62 | 22 | 757 | 792 |
| 781 | 790 | 10 | YVPSALNPAD | 685 | A*3001 | 14 | 0.18 | 3 | 22 | 757 | 792 |
| | | | | | Cumulative Class I-BCI score: | | | 6817 | | | |
| 754 | 762 | 9 | VLSRKYTSF | 638 | B*0801 | 68 | 1.77 | 120 | 23 | 754 | 789 |
| 754 | 762 | 9 | VLSRKYTSF | 638 | B*1501 | 17 | 1.77 | 30 | 23 | 754 | 789 |
| 755 | 762 | 8 | LSRKYTSF | 639 | B*0801 | 61 | 1.77 | 108 | 23 | 754 | 789 |
| 755 | 762 | 8 | LSRKYTSF | 639 | B*1501 | 98 | 1.77 | 174 | 23 | 754 | 789 |
| 755 | 762 | 8 | LSRKYTSF | 639 | B*1502 | 85 | 1.77 | 150 | 23 | 754 | 789 |
| 755 | 762 | 8 | LSRKYTSF | 639 | B*1525 | 81 | 1.77 | 144 | 23 | 754 | 789 |
| 755 | 762 | 8 | LSRKYTSF | 639 | B*4601 | 59 | 1.77 | 104 | 23 | 754 | 789 |
| 755 | 762 | 8 | LSRKYTSF | 639 | B*5701 | 61 | 1.77 | 107 | 23 | 754 | 789 |
| 755 | 762 | 8 | LSRKYTSF | 639 | B*5802 | 46 | 1.77 | 82 | 23 | 754 | 789 |
| 754 | 764 | 11 | VLSRKYTSFPW | 640 | A*3201 | 17 | 0.99 | 16 | 23 | 754 | 789 |
| 754 | 764 | 11 | VLSRKYTSFPW | 640 | B*5701 | 55 | 0.99 | 54 | 23 | 754 | 789 |
| 754 | 764 | 11 | VLSRKYTSFPW | 640 | B*5801 | 56 | 0.99 | 55 | 23 | 754 | 789 |
| 754 | 764 | 11 | VLSRKYTSFPW | 640 | B*5802 | 22 | 0.99 | 21 | 23 | 754 | 789 |
| 755 | 764 | 10 | LSRKYTSFPW | 641 | B*1525 | 10 | 0.99 | 10 | 23 | 754 | 789 |
| 755 | 764 | 10 | LSRKYTSFPW | 641 | B*5802 | 96 | 0.99 | 94 | 23 | 754 | 789 |
| 756 | 764 | 9 | SRKYTSFPW | 642 | B*2702 | 81 | 0.99 | 80 | 23 | 754 | 789 |
| 757 | 764 | 8 | RKYTSFPW | 643 | B*1301 | 52 | 0.99 | 51 | 23 | 754 | 789 |
| 757 | 764 | 8 | RKYTSFPW | 643 | B*2702 | 94 | 0.99 | 93 | 23 | 754 | 789 |
| 757 | 764 | 8 | RKYTSFPW | 643 | B*4402 | 4 | 0.99 | 4 | 23 | 754 | 789 |
| 757 | 764 | 8 | RKYTSFPW | 643 | B*4403 | 12 | 0.99 | 12 | 23 | 754 | 789 |
| 757 | 764 | 8 | RKYTSFPW | 643 | B*5701 | 3 | 0.99 | 3 | 23 | 754 | 789 |
| 757 | 764 | 8 | RKYTSFPW | 643 | B*5802 | 12 | 0.99 | 11 | 23 | 754 | 789 |
| 755 | 765 | 11 | LSRKYTSFPWL | 644 | A*3001 | 36 | 1.24 | 45 | 23 | 754 | 789 |
| 755 | 765 | 11 | LSRKYTSFPWL | 644 | B*0801 | 36 | 1.24 | 44 | 23 | 754 | 789 |
| 756 | 765 | 10 | SRKYTSFPWL | 645 | A*3001 | 21 | 1.24 | 26 | 23 | 754 | 789 |
| 756 | 765 | 10 | SRKYTSFPWL | 645 | B*1402 | 24 | 1.24 | 30 | 23 | 754 | 789 |
| 756 | 765 | 10 | SRKYTSFPWL | 645 | B*2702 | 46 | 1.24 | 57 | 23 | 754 | 789 |
| 756 | 765 | 10 | SRKYTSFPWL | 645 | B*2705 | 10 | 1.24 | 13 | 23 | 754 | 789 |
| 757 | 765 | 9 | RKYTSFPWL | 646 | B*1402 | 8 | 1.24 | 10 | 23 | 754 | 789 |

TABLE 4a-continued

Predicted HLA class I-restricted CD8+ cytotoxic T cell epitopes contained in SLP sequences from HBV polymerase protein.

HLA class I binding peptides in SLP sequences derived from HBV Polymerase protein

| | | | | | | | | | Peptide of invention (SLP) | | |
|---|---|---|---|---|---|---|---|---|---|---|---|
| Start | End | Length | Sequence[A] | SEQ ID NO: | HLA class I molecule | Class I-B score[B] | C-score[C] | Class I-BCI score[D] | SLP# | SLP Start | SLP End |
| 757 | 765 | 9 | RKYTSFPWL | 646 | B*2702 | 4 | 1.24 | 4 | 23 | 754 | 789 |
| 757 | 765 | 9 | RKYTSFPWL | 646 | B*4801 | 87 | 1.24 | 108 | 23 | 754 | 789 |
| 758 | 765 | 8 | KYTSFPWL | 647 | A*2301 | 81 | 1.24 | 101 | 23 | 754 | 789 |
| 758 | 765 | 8 | KYTSFPWL | 647 | A*2402 | 77 | 1.24 | 96 | 23 | 754 | 789 |
| 756 | 766 | 11 | SRKYTSFPWLL | 648 | B*1402 | 64 | 1.92 | 122 | 23 | 754 | 789 |
| 756 | 766 | 11 | SRKYTSFPWLL | 648 | B*2702 | 80 | 1.92 | 152 | 23 | 754 | 789 |
| 756 | 766 | 11 | SRKYTSFPWLL | 648 | B*3901 | 26 | 1.92 | 50 | 23 | 754 | 789 |
| 757 | 766 | 10 | RKYTSFPWLL | 649 | B*1302 | 8 | 1.92 | 16 | 23 | 754 | 789 |
| 757 | 766 | 10 | RKYTSFPWLL | 649 | B*1402 | 63 | 1.92 | 120 | 23 | 754 | 789 |
| 757 | 766 | 10 | RKYTSFPWLL | 649 | B*2702 | 70 | 1.92 | 134 | 23 | 754 | 789 |
| 757 | 766 | 10 | RKYTSFPWLL | 649 | B*3901 | 17 | 1.92 | 32 | 23 | 754 | 789 |
| 757 | 766 | 10 | RKYTSFPWLL | 649 | B*4801 | 75 | 1.92 | 144 | 23 | 754 | 789 |
| 758 | 766 | 9 | KYTSFPWLL | 650 | A*2301 | 97 | 1.92 | 185 | 23 | 754 | 789 |
| 758 | 766 | 9 | KYTSFPWLL | 650 | A*2402 | 96 | 1.92 | 185 | 23 | 754 | 789 |
| 759 | 766 | 8 | YTSFPWLL | 651 | A*0101 | 57 | 1.92 | 108 | 23 | 754 | 789 |
| 759 | 766 | 8 | YTSFPWLL | 651 | A*2601 | 18 | 1.92 | 34 | 23 | 754 | 789 |
| 759 | 766 | 8 | YTSFPWLL | 651 | B*5801 | 5 | 1.92 | 10 | 23 | 754 | 789 |
| 757 | 767 | 11 | RKYTSFPWLLG | 652 | B*2705 | 48 | 0.64 | 31 | 23 | 754 | 789 |
| 758 | 767 | 10 | KYTSFPWLLG | 653 | A*3201 | 11 | 0.64 | 7 | 23 | 754 | 789 |
| 759 | 767 | 9 | YTSFPWLLG | 654 | A*0101 | 9 | 0.64 | 6 | 23 | 754 | 789 |
| 762 | 769 | 8 | FPWLLGCT | 655 | B*3501 | 65 | 0.19 | 13 | 23 | 754 | 789 |
| 762 | 769 | 8 | FPWLLGCT | 655 | B*3503 | 8 | 0.19 | 2 | 23 | 754 | 789 |
| 762 | 769 | 8 | FPWLLGCT | 655 | B*5101 | 35 | 0.19 | 7 | 23 | 754 | 789 |
| 762 | 769 | 8 | FPWLLGCT | 655 | B*5501 | 66 | 0.19 | 13 | 23 | 754 | 789 |
| 762 | 769 | 8 | FPWLLGCT | 655 | B*5601 | 85 | 0.19 | 16 | 23 | 754 | 789 |
| 762 | 770 | 9 | FPWLLGCTA | 656 | B*1402 | 14 | 1.76 | 25 | 23 | 754 | 789 |
| 762 | 770 | 9 | FPWLLGCTA | 656 | B*3501 | 39 | 1.76 | 68 | 23 | 754 | 789 |
| 762 | 770 | 9 | FPWLLGCTA | 656 | B*3503 | 88 | 1.76 | 155 | 23 | 754 | 789 |
| 762 | 770 | 9 | FPWLLGCTA | 656 | B*5101 | 33 | 1.76 | 59 | 23 | 754 | 789 |
| 762 | 771 | 10 | FPWLLGCTAN | 657 | B*0702 | 7 | 0.39 | 3 | 23 | 754 | 789 |
| 762 | 771 | 10 | FPWLLGCTAN | 657 | B*3501 | 79 | 0.39 | 31 | 23 | 754 | 789 |
| 762 | 771 | 10 | FPWLLGCTAN | 657 | B*3503 | 24 | 0.39 | 9 | 23 | 754 | 789 |
| 762 | 771 | 10 | FPWLLGCTAN | 657 | B*5101 | 57 | 0.39 | 22 | 23 | 754 | 789 |
| 762 | 771 | 10 | FPWLLGCTAN | 657 | B*5301 | 52 | 0.39 | 20 | 23 | 754 | 789 |
| 762 | 771 | 10 | FPWLLGCTAN | 657 | B*5501 | 52 | 0.39 | 20 | 23 | 754 | 789 |

TABLE 4a-continued

Predicted HLA class I-restricted CD8+ cytotoxic T cell epitopes contained in SLP sequences from HBV polymerase protein.

HLA class I binding peptides in SLP sequences derived from HBV Polymerase protein

| Start | End | Length | Sequence [A] | SEQ ID NO: | HLA class I molecule | Class I-B score[B] | C-score[C] | Class I-BCI score[D] | Peptide of invention (SLP) | | |
|---|---|---|---|---|---|---|---|---|---|---|---|
| | | | | | | | | | SLP# | SLP Start | SLP End |
| 762 | 771 | 10 | FPWLLGCTAN | 657 | B*5601 | 69 | 0.39 | 27 | 23 | 754 | 789 |
| 762 | 772 | 11 | FPWLLGCTANW | 658 | B*1402 | 55 | 1.72 | 94 | 23 | 754 | 789 |
| 762 | 772 | 11 | FPWLLGCTANW | 658 | B*1801 | 48 | 1.72 | 82 | 23 | 754 | 789 |
| 762 | 772 | 11 | FPWLLGCTANW | 658 | B*3501 | 93 | 1.72 | 161 | 23 | 754 | 789 |
| 762 | 772 | 11 | FPWLLGCTANW | 658 | B*3503 | 81 | 1.72 | 140 | 23 | 754 | 789 |
| 762 | 772 | 11 | FPWLLGCTANW | 658 | B*3801 | 63 | 1.72 | 109 | 23 | 754 | 789 |
| 762 | 772 | 11 | FPWLLGCTANW | 658 | B*5101 | 87 | 1.72 | 149 | 23 | 754 | 789 |
| 762 | 772 | 11 | FPWLLGCTANW | 658 | B*5501 | 8 | 1.72 | 14 | 23 | 754 | 789 |
| 762 | 772 | 11 | FPWLLGCTANW | 658 | B*5601 | 50 | 1.72 | 86 | 23 | 754 | 789 |
| 763 | 772 | 10 | PWLLGCTANW | 659 | A*2301 | 67 | 1.72 | 116 | 23 | 754 | 789 |
| 763 | 772 | 10 | PWLLGCTANW | 659 | A*2402 | 32 | 1.72 | 54 | 23 | 754 | 789 |
| 764 | 772 | 9 | WLLGCTANW | 660 | B*5701 | 26 | 1.72 | 44 | 23 | 754 | 789 |
| 764 | 773 | 10 | WLLGcTANWI | 661 | A*0201 | 91 | 0.22 | 20 | 23 | 754 | 789 |
| 765 | 773 | 9 | LLGCTANWI | 662 | A*0201 | 71 | 0.22 | 15 | 23 | 754 | 789 |
| 764 | 774 | 11 | WLLGCTANWIL | 663 | B*3801 | 18 | 1.41 | 26 | 23 | 754 | 789 |
| 764 | 774 | 11 | WLLGCTANWIL | 663 | B*3901 | 74 | 1.41 | 104 | 23 | 754 | 789 |
| 764 | 774 | 11 | WLLGCTANWIL | 663 | B*4801 | 40 | 1.41 | 57 | 23 | 754 | 789 |
| 765 | 774 | 10 | LLGCtANWIL | 664 | A*0201 | 64 | 1.41 | 90 | 23 | 754 | 789 |
| 765 | 775 | 11 | LLGCTANWILR | 665 | A*7401 | 30 | 1.01 | 31 | 23 | 754 | 789 |
| 766 | 775 | 10 | LGCTANWILR | 666 | A*3201 | 33 | 1.01 | 34 | 23 | 754 | 789 |
| 768 | 775 | 8 | CTANWILR | 667 | A*1101 | 72 | 1.01 | 72 | 23 | 754 | 789 |
| 768 | 775 | 8 | CTANWILR | 667 | A*3101 | 53 | 1.01 | 54 | 23 | 754 | 789 |
| 768 | 775 | 8 | CTANWILR | 667 | A*3303 | 79 | 1.01 | 80 | 23 | 754 | 789 |
| 768 | 775 | 8 | CTANWILR | 667 | A*6801 | 94 | 1.01 | 95 | 23 | 754 | 789 |
| 768 | 775 | 8 | CTANWILR | 667 | A*7401 | 74 | 1.01 | 75 | 23 | 754 | 789 |
| 769 | 779 | 11 | TANWILRGTSF | 668 | B*1502 | 33 | 1.20 | 40 | 23 | 754 | 789 |
| 769 | 779 | 11 | TANWILRGTSF | 668 | B*3501 | 11 | 1.20 | 13 | 23 | 754 | 789 |
| 769 | 779 | 11 | TANWILRGTSF | 668 | B*4601 | 25 | 1.20 | 29 | 23 | 754 | 789 |
| 769 | 779 | 11 | TANWILRGTSF | 668 | B*5802 | 20 | 1.20 | 24 | 23 | 754 | 789 |
| 770 | 779 | 10 | ANWILRGTSF | 669 | B*4402 | 8 | 1.20 | 9 | 23 | 754 | 789 |
| 771 | 779 | 9 | NWILRGTSF | 670 | A*2301 | 2 | 1.20 | 2 | 23 | 754 | 789 |
| 771 | 779 | 9 | NWILRGTSF | 670 | A*2402 | 30 | 1.20 | 36 | 23 | 754 | 789 |
| 772 | 779 | 8 | WILRGTSF | 671 | B*0801 | 7 | 1.20 | 8 | 23 | 754 | 789 |
| 772 | 779 | 8 | WILRGTSF | 671 | B*1501 | 52 | 1.20 | 62 | 23 | 754 | 789 |

TABLE 4a-continued

Predicted HLA class I-restricted CD8+ cytotoxic T cell epitopes contained in SLP sequences from HBV polymerase protein.

HLA class I binding peptides in SLP sequences derived from HBV Polymerase protein

| Start | End | Length | Sequence[A] | SEQ ID NO: | HLA class I molecule | Class I-B score[B] | C-score[C] | Class TABLE 4a-continued Predicted HLA class I-restricted CD8+ cytotoxic T cell epitopes contained in SLP sequences from HBV polymerase protein.

HLA class I binding peptides in SLP sequences derived from HBV Polymerase protein

| Start | End | Length | Sequence [A] | SEQ ID NO: | HLA class I molecule | Class I-B score[B] | C-score[C] | Class I-BCI score[D] | SLP# | SLP Start | SLP End |
|---|---|---|---|---|---|---|---|---|---|---|---|
| 779 | 789 | 11 | FVYVPSALNPA | 682 | B*5601 | 74 | 0.68 | 51 | 23 | 754 | 789 |
| 781 | 789 | 9 | YVPSALNPA | 683 | A*0206 | 42 | 0.68 | 28 | 23 | 754 | 789 |
| 782 | 789 | 8 | VPSALNPA | 684 | B*0702 | 22 | 0.68 | 15 | 23 | 754 | 789 |
| 782 | 789 | 8 | VPSALNPA | 684 | B*3503 | 1 | 0.68 | 1 | 23 | 754 | 789 |
| 782 | 789 | 8 | VPSALNPA | 684 | B*5101 | 5 | 0.68 | 3 | 23 | 754 | 789 |
| 782 | 789 | 8 | VPSALNPA | 684 | B*5501 | 80 | 0.68 | 55 | 23 | 754 | 789 |
| 782 | 789 | 8 | VPSALNPA | 684 | B*5601 | 91 | 0.68 | 62 | 23 | 754 | 789 |
| | | | | | Cumulative Class I-BCI score: | | | 8553 | | | |

"Start" and "End" are relative to the amino acid sequence of HBV polymerase as depicted in SEQ ID NO: 1
[A] Peptide amino acid sequence. Each HLA class I binding peptide of HBV polymerase is listed separately for each HLA class I molecule to which it is predicted to bind, and can be listed multiple times for that reason.
[B] Class I-B score. See Material and Methods (Examples section).
[C] C-score. See Material and Methods (Examples section).
[D] Class I-BCI score. See Material and Methods (Examples section).
[E] Cumulative Class I-BCI score. See Material and Methods (Examples section).

TABLE 4b

Predicted HLA class II-restricted CD4+ T cell epitopes contained in SLP sequences from HBV polymerase protein.

HLA class II binding peptides in SLP sequences derived from HBV Polymerase

| Start | End | Sequence [A] | SEQ ID NO: | HLA-DRB1 molecule | Class II-B score[B] | SLP# | SLP Start | SLP End |
|---|---|---|---|---|---|---|---|---|
| 1 | 15 | MPLSYQHFRKLLLLD | 686 | *0701 | 79 | 1 | 1 | 30 |
| 1 | 15 | MPLSYQHFRKLLLLD | 686 | *1101 | 86 | 1 | 1 | 30 |
| 1 | 15 | MPLSYQHFRKLLLLD | 686 | *1501 | 9 | 1 | 1 | 30 |
| 2 | 16 | PLSYQHFRKLLLLDD | 687 | *0701 | 40 | 1 | 1 | 30 |
| 2 | 16 | PLSYQHFRKLLLLDD | 687 | *1101 | 84 | 1 | 1 | 30 |
| 2 | 16 | PLSYQHFRKLLLLDD | 687 | *1501 | 4 | 1 | 1 | 30 |
| 3 | 17 | LSYQHFRKLLLLDDG | 688 | *0701 | 9 | 1 | 1 | 30 |
| 3 | 17 | LSYQHFRKLLLLDDG | 688 | *1101 | 83 | 1 | 1 | 30 |
| 3 | 17 | LSYQHFRKLLLLDDG | 688 | *1501 | 3 | 1 | 1 | 30 |
| 4 | 18 | SYQHFRKLLLLDDGT | 689 | *1101 | 81 | 1 | 1 | 30 |
| 5 | 19 | YQHFRKLLLLDDGTE | 690 | *1101 | 80 | 1 | 1 | 30 |
| 6 | 20 | QHFRKLLLLDDGTEA | 691 | *0301 | 31 | 1 | 1 | 30 |
| 6 | 20 | QHFRKLLLLDDGTEA | 691 | *1101 | 56 | 1 | 1 | 30 |
| 7 | 21 | HFRKLLLLDDGTEAG | 692 | *0301 | 30 | 1 | 1 | 30 |
| 8 | 22 | FRKLLLLDDGTEAGP | 693 | *0301 | 29 | 1 | 1 | 30 |
| 9 | 23 | RKLLLLDDGTEAGPL | 694 | *0301 | 27 | 1 | 1 | 30 |

TABLE 4b-continued

Predicted HLA class II-restricted CD4⁺ T cell epitopes contained in SLP sequences from HBV polym TABLE 4b-continued Predicted HLA class II-restricted CD4+ T cell epitopes contained in SLP sequences from HBV polymerase protein.

| HLA class II binding peptides in SLP sequences derived from HBV Polymerase | | | | | | Peptide of invention (SLP) | | |
|---|---|---|---|---|---|---|---|---|
| Start | End | Sequence [A] | SEQ ID NO: | HLA-DRB1 molecule | Class II-B score[B] | SLP# | SLP Start | SLP End |
| | | Cumulative Class II-B score: | | | 1323 | | | |
| 103 | 117 | VNEKRRLKLIMPARF | 705 | *0101 | 47 | 3 | 103 | 135 |
| 103 | 117 | VNEKRRLKLIMPARF | 705 | *0102 | 33 | 3 | 103 | 135 |
| 103 | 117 | VNEKRRLKLIMPARF | 705 | *0104 | 8 | 3 | 103 | 135 |
| 103 | 117 | VNEKRRLKLIMPARF | 705 | *0106 | 50 | 3 | 103 | 135 |
| 103 | 117 | VNEKRRLKLIMPARF | 705 | *0301 | 36 | 3 | 103 | 135 |
| 103 | 117 | VNEKRRLKLIMPARF | 705 | *0701 | 17 | 3 | 103 | 135 |
| 103 | 117 | VNEKRRLKLIMPARF | 705 | *1301 | 7 | 3 | 103 | 135 |
| 103 | 117 | VNEKRRLKLIMPARF | 705 | *1501 | 64 | 3 | 103 | 135 |
| 104 | 118 | NEKRRLKLIMPARFY | 706 | *0101 | 53 | 3 | 103 | 135 |
| 104 | 118 | NEKRRLKLIMPARFY | 706 | *0102 | 83 | 3 | 103 | 135 |
| 104 | 118 | NEKRRLKLIMPARFY | 706 | *0104 | 78 | 3 | 103 | 135 |
| 104 | 118 | NEKRRLKLIMPARFY | 706 | *0106 | 83 | 3 | 103 | 135 |
| 104 | 118 | NEKRRLKLIMPARFY | 706 | *0701 | 27 | 3 | 103 | 135 |
| 104 | 118 | NEKRRLKLIMPARFY | 706 | *1301 | 64 | 3 | 103 | 135 |
| 104 | 118 | NEKRRLKLIMPARFY | 706 | *1501 | 76 | 3 | 103 | 135 |
| 105 | 119 | EKRRLKLIMPARFYP | 707 | *0101 | 46 | 3 | 103 | 135 |
| 105 | 119 | EKRRLKLIMPARFYP | 707 | *0102 | 93 | 3 | 103 | 135 |
| 105 | 119 | EKRRLKLIMPARFYP | 707 | *0104 | 85 | 3 | 103 | 135 |
| 105 | 119 | EKRRLKLIMPARFYP | 707 | *0106 | 85 | 3 | 103 | 135 |
| 105 | 119 | EKRRLKLIMPARFYP | 707 | *0701 | 3 | 3 | 103 | 135 |
| 105 | 119 | EKRRLKLIMPARFYP | 707 | *1101 | 8 | 3 | 103 | 135 |
| 105 | 119 | EKRRLKLIMPARFYP | 707 | *1301 | 61 | 3 | 103 | 135 |
| 105 | 119 | EKRRLKLIMPARFYP | 707 | *1501 | 71 | 3 | 103 | 135 |
| 106 | 120 | KRRLKLIMPARFYPT | 708 | *0101 | 49 | 3 | 103 | 135 |
| 106 | 120 | KRRLKLIMPARFYPT | 708 | *0102 | 100 | 3 | 103 | 135 |
| 106 | 120 | KRRLKLIMPARFYPT | 708 | *0103 | 4 | 3 | 103 | 135 |
| 106 | 120 | KRRLKLIMPARFYPT | 708 | *0104 | 100 | 3 | 103 | 135 |
| 106 | 120 | KRRLKLIMPARFYPT | 708 | *0105 | 45 | 3 | 103 | 135 |
| 106 | 120 | KRRLKLIMPARFYPT | 708 | *0106 | 93 | 3 | 103 | 135 |
| 106 | 120 | KRRLKLIMPARFYPT | 708 | *0107 | 45 | 3 | 103 | 135 |
| 106 | 120 | KRRLKLIMPARFYPT | 708 | *1101 | 25 | 3 | 103 | 135 |
| 106 | 120 | KRRLKLIMPARFYPT | 708 | *1301 | 71 | 3 | 103 | 135 |
| 106 | 120 | KRRLKLIMPARFYPT | 708 | *1501 | 73 | 3 | 103 | 135 |
| 107 | 121 | RRLKLIMPARFYPTH | 709 | *0101 | 44 | 3 | 103 | 135 |

TABLE 4b-continued

Predicted HLA class II-restricted CD4+ T cell epitopes contained in SLP sequences from HBV polymerase protein.

HLA class II binding peptides in SLP sequences derived from HBV Polymerase

| Start | End | Sequence [A] | SEQ ID NO: | HLA-DRB1 molecule | Class II-B score[B] | SLP# | SLP Start | SLP End |
|---|---|---|---|---|---|---|---|---|
| 107 | 121 | RRLKLIMPARFYPTH | 709 | *0102 | 80 | 3 | 103 | 135 |
| 107 | 121 | RRLKLIMPARFYPTH | 709 | *0104 | 88 | 3 | 103 | 135 |
| 107 | 121 | RRLKLIMPARFYPTH | 709 | *0106 | 78 | 3 | 103 | 135 |
| 107 | 121 | RRLKLIMPARFYPTH | 709 | *1301 | 32 | 3 | 103 | 135 |
| 107 | 121 | RRLKLIMPARFYPTH | 709 | *1501 | 69 | 3 | 103 | 135 |
| 108 | 122 | RLKLIMPARFYPTHT | 710 | *0102 | 53 | 3 | 103 | 135 |
| 108 | 122 | RLKLIMPARFYPTHT | 710 | *0104 | 53 | 3 | 103 | 135 |
| 108 | 122 | RLKLIMPARFYPTHT | 710 | *0106 | 60 | 3 | 103 | 135 |
| 108 | 122 | RLKLIMPARFYPTHT | 710 | *1501 | 41 | 3 | 103 | 135 |
| 109 | 123 | LKLIMPARFYPTHTK | 711 | *1501 | 40 | 3 | 103 | 135 |
| 111 | 125 | LIMPARFYPTHTKYL | 712 | *0701 | 93 | 3 | 103 | 135 |
| 112 | 126 | IMPARFYPTHTKYLP | 713 | *0701 | 91 | 3 | 103 | 135 |
| 113 | 127 | MPARFYPTHTKYLPL | 714 | *0701 | 96 | 3 | 103 | 135 |
| 114 | 128 | PARFYPTHTKYLPLD | 715 | *0701 | 94 | 3 | 103 | 135 |
| 115 | 129 | ARFYPTHTKYLPLDK | 716 | *0701 | 90 | 3 | 103 | 135 |
| 116 | 130 | RFYPTHTKYLPLDKG | 717 | *0701 | 86 | 3 | 103 | 135 |
| 117 | 131 | FYPTHTKYLPLDKGI | 718 | *0701 | 81 | 3 | 103 | 135 |
| 121 | 135 | HTKYLPLDKGIKPYY | 719 | *1101 | 23 | 3 | 103 | 135 |
| | | Cumulative Class II-B score: | | | 3070 | | | |
| 121 | 135 | HTKYLPLDKGIKPYY | 719 | *1101 | 23 | 4 | 118 | 150 |
| 122 | 136 | TKYLPLDKGIKPYYP | 720 | *1101 | 21 | 4 | 118 | 150 |
| 130 | 144 | GIKPYYPDQVVNHYF | 721 | *0401 | 26 | 4 | 118 | 150 |
| 131 | 145 | IKPYYPDQVVNHYFQ | 722 | *0401 | 51 | 4 | 118 | 150 |
| 132 | 146 | KPYYPDQVVNHYFQT | 723 | *0401 | 21 | 4 | 118 | 150 |
| | | Cumulative Class II-B score: | | | 143 | | | |
| 139 | 153 | VVNHYFQTRHYLHTL | 726 | *1101 | 87 | 5 | 139 | 177 |
| 139 | 153 | VVNHYFQTRHYLHTL | 726 | *1501 | 70 | 5 | 139 | 177 |
| 140 | 154 | VNHYFQTRHYLHTLW | 727 | *0701 | 70 | 5 | 139 | 177 |
| 140 | 154 | VNHYFQTRHYLHTLW | 727 | *1101 | 76 | 5 | 139 | 177 |
| 140 | 154 | VNHYFQTRHYLHTLW | 727 | *1501 | 58 | 5 | 139 | 177 |
| 141 | 155 | NHYFQTRHYLHTLWK | 728 | *0701 | 40 | 5 | 139 | 177 |
| 141 | 155 | NHYFQTRHYLHTLWK | 728 | *1101 | 79 | 5 | 139 | 177 |
| 141 | 155 | NHYFQTRHYLHTLWK | 728 | *1501 | 28 | 5 | 139 | 177 |
| 142 | 156 | HYFQTRHYLHTLWKA | 729 | *1101 | 54 | 5 | 139 | 177 |
| 142 | 156 | HYFQTRHYLHTLWKA | 729 | *1501 | 30 | 5 | 139 | 177 |

TABLE 4b-continued

Predicted HLA class II-restricted CD4[+] T cell epitopes contained in SLP sequences from HBV polymerase protein.

HLA class II binding peptides in SLP sequences derived from HBV Polymerase

| Start | End | Sequence [A] | SEQ ID NO: | HLA-DRB1 molecule | Class II-B score[B] | SLP# | Peptide of invention (SLP) SLP Start | SLP End |
|---|---|---|---|---|---|---|---|---|
| 143 | 157 | YFQTRHYLHTLWKAG | 730 | *1101 | 24 | 5 | 139 | 177 |
| 144 | 158 | FQTRHYLHTLWKAGI | 731 | *1101 | 55 | 5 | 139 | 177 |
| 144 | 158 | FQTRHYLHTLWKAGI | 731 | *1501 | 5 | 5 | 139 | 177 |
| 145 | 159 | QTRHYLHTLWKAGIL | 732 | *1101 | 78 | 5 | 139 | 177 |
| 145 | 159 | QTRHYLHTLWKAGIL | 732 | *1501 | 38 | 5 | 139 | 177 |
| 146 | 160 | TRHYLHTLWKAGILY | 733 | *1101 | 88 | 5 | 139 | 177 |
| 146 | 160 | TRHYLHTLWKAGILY | 733 | *1501 | 45 | 5 | 139 | 177 |
| 147 | 161 | RHYLHTLWKAGILYK | 734 | *1101 | 85 | 5 | 139 | 177 |
| 147 | 161 | RHYLHTLWKAGILYK | 734 | *1501 | 40 | 5 | 139 | 177 |
| 148 | 162 | HYLHTLWKAGILYKR | 735 | *1101 | 50 | 5 | 139 | 177 |
| 154 | 168 | WKAGILYKRETTRSA | 736 | *0401 | 81 | 5 | 139 | 177 |
| 155 | 169 | KAGILYKRETTRSAS | 737 | *0401 | 83 | 5 | 139 | 177 |
| 156 | 170 | AGILYKRETTRSASF | 738 | *0401 | 84 | 5 | 139 | 177 |
| 157 | 171 | GILYKRETTRSASFC | 739 | *0401 | 80 | 5 | 139 | 177 |
| 158 | 172 | ILYKRETTRSASFCG | 740 | *0401 | 79 | 5 | 139 | 177 |
| 159 | 173 | LYKRETTRSASFCGS | 741 | *0401 | 14 | 5 | 139 | 177 |
| | | Cumulative Class II-B score: | | | 1519 | | | |
| 143 | 157 | YFQTRHYLHTLWKAG | 730 | *1101 | 24 | 6 | 143 | 177 |
| 144 | 158 | FQTRHYLHTLWKAGI | 731 | *1101 | 55 | 6 | 143 | 177 |
| 144 | 158 | FQTRHYLHTLWKAGI | 731 | *1501 | 5 | 6 | 143 | 177 |
| 145 | 159 | QTRHYLHTLWKAGIL | 732 | *1101 | 78 | 6 | 143 | 177 |
| 145 | 159 | QTRHYLHTLWKAGIL | 732 | *1501 | 38 | 6 | 143 | 177 |
| 146 | 160 | TRHYLHTLWKAGILY | 733 | *1101 | 88 | 6 | 143 | 177 |
| 146 | 160 | TRHYLHTLWKAGILY | 733 | *1501 | 45 | 6 | 143 | 177 |
| 147 | 161 | RHYLHTLWKAGILYK | 734 | *1101 | 85 | 6 | 143 | 177 |
| 147 | 161 | RHYLHTLWKAGILYK | 734 | *1501 | 40 | 6 | 143 | 177 |
| 148 | 162 | HYLHTLWKAGILYKR | 735 | *1101 | 50 | 6 | 143 | 177 |
| 154 | 168 | WKAGILYKRETTRSA | 736 | *0401 | 81 | 6 | 143 | 177 |
| 155 | 169 | KAGILYKRETTRSAS | 737 | *0401 | 83 | 6 | 143 | 177 |
| 156 | 170 | AGILYKRETTRSASF | 738 | *0401 | 84 | 6 | 143 | 177 |
| 157 | 171 | GILYKRETTRSASFC | 739 | *0401 | 80 | 6 | 143 | 177 |
| 158 | 172 | ILYKRETTRSASFCG | 740 | *0401 | 79 | 6 | 143 | 177 |
| 159 | 173 | LYKRETTRSASFCGS | 741 | *0401 | 14 | 6 | 143 | 177 |
| | | Cumulative Class II-B score: | | | 928 | | | |
| 137 | 151 | DQVVNHYFQTRHYLH | 724 | *0701 | 53 | 7 | 137 | 170 |
| 137 | 151 | DQVVNHYFQTRHYLH | 724 | *1101 | 75 | 7 | 137 | 170 |

TABLE 4b-continued

Predicted HLA class II-restricted CD4+ T cell epitopes contained in SLP sequences from HBV polymerase protein.

| HLA class II binding peptides in SLP sequences derived from HBV Polymerase | | | | | | Peptide of invention (SLP) | | |
|---|---|---|---|---|---|---|---|---|
| Start | End | Sequence [A] | SEQ ID NO: | HLA-DRB1 molecule | Class II-B score[B] | SLP# | SLP Start | SLP End |
| 137 | 151 | DQVVNHYFQTRHYLH | 724 | *1501 | 63 | 7 | 137 | 170 |
| 138 | 152 | QVVNHYFQTRHYLHT | 725 | *0701 | 63 | 7 | 137 | 170 |
| 138 | 152 | QVVNHYFQTRHYLHT | 725 | *1101 | 59 | 7 | 137 | 170 |
| 138 | 152 | QVVNHYFQTRHYLHT | 725 | *1501 | 73 | 7 | 137 | 170 |
| 139 | 153 | VVNHYFQTRHYLHTL | 726 | *0701 | 88 | 7 | 137 | 170 |
| 139 | 153 | VVNHYFQTRHYLHTL | 726 | *1101 | 87 | 7 | 137 | 170 |
| 139 | 153 | VVNHYFQTRHYLHTL | 726 | *1501 | 70 | 7 | 137 | 170 |
| 140 | 154 | VNHYFQTRHYLHTLW | 727 | *0701 | 70 | 7 | 137 | 170 |
| 140 | 154 | VNHYFQTRHYLHTLW | 727 | *1101 | 76 | 7 | 137 | 170 |
| 140 | 154 | VNHYFQTRHYLHTLW | 727 | *1501 | 58 | 7 | 137 | 170 |
| 141 | 155 | NHYFQTRHYLHTLWK | 728 | *0701 | 40 | 7 | 137 | 170 |
| 141 | 155 | NHYFQTRHYLHTLWK | 728 | *1101 | 79 | 7 | 137 | 170 |
| 141 | 155 | NHYFQTRHYLHTLWK | 728 | *1501 | 28 | 7 | 137 | 170 |
| 142 | 156 | HYFQTRHYLHTLWKA | 729 | *1101 | 54 | 7 | 137 | 170 |
| 142 | 156 | HYFQTRHYLHTLWKA | 729 | *1501 | 30 | 7 | 137 | 170 |
| 143 | 157 | YFQTRHYLHTLWKAG | 730 | *1101 | 24 | 7 | 137 | 170 |
| 144 | 158 | FQTRHYLHTLWKAGI | 731 | *1101 | 55 | 7 | 137 | 170 |
| 144 | 158 | FQTRHYLHTLWKAGI | 731 | *1501 | 5 | 7 | 137 | 170 |
| 145 | 159 | QTRHYLHTLWKAGIL | 732 | *1101 | 78 | 7 | 137 | 170 |
| 145 | 159 | QTRHYLHTLWKAGIL | 732 | *1501 | 38 | 7 | 137 | 170 |
| 146 | 160 | TRHYLHTLWKAGILY | 733 | *1101 | 88 | 7 | 137 | 170 |
| 146 | 160 | TRHYLHTLWKAGILY | 733 | *1501 | 45 | 7 | 137 | 170 |
| 147 | 161 | RHYLHTLWKAGILYK | 734 | *1101 | 85 | 7 | 137 | 170 |
| 147 | 161 | RHYLHTLWKAGILYK | 734 | *1501 | 40 | 7 | 137 | 170 |
| 148 | 162 | HYLHTLWKAGILYKR | 735 | *1101 | 50 | 7 | 137 | 170 |
| 154 | 168 | WKAGILYKRETTRSA | 736 | *0401 | 81 | 7 | 137 | 170 |
| 155 | 169 | KAGILYKRETTRSAS | 737 | *0401 | 83 | 7 | 137 | 170 |
| 156 | 170 | AGILYKRETTRSASF | 738 | *0401 | 84 | 7 | 137 | 170 |
| | | Cumulative Class II-B score: | | | 1817 | | | |
| 324 | 338 | SCWWLQFRNSKPCSE | 742 | *0401 | 3 | 8 | 316 | 347 |
| 385 | 399 | TAESRLVVDFSQFSR | 743 | *0301 | 97 | 9 | 385 | 417 |
| 386 | 400 | AESRLVVDFSQFSRG | 744 | *0301 | 87 | 9 | 385 | 417 |
| 387 | 401 | ESRLVVDFSQFSRGI | 745 | *0301 | 96 | 9 | 385 | 417 |
| 388 | 402 | SRLVVDFSQFSRGIS | 746 | *0301 | 94 | 9 | 385 | 417 |

TABLE 4b-continued

Predicted HLA class II-restricted CD4[+] T cell epitopes contained in SLP sequences from HBV polymerase protein.

HLA class II binding peptides in SLP sequences derived from HBV Polymerase

| Start | End | Sequence [A] | SEQ ID NO: | HLA-DRB1 molecule | Class II-B score[B] | SLP# | SLP Start | SLP End |
|---|---|---|---|---|---|---|---|---|
| 389 | 403 | RLVVDFSQFSRGISR | 747 | *0301 | 77 | 9 | 385 | 417 |
| 390 | 404 | LVVDFSQFSRGISRV | 748 | *0301 | 76 | 9 | 385 | 417 |
| | | Cumulative Class II-B score: | | | 527 | | | |
| 421 | 435 | LSSNLSWLSLDVSAA | 749 | *0401 | 27 | 10 | 419 | 456 |
| 422 | 436 | SSNLSWLSLDVSAAF | 750 | *0301 | 57 | 10 | 419 | 456 |
| 422 | 436 | SSNLSWLSLDVSAAF | 750 | *0401 | 71 | 10 | 419 | 456 |
| 423 | 437 | SNLSWLSLDVSAAFY | 751 | *0301 | 56 | 10 | 419 | 456 |
| 423 | 437 | SNLSWLSLDVSAAFY | 751 | *0401 | 70 | 10 | 419 | 456 |
| 424 | 438 | NLSWLSLDVSAAFYH | 752 | *0301 | 54 | 10 | 419 | 456 |
| 424 | 438 | NLSWLSLDVSAAFYH | 752 | *0401 | 69 | 10 | 419 | 456 |
| 425 | 439 | LSWLSLDVSAAFYHI | 753 | *0301 | 53 | 10 | 419 | 456 |
| 425 | 439 | LSWLSLDVSAAFYHI | 753 | *0401 | 67 | 10 | 419 | 456 |
| 425 | 439 | LSWLSLDVSAAFYHI | 753 | *1301 | 18 | 10 | 419 | 456 |
| 426 | 440 | SWLSLDVSAAFYHIP | 754 | *0301 | 51 | 10 | 419 | 456 |
| 426 | 440 | SWLSLDVSAAFYHIP | 754 | *0401 | 66 | 10 | 419 | 456 |
| 427 | 441 | WLSLDVSAAFYHIPL | 755 | *0301 | 50 | 10 | 419 | 456 |
| 427 | 441 | WLSLDVSAAFYHIPL | 755 | *0401 | 17 | 10 | 419 | 456 |
| 428 | 442 | LSLDVSAAFYHIPLH | 756 | *0301 | 49 | 10 | 419 | 456 |
| 432 | 446 | VSAAFYHIPLHPAAM | 757 | *0101 | 8 | 10 | 419 | 456 |
| 432 | 446 | VSAAFYHIPLHPAAM | 757 | *0105 | 8 | 10 | 419 | 456 |
| 432 | 446 | VSAAFYHIPLHPAAM | 757 | *0107 | 8 | 10 | 419 | 456 |
| 433 | 447 | SAAFYHIPLHPAAMP | 758 | *0101 | 35 | 10 | 419 | 456 |
| 433 | 447 | SAAFYHIPLHPAAMP | 758 | *0105 | 35 | 10 | 419 | 456 |
| 433 | 447 | SAAFYHIPLHPAAMP | 758 | *0107 | 35 | 10 | 419 | 456 |
| 433 | 447 | SAAFYHIPLHPAAMP | 758 | *1101 | 3 | 10 | 419 | 456 |
| 434 | 448 | AAFYHIPLHPAAMPH | 759 | *0101 | 13 | 10 | 419 | 456 |
| 434 | 448 | AAFYHIPLHPAAMPH | 759 | *0105 | 13 | 10 | 419 | 456 |
| 434 | 448 | AAFYHIPLHPAAMPH | 759 | *0107 | 13 | 10 | 419 | 456 |
| | | Cumulative Class II-B score: | | | 943 | | | |
| 422 | 436 | SSNLSWLSLDVSAAF | 750 | *0301 | 57 | 11 | 422 | 459 |
| 422 | 436 | SSNLSWLSLDVSAAF | 750 | *0401 | 71 | 11 | 422 | 459 |
| 423 | 437 | SNLSWLSLDVSAAFY | 751 | *0301 | 56 | 11 | 422 | 459 |
| 423 | 437 | SNLSWLSLDVSAAFY | 751 | *0401 | 70 | 11 | 422 | 459 |
| 424 | 438 | NLSWLSLDVSAAFYH | 752 | *0301 | 54 | 11 | 422 | 459 |
| 424 | 438 | NLSWLSLDVSAAFYH | 752 | *0401 | 69 | 11 | 422 | 459 |

TABLE 4b-continued

Predicted HLA class II-restricted CD4+ T cell epitopes contained in SLP sequences from HBV polymerase protein.

HLA class II binding peptides in SLP sequences derived from HBV Polymerase

| Start | End | Sequence [A] | SEQ ID NO: | HLA-DRB1 molecule | Class II-B score[B] | SLP# | SLP Start | SLP End |
|---|---|---|---|---|---|---|---|---|
| 425 | 439 | LSWLSLDVSAAFYHI | 753 | *0301 | 53 | 11 | 422 | 459 |
| 425 | 439 | LSWLSLDVSAAFYHI | 753 | *0401 | 67 | 11 | 422 | 459 |
| 425 | 439 | LSWLSLDVSAAFYHI | 753 | *1301 | 18 | 11 | 422 | 459 |
| 426 | 440 | SWLSLDVSAAFYHIP | 754 | *0301 | 51 | 11 | 422 | 459 |
| 426 | 440 | SWLSLDVSAAFYHIP | 754 | *0401 | 66 | 11 | 422 | 459 |
| 427 | 441 | WLSLDVSAAFYHIPL | 755 | *0301 | 50 | 11 | 422 | 459 |
| 427 | 441 | WLSLDVSAAFYHIPL | 755 | *0401 | 17 | 11 | 422 | 459 |
| 428 | 442 | LSLDVSAAFYHIPLH | 756 | *0301 | 49 | 11 | 422 | 459 |
| 432 | 446 | VSAAFYHIPLHPAAM | 757 | *0101 | 8 | 11 | 422 | 459 |
| 432 | 446 | VSAAFYHIPLHPAAM | 757 | *0105 | 8 | 11 | 422 | 459 |
| 432 | 446 | VSAAFYHIPLHPAAM | 757 | *0107 | 8 | 11 | 422 | 459 |
| 433 | 447 | SAAFYHIPLHPAAMP | 758 | *0101 | 35 | 11 | 422 | 459 |
| 433 | 447 | SAAFYHIPLHPAAMP | 758 | *0105 | 35 | 11 | 422 | 459 |
| 433 | 447 | SAAFYHIPLHPAAMP | 758 | *0107 | 35 | 11 | 422 | 459 |
| 433 | 447 | SAAFYHIPLHPAAMP | 758 | *1101 | 3 | 11 | 422 | 459 |
| 434 | 448 | AAFYHIPLHPAAMPH | 759 | *0101 | 13 | 11 | 422 | 459 |
| 434 | 448 | AAFYHIPLHPAAMPH | 759 | *0105 | 13 | 11 | 422 | 459 |
| 434 | 448 | AAFYHIPLHPAAMPH | 759 | *0107 | 13 | 11 | 422 | 459 |
| 444 | 458 | AAMPHLLIGSSGLSR | 760 | *0101 | 9 | 11 | 422 | 459 |
| 444 | 458 | AAMPHLLIGSSGLSR | 760 | *0301 | 64 | 11 | 422 | 459 |
| 445 | 459 | AMPHLLIGSSGLSRY | 761 | *0101 | 7 | 11 | 422 | 459 |
| 445 | 459 | AMPFILLIGSSGLSRY | 761 | *0301 | 63 | 11 | 422 | 459 |
| | | Cumulative Class II-B score: | | | 1058 | | | |
| 427 | 441 | WLSLDVSAAFYHIPL | 755 | *0301 | 50 | 12 | 427 | 459 |
| 427 | 441 | WLSLDVSAAFYHIPL | 755 | *0401 | 17 | 12 | 427 | 459 |
| 428 | 442 | LSLDVSAAFYHIPLH | 756 | *0301 | 49 | 12 | 427 | 459 |
| 432 | 446 | VSAAFYHIPLHPAAM | 757 | *0101 | 8 | 12 | 427 | 459 |
| 432 | 446 | VSAAFYHIPLHPAAM | 757 | *0105 | 8 | 12 | 427 | 459 |
| 432 | 446 | VSAAFYHIPLHPAAM | 757 | *0107 | 8 | 12 | 427 | 459 |
| 433 | 447 | SAAFYHIPLHPAAMP | 758 | *0101 | 35 | 12 | 427 | 459 |
| 433 | 447 | SAAFYHIPLHPAAMP | 758 | *0105 | 35 | 12 | 427 | 459 |
| 433 | 447 | SAAFYHIPLHPAAMP | 758 | *0107 | 35 | 12 | 427 | 459 |
| 433 | 447 | SAAFYHIPLHPAAMP | 758 | *1101 | 3 | 12 | 427 | 459 |
| 434 | 448 | AAFYHIPLHPAAMPH | 759 | *0101 | 13 | 12 | 427 | 459 |
| 434 | 448 | AAFYHIPLHPAAMPH | 759 | *0105 | 13 | 12 | 427 | 459 |

TABLE 4b-continued

Predicted HLA class II-restricted CD4+ T cell epitopes contained in SLP sequences from HBV polymerase protein.

HLA class II binding peptides in SLP sequences derived from HBV Polymerase

| Start | End | Sequence [A] | SEQ ID NO: | HLA-DRB1 molecule | Class II-B score[B] | SLP# | SLP Start | SLP End |
|---|---|---|---|---|---|---|---|---|
| 434 | 448 | AAFYHIPLHPAAMPH | 759 | *0107 | 13 | 12 | 427 | 459 |
| 444 | 458 | AAMPHLLIGSSGLSR | 760 | *0101 | 9 | 12 | 427 | 459 |
| 444 | 458 | AAMPHLLIGSSGLSR | 760 | *0301 | 64 | 12 | 427 | 459 |
| 445 | 459 | AMPHLLIGSSGLSRY | 761 | *0101 | 7 | 12 | 427 | 459 |
| 445 | 459 | AMPHLLIGSSGLSRY | 761 | *0301 | 63 | 12 | 427 | 459 |
| | | Cumulative Class II-B score: | | | 426 | | | |
| 483 | 497 | SCSRQLYVSLMLLYK | 762 | *1101 | 94 | 13 | 481 | 514 |
| 484 | 498 | CSRQLYVSLMLLYKT | 763 | *1101 | 93 | 13 | 481 | 514 |
| 484 | 498 | CSRQLYVSLMLLYKT | 763 | *1501 | 20 | 13 | 481 | 514 |
| 485 | 499 | SRQLYVSLMLLYKTY | 764 | *1101 | 91 | 13 | 481 | 514 |
| 485 | 499 | SRQLYVSLMLLYKTY | 764 | *1501 | 10 | 13 | 481 | 514 |
| 486 | 500 | RQLYVSLMLLYKTYG | 765 | *0301 | 47 | 13 | 481 | 514 |
| 486 | 500 | RQLYVSLMLLYKTYG | 765 | *1101 | 100 | 13 | 481 | 514 |
| 486 | 500 | RQLYVSLMLLYKTYG | 765 | *1301 | 21 | 13 | 481 | 514 |
| 486 | 500 | RQLYVSLMLLYKTYG | 765 | *1501 | 23 | 13 | 481 | 514 |
| 487 | 501 | QLYVSLMLLYKTYGW | 766 | *0301 | 10 | 13 | 481 | 514 |
| 487 | 501 | QLYVSLMLLYKTYGW | 766 | *1101 | 99 | 13 | 481 | 514 |
| 487 | 501 | QLYVSLMLLYKTYGW | 766 | *1301 | 20 | 13 | 481 | 514 |
| 487 | 501 | QLYVSLMLLYKTYGW | 766 | *1501 | 61 | 13 | 481 | 514 |
| 488 | 502 | LYVSLMLLYKTYGWK | 767 | *0301 | 9 | 13 | 481 | 514 |
| 488 | 502 | LYVSLMLLYKTYGWK | 767 | *1101 | 97 | 13 | 481 | 514 |
| 488 | 502 | LYVSLMLLYKTYGWK | 767 | *1301 | 19 | 13 | 481 | 514 |
| 488 | 502 | LYVSLMLLYKTYGWK | 767 | *1501 | 60 | 13 | 481 | 514 |
| 489 | 503 | YVSLMLLYKTYGWKL | 768 | *0701 | 100 | 13 | 481 | 514 |
| 489 | 503 | YVSLMLLYKTYGWKL | 768 | *1101 | 96 | 13 | 481 | 514 |
| 489 | 503 | YVSLMLLYKTYGWKL | 768 | *1301 | 17 | 13 | 481 | 514 |
| 489 | 503 | YVSLMLLYKTYGWKL | 768 | *1501 | 99 | 13 | 481 | 514 |
| 490 | 504 | VSLMLLYKTYGWKLH | 769 | *0701 | 99 | 13 | 481 | 514 |
| 490 | 504 | VSLMLLYKTYGWKLH | 769 | *1301 | 16 | 13 | 481 | 514 |
| 490 | 504 | VSLMLLYKTYGWKLH | 769 | *1501 | 100 | 13 | 481 | 514 |
| 491 | 505 | SLMLLYKTYGWKLHL | 770 | *0701 | 97 | 13 | 481 | 514 |
| 491 | 505 | SLMLLYKTYGWKLHL | 770 | *1301 | 14 | 13 | 481 | 514 |
| 491 | 505 | SLMLLYKTYGWKLHL | 770 | *1501 | 97 | 13 | 481 | 514 |
| 492 | 506 | LMLLYKTYGWKLHLY | 771 | *0106 | 3 | 13 | 481 | 514 |
| 492 | 506 | LMLLYKTYGWKLHLY | 771 | *0701 | 89 | 13 | 481 | 514 |

TABLE 4b-continued

Predicted HLA class II-restricted CD4+ T cell epitopes contained in SLP sequences from HBV polymerase protein.

HLA class II binding peptides in SLP sequences derived from HBV Polymerase

| Start | End | Sequence [A] | SEQ ID NO: | HLA-DRB1 molecule | Class II-B score[B] | SLP# | SLP Start | SLP End |
|---|---|---|---|---|---|---|---|---|
| 492 | 506 | LMLLYKTYGWKLHLY | 771 | *1101 | 5 | 13 | 481 | 514 |
| 492 | 506 | LMLLYKTYGWKLHLY | 771 | *1301 | 13 | 13 | 481 | 514 |
| 492 | 506 | LMLLYKTYGWKLHLY | 771 | *1501 | 77 | 13 | 481 | 514 |
| 493 | 507 | MLLYKTYGWKLHLYS | 772 | *0701 | 87 | 13 | 481 | 514 |
| 493 | 507 | MLLYKTYGWKLHLYS | 772 | *1101 | 9 | 13 | 481 | 514 |
| 493 | 507 | MLLYKTYGWKLHLYS | 772 | *1501 | 66 | 13 | 481 | 514 |
| 494 | 508 | LLYKTYGWKLHLYSH | 773 | *0701 | 84 | 13 | 481 | 514 |
| 494 | 508 | LLYKTYGWKLHLYSH | 773 | *1101 | 7 | 13 | 481 | 514 |
| 494 | 508 | LLYKTYGWKLHLYSH | 773 | *1501 | 85 | 13 | 481 | 514 |
| 495 | 509 | LYKTYGWKLHLYSHP | 774 | *0701 | 74 | 13 | 481 | 514 |
| 495 | 509 | LYKTYGWKLHLYSHP | 774 | *1101 | 6 | 13 | 481 | 514 |
| 495 | 509 | LYKTYGWKLHLYSHP | 774 | *1501 | 13 | 13 | 481 | 514 |
| 496 | 510 | YKTYGWKLHLYSHPI | 775 | *1101 | 4 | 13 | 481 | 514 |
| 497 | 511 | KTYGWKLHLYSHPIV | 776 | *0101 | 30 | 13 | 481 | 514 |
| 497 | 511 | KTYGWKLHLYSHPIV | 776 | *0701 | 13 | 13 | 481 | 514 |
| 497 | 511 | KTYGWKLHLYSHPIV | 776 | *1101 | 3 | 13 | 481 | 514 |
| 497 | 511 | KTYGWKLHLYSHPIV | 776 | *1501 | 90 | 13 | 481 | 514 |
| 498 | 512 | TYGWKLHLYSHPIVL | 777 | *0101 | 70 | 13 | 481 | 514 |
| 498 | 512 | TYGWKLHLYSHPIVL | 777 | *0701 | 71 | 13 | 481 | 514 |
| 498 | 512 | TYGWKLHLYSHPIVL | 777 | *1101 | 1 | 13 | 481 | 514 |
| 498 | 512 | TYGWKLHLYSHPIVL | 777 | *1501 | 89 | 13 | 481 | 514 |
| 499 | 513 | YGWKLHLYSHPIVLG | 778 | *0101 | 81 | 13 | 481 | 514 |
| 499 | 513 | YGWKLHLYSHPIVLG | 778 | *0701 | 24 | 13 | 481 | 514 |
| 499 | 513 | YGWKLHLYSHPIVLG | 778 | *1301 | 50 | 13 | 481 | 514 |
| 499 | 513 | YGWKLHLYSHPIVLG | 778 | *1501 | 87 | 13 | 481 | 514 |
| 500 | 514 | GWKLHLYSHPIVLGF | 779 | *0101 | 66 | 13 | 481 | 514 |
| 500 | 514 | GWKLHLYSHPIVLGF | 779 | *0701 | 7 | 13 | 481 | 514 |
| 500 | 514 | GWKLHLYSHPIVLGF | 779 | *1301 | 49 | 13 | 481 | 514 |
| 500 | 514 | GWKLHLYSHPIVLGF | 779 | *1501 | 86 | 13 | 481 | 514 |
|   |   | Cumulative Class II-B score: |   |   | 3046 |   |   |   |
| 524 | 538 | SPFLLAQFTSAICSV | 780 | *0101 | 61 | 14 | 524 | 559 |
| 524 | 538 | SPFLLAQFTSAICSV | 780 | *0401 | 43 | 14 | 524 | 559 |
| 524 | 538 | SPFLLAQFTSAICSV | 780 | *1501 | 16 | 14 | 524 | 559 |
| 525 | 539 | PFLLAQFTSAICSVV | 781 | *0101 | 24 | 14 | 524 | 559 |
| 525 | 539 | PFLLAQFTSAICSVV | 781 | *0401 | 41 | 14 | 524 | 559 |

TABLE 4b-continued

Predicted HLA class II-restricted CD4+ T cell epitopes contained in SLP sequences from HBV polymerase protein.

HLA class II binding peptides in SLP sequences derived from HBV Polymerase

| Start | End | Sequence [A] | SEQ ID NO: | HLA-DRB1 molecule | Class II-B score[B] | SLP# | SLP Start | SLP End |
|---|---|---|---|---|---|---|---|---|
| 525 | 539 | PFLLAQFTSAICSVV | 781 | *0701 | 59 | 14 | 524 | 559 |
| 525 | 539 | PFLLAQFTSAICSVV | 781 | *1501 | 14 | 14 | 524 | 559 |
| 526 | 540 | FLLAQFTSAICSVVR | 782 | *0401 | 13 | 14 | 524 | 559 |
| 526 | 540 | FLLAQFTSAICSVVR | 782 | *0701 | 53 | 14 | 524 | 559 |
| 527 | 541 | LLAQFTSAICSVVRR | 783 | *0701 | 49 | 14 | 524 | 559 |
| 528 | 542 | LAQFTSAICSVVRRA | 784 | *0701 | 43 | 14 | 524 | 559 |
| 529 | 543 | AQFTSAICSVVRRAF | 785 | *0701 | 51 | 14 | 524 | 559 |
| 533 | 547 | SAICSVVRRAFPHCL | 786 | *0701 | 47 | 14 | 524 | 559 |
| 533 | 547 | SAICSVVRRAFPHCL | 786 | *1301 | 60 | 14 | 524 | 559 |
| 534 | 548 | AICSVVRRAFPHCLA | 787 | *0701 | 16 | 14 | 524 | 559 |
| 534 | 548 | AICSVVRRAFPHCLA | 787 | *1301 | 59 | 14 | 524 | 559 |
| 535 | 549 | ICSVVRRAFPHCLAF | 788 | *0106 | 10 | 14 | 524 | 559 |
| 535 | 549 | ICSVVRRAFPHCLAF | 788 | *0701 | 21 | 14 | 524 | 559 |
| 535 | 549 | ICSVVRRAFPHCLAF | 788 | *1301 | 57 | 14 | 524 | 559 |
| 536 | 550 | CSVVRRAFPHCLAFS | 789 | *0103 | 30 | 14 | 524 | 559 |
| 536 | 550 | CSVVRRAFPHCLAFS | 789 | *0106 | 30 | 14 | 524 | 559 |
| 536 | 550 | CSVVRRAFPHCLAFS | 789 | *1301 | 56 | 14 | 524 | 559 |
| 537 | 551 | SVVRRAFPHCLAFSY | 790 | *1301 | 54 | 14 | 524 | 559 |
| 538 | 552 | VVRRAFPHCLAFSYM | 791 | *1301 | 53 | 14 | 524 | 559 |
| 539 | 553 | VRRAFPHCLAFSYMD | 792 | *1301 | 51 | 14 | 524 | 559 |
| 545 | 559 | HCLAFSYMDDVVLGA | 793 | *0401 | 30 | 14 | 524 | 559 |
| | | Cumulative Class II-B score: | | | 1042 | | | |
| 526 | 540 | FLLAQFTSAICSVVR | 782 | *0401 | 13 | 15 | 526 | 559 |
| 526 | 540 | FLLAQFTSAICSVVR | 782 | *0701 | 53 | 15 | 526 | 559 |
| 527 | 541 | LLAQFTSAICSVVRR | 783 | *0701 | 49 | 15 | 526 | 559 |
| 528 | 542 | LAQFTSAICSVVRRA | 784 | *0701 | 43 | 15 | 526 | 559 |
| 529 | 543 | AQFTSAICSVVRRAF | 785 | *0701 | 51 | 15 | 526 | 559 |
| 533 | 547 | SAICSVVRRAFPHCL | 786 | *0701 | 47 | 15 | 526 | 559 |
| 533 | 547 | SAICSVVRRAFPHCL | 786 | *1301 | 60 | 15 | 526 | 559 |
| 534 | 548 | AICSVVRRAFPHCLA | 787 | *0701 | 16 | 15 | 526 | 559 |
| 534 | 548 | AICSVVRRAFPHCLA | 787 | *1301 | 59 | 15 | 526 | 559 |
| 535 | 549 | ICSVVRRAFPHCLAF | 788 | *0106 | 10 | 15 | 526 | 559 |
| 535 | 549 | ICSVVRRAFPHCLAF | 788 | *0701 | 21 | 15 | 526 | 559 |
| 535 | 549 | ICSVVRRAFPHCLAF | 788 | *1301 | 57 | 15 | 526 | 559 |
| 536 | 550 | CSVVRRAFPHCLAFS | 789 | *0103 | 30 | 15 | 526 | 559 |

TABLE 4b-continued

Predicted HLA class II-restricted CD4+ T cell epitopes contained in SLP sequences from HBV polymerase protein.

HLA class II binding peptides in SLP sequences derived from HBV Polymerase

| Start | End | Sequence [A] | SEQ ID NO: | HLA-DRB1 molecule | Class II-B score[B] | SLP# | SLP Start | SLP End |
|---|---|---|---|---|---|---|---|---|
| 536 | 550 | CSVVRRAFPHCLAFS | 789 | *0106 | 30 | 15 | 526 | 559 |
| 536 | 550 | CSVVRRAFPHCLAFS | 789 | *1301 | 56 | 15 | 526 | 559 |
| 537 | 551 | SVVRRAFPHCLAFSY | 790 | *1301 | 54 | 15 | 526 | 559 |
| 538 | 552 | VVRRAFPHCLAFSYM | 791 | *1301 | 53 | 15 | 526 | 559 |
| 539 | 553 | VRRAFPHCLAFSYMD | 792 | *1301 | 51 | 15 | 526 | 559 |
| 545 | 559 | HCLAFSYMDDVVLGA | 793 | *0401 | 30 | 15 | 526 | 559 |
|  |  | Cumulative Class II-B score: |  |  | 783 |  |  |  |
| 565 | 579 | RESLYTAVTNFLLSL | 794 | *0103 | 9 | 16 | 565 | 598 |
| 565 | 579 | RESLYTAVTNFLLSL | 794 | *0701 | 67 | 16 | 565 | 598 |
| 566 | 580 | ESLYTAVTNFLLSLG | 795 | *0701 | 66 | 16 | 565 | 598 |
| 567 | 581 | SLYTAVTNFLLSLGI | 796 | *0701 | 64 | 16 | 565 | 598 |
| 568 | 582 | LYTAVTNFLLSLGIH | 797 | *0701 | 63 | 16 | 565 | 598 |
| 569 | 583 | YTAVTNFLLSLGIHL | 798 | *0101 | 90 | 16 | 565 | 598 |
| 569 | 583 | YTAVTNFLLSLGIHL | 798 | *0701 | 61 | 16 | 565 | 598 |
| 569 | 583 | YTAVTNFLLSLGIHL | 798 | *1501 | 37 | 16 | 565 | 598 |
| 570 | 584 | TAVTNFLLSLGIHLN | 799 | *0101 | 91 | 16 | 565 | 598 |
| 570 | 584 | TAVTNFLLSLGIHLN | 799 | *0102 | 28 | 16 | 565 | 598 |
| 570 | 584 | TAVTNFLLSLGIHLN | 799 | *0104 | 23 | 16 | 565 | 598 |
| 570 | 584 | TAVTNFLLSLGIHLN | 799 | *1501 | 49 | 16 | 565 | 598 |
| 571 | 585 | AVTNFLLSLGIHLNP | 800 | *0101 | 89 | 16 | 565 | 598 |
| 571 | 585 | AVTNFLLSLGIHLNP | 800 | *0102 | 35 | 16 | 565 | 598 |
| 571 | 585 | AVTNFLLSLGIHLNP | 800 | *0104 | 25 | 16 | 565 | 598 |
| 571 | 585 | AVTNFLLSLGIHLNP | 800 | *1501 | 46 | 16 | 565 | 598 |
| 572 | 586 | VTNFLLSLGIHLNPN | 801 | *0101 | 84 | 16 | 565 | 598 |
| 572 | 586 | VTNFLLSLGIHLNPN | 801 | *0102 | 38 | 16 | 565 | 598 |
| 572 | 586 | VTNFLLSLGIHLNPN | 801 | *0104 | 38 | 16 | 565 | 598 |
| 572 | 586 | VTNFLLSLGIHLNPN | 801 | *0106 | 5 | 16 | 565 | 598 |
| 572 | 586 | VTNFLLSLGIHLNPN | 801 | *1501 | 63 | 16 | 565 | 598 |
| 573 | 587 | TNFLLSLGIHLNPNK | 802 | *0101 | 83 | 16 | 565 | 598 |
| 573 | 587 | TNFLLSLGIHLNPNK | 802 | *0102 | 10 | 16 | 565 | 598 |
| 573 | 587 | TNFLLSLGIHLNPNK | 802 | *0104 | 5 | 16 | 565 | 598 |
| 573 | 587 | TNFLLSLGIHLNPNK | 802 | *0401 | 4 | 16 | 565 | 598 |
| 573 | 587 | TNFLLSLGIHLNPNK | 802 | *1501 | 43 | 16 | 565 | 598 |
| 574 | 588 | NFLLSLGIHLNPNKT | 803 | *0101 | 33 | 16 | 565 | 598 |
| 574 | 588 | NFLLSLGIHLNPNKT | 803 | *1501 | 30 | 16 | 565 | 598 |

TABLE 4b-continued

Predicted HLA class II-restricted CD4+ T cell epitopes contained in SLP sequences from HBV polymerase protein.

HLA class II binding peptides in SLP sequences derived from HBV Polymerase

| Start | End | Sequence [A] | SEQ ID NO: | HLA-DRB1 molecule | Class II-B score[B] | SLP# | SLP Start | SLP End |
|---|---|---|---|---|---|---|---|---|
| 575 | 589 | FLLSLGIHLNPNKTK | 804 | *0101 | 23 | 16 | 565 | 598 |
| 575 | 589 | FLLSLGIHLNPNKTK | 804 | *1501 | 29 | 16 | 565 | 598 |
| 576 | 590 | LLSLGIHLNPNKTKR | 805 | *1301 | 25 | 16 | 565 | 598 |
| 577 | 591 | LSLGIHLNPNKTKRW | 806 | *1301 | 50 | 16 | 565 | 598 |
| 578 | 592 | SLGIHLNPNKTKRWG | 807 | *1301 | 43 | 16 | 565 | 598 |
| 579 | 593 | LGIHLNPNKTKRWGY | 808 | *1301 | 36 | 16 | 565 | 598 |
|  |  | Cumulative Class II-B score: |  |  | 1482 |  |  |  |
| 589 | 603 | KRWGYSLNFMGYIIG | 809 | *1501 | 57 | 17 | 584 | 617 |
| 590 | 604 | RWGYSLNFMGYIIGS | 810 | *1501 | 56 | 17 | 584 | 617 |
| 591 | 605 | WGYSLNFMGYIIGSW | 811 | *1501 | 34 | 17 | 584 | 617 |
| 592 | 606 | GYSLNFMGYIIGSWG | 812 | *1501 | 21 | 17 | 584 | 617 |
| 593 | 607 | YSLNFMGYIIGSWGT | 813 | *1501 | 24 | 17 | 584 | 617 |
| 594 | 608 | SLNFMGYIIGSWGTL | 814 | *1501 | 11 | 17 | 584 | 617 |
| 595 | 609 | LNFMGYIIGSWGTLP | 815 | *1501 | 19 | 17 | 584 | 617 |
|  |  | Cumulative Class II-B score: |  |  | 223 |  |  |  |
| 653 | 667 | YPALMPLYACIQAKQ | 816 | *1101 | 11 | 18 | 653 | 691 |
| 656 | 670 | LMPLYACIQAKQAFT | 817 | *0101 | 58 | 18 | 653 | 691 |
| 656 | 670 | LMPLYACIQAKQAFT | 817 | *0105 | 58 | 18 | 653 | 691 |
| 656 | 670 | LMPLYACIQAKQAFT | 817 | *0107 | 58 | 18 | 653 | 691 |
| 657 | 671 | MPLYACIQAKQAFTF | 818 | *0101 | 75 | 18 | 653 | 691 |
| 657 | 671 | MPLYACIQAKQAFTF | 818 | *0105 | 75 | 18 | 653 | 691 |
| 657 | 671 | MPLYACIQAKQAFTF | 818 | *0107 | 75 | 18 | 653 | 691 |
| 657 | 671 | MPLYACIQAKQAFTF | 818 | *1301 | 41 | 18 | 653 | 691 |
| 658 | 672 | PLYACIQAKQAFTFS | 819 | *0101 | 48 | 18 | 653 | 691 |
| 658 | 672 | PLYACIQAKQAFTFS | 819 | *0105 | 48 | 18 | 653 | 691 |
| 658 | 672 | PLYACIQAKQAFTFS | 819 | *0107 | 48 | 18 | 653 | 691 |
| 658 | 672 | PLYACIQAKQAFTFS | 819 | *1301 | 40 | 18 | 653 | 691 |
| 659 | 673 | LYACIQAKQAFTFSP | 820 | *1301 | 39 | 18 | 653 | 691 |
| 660 | 674 | YACIQAKQAFTFSPT | 821 | *1301 | 37 | 18 | 653 | 691 |
| 661 | 675 | ACIQAKQAFTFSPTY | 822 | *1301 | 36 | 18 | 653 | 691 |
| 662 | 676 | CIQAKQAFTFSPTYK | 823 | *1301 | 34 | 18 | 653 | 691 |
| 663 | 677 | IQAKQAFTFSPTYKA | 824 | *0701 | 6 | 18 | 653 | 691 |
| 663 | 677 | IQAKQAFTFSPTYKA | 824 | *1301 | 33 | 18 | 653 | 691 |
| 664 | 678 | QAKQAFTFSPTYKAF | 825 | *0401 | 44 | 18 | 653 | 691 |
| 664 | 678 | QAKQAFTFSPTYKAF | 825 | *0701 | 37 | 18 | 653 | 691 |
| 665 | 679 | AKQAFTFSPTYKAFL | 826 | *0401 | 79 | 18 | 653 | 691 |

TABLE 4b-continued

Predicted HLA class II-restricted CD4+ T cell epitopes contained in SLP sequences from HBV polymerase protein.

HLA class II binding peptides in SLP sequences derived from HBV Polymerase

| Start | End | Sequence[A] | SEQ ID NO: | HLA-DRB1 molecule | Class II-B score[B] | SLP# | SLP Start | SLP End |
|---|---|---|---|---|---|---|---|---|
| 665 | 679 | AKQAFTFSPTYKAFL | 826 | *0701 | 77 | 18 | 653 | 691 |
| 666 | 680 | KQAFTFSPTYKAFLS | 827 | *0401 | 33 | 18 | 653 | 691 |
| 666 | 680 | KQAFTFSPTYKAFLS | 827 | *0701 | 60 | 18 | 653 | 691 |
| 666 | 680 | KQAFTFSPTYKAFLS | 827 | *1101 | 13 | 18 | 653 | 691 |
| 666 | 680 | KQAFTFSPTYKAFLS | 827 | *1501 | 8 | 18 | 653 | 691 |
| 667 | 681 | QAFTFSPTYKAFLSK | 828 | *0401 | 54 | 18 | 653 | 691 |
| 667 | 681 | QAFTFSPTYKAFLSK | 828 | *0701 | 46 | 18 | 653 | 691 |
| 668 | 682 | AFTFSPTYKAFLSKQ | 829 | *0701 | 14 | 18 | 653 | 691 |
| 669 | 683 | FTFSPTYKAFLSKQY | 830 | *0701 | 19 | 18 | 653 | 691 |
| 672 | 686 | SPTYKAFLSKQYMNL | 831 | *1501 | 3 | 18 | 653 | 691 |
| 673 | 687 | PTYKAFLSKQYMNLY | 832 | *1501 | 23 | 18 | 653 | 691 |
| 677 | 691 | AFLSKQYMNLYPVAR | 833 | *0101 | 40 | 18 | 653 | 691 |
| | | Cumulative Class II-B score: | | | 1365 | | | |
| 657 | 671 | MPLYACIQAKQAFTF | 818 | *0101 | 75 | 19 | 657 | 691 |
| 657 | 671 | MPLYACIQAKQAFTF | 818 | *0105 | 75 | 19 | 657 | 691 |
| 657 | 671 | MPLYACIQAKQAFTF | 818 | *0107 | 75 | 19 | 657 | 691 |
| 657 | 671 | MPLYACIQAKQAFTF | 818 | *1301 | 41 | 19 | 657 | 691 |
| 658 | 672 | PLYACIQAKQAFTFS | 819 | *0101 | 48 | 19 | 657 | 691 |
| 658 | 672 | PLYACIQAKQAFTFS | 819 | *0105 | 48 | 19 | 657 | 691 |
| 658 | 672 | PLYACIQAKQAFTFS | 819 | *0107 | 48 | 19 | 657 | 691 |
| 658 | 672 | PLYACIQAKQAFTFS | 819 | *1301 | 40 | 19 | 657 | 691 |
| 659 | 673 | LYACIQAKQAFTFSP | 820 | *1301 | 39 | 19 | 657 | 691 |
| 660 | 674 | YACIQAKQAFTFSPT | 821 | *1301 | 37 | 19 | 657 | 691 |
| 661 | 675 | ACIQAKQAFTFSPTY | 822 | *1301 | 36 | 19 | 657 | 691 |
| 662 | 676 | CIQAKQAFTFSPTYK | 823 | *1301 | 34 | 19 | 657 | 691 |
| 663 | 677 | IQAKQAFTFSPTYKA | 824 | *0701 | 6 | 19 | 657 | 691 |
| 663 | 677 | IQAKQAFTFSPTYKA | 824 | *1301 | 33 | 19 | 657 | 691 |
| 664 | 678 | QAKQAFTFSPTYKAF | 825 | *0401 | 44 | 19 | 657 | 691 |
| 664 | 678 | QAKQAFTFSPTYKAF | 825 | *0701 | 37 | 19 | 657 | 691 |
| 665 | 679 | AKQAFTFSPTYKAFL | 826 | *0401 | 79 | 19 | 657 | 691 |
| 665 | 679 | AKQAFTFSPTYKAFL | 826 | *0701 | 77 | 19 | 657 | 691 |
| 666 | 680 | KQAFTFSPTYKAFLS | 827 | *0401 | 33 | 19 | 657 | 691 |
| 666 | 680 | KQAFTFSPTYKAFLS | 827 | *0701 | 60 | 19 | 657 | 691 |
| 666 | 680 | KQAFTFSPTYKAFLS | 827 | *1101 | 13 | 19 | 657 | 691 |
| 666 | 680 | KQAFTFSPTYKAFLS | 827 | *1501 | 8 | 19 | 657 | 691 |

TABLE 4b-continued

Predicted HLA class II-restricted CD4+ T cell epitopes contained in SLP sequences from HBV polymerase protein.

HLA class II binding peptides in SLP sequences derived from HBV Polymerase

| Start | End | Sequence [A] | SEQ ID NO: | HLA-DRB1 molecule | Class II-B score[B] | Peptide of invention (SLP) SLP# | SLP Start | SLP End |
|---|---|---|---|---|---|---|---|---|
| 667 | 681 | QAFTFSPTYKAFLSK | 828 | *0401 | 54 | 19 | 657 | 691 |
| 667 | 681 | QAFTFSPTYKAFLSK | 828 | *0701 | 46 | 19 | 657 | 691 |
| 668 | 682 | AFTFSPTYKAFLSKQ | 829 | *0701 | 14 | 19 | 657 | 691 |
| 669 | 683 | FTFSPTYKAFLSKQY | 830 | *0701 | 19 | 19 | 657 | 691 |
| 672 | 686 | SPTYKAFLSKQYMNL | 831 | *1501 | 3 | 19 | 657 | 691 |
| 673 | 687 | PTYKAFLSKQYMNLY | 832 | *1501 | 23 | 19 | 657 | 691 |
| 677 | 691 | AFLSKQYMNLYPVAR | 833 | *0101 | 40 | 19 | 657 | 691 |
|  |  | Cumulative Class II-B score: |  |  | 1181 |  |  |  |
| 717 | 731 | MRGTFVAPLPIHTAE | 834 | *0101 | 10 | 20 | 715 | 746 |
| 717 | 731 | MRGTFVAPLPIHTAE | 834 | *0105 | 10 | 20 | 715 | 746 |
| 717 | 731 | MRGTFVAPLPIHTAE | 834 | *0107 | 10 | 20 | 715 | 746 |
| 718 | 732 | RGTFVAPLPIHTAEL | 835 | *0101 | 4 | 20 | 715 | 746 |
| 718 | 732 | RGTFVAPLPIHTAEL | 835 | *0102 | 20 | 20 | 715 | 746 |
| 718 | 732 | RGTFVAPLPIHTAEL | 835 | *0104 | 30 | 20 | 715 | 746 |
| 718 | 732 | RGTFVAPLPIHTAEL | 835 | *0105 | 60 | 20 | 715 | 746 |
| 718 | 732 | RGTFVAPLPIHTAEL | 835 | *0106 | 33 | 20 | 715 | 746 |
| 718 | 732 | RGTFVAPLPIHTAEL | 835 | *0107 | 60 | 20 | 715 | 746 |
| 719 | 733 | GTFVAPLPIHTAELL | 836 | *0101 | 6 | 20 | 715 | 746 |
| 732 | 746 | LLAACFARSRSGAKL | 837 | *0701 | 1 | 20 | 715 | 746 |
|  |  | Cumulative Class II-B score: |  |  | 244 |  |  |  |
| 767 | 781 | GCTANWILRGTSFVY | 838 | *1501 | 1 | 21 | 754 | 791 |
| 768 | 782 | CTANWILRGTSFVYV | 839 | *1301 | 21 | 21 | 754 | 791 |
| 768 | 782 | CTANWILRGTSFVYV | 839 | *1501 | 10 | 21 | 754 | 791 |
| 773 | 787 | ILRGTSFVYVPSALN | 840 | *0101 | 100 | 21 | 754 | 791 |
| 773 | 787 | ILRGTSFVYVPSALN | 840 | *0401 | 23 | 21 | 754 | 791 |
| 773 | 787 | ILRGTSFVYVPSALN | 840 | *0701 | 31 | 21 | 754 | 791 |
| 774 | 788 | LRGTSFVYVPSALNP | 841 | *0101 | 96 | 21 | 754 | 791 |
| 774 | 788 | LRGTSFVYVPSALNP | 841 | *0105 | 40 | 21 | 754 | 791 |
| 774 | 788 | LRGTSFVYVPSALNP | 841 | *0107 | 40 | 21 | 754 | 791 |
| 774 | 788 | LRGTSFVYVPSALNP | 841 | *0401 | 56 | 21 | 754 | 791 |
| 774 | 788 | LRGTSFVYVPSALNP | 841 | *0701 | 23 | 21 | 754 | 791 |
| 775 | 789 | RGTSFVYVPSALNPA | 842 | *0101 | 99 | 21 | 754 | 791 |
| 775 | 789 | RGTSFVYVPSALNPA | 842 | *0102 | 30 | 21 | 754 | 791 |
| 775 | 789 | RGTSFVYVPSALNPA | 842 | *0104 | 43 | 21 | 754 | 791 |
| 775 | 789 | RGTSFVYVPSALNPA | 842 | *0105 | 93 | 21 | 754 | 791 |

TABLE 4b-continued

Predicted HLA class II-restricted CD4[+] T cell epitopes contained in SLP sequences from HBV polymerase protein.

HLA class II binding peptides in SLP sequences derived from HBV Polymerase

| Start | End | Sequence [A] | SEQ ID NO: | HLA-DRB1 molecule | Class II-B score[B] | SLP# | SLP Start | SLP End |
|---|---|---|---|---|---|---|---|---|
| 775 | 789 | RGTSFVYVPSALNPA | 842 | *0107 | 93 | 21 | 754 | 791 |
| 775 | 789 | RGTSFVYVPSALNPA | 842 | *0401 | 76 | 21 | 754 | 791 |
| 775 | 789 | RGTSFVYVPSALNPA | 842 | *0701 | 29 | 21 | 754 | 791 |
| 776 | 790 | GTSFVYVPSALNPAD | 843 | *0101 | 97 | 21 | 754 | 791 |
| 776 | 790 | GTSFVYVPSALNPAD | 843 | *0102 | 13 | 21 | 754 | 791 |
| 776 | 790 | GTSFVYVPSALNPAD | 843 | *0104 | 28 | 21 | 754 | 791 |
| 776 | 790 | GTSFVYVPSALNPAD | 843 | *0105 | 85 | 21 | 754 | 791 |
| 776 | 790 | GTSFVYVPSALNPAD | 843 | *0107 | 85 | 21 | 754 | 791 |
| 776 | 790 | GTSFVYVPSALNPAD | 843 | *0401 | 74 | 21 | 754 | 791 |
| 776 | 790 | GTSFVYVPSALNPAD | 843 | *0701 | 4 | 21 | 754 | 791 |
| 777 | 791 | TSFVYVPSALNPADD | 844 | *0101 | 94 | 21 | 754 | 791 |
| 777 | 791 | TSFVYVPSALNPADD | 844 | *0105 | 68 | 21 | 754 | 791 |
| 777 | 791 | TSFVYVPSALNPADD | 844 | *0107 | 68 | 21 | 754 | 791 |
| 777 | 791 | TSFVYVPSALNPADD | 844 | *0401 | 73 | 21 | 754 | 791 |
| | | Cumulative Class II-B score: | | | 1591 | | | |
| 767 | 781 | GCTANWILRGTSFVY | 838 | *1501 | 1 | 22 | 757 | 792 |
| 768 | 782 | CTANWILRGTSFVYV | 839 | *1301 | 21 | 22 | 757 | 792 |
| 768 | 782 | CTANWILRGTSFVYV | 839 | *1501 | 10 | 22 | 757 | 792 |
| 773 | 787 | ILRGTSFVYVPSALN | 840 | *0101 | 100 | 22 | 757 | 792 |
| 773 | 787 | ILRGTSFVYVPSALN | 840 | *0401 | 23 | 22 | 757 | 792 |
| 773 | 787 | ILRGTSFVYVPSALN | 840 | *0701 | 31 | 22 | 757 | 792 |
| 774 | 788 | LRGTSFVYVPSALNP | 841 | *0101 | 96 | 22 | 757 | 792 |
| 774 | 788 | LRGTSFVYVPSALNP | 841 | *0105 | 40 | 22 | 757 | 792 |
| 774 | 788 | LRGTSFVYVPSALNP | 841 | *0107 | 40 | 22 | 757 | 792 |
| 774 | 788 | LRGTSFVYVPSALNP | 841 | *0401 | 56 | 22 | 757 | 792 |
| 774 | 788 | LRGTSFVYVPSALNP | 841 | *0701 | 23 | 22 | 757 | 792 |
| 775 | 789 | RGTSFVYVPSALNPA | 842 | *0101 | 99 | 22 | 757 | 792 |
| 775 | 789 | RGTSFVYVPSALNPA | 842 | *0102 | 30 | 22 | 757 | 792 |
| 775 | 789 | RGTSFVYVPSALNPA | 842 | *0104 | 43 | 22 | 757 | 792 |
| 775 | 789 | RGTSFVYVPSALNPA | 842 | *0105 | 93 | 22 | 757 | 792 |
| 775 | 789 | RGTSFVYVPSALNPA | 842 | *0107 | 93 | 22 | 757 | 792 |
| 775 | 789 | RGTSFVYVPSALNPA | 842 | *0401 | 76 | 22 | 757 | 792 |
| 775 | 789 | RGTSFVYVPSALNPA | 842 | *0701 | 29 | 22 | 757 | 792 |
| 776 | 790 | GTSFVYVPSALNPAD | 843 | *0101 | 97 | 22 | 757 | 792 |
| 776 | 790 | GTSFVYVPSALNPAD | 843 | *0102 | 13 | 22 | 757 | 792 |

TABLE 4b-continued

Predicted HLA class II-restricted CD4+ T cell epitopes contained in SLP sequences from HBV polymerase protein.

HLA class II binding peptides in SLP sequences derived from HBV Polymerase

| Start | End | Sequence [A] | SEQ ID NO: | HLA-DRB1 molecule | Class II-B score[B] | SLP# | SLP Start | SLP End |
|---|---|---|---|---|---|---|---|---|
| 776 | 790 | GTSFVYVPSALNPAD | 843 | *0104 | 28 | 22 | 757 | 792 |
| 776 | 790 | GTSFVYVPSALNPAD | 843 | *0105 | 85 | 22 | 757 | 792 |
| 776 | 790 | GTSFVYVPSALNPAD | 843 | *0107 | 85 | 22 | 757 | 792 |
| 776 | 790 | GTSFVYVPSALNPAD | 843 | *0401 | 74 | 22 | 757 | 792 |
| 776 | 790 | GTSFVYVPSALNPAD | 843 | *0701 | 4 | 22 | 757 | 792 |
| 777 | 791 | TSFVYVPSALNPADD | 844 | *0101 | 94 | 22 | 757 | 792 |
| 777 | 791 | TSFVYVPSALNPADD | 844 | *0105 | 68 | 22 | 757 | 792 |
| 777 | 791 | TSFVYVPSALNPADD | 844 | *0107 | 68 | 22 | 757 | 792 |
| 777 | 791 | TSFVYVPSALNPADD | 844 | *0401 | 73 | 22 | 757 | 792 |
| 778 | 792 | SFVYVPSALNPADDP | 845 | *0101 | 54 | 22 | 757 | 792 |
| 778 | 792 | SFVYVPSALNPADDP | 845 | *0401 | 64 | 22 | 757 | 792 |
| | | Cumulative Class II-B score: | | | 1709 | | | |
| 767 | 781 | GCTANWILRGTSFVY | 838 | *1501 | 1 | 23 | 754 | 789 |
| 768 | 782 | CTANWILRGTSFVYV | 839 | *1301 | 21 | 23 | 754 | 789 |
| 768 | 782 | CTANWILRGTSFVYV | 839 | *1501 | 10 | 23 | 754 | 789 |
| 773 | 787 | ILRGTSFVYVPSALN | 840 | *0101 | 100 | 23 | 754 | 789 |
| 773 | 787 | ILRGTSFVYVPSALN | 840 | *0401 | 23 | 23 | 754 | 789 |
| 773 | 787 | ILRGTSFVYVPSALN | 840 | *0701 | 31 | 23 | 754 | 789 |
| 774 | 788 | LRGTSFVYVPSALNP | 841 | *0101 | 96 | 23 | 754 | 789 |
| 774 | 788 | LRGTSFVYVPSALNP | 841 | *0105 | 40 | 23 | 754 | 789 |
| 774 | 788 | LRGTSFVYVPSALNP | 841 | *0107 | 40 | 23 | 754 | 789 |
| 774 | 788 | LRGTSFVYVPSALNP | 841 | *0401 | 56 | 23 | 754 | 789 |
| 774 | 788 | LRGTSFVYVPSALNP | 841 | *0701 | 23 | 23 | 754 | 789 |
| 775 | 789 | RGTSFVYVPSALNPA | 842 | *0101 | 99 | 23 | 754 | 789 |
| 775 | 789 | RGTSFVYVPSALNPA | 842 | *0102 | 30 | 23 | 754 | 789 |
| 775 | 789 | RGTSFVYVPSALNPA | 842 | *0104 | 43 | 23 | 754 | 789 |
| 775 | 789 | RGTSFVYVPSALNPA | 842 | *0105 | 93 | 23 | 754 | 789 |
| 775 | 789 | RGTSFVYVPSALNPA | 842 | *0107 | 93 | 23 | 754 | 789 |
| 775 | 789 | RGTSFVYVPSALNPA | 842 | *0401 | 76 | 23 | 754 | 789 |
| 775 | 789 | RGTSFVYVPSALNPA | 842 | *0701 | 29 | 23 | 754 | 789 |
| | | Cumulative Class II-B score: | | | 903 | | | |

"Start" and "End" are relative to the amino acid sequence of human HBV polymerase as depicted in SEQ ID NO: 1
[A] Peptide amino acid sequence. Each HLA-DRB1 binding peptide of HBV polymerase is listed separately for each HLA class II molecule to which it is predicted to bind, and each peptide can be listed multiple times for that reason.
[B] Class II-B score. See Material and Methods (Examples section).
[C] Cumulative Class II-B score. See Material and Methods (Examples section).

TABLE 5a

Predicted HLA class I-restricted CD8+ cytotoxic T cell epitopes contained in SLP sequences from HBV Core protein.

| HLA class I binding peptides in SLP sequences derived from HBV Core protein | | | | | | | | | Peptide of invention (SLP) | | |
|---|---|---|---|---|---|---|---|---|---|---|---|
| Start | End | Length | Sequence[A] | SEQ ID NO: | HLA class I molecule | Class I-B score[B] | C-score[C] | Class I-BCI score[D] | SLP# | SLP Start | SLP End |
| 107 | 117 | 11 | DPASRDLVVNY | 846 | B*3501 | 100 | 1.68 | 168 | 24 | 107 | 141 |
| 107 | 117 | 11 | DPASRDLVVNY | 846 | B*3503 | 30 | 1.68 | 50 | 24 | 107 | 141 |
| 107 | 117 | 11 | DPASRDLVVNY | 846 | B*5301 | 79 | 1.68 | 132 | 24 | 107 | 141 |
| 108 | 117 | 10 | PASRDLVVNY | 847 | B*5701 | 100 | 1.68 | 168 | 24 | 107 | 141 |
| 108 | 117 | 10 | PASRDLVVNY | 847 | B*5801 | 100 | 1.68 | 168 | 24 | 107 | 141 |
| 109 | 117 | 9 | ASRDLVVNY | 848 | A*3002 | 45 | 1.68 | 76 | 24 | 107 | 141 |
| 109 | 117 | 9 | ASRDLVVNY | 848 | B*1501 | 40 | 1.68 | 67 | 24 | 107 | 141 |
| 109 | 117 | 9 | ASRDLVVNY | 848 | B*1525 | 10 | 1.68 | 17 | 24 | 107 | 141 |
| 111 | 118 | 8 | RDLVVNYV | 849 | B*1302 | 63 | 1.72 | 108 | 24 | 107 | 141 |
| 113 | 122 | 10 | LVVNYVNTNV | 850 | A*0206 | 29 | 1.04 | 30 | 24 | 107 | 141 |
| 113 | 122 | 10 | LVVNYVNTNV | 850 | A*6802 | 75 | 1.04 | 78 | 24 | 107 | 141 |
| 114 | 122 | 9 | VVNYVNTNV | 851 | A*6802 | 38 | 1.04 | 39 | 24 | 107 | 141 |
| 113 | 123 | 11 | LVVNYVNTNVG | 852 | A*6802 | 25 | 0.09 | 2 | 24 | 107 | 141 |
| 116 | 124 | 9 | NYVNTNVGL | 853 | A*2301 | 63 | 1.89 | 118 | 24 | 107 | 141 |
| 117 | 125 | 9 | YVNTNVGLK | 854 | A*0301 | 100 | 0.33 | 33 | 24 | 107 | 141 |
| 117 | 125 | 9 | YVNTNVGLK | 854 | A*1101 | 100 | 0.33 | 33 | 24 | 107 | 141 |
| 117 | 125 | 9 | YVNTNVGLK | 854 | A*6801 | 62 | 0.33 | 20 | 24 | 107 | 141 |
| 116 | 126 | 11 | NYVNTNVGLKI | 855 | A*2301 | 44 | 1.53 | 67 | 24 | 107 | 141 |
| 116 | 126 | 11 | NYVNTNVGLKI | 855 | A*2402 | 63 | 1.53 | 96 | 24 | 107 | 141 |
| 120 | 129 | 10 | TNVGlKIRQL | 856 | B*0801 | 50 | 1.67 | 83 | 24 | 107 | 141 |
| 121 | 129 | 9 | NVGLKIRQL | 857 | B*0702 | 75 | 1.67 | 125 | 24 | 107 | 141 |
| 121 | 130 | 10 | NVGLKIRQLL | 858 | B*0702 | 83 | 1.23 | 103 | 24 | 107 | 141 |
| 123 | 130 | 8 | GLKIRQLL | 859 | B*0801 | 70 | 1.23 | 86 | 24 | 107 | 141 |
| 122 | 131 | 10 | VGLKIRQLLW | 860 | B*5802 | 55 | 1.66 | 91 | 24 | 107 | 141 |
| 123 | 132 | 10 | GLKIRQLLWF | 861 | A*0301 | 25 | 1.02 | 25 | 24 | 107 | 141 |
| 125 | 132 | 8 | KIRQLLWF | 862 | A*3201 | 75 | 1.02 | 76 | 24 | 107 | 141 |
| 125 | 132 | 8 | KIRQLLWF | 862 | B*1501 | 20 | 1.02 | 20 | 24 | 107 | 141 |
| 125 | 132 | 8 | KIRQLLWF | 862 | B*1525 | 40 | 1.02 | 41 | 24 | 107 | 141 |
| 126 | 134 | 9 | IRQLLWFHI | 863 | B*2702 | 86 | 1.69 | 145 | 24 | 107 | 141 |
| 126 | 134 | 9 | IRQLLWFHI | 863 | B*2705 | 84 | 1.69 | 142 | 24 | 107 | 141 |
| 127 | 134 | 8 | RQLLWFHI | 864 | A*2301 | 81 | 1.69 | 138 | 24 | 107 | 141 |
| 127 | 134 | 8 | RQLLWFHI | 864 | A*2402 | 69 | 1.69 | 116 | 24 | 107 | 141 |
| 127 | 134 | 8 | RQLLWFHI | 864 | A*3201 | 63 | 1.69 | 106 | 24 | 107 | 141 |
| 127 | 134 | 8 | RQLLWFHI | 864 | B*1301 | 90 | 1.69 | 152 | 24 | 107 | 141 |
| 127 | 134 | 8 | RQLLWFHI | 864 | B*2702 | 100 | 1.69 | 169 | 24 | 107 | 141 |

TABLE 5a-continued

Predicted HLA class I-restricted CD8+ cytotoxic T cell epitopes contained in SLP sequences from HBV Core protein.

| | | | HLA class I binding peptides in SLP sequences derived from HBV Core protein | | | | | | Peptide of invention (SLP) | | |
|---|---|---|---|---|---|---|---|---|---|---|---|
| Start | End | Length | Sequence [A] | SEQ ID NO: | HLA class I molecule | Class I-B score[B] | C-score[C] | Class I-BCI score[D] | SLP# | SLP Start | SLP End |
| 127 | 134 | 8 | RQLLWFHI | 864 | B*3701 | 73 | 1.69 | 124 | 24 | 107 | 141 |
| 127 | 134 | 8 | RQLLWFHI | 864 | B*4002 | 57 | 1.69 | 97 | 24 | 107 | 141 |
| 127 | 134 | 8 | RQLLWFHI | 864 | B*4801 | 100 | 1.69 | 169 | 24 | 107 | 141 |
| 127 | 134 | 8 | RQLLWFHI | 864 | B*4901 | 47 | 1.69 | 80 | 24 | 107 | 141 |
| 127 | 134 | 8 | RQLLWFHI | 864 | B*5001 | 47 | 1.69 | 79 | 24 | 107 | 141 |
| 127 | 134 | 8 | RQLLWFHI | 864 | B*5201 | 78 | 1.69 | 132 | 24 | 107 | 141 |
| 126 | 135 | 10 | IRQLLWFHIS | 865 | B*2705 | 3 | 0.55 | 2 | 24 | 107 | 141 |
| 127 | 135 | 9 | RQLLWFHIS | 866 | B*4801 | 14 | 0.55 | 8 | 24 | 107 | 141 |
| 127 | 136 | 10 | RQLLWFHISC | 867 | B*4801 | 29 | 0.82 | 24 | 24 | 107 | 141 |
| 128 | 136 | 9 | QLLWFHISC | 868 | A*0201 | 75 | 0.82 | 62 | 24 | 107 | 141 |
| 129 | 136 | 8 | LLWFHISC | 869 | A*0201 | 60 | 0.82 | 49 | 24 | 107 | 141 |
| 127 | 137 | 11 | RQLLWFHISCL | 870 | B*1301 | 35 | 1.95 | 68 | 24 | 107 | 141 |
| 127 | 137 | 11 | RQLLWFHISCL | 870 | B*1302 | 50 | 1.95 | 98 | 24 | 107 | 141 |
| 127 | 137 | 11 | RQLLWFHISCL | 870 | B*1402 | 38 | 1.95 | 75 | 24 | 107 | 141 |
| 127 | 137 | 11 | RQLLWFHISCL | 870 | B*2702 | 71 | 1.95 | 139 | 24 | 107 | 141 |
| 127 | 137 | 11 | RQLLWFHISCL | 870 | B*3701 | 40 | 1.95 | 78 | 24 | 107 | 141 |
| 127 | 137 | 11 | RQLLWFHISCL | 870 | B*3901 | 64 | 1.95 | 125 | 24 | 107 | 141 |
| 127 | 137 | 11 | RQLLWFHISCL | 870 | B*4001 | 7 | 1.95 | 13 | 24 | 107 | 141 |
| 127 | 137 | 11 | RQLLWFHISCL | 870 | B*4002 | 14 | 1.95 | 28 | 24 | 107 | 141 |
| 128 | 137 | 10 | QLLWFHISCL | 871 | A*0201 | 20 | 1.95 | 39 | 24 | 107 | 141 |
| 129 | 137 | 9 | LLWFHISCL | 872 | A*0201 | 50 | 1.95 | 98 | 24 | 107 | 141 |
| 129 | 137 | 9 | LLWFHISCL | 872 | B*0801 | 50 | 1.95 | 98 | 24 | 107 | 141 |
| 130 | 137 | 8 | LWFHISCL | 873 | A*2301 | 13 | 1.95 | 24 | 24 | 107 | 141 |
| 130 | 137 | 8 | LWFHISCL | 873 | A*2402 | 13 | 1.95 | 24 | 24 | 107 | 141 |
| 129 | 138 | 10 | LLWFHISCLT | 874 | A*0201 | 56 | 0.32 | 18 | 24 | 107 | 141 |
| 129 | 139 | 11 | LLWFHISCLTF | 875 | A*3201 | 81 | 1.49 | 121 | 24 | 107 | 141 |
| 129 | 139 | 11 | LLWFHISCLTF | 875 | B*1501 | 100 | 1.49 | 149 | 24 | 107 | 141 |
| 129 | 139 | 11 | LLWFHISCLTF | 875 | B*1502 | 78 | 1.49 | 116 | 24 | 107 | 141 |
| 129 | 139 | 11 | LLWFHISCLTF | 875 | B*1525 | 100 | 1.49 | 149 | 24 | 107 | 141 |
| 130 | 139 | 10 | LWFHISCLTF | 876 | A*2301 | 100 | 1.49 | 149 | 24 | 107 | 141 |
| 130 | 139 | 10 | LWFHISCLTF | 876 | A*2402 | 100 | 1.49 | 149 | 24 | 107 | 141 |
| 130 | 139 | 10 | LWFHISCLTF | 876 | A*2902 | 86 | 1.49 | 127 | 24 | 107 | 141 |
| 130 | 139 | 10 | LWFHISCLTF | 876 | B*2702 | 43 | 1.49 | 64 | 24 | 107 | 141 |
| 132 | 139 | 8 | FHISCLTF | 877 | A*2301 | 56 | 1.49 | 84 | 24 | 107 | 141 |
| 132 | 139 | 8 | FHISCLTF | 877 | B*1402 | 54 | 1.49 | 80 | 24 | 107 | 141 |

TABLE 5a-continued

Predicted HLA class I-restricted CD8+ cytotoxic T cell epitopes contained in SLP sequences from HBV Core protein.

| | | | HLA class I binding peptides in SLP sequences derived from HBV Core protein | | | | | | Peptide of invention (SLP) | | |
|---|---|---|---|---|---|---|---|---|---|---|---|
| Start | End | Length | Sequence [A] | SEQ ID NO: | HLA class I molecule | Class I-B score[B] | C-score[C] | Class I-BCI score[D] | SLP# | SLP Start | SLP End |
| 132 | 139 | 8 | FHISCLTF | 877 | B*3503 | 40 | 1.49 | 59 | 24 | 107 | 141 |
| 132 | 139 | 8 | FHISCLTF | 877 | B*3801 | 100 | 1.49 | 149 | 24 | 107 | 141 |
| 132 | 139 | 8 | FHISCLTF | 877 | B*3901 | 57 | 1.49 | 85 | 24 | 107 | 141 |
| 131 | 141 | 11 | WFHISCLTFGR | 878 | A*3101 | 29 | 1.41 | 42 | 24 | 107 | 141 |
| 131 | 141 | 11 | WFHISCLTFGR | 878 | A*3303 | 52 | 1.41 | 74 | 24 | 107 | 141 |
| 132 | 141 | 10 | FHISCLTFGR | 879 | A*3101 | 35 | 1.41 | 50 | 24 | 107 | 141 |
| 133 | 141 | 9 | HISCLTFGR | 880 | A*3101 | 82 | 1.41 | 116 | 24 | 107 | 141 |
| 133 | 141 | 9 | HISCLTFGR | 880 | A*3303 | 95 | 1.41 | 135 | 24 | 107 | 141 |
| 133 | 141 | 9 | HISCLTFGR | 880 | A*6801 | 85 | 1.41 | 120 | 24 | 107 | 141 |
| 133 | 141 | 9 | HISCLTFGR | 880 | A*7401 | 100 | 1.41 | 141 | 24 | 107 | 141 |
| 134 | 141 | 8 | ISCLTFGR | 881 | A*3101 | 88 | 1.41 | 125 | 24 | 107 | 141 |
| 134 | 141 | 8 | ISCLTFGR | 881 | A*3303 | 29 | 1.41 | 40 | 24 | 107 | 141 |
| 134 | 141 | 8 | ISCLTFGR | 881 | A*6801 | 31 | 1.41 | 43 | 24 | 107 | 141 |
| 134 | 141 | 8 | ISCLTFGR | 881 | A*7401 | 50 | 1.41 | 71 | 24 | 107 | 141 |
| | | | | | Cumulative Class I-BCI score[E]: | | | 7277 | | | |
| 136 | 145 | 10 | CLTFGRETVL | 882 | B*0801 | 100 | 1.87 | 187 | 25 | 136 | 169 |
| 137 | 147 | 11 | LTFGRETVLEY | 883 | A*0101 | 80 | 1.68 | 134 | 25 | 136 | 169 |
| 137 | 147 | 11 | LTFGRETVLEY | 883 | A*0301 | 67 | 1.68 | 112 | 25 | 136 | 169 |
| 137 | 147 | 11 | LTFGRETVLEY | 883 | A*2501 | 80 | 1.68 | 134 | 25 | 136 | 169 |
| 137 | 147 | 11 | LTFGRETVLEY | 883 | A*2601 | 60 | 1.68 | 101 | 25 | 136 | 169 |
| 137 | 147 | 11 | LTFGRETVLEY | 883 | A*2902 | 100 | 1.68 | 168 | 25 | 136 | 169 |
| 137 | 147 | 11 | LTFGRETVLEY | 883 | A*3002 | 100 | 1.68 | 168 | 25 | 136 | 169 |
| 137 | 147 | 11 | LTFGRETVLEY | 883 | B*1501 | 90 | 1.68 | 151 | 25 | 136 | 169 |
| 137 | 147 | 11 | LTFGRETVLEY | 883 | B*1502 | 100 | 1.68 | 168 | 25 | 136 | 169 |
| 137 | 147 | 11 | LTFGRETVLEY | 883 | B*4601 | 67 | 1.68 | 112 | 25 | 136 | 169 |
| 137 | 147 | 11 | LTFGRETVLEY | 883 | B*5701 | 38 | 1.68 | 63 | 25 | 136 | 169 |
| 137 | 147 | 11 | LTFGRETVLEY | 883 | B*5802 | 36 | 1.68 | 61 | 25 | 136 | 169 |
| 139 | 147 | 9 | FGRETVLEY | 884 | B*1525 | 90 | 1.68 | 151 | 25 | 136 | 169 |
| 139 | 147 | 9 | FGRETVLEY | 884 | B*4601 | 100 | 1.68 | 168 | 25 | 136 | 169 |
| 138 | 148 | 11 | TFGRETVLEYL | 885 | A*2301 | 6 | 1.23 | 8 | 25 | 136 | 169 |
| 138 | 148 | 11 | TFGRETVLEYL | 885 | A*2402 | 31 | 1.23 | 38 | 25 | 136 | 169 |
| 139 | 148 | 10 | FGRETVLEYL | 886 | B*0702 | 100 | 1.23 | 123 | 25 | 136 | 169 |
| 140 | 148 | 9 | GRETVLEYL | 887 | B*2702 | 21 | 1.23 | 26 | 25 | 136 | 169 |
| 141 | 148 | 8 | RETVLEYL | 888 | B*1301 | 60 | 1.23 | 74 | 25 | 136 | 169 |
| 141 | 148 | 8 | RETVLEYL | 888 | B*3701 | 33 | 1.23 | 41 | 25 | 136 | 169 |
| 141 | 148 | 8 | RETVLEYL | 888 | B*4001 | 100 | 1.23 | 123 | 25 | 136 | 169 |

TABLE 5a-continued

Predicted HLA class I-restricted CD8+ cytotoxic T cell epitopes contained in SLP sequences from HBV Core protein.

| HLA class I binding peptides in SLP sequences derived from HBV Core protein | | | | | | | | | Peptide of invention (SLP) | | |
|---|---|---|---|---|---|---|---|---|---|---|---|
| Start | End | Length | Sequence [A] | SEQ ID NO: | HLA class I molecule | Class I-B score[B] | C-score[C] | Class I-BCI score[D] | SLP# | SLP Start | SLP End |
| 141 | 148 | 8 | RETVLEYL | 888 | B*4002 | 93 | 1.23 | 114 | 25 | 136 | 169 |
| 141 | 148 | 8 | RETVLEYL | 888 | B*4402 | 8 | 1.23 | 10 | 25 | 136 | 169 |
| 141 | 148 | 8 | RETVLEYL | 888 | B*4403 | 54 | 1.23 | 66 | 25 | 136 | 169 |
| 141 | 148 | 8 | RETVLEYL | 888 | B*4801 | 7 | 1.23 | 9 | 25 | 136 | 169 |
| 141 | 148 | 8 | RETVLEYL | 888 | B*4901 | 6 | 1.23 | 7 | 25 | 136 | 169 |
| 139 | 149 | 11 | FGRETVLEYLV | 889 | A*0201 | 45 | 1.23 | 55 | 25 | 136 | 169 |
| 141 | 149 | 9 | RETVLEYLV | 890 | B*1301 | 30 | 1.23 | 37 | 25 | 136 | 169 |
| 141 | 149 | 9 | RETVLEYLV | 890 | B*1302 | 38 | 1.23 | 46 | 25 | 136 | 169 |
| 141 | 149 | 9 | RETVLEYLV | 890 | B*3701 | 27 | 1.23 | 33 | 25 | 136 | 169 |
| 141 | 149 | 9 | RETVLEYLV | 890 | B*4001 | 67 | 1.23 | 82 | 25 | 136 | 169 |
| 141 | 149 | 9 | RETVLEYLV | 890 | B*4002 | 79 | 1.23 | 96 | 25 | 136 | 169 |
| 141 | 149 | 9 | RETVLEYLV | 890 | B*4901 | 71 | 1.23 | 87 | 25 | 136 | 169 |
| 141 | 149 | 9 | RETVLEYLV | 890 | B*5001 | 27 | 1.23 | 33 | 25 | 136 | 169 |
| 142 | 149 | 8 | ETVLEYLV | 891 | A*2501 | 20 | 1.23 | 25 | 25 | 136 | 169 |
| 142 | 149 | 8 | ETVLEYLV | 891 | A*2601 | 50 | 1.23 | 61 | 25 | 136 | 169 |
| 141 | 150 | 10 | RETVLEYLVS | 892 | B*4002 | 7 | 0.57 | 4 | 25 | 136 | 169 |
| 141 | 151 | 11 | RETVLEYLVSF | 893 | B*1301 | 45 | 1.50 | 67 | 25 | 136 | 169 |
| 141 | 151 | 11 | RETVLEYLVSF | 893 | B*1801 | 88 | 1.50 | 131 | 25 | 136 | 169 |
| 141 | 151 | 11 | RETVLEYLVSF | 893 | B*2702 | 50 | 1.50 | 75 | 25 | 136 | 169 |
| 141 | 151 | 11 | RETVLEYLVSF | 893 | B*4001 | 80 | 1.50 | 120 | 25 | 136 | 169 |
| 141 | 151 | 11 | RETVLEYLVSF | 893 | B*4002 | 86 | 1.50 | 128 | 25 | 136 | 169 |
| 141 | 151 | 11 | RETVLEYLVSF | 893 | B*4402 | 67 | 1.50 | 100 | 25 | 136 | 169 |
| 141 | 151 | 11 | RETVLEYLVSF | 893 | B*4403 | 77 | 1.50 | 115 | 25 | 136 | 169 |
| 141 | 151 | 11 | RETVLEYLVSF | 893 | B*4901 | 35 | 1.50 | 53 | 25 | 136 | 169 |
| 141 | 151 | 11 | RETVLEYLVSF | 893 | B*5001 | 60 | 1.50 | 90 | 25 | 136 | 169 |
| 142 | 151 | 10 | ETVLEYLVSF | 894 | A*2501 | 100 | 1.50 | 150 | 25 | 136 | 169 |
| 142 | 151 | 10 | ETVLEYLVSF | 894 | A*2601 | 100 | 1.50 | 150 | 25 | 136 | 169 |
| 143 | 151 | 9 | TVLEYLVSF | 895 | A*3201 | 50 | 1.50 | 75 | 25 | 136 | 169 |
| 143 | 151 | 9 | TVLEYLVSF | 895 | B*1525 | 20 | 1.50 | 30 | 25 | 136 | 169 |
| 145 | 152 | 8 | LEYLVSFG | 896 | B*4901 | 18 | 0.48 | 8 | 25 | 136 | 169 |
| 143 | 153 | 11 | TVLEYLVSFGV | 897 | A*0201 | 90 | 1.80 | 162 | 25 | 136 | 169 |
| 143 | 153 | 11 | TVLEYLVSFGV | 897 | A*6802 | 100 | 1.80 | 180 | 25 | 136 | 169 |
| 144 | 153 | 10 | VLEYLVSFGV | 898 | A*0201 | 65 | 1.80 | 117 | 25 | 136 | 169 |
| 145 | 153 | 9 | LEYLVSFGV | 899 | A*0201 | 67 | 1.80 | 120 | 25 | 136 | 169 |
| 145 | 153 | 9 | LEYLVSFGV | 899 | B*1301 | 75 | 1.80 | 135 | 25 | 136 | 169 |

TABLE 5a-continued

Predicted HLA class I-restricted CD8+ cytotoxic T cell epitopes contained in SLP sequences from HBV Core protein.

| | | | HLA class I binding peptides in SLP sequences derived from HBV Core protein | | | | | | Peptide of invention (SLP) | | |
|---|---|---|---|---|---|---|---|---|---|---|---|
| Start | End | Length | Sequence [A] | SEQ ID NO: | HLA class I molecule | Class I-B score [B] | C-score [C] | Class I-BCI score [D] | SLP# | SLP Start | SLP End |
| 145 | 153 | 9 | LEYLVSFGV | 899 | B*1801 | 63 | 1.80 | 113 | 25 | 136 | 169 |
| 145 | 153 | 9 | LEYLVSFGV | 899 | B*3701 | 67 | 1.80 | 120 | 25 | 136 | 169 |
| 145 | 153 | 9 | LEYLVSFGV | 899 | B*4001 | 73 | 1.80 | 132 | 25 | 136 | 169 |
| 145 | 153 | 9 | LEYLVSFGV | 899 | B*4002 | 29 | 1.80 | 51 | 25 | 136 | 169 |
| 145 | 153 | 9 | LEYLVSFGV | 899 | B*4402 | 42 | 1.80 | 75 | 25 | 136 | 169 |
| 145 | 153 | 9 | LEYLVSFGV | 899 | B*4901 | 94 | 1.80 | 170 | 25 | 136 | 169 |
| 145 | 153 | 9 | LEYLVSFGV | 899 | B*5001 | 87 | 1.80 | 156 | 25 | 136 | 169 |
| 145 | 153 | 9 | LEYLVSFGV | 899 | B*5201 | 56 | 1.80 | 100 | 25 | 136 | 169 |
| 145 | 154 | 10 | LEYLVSFGVW | 900 | B*1301 | 65 | 1.34 | 87 | 25 | 136 | 169 |
| 145 | 154 | 10 | LEYLVSFGVW | 900 | B*1302 | 13 | 1.34 | 17 | 25 | 136 | 169 |
| 145 | 154 | 10 | LEYLVSFGVW | 900 | B*3801 | 11 | 1.34 | 15 | 25 | 136 | 169 |
| 145 | 154 | 10 | LEYLVSFGVW | 900 | B*4402 | 92 | 1.34 | 123 | 25 | 136 | 169 |
| 145 | 154 | 10 | LEYLVSFGVW | 900 | B*4403 | 92 | 1.34 | 124 | 25 | 136 | 169 |
| 145 | 154 | 10 | LEYLVSFGVW | 900 | B*4901 | 88 | 1.34 | 118 | 25 | 136 | 169 |
| 145 | 154 | 10 | LEYLVSFGVW | 900 | B*5201 | 22 | 1.34 | 30 | 25 | 136 | 169 |
| 146 | 154 | 9 | EYLVSFGVW | 901 | A*2301 | 69 | 1.34 | 92 | 25 | 136 | 169 |
| 146 | 154 | 9 | EYLVSFGVW | 901 | A*2402 | 81 | 1.34 | 109 | 25 | 136 | 169 |
| 147 | 154 | 8 | YLVSFGVW | 902 | B*5701 | 13 | 1.34 | 17 | 25 | 136 | 169 |
| 147 | 154 | 8 | YLVSFGVW | 902 | B*5801 | 36 | 1.34 | 48 | 25 | 136 | 169 |
| 145 | 155 | 11 | LEYLVSFGVWI | 903 | B*1301 | 85 | 1.63 | 139 | 25 | 136 | 169 |
| 145 | 155 | 11 | LEYLVSFGVWI | 903 | B*1302 | 88 | 1.63 | 143 | 25 | 136 | 169 |
| 145 | 155 | 11 | LEYLVSFGVWI | 903 | B*1801 | 50 | 1.63 | 82 | 25 | 136 | 169 |
| 145 | 155 | 11 | LEYLVSFGVWI | 903 | B*3701 | 80 | 1.63 | 130 | 25 | 136 | 169 |
| 145 | 155 | 11 | LEYLVSFGVWI | 903 | B*3801 | 78 | 1.63 | 127 | 25 | 136 | 169 |
| 145 | 155 | 11 | LEYLVSFGVWI | 903 | B*4001 | 60 | 1.63 | 98 | 25 | 136 | 169 |
| 145 | 155 | 11 | LEYLVSFGVWI | 903 | B*4002 | 43 | 1.63 | 70 | 25 | 136 | 169 |
| 145 | 155 | 11 | LEYLVSFGVWI | 903 | B*4402 | 50 | 1.63 | 82 | 25 | 136 | 169 |
| 145 | 155 | 11 | LEYLVSFGVWI | 903 | B*4403 | 62 | 1.63 | 100 | 25 | 136 | 169 |
| 145 | 155 | 11 | LEYLVSFGVWI | 903 | B*4901 | 100 | 1.63 | 163 | 25 | 136 | 169 |
| 145 | 155 | 11 | LEYLVSFGVWI | 903 | B*5001 | 80 | 1.63 | 130 | 25 | 136 | 169 |
| 145 | 155 | 11 | LEYLVSFGVWI | 903 | B*5201 | 89 | 1.63 | 145 | 25 | 136 | 169 |
| 147 | 155 | 9 | YLVSFGVWI | 904 | A*0201 | 75 | 1.63 | 122 | 25 | 136 | 169 |
| 146 | 156 | 11 | EYLVSFGVWIR | 905 | A*3303 | 71 | 1.61 | 115 | 25 | 136 | 169 |
| 147 | 156 | 10 | YLVSFGVWIR | 906 | A*0301 | 100 | 1.61 | 161 | 25 | 136 | 169 |
| 147 | 156 | 10 | YLVSFGVWIR | 906 | A*6801 | 54 | 1.61 | 87 | 25 | 136 | 169 |

TABLE 5a-continued

Predicted HLA class I-restricted CD8+ cytotoxic T cell epitopes contained in SLP sequences from HBV Core protein.

| | | | HLA class I binding peptides in SLP sequences derived from HBV Core protein | | | | | | Peptide of invention (SLP) | | |
|---|---|---|---|---|---|---|---|---|---|---|---|
| Start | End | Length | Sequence [A] | SEQ ID NO: | HLA class I molecule | Class I-B score[B] | C-score[C] | Class I-BCI score[D] | SLP# | SLP Start | SLP End |
| 148 | 156 | 9 | LVSFGVWIR | 907 | A*3101 | 12 | 1.61 | 19 | 25 | 136 | 169 |
| 148 | 156 | 9 | LVSFGVWIR | 907 | A*3303 | 38 | 1.61 | 61 | 25 | 136 | 169 |
| 148 | 156 | 9 | LVSFGVWIR | 907 | A*6801 | 23 | 1.61 | 37 | 25 | 136 | 169 |
| 148 | 156 | 9 | LVSFGVWIR | 907 | A*7401 | 40 | 1.61 | 64 | 25 | 136 | 169 |
| 149 | 156 | 8 | VSFGVWIR | 908 | A*1101 | 13 | 1.61 | 20 | 25 | 136 | 169 |
| 149 | 156 | 8 | VSFGVWIR | 908 | A*3101 | 59 | 1.61 | 95 | 25 | 136 | 169 |
| 149 | 156 | 8 | VSFGVWIR | 908 | A*3303 | 48 | 1.61 | 77 | 25 | 136 | 169 |
| 149 | 156 | 8 | VSFGVWIR | 908 | A*6801 | 77 | 1.61 | 124 | 25 | 136 | 169 |
| 149 | 156 | 8 | VSFGVWIR | 908 | A*7401 | 80 | 1.61 | 129 | 25 | 136 | 169 |
| 148 | 157 | 10 | LVSFGVWIRT | 909 | A*3201 | 88 | 0.42 | 37 | 25 | 136 | 169 |
| 148 | 158 | 11 | LVSFGVWIRTP | 910 | A*6802 | 63 | 0.28 | 17 | 25 | 136 | 169 |
| 151 | 160 | 10 | FGVWIRTPPA | 911 | B*5501 | 55 | 0.99 | 54 | 25 | 136 | 169 |
| 151 | 160 | 10 | FGVWIRTPPA | 911 | B*5601 | 64 | 0.99 | 63 | 25 | 136 | 169 |
| 151 | 161 | 11 | FGVWIRTPPAY | 912 | A*2902 | 57 | 1.46 | 83 | 25 | 136 | 169 |
| 151 | 161 | 11 | FGVWIRTPPAY | 912 | B*1502 | 56 | 1.46 | 81 | 25 | 136 | 169 |
| 151 | 161 | 11 | FGVWIRTPPAY | 912 | B*3501 | 89 | 1.46 | 130 | 25 | 136 | 169 |
| 151 | 161 | 11 | FGVWIRTPPAY | 912 | B*4601 | 33 | 1.46 | 49 | 25 | 136 | 169 |
| 152 | 161 | 10 | GVWIRTPPAY | 913 | A*3001 | 67 | 1.46 | 97 | 25 | 136 | 169 |
| 152 | 161 | 10 | GVWIRTPPAY | 913 | B*1502 | 22 | 1.46 | 32 | 25 | 136 | 169 |
| 153 | 161 | 9 | VWIRTPPAY | 914 | A*2902 | 79 | 1.46 | 114 | 25 | 136 | 169 |
| 153 | 161 | 9 | VWIRTPPAY | 914 | A*3002 | 91 | 1.46 | 132 | 25 | 136 | 169 |
| 154 | 161 | 8 | WIRTPPAY | 915 | A*2601 | 30 | 1.46 | 44 | 25 | 136 | 169 |
| 154 | 161 | 8 | WIRTPPAY | 915 | A*2902 | 14 | 1.46 | 21 | 25 | 136 | 169 |
| 154 | 161 | 8 | WIRTPPAY | 915 | B*1501 | 70 | 1.46 | 102 | 25 | 136 | 169 |
| 154 | 161 | 8 | WIRTPPAY | 915 | B*1502 | 89 | 1.46 | 130 | 25 | 136 | 169 |
| 154 | 161 | 8 | WIRTPPAY | 915 | B*1525 | 50 | 1.46 | 73 | 25 | 136 | 169 |
| 152 | 162 | 11 | GVWIRTPPAYR | 916 | A*0301 | 33 | 0.95 | 32 | 25 | 136 | 169 |
| 152 | 162 | 11 | GVWIRTPPAYR | 916 | A*1101 | 38 | 0.95 | 36 | 25 | 136 | 169 |
| 152 | 162 | 11 | GVWIRTPPAYR | 916 | A*3101 | 100 | 0.95 | 95 | 25 | 136 | 169 |
| 152 | 162 | 11 | GVWIRTPPAYR | 916 | A*3303 | 76 | 0.95 | 72 | 25 | 136 | 169 |
| 152 | 162 | 11 | GVWIRTPPAYR | 916 | A*7401 | 90 | 0.95 | 86 | 25 | 136 | 169 |
| 153 | 162 | 10 | VWIRTPPAYR | 917 | A*3101 | 6 | 0.95 | 6 | 25 | 136 | 169 |
| 153 | 162 | 10 | VWIRTPPAYR | 917 | A*3303 | 33 | 0.95 | 32 | 25 | 136 | 169 |
| 154 | 162 | 9 | WIRTPPAYR | 918 | A*3303 | 90 | 0.95 | 86 | 25 | 136 | 169 |
| 154 | 162 | 9 | WIRTPPAYR | 918 | A*7401 | 70 | 0.95 | 67 | 25 | 136 | 169 |

TABLE 5a-continued

Predicted HLA class I-restricted CD8[+] cytotoxic T cell epitopes contained in SLP sequences from HBV Core protein.

| | | | HLA class I binding peptides in SLP sequences derived from HBV Core protein | | | | | | Peptide of invention (SLP) | | |
|---|---|---|---|---|---|---|---|---|---|---|---|
| Start | End | Length | Sequence[A] | SEQ ID NO: | HLA class I molecule | Class I-B score[B] | C-score[C] | Class I-BCI score[D] | SLP# | SLP Start | SLP End |
| 156 | 165 | 10 | RTPPAYRPPN | 919 | A*3001 | 83 | 0.09 | 7 | 25 | 136 | 169 |
| 158 | 168 | 11 | PPAYRPPNAPI | 920 | B*0702 | 17 | 1.00 | 17 | 25 | 136 | 169 |
| 160 | 168 | 9 | AYRPPNAPI | 921 | A*2402 | 25 | 1.00 | 25 | 25 | 136 | 169 |
| 160 | 168 | 9 | AYRPPNAPI | 921 | A*3001 | 42 | 1.00 | 41 | 25 | 136 | 169 |
| 160 | 169 | 10 | AYRPPNAPIL | 922 | A*2402 | 6 | 1.90 | 12 | 25 | 136 | 169 |
| 160 | 169 | 10 | AYRPPNAPIL | 922 | B*0702 | 50 | 1.90 | 95 | 25 | 136 | 169 |
| 161 | 169 | 9 | YRPPNAPIL | 923 | B*3901 | 36 | 1.90 | 68 | 25 | 136 | 169 |
| | | | | | Cumulative BCI Class I-score: | | | 11331 | | | |

"Start" and "End" are relative to the amino acid sequence of HBV core protein as depicted in SEQ ID NO: 4
[A] Peptide amino acid sequence. Each HLA class I binding peptide of HBV core protein is listed separately for each HLA class I molecule to which it is predicted to bind, and can be listed multiple times for that reason.
[B] Class I-B score. See Material and Methods of Examples section.
[C] C-score. See Material and Methods of Examples section.
[D] Class I-BCI score. See Material and Methods (Examples section).
[E] Cumulative Class I-BCI score. See Material and Methods (Examples section).

TABLE 5b

Predicted HLA class II-restricted CD4[+] T cell epitopes contained in SLP sequences from HBV Core protein.

| | | HLA class II binding peptides in SLP sequences derived from HBV Core protein | | | | Peptide of invention (SLP) | | |
|---|---|---|---|---|---|---|---|---|
| Start | End | Sequence[A] | SEQ ID NO: | HLA-DRB1 molecule | Class II-B score[B] | SLP# | SLP Start | SLP End |
| 107 | 121 | DPASRDLVVNYVNTN | 924 | *0301 | 46 | 24 | 107 | 141 |
| 108 | 122 | PASRDLVVNYVNTNV | 925 | *0401 | 69 | 24 | " | " |
| 108 | 122 | PASRDLVVNYVNTNV | " | *1301 | 10 | 24 | " | " |
| 109 | 123 | ASRDLVVNYVNTNVG | 926 | *0401 | 85 | 24 | " | " |
| 109 | 123 | ASRDLVVNYVNTNVG | " | *1301 | 20 | 24 | " | " |
| 110 | 124 | SRDLVVNYVNTNVGL | 927 | *0401 | 92 | 24 | " | " |
| 110 | 124 | SRDLVVNYVNTNVGL | " | *1301 | 40 | 24 | " | " |
| 111 | 125 | RDLVVNYVNTNVGLK | 928 | *0103 | 17 | 24 | " | " |
| 111 | 125 | RDLVVNYVNTNVGLK | " | *0401 | 100 | 24 | " | " |
| 111 | 125 | RDLVVNYVNTNVGLK | " | *1301 | 50 | 24 | " | " |
| 112 | 126 | DLVVNYVNTNVGLKI | 929 | *0103 | 50 | 24 | " | " |
| 112 | 126 | DLVVNYVNTNVGLKI | " | *0106 | 25 | 24 | " | " |
| 112 | 126 | DLVVNYVNTNVGLKI | " | *0301 | 62 | 24 | " | " |
| 112 | 126 | DLVVNYVNTNVGLKI | " | *0401 | 77 | 24 | " | " |
| 112 | 126 | DLVVNYVNTNVGLKI | " | *0701 | 15 | 24 | " | " |
| 112 | 126 | DLVVNYVNTNVGLKI | " | *1301 | 80 | 24 | " | " |

TABLE 5b-continued

Predicted HLA class II-restricted CD4+ T cell epitopes contained in SLP sequences from HBV Core protein.

| | | HLA class II binding peptides in SLP sequences derived from HBV Core protein | | | | Peptide of invention (SLP) | | |
|---|---|---|---|---|---|---|---|---|
| Start | End | Sequence[A] | SEQ ID NO: | HLA-DRB1 molecule | Class II-B score[B] | SLP# | SLP Start | SLP End |
| 113 | 127 | LVVNYVNTNVGLKIR | 930 | *0103 | 100 | 24 | " | " |
| 113 | 127 | LVVNYVNTNVGLKIR | " | *0104 | 35 | 24 | " | " |
| 113 | 127 | LVVNYVNTNVGLKIR | " | *0106 | 75 | 24 | " | " |
| 113 | 127 | LVVNYVNTNVGLKIR | " | *0301 | 69 | 24 | " | " |
| 113 | 127 | LVVNYVNTNVGLKIR | " | *0701 | 50 | 24 | " | " |
| 113 | 127 | LVVNYVNTNVGLKIR | " | *1301 | 100 | 24 | " | " |
| 114 | 128 | VVNYVNTNVGLKIRQ | 931 | *0103 | 83 | 24 | " | " |
| 114 | 128 | VVNYVNTNVGLKIRQ | " | *0104 | 45 | 24 | " | " |
| 114 | 128 | VVNYVNTNVGLKIRQ | " | *0106 | 80 | 24 | " | " |
| 114 | 128 | VVNYVNTNVGLKIRQ | " | *1301 | 90 | 24 | " | " |
| 115 | 129 | VNYVNTNVGLKIRQL | 932 | *0101 | 21 | 24 | " | " |
| 115 | 129 | VNYVNTNVGLKIRQL | " | *0102 | 10 | 24 | " | " |
| 115 | 129 | VNYVNTNVGLKIRQL | " | *0103 | 67 | 24 | " | " |
| 115 | 129 | VNYVNTNVGLKIRQL | " | *0104 | 65 | 24 | " | " |
| 115 | 129 | VNYVNTNVGLKIRQL | " | *0105 | 19 | 24 | " | " |
| 115 | 129 | VNYVNTNVGLKIRQL | " | *0106 | 85 | 24 | " | " |
| 115 | 129 | VNYVNTNVGLKIRQL | " | *0107 | 21 | 24 | " | " |
| 115 | 129 | VNYVNTNVGLKIRQL | " | *0701 | 33 | 24 | " | " |
| 115 | 129 | VNYVNTNVGLKIRQL | " | *1301 | 70 | 24 | " | " |
| 116 | 130 | NYVNTNVGLKIRQLL | 933 | *0103 | 33 | 24 | " | " |
| 116 | 130 | NYVNTNVGLKIRQLL | " | *0104 | 25 | 24 | " | " |
| 116 | 130 | NYVNTNVGLKIRQLL | " | *0106 | 65 | 24 | " | " |
| 116 | 130 | NYVNTNVGLKIRQLL | " | *1301 | 60 | 24 | " | " |
| 117 | 131 | YVNTNVGLKIRQLLW | 934 | *1101 | 54 | 24 | " | " |
| 117 | 131 | YVNTNVGLKIRQLLW | " | *1301 | 30 | 24 | " | " |
| 118 | 132 | VNTNVGLKIRQLLWF | 935 | *0301 | 38 | 24 | " | " |
| 118 | 132 | VNTNVGLKIRQLLWF | " | *1301 | 46 | 24 | " | " |
| 119 | 133 | NTNVGLKIRQLLWFH | 936 | *0301 | 31 | 24 | " | " |
| 119 | 133 | NTNVGLKIRQLLWFH | " | *1301 | 38 | 24 | " | " |
| 120 | 134 | TNVGLKIRQLLWFHI | 937 | *0102 | 70 | 24 | " | " |
| 120 | 134 | TNVGLKIRQLLWFHI | " | *0104 | 55 | 24 | " | " |
| 120 | 134 | TNVGLKIRQLLWFHI | " | *0106 | 40 | 24 | " | " |
| 120 | 134 | TNVGLKIRQLLWFHI | " | *0301 | 23 | 24 | " | " |
| 120 | 134 | TNVGLKIRQLLWFHI | " | *0701 | 38 | 24 | " | " |
| 120 | 134 | TNVGLKIRQLLWFHI | " | *1301 | 31 | 24 | " | " |

TABLE 5b-continued

Predicted HLA class II-restricted CD4+ T cell epitopes contained in SLP sequences from HBV Core protein.

| | | HLA class II binding peptides in SLP sequences derived from HBV Core protein | | | | Peptide of invention (SLP) | | |
|---|---|---|---|---|---|---|---|---|
| Start | End | Sequence[A] | SEQ ID NO: | HLA-DRB1 molecule | Class II-B score[B] | SLP# | SLP Start | SLP End |
| 120 | 134 | TNVGLKIRQLLWFHI | " | *1501 | 38 | 24 | " | " |
| 121 | 135 | NVGLKIRQLLWFHIS | 938 | *0101 | 11 | 24 | " | " |
| 121 | 135 | NVGLKIRQLLWFHIS | " | *0102 | 85 | 24 | " | " |
| 121 | 135 | NVGLKIRQLLWFHIS | " | *0104 | 75 | 24 | " | " |
| 121 | 135 | NVGLKIRQLLWFHIS | " | *0105 | 10 | 24 | " | " |
| 121 | 135 | NVGLKIRQLLWFHIS | " | *0106 | 50 | 24 | " | " |
| 121 | 135 | NVGLKIRQLLWFHIS | " | *0107 | 11 | 24 | " | " |
| 121 | 135 | NVGLKIRQLLWFHIS | " | *0301 | 15 | 24 | " | " |
| 121 | 135 | NVGLKIRQLLWFHIS | " | *0701 | 23 | 24 | " | " |
| 121 | 135 | NVGLKIRQLLWFHIS | " | *1301 | 23 | 24 | " | " |
| 121 | 135 | NVGLKIRQLLWFHIS | " | *1501 | 85 | 24 | " | " |
| 122 | 136 | VGLKIRQLLWFHISC | 939 | *0102 | 65 | 24 | " | " |
| 122 | 136 | VGLKIRQLLWFHISC | " | *0104 | 50 | 24 | " | " |
| 122 | 136 | VGLKIRQLLWFHISC | " | *0106 | 20 | 24 | " | " |
| 122 | 136 | VGLKIRQLLWFHISC | " | *0301 | 8 | 24 | " | " |
| 122 | 136 | VGLKIRQLLWFHISC | " | *1301 | 15 | 24 | " | " |
| 122 | 136 | VGLKIRQLLWFHISC | " | *1501 | 46 | 24 | " | " |
| 123 | 137 | GLKIRQLLWFHISCL | 940 | *0101 | 31 | 24 | " | " |
| 123 | 137 | GLKIRQLLWFHISCL | " | *0102 | 75 | 24 | " | " |
| 123 | 137 | GLKIRQLLWFHISCL | " | *0104 | 80 | 24 | " | " |
| 123 | 137 | GLKIRQLLWFHISCL | " | *0106 | 55 | 24 | " | " |
| 123 | 137 | GLKIRQLLWFHISCL | " | *0701 | 100 | 24 | " | " |
| 123 | 137 | GLKIRQLLWFHISCL | " | *1301 | 8 | 24 | " | " |
| 123 | 137 | GLKIRQLLWFHISCL | " | *1501 | 100 | 24 | " | " |
| 124 | 138 | LKIRQLLWFHISCLT | 941 | *0101 | 26 | 24 | " | " |
| 124 | 138 | LKIRQLLWFHISCLT | " | *0102 | 80 | 24 | " | " |
| 124 | 138 | LKIRQLLWFHISCLT | " | *0104 | 70 | 24 | " | " |
| 124 | 138 | LKIRQLLWFHISCLT | " | *0105 | 24 | 24 | " | " |
| 124 | 138 | LKIRQLLWFHISCLT | " | *0106 | 60 | 24 | " | " |
| 124 | 138 | LKIRQLLWFHISCLT | " | *0107 | 26 | 24 | " | " |
| 124 | 138 | LKIRQLLWFHISCLT | " | *0701 | 92 | 24 | " | " |
| 124 | 138 | LKIRQLLWFHISCLT | " | *1501 | 92 | 24 | " | " |
| 125 | 139 | KIRQLLWFHISCLTF | 942 | *0101 | 5 | 24 | " | " |
| 125 | 139 | KIRQLLWFHISCLTF | " | *0102 | 50 | 24 | " | " |
| 125 | 139 | KIRQLLWFHISCLTF | " | *0104 | 40 | 24 | " | " |

TABLE 5b-continued

Predicted HLA class II-restricted CD4+ T cell epitopes contained in SLP sequences from HBV Core protein.

| | | HLA class II binding peptides in SLP sequences derived from HBV Core protein | | | | Peptide of invention (SLP) | | |
|---|---|---|---|---|---|---|---|---|
| Start | End | Sequence[A] | SEQ ID NO: | HLA-DRB1 molecule | Class II-B score[B] | SLP# | SLP Start | SLP End |
| 125 | 139 | KIRQLLWFHISCLTF | " | *0105 | 5 | 24 | " | " |
| 125 | 139 | KIRQLLWFHISCLTF | " | *0106 | 35 | 24 | " | " |
| 125 | 139 | KIRQLLWFHISCLTF | " | *0107 | 5 | 24 | " | " |
| 125 | 139 | KIRQLLWFHISCLTF | " | *0701 | 85 | 24 | " | " |
| 125 | 139 | KIRQLLWFHISCLTF | " | *1501 | 31 | 24 | " | " |
| 126 | 140 | IRQLLWFHISCLTFG | 943 | *0102 | 40 | 24 | " | " |
| 126 | 140 | IRQLLWFHISCLTFG | " | *0701 | 46 | 24 | " | " |
| 126 | 140 | IRQLLWFHISCLTFG | " | *1101 | 69 | 24 | " | " |
| 127 | 141 | RQLLWFHISCLTFGR | 944 | *0701 | 8 | 24 | " | " |
| 127 | 141 | RQLLWFHISCLTFGR | " | *1101 | 46 | 24 | " | " |
| | | Cumulative Class II-B score[C]: | | | 4649 | | | |
| 139 | 153 | FGRETVLEYLVSFGV | 945 | *0101 | 42 | 25 | 136 | 169 |
| 139 | 153 | FGRETVLEYLVSFGV | " | *0102 | 35 | 25 | " | " |
| 139 | 153 | FGRETVLEYLVSFGV | " | *0105 | 38 | 25 | " | " |
| 139 | 153 | FGRETVLEYLVSFGV | " | *0107 | 42 | 25 | " | " |
| 139 | 153 | FGRETVLEYLVSFGV | " | *0701 | 69 | 25 | " | " |
| 139 | 153 | FGRETVLEYLVSFGV | " | *1501 | 23 | 25 | " | " |
| 140 | 154 | GRETVLEYLVSFGVW | 946 | *0101 | 46 | 25 | " | " |
| 140 | 154 | GRETVLEYLVSFGVW | " | *0102 | 55 | 25 | " | " |
| 140 | 154 | GRETVLEYLVSFGVW | " | *0104 | 60 | 25 | " | " |
| 140 | 154 | GRETVLEYLVSFGVW | " | *0105 | 67 | 25 | " | " |
| 140 | 154 | GRETVLEYLVSFGVW | " | *0106 | 45 | 25 | " | " |
| 140 | 154 | GRETVLEYLVSFGVW | " | *0107 | 74 | 25 | " | " |
| 140 | 154 | GRETVLEYLVSFGVW | " | *0701 | 62 | 25 | " | " |
| 140 | 154 | GRETVLEYLVSFGVW | " | *1501 | 15 | 25 | " | " |
| 141 | 155 | RETVLEYLVSFGVWI | 947 | *0101 | 92 | 25 | " | " |
| 141 | 155 | RETVLEYLVSFGVWI | " | *0102 | 95 | 25 | " | " |
| 141 | 155 | RETVLEYLVSFGVWI | " | *0104 | 90 | 25 | " | " |
| 141 | 155 | RETVLEYLVSFGVWI | " | *0105 | 81 | 25 | " | " |
| 141 | 155 | RETVLEYLVSFGVWI | " | *0106 | 90 | 25 | " | " |
| 141 | 155 | RETVLEYLVSFGVWI | " | *0107 | 89 | 25 | " | " |
| 141 | 155 | RETVLEYLVSFGVWI | " | *0701 | 77 | 25 | " | " |
| 141 | 155 | RETVLEYLVSFGVWI | " | *1501 | 8 | 25 | " | " |
| 142 | 156 | ETVLEYLVSFGVWIR | 948 | *0101 | 100 | 25 | " | " |
| 142 | 156 | ETVLEYLVSFGVWIR | " | *0102 | 100 | 25 | " | " |

TABLE 5b-continued

Predicted HLA class II-restricted CD4+ T cell epitopes contained in SLP sequences from HBV Core protein.

| | | HLA class II binding peptides in SLP sequences derived from HBV Core protein | | | | Peptide of invention (SLP) | | |
|---|---|---|---|---|---|---|---|---|
| Start | End | Sequence[A] | SEQ ID NO: | HLA-DRB1 molecule | Class II-B score[B] | SLP# | SLP Start | SLP End |
| 142 | 156 | ETVLEYLVSFGVWIR | " | *0104 | 100 | 25 | " | " |
| 142 | 156 | ETVLEYLVSFGVWIR | " | *0105 | 90 | 25 | " | " |
| 142 | 156 | ETVLEYLVSFGVWIR | " | *0106 | 100 | 25 | " | " |
| 142 | 156 | ETVLEYLVSFGVWIR | " | *0107 | 100 | 25 | " | " |
| 142 | 156 | ETVLEYLVSFGVWIR | " | *0701 | 54 | 25 | " | " |
| 142 | 156 | ETVLEYLVSFGVWIR | " | *1301 | 100 | 25 | " | " |
| 142 | 156 | ETVLEYLVSFGVWIR | " | *1501 | 77 | 25 | " | " |
| 143 | 157 | TVLEYLVSFGVWIRT | 949 | *0101 | 85 | 25 | " | " |
| 143 | 157 | TVLEYLVSFGVWIRT | " | *0102 | 90 | 25 | " | " |
| 143 | 157 | TVLEYLVSFGVWIRT | " | *0104 | 95 | 25 | " | " |
| 143 | 157 | TVLEYLVSFGVWIRT | " | *0105 | 86 | 25 | " | " |
| 143 | 157 | TVLEYLVSFGVWIRT | " | *0106 | 95 | 25 | " | " |
| 143 | 157 | TVLEYLVSFGVWIRT | " | *0107 | 95 | 25 | " | " |
| 143 | 157 | TVLEYLVSFGVWIRT | " | *0701 | 31 | 25 | " | " |
| 143 | 157 | TVLEYLVSFGVWIRT | " | *1301 | 92 | 25 | " | " |
| 143 | 157 | TVLEYLVSFGVWIRT | " | *1501 | 69 | 25 | " | " |
| 144 | 158 | VLEYLVSFGVWIRTP | 950 | *0101 | 69 | 25 | " | " |
| 144 | 158 | VLEYLVSFGVWIRTP | " | *0102 | 60 | 25 | " | " |
| 144 | 158 | VLEYLVSFGVWIRTP | " | *0104 | 85 | 25 | " | " |
| 144 | 158 | VLEYLVSFGVWIRTP | " | *0105 | 76 | 25 | " | " |
| 144 | 158 | VLEYLVSFGVWIRTP | " | *0106 | 70 | 25 | " | " |
| 144 | 158 | VLEYLVSFGVWIRTP | " | *0107 | 84 | 25 | " | " |
| 144 | 158 | VLEYLVSFGVWIRTP | " | *1301 | 85 | 25 | " | " |
| 144 | 158 | VLEYLVSFGVWIRTP | " | *1501 | 62 | 25 | " | " |
| 145 | 159 | LEYLVSFGVWIRTPP | 951 | *0101 | 62 | 25 | " | " |
| 145 | 159 | LEYLVSFGVWIRTPP | " | *0102 | 15 | 25 | " | " |
| 145 | 159 | LEYLVSFGVWIRTPP | " | *0104 | 20 | 25 | " | " |
| 145 | 159 | LEYLVSFGVWIRTPP | " | *0105 | 48 | 25 | " | " |
| 145 | 159 | LEYLVSFGVWIRTPP | " | *0107 | 53 | 25 | " | " |
| 145 | 159 | LEYLVSFGVWIRTPP | " | *1301 | 77 | 25 | " | " |
| 145 | 159 | LEYLVSFGVWIRTPP | " | *1501 | 54 | 25 | " | " |
| 146 | 160 | EYLVSFGVWIRTPPA | 952 | *1301 | 69 | 25 | " | " |
| 147 | 161 | YLVSFGVWIRTPPAY | 953 | *1301 | 62 | 25 | " | " |
| 148 | 162 | LVSFGVWIRTPPAYR | 954 | *0101 | 32 | 25 | " | " |
| 148 | 162 | LVSFGVWIRTPPAYR | " | *0105 | 29 | 25 | " | " |

TABLE 5b-continued

Predicted HLA class II-restricted CD4+ T cell epitopes contained in SLP sequences from H TABLE 6a Predicted HLA class I-restricted CD8+ cytotoxic T cell epitopes
contained in SLP sequences from HBV X protein (consensus sequence).

| | | | HLA class I binding peptides in SLP sequences derived from HBV X protein (consensus sequence) | | | | | | Peptide of invention (SLP) | | |
|---|---|---|---|---|---|---|---|---|---|---|---|
| Start | End | Length | Sequence[A] | SEQ ID NO: | HLA class I molecule | Class I-B score[B] | C-score[C] | Class I-BCI score[D] | SLP# | SLP Start | SLP End |
| 36 | 44 | 9 | ALPSPSPSA | 959 | A*0201 | 20 | 0,97 | 19 | 26 | 36 | 68 |
| 37 | 44 | 8 | LPSPSPSA | 960 | B*3501 | 92 | " | 89 | 26 | " | " |
| 37 | 44 | 8 | LPSPSPSA | " | B*5101 | 82 | " | 79 | 26 | " | " |
| 37 | 44 | 8 | LPSPSPSA | " | B*5501 | 63 | " | 61 | 26 | " | " |
| 37 | 44 | 8 | LPSPSPSA | " | B*5601 | 92 | " | 89 | 26 | " | " |
| 36 | 45 | 10 | ALPSPSPSAV | 961 | A*0201 | 90 | 1,49 | 134 | 26 | " | " |
| 37 | 45 | 9 | LPSPSPSAV | 962 | B*3503 | 75 | " | 112 | 26 | " | " |
| 37 | 45 | 9 | LPSPSPSAV | " | B*5101 | 100 | " | 149 | 26 | " | " |
| 37 | 45 | 9 | LPSPSPSAV | " | B*5501 | 94 | " | 139 | 26 | " | " |
| 37 | 45 | 9 | LPSPSPSAV | " | B*5601 | 46 | " | 69 | 26 | " | " |
| 37 | 45 | 9 | LPSPSPSAV | " | B*0701 | 50 | " | 74 | 26 | " | " |
| 37 | 47 | 11 | LPSPSPSAVPA | 963 | A*6802 | 20 | 1,05 | 21 | 26 | " | " |
| 37 | 47 | 11 | LPSPSPSAVPA | " | B*3501 | 33 | " | 35 | 26 | " | " |
| 37 | 47 | 11 | LPSPSPSAVPA | " | B*3503 | 58 | " | 61 | 26 | " | " |
| 37 | 47 | 11 | LPSPSPSAVPA | " | B*5101 | 55 | " | 57 | 26 | " | " |
| 37 | 47 | 11 | LPSPSPSAVPA | " | B*5501 | 88 | " | 92 | 26 | " | " |
| 37 | 47 | 11 | LPSPSPSAVPA | " | B*5601 | 77 | " | 81 | 26 | " | " |
| 37 | 47 | 11 | LPSPSPSAVPA | " | B*0701 | 25 | " | 26 | 26 | " | " |
| 39 | 47 | 9 | SPSPSAVPA | 964 | B*5501 | 56 | " | 59 | 26 | " | " |
| 39 | 47 | 9 | SPSPSAVPA | " | B*5601 | 85 | " | 89 | 26 | " | " |
| 41 | 51 | 11 | SPSAVPADHGA | 965 | B*5501 | 6 | 1,30 | 8 | 26 | " | " |
| 41 | 51 | 11 | SPSAVPADHGA | " | B*5601 | 8 | " | 10 | 26 | " | " |
| 44 | 53 | 10 | AVPADHGAHL | 966 | B*0701 | 75 | 1,87 | 140 | 26 | " | " |
| 45 | 53 | 9 | VPADHGAHL | 967 | B*1402 | 43 | " | 80 | 26 | " | " |
| 45 | 53 | 9 | VPADHGAHL | " | B*3503 | 42 | " | 78 | 26 | " | " |
| 45 | 53 | 9 | VPADHGAHL | " | B*5501 | 31 | " | 59 | 26 | " | " |
| 45 | 53 | 9 | VPADHGAHL | " | B*0701 | 100 | " | 187 | 26 | " | " |
| 45 | 55 | 11 | VPADHGAHLSL | 968 | B*1402 | 93 | 1,93 | 180 | 26 | " | " |
| 45 | 55 | 11 | VPADHGAHLSL | " | B*3501 | 67 | " | 129 | 26 | " | " |
| 45 | 55 | 11 | VPADHGAHLSL | " | B*3503 | 100 | " | 193 | 26 | " | " |
| 45 | 55 | 11 | VPADHGAHLSL | " | B*5101 | 73 | " | 141 | 26 | " | " |
| 45 | 55 | 11 | VPADHGAHLSL | " | B*5301 | 29 | " | 55 | 26 | " | " |
| 45 | 55 | 11 | VPADHGAHLSL | " | B*5501 | 50 | " | 97 | 26 | " | " |
| 45 | 55 | 11 | VPADHGAHLSL | " | B*0701 | 100 | " | 193 | 26 | " | " |
| 47 | 55 | 9 | ADHGAHLSL | 969 | B*4002 | 14 | " | 28 | 26 | " | " |

TABLE 6a-continued

Predicted HLA class I-restricted CD8⁺ cytotoxic T cell epitopes
contained in SLP sequences from HBV X protein (consensus sequence).

| | HLA class I binding peptides in SLP sequences derived from HBV X protein (consensus sequence) | | | | | | | | Peptide of invention (SLP) | | |
|---|---|---|---|---|---|---|---|---|---|---|---|
| Start | End | Length | Sequence[A] | SEQ ID NO: | HLA class I molecule | Class I-B score[B] | C-score[C] | Class I-BCI score[D] | SLP# | SLP Start | SLP End |
| 48 | 55 | 8 | DHGAHLSL | 970 | B*1402 | 79 | " | 152 | 26 | " | " |
| 49 | 56 | 8 | HGAHLSLR | 971 | A*3303 | 73 | 0,63 | 46 | 26 | " | " |
| 49 | 56 | 8 | HGAHLSLR | " | A*6801 | 33 | " | 21 | 26 | " | " |
| 50 | 58 | 9 | GAHLSLRGL | 972 | B*0701 | 25 | 1,33 | 33 | 26 | " | " |
| 51 | 58 | 8 | AHLSLRGL | 973 | B*1402 | 29 | " | 38 | 26 | " | " |
| 51 | 58 | 8 | AHLSLRGL | " | B*3901 | 9 | " | 12 | 26 | " | " |
| 51 | 60 | 10 | AHLSLRGLPV | 974 | B*1402 | 71 | 1,05 | 75 | 26 | " | " |
| 51 | 60 | 10 | AHLSLRGLPV | " | B*3901 | 36 | " | 38 | 26 | " | " |
| 52 | 60 | 9 | HLSLRGLPV | 975 | B*0801 | 40 | " | 42 | 26 | " | " |
| 53 | 60 | 8 | LSLRGLPV | 976 | A*0201 | 36 | " | 38 | 26 | " | " |
| 53 | 60 | 8 | LSLRGLPV | " | B*5201 | 33 | " | 35 | 26 | " | " |
| 52 | 61 | 10 | HLSLRGLPVC | 977 | A*3001 | 88 | 0,87 | 77 | 26 | " | " |
| 53 | 61 | 9 | LSLRGLPVC | 978 | B*5802 | 10 | " | 9 | 26 | " | " |
| 53 | 63 | 11 | LSLRGLPVCAF | 979 | B*1502 | 71 | 1,48 | 106 | 26 | " | " |
| 53 | 63 | 11 | LSLRGLPVCAF | " | B*1525 | 85 | " | 125 | 26 | " | " |
| 53 | 63 | 11 | LSLRGLPVCAF | " | B*4601 | 50 | " | 74 | 26 | " | " |
| 53 | 63 | 11 | LSLRGLPVCAF | " | B*5701 | 100 | " | 148 | 26 | " | " |
| 53 | 63 | 11 | LSLRGLPVCAF | " | B*5801 | 90 | " | 133 | 26 | " | " |
| 53 | 63 | 11 | LSLRGLPVCAF | " | B*5802 | 30 | " | 44 | 26 | " | " |
| 54 | 63 | 10 | SLRGlPVCAF | 980 | A*0301 | 100 | " | 148 | 26 | " | " |
| 54 | 63 | 10 | SLRGLPVCAF | 981 | B*1501 | 86 | " | 127 | 26 | " | " |
| 54 | 63 | 10 | SLRGLPVCAF | " | B*1502 | 86 | " | 127 | 26 | " | " |
| 54 | 63 | 10 | SLRGLPVCAF | " | B*1525 | 54 | " | 80 | 26 | " | " |
| 54 | 63 | 10 | SLRGLPVCAF | " | B*4601 | 36 | " | 53 | 26 | " | " |
| 56 | 63 | 8 | RGLPVCAF | 982 | A*2301 | 25 | " | 37 | 26 | " | " |
| 56 | 63 | 8 | RGLPVCAF | " | A*3201 | 20 | " | 30 | 26 | " | " |
| 58 | 65 | 8 | LPVCAFSS | 983 | B*5101 | 45 | 0,59 | 27 | 26 | " | " |
| 58 | 65 | 8 | LPVCAFSS | " | B*5501 | 13 | " | 7 | 26 | " | " |
| 58 | 65 | 8 | LPVCAFSS | " | B*5601 | 31 | " | 18 | 26 | " | " |
| 56 | 66 | 11 | RGLPVCAFSSA | 984 | A*3001 | 29 | 0,95 | 28 | 26 | " | " |
| 57 | 66 | 10 | GLPVCAFSSA | 985 | A*0201 | 20 | " | 19 | 26 | " | " |
| 58 | 66 | 9 | LPVCAFSSA | 986 | B*3503 | 83 | " | 79 | 26 | " | " |
| 58 | 66 | 9 | LPVCAFSSA | " | B*5101 | 91 | " | 86 | 26 | " | " |
| 58 | 66 | 9 | LPVCAFSSA | " | B*5501 | 100 | " | 95 | 26 | " | " |
| 58 | 66 | 9 | LPVCAFSSA | " | B*5601 | 100 | " | 95 | 26 | " | " |

TABLE 6a-continued

Predicted HLA class I-restricted CD8+ cytotoxic T cell epitopes
contained in SLP sequences from HBV X protein (consensus sequence).

| | HLA class I binding peptides in SLP sequences derived from HBV X protein (consensus sequence) | | | | | | | | Peptide of invention (SLP) | | |
|---|---|---|---|---|---|---|---|---|---|---|---|
| Start | End | Length | Sequence[A] | SEQ ID NO: | HLA class I molecule | Class I-B score[B] | C-score[C] | Class I-BCI score[D] | SLP# | SLP Start | SLP End |
| 58 | 67 | 10 | LPVCAFSSAG | 987 | B*3501 | 58 | 0,11 | 6 | 26 | " | " |
| 58 | 67 | 10 | LPVCAFSSAG | " | B*3503 | 8 | " | 1 | 26 | " | " |
| 58 | 67 | 10 | LPVCAFSSAG | " | B*5501 | 19 | " | 2 | 26 | " | " |
| | | | | | Cumulative Class I-BCI score[E]: | | | 5422 | | | |
| 61 | 70 | 10 | CAFSSAGPCA | 988 | A*3001 | 76 | 0,45 | 35 | 27 | 61 | 95 |
| 61 | 71 | 11 | CAFSSAGPCAL | 989 | B*1402 | 57 | 1,74 | 99 | 27 | " | " |
| 61 | 71 | 11 | CAFSSAGPCAL | " | B*3901 | 64 | " | 111 | 27 | " | " |
| 61 | 71 | 11 | CAFSSAGPCAL | " | B*4801 | 57 | " | 99 | 27 | " | " |
| 63 | 71 | 9 | FSSAGPCAL | 990 | B*3901 | 100 | " | 174 | 27 | " | " |
| 63 | 71 | 9 | FSSAGPCAL | " | B*4601 | 71 | " | 124 | 27 | " | " |
| 62 | 72 | 11 | AFSSAGPCALR | 991 | A*3101 | 40 | 1,24 | 50 | 27 | " | " |
| 63 | 72 | 10 | FSSAGPCALR | 992 | A*3303 | 60 | " | 74 | 27 | " | " |
| 63 | 72 | 10 | FSSAGPCALR | " | A*6801 | 100 | " | 124 | 27 | " | " |
| 64 | 72 | 9 | SSAGPCALR | 993 | A*3303 | 87 | " | 107 | 27 | " | " |
| 64 | 72 | 9 | SSAGPCALR | " | A*6801 | 56 | " | 69 | 27 | " | " |
| 63 | 73 | 11 | FSSAGPCALRF | 994 | A*0101 | 38 | 1,58 | 59 | 27 | " | " |
| 63 | 73 | 11 | FSSAGPCALRF | " | B*1501 | 14 | " | 23 | 27 | " | " |
| 63 | 73 | 11 | FSSAGPCALRF | " | B*1502 | 43 | " | 68 | 27 | " | " |
| 63 | 73 | 11 | FSSAGPCALRF | " | B*1525 | 15 | " | 24 | 27 | " | " |
| 63 | 73 | 11 | FSSAGPCALRF | " | B*3501 | 50 | " | 79 | 27 | " | " |
| 63 | 73 | 11 | FSSAGPCALRF | " | B*4601 | 86 | " | 136 | 27 | " | " |
| 63 | 73 | 11 | FSSAGPCALRF | " | B*5301 | 86 | " | 136 | 27 | " | " |
| 63 | 73 | 11 | FSSAGPCALRF | " | B*5701 | 67 | " | 105 | 27 | " | " |
| 63 | 73 | 11 | FSSAGPCALRF | " | B*5801 | 100 | " | 158 | 27 | " | " |
| 63 | 73 | 11 | FSSAGPCALRF | " | B*5802 | 50 | " | 79 | 27 | " | " |
| 64 | 73 | 10 | SSAGPCALRF | 995 | B*5802 | 20 | " | 32 | 27 | " | " |
| 65 | 73 | 9 | SAGPCALRF | 996 | A*0101 | 25 | " | 40 | 27 | " | " |
| 65 | 73 | 9 | SAGPCALRF | " | B*5701 | 17 | " | 26 | 27 | " | " |
| 69 | 77 | 9 | CALRFTSAR | 997 | A*3101 | 30 | 1,06 | 32 | 27 | " | " |
| 69 | 77 | 9 | CALRFTSAR | " | A*3303 | 100 | " | 106 | 27 | " | " |
| 69 | 77 | 9 | CALRFTSAR | " | A*6801 | 11 | " | 12 | 27 | " | " |
| 69 | 77 | 9 | CALRFTSAR | " | A*7401 | 100 | " | 106 | 27 | " | " |
| 70 | 77 | 8 | ALRFTSAR | 998 | A*3001 | 18 | " | 19 | 27 | " | " |
| 70 | 77 | 8 | ALRFTSAR | " | A*3101 | 70 | " | 74 | 27 | " | " |
| 70 | 77 | 8 | ALRFTSAR | " | A*3303 | 53 | " | 56 | 27 | " | " |

TABLE 6a-continued

Predicted HLA class I-restricted CD8+ cytotoxic T cell epitopes
contained in SLP sequences from HBV X protein (consensus sequence).

| | | | HLA class I binding peptides in SLP sequences derived from HBV X protein (consensus sequence) | | | | | | Peptide of invention (SLP) | | |
|---|---|---|---|---|---|---|---|---|---|---|---|
| Start | End | Length | Sequence[A] | SEQ ID NO: | HLA class I molecule | Class I-B score[B] | C-score[C] | Class I-BCI score[D] | SLP# | SLP Start | SLP End |
| 70 | 77 | 8 | ALRFTSAR | " | A*7401 | 90 | " | 95 | 27 | " | " |
| 70 | 77 | 8 | ALRFTSAR | " | A*0301 | 81 | " | 86 | 27 | " | " |
| 69 | 78 | 10 | CALRFTSARR | 999 | A*3101 | 90 | 1,59 | 143 | 27 | " | " |
| 69 | 78 | 10 | CALRFTSARR | " | A*3303 | 93 | " | 148 | 27 | " | " |
| 69 | 78 | 10 | CALRFTSARR | " | A*7401 | 60 | " | 95 | 27 | " | " |
| 70 | 78 | 9 | ALRFTSARR | 1000 | A*3101 | 20 | " | 32 | 27 | " | " |
| 70 | 78 | 9 | ALRFTSARR | " | A*3303 | 7 | " | 11 | 27 | " | " |
| 70 | 78 | 9 | ALRFTSARR | " | A*7401 | 80 | " | 127 | 27 | " | " |
| 70 | 78 | 9 | ALRFTSARR | " | A*0301 | 50 | " | 80 | 27 | " | " |
| 71 | 78 | 8 | LRFTSARR | 1001 | B*2705 | 10 | " | 16 | 27 | " | " |
| 70 | 79 | 10 | ALRFTSARRM | 1002 | B*0701 | 50 | 1,80 | 90 | 27 | " | " |
| 70 | 79 | 10 | ALRFTSARRM | " | B*0801 | 67 | " | 120 | 27 | " | " |
| 71 | 79 | 9 | LRFTSARRM | 1003 | B*1402 | 7 | " | 13 | 27 | " | " |
| 71 | 79 | 9 | LRFTSARRM | " | B*2702 | 75 | " | 135 | 27 | " | " |
| 71 | 79 | 9 | LRFTSARRM | " | B*2705 | 60 | " | 108 | 27 | " | " |
| 77 | 84 | 8 | RRMETTVN | 1004 | B*2702 | 38 | 0,84 | 31 | 27 | " | " |
| 75 | 85 | 11 | SARRMETTVNA | 1005 | A*3001 | 6 | 1,44 | 8 | 27 | " | " |
| 77 | 85 | 9 | RRMETTVNA | 1006 | B*2702 | 50 | " | 72 | 27 | " | " |
| 77 | 85 | 9 | RRMETTVNA | " | B*2705 | 40 | " | 58 | 27 | " | " |
| 77 | 86 | 10 | RRMETTVNAH | 1007 | B*2702 | 63 | 0,74 | 46 | 27 | " | " |
| 79 | 86 | 8 | METTVNAH | 1008 | A*6802 | 60 | " | 44 | 27 | " | " |
| 79 | 86 | 8 | METTVNAH | " | B*1801 | 67 | " | 49 | 27 | " | " |
| 79 | 86 | 8 | METTVNAH | " | B*4403 | 33 | " | 25 | 27 | " | " |
| 77 | 87 | 11 | RRMETTVNAHQ | 1009 | B*2702 | 25 | 0,30 | 7 | 27 | " | " |
| 79 | 87 | 9 | METTVNAHQ | 1010 | B*4403 | 44 | " | 13 | 27 | " | " |
| 78 | 88 | 11 | RMETTVNAHQI | 1011 | A*3201 | 40 | 0,68 | 27 | 27 | " | " |
| 79 | 88 | 10 | METTVNAHQI | 1012 | B*1301 | 100 | " | 68 | 27 | " | " |
| 79 | 88 | 10 | METTVNAHQI | " | B*1302 | 67 | " | 45 | 27 | " | " |
| 79 | 88 | 10 | METTVNAHQI | " | B*1801 | 33 | " | 23 | 27 | " | " |
| 79 | 88 | 10 | METTVNAHQI | " | B*3701 | 100 | " | 68 | 27 | " | " |
| 79 | 88 | 10 | METTVNAHQI | " | B*3801 | 100 | " | 68 | 27 | " | " |
| 79 | 88 | 10 | METTVNAHQI | " | B*4901 | 100 | " | 68 | 27 | " | " |
| 79 | 88 | 10 | METTVNAHQI | " | B*5001 | 100 | " | 68 | 27 | " | " |
| 79 | 88 | 10 | METTVNAHQI | " | B*5201 | 100 | " | 68 | 27 | " | " |
| 80 | 88 | 9 | ETTVNAHQI | 1013 | A*6802 | 40 | " | 27 | 27 | " | " |

TABLE 6a-continued

Predicted HLA class I-restricted CD8+ cytotoxic T cell epitopes
contained in SLP sequences from HBV X protein (consensus sequence).

| | | | HLA class I binding peptides in SLP sequences derived from HBV X protein (consensus sequence) | | | | | | Peptide of invention (SLP) | | |
|---|---|---|---|---|---|---|---|---|---|---|---|
| Start | End | Length | Sequence[A] | SEQ ID NO: | HLA class I molecule | Class I-B score[B] | C-score[C] | Class I-BCI score[D] | SLP# | SLP Start | SLP End |
| 79 | 89 | 11 | METTVNAHQIL | 1014 | B*1301 | 75 | 0,67 | 50 | 27 | " | " |
| 79 | 89 | 11 | METTVNAHQIL | " | B*1801 | 100 | " | 67 | 27 | " | " |
| 79 | 89 | 11 | METTVNAHQIL | " | B*3701 | 92 | " | 61 | 27 | " | " |
| 79 | 89 | 11 | METTVNAHQIL | " | B*3801 | 80 | " | 53 | 27 | " | " |
| 79 | 89 | 11 | METTVNAHQIL | " | B*4001 | 90 | " | 60 | 27 | " | " |
| 79 | 89 | 11 | METTVNAHQIL | " | B*4002 | 43 | " | 29 | 27 | " | " |
| 79 | 89 | 11 | METTVNAHQIL | " | B*4402 | 40 | " | 27 | 27 | " | " |
| 79 | 89 | 11 | METTVNAHQIL | " | B*4403 | 67 | " | 45 | 27 | " | " |
| 79 | 89 | 11 | METTVNAHQIL | " | B*4801 | 43 | " | 29 | 27 | " | " |
| 79 | 89 | 11 | METTVNAHQIL | " | B*4901 | 78 | " | 52 | 27 | " | " |
| 79 | 89 | 11 | METTVNAHQIL | " | B*5001 | 20 | " | 13 | 27 | " | " |
| 80 | 89 | 10 | ETTVNAHQIL | 1015 | A*2501 | 40 | " | 27 | 27 | " | " |
| 81 | 91 | 11 | TTVNAHQILPK | 1016 | A*1101 | 67 | 0,39 | 26 | 27 | " | " |
| 81 | 91 | 11 | TTVNAHQILPK | " | A*6801 | 44 | " | 17 | 27 | " | " |
| 81 | 91 | 11 | TTVNAHQILPK | " | A*0301 | 6 | " | 2 | 27 | " | " |
| 82 | 91 | 10 | TVNAHQILPK | 1017 | A*1101 | 92 | " | 36 | 27 | " | " |
| 82 | 91 | 10 | TVNAHQILPK | " | A*0301 | 100 | " | 39 | 27 | " | " |
| 82 | 92 | 11 | TVNAHQILPKV | 1018 | A*0201 | 27 | 1,32 | 36 | 27 | " | " |
| 84 | 93 | 10 | NAHQILPKVL | 1019 | B*0701 | 25 | 1,59 | 40 | 27 | " | " |
| 85 | 93 | 9 | AHQILPKVL | 1020 | B*3801 | 60 | " | 95 | 27 | " | " |
| 85 | 93 | 9 | AHQILPKVL | " | B*3901 | 18 | " | 29 | 27 | " | " |
| 86 | 93 | 8 | HQILPKVL | 1021 | B*3901 | 91 | " | 144 | 27 | " | " |
| 86 | 93 | 8 | HQILPKVL | " | B*4801 | 100 | " | 159 | 27 | " | " |
| 86 | 95 | 10 | HQILPKVLHK | 1022 | A*1101 | 42 | 1,60 | 67 | 27 | " | " |
| 86 | 95 | 10 | HQILPKVLHK | " | A*0301 | 33 | " | 53 | 27 | " | " |
| 87 | 95 | 9 | QILPKVLHK | 1023 | A*1101 | 50 | " | 80 | 27 | " | " |
| 87 | 95 | 9 | QILPKVLHK | " | A*0101 | 75 | " | 120 | 27 | " | " |
| 87 | 95 | 9 | QILPKVLHK | " | A*0301 | 100 | " | 160 | 27 | " | " |
| 88 | 95 | 8 | ILPKVLHK | 1024 | A*0201 | 82 | " | 131 | 27 | " | " |
| 88 | 95 | 8 | ILPKVLHK | " | A*0301 | 63 | " | 100 | 27 | " | " |
| | | | | | Cumulative Class I-BCI score: | | | 6468 | | | |
| 86 | 93 | 8 | HQILPKVL | 1021 | B*3901 | 91 | " | 144 | 28 | 86 | 120 |
| 86 | 93 | 8 | HQILPKVL | " | B*4801 | 100 | " | 159 | 28 | " | " |
| 86 | 95 | 10 | HQILPKVLHK | 1022 | A*1101 | 42 | 1,60 | 67 | 28 | " | " |

TABLE 6a-continued

Predicted HLA class I-restricted CD8+ cytotoxic T cell epitopes
contained in SLP sequences from HBV X protein (consensus sequence).

| | | | HLA class I binding peptides in SLP sequences derived from HBV X protein (consensus sequence) | | | | | | Peptide of invention (SLP) | | |
|---|---|---|---|---|---|---|---|---|---|---|---|
| Start | End | Length | Sequence[A] | SEQ ID NO: | HLA class I molecule | Class I-B score[B] | C-score[C] | Class I-BCI score[D] | SLP# | SLP Start | SLP End |
| 86 | 95 | 10 | HQILPKVLHK | " | A*0301 | 33 | " | 53 | 28 | " | " |
| 87 | 95 | 9 | QILPKVLHK | 1023 | A*1101 | 50 | " | 80 | 28 | " | " |
| 87 | 95 | 9 | QILPKVLHK | " | A*0101 | 75 | " | 120 | 28 | " | " |
| 87 | 95 | 9 | QILPKVLHK | " | A*0301 | 100 | " | 160 | 28 | " | " |
| 88 | 95 | 8 | ILPKVLHK | 1024 | A*0201 | 82 | " | 131 | 28 | " | " |
| 88 | 95 | 8 | ILPKVLHK | " | A*0301 | 63 | " | 100 | 28 | " | " |
| 86 | 96 | 11 | HQILPKVLHKR | 1025 | A*3101 | 50 | 1,87 | 94 | 28 | " | " |
| 86 | 96 | 11 | HQILPKVLHKR | " | A*3303 | 47 | " | 87 | 28 | " | " |
| 87 | 96 | 10 | QILPKVLHKR | 1026 | A*3101 | 60 | " | 112 | 28 | " | " |
| 87 | 96 | 10 | QILPKVLHKR | " | A*3303 | 67 | " | 125 | 28 | " | " |
| 88 | 96 | 9 | ILPKVLHKR | 1027 | A*3303 | 27 | " | 50 | 28 | " | " |
| 88 | 96 | 9 | ILPKVLHKR | " | A*0301 | 75 | " | 141 | 28 | " | " |
| 89 | 96 | 8 | LPKVLHKR | 1028 | B*0701 | 42 | " | 78 | 28 | " | " |
| 88 | 97 | 10 | ILPKVLHKRT | 1029 | A*0201 | 30 | 0,47 | 14 | 28 | " | " |
| 89 | 98 | 10 | LPKVLHKRTL | 1030 | B*5101 | 64 | 1,61 | 103 | 28 | " | " |
| 89 | 98 | 10 | LPKVIHKRTL | " | B*0701 | 88 | " | 141 | 28 | " | " |
| 89 | 98 | 10 | LPKVIHKRTL | " | B*0801 | 100 | " | 161 | 28 | " | " |
| 91 | 98 | 8 | KVLHKRTL | 1031 | B*0801 | 10 | " | 16 | 28 | " | " |
| 91 | 100 | 10 | KVLHKRTLGL | 1032 | A*0201 | 70 | 1,91 | 134 | 28 | " | " |
| 91 | 100 | 10 | KVLHKRTLGL | " | B*0701 | 38 | " | 72 | 28 | " | " |
| 91 | 100 | 10 | KVLHKRTLGL | " | B*0801 | 33 | " | 64 | 28 | " | " |
| 92 | 100 | 9 | VLHKRTLGL | 1033 | A*0201 | 90 | " | 172 | 28 | " | " |
| 92 | 100 | 9 | VLHKRTLGL | " | B*0801 | 100 | " | 191 | 28 | " | " |
| 92 | 102 | 11 | VLHKRTLGLSA | 1034 | B*0801 | 70 | 1,09 | 76 | 28 | " | " |
| 95 | 102 | 8 | KRTLGLSA | 1035 | B*2702 | 13 | " | 14 | 28 | " | " |
| 93 | 103 | 11 | LHKRTLGLSAM | 1036 | B*1402 | 86 | 1,72 | 148 | 28 | " | " |
| 93 | 103 | 11 | LHKRTLGLSAM | " | B*0801 | 20 | " | 34 | 28 | " | " |
| 94 | 103 | 10 | HKRTLGLSAM | 1037 | B*1402 | 50 | " | 86 | 28 | " | " |
| 95 | 103 | 9 | KRTLGLSAM | 1038 | B*2702 | 88 | " | 151 | 28 | " | " |
| 96 | 103 | 8 | RTLGLSAM | 1039 | A*2501 | 20 | " | 34 | 28 | " | " |
| 96 | 103 | 8 | RTLGLSAM | " | A*3201 | 100 | " | 172 | 28 | " | " |
| 96 | 103 | 8 | RTLGLSAM | " | B*1502 | 29 | " | 49 | 28 | " | " |
| 96 | 103 | 8 | RTLGLSAM | " | B*1525 | 23 | " | 40 | 28 | " | " |
| 96 | 103 | 8 | RTLGLSAM | " | B*4601 | 93 | " | 160 | 28 | " | " |
| 96 | 103 | 8 | RTLGLSAM | " | B*5701 | 33 | " | 57 | 28 | " | " |

TABLE 6a-continued

Predicted HLA class I-restricted CD8+ cytotoxic T cell epitopes
contained in SLP sequences from HBV X protein (consensus sequence).

| | | | HLA class I binding peptides in SLP sequences derived from HBV X protein (consensus sequence) | | | | | | Peptide of invention (SLP) | | |
|---|---|---|---|---|---|---|---|---|---|---|---|
| Start | End | Length | Sequence[A] | SEQ ID NO: | HLA class I molecule | Class I-B score[B] | C-score[C] | Class I-BCI score[D] | SLP# | SLP Start | SLP End |
| 96 | 103 | 8 | RTLGLSAM | " | B*5801 | 80 | " | 138 | 28 | " | " |
| 97 | 104 | 8 | TLGLSAMS | 1040 | A*0201 | 9 | 0,51 | 5 | 28 | " | " |
| 97 | 105 | 9 | TLGLAAMST | 1041 | A*0201 | 50 | 0,88 | 44 | 28 | " | " |
| 97 | 106 | 10 | TLGLSAMSTT | 1042 | A*0201 | 40 | 0,27 | 11 | 28 | " | " |
| 99 | 108 | 10 | GLSAMSTTDL | 1043 | A*0201 | 50 | 1,60 | 80 | 28 | " | " |
| 100 | 110 | 11 | LSAMSTTDLEA | 1044 | A*0206 | 100 | 1,07 | 107 | 28 | " | " |
| 101 | 111 | 11 | SAMSTTDLEAY | 1045 | A*2902 | 75 | 0,70 | 53 | 28 | " | " |
| 101 | 111 | 11 | SAMSTTDLEAY | " | A*3002 | 100 | " | 70 | 28 | " | " |
| 101 | 111 | 11 | SAMSTTDLEAY | " | B*1501 | 100 | " | 70 | 28 | " | " |
| 101 | 111 | 11 | SAMSTTDLEAY | " | B*1502 | 100 | " | 70 | 28 | " | " |
| 101 | 111 | 11 | SAMSTTDLEAY | " | B*1525 | 100 | " | 70 | 28 | " | " |
| 101 | 111 | 11 | SAMSTTDLEAY | " | B*4601 | 100 | " | 70 | 28 | " | " |
| 101 | 111 | 11 | SAMSTTDLEAY | " | B*5301 | 57 | " | 40 | 28 | " | " |
| 101 | 111 | 11 | SAMSTTDLEAY | " | B*5801 | 60 | " | 42 | 28 | " | " |
| 102 | 111 | 10 | AMSTTDLEAY | 1046 | A*0301 | 50 | " | 35 | 28 | " | " |
| 103 | 111 | 9 | MSTTDLEAY | 1047 | A*2601 | 25 | " | 18 | 28 | " | " |
| 103 | 111 | 9 | MSTTDLEAY | " | A*0101 | 88 | " | 62 | 28 | " | " |
| 103 | 111 | 9 | MSTTDLEAY | " | B*3501 | 83 | " | 59 | 28 | " | " |
| 104 | 111 | 8 | STTDLEAY | 1048 | A*2501 | 100 | " | 70 | 28 | " | " |
| 102 | 112 | 11 | AMSTTDLEAYF | 1049 | A*3002 | 20 | 1,45 | 29 | 28 | " | " |
| 102 | 112 | 11 | AMSTTDLEAYF | " | B*1501 | 71 | " | 104 | 28 | " | " |
| 102 | 112 | 11 | AMSTTDLEAYF | " | B*1502 | 14 | " | 21 | 28 | " | " |
| 102 | 112 | 11 | AMSTTDLEAYF | " | B*1525 | 62 | " | 89 | 28 | " | " |
| 102 | 112 | 11 | AMSTTDLEAYF | " | B*4601 | 7 | " | 10 | 28 | " | " |
| 103 | 112 | 10 | MSTTDLEAYF | 1050 | A*0101 | 13 | " | 18 | 28 | " | " |
| 103 | 112 | 10 | MSTTDLEAYF | " | B*3501 | 42 | " | 61 | 28 | " | " |
| 103 | 112 | 10 | MSTTDLEAYF | " | B*4601 | 43 | " | 62 | 28 | " | " |
| 103 | 112 | 10 | MSTTDLEAYF | " | B*5301 | 14 | " | 21 | 28 | " | " |
| 103 | 112 | 10 | MSTTDLEAYF | " | B*5802 | 40 | " | 58 | 28 | " | " |
| 104 | 112 | 9 | STTDLEAYF | 1051 | A*2501 | 60 | " | 87 | 28 | " | " |
| 104 | 112 | 9 | STTDLEAYF | " | A*2601 | 50 | " | 73 | 28 | " | " |
| 105 | 112 | 8 | TTDLEAYF | 1052 | A*0101 | 75 | " | 109 | 28 | " | " |
| 103 | 113 | 11 | MSTTDLEAYFK | 1053 | A*1101 | 75 | 0,43 | 32 | 28 | " | " |
| 103 | 113 | 11 | MSTTDLEAYFK | " | A*6801 | 67 | " | 29 | 28 | " | " |
| 104 | 113 | 10 | STTDLEAYFK | 1054 | A*1101 | 100 | " | 43 | 28 | " | " |

TABLE 6a-continued

Predicted HLA class I-restricted CD8+ cytotoxic T cell epitopes
contained in SLP sequences from HBV X protein (consensus sequence).

| | | | HLA class I binding peptides in SLP sequences derived from HBV X protein (consensus sequence) | | | | | Peptide of invention (SLP) | | |
|---|---|---|---|---|---|---|---|---|---|---|
| Start | End | Length | Sequence[A] | SEQ ID NO: | HLA class I molecule | Class I-B score[B] | C-score[C] | Class I-BCI score[D] | SLP# | SLP Start | SLP End |
| 104 | 113 | 10 | STTDLEAYFK | " | A*6801 | 89 | " | 38 | 28 | " | " |
| 104 | 113 | 10 | STTDLEAYFK | " | A*0301 | 19 | " | 8 | 28 | " | " |
| 105 | 113 | 9 | TTDLEAYFK | 1055 | A*1101 | 83 | " | 36 | 28 | " | " |
| 105 | 113 | 9 | TTDLEAYFK | " | A*6801 | 22 | " | 10 | 28 | " | " |
| 105 | 113 | 9 | TTDLEAYFK | " | A*0101 | 100 | " | 43 | 28 | " | " |
| 105 | 113 | 9 | TTDLEAYFK | " | A*0301 | 25 | " | 11 | 28 | " | " |
| 106 | 116 | 11 | TDLEAYFKDCV | 1056 | A*0201 | 64 | 0,18 | 12 | 28 | " | " |
| 106 | 116 | 11 | TDLEAYFKDCV | " | B*3701 | 33 | " | 6 | 28 | " | " |
| 108 | 116 | 9 | LEAYFKDCV | 1057 | A*0201 | 10 | " | 2 | 28 | " | " |
| 108 | 116 | 9 | LEAYFKDCV | " | B*1301 | 25 | " | 5 | 28 | " | " |
| 108 | 116 | 9 | LEAYFKDCV | " | B*3701 | 75 | " | 14 | 28 | " | " |
| 108 | 116 | 9 | LEAYFKDCV | " | B*4001 | 40 | " | 7 | 28 | " | " |
| 108 | 116 | 9 | LEAYFKDCV | " | B*4901 | 89 | " | 16 | 28 | " | " |
| 108 | 116 | 9 | LEAYFKDCV | " | B*5001 | 80 | " | 15 | 28 | " | " |
| 109 | 116 | 8 | EAYFKDCV | 1058 | B*0801 | 40 | " | 7 | 28 | " | " |
| 108 | 117 | 10 | LEAYFKDCVF | 1059 | B*1301 | 63 | 1,37 | 85 | 28 | " | " |
| 108 | 117 | 10 | LEAYFKDCVF | " | B*3701 | 42 | " | 57 | 28 | " | " |
| 108 | 117 | 10 | LEAYFKDCVF | " | B*4001 | 20 | " | 27 | 28 | " | " |
| 108 | 117 | 10 | LEAYFKDCVF | " | B*4402 | 80 | " | 109 | 28 | " | " |
| 108 | 117 | 10 | LEAYFKDCVF | " | B*4403 | 89 | " | 121 | 28 | " | " |
| 108 | 117 | 10 | LEAYFKDCVF | " | B*4901 | 67 | " | 91 | 28 | " | " |
| 108 | 117 | 10 | LEAYFKDCVF | " | B*5001 | 60 | " | 82 | 28 | " | " |
| 110 | 117 | 8 | AYFKDCVF | 1060 | A*2301 | 100 | " | 137 | 28 | " | " |
| 110 | 117 | 8 | AYFKDCVF | " | A*2402 | 100 | " | 137 | 28 | " | " |
| 109 | 118 | 10 | EAYFKDCVFK | 1061 | A*1101 | 25 | 1,38 | 34 | 28 | " | " |
| 109 | 118 | 10 | EAYFKDCVFK | " | A*6801 | 78 | " | 107 | 28 | " | " |
| 110 | 118 | 9 | AYFKDCVFK | 1062 | A*1101 | 8 | " | 11 | 28 | " | " |
| 111 | 118 | 8 | YFKDCVFK | 1063 | A*3101 | 10 | " | 14 | 28 | " | " |
| 111 | 118 | 8 | YFKDCVFK | " | A*3303 | 80 | " | 110 | 28 | " | " |
| 110 | 120 | 11 | AYFKDCVFKDW | 1064 | A*2301 | 75 | 1,74 | 131 | 28 | " | " |
| 110 | 120 | 11 | AYFKDCVFKDW | " | A*2402 | 67 | " | 116 | 28 | " | " |
| | | | | | Cumulative Class I-BCI score: | | | 7354 | | | |
| 108 | 117 | 10 | LEAYFKDCVF | 1059 | B*1301 | 63 | 1,37 | 85 | 29 | 108 | 141 |
| 108 | 117 | 10 | LEAYFKDCVF | " | B*3701 | 42 | " | 57 | 29 | " | " |
| 108 | 117 | 10 | LEAYFKDCVF | " | B*4001 | 20 | " | 27 | 29 | " | " |

TABLE 6a-continued

Predicted HLA class I-restricted CD8[+] cytotoxic T cell epitopes
contained in SLP sequences from HBV X protein (consensus sequence).

| | | | HLA class I binding peptides in SLP sequences derived from HBV X protein (consensus sequence) | | | | | | Peptide of invention (SLP) | | |
|---|---|---|---|---|---|---|---|---|---|---|---|
| Start | End | Length | Sequence[A] | SEQ ID NO: | HLA class I molecule | Class I-B score[B] | C-score[C] | Class I-BCI score[D] | SLP# | SLP Start | SLP End |
| 108 | 117 | 10 | LEAYFKDCVF | " | B*4402 | 80 | " | 109 | 29 | " | " |
| 108 | 117 | 10 | LEAYFKDCVF | " | B*4403 | 89 | " | 121 | 29 | " | " |
| 108 | 117 | 10 | LEAYFKDCVF | " | B*4901 | 67 | " | 91 | 29 | " | " |
| 108 | 117 | 10 | LEAYFKDCVF | " | B*5001 | 60 | " | 82 | 29 | " | " |
| 110 | 117 | 8 | AYFKDCVF | 1060 | A*2301 | 100 | " | 137 | 29 | " | " |
| 110 | 117 | 8 | AYFKDCVF | " | A*2402 | 100 | " | 137 | 29 | " | " |
| 109 | 118 | 10 | EAYFKDCVFK | 1061 | A*1101 | 25 | 1,38 | 34 | 29 | " | " |
| 109 | 118 | 10 | EAYFKDCVFK | " | A*6801 | 78 | " | 107 | 29 | " | " |
| 110 | 118 | 9 | AYFKDCVFK | 1062 | A*1101 | 8 | " | 11 | 29 | " | " |
| 111 | 118 | 8 | YFKDCVFK | 1063 | A*3101 | 10 | " | 14 | 29 | " | " |
| 111 | 118 | 8 | YFKDCVFK | " | A*3303 | 80 | " | 110 | 29 | " | " |
| 110 | 120 | 11 | AYFKDCVFKDW | 1064 | A*2301 | 75 | 1,74 | 131 | 29 | " | " |
| 110 | 120 | 11 | AYFKDCVFKDW | " | A*2402 | 67 | " | 116 | 29 | " | " |
| 114 | 123 | 10 | DCVFKDWEEL | 1065 | A*3201 | 60 | 1,30 | 78 | 29 | " | " |
| 115 | 123 | 9 | CVFKDWEEL | 1066 | A*0201 | 40 | " | 52 | 29 | " | " |
| 115 | 123 | 9 | CVFKDWEEL | " | B*0701 | 50 | " | 65 | 29 | " | " |
| 118 | 127 | 10 | KDWEELGEEI | 1067 | B*1301 | 88 | 0,73 | 63 | 29 | " | " |
| 118 | 127 | 10 | KDWEELGEEI | " | B*1302 | 100 | " | 73 | 29 | " | " |
| 118 | 127 | 10 | KDWEELGEEI | " | B*5201 | 67 | " | 48 | 29 | " | " |
| 120 | 127 | 8 | WEELGEEI | 1068 | B*1301 | 50 | " | 36 | 29 | " | " |
| 120 | 127 | 8 | WEELGEEI | " | B*4001 | 70 | " | 51 | 29 | " | " |
| 120 | 127 | 8 | WEELGEEI | " | B*4901 | 56 | " | 40 | 29 | " | " |
| 119 | 129 | 11 | DWEELGEEIRL | 1069 | A*0201 | 55 | 1,70 | 93 | 29 | " | " |
| 120 | 129 | 10 | WEELGEEIRL | 1070 | B*3801 | 20 | " | 34 | 29 | " | " |
| 120 | 129 | 10 | WEELGEEIRL | " | B*4001 | 10 | " | 17 | 29 | " | " |
| 121 | 129 | 9 | EELGEEIRL | 1071 | B*4001 | 60 | " | 102 | 29 | " | " |
| 121 | 129 | 9 | EELGEEIRL | " | B*4403 | 22 | " | 38 | 29 | " | " |
| 121 | 131 | 11 | EELGEEIRLKV | 1072 | B*1801 | 17 | 1,00 | 17 | 29 | " | " |
| 121 | 131 | 11 | EELGEEIRLKV | " | B*3701 | 50 | " | 50 | 29 | " | " |
| 122 | 131 | 10 | ELGEEIRLKV | 1073 | A*0201 | 60 | " | 60 | 29 | " | " |
| 124 | 131 | 8 | GEEIRLKV | 1074 | B*4901 | 11 | " | 11 | 29 | " | " |
| 123 | 132 | 10 | LGEEIRLKVF | 1075 | A*0101 | 50 | 1,36 | 68 | 29 | " | " |
| 124 | 132 | 9 | GEEIRLKVF | 1076 | B*4402 | 60 | " | 82 | 29 | " | " |
| 124 | 132 | 9 | GEEIRLKVF | " | B*4403 | 11 | " | 15 | 29 | " | " |
| 125 | 132 | 8 | EEIRLKVF | 1077 | B*1801 | 83 | " | 113 | 29 | " | " |

TABLE 6a-continued

Predicted HLA class I-restricted CD8+ cytotoxic T cell epitopes
contained in SLP sequences from HBV X protein (consensus sequence).

| | | | HLA class I binding peptides in SLP sequences derived from HBV X protein (consensus sequence) | | | | | | Peptide of invention (SLP) | | |
|---|---|---|---|---|---|---|---|---|---|---|---|
| Start | End | Length | Sequence[A] | SEQ ID NO: | HLA class I molecule | Class I-B score[B] | C-score[C] | Class I-BCI score[D] | SLP# | SLP Start | SLP End |
| 125 | 132 | 8 | EEIRLKVF | " | B*4402 | 20 | " | 27 | 29 | " | " |
| 125 | 132 | 8 | EEIRLKVF | " | B*4403 | 56 | " | 75 | 29 | " | " |
| 123 | 133 | 11 | LGEEIRLKVFV | 1078 | A*0206 | 50 | 1,07 | 54 | 29 | " | " |
| 123 | 133 | 11 | LGEEIRLKVFV | " | A*0201 | 91 | " | 98 | 29 | " | " |
| 125 | 133 | 9 | EEIRLKVFV | 1079 | B*3701 | 58 | " | 63 | 29 | " | " |
| 125 | 133 | 9 | EEIRLKVFV | " | B*4001 | 30 | " | 32 | 29 | " | " |
| 125 | 133 | 9 | EEIRLKVFV | " | B*4403 | 78 | " | 84 | 29 | " | " |
| 126 | 133 | 8 | EIRLKVFV | 1080 | B*0801 | 100 | " | 107 | 29 | " | " |
| 125 | 134 | 10 | EEIRLKVFVL | 1081 | B*1801 | 50 | 1,85 | 93 | 29 | " | " |
| 125 | 134 | 10 | EEIRLKVFVL | " | B*3701 | 83 | " | 154 | 29 | " | " |
| 125 | 134 | 10 | EEIRLKVFVL | " | B*3801 | 40 | " | 74 | 29 | " | " |
| 125 | 134 | 10 | EEIRLKVFVL | " | B*4001 | 100 | " | 185 | 29 | " | " |
| 125 | 134 | 10 | EEIRLKVFVL | " | B*4002 | 71 | " | 132 | 29 | " | " |
| 125 | 134 | 10 | EEIRLKVFVL | " | B*4402 | 100 | " | 185 | 29 | " | " |
| 125 | 134 | 10 | EEIRLKVFVL | " | B*4403 | 100 | " | 185 | 29 | " | " |
| 126 | 134 | 9 | EIRLKVFVL | 1082 | B*0701 | 63 | " | 116 | 29 | " | " |
| 126 | 134 | 9 | EIRLKVFVL | " | B*0801 | 100 | " | 185 | 29 | " | " |
| 127 | 134 | 8 | IRLKVFVL | 1083 | A*0206 | 25 | " | 46 | 29 | " | " |
| 127 | 134 | 8 | IRLKVFVL | " | B*1402 | 64 | " | 119 | 29 | " | " |
| 127 | 134 | 8 | IRLKVFVL | " | B*2702 | 100 | " | 185 | 29 | " | " |
| 127 | 134 | 8 | IRLKVFVL | " | B*3901 | 82 | " | 151 | 29 | " | " |
| 129 | 136 | 8 | LKVFVLGG | 1084 | A*0206 | 75 | 0,47 | 35 | 29 | " | " |
| 128 | 138 | 11 | RLKVFVLGGCR | 1085 | A*3101 | 80 | 0,64 | 51 | 29 | " | " |
| 128 | 138 | 11 | RLKVFVLGGCR | " | A*7401 | 30 | " | 19 | 29 | " | " |
| 128 | 138 | 11 | RLKVFVLGGCR | " | A*0301 | 13 | " | 8 | 29 | " | " |
| 130 | 138 | 9 | KVFVLGGCR | 1086 | A*3101 | 100 | " | 64 | 29 | " | " |
| 130 | 138 | 9 | KVFVLGGCR | " | A*7401 | 50 | " | 32 | 29 | " | " |
| 130 | 140 | 11 | KVFVLGGCRHK | 1087 | A*1101 | 58 | 1,05 | 61 | 29 | " | " |
| 130 | 140 | 11 | KVFVLGGCRHK | " | A*3001 | 94 | " | 99 | 29 | " | " |
| 130 | 140 | 11 | KVFVLGGCRHK | " | A*0301 | 94 | " | 98 | 29 | " | " |
| 133 | 140 | 8 | VLGGCRHK | 1088 | A*0201 | 18 | " | 19 | 29 | " | " |
| 133 | 140 | 8 | VLGGCRHK | " | A*0301 | 44 | " | 46 | 29 | " | " |
| 132 | 141 | 10 | FVLGGCRHKL | 1089 | A*0201 | 80 | 1,66 | 133 | 29 | " | " |
| 132 | 141 | 10 | FVLGGCRHKL | " | B*0701 | 63 | " | 104 | 29 | " | " |
| 133 | 141 | 9 | VLGGCRHKL | 1090 | A*0201 | 100 | " | 166 | 29 | " | " |

TABLE 6a-continued

Predicted HLA class I-restricted CD8+ cytotoxic T cell epitopes contained in SLP sequences from HBV X protein (consensus sequence).

| | | HLA class I binding peptides in SLP sequences derived from HBV X protein (consensus sequence) | | | | | | Peptide of invention (SLP) | | |
|---|---|---|---|---|---|---|---|---|---|---|
| Start | End | Length Sequence[A] | SEQ ID NO: | HLA class I molecule | Class I-B score[B] | C-score[C] | Class I-BCI score[D] | SLP# | SLP Start | SLP End |
| | | | | Cumulative Class I-BCI score: | | | 5862 | | | |

"Start" and "End" are relative to the amino acid sequence of HBV X protein, consensus sequence, as depicted in SEQ ID NO: 45
[A]Peptide amino acid sequence. Each HLA class I binding peptide of HBV X protein is listed separately for each HLA class I molecule to which it is predicted to bind, and can be listed multiple times for that reason.
[B]Class I-B score. See Material and Methods (Examples section).
[C]C-score. See Material and Methods (Examples section).
[D]Class I-BCI score. See Material and Methods (Examples section).
[E]Cumulative Class I-BCI score. See Material and Methods (Examples section).

TABLE 6b

Predicted HLA class II-restricted CD4+ T cell epitopes contained in SLP sequences from HBV X protein (consensus sequence).

| HLA class II binding peptides in SLP derived from HBV X protein (consens. seq.) | | | | | | Peptide of invention (SLP) | | |
|---|---|---|---|---|---|---|---|---|
| Start | End | Sequence[A] | SEQ ID NO: | HLA-DRB1 molecule | Class II-B score[B] | SLP# | SLP Start | SLP End |
| 46 | 60 | PADHGAHLSRGLPV | 1091 | *0701 | 8 | 26 | 36 | 68 |
| 47 | 61 | ADHGAHLSRGLPVC | 1092 | *0101 | 13 | 26 | " | " |
| 47 | 61 | ADHGAHLSRGLPVC | " | *0102 | 20 | 26 | " | " |
| 47 | 61 | ADHGAHLSRGLPVC | " | *0105 | 13 | 26 | " | " |
| 47 | 61 | ADHGAHLSRGLPVC | " | *0107 | 13 | 26 | " | " |
| 48 | 62 | DHGAHLSRGLPVCA | 1093 | *0101 | 87 | 26 | " | " |
| 48 | 62 | DHGAHLSRGLPVCA | " | *0102 | 67 | 26 | " | " |
| 48 | 62 | DHGAHLSRGLPVCA | " | *0104 | 43 | 26 | " | " |
| 48 | 62 | DHGAHLSRGLPVCA | " | *0105 | 87 | 26 | " | " |
| 48 | 62 | DHGAHLSRGLPVCA | " | *0106 | 53 | 26 | " | " |
| 48 | 62 | DHGAHLSRGLPVCA | " | *0107 | 87 | 26 | " | " |
| 49 | 63 | HGAHLSRGLPVCAF | 1094 | *0101 | 100 | 26 | " | " |
| 49 | 63 | HGAHLSRGLPVCAF | " | *0102 | 93 | 26 | " | " |
| 49 | 63 | HGAHLSRGLPVCAF | " | *0103 | 40 | 26 | " | " |
| 49 | 63 | HGAHLSRGLPVCAF | " | *0104 | 90 | 26 | " | " |
| 49 | 63 | HGAHLSRGLPVCAF | " | *0105 | 90 | 26 | " | " |
| 49 | 63 | HGAHLSRGLPVCAF | " | *0106 | 90 | 26 | " | " |
| 49 | 63 | HGAHLSRGLPVCAF | " | *0107 | 90 | 26 | " | " |
| 49 | 63 | HGAHLSRGLPVCAF | " | *1101 | 85 | 26 | " | " |
| 49 | 63 | HGAHLSRGLPVCAF | " | *1301 | 100 | 26 | " | " |
| 49 | 63 | HGAHLSRGLPVCAF | " | *1501 | 46 | 26 | " | " |
| 50 | 64 | GAHLSRGLPVCAFS | 1095 | *0101 | 77 | 26 | " | " |

TABLE 6b-continued

Predicted HLA class II-restricted CD4[+] T cell epitopes contained in SLP sequences from HBV X protein (consensus sequence).

| | | HLA class II binding peptides in SLP derived from HBV X protein (consens. seq.) | | | | Peptide of invention (SLP) | | |
|---|---|---|---|---|---|---|---|---|
| Start | End | Sequence[A] | SEQ ID NO: | HLA-DRB1 molecule | Class II-B score[B] | SLP# | SLP Start | SLP End |
| 50 | 64 | GAHLSLRGLPVCAFS | " | *0102 | 97 | 26 | " | " |
| 50 | 64 | GAHLSLRGLPVCAFS | " | *0103 | 70 | 26 | " | " |
| 50 | 64 | GAHLSLRGLPVCAFS | " | *0104 | 93 | 26 | " | " |
| 50 | 64 | GAHLSLRGLPVCAFS | " | *0105 | 93 | 26 | " | " |
| 50 | 64 | GAHLSLRGLPVCAFS | " | *0106 | 97 | 26 | " | " |
| 50 | 64 | GAHLSLRGLPVCAFS | " | *0107 | 93 | 26 | " | " |
| 50 | 64 | GAHLSLRGLPVCAFS | " | *1101 | 77 | 26 | " | " |
| 50 | 64 | GAHLSLRGLPVCAFS | " | *1301 | 92 | 26 | " | " |
| 50 | 64 | GAHLSLRGLPVCAFS | " | *1501 | 54 | 26 | " | " |
| 51 | 65 | AHLSLRGLPVCAFSS | 1096 | *0101 | 100 | 26 | " | " |
| 51 | 65 | AHLSLRGLPVCAFSS | " | *0102 | 100 | 26 | " | " |
| 51 | 65 | AHLSLRGLPVCAFSS | " | *0103 | 100 | 26 | " | " |
| 51 | 65 | AHLSLRGLPVCAFSS | " | *0104 | 100 | 26 | " | " |
| 51 | 65 | AHLSLRGLPVCAFSS | " | *0105 | 100 | 26 | " | " |
| 51 | 65 | AHLSLRGLPVCAFSS | " | *0106 | 100 | 26 | " | " |
| 51 | 65 | AHLSLRGLPVCAFSS | " | *0107 | 100 | 26 | " | " |
| 51 | 65 | AHLSLRGLPVCAFSS | " | *1301 | 85 | 26 | " | " |
| 52 | 66 | HLSLRGLPVCAFSSA | 1097 | *0101 | 97 | 26 | " | " |
| 52 | 66 | HLSLRGLPVCAFSSA | " | *0102 | 90 | 26 | " | " |
| 52 | 66 | HLSLRGLPVCAFSSA | " | *0103 | 90 | 26 | " | " |
| 52 | 66 | HLSLRGLPVCAFSSA | " | *0104 | 97 | 26 | " | " |
| 52 | 66 | HLSLRGLPVCAFSSA | " | *0105 | 97 | 26 | " | " |
| 52 | 66 | HLSLRGLPVCAFSSA | " | *0106 | 93 | 26 | " | " |
| 52 | 66 | HLSLRGLPVCAFSSA | " | *0107 | 97 | 26 | " | " |
| 52 | 66 | HLSLRGLPVCAFSSA | " | *1301 | 77 | 26 | " | " |
| 53 | 67 | LSLRGLPVCAFSSAG | 1098 | *0101 | 83 | 26 | " | " |
| 53 | 67 | LSLRGLPVCAFSSAG | " | *0102 | 50 | 26 | " | " |
| 53 | 67 | LSLRGLPVCAFSSAG | " | *0104 | 77 | 26 | " | " |
| 53 | 67 | LSLRGLPVCAFSSAG | " | *0105 | 83 | 26 | " | " |
| 53 | 67 | LSLRGLPVCAFSSAG | " | *0106 | 73 | 26 | " | " |
| 53 | 67 | LSLRGLPVCAFSSAG | " | *0107 | 83 | 26 | " | " |
| 53 | 67 | LSLRGLPVCAFSSAG | " | *1301 | 69 | 26 | " | " |
| 54 | 68 | SLRGLPVCAFSSAGP | 1099 | *0101 | 37 | 26 | " | " |
| 54 | 68 | SLRGLPVCAFSSAGP | " | *0102 | 7 | 26 | " | " |
| 54 | 68 | SLRGLPVCAFSSAGP | " | *0104 | 30 | 26 | " | " |

TABLE 6b-continued

Predicted HLA class II-restricted CD4+ T cell epitopes contained in SLP sequences from HBV X protein (consensus sequence).

| | | HLA class II binding peptides in SLP derived from HBV X protein (consens. seq.) | | | | Peptide of invention (SLP) | | |
|---|---|---|---|---|---|---|---|---|
| Start | End | Sequence[A] | SEQ ID NO: | HLA-DRB1 molecule | Class II-B score[B] | SLP# | SLP Start | SLP End |
| 54 | 68 | SLRGLPVCAFSSAGP | " | *0105 | 37 | 26 | " | " |
| 54 | 68 | SLRGLPVCAFSSAGP | " | *0106 | 7 | 26 | " | " |
| 54 | 68 | SLRGLPVCAFSSAGP | " | *0107 | 37 | 26 | " | " |
| 54 | 68 | SLRGLPVCAFSSAGP | " | *1301 | 62 | 26 | " | " |
| | | Cumulative Class II-B score[C]: | | | 4414 | | | |
| 61 | 75 | CAFSSAGPCALRFTS | 1100 | *0101 | 20 | 27 | 61 | 95 |
| 61 | 75 | CAFSSAGPCALRFTS | " | *0105 | 20 | 27 | " | " |
| 61 | 75 | CAFSSAGPCALRFTS | " | *0107 | 20 | 27 | " | " |
| 61 | 75 | CAFSSAGPCALRFTS | " | *0701 | 15 | 27 | " | " |
| 64 | 78 | SSAGPCALRFTSARR | 1101 | *1501 | 69 | 27 | " | " |
| 65 | 79 | SAGPCALRFTSARRM | 1102 | *0101 | 23 | 27 | " | " |
| 65 | 79 | SAGPCALRFTSARRM | " | *0102 | 23 | 27 | " | " |
| 65 | 79 | SAGPCALRFTSARRM | " | *0104 | 27 | 27 | " | " |
| 65 | 79 | SAGPCALRFTSARRM | " | *0106 | 23 | 27 | " | " |
| 65 | 79 | SAGPCALRFTSARRM | " | *0401 | 31 | 27 | " | " |
| 65 | 79 | SAGPCALRFTSARRM | " | *0701 | 85 | 27 | " | " |
| 65 | 79 | SAGPCALRFTSARRM | " | *1301 | 46 | 27 | " | " |
| 65 | 79 | SAGPCALRFTSARRM | " | *1501 | 92 | 27 | " | " |
| 66 | 80 | AGPCALRFTSARRME | 1103 | *0101 | 69 | 27 | " | " |
| 66 | 80 | AGPCALRFTSARRME | " | *0102 | 37 | 27 | " | " |
| 66 | 80 | AGPCALRFTSARRME | " | *0104 | 40 | 27 | " | " |
| 66 | 80 | AGPCALRFTSARRME | " | *0105 | 3 | 27 | " | " |
| 66 | 80 | AGPCALRFTSARRME | " | *0106 | 37 | 27 | " | " |
| 66 | 80 | AGPCALRFTSARRME | " | *0107 | 3 | 27 | " | " |
| 66 | 80 | AGPCALRFTSARRME | " | *0401 | 46 | 27 | " | " |
| 66 | 80 | AGPCALRFTSARRME | " | *0701 | 69 | 27 | " | " |
| 66 | 80 | AGPCALRFTSARRME | " | *1301 | 38 | 27 | " | " |
| 66 | 80 | AGPCALRFTSARRME | " | *1501 | 85 | 27 | " | " |
| 67 | 81 | GPCALRFTSARRMET | 1104 | *0101 | 62 | 27 | " | " |
| 67 | 81 | GPCALRFTSARRMET | " | *0102 | 57 | 27 | " | " |
| 67 | 81 | GPCALRFTSARRMET | " | *0104 | 70 | 27 | " | " |
| 67 | 81 | GPCALRFTSARRMET | " | *0105 | 43 | 27 | " | " |
| 67 | 81 | GPCALRFTSARRMET | " | *0106 | 80 | 27 | " | " |
| 67 | 81 | GPCALRFTSARRMET | " | *0107 | 43 | 27 | " | " |
| 67 | 81 | GPCALRFTSARRMET | " | *0301 | 46 | 27 | " | " |

TABLE 6b-continued

Predicted HLA class II-restricted CD4+ T cell epitopes contained in SLP sequences from HBV X protein (consensus sequence).

| | | HLA class II binding peptides in SLP derived from HBV X protein (consens. seq.) | | | | Peptide of invention (SLP) | | |
|---|---|---|---|---|---|---|---|---|
| Start | End | Sequence[A] | SEQ ID NO: | HLA-DRB1 molecule | Class II-B score[B] | SLP# | SLP Start | SLP End |
| 67 | 81 | GPCALRFTSARRMET | " | *0401 | 92 | 27 | " | " |
| 67 | 81 | GPCALRFTSARRMET | " | *0701 | 77 | 27 | " | " |
| 67 | 81 | GPCALRFTSARRMET | " | *1101 | 8 | 27 | " | " |
| 67 | 81 | GPCALRFTSARRMET | " | *1301 | 31 | 27 | " | " |
| 67 | 81 | GPCALRFTSARRMET | " | *1501 | 100 | 27 | " | " |
| 68 | 82 | PCALRFTSARRMETT | 1105 | *0101 | 54 | 27 | " | " |
| 68 | 82 | PCALRFTSARRMETT | " | *0102 | 60 | 27 | " | " |
| 68 | 82 | PCALRFTSARRMETT | " | *0104 | 83 | 27 | " | " |
| 68 | 82 | PCALRFTSARRMETT | " | *0105 | 57 | 27 | " | " |
| 68 | 82 | PCALRFTSARRMETT | " | *0106 | 83 | 27 | " | " |
| 68 | 82 | PCALRFTSARRMETT | " | *0107 | 57 | 27 | " | " |
| 68 | 82 | PCALRFTSARRMETT | " | *0301 | 38 | 27 | " | " |
| 68 | 82 | PCALRFTSARRMETT | " | *0401 | 69 | 27 | " | " |
| 68 | 82 | PCALRFTSARRMETT | " | *0701 | 100 | 27 | " | " |
| 68 | 82 | PCALRFTSARRMETT | " | *1101 | 31 | 27 | " | " |
| 68 | 82 | PCALRFTSARRMETT | " | *1301 | 23 | 27 | " | " |
| 68 | 82 | PCALRFTSARRMETT | " | *1501 | 77 | 27 | " | " |
| 69 | 83 | CALRFTSARRMETTV | 1106 | *0101 | 46 | 27 | " | " |
| 69 | 83 | CALRFTSARRMETTV | " | *0102 | 43 | 27 | " | " |
| 69 | 83 | CALRFTSARRMETTV | " | *0104 | 67 | 27 | " | " |
| 69 | 83 | CALRFTSARRMETTV | " | *0105 | 47 | 27 | " | " |
| 69 | 83 | CALRFTSARRMETTV | " | *0106 | 57 | 27 | " | " |
| 69 | 83 | CALRFTSARRMETTV | " | *0107 | 47 | 27 | " | " |
| 69 | 83 | CALRFTSARRMETTV | " | *0301 | 31 | 27 | " | " |
| 69 | 83 | CALRFTSARRMETTV | " | *0401 | 23 | 27 | " | " |
| 69 | 83 | CALRFTSARRMETTV | " | *0701 | 92 | 27 | " | " |
| 69 | 83 | CALRFTSARRMETTV | " | *1101 | 38 | 27 | " | " |
| 69 | 83 | CALRFTSARRMETTV | " | *1301 | 15 | 27 | " | " |
| 69 | 83 | CALRFTSARRMETTV | " | *1501 | 62 | 27 | " | " |
| 70 | 84 | ALRFTSARRMETTVN | 1107 | *0101 | 38 | 27 | " | " |
| 70 | 84 | ALRFTSARRMETTVN | " | *0102 | 17 | 27 | " | " |
| 70 | 84 | ALRFTSARRMETTVN | " | *0104 | 37 | 27 | " | " |
| 70 | 84 | ALRFTSARRMETTVN | " | *0106 | 3 | 27 | " | " |
| 70 | 84 | ALRFTSARRMETTVN | " | *0301 | 62 | 27 | " | " |
| 70 | 84 | ALRFTSARRMETTVN | " | *0401 | 8 | 27 | " | " |

TABLE 6b-continued

Predicted HLA class II-restricted CD4⁺ T cell epitopes contained in SLP sequences from HBV X protein (consensus sequence).

| | | HLA class II binding peptides in SLP derived from HBV X protein (consens. seq.) | | | | Peptide of invention (SLP) | | |
|---|---|---|---|---|---|---|---|---|
| Start | End | Sequence[A] | SEQ ID NO: | HLA-DRB1 molecule | Class II-B score[B] | SLP# | SLP Start | SLP End |
| 70 | 84 | ALRFTSARRMETTVN | " | *0701 | 62 | 27 | " | " |
| 70 | 84 | ALRFTSARRMETTVN | " | *1101 | 46 | 27 | " | " |
| 70 | 84 | ALRFTSARRMETTVN | " | *1301 | 8 | 27 | " | " |
| 70 | 84 | ALRFTSARRMETTVN | " | *1501 | 23 | 27 | " | " |
| 71 | 85 | LRFTSARRMETTVNA | 1108 | *0301 | 23 | 27 | " | " |
| 71 | 85 | LRFTSARRMETTVNA | " | *0401 | 15 | 27 | " | " |
| 71 | 85 | LRFTSARRMETTVNA | " | *0701 | 54 | 27 | " | " |
| 71 | 85 | LRFTSARRMETTVNA | " | *1101 | 23 | 27 | " | " |
| 73 | 87 | FTSARRMETTVNAHQ | 1109 | *0401 | 85 | 27 | " | " |
| 74 | 88 | TSARRMETTVNAHQI | 1110 | *0401 | 100 | 27 | " | " |
| 75 | 89 | SARRMETTVNAHQIL | 1111 | *0401 | 38 | 27 | " | " |
| 75 | 89 | SARRMETTVNAHQIL | " | *1301 | 40 | 27 | " | " |
| 76 | 90 | ARRMETTVNAHQILP | 1112 | *0401 | 80 | 27 | " | " |
| 76 | 90 | ARRMETTVNAHQILP | " | *1301 | 10 | 27 | " | " |
| 77 | 91 | RRMETTVNAHQILPK | 1113 | *1301 | 50 | 27 | " | " |
| 78 | 92 | RMETTVNAHQILPKV | 1114 | *1301 | 20 | 27 | " | " |
| 81 | 95 | TTVNAHQILPKVLHK | 1115 | *1101 | 15 | 27 | " | " |
| | | Cumulative Class II-B score: | | | 3788 | | | |
| 86 | 100 | HQILPKVLHKRTLGL | 1116 | *1101 | 54 | 28 | 86 | 120 |
| 87 | 101 | QILPKVLHKRTLGLS | 1117 | *0102 | 10 | 28 | " | " |
| 87 | 101 | QILPKVLHKRTLGLS | " | *1101 | 22 | 28 | " | " |
| 87 | 101 | QILPKVLHKRTLGLS | " | *1301 | 70 | 28 | " | " |
| 88 | 102 | ILPKVLHKRTLGLSA | 1118 | *0102 | 53 | 28 | " | " |
| 88 | 102 | ILPKVLHKRTLGLSA | " | *0104 | 17 | 28 | " | " |
| 88 | 102 | ILPKVLHKRTLGLSA | " | *0106 | 33 | 28 | " | " |
| 88 | 102 | ILPKVLHKRTLGLSA | " | *1101 | 44 | 28 | " | " |
| 88 | 102 | ILPKVLHKRTLGLSA | " | *1301 | 80 | 28 | " | " |
| 89 | 103 | LPKVLHKRTLGLSAM | 1119 | *0101 | 10 | 28 | " | " |
| 89 | 103 | LPKVLHKRTLGLSAM | " | *0102 | 77 | 28 | " | " |
| 89 | 103 | LPKVLHKRTLGLSAM | " | *0104 | 60 | 28 | " | " |
| 89 | 103 | LPKVLHKRTLGLSAM | " | *0105 | 10 | 28 | " | " |
| 89 | 103 | LPKVLHKRTLGLSAM | " | *0106 | 77 | 28 | " | " |
| 89 | 103 | LPKVLHKRTLGLSAM | " | *0107 | 10 | 28 | " | " |
| 89 | 103 | LPKVLHKRTLGLSAM | " | *0701 | 10 | 28 | " | " |
| 89 | 103 | LPKVLHKRTLGLSAM | " | *1101 | 78 | 28 | " | " |

TABLE 6b-continued

Predicted HLA class II-restricted CD4+ T cell epitopes contained in SLP sequences from HBV X protein (consensus sequence).

| | | HLA class II binding peptides in SLP derived from HBV X protein (consens. seq.) | | | | Peptide of invention (SLP) | | |
|---|---|---|---|---|---|---|---|---|
| Start | End | Sequence[A] | SEQ ID NO: | HLA-DRB1 molecule | Class II-B score[B] | SLP# | SLP Start | SLP End |
| 89 | 103 | LPKVLHKRTLGLSAM | " | *1301 | 100 | 28 | " | " |
| 89 | 103 | LPKVLHKRTLGLSAM | " | *1501 | 40 | 28 | " | " |
| 90 | 104 | PKVLHKRTLGLSAMS | 1120 | *0101 | 33 | 28 | " | " |
| 90 | 104 | PKVLHKRTLGLSAMS | " | *0102 | 73 | 28 | " | " |
| 90 | 104 | PKVLHKRTLGLSAMS | " | *0104 | 63 | 28 | " | " |
| 90 | 104 | PKVLHKRTLGLSAMS | " | *0105 | 33 | 28 | " | " |
| 90 | 104 | PKVLHKRTLGLSAMS | " | *0106 | 67 | 28 | " | " |
| 90 | 104 | PKVLHKRTLGLSAMS | " | *0107 | 33 | 28 | " | " |
| 90 | 104 | PKVLHKRTLGLSAMS | " | *1101 | 72 | 28 | " | " |
| 90 | 104 | PKVLHKRTLGLSAMS | " | *1301 | 90 | 28 | " | " |
| 91 | 105 | KVLHKRTLGLSAMST | 1121 | *0101 | 63 | 28 | " | " |
| 91 | 105 | KVLHKRTLGLSAMST | " | *0102 | 70 | 28 | " | " |
| 91 | 105 | KVLHKRTLGLSAMST | " | *0104 | 50 | 28 | " | " |
| 91 | 105 | KVLHKRTLGLSAMST | " | *0105 | 63 | 28 | " | " |
| 91 | 105 | KVLHKRTLGLSAMST | " | *0106 | 60 | 28 | " | " |
| 91 | 105 | KVLHKRTLGLSAMST | " | *0107 | 63 | 28 | " | " |
| 91 | 105 | KVLHKRTLGLSAMST | " | *1101 | 11 | 28 | " | " |
| 91 | 105 | KVLHKRTLGLSAMST | " | *1301 | 60 | 28 | " | " |
| 92 | 106 | VLHKRTLGLSAMSTT | 1122 | *0101 | 15 | 28 | " | " |
| 92 | 106 | VLHKRTLGLSAMSTT | " | *0102 | 47 | 28 | " | " |
| 92 | 106 | VLHKRTLGLSAMSTT | " | *0104 | 23 | 28 | " | " |
| 92 | 106 | VLHKRTLGLSAMSTT | " | *0105 | 73 | 28 | " | " |
| 92 | 106 | VLHKRTLGLSAMSTT | " | *0106 | 43 | 28 | " | " |
| 92 | 106 | VLHKRTLGLSAMSTT | " | *0107 | 73 | 28 | " | " |
| 93 | 107 | LHKRTLGLSAMSTTD | 1123 | *0101 | 60 | 28 | " | " |
| 93 | 107 | LHKRTLGLSAMSTTD | " | *0102 | 27 | 28 | " | " |
| 93 | 107 | LHKRTLGLSAMSTTD | " | *0105 | 60 | 28 | " | " |
| 93 | 107 | LHKRTLGLSAMSTTD | " | *0107 | 60 | 28 | " | " |
| 94 | 108 | HKRTLGLSAMSTTDL | 1124 | *0101 | 92 | 28 | " | " |
| 94 | 108 | HKRTLGLSAMSTTDL | " | *0102 | 33 | 28 | " | " |
| 94 | 108 | HKRTLGLSAMSTTDL | " | *0104 | 3 | 28 | " | " |
| 94 | 108 | HKRTLGLSAMSTTDL | " | *0105 | 67 | 28 | " | " |
| 94 | 108 | HKRTLGLSAMSTTDL | " | *0106 | 40 | 28 | " | " |
| 94 | 108 | HKRTLGLSAMSTTDL | " | *0107 | 67 | 28 | " | " |
| 94 | 108 | HKRTLGLSAMSTTDL | " | *0401 | 77 | 28 | " | " |

TABLE 6b-continued

Predicted HLA class II-restricted CD4⁺ T cell epitopes contained in SLP sequences from HBV X protein (consensus sequence).

| | | HLA class II binding peptides in SLP derived from HBV X protein (consens. seq.) | | | | Peptide of invention (SLP) | | |
|---|---|---|---|---|---|---|---|---|
| Start | End | Sequence$^A$ | SEQ ID NO: | HLA-DRB1 molecule | Class II-B score$^B$ | SLP# | SLP Start | SLP End |
| 95 | 109 | KRTLGLSAMSTTDLE | 1125 | *0101 | 31 | 28 | " | " |
| 95 | 109 | KRTLGLSAMSTTDLE | " | *0105 | 23 | 28 | " | " |
| 95 | 109 | KRTLGLSAMSTTDLE | " | *0106 | 17 | 28 | " | " |
| 95 | 109 | KRTLGLSAMSTTDLE | " | *0107 | 23 | 28 | " | " |
| 95 | 109 | KRTLGLSAMSTTDLE | " | *0401 | 54 | 28 | " | " |
| 96 | 110 | RTLGLSAMSTTDLEA | 1126 | *0101 | 8 | 28 | " | " |
| 96 | 110 | RTLGLSAMSTTDLEA | " | *0105 | 30 | 28 | " | " |
| 96 | 110 | RTLGLSAMSTTDLEA | " | *0106 | 27 | 28 | " | " |
| 96 | 110 | RTLGLSAMSTTDLEA | " | *0107 | 30 | 28 | " | " |
| 96 | 110 | RTLGLSAMSTTDLEA | " | *0401 | 62 | 28 | " | " |
| 97 | 111 | TLGLSAMSTTDLEAY | 1127 | *0101 | 17 | 28 | " | " |
| 97 | 111 | TLGLSAMSTTDLEAY | " | *0105 | 17 | 28 | " | " |
| 97 | 111 | TLGLSAMSTTDLEAY | " | *0106 | 20 | 28 | " | " |
| 97 | 111 | TLGLSAMSTTDLEAY | " | *0107 | 17 | 28 | " | " |
| 97 | 111 | TLGLSAMSTTDLEAY | " | *0401 | 50 | 28 | " | " |
| 105 | 119 | TTDLEAYFKDCVFKD | 1128 | *0301 | 69 | 28 | " | " |
| 106 | 120 | TDLEAYFKDCVFKDW | 1129 | *0301 | 54 | 28 | " | " |
| | | Cumulative Class II-B score: | | | 3170 | | | |
| 108 | 122 | LEAYFKDCVFKDWEE | 1130 | *0301 | 15 | 29 | 108 | 141 |
| 110 | 124 | AYFKDCVFKDWEELG | 1131 | *0301 | 100 | 29 | " | " |
| 111 | 125 | YFKDCVFKDWEELGE | 1132 | *0301 | 92 | 29 | " | " |
| 119 | 133 | DWEELGEEIRLKVFV | 1133 | *0301 | 77 | 29 | " | " |
| 120 | 134 | WEELGEEIRLKVFVL | 1134 | *0301 | 85 | 29 | " | " |
| 120 | 134 | WEELGEEIRLKVFVL | " | *1501 | 8 | 29 | " | " |
| 121 | 135 | EELGEEIRLKVFVLG | 1135 | *1501 | 31 | 29 | " | " |
| 123 | 137 | LGEEIRLKVFVLGGC | 1136 | *1501 | 15 | 29 | " | " |
| 124 | 138 | GEEIRLKVFVLGGCR | 1137 | *1501 | 38 | 29 | " | " |
| 125 | 139 | EEIRLKVFVLGGCRH | 1138 | *0102 | 3 | 29 | " | " |
| 126 | 140 | EIRLKVFVLGGCRHK | 1139 | *0102 | 40 | 29 | " | " |
| 126 | 140 | EIRLKVFVLGGCRHK | " | *0104 | 20 | 29 | " | " |
| 126 | 140 | EIRLKVFVLGGCRHK | " | *1501 | 10 | 29 | " | " |
| 127 | 141 | IRLKVFVLGGCRHKL | 1140 | *0101 | 40 | 29 | " | " |
| 127 | 141 | IRLKVFVLGGCRHKL | " | *0102 | 80 | 29 | " | " |
| 127 | 141 | IRLKVFVLGGCRHKL | " | *0104 | 73 | 29 | " | " |
| 127 | 141 | IRLKVFVLGGCRHKL | " | *0105 | 40 | 29 | " | " |

TABLE 6b-continued

Predicted HLA class II-restricted CD4+ T cell epitopes contained in SLP sequences from HBV X protein (consensus sequence).

| | | HLA class II binding peptides in SLP derived from HBV X protein (consens. seq.) | | | | Peptide of invention (SLP) | | |
|---|---|---|---|---|---|---|---|---|
| Start | End | Sequence[A] | SEQ ID NO: | HLA-DRB1 molecule | Class II-B score[B] | SLP# | SLP Start | SLP End |
| 127 | 141 | IRLKVFVLGGCRHKL | " | *0106 | 70 | 29 | " | " |
| 127 | 141 | IRLKVFVLGGCRHKL | " | *0107 | 40 | 29 | " | " |
| 127 | 141 | IRLKVFVLGGCRHKL | " | *1101 | 56 | 29 | " | " |
| 127 | 141 | IRLKVFVLGGCRHKL | " | *1501 | 90 | 29 | " | " |
| | | Cumulative Class II-B score: | | | 1024 | | | |

"Start" and "End" are relative to the amino acid sequence of human HBV X protein as depicted in SEQ ID NO: 45
[A]Peptide amino acid sequence. Each HLA-DRB1 binding peptide of HBV X protein is listed separately for each HLA class II molecule to which it is predicted to bind, and each peptide can be listed multiple times for that reason.
[B]Class II-B score. See *Material and Methods* (Examples section).
[C]Cumulative Class II-B score. See *Material and Methods* (Examples section).

TABLE 7a

Predicted HLA class I-restricted CD8+ cytotoxic T cell epitopes contained in SLP sequences from HBV large surface protein.

| | | | HLA class I binding peptides contained in SLP sequences derived from HBV Surface antigen | | | | | | Peptide of invention (SLP) | | |
|---|---|---|---|---|---|---|---|---|---|---|---|
| Start | End | Length | Sequence[A] | SEQ ID NO: | HLA class 1 molecule | Class I-B score[B] | C-score[C] | Class I-BCI score[D] | SLP# | SLP Start | SLP End |
| 175 | 182 | 8 | MENITSGF | 1146 | B*4901 | 40 | 1,40 | 56 | 30 | 175 | 210 |
| 175 | 182 | 8 | MENITSGF | " | B*5001 | 35 | 1,40 | 49 | " | " | " |
| 175 | 182 | 8 | MENITSGF | " | B*1801 | 30 | 1,40 | 42 | " | " | " |
| 175 | 183 | 9 | MENITSGFL | 1147 | B*4403 | 90 | 0,93 | 84 | " | " | " |
| 175 | 183 | 9 | MENITSGFL | " | B*4402 | 85 | 0,93 | 79 | " | " | " |
| 175 | 183 | 9 | MENITSGFL | " | B*4001 | 75 | 0,93 | 70 | " | " | " |
| 175 | 183 | 9 | MENITSGFL | " | B*5001 | 25 | 0,93 | 23 | " | " | " |
| 175 | 183 | 9 | MENITSGFL | " | B*4901 | 20 | 0,93 | 19 | " | " | " |
| 175 | 184 | 10 | MENITSGFLG | 1148 | B*4402 | 75 | 0,59 | 44 | " | " | " |
| 175 | 184 | 10 | MENITSGFLG | " | B*4403 | 60 | 0,59 | 35 | " | " | " |
| 175 | 185 | 11 | MENITSGFLGP | 1149 | B*4402 | 35 | 0,19 | 7 | " | " | " |
| 175 | 186 | 12 | MENITSGFLGPL | 1150 | B*4001 | 90 | 0,80 | 72 | " | " | " |
| 175 | 186 | 12 | MENITSGFLGPL | " | B*4002 | 80 | 0,80 | 64 | " | " | " |
| 175 | 186 | 12 | MENITSGFLGPL | " | B*4402 | 80 | 0,80 | 64 | " | " | " |
| 175 | 186 | 12 | MENITSGFLGPL | " | B*4403 | 80 | 0,80 | 64 | " | " | " |
| 175 | 186 | 12 | MENITSGFLGPL | " | B*1801 | 70 | 0,80 | 56 | " | " | " |
| 175 | 186 | 12 | MENITSGFLGPL | " | B*3701 | 60 | 0,80 | 48 | " | " | " |
| 175 | 186 | 12 | MENITSGFLGPL | " | B*5001 | 55 | 0,80 | 44 | " | " | " |
| 175 | 186 | 12 | MENITSGFLGPL | " | B*4901 | 30 | 0,80 | 24 | " | " | " |
| 176 | 186 | 11 | ENITSGFLGPL | 1151 | A*6802 | 20 | 0,80 | 16 | " | " | " |

TABLE 7a-continued

Predicted HLA class I-restricted CD8+ cytotoxic T cell epitopes contained in SLP sequences from HBV large surface protein.

| | | | HLA class I binding peptides contained in SLP sequences derived from HBV Surface antigen | | | | | | Peptide of invention (SLP) | | |
|---|---|---|---|---|---|---|---|---|---|---|---|
| Start | End | Length | Sequence[A] | SEQ ID NO: | HLA class 1 molecule | Class I-B score[B] | C-score[C] | Class I-BCI score[D] | SLP# | SLP Start | SLP End |
| 175 | 187 | 13 | MENITSGFLGPLL | 1152 | B*4402 | 95 | 0,77 | 73 | " | " | " |
| 175 | 187 | 13 | MENITSGFLGPLL | " | B*4403 | 95 | 0,77 | 73 | " | " | " |
| 175 | 187 | 13 | MENITSGFLGPLL | " | B*4001 | 85 | 0,77 | 66 | " | " | " |
| 175 | 187 | 13 | MENITSGFLGPLL | " | B*5001 | 75 | 0,77 | 58 | " | " | " |
| 175 | 187 | 13 | MENITSGFLGPLL | " | B*3701 | 70 | 0,77 | 54 | " | " | " |
| 175 | 187 | 13 | MENITSGFLGPLL | " | B*4002 | 65 | 0,77 | 50 | " | " | " |
| 175 | 187 | 13 | MENITSGFLGPLL | " | B*4901 | 60 | 0,77 | 46 | " | " | " |
| 175 | 187 | 13 | MENITSGFLGPLL | " | B*1801 | 40 | 0,77 | 31 | " | " | " |
| 175 | 187 | 13 | MENITSGFLGPLL | " | B*1301 | 25 | 0,77 | 19 | " | " | " |
| 178 | 187 | 10 | ITSGFLGPLL | 1153 | A*3001 | 15 | 0,77 | 12 | " | " | " |
| 175 | 188 | 14 | MENITSGFLGPLLV | 1154 | B*4901 | 95 | 1,48 | 141 | " | " | " |
| 175 | 188 | 14 | MENITSGFLGPLLV | " | B*4402 | 90 | 1,48 | 133 | " | " | " |
| 175 | 188 | 14 | MENITSGFLGPLLV | " | B*4403 | 85 | 1,48 | 126 | " | " | " |
| 175 | 188 | 14 | MENITSGFLGPLLV | " | B*5001 | 80 | 1,48 | 119 | " | " | " |
| 175 | 188 | 14 | MENITSGFLGPLLV | " | B*4001 | 65 | 1,48 | 96 | " | " | " |
| 175 | 188 | 14 | MENITSGFLGPLLV | " | B*3701 | 50 | 1,48 | 74 | " | " | " |
| 175 | 188 | 14 | MENITSGFLGPLLV | " | B*4002 | 10 | 1,48 | 15 | " | " | " |
| 182 | 193 | 12 | FLGPLLVLQAGF | 1155 | B*1501 | 30 | 1,17 | 35 | " | " | " |
| 186 | 193 | 8 | LLVLQAGF | 1156 | B*1501 | 10 | 1,17 | 12 | " | " | " |
| 187 | 194 | 8 | LVLQAGFF | 1157 | A*2601 | 15 | 0,99 | 15 | " | " | " |
| 182 | 195 | 14 | FLGPLLVLQAGFFL | 1158 | A*0201 | 63 | 1,59 | 100 | " | " | " |
| 182 | 195 | 14 | FLGPLLVLQAGFFL | " | A*0206 | 55 | 1,59 | 87 | " | " | " |
| 186 | 195 | 10 | LLVLqAGFFL | 1159 | A*0201 | 66 | 1,59 | 104 | " | " | " |
| 187 | 195 | 9 | LVLQAGFFL | 1160 | A*0201 | 20 | 1,59 | 32 | " | " | " |
| 187 | 196 | 10 | LVLQAGFFLL | 1161 | A*0206 | 20 | 1,85 | 37 | " | " | " |
| 188 | 196 | 9 | VLQAGFFLL | 1162 | A*0201 | 26 | 1,85 | 48 | " | " | " |
| 189 | 196 | 8 | LQAGFFLL | 1163 | B*3701 | 85 | 1,85 | 157 | " | " | " |
| 189 | 196 | 8 | LQAGFFLL | " | B*4801 | 60 | 1,85 | 111 | " | " | " |
| 189 | 196 | 8 | LQAGFFLL | " | B*1301 | 50 | 1,85 | 92 | " | " | " |
| 189 | 196 | 8 | LQAGFFLL | " | B*3901 | 45 | 1,85 | 83 | " | " | " |
| 189 | 196 | 8 | LQAGFFLL | " | B*1302 | 40 | 1,85 | 74 | " | " | " |
| 189 | 196 | 8 | LQAGFFLL | " | B*3801 | 35 | 1,85 | 65 | " | " | " |
| 189 | 196 | 8 | LQAGFFLL | " | B*5001 | 30 | 1,85 | 55 | " | " | " |
| 187 | 198 | 12 | LVLQAGFFLLTR | 1164 | A*7401 | 30 | 1,36 | 41 | " | " | " |
| 187 | 198 | 12 | LVLQAGFFLLTR | " | A*3101 | 10 | 1,36 | 14 | " | " | " |

TABLE 7a-continued

Predicted HLA class I-restricted CD8+ cytotoxic T cell epitopes
contained in SLP sequences from HBV large surface protein.

| | | | HLA class I binding peptides contained in SLP sequences derived from HBV Surface antigen | | | | | Peptide of invention (SLP) | | |
|---|---|---|---|---|---|---|---|---|---|---|
| Start | End | Length | Sequence[A] | SEQ ID NO: | HLA class 1 molecule | Class I-B score[B] | C-score[C] | Class I-BCI score[D] | SLP# | SLP Start | SLP End |
| 187 | 198 | 12 | LVLQAGFFLLTR | " | A*1101 | 5 | 1,36 | 7 | " | " | " |
| 188 | 198 | 11 | VLQAGFFLLTR | 1165 | A*7401 | 90 | 1,36 | 122 | " | " | " |
| 189 | 198 | 10 | LQAGFFLLTR | 1166 | A*3101 | 80 | 1,36 | 109 | " | " | " |
| 189 | 198 | 10 | LQAGFFLLTR | " | A*7401 | 65 | 1,36 | 88 | " | " | " |
| 189 | 198 | 10 | LQAGFFLLTR | " | A*1101 | 15 | 1,36 | 20 | " | " | " |
| 190 | 198 | 9 | QAGFFLLTR | 1167 | A*7401 | 10 | 1,36 | 14 | " | " | " |
| 191 | 198 | 8 | AGFFLLTR | 1168 | A*7401 | 70 | 1,36 | 95 | " | " | " |
| 189 | 199 | 11 | LQAGFFLLTRI | 1169 | B*5201 | 95 | 1,36 | 129 | " | " | " |
| 189 | 199 | 11 | LQAGFFLLTRI | " | B*1302 | 85 | 1,36 | 115 | " | " | " |
| 189 | 199 | 11 | LQAGFFLLTRI | " | B*4901 | 50 | 1,36 | 68 | " | " | " |
| 189 | 199 | 11 | LQAGFFLLTRI | " | B*1301 | 30 | 1,36 | 41 | " | " | " |
| 189 | 199 | 11 | LQAGFFLLTRI | " | B*4001 | 25 | 1,36 | 34 | " | " | " |
| 189 | 199 | 11 | LQAGFFLLTRI | " | B*5001 | 15 | 1,36 | 20 | " | " | " |
| 189 | 199 | 11 | LQAGFFLLTRI | " | B*3701 | 10 | 1,36 | 14 | " | " | " |
| 189 | 200 | 12 | LQAGFFLLTRIL | 1170 | B*4001 | 60 | 1,90 | 114 | " | " | " |
| 189 | 200 | 12 | LQAGFFLLTRIL | " | B*3701 | 40 | 1,90 | 76 | " | " | " |
| 189 | 200 | 12 | LQAGFFLLTRIL | " | B*4801 | 40 | 1,90 | 76 | " | " | " |
| 189 | 200 | 12 | LQAGFFLLTRIL | " | B*3901 | 30 | 1,90 | 57 | " | " | " |
| 189 | 200 | 12 | LQAGFFLLTRIL | " | B*5001 | 5 | 1,90 | 9 | " | " | " |
| 189 | 202 | 14 | LQAGFFLLTRILTI | 1171 | B*5201 | 80 | 1,73 | 139 | " | " | " |
| 189 | 202 | 14 | LQAGFFLLTRILTI | " | B*4901 | 65 | 1,73 | 113 | " | " | " |
| 189 | 202 | 14 | LQAGFFLLTRILTI | " | B*5001 | 65 | 1,73 | 113 | " | " | " |
| 189 | 202 | 14 | LQAGFFLLTRILTI | " | B*1301 | 60 | 1,73 | 104 | " | " | " |
| 189 | 202 | 14 | LQAGFFLLTRILTI | " | B*1302 | 55 | 1,73 | 95 | " | " | " |
| 189 | 202 | 14 | LQAGFFLLTRILTI | " | A*0206 | 50 | 1,73 | 87 | " | " | " |
| 189 | 202 | 14 | LQAGFFLLTRILTI | " | B*3701 | 45 | 1,73 | 78 | " | " | " |
| 189 | 202 | 14 | LQAGFFLLTRILTI | " | B*4001 | 45 | 1,73 | 78 | " | " | " |
| 191 | 202 | 12 | AGFFLLTRILTI | 1172 | B*5201 | 50 | 1,73 | 87 | " | " | " |
| 194 | 202 | 9 | FLLTRILTI | 1173 | B*0801 | 80 | 1,73 | 139 | " | " | " |
| 194 | 202 | 9 | FLLTRILTI | " | A*0201 | 37 | 1,73 | 64 | " | " | " |
| 194 | 206 | 13 | FLLTRILTIPQSL | 1174 | B*0801 | 100 | 1,23 | 123 | " | " | " |
| 194 | 206 | 13 | FLLTRILTIPQSL | " | A*0201 | 29 | 1,23 | 35 | " | " | " |
| 195 | 206 | 12 | LLTRILTIPQSL | 1175 | B*1402 | 70 | 1,23 | 86 | " | " | " |
| 196 | 206 | 11 | LTRILTIPQSL | 1176 | A*3001 | 25 | 1,23 | 31 | " | " | " |
| 196 | 206 | 11 | LTRILTIPQSL | " | B*1402 | 10 | 1,23 | 12 | " | " | " |

TABLE 7a-continued

Predicted HLA class I-restricted CD8+ cytotoxic T cell epitopes
contained in SLP sequences from HBV large surface protein.

| | | | HLA class I binding peptides contained in SLP sequences derived from HBV Surface antigen | | | | | | Peptide of invention (SLP) | | |
|---|---|---|---|---|---|---|---|---|---|---|---|
| Start | End | Length | Sequence[A] | SEQ ID NO: | HLA class 1 molecule | Class I-B score[B] | C-score[C] | Class I-BCI score[D] | SLP# | SLP Start | SLP End |
| 197 | 206 | 10 | TRILTIPQSL | 1177 | B*3901 | 100 | 1,23 | 123 | " | " | " |
| 197 | 206 | 10 | TRILTIPQSL | " | B*2705 | 5 | 1,23 | 6 | " | " | " |
| 196 | 209 | 14 | LTRILTIPQSLDSW | 1178 | B*5701 | 75 | 1,47 | 111 | " | " | " |
| 196 | 209 | 14 | LTRILTIPQSLDSW | " | B*5802 | 40 | 1,47 | 59 | " | " | " |
| 198 | 209 | 12 | RILTIPQSLDSW | 1179 | B*5801 | 65 | 1,47 | 96 | " | " | " |
| 198 | 209 | 12 | RILTIPQSLDSW | " | A*3201 | 60 | 1,47 | 88 | " | " | " |
| 198 | 209 | 12 | RILTIPQSLDSW | " | B*5701 | 50 | 1,47 | 74 | " | " | " |
| 200 | 209 | 10 | LTIPQSLDSW | 1180 | B*5802 | 90 | 1,47 | 133 | " | " | " |
| 200 | 209 | 10 | LTIPQSLDSW | " | A*2501 | 40 | 1,47 | 59 | " | " | " |
| 197 | 210 | 14 | TRILTIPQSLDSWW | 1181 | B*4402 | 20 | 0,79 | 16 | " | " | " |
| 197 | 210 | 14 | TRILTIPQSLDSWW | " | B*4403 | 15 | 0,79 | 12 | " | " | " |
| 198 | 210 | 13 | RILTIPQSLDSWW | 1182 | B*5801 | 60 | 0,79 | 47 | " | " | " |
| 198 | 210 | 13 | RILTIPQSLDSWW | " | B*5701 | 40 | 0,79 | 31 | " | " | " |
| 200 | 210 | 11 | LTIPQSLDSWW | 1183 | B*5802 | 75 | 0,79 | 59 | " | " | " |
| 200 | 210 | 11 | LTIPQSLDSWW | " | B*5801 | 40 | 0,79 | 31 | " | " | " |
| 202 | 210 | 9 | IPQSLDSWW | 1184 | B*5301 | 50 | 0,79 | 39 | " | " | " |
| | | | | | Cumulative Class I-BCI score: | | | 6882 | | | |
| 239 | 246 | 8 | CPPICPGY | 1185 | B*3501 | 45 | 1,44 | 65 | 31 | 239 | 274 |
| 239 | 248 | 10 | CPPICPGYRW | 1186 | B*5301 | 85 | 1,94 | 165 | " | " | " |
| 240 | 251 | 12 | PPICPGYRWMCL | 1187 | B*3503 | 50 | 1,46 | 73 | " | " | " |
| 243 | 251 | 9 | CPGYRWMCL | 1188 | B*0801 | 75 | 1,46 | 110 | " | " | " |
| 243 | 251 | 9 | CPGYRWMCL | " | B*1402 | 50 | 1,46 | 73 | " | " | " |
| 243 | 252 | 10 | CPGYRWMCLR | 1189 | A*3303 | 5 | 1,04 | 5 | " | " | " |
| 244 | 252 | 9 | PGYRWMCLR | 1190 | A*3101 | 5 | 1,04 | 5 | " | " | " |
| 245 | 252 | 8 | GYRWMCLR | 1191 | A*3101 | 95 | 1,04 | 99 | " | " | " |
| 245 | 252 | 8 | GYRWMCLR | " | A*3303 | 10 | 1,04 | 10 | " | " | " |
| 245 | 253 | 9 | GYRWMCLRR | 1192 | A*3101 | 45 | 0,95 | 43 | " | " | " |
| 245 | 254 | 10 | GYRWMCLRRF | 1193 | A*2402 | 10 | 1,01 | 10 | " | " | " |
| 246 | 254 | 9 | YRWMCLRRF | 1194 | B*2702 | 40 | 1,01 | 41 | " | " | " |
| 246 | 254 | 9 | YRWMCLRRF | " | B*2705 | 40 | 1,01 | 41 | " | " | " |
| 245 | 255 | 11 | GYRWMCLRRFI | 1195 | A*3001 | 35 | 0,99 | 35 | " | " | " |
| 246 | 255 | 10 | YRWMCLRRFI | 1196 | B*1402 | 90 | 0,99 | 89 | " | " | " |
| 246 | 255 | 10 | YRWMCLRRFI | " | B*2702 | 85 | 0,99 | 84 | " | " | " |
| 246 | 255 | 10 | YRWMCLRRFI | " | B*2705 | 20 | 0,99 | 20 | " | " | " |
| 243 | 256 | 14 | CPGYRWMCLRRFII | 1197 | B*0801 | 65 | 0,86 | 56 | " | " | " |

TABLE 7a-continued

Predicted HLA class I-restricted CD8+ cytotoxic T cell epitopes
contained in SLP sequences from H TABLE 7a-continued Predicted HLA class I-restricted CD8+ cytotoxic T cell epitopes
contained in SLP sequences from HBV large surface protein.

| | | | HLA class I binding peptides contained in SLP sequences derived from HBV Surface antigen | | | | | | Peptide of invention (SLP) | |

TABLE 7a-continued

Predicted HLA class I-restricted CD8+ cytotoxic T cell epitopes
contained in SLP sequences from HB TABLE 7a-continued Predicted HLA class I-restricted CD8+ cytotoxic T cell epitopes
contained in SLP sequences from HBV large surface protein.

| | HLA class I binding peptides contained in SLP sequences derived from HBV Surface antigen | | | | | | | | Peptide of invention (SLP) | | |
|---|---|---|---|---|---|---|---|---|---|---|---|
| Start | End | Length | Sequence[A] | SEQ ID NO: | HLA class 1 molecule | Class I-B score[B] | C-score[C] | Class I-BCI score[D] | SLP# | SLP Start | SLP End |
| 261 | 274 | 14 | LLLCLIFLLVLLDY | 1258 | A*2902 | 80 | 1,83 | 147 | " | " | " |
| 262 | 274 | 13 | LLCLIFLLVLLDY | 1259 | A*2902 | 90 | 1,83 | 165 | " | " | " |
| 262 | 274 | 13 | LLCLIFLLVLLDY | " | A*0101 | 75 | 1,83 | 138 | " | " | " |
| 264 | 274 | 11 | CLIFLLVLLDY | 1260 | A*0101 | 85 | 1,83 | 156 | " | " | " |
| 265 | 274 | 10 | LIFLLVLLDY | 1261 | A*0101 | 55 | 1,83 | 101 | " | " | " |
| 265 | 274 | 10 | LIFLLVLLDY | " | A*0301 | 35 | 1,83 | 64 | " | " | " |
| 266 | 274 | 9 | IFLLVLLDY | 1262 | A*2902 | 70 | 1,83 | 128 | " | " | " |
| 267 | 274 | 8 | FLLVLLDY | 1263 | B*1502 | 60 | 1,83 | 110 | " | " | " |
| | | | | | Cumulative Class I-BCI score: | | | 10214 | | | |
| 324 | 331 | 8 | IPIPSSWA | 1264 | B*5601 | 85 | 0,15 | 13 | 32 | 323 | 358 |
| 324 | 331 | 8 | IPIPSSWA | " | B*5501 | 55 | 0,16 | 9 | " | " | " |
| 324 | 332 | 9 | IPIPSSWAF | 1265 | B*3501 | 70 | 1,87 | 131 | " | " | " |
| 324 | 332 | 9 | IPIPSSWAF | " | B*3503 | 55 | 1,87 | 103 | " | " | " |
| 324 | 332 | 9 | IPIPSSWAF | " | B*5301 | 45 | 1,87 | 84 | " | " | " |
| 324 | 333 | 10 | IPIPSSWAFA | 1266 | B*5601 | 100 | 1,02 | 102 | " | " | " |
| 324 | 333 | 10 | IPIPSSWAFA | " | B*5501 | 85 | 1,02 | 87 | " | " | " |
| 326 | 333 | 8 | IPSSWAFA | 1267 | B*5601 | 45 | 1,02 | 46 | " | " | " |
| 326 | 333 | 8 | IPSSWAFA | " | B*5501 | 40 | 1,02 | 41 | " | " | " |
| 323 | 334 | 12 | CIPIPSSWAFAK | 1268 | A*0301 | 80 | 1,04 | 83 | " | " | " |
| 323 | 334 | 12 | CIPIPSSWAFAK | " | A*1101 | 30 | 1,04 | 31 | " | " | " |
| 324 | 334 | 11 | IPIPSSWAFAK | 1269 | B*3501 | 15 | 1,04 | 16 | " | " | " |
| 326 | 334 | 9 | IPSSWAFAK | 1270 | A*1101 | 10 | 1,04 | 10 | " | " | " |
| 327 | 334 | 8 | PSSWAFAK | 1271 | A*0301 | 45 | 1,04 | 47 | " | " | " |
| 324 | 335 | 12 | IPIPSSWAFAKY | 1272 | B*3503 | 85 | 1,90 | 161 | " | " | " |
| 324 | 335 | 12 | IPIPSSWAFAKY | " | B*3501 | 80 | 1,90 | 152 | " | " | " |
| 324 | 335 | 12 | IPIPSSWAFAKY | " | B*5301 | 25 | 1,90 | 47 | " | " | " |
| 325 | 335 | 11 | PIPSSWAFAKY | 1273 | A*2501 | 30 | 1,90 | 57 | " | " | " |
| 326 | 335 | 10 | IPSSWAFAKY | 1274 | B*3501 | 35 | 1,90 | 66 | " | " | " |
| 327 | 335 | 9 | PSSWAFAKY | 1275 | A*0101 | 65 | 1,90 | 123 | " | " | " |
| 327 | 335 | 9 | PSSWAFAKY | " | A*3002 | 45 | 1,90 | 85 | " | " | " |
| 328 | 335 | 8 | SSWAFAKY | 1276 | A*2501 | 75 | 1,90 | 142 | " | " | " |
| 328 | 335 | 8 | SSWAFAKY | " | A*3002 | 75 | 1,90 | 142 | " | " | " |
| 328 | 335 | 8 | SSWAFAKY | " | A*2902 | 55 | 1,90 | 104 | " | " | " |
| 324 | 336 | 13 | IPIPSSWAFAKYL | 1277 | B*3503 | 80 | 1,06 | 85 | " | " | " |

TABLE 7a-continued

Predicted HLA class I-restricted CD8+ cytotoxic T cell epitopes
contained in SLP sequences from HBV large surface protein.

| | | | HLA class I binding peptides contained in SLP sequences derived from HBV Surface antigen | | | | | | Peptide of invention (SLP) | | |
|---|---|---|---|---|---|---|---|---|---|---|---|
| Start | End | Length | Sequence[A] | SEQ ID NO: | HLA class 1 molecule | Class I-B score[B] | C-score[C] | Class I-BCI score[D] | SLP# | SLP Start | SLP End |
| 324 | 336 | 13 | IPIPSSWAFAKYL | " | B*5101 | 65 | 1,06 | 69 | " | " | " |
| 324 | 337 | 14 | IPIPSSWAFAKYLW | 1278 | B*5301 | 55 | 1,58 | 87 | " | " | " |
| 324 | 337 | 14 | IPIPSSWAFAKYLW | " | B*5101 | 20 | 1,58 | 32 | " | " | " |
| 324 | 337 | 14 | IPIPSSWAFAKYLW | " | B*5701 | 5 | 1,58 | 8 | " | " | " |
| 326 | 337 | 12 | IPSSWAFAKYLW | 1279 | B*5301 | 100 | 1,58 | 158 | " | " | " |
| 326 | 337 | 12 | IPSSWAFAKYLW | " | B*5802 | 10 | 1,58 | 16 | " | " | " |
| 328 | 337 | 10 | SSWAFAKYLW | 1280 | B*5802 | 100 | 1,58 | 158 | " | " | " |
| 328 | 337 | 10 | SSWAFAKYLW | " | B*5701 | 95 | 1,58 | 150 | " | " | " |
| 328 | 337 | 10 | SSWAFAKYLW | " | B*4403 | 45 | 1,58 | 71 | " | " | " |
| 328 | 337 | 10 | SSWAFAKYLW | " | B*5801 | 35 | 1,58 | 55 | " | " | " |
| 328 | 337 | 10 | SSWAFAKYLW | " | B*4402 | 15 | 1,58 | 24 | " | " | " |
| 330 | 337 | 8 | WAFAKYLW | 1281 | B*5801 | 85 | 1,58 | 134 | " | " | " |
| 330 | 337 | 8 | WAFAKYLW | " | B*5701 | 65 | 1,58 | 103 | " | " | " |
| 330 | 337 | 8 | WAFAKYLW | " | B*5802 | 50 | 1,58 | 79 | | | |
| 326 | 339 | 14 | IPSSWAFAKYLWEW | 1282 | B*5301 | 95 | 1,83 | 174 | " | " | " |
| 328 | 339 | 12 | SSWAFAKYLWEW | 1283 | B*5701 | 100 | 1,83 | 183 | " | " | " |
| 328 | 339 | 12 | SSWAFAKYLWEW | " | B*5801 | 95 | 1,83 | 174 | " | " | " |
| 328 | 339 | 12 | SSWAFAKYLWEW | " | B*5802 | 65 | 1,83 | 119 | " | " | " |
| 328 | 339 | 12 | SSWAFAKYLWEW | " | A*3201 | 55 | 1,83 | 101 | " | " | " |
| 328 | 339 | 12 | SSWAFAKYLWEW | " | B*4403 | 50 | 1,83 | 91 | " | " | " |
| 328 | 339 | 12 | SSWAFAKYLWEW | " | B*4402 | 10 | 1,83 | 18 | " | " | " |
| 330 | 339 | 10 | WAFAKYLWEW | 1284 | B*5802 | 85 | 1,83 | 156 | " | " | " |
| 330 | 339 | 10 | WAFAKYLWEW | " | B*5201 | 70 | 1,83 | 128 | " | " | " |
| 331 | 339 | 9 | AFAKYLWEW | 1285 | B*4402 | 50 | 1,83 | 91 | " | " | " |
| 331 | 339 | 9 | AFAKYLWEW | " | B*4403 | 40 | 1,83 | 73 | " | " | " |
| 332 | 339 | 8 | FAKYLWEW | 1286 | B*4601 | 40 | 1,83 | 73 | " | " | " |
| 332 | 339 | 8 | FAKYLWEW | " | B*5701 | 30 | 1,83 | 55 | " | " | " |
| 330 | 342 | 13 | WAFAKYLWEWASV | 1287 | A*6802 | 85 | 1,92 | 164 | " | " | " |
| 330 | 342 | 13 | WAFAKYLWEWASV | " | B*1402 | 20 | 1,92 | 38 | " | " | " |
| 332 | 342 | 11 | FAKYLWEWASV | 1288 | B*4601 | 50 | 1,92 | 96 | " | " | " |
| 330 | 343 | 14 | WAFAKYLWEWASVR | 1289 | A*3303 | 80 | 1,07 | 85 | " | " | " |
| 330 | 343 | 14 | WAFAKYLWEWASVR | " | A*6801 | 50 | 1,07 | 53 | " | " | " |
| 330 | 343 | 14 | WAFAKYLWEWASVR | " | A*7401 | 15 | 1,07 | 16 | " | " | " |
| 331 | 343 | 13 | AFAKYLWEWASVR | 1290 | A*3101 | 70 | 1,07 | 75 | " | " | " |
| 331 | 343 | 13 | AFAKYLWEWASVR | " | A*3303 | 35 | 1,07 | 37 | " | " | " |

TABLE 7a-continued

Predicted HLA class I-restricted CD8+ cytotoxic T cell epitopes
contained in SLP sequences from HBV large surface protein.

| | | | HLA class I binding peptides contained in SLP sequences derived from HBV Surface antigen | | | | | | Peptide of invention (SLP) | | |
|---|---|---|---|---|---|---|---|---|---|---|---|
| Start | End | Length | Sequence[A] | SEQ ID NO: | HLA class 1 molecule | Class I-B score[B] | C-score[C] | Class I-BCI score[D] | SLP# | SLP Start | SLP End |
| 332 | 343 | 12 | FAKYLWEWASVR | 1291 | A*3303 | 85 | 1,07 | 91 | " | " | " |
| 332 | 343 | 12 | FAKYLWEWASVR | " | A*6801 | 60 | 1,07 | 64 | " | " | " |
| 332 | 343 | 12 | FAKYLWEWASVR | " | A*3101 | 55 | 1,07 | 59 | " | " | " |
| 334 | 343 | 10 | KYLWEWASVR | 1292 | A*3101 | 100 | 1,07 | 107 | " | " | " |
| 335 | 343 | 9 | YLWEWASVR | 1293 | A*7401 | 85 | 1,07 | 91 | " | " | " |
| 335 | 343 | 9 | YLWEWASVR | " | A*3303 | 40 | 1,07 | 43 | " | " | " |
| 335 | 343 | 9 | YLWEWASVR | " | A*3101 | 35 | 1,07 | 37 | " | " | " |
| 335 | 343 | 9 | YLWEWASVR | " | A*0301 | 20 | 1,07 | 21 | " | " | " |
| 331 | 344 | 14 | AFAKYLWEWASVRF | 1294 | A*2402 | 30 | 1,86 | 56 | " | " | " |
| 331 | 344 | 14 | AFAKYLWEWASVRF | " | A*2301 | 5 | 1,86 | 9 | " | " | " |
| 332 | 344 | 13 | FAKYLWEWASVRF | 1295 | B*4601 | 75 | 1,86 | 139 | " | " | " |
| 335 | 344 | 10 | YLWEWASVRF | 1296 | B*1502 | 90 | 1,86 | 167 | " | " | " |
| 335 | 344 | 10 | YLWEWASVRF | " | B*1525 | 45 | 1,86 | 84 | " | " | " |
| 337 | 344 | 8 | WEWASVRF | 1297 | B*3701 | 80 | 1,86 | 149 | " | " | " |
| 337 | 344 | 8 | WEWASVRF | " | B*4901 | 80 | 1,86 | 149 | " | " | " |
| 337 | 344 | 8 | WEWASVRF | " | B*5001 | 50 | 1,86 | 93 | " | " | " |
| 337 | 344 | 8 | WEWASVRF | " | B*1301 | 45 | 1,86 | 84 | " | " | " |
| 337 | 344 | 8 | WEWASVRF | " | B*4403 | 5 | 1,86 | 9 | " | " | " |
| 337 | 345 | 9 | WEWASVRFS | 1298 | B*4403 | 65 | 0,50 | 33 | " | " | " |
| 337 | 345 | 9 | WEWASVRFS | " | B*5001 | 60 | 0,50 | 30 | " | " | " |
| 337 | 345 | 9 | WEWASVRFS | " | B*4002 | 55 | 0,50 | 28 | " | " | " |
| 337 | 345 | 9 | WEWASVRFS | " | B*4901 | 15 | 0,50 | 8 | " | " | " |
| 333 | 346 | 14 | AKYLWEWASVRFSW | 1299 | B*4403 | 35 | 1,50 | 52 | " | " | " |
| 334 | 346 | 13 | KYLWEWASVRFSW | 1300 | A*2402 | 95 | 1,50 | 142 | " | " | " |
| 334 | 346 | 13 | KYLWEWASVRFSW | " | A*2301 | 75 | 1,50 | 112 | " | " | " |
| 335 | 346 | 12 | YLWEWASVRFSW | 1301 | A*3201 | 80 | 1,50 | 120 | " | " | " |
| 335 | 346 | 12 | YLWEWASVRFSW | " | B*1302 | 75 | 1,50 | 112 | " | " | " |
| 335 | 346 | 12 | YLWEWASVRFSW | " | B*5201 | 45 | 1,50 | 67 | " | " | " |
| 337 | 346 | 10 | WEWASVRFSW | 1302 | B*1301 | 100 | 1,50 | 150 | " | " | " |
| 337 | 346 | 10 | WEWASVRFSW | " | B*4402 | 100 | 1,50 | 150 | " | " | " |
| 337 | 346 | 10 | WEWASVRFSW | " | B*4403 | 100 | 1,50 | 150 | " | " | " |
| 337 | 346 | 10 | WEWASVRFSW | " | B*1302 | 90 | 1,50 | 135 | " | " | " |
| 337 | 346 | 10 | WEWASVRFSW | " | B*4002 | 90 | 1,50 | 135 | " | " | " |
| 337 | 346 | 10 | WEWASVRFSW | " | B*4901 | 75 | 1,50 | 112 | " | " | " |
| 339 | 346 | 8 | WASVRFSW | 1303 | B*5801 | 50 | 1,50 | 75 | " | " | " |

TABLE 7a-continued

Predicted HLA class I-restricted CD8+ cytotoxic T cell epitopes contained in SLP sequences from HBV large surface protein.

| | | | HLA class I binding peptides contained in SLP sequences derived from HBV Surface antigen | | | | | | Peptide of invention (SLP) | | |
|---|---|---|---|---|---|---|---|---|---|---|---|
| Start | End | Length | Sequence[A] | SEQ ID NO: | HLA class 1 molecule | Class I-B score[B] | C-score[C] | Class I-BCI score[D] | SLP# | SLP Start | SLP End |
| 334 | 347 | 14 | KYLWEWASVRFSWL | 1304 | A*2402 | 90 | 1,37 | 123 | " | " | " |
| 334 | 347 | 14 | KYLWEWASVRFSWL | " | A*2301 | 40 | 1,37 | 55 | " | " | " |
| 335 | 347 | 13 | YLWEWASVRFSWL | 1305 | A*0201 | 100 | 1,37 | 137 | " | " | " |
| 335 | 347 | 13 | YLWEWASVRFSWL | " | A*0206 | 60 | 1,37 | 82 | " | " | " |
| 337 | 347 | 11 | WEWASVRFSWL | 1306 | B*4001 | 95 | 1,37 | 130 | " | " | " |
| 337 | 347 | 11 | WEWASVRFSWL | " | B*3701 | 90 | 1,37 | 123 | " | " | " |
| 337 | 347 | 11 | WEWASVRFSWL | " | B*5001 | 90 | 1,37 | 123 | " | " | " |
| 337 | 347 | 11 | WEWASVRFSWL | " | B*4002 | 85 | 1,37 | 117 | " | " | " |
| 337 | 347 | 11 | WEWASVRFSWL | " | B*4901 | 85 | 1,37 | 117 | " | " | " |
| 337 | 347 | 11 | WEWASVRFSWL | " | B*1301 | 80 | 1,37 | 110 | " | " | " |
| 337 | 347 | 11 | WEWASVRFSWL | " | B*4402 | 55 | 1,37 | 75 | " | " | " |
| 337 | 347 | 11 | WEWASVRFSWL | " | B*1302 | 10 | 1,37 | 14 | " | " | " |
| 339 | 347 | 9 | WASVRFSWL | 1307 | B*0801 | 50 | 1,37 | 69 | " | " | " |
| 337 | 348 | 12 | WEWASVRFSWLS | 1308 | B*1801 | 80 | 0,54 | 43 | " | " | " |
| 337 | 348 | 12 | WEWASVRFSWLS | " | B*4002 | 70 | 0,54 | 38 | " | " | " |
| 337 | 348 | 12 | WEWASVRFSWLS | " | B*4901 | 45 | 0,54 | 24 | " | " | " |
| 337 | 348 | 12 | WEWASVRFSWLS | " | B*5001 | 45 | 0,54 | 24 | " | " | " |
| 337 | 348 | 12 | WEWASVRFSWLS | " | B*4403 | 20 | 0,54 | 11 | " | " | " |
| 337 | 348 | 12 | WEWASVRFSWLS | " | B*3701 | 5 | 0,54 | 3 | " | " | " |
| 341 | 348 | 8 | SVRFSWLS | 1309 | A*3001 | 40 | 0,54 | 22 | " | " | " |
| 337 | 349 | 13 | WEWASVRFSWLSL | 1310 | B*1801 | 100 | 1,61 | 161 | " | " | " |
| 337 | 349 | 13 | WEWASVRFSWLSL | " | B*3701 | 100 | 1,61 | 161 | " | " | " |
| 337 | 349 | 13 | WEWASVRFSWLSL | " | B*4001 | 100 | 1,61 | 161 | " | " | " |
| 337 | 349 | 13 | WEWASVRFSWLSL | " | B*4002 | 100 | 1,61 | 161 | " | " | " |
| 337 | 349 | 13 | WEWASVRFSWLSL | " | B*4901 | 100 | 1,61 | 161 | " | " | " |
| 337 | 349 | 13 | WEWASVRFSWLSL | " | B*5001 | 100 | 1,61 | 161 | " | " | " |
| 337 | 349 | 13 | WEWASVRFSWLSL | " | B*1301 | 90 | 1,61 | 145 | " | " | " |
| 337 | 349 | 13 | WEWASVRFSWLSL | " | B*4403 | 75 | 1,61 | 120 | " | " | " |
| 337 | 349 | 13 | WEWASVRFSWLSL | " | B*4402 | 70 | 1,61 | 112 | " | " | " |
| 339 | 349 | 11 | WASVRFSWLSL | 1311 | B*1402 | 85 | 1,61 | 137 | " | " | " |
| 341 | 349 | 9 | SVRFSWLSL | 1312 | A*3001 | 90 | 1,61 | 145 | " | " | " |
| 341 | 349 | 9 | SVRFSWLSL | " | B*0702 | 80 | 1,61 | 129 | " | " | " |
| 342 | 349 | 8 | VRFSWLSL | 1313 | B*3901 | 70 | 1,61 | 112 | " | " | " |
| 337 | 350 | 14 | WEWASVRFSWLSLL | 1314 | B*3701 | 95 | 1,15 | 109 | " | " | " |
| 337 | 350 | 14 | WEWASVRFSWLSLL | " | B*4002 | 95 | 1,15 | 109 | " | " | " |

TABLE 7a-continued

Predicted HLA class I-restricted CD8+ cytotoxic T cell epitopes
contained in SLP sequences from HBV large surface protein.

| | | | HLA class I binding peptides contained in SLP sequences derived from HBV Surface antigen | | | | | | Peptide of invention (SLP) | | |
|---|---|---|---|---|---|---|---|---|---|---|---|
| Start | End | Length | Sequence[A] | SEQ ID NO: | HLA class 1 molecule | Class I-B score[B] | C-score[C] | Class I-BCI score[D] | SLP# | SLP Start | SLP End |
| 337 | 350 | 14 | WEWASVRFSWLSLL | " | B*5001 | 95 | 1,15 | 109 | " | " | " |
| 337 | 350 | 14 | WEWASVRFSWLSLL | " | B*1801 | 90 | 1,15 | 104 | " | " | " |
| 337 | 350 | 14 | WEWASVRFSWLSLL | " | B*4901 | 90 | 1,15 | 104 | " | " | " |
| 337 | 350 | 14 | WEWASVRFSWLSLL | " | B*1301 | 85 | 1,15 | 98 | " | " | " |
| 337 | 350 | 14 | WEWASVRFSWLSLL | " | B*4001 | 80 | 1,15 | 92 | " | " | " |
| 337 | 350 | 14 | WEWASVRFSWLSLL | " | B*4403 | 70 | 1,15 | 81 | " | " | " |
| 337 | 350 | 14 | WEWASVRFSWLSLL | " | B*4801 | 70 | 1,15 | 81 | " | " | " |
| 337 | 350 | 14 | WEWASVRFSWLSLL | " | B*4402 | 60 | 1,15 | 69 | " | " | " |
| 337 | 350 | 14 | WEWASVRFSWLSLL | " | B*1302 | 50 | 1,15 | 58 | " | " | " |
| 342 | 350 | 9 | VRFSWLSLL | 1315 | B*3801 | 65 | 1,15 | 75 | " | " | " |
| 342 | 350 | 9 | VRFSWLSLL | " | B*2702 | 20 | 1,15 | 23 | " | " | " |
| 339 | 351 | 13 | WASVRFSWLSLLV | 1316 | B*5101 | 30 | 1,47 | 44 | " | " | " |
| 341 | 351 | 11 | SVRFSWLSLLV | 1317 | A*3001 | 85 | 1,47 | 125 | " | " | " |
| 340 | 353 | 14 | ASVRFSWLSLLVPF | 1318 | B*4601 | 30 | 0,19 | 6 | " | " | " |
| 340 | 353 | 14 | ASVRFSWLSLLVPF | " | B*1525 | 15 | 0,19 | 3 | " | " | " |
| 341 | 353 | 13 | SVRFSWLSLLVPF | 1319 | B*1501 | 80 | 0,19 | 15 | " | " | " |
| 341 | 353 | 13 | SVRFSWLSLLVPF | " | B*1525 | 60 | 0,19 | 11 | " | " | " |
| 341 | 353 | 13 | SVRFSWLSLLVPF | " | B*1502 | 25 | 0,19 | 5 | " | " | " |
| 341 | 353 | 13 | SVRFSWLSLLVPF | " | A*3001 | 20 | 0,19 | 4 | " | " | " |
| 342 | 353 | 12 | VRFSWLSLLVPF | 1320 | B*2702 | 65 | 0,19 | 12 | " | " | " |
| 342 | 353 | 12 | VRFSWLSLLVPF | " | B*2705 | 55 | 0,19 | 10 | " | " | " |
| 343 | 353 | 11 | RFSWLSLLVPF | 1321 | A*3201 | 85 | 0,19 | 16 | " | " | " |
| 343 | 353 | 11 | RFSWLSLLVPF | " | A*2402 | 80 | 0,19 | 15 | " | " | " |
| 344 | 353 | 10 | FSWLSLLVPF | 1322 | B*4601 | 100 | 0,19 | 19 | " | " | " |
| 344 | 353 | 10 | FSWLSLLVPF | " | B*1525 | 55 | 0,19 | 10 | " | " | " |
| 346 | 353 | 8 | WLSLLVPF | 1323 | B*1502 | 10 | 0,19 | 2 | " | " | " |
| 341 | 354 | 14 | SVRFSWLSLLVPFV | 1324 | A*3001 | 95 | 1,30 | 124 | " | " | " |
| 342 | 354 | 13 | VRFSWLSLLVPFV | 1325 | B*2705 | 15 | 1,30 | 20 | " | " | " |
| 346 | 354 | 9 | WLSLLVPFV | 1326 | A*0201 | 94 | 1,30 | 123 | " | " | " |
| 343 | 356 | 14 | RFSWLSLLVPFVQW | 1327 | A*2402 | 25 | 1,92 | 48 | " | " | " |
| 344 | 356 | 13 | FSWLSLLVPFVQW | 1328 | B*5801 | 90 | 1,92 | 173 | " | " | " |
| 344 | 356 | 13 | FSWLSLLVPFVQW | " | B*5701 | 85 | 1,92 | 163 | " | " | " |
| 344 | 356 | 13 | FSWLSLLVPFVQW | " | B*5802 | 60 | 1,92 | 115 | " | " | " |
| 344 | 356 | 13 | FSWLSLLVPFVQW | " | B*5201 | 40 | 1,92 | 77 | " | " | " |
| 347 | 356 | 10 | LSLLVPFVQW | 1329 | B*5802 | 80 | 1,92 | 154 | " | " | " |

TABLE 7a-continued

Predicted HLA class I-restricted CD8+ cytotoxic T cell epitopes
contained in SLP sequences from HBV large surface protein.

| | HLA class I binding peptides contained in SLP sequences derived from HBV Surface antigen | | | | | | | | Peptide of invention (SLP) | | |
|---|---|---|---|---|---|---|---|---|---|---|---|
| Start | End | Length | Sequence[A] | SEQ ID NO: | HLA class 1 molecule | Class I-B score[B] | C-score[C] | Class I-BCI score[D] | SLP# | SLP Start | SLP End |
| 344 | 357 | 14 | FSWLSLLVPFVQWF | 1330 | B*4601 | 65 | 1,38 | 89 | " | " | " |
| 345 | 357 | 13 | SWLSLLVPFVQWF | 1331 | A*2301 | 45 | 1,38 | 62 | " | " | " |
| 345 | 357 | 13 | SWLSLLVPFVQWF | " | A*2402 | 35 | 1,38 | 48 | " | " | " |
| 347 | 357 | 11 | LSLLVPFVQWF | 1332 | B*5802 | 20 | 1,38 | 28 | " | " | " |
| 348 | 357 | 10 | SLLVPFVQWF | 1333 | B*1502 | 50 | 1,38 | 69 | " | " | " |
| 349 | 357 | 9 | LLVPFVQWF | 1334 | B*1501 | 45 | 1,38 | 62 | " | " | " |
| 349 | 357 | 9 | LLVPFVQWF | " | B*1525 | 10 | 1,38 | 14 | " | " | " |
| 346 | 358 | 13 | WLSLLVPFVQWFV | 1335 | A*0201 | 80 | 1,65 | 132 | " | " | " |
| 346 | 358 | 13 | WLSLLVPFVQWFV | " | A*0206 | 25 | 1,65 | 41 | " | " | " |
| 349 | 358 | 10 | LLVPfVQWFV | 1336 | A*0201 | 97 | 1,65 | 161 | " | " | " |
| 349 | 358 | 10 | LLVPFVQWFV | " | A*0206 | 90 | 1,65 | 149 | " | " | " |
| 350 | 358 | 9 | LVPFVQWFV | 1337 | A*6802 | 100 | 1,65 | 165 | " | " | " |
| 350 | 358 | 9 | LVPFVQWFV | " | A*0201 | 43 | 1,65 | 71 | " | " | " |
| | | | | | Cumulative Class I-BCI score: | | | 14976 | | | |
| 327 | 334 | 8 | PSSWAFAK | 1271 | A*0301 | 45 | 1,04 | 47 | 33 | 327 | 358 |
| 327 | 335 | 9 | PSSWAFAKY | 1275 | A*0101 | 65 | 1,90 | 123 | " | " | " |
| 327 | 335 | 9 | PSSWAFAKY | " | A*3002 | 45 | 1,90 | 85 | " | " | " |
| 328 | 335 | 8 | SSWAFAKY | 1276 | A*2501 | 75 | 1,90 | 142 | " | " | " |
| 328 | 335 | 8 | SSWAFAKY | " | A*3002 | 75 | 1,90 | 142 | " | " | " |
| 328 | 335 | 8 | SSWAFAKY | " | A*2902 | 55 | 1,90 | 104 | " | " | " |
| 328 | 337 | 10 | SSWAFAKYLW | 1280 | B*5802 | 100 | 1,58 | 158 | " | " | " |
| 328 | 337 | 10 | SSWAFAKYLW | " | B*5701 | 95 | 1,58 | 150 | " | " | " |
| 328 | 337 | 10 | SSWAFAKYLW | " | B*4403 | 45 | 1,58 | 71 | " | " | " |
| 328 | 337 | 10 | SSWAFAKYLW | " | B*5801 | 35 | 1,58 | 55 | " | " | " |
| 328 | 337 | 10 | SSWAFAKYLW | " | B*4402 | 15 | 1,58 | 24 | " | " | " |
| 330 | 337 | 8 | WAFAKYLW | 1281 | B*5801 | 85 | 1,58 | 134 | " | " | " |
| 330 | 337 | 8 | WAFAKYLW | " | B*5701 | 65 | 1,58 | 103 | " | " | " |
| 330 | 337 | 8 | WAFAKYLW | " | B*5802 | 50 | 1,58 | 79 | " | " | " |
| 328 | 339 | 12 | SSWAFAKYLWEW | 1283 | B*5701 | 100 | 1,83 | 183 | " | " | " |
| 328 | 339 | 12 | SSWAFAKYLWEW | " | B*5801 | 95 | 1,83 | 174 | " | " | " |
| 328 | 339 | 12 | SSWAFAKYLWEW | " | B*5802 | 65 | 1,83 | 119 | " | " | " |
| 328 | 339 | 12 | SSWAFAKYLWEW | " | A*3201 | 55 | 1,83 | 101 | " | " | " |
| 328 | 339 | 12 | SSWAFAKYLWEW | " | B*4403 | 50 | 1,83 | 91 | " | " | " |
| 328 | 339 | 12 | SSWAFAKYLWEW | " | B*4402 | 10 | 1,83 | 18 | " | " | " |
| 330 | 339 | 10 | WAFAKYLWEW | 1284 | B*5802 | 85 | 1,83 | 156 | " | " | " |

TABLE 7a-continued

Predicted HLA class I-restricted CD8+ cytotoxic T cell epitopes
contained in SLP sequences from HBV large TABLE 7a-continued Predicted HLA class I-restricted CD8+ cytotoxic T cell epitopes contained in SLP sequences from HBV large surface protein.

| | | | HLA class I binding peptides contained in SLP sequences derived from HBV Surface antigen | | | | | | Peptide of invention (SLP) | | |
|---|---|---|---|---|---|---|---|---|---|---|---|
| Start | End | Length | Sequence[A] | SEQ ID NO: | HLA class 1 molecule | Class I-B score[B] | C-score[C] | Class I-BCI score[D] | SLP# | SLP Start | SLP End |
| 333 | 346 | 14 | AKYLWEWASVRFSW | 1299 | B*4403 | 35 | 1,50 | 52 | " | " | " |
| 334 | 346 | 13 | KYLWEWASVRFSW | 1300 | A*2402 | 95 | 1,50 | 142 | " | " | " |
| 334 | 346 | 13 | KYLWEWASVRFSW | " | A*2301 | 75 | 1,50 | 112 | " | " | " |
| 335 | 346 | 12 | YLWEWASVRFSW | 1301 | A*3201 | 80 | 1,50 | 120 | " | " | " |
| 335 | 346 | 12 | YLWEWASVRFSW | " | B*1302 | 75 | 1,50 | 112 | " | " | " |
| 335 | 346 | 12 | YLWEWASVRFSW | " | B*5201 | 45 | 1,50 | 67 | " | " | " |
| 337 | 346 | 10 | WEWASVRFSW | 1302 | B*1301 | 100 | 1,50 | 150 | " | " | " |
| 337 | 346 | 10 | WEWASVRFSW | " | B*4402 | 100 | 1,50 | 150 | " | " | " |
| 337 | 346 | 10 | WEWASVRFSW | " | B*4403 | 100 | 1,50 | 150 | " | " | " |
| 337 | 346 | 10 | WEWASVRFSW | " | B*1302 | 90 | 1,50 | 135 | " | " | " |
| 337 | 346 | 10 | WEWASVRFSW | " | B*4002 | 90 | 1,50 | 135 | " | " | " |
| 337 | 346 | 10 | WEWASVRFSW | " | B*4901 | 75 | 1,50 | 112 | " | " | " |
| 339 | 346 | 8 | WASVRFSW | 1303 | B*5801 | 50 | 1,50 | 75 | " | " | " |
| 334 | 347 | 14 | KYLWEWASVRFSWL | 1304 | A*2402 | 90 | 1,37 | 123 | " | " | " |
| 334 | 347 | 14 | KYLWEWASVRFSWL | " | A*2301 | 40 | 1,37 | 55 | " | " | " |
| 335 | 347 | 13 | YLWEWASVRFSWL | 1305 | A*0201 | 100 | 1,37 | 137 | " | " | " |
| 335 | 347 | 13 | YLWEWASVRFSWL | " | A*0206 | 60 | 1,37 | 82 | " | " | " |
| 337 | 347 | 11 | WEWASVRFSWL | 1306 | B*4001 | 95 | 1,37 | 130 | " | " | " |
| 337 | 347 | 11 | WEWASVRFSWL | " | B*3701 | 90 | 1,37 | 123 | " | " | " |
| 337 | 347 | 11 | WEWASVRFSWL | " | B*5001 | 90 | 1,37 | 123 | " | " | " |
| 337 | 347 | 11 | WEWASVRFSWL | " | B*4002 | 85 | 1,37 | 117 | " | " | " |
| 337 | 347 | 11 | WEWASVRFSWL | " | B*4901 | 85 | 1,37 | 117 | " | " | " |
| 337 | 347 | 11 | WEWASVRFSWL | " | B*1301 | 80 | 1,37 | 110 | " | " | " |
| 337 | 347 | 11 | WEWASVRFSWL | " | B*4402 | 55 | 1,37 | 75 | " | " | " |
| 337 | 347 | 11 | WEWASVRFSWL | " | B*1302 | 10 | 1,37 | 14 | " | " | " |
| 339 | 347 | 9 | WASVRFSWL | 1307 | B*0801 | 50 | 1,37 | 69 | " | " | " |
| 337 | 348 | 12 | WEWASVRFSWLS | 1308 | B*1801 | 80 | 0,54 | 43 | " | " | " |
| 337 | 348 | 12 | WEWASVRFSWLS | " | B*4002 | 70 | 0,54 | 38 | " | " | " |
| 337 | 348 | 12 | WEWASVRFSWLS | " | B*4901 | 45 | 0,54 | 24 | " | " | " |
| 337 | 348 | 12 | WEWASVRFSWLS | " | B*5001 | 45 | 0,54 | 24 | " | " | " |
| 337 | 348 | 12 | WEWASVRFSWLS | " | B*4403 | 20 | 0,54 | 11 | " | " | " |
| 337 | 348 | 12 | WEWASVRFSWLS | " | B*3701 | 5 | 0,54 | 3 | " | " | " |
| 341 | 348 | 8 | SVRFSWLS | 1309 | A*3001 | 40 | 0,54 | 22 | " | " | " |
| 337 | 349 | 13 | WEWASVRFSWLSL | 1310 | B*1801 | 100 | 1,61 | 161 | " | " | " |
| 337 | 349 | 13 | WEWASVRFSWLSL | " | B*3701 | 100 | 1,61 | 161 | " | " | " |

TABLE 7a-continued

Predicted HLA class I-restricted CD8+ cytotoxic T cell epitopes
contained in SLP sequences from H TABLE 7a-continued Predicted HLA class I-restricted CD8⁺ cytotoxic T cell epitopes contained in SLP sequences from HBV large surface protein.

| | | | HLA class I binding peptides contained in SLP sequences derived from HBV Surface antigen | | | | | | Peptide of invention (SLP) | | |
|---|---|---|---|---|---|---|---|---|---|---|---|
| Start | End | Length | Sequence[A] | SEQ ID NO: | HLA class 1 molecule | Class I-B score[B] | C-score[C] | Class I-BCI score[D] | SLP# | SLP Start | SLP End |
| 343 | 353 | 11 | RFSWLSLLVPF | | A*2402 | 80 | 0,19 | 15 | " | " | " |
| 344 | 353 | 10 | FSWLSLLVPF | 1322 | B*4601 | 100 | 0,19 | 19 | " | " | " |
| 344 | 353 | 10 | FSWLSLLVPF | " | B*1525 | 55 | 0,19 | 10 | " | " | " |
| 346 | 353 | 8 | WLSLLVPF | 1323 | B*1502 | 10 | 0,19 | 2 | " | " | " |
| 341 | 354 | 14 | SVRFSWLSLLVPFV | 1324 | A*3001 | 95 | 1,30 | 124 | " | " | " |
| 342 | 354 | 13 | VRFSWLSLLVPFV | 1325 | B*2705 | 15 | 1,30 | 20 | " | " | " |
| 346 | 354 | 9 | WLSLLVPFV | 1326 | A*0201 | 94 | 1,30 | 123 | " | " | " |
| 343 | 356 | 14 | RFSWLSLLVPFVQW | 1327 | A*2402 | 25 | 1,92 | 48 | " | " | " |
| 344 | 356 | 13 | FSWLSLLVPFVQW | 1328 | B*5801 | 90 | 1,92 | 173 | " | " | " |
| 344 | 356 | 13 | FSWLSLLVPFVQW | " | B*5701 | 85 | 1,92 | 163 | " | " | " |
| 344 | 356 | 13 | FSWLSLLVPFVQW | " | B*5802 | 60 | 1,92 | 115 | " | " | " |
| 344 | 356 | 13 | FSWLSLLVPFVQW | " | B*5201 | 40 | 1,92 | 77 | " | " | " |
| 347 | 356 | 10 | LSLLVPFVQW | 1329 | B*5802 | 80 | 1,92 | 154 | " | " | " |
| 344 | 357 | 14 | FSWLSLLVPFVQWF | 1330 | B*4601 | 65 | 1,38 | 89 | " | " | " |
| 345 | 357 | 13 | SWLSLLVPFVQWF | 1331 | A*2301 | 45 | 1,38 | 62 | " | " | " |
| 345 | 357 | 13 | SWLSLLVPFVQWF | " | A*2402 | 35 | 1,38 | 48 | " | " | " |
| 347 | 357 | 11 | LSLLVPFVQWF | 1332 | B*5802 | 20 | 1,38 | 28 | " | " | " |
| 348 | 357 | 10 | SLLVPFVQWF | 1333 | B*1502 | 50 | 1,38 | 69 | " | " | " |
| 349 | 357 | 9 | LLVPFVQWF | 1334 | B*1501 | 45 | 1,38 | 62 | " | " | " |
| 349 | 357 | 9 | LLVPFVQWF | " | B*1525 | 10 | 1,38 | 14 | " | " | " |
| 346 | 358 | 13 | WLSLLVPFVQWFV | 1335 | A*0201 | 80 | 1,65 | 132 | " | " | " |
| 346 | 358 | 13 | WLSLLVPFVQWFV | " | A*0206 | 25 | 1,65 | 41 | " | " | " |
| 349 | 358 | 10 | LLVPfVQWFV | 1336 | A*0201 | 97 | 1,65 | 161 | " | " | " |
| 349 | 358 | 10 | LLVPFVQWFV | " | A*0206 | 90 | 1,65 | 149 | " | " | " |
| 350 | 358 | 9 | LVPFVQWFV | 1337 | A*6802 | 100 | 1,65 | 165 | " | " | " |
| 350 | 358 | 9 | LVPFVQWFV | " | A*0201 | 43 | 1,65 | 71 | " | " | " |
| | | | | | Cumulative Class I-BCI score: | | | 13107 | | | |
| 328 | 335 | 8 | SSWAFAKY | 1276 | A*2501 | 75 | 1,90 | 142 | 34 | 328 | 358 |
| 328 | 335 | 8 | SSWAFAKY | " | A*3002 | 75 | 1,90 | 142 | " | " | " |
| 328 | 335 | 8 | SSWAFAKY | " | A*2902 | 55 | 1,90 | 104 | " | " | " |
| 328 | 337 | 10 | SSWAFAKYLW | 1280 | B*5802 | 100 | 1,58 | 158 | " | " | " |
| 328 | 337 | 10 | SSWAFAKYLW | " | B*5701 | 95 | 1,58 | 150 | " | " | " |
| 328 | 337 | 10 | SSWAFAKYLW | " | B*4403 | 45 | 1,58 | 71 | " | " | " |
| 328 | 337 | 10 | SSWAFAKYLW | " | B*5801 | 35 | 1,58 | 55 | " | " | " |

TABLE 7a-continued

Predicted HLA class I-restricted CD8+ cytotoxic T cell epitopes contained in SLP sequences from HBV large surface protein.

| | | | HLA class I binding peptides contained in SLP sequences derived from HBV Surface antigen | | | | | Peptide of invention (SLP) | | |
|---|---|---|---|---|---|---|---|---|---|---|
| Start | End | Length | Sequence[A] | SEQ ID NO: | HLA class 1 molecule | Class I-B score[B] | C-score[C] | Class I-BCI score[D] | SLP# | SLP Start | SLP End |
| 328 | 337 | 10 | SSWAFAKYLW | " | B*4402 | 15 | 1,58 | 24 | " | " | " |
| 330 | 337 | 8 | WAFAKYLW | 1281 | B*5801 | 85 | 1,58 | 134 | " | " | " |
| 330 | 337 | 8 | WAFAKYLW | " | B*5701 | 65 | 1,58 | 103 | " | " | " |
| 330 | 337 | 8 | WAFAKYLW | " | B*5802 | 50 | 1,58 | 79 | " | " | " |
| 328 | 339 | 12 | SSWAFAKYLWEW | 1283 | B*5701 | 100 | 1,83 | 183 | " | " | " |
| 328 | 339 | 12 | SSWAFAKYLWEW | " | B*5801 | 95 | 1,83 | 174 | " | " | " |
| 328 | 339 | 12 | SSWAFAKYLWEW | " | B*5802 | 65 | 1,83 | 119 | " | " | " |
| 328 | 339 | 12 | SSWAFAKYLWEW | " | A*3201 | 55 | 1,83 | 101 | " | " | " |
| 328 | 339 | 12 | SSWAFAKYLWEW | " | B*4403 | 50 | 1,83 | 91 | " | " | " |
| 328 | 339 | 12 | SSWAFAKYLWEW | " | B*4402 | 10 | 1,83 | 18 | " | " | " |
| 330 | 339 | 10 | WAFAKYLWEW | 1284 | B*5802 | 85 | 1,83 | 156 | " | " | " |
| 330 | 339 | 10 | WAFAKYLWEW | " | B*5201 | 70 | 1,83 | 128 | " | " | " |
| 331 | 339 | 9 | AFAKYLWEW | 1285 | B*4402 | 50 | 1,83 | 91 | " | " | " |
| 331 | 339 | 9 | AFAKYLWEW | " | B*4403 | 40 | 1,83 | 73 | " | " | " |
| 332 | 339 | 8 | FAKYLWEW | 1286 | B*4601 | 40 | 1,83 | 73 | " | " | " |
| 332 | 339 | 8 | FAKYLWEW | " | B*5701 | 30 | 1,83 | 55 | " | " | " |
| 330 | 342 | 13 | WAFAKYLWEWASV | 1287 | A*6802 | 85 | 1,92 | 164 | " | " | " |
| 330 | 342 | 13 | WAFAKYLWEWASV | " | B*1402 | 20 | 1,92 | 38 | " | " | " |
| 332 | 342 | 11 | FAKYLWEWASV | 1288 | B*4601 | 50 | 1,92 | 96 | " | " | " |
| 330 | 343 | 14 | WAFAKYLWEWASVR | 1289 | A*3303 | 80 | 1,07 | 85 | " | " | " |
| 330 | 343 | 14 | WAFAKYLWEWASVR | " | A*6801 | 50 | 1,07 | 53 | " | " | " |
| 330 | 343 | 14 | WAFAKYLWEWASVR | " | A*7401 | 15 | 1,07 | 16 | " | " | " |
| 331 | 343 | 13 | AFAKYLWEWASVR | 1290 | A*3101 | 70 | 1,07 | 75 | " | " | " |
| 331 | 343 | 13 | AFAKYLWEWASVR | " | A*3303 | 35 | 1,07 | 37 | " | " | " |
| 332 | 343 | 12 | FAKYLWEWASVR | 1291 | A*3303 | 85 | 1,07 | 91 | " | " | " |
| 332 | 343 | 12 | FAKYLWEWASVR | " | A*6801 | 60 | 1,07 | 64 | " | " | " |
| 332 | 343 | 12 | FAKYLWEWASVR | " | A*3101 | 55 | 1,07 | 59 | " | " | " |
| 334 | 343 | 10 | KYLWEWASVR | 1292 | A*3101 | 100 | 1,07 | 107 | " | " | " |
| 335 | 343 | 9 | YLWEWASVR | 1293 | A*7401 | 85 | 1,07 | 91 | " | " | " |
| 335 | 343 | 9 | YLWEWASVR | " | A*3303 | 40 | 1,07 | 43 | " | " | " |
| 335 | 343 | 9 | YLWEWASVR | " | A*3101 | 35 | 1,07 | 37 | " | " | " |
| 335 | 343 | 9 | YLWEWASVR | " | A*0301 | 20 | 1,07 | 21 | " | " | " |
| 331 | 344 | 14 | AFAKYLWEWASVRF | 1294 | A*2402 | 30 | 1,86 | 56 | " | " | " |
| 331 | 344 | 14 | AFAKYLWEWASVRF | " | A*2301 | 5 | 1,86 | 9 | " | " | " |
| 332 | 344 | 13 | FAKYLWEWASVRF | 1295 | B*4601 | 75 | 1,86 | 139 | " | " | " |

TABLE 7a-continued

Predicted HLA class I-restricted CD8+ cytotoxic T cell epitopes
contained in SLP sequences from HBV large surface protein.

| | | | HLA class I binding peptides contained in SLP sequences derived from HBV Surface antigen | | | | | | Peptide of invention (SLP) | | |
|---|---|---|---|---|---|---|---|---|---|---|---|
| Start | End | Length | Sequence[A] | SEQ ID NO: | HLA class 1 molecule | Class I-B score[B] | C-score[C] | Class I-BCI score[D] | SLP# | SLP Start | SLP End |
| 335 | 344 | 10 | YLWEWASVRF | 1296 | B*1502 | 90 | 1,86 | 167 | " | " | " |
| 335 | 344 | 10 | YLWEWASVRF | " | B*1525 | 45 | 1,86 | 84 | " | " | " |
| 337 | 344 | 8 | WEWASVRF | 1297 | B*3701 | 80 | 1,86 | 149 | " | " | " |
| 337 | 344 | 8 | WEWASVRF | " | B*4901 | 80 | 1,86 | 149 | " | " | " |
| 337 | 344 | 8 | WEWASVRF | " | B*5001 | 50 | 1,86 | 93 | " | " | " |
| 337 | 344 | 8 | WEWASVRF | " | B*1301 | 45 | 1,86 | 84 | " | " | " |
| 337 | 344 | 8 | WEWASVRF | " | B*4403 | 5 | 1,86 | 9 | " | " | " |
| 337 | 345 | 9 | WEWASVRFS | 1298 | B*4403 | 65 | 0,50 | 33 | " | " | " |
| 337 | 345 | 9 | WEWASVRFS | " | B*5001 | 60 | 0,50 | 30 | " | " | " |
| 337 | 345 | 9 | WEWASVRFS | " | B*4002 | 55 | 0,50 | 28 | " | " | " |
| 337 | 345 | 9 | WEWASVRFS | " | B*4901 | 15 | 0,50 | 8 | " | " | " |
| 333 | 346 | 14 | AKYLWEWASVRFSW | 1299 | B*4403 | 35 | 1,50 | 52 | " | " | " |
| 334 | 346 | 13 | KYLWEWASVRFSW | 1300 | A*2402 | 95 | 1,50 | 142 | " | " | " |
| 334 | 346 | 13 | KYLWEWASVRFSW | " | A*2301 | 75 | 1,50 | 112 | " | " | " |
| 335 | 346 | 12 | YLWEWASVRFSW | 1301 | A*3201 | 80 | 1,50 | 120 | " | " | " |
| 335 | 346 | 12 | YLWEWASVRFSW | " | B*1302 | 75 | 1,50 | 112 | " | " | " |
| 335 | 346 | 12 | YLWEWASVRFSW | " | B*5201 | 45 | 1,50 | 67 | " | " | " |
| 337 | 346 | 10 | WEWASVRFSW | 1302 | B*1301 | 100 | 1,50 | 150 | " | " | " |
| 337 | 346 | 10 | WEWASVRFSW | " | B*4402 | 100 | 1,50 | 150 | " | " | " |
| 337 | 346 | 10 | WEWASVRFSW | " | B*4403 | 100 | 1,50 | 150 | " | " | " |
| 337 | 346 | 10 | WEWASVRFSW | " | B*1302 | 90 | 1,50 | 135 | " | " | " |
| 337 | 346 | 10 | WEWASVRFSW | " | B*4002 | 90 | 1,50 | 135 | " | " | " |
| 337 | 346 | 10 | WEWASVRFSW | " | B*4901 | 75 | 1,50 | 112 | " | " | " |
| 339 | 346 | 8 | WASVRFSW | 1303 | B*5801 | 50 | 1,50 | 75 | " | " | " |
| 334 | 347 | 14 | KYLWEWASVRFSWL | 1304 | A*2402 | 90 | 1,37 | 123 | " | " | " |
| 334 | 347 | 14 | KYLWEWASVRFSWL | " | A*2301 | 40 | 1,37 | 55 | " | " | " |
| 335 | 347 | 13 | YLWEWASVRFSWL | 1305 | A*0201 | 100 | 1,37 | 137 | " | " | " |
| 335 | 347 | 13 | YLWEWASVRFSWL | " | A*0206 | 60 | 1,37 | 82 | " | " | " |
| 337 | 347 | 11 | WEWASVRFSWL | 1306 | B*4001 | 95 | 1,37 | 130 | " | " | " |
| 337 | 347 | 11 | WEWASVRFSWL | " | B*3701 | 90 | 1,37 | 123 | " | " | " |
| 337 | 347 | 11 | WEWASVRFSWL | " | B*5001 | 90 | 1,37 | 123 | " | " | " |
| 337 | 347 | 11 | WEWASVRFSWL | " | B*4002 | 85 | 1,37 | 117 | " | " | " |
| 337 | 347 | 11 | WEWASVRFSWL | " | B*4901 | 85 | 1,37 | 117 | " | " | " |
| 337 | 347 | 11 | WEWASVRFSWL | " | B*1301 | 80 | 1,37 | 110 | " | " | " |
| 337 | 347 | 11 | WEWASVRFSWL | " | B*4402 | 55 | 1,37 | 75 | " | " | " |

TABLE 7a-continued

Predicted HLA class I-restricted CD8+ cytotoxic T cell epitopes
contained in SLP sequences from HBV large surface protein.

| | | | HLA class I binding peptides contained in SLP sequences derived from HBV Surface antigen | | | | | | Peptide of invention (SLP) | | |
|---|---|---|---|---|---|---|---|---|---|---|---|
| Start | End | Length | Sequence[A] | SEQ ID NO: | HLA class 1 molecule | Class I-B score[B] | C-score[C] | Class I-BCI score[D] | SLP# | SLP Start | SLP End |
| 337 | 347 | 11 | WEWASVRFSWL | " | B*1302 | 10 | 1,37 | 14 | " | " | " |
| 339 | 347 | 9 | WASVRFSWL | 1307 | B*0801 | 50 | 1,37 | 69 | " | " | " |
| 337 | 348 | 12 | WEWASVRFSWLS | 1308 | B*1801 | 80 | 0,54 | 43 | " | " | " |
| 337 | 348 | 12 | WEWASVRFSWLS | " | B*4002 | 70 | 0,54 | 38 | " | " | " |
| 337 | 348 | 12 | WEWASVRFSWLS | " | B*4901 | 45 | 0,54 | 24 | " | " | " |
| 337 | 348 | 12 | WEWASVRFSWLS | " | B*5001 | 45 | 0,54 | 24 | " | " | " |
| 337 | 348 | 12 | WEWASVRFSWLS | " | B*4403 | 20 | 0,54 | 11 | " | " | " |
| 337 | 348 | 12 | WEWASVRFSWLS | " | B*3701 | 5 | 0,54 | 3 | " | " | " |
| 341 | 348 | 8 | SVRFSWLS | 1309 | A*3001 | 40 | 0,54 | 22 | " | " | " |
| 337 | 349 | 13 | WEWASVRFSWLSL | 1310 | B*1801 | 100 | 1,61 | 161 | " | " | " |
| 337 | 349 | 13 | WEWASVRFSWLSL | " | B*3701 | 100 | 1,61 | 161 | " | " | " |
| 337 | 349 | 13 | WEWASVRFSWLSL | " | B*4001 | 100 | 1,61 | 161 | " | " | " |
| 337 | 349 | 13 | WEWASVRFSWLSL | " | B*4002 | 100 | 1,61 | 161 | " | " | " |
| 337 | 349 | 13 | WEWASVRFSWLSL | " | B*4901 | 100 | 1,61 | 161 | " | " | " |
| 337 | 349 | 13 | WEWASVRFSWLSL | " | B*5001 | 100 | 1,61 | 161 | " | " | " |
| 337 | 349 | 13 | WEWASVRFSWLSL | " | B*1301 | 90 | 1,61 | 145 | " | " | " |
| 337 | 349 | 13 | WEWASVRFSWLSL | " | B*4403 | 75 | 1,61 | 120 | " | " | " |
| 337 | 349 | 13 | WEWASVRFSWLSL | " | B*4402 | 70 | 1,61 | 112 | " | " | " |
| 339 | 349 | 11 | WASVRFSWLSL | 1311 | B*1402 | 85 | 1,61 | 137 | " | " | " |
| 341 | 349 | 9 | SVRFSWLSL | 1312 | A*3001 | 90 | 1,61 | 145 | " | " | " |
| 341 | 349 | 9 | SVRFSWLSL | " | B*0702 | 80 | 1,61 | 129 | " | " | " |
| 342 | 349 | 8 | VRFSWLSL | 1313 | B*3901 | 70 | 1,61 | 112 | " | " | " |
| 337 | 350 | 14 | WEWASVRFSWLSLL | 1314 | B*3701 | 95 | 1,15 | 109 | " | " | " |
| 337 | 350 | 14 | WEWASVRFSWLSLL | " | B*4002 | 95 | 1,15 | 109 | " | " | " |
| 337 | 350 | 14 | WEWASVRFSWLSLL | " | B*5001 | 95 | 1,15 | 109 | " | " | " |
| 337 | 350 | 14 | WEWASVRFSWLSLL | " | B*1801 | 90 | 1,15 | 104 | " | " | " |
| 337 | 350 | 14 | WEWASVRFSWLSLL | " | B*4901 | 90 | 1,15 | 104 | " | " | " |
| 337 | 350 | 14 | WEWASVRFSWLSLL | " | B*1301 | 85 | 1,15 | 98 | " | " | " |
| 337 | 350 | 14 | WEWASVRFSWLSLL | " | B*4001 | 80 | 1,15 | 92 | " | " | " |
| 337 | 350 | 14 | WEWASVRFSWLSLL | " | B*4403 | 70 | 1,15 | 81 | " | " | " |
| 337 | 350 | 14 | WEWASVRFSWLSLL | " | B*4801 | 70 | 1,15 | 81 | " | " | " |
| 337 | 350 | 14 | WEWASVRFSWLSLL | " | B*4402 | 60 | 1,15 | 69 | " | " | " |
| 337 | 350 | 14 | WEWASVRFSWLSLL | " | B*1302 | 50 | 1,15 | 58 | " | " | " |
| 342 | 350 | 9 | VRFSWLSLL | 1315 | B*3801 | 65 | 1,15 | 75 | " | " | " |
| 342 | 350 | 9 | VRFSWLSLL | " | B*2702 | 20 | 1,15 | 23 | " | " | " |

TABLE 7a-continued

Predicted HLA class I-restricted CD8+ cytotoxic T cell epitopes
contained in SLP sequences from HBV large surface protein.

| | | | HLA class I binding peptides contained in SLP sequences derived from HBV Surface antigen | | | | | Peptide of invention (SLP) | | |
|---|---|---|---|---|---|---|---|---|---|---|
| Start | End | Length | Sequence[A] | SEQ ID NO: | HLA class 1 molecule | Class I-B score[B] | C-score[C] | Class I-BCI score[D] | SLP# | SLP Start | SLP End |
| 339 | 351 | 13 | WASVRFSWLSLLV | 1316 | B*5101 | 30 | 1,47 | 44 | " | " | " |
| 341 | 351 | 11 | SVRFSWLSLLV | 1317 | A*3001 | 85 | 1,47 | 125 | " | " | " |
| 340 | 353 | 14 | ASVRFSWLSLLVPF | 1318 | B*4601 | 30 | 0,19 | 6 | " | " | " |
| 340 | 353 | 14 | ASVRFSWLSLLVPF | " | B*1525 | 15 | 0,19 | 3 | " | " | " |
| 341 | 353 | 13 | SVRFSWLSLLVPF | 1319 | B*1501 | 80 | 0,19 | 15 | " | " | " |
| 341 | 353 | 13 | SVRFSWLSLLVPF | " | B*1525 | 60 | 0,19 | 11 | " | " | " |
| 341 | 353 | 13 | SVRFSWLSLLVPF | " | B*1502 | 25 | 0,19 | 5 | " | " | " |
| 341 | 353 | 13 | SVRFSWLSLLVPF | " | A*3001 | 20 | 0,19 | 4 | " | " | " |
| 342 | 353 | 12 | VRFSWLSLLVPF | 1320 | B*2702 | 65 | 0,19 | 12 | " | " | " |
| 342 | 353 | 12 | VRFSWLSLLVPF | " | B*2705 | 55 | 0,19 | 10 | " | " | " |
| 343 | 353 | 11 | RFSWLSLLVPF | 1321 | A*3201 | 85 | 0,19 | 16 | " | " | " |
| 343 | 353 | 11 | RFSWLSLLVPF | " | A*2402 | 80 | 0,19 | 15 | " | " | " |
| 344 | 353 | 10 | FSWLSLLVPF | 1322 | B*4601 | 100 | 0,19 | 19 | " | " | " |
| 344 | 353 | 10 | FSWLSLLVPF | " | B*1525 | 55 | 0,19 | 10 | " | " | " |
| 346 | 353 | 8 | WLSLLVPF | 1323 | B*1502 | 10 | 0,19 | 2 | " | " | " |
| 341 | 354 | 14 | SVRFSWLSLLVPFV | 1324 | A*3001 | 95 | 1,30 | 124 | " | " | " |
| 342 | 354 | 13 | VRFSWLSLLVPFV | 1325 | B*2705 | 15 | 1,30 | 20 | " | " | " |
| 346 | 354 | 9 | WLSLLVPFV | 1326 | A*0201 | 94 | 1,30 | 123 | " | " | " |
| 343 | 356 | 14 | RFSWLSLLVPFVQW | 1327 | A*2402 | 25 | 1,92 | 48 | " | " | " |
| 344 | 356 | 13 | FSWLSLLVPFVQW | 1328 | B*5801 | 90 | 1,92 | 173 | " | " | " |
| 344 | 356 | 13 | FSWLSLLVPFVQW | " | B*5701 | 85 | 1,92 | 163 | " | " | " |
| 344 | 356 | 13 | FSWLSLLVPFVQW | " | B*5802 | 60 | 1,92 | 115 | " | " | " |
| 344 | 356 | 13 | FSWLSLLVPFVQW | " | B*5201 | 40 | 1,92 | 77 | " | " | " |
| 347 | 356 | 10 | LSLLVPFVQW | 1329 | B*5802 | 80 | 1,92 | 154 | " | " | " |
| 344 | 357 | 14 | FSWLSLLVPFVQWF | 1330 | B*4601 | 65 | 1,38 | 89 | " | " | " |
| 345 | 357 | 13 | SWLSLLVPFVQWF | 1331 | A*2301 | 45 | 1,38 | 62 | " | " | " |
| 345 | 357 | 13 | SWLSLLVPFVQWF | " | A*2402 | 35 | 1,38 | 48 | " | " | " |
| 347 | 357 | 11 | LSLLVPFVQWF | 1332 | B*5802 | 20 | 1,38 | 28 | " | " | " |
| 348 | 357 | 10 | SLLVPFVQWF | 1333 | B*1502 | 50 | 1,38 | 69 | " | " | " |
| 349 | 357 | 9 | LLVPFVQWF | 1334 | B*1501 | 45 | 1,38 | 62 | " | " | " |
| 349 | 357 | 9 | LLVPFVQWF | " | B*1525 | 10 | 1,38 | 14 | " | " | " |
| 346 | 358 | 13 | WLSLLVPFVQWFV | 1335 | A*0201 | 80 | 1,65 | 132 | " | " | " |
| 346 | 358 | 13 | WLSLLVPFVQWFV | " | A*0206 | 25 | 1,65 | 41 | " | " | " |
| 349 | 358 | 10 | LLVPfVQWFV | 1336 | A*0201 | 97 | 1,65 | 161 | " | " | " |
| 349 | 358 | 10 | LLVPFVQWFV | " | A*0206 | 90 | 1,65 | 149 | " | " | " |

TABLE 7a-continued

Predicted HLA class I-restricted CD8+ cytotoxic T cell epitopes
contained in SLP sequences from HBV large surface protein.

| | | | HLA class I binding peptides contained in SLP sequences derived from HBV Surface antigen | | | | | | Peptide of invention (SLP) | | |
|---|---|---|---|---|---|---|---|---|---|---|---|
| Start | End | Length | Sequence[A] | SEQ ID NO: | HLA class 1 molecule | Class I-B score[B] | C-score[C] | Class I-BCI score[D] | SLP# | SLP Start | SLP End |
| 350 | 358 | 9 | LVPFVQWFV | 1337 | A*6802 | 100 | 1,65 | 165 | " | " | " |
| 350 | 358 | 9 | LVPFVQWFV | " | A*0201 | 43 | 1,65 | 71 | " | " | " |
| | | | | | Cumulative Class I-BCI score: | | | 12851 | | | |
| 366 | 373 | 8 | LSAIWMMW | 1338 | B*5801 | 100 | 1,78 | 178 | 35 | 365 | 400 |
| 366 | 373 | 8 | LSAIWMMW | " | B*5701 | 60 | 1,78 | 107 | " | " | " |
| 366 | 373 | 8 | LSAIWMMW | " | B*5802 | 45 | 1,78 | 80 | " | " | " |
| 365 | 374 | 10 | WLSAIWMMWY | 1339 | A*0101 | 90 | 1,38 | 124 | " | " | " |
| 365 | 374 | 10 | WLSAIWMMWY | " | A*0301 | 70 | 1,38 | 96 | " | " | " |
| 366 | 374 | 9 | LSAIWMMWY | 1340 | A*0101 | 100 | 1,38 | 138 | " | " | " |
| 367 | 374 | 8 | SAIWMMWY | 1341 | A*2501 | 90 | 1,38 | 124 | " | " | " |
| 367 | 374 | 8 | SAIWMMWY | " | A*3002 | 60 | 1,38 | 83 | " | " | " |
| 366 | 375 | 10 | LSAIWMMWYW | 1342 | B*5802 | 95 | 1,46 | 139 | " | " | " |
| 366 | 375 | 10 | LSAIWMMWYW | " | B*5801 | 75 | 1,46 | 110 | " | " | " |
| 367 | 375 | 9 | SAIWMMWYW | 1343 | B*5801 | 80 | 1,46 | 117 | " | " | " |
| 367 | 375 | 9 | SAIWMMWYW | " | B*4403 | 55 | 1,46 | 81 | " | " | " |
| 367 | 375 | 9 | SAIWMMWYW | " | B*5701 | 55 | 1,46 | 81 | " | " | " |
| 367 | 375 | 9 | SAIWMMWYW | " | B*4402 | 45 | 1,46 | 66 | " | " | " |
| 367 | 375 | 9 | SAIWMMWYW | " | B*5301 | 40 | 1,46 | 59 | " | " | " |
| 368 | 375 | 8 | AIWMMWYW | 1344 | B*5701 | 25 | 1,46 | 37 | " | " | " |
| 370 | 379 | 10 | WMMWYWGPSL | 1345 | B*0801 | 95 | 1,46 | 138 | " | " | " |
| 370 | 379 | 10 | WMMWYWGPSL | " | B*3801 | 95 | 1,46 | 138 | " | " | " |
| 370 | 379 | 10 | WMMWYWGPSL | " | B*3901 | 95 | 1,46 | 138 | " | " | " |
| 370 | 379 | 10 | WMMWYWGPSL | " | B*4801 | 80 | 1,46 | 117 | " | " | " |
| 370 | 379 | 10 | WMMWYWGPSL | " | B*3701 | 65 | 1,46 | 95 | " | " | " |
| 370 | 379 | 10 | WMMWYWGPSL | " | B*1301 | 40 | 1,46 | 58 | " | " | " |
| 370 | 379 | 10 | WMMWYWGPSL | " | B*1525 | 20 | 1,46 | 29 | " | " | " |
| 371 | 379 | 9 | MMWYWGPSL | 1346 | B*4801 | 85 | 1,46 | 124 | " | " | " |
| 371 | 379 | 9 | MMWYWGPSL | " | B*1525 | 75 | 1,46 | 109 | " | " | " |
| 371 | 379 | 9 | MMWYWGPSL | " | A*0201 | 46 | 1,46 | 67 | " | " | " |
| 371 | 379 | 9 | MMWYWGPSL | " | A*3201 | 45 | 1,46 | 66 | " | " | " |
| 371 | 379 | 9 | MMWYWGPSL | " | B*1501 | 40 | 1,46 | 58 | " | " | " |
| 371 | 379 | 9 | MMWYWGPSL | " | B*3901 | 40 | 1,46 | 58 | " | " | " |
| 367 | 380 | 14 | SAIWMMWYWGPSLY | 1347 | A*2601 | 95 | 1,93 | 183 | " | " | " |
| 367 | 380 | 14 | SAIWMMWYWGPSLY | " | A*1101 | 80 | 1,93 | 154 | " | " | " |
| 367 | 380 | 14 | SAIWMMWYWGPSLY | " | B*3501 | 75 | 1,93 | 145 | " | " | " |

TABLE 7a-continued

Predicted HLA class I-restricted CD8+ cytotoxic T cell epitopes
contained in SLP sequences from H TABLE 7a-continued Predicted HLA class I-restricted CD8+ cytotoxic T cell epitopes
contained in SLP sequences from HBV large surface protein.

| | | | HLA class I binding peptides contained in SLP sequences derived from HBV Surface antigen | | | | | | Peptide of invention (SLP) | | |
|---|---|---|---|---|---|---|---

TABLE 7a-continued

Predicted HLA class I-restricted CD8+ cytotoxic T cell epitopes
contained in SLP sequences from HBV large surface protein.

| | | | HLA class I binding peptides contained in SLP sequences derived from HBV Surface antigen | | | | | Peptide of invention (SLP) | | |
|---|---|---|---|---|---|---|---|---|---|---|

TABLE 7a-continued

Predicted HLA class I-restricted CD8+ cytotoxic T cell epitopes contained in SLP sequences from HBV large surface protein.

| | HLA class I binding peptides contained in SLP sequences derived from HBV Surface antigen | | | | | | | | Peptide of invention (SLP) | | |
|---|---|---|---|---|---|---|---|---|---|---|---|
| Start | End | Length | Sequence[A] | SEQ ID NO: | HLA class 1 molecule | Class I-B score[B] | C-score[C] | Class I-BCI score[D] | SLP# | SLP Start | SLP End |
| 371 | 380 | 10 | MMWYWGPSLY | 1350 | A*0301 | 100 | 1,93 | 193 | 36 | 371 | 400 |
| 371 | 380 | 10 | MMWYWGPSLY | " | A*3002 | 90 | 1,93 | 174 | " | " | " |
| 371 | 380 | 10 | MMWYWGPSLY | " | B*1525 | 90 | 1,93 | 174 | " | " | " |
| 371 | 380 | 10 | MMWYWGPSLY | " | A*7401 | 80 | 1,93 | 154 | " | " | " |
| 371 | 380 | 10 | MMWYWGPSLY | " | A*2902 | 65 | 1,93 | 125 | " | " | " |
| 372 | 380 | 9 | MWYWGPSLY | 1351 | A*2902 | 100 | 1,93 | 193 | " | " | " |
| 371 | 382 | 12 | MMWYWGPSLYSI | 1354 | A*3201 | 100 | 0,77 | 77 | " | " | " |
| 371 | 382 | 12 | MMWYWGPSLYSI | " | B*5201 | 100 | 0,77 | 77 | " | " | " |
| 371 | 382 | 12 | MMWYWGPSLYSI | " | B*1302 | 95 | 0,77 | 73 | " | " | " |
| 371 | 382 | 12 | MMWYWGPSLYSI | " | A*0201 | 86 | 0,77 | 66 | " | " | " |
| 371 | 382 | 12 | MMWYWGPSLYSI | " | A*7401 | 75 | 0,77 | 58 | " | " | " |
| 371 | 382 | 12 | MMWYWGPSLYSI | " | B*4801 | 75 | 0,77 | 58 | " | " | " |
| 371 | 382 | 12 | MMWYWGPSLYSI | " | B*1301 | 70 | 0,77 | 54 | " | " | " |
| 370 | 383 | 14 | WMMWYWGPSLYSIV | 1355 | A*0206 | 70 | 0,79 | 55 | " | " | " |
| 370 | 383 | 14 | WMMWYWGPSLYSIV | " | A*0201 | 51 | 0,79 | 40 | " | " | " |
| 370 | 383 | 14 | WMMWYWGPSLYSIV | " | B*0801 | 45 | 0,79 | 35 | " | " | " |
| 370 | 383 | 14 | WMMWYWGPSLYSIV | " | B*3901 | 10 | 0,79 | 8 | " | " | " |
| 370 | 383 | 14 | WMMWYWGPSLYSIV | " | B*3801 | 5 | 0,79 | 4 | " | " | " |
| 371 | 383 | 13 | MMWYWGPSLYSIV | 1356 | A*0201 | 69 | 0,79 | 54 | " | " | " |
| 371 | 383 | 13 | MMWYWGPSLYSIV | " | B*1302 | 25 | 0,79 | 20 | " | " | " |
| 371 | 383 | 13 | MMWYWGPSLYSIV | " | B*4801 | 25 | 0,79 | 20 | " | " | " |
| 373 | 386 | 14 | WYWGPSLYSIVSPF | 1357 | B*1502 | 80 | 0,72 | 58 | " | " | " |
| 373 | 386 | 14 | WYWGPSLYSIVSPF | " | A*2301 | 55 | 0,72 | 40 | " | " | " |
| 373 | 386 | 14 | WYWGPSLYSIVSPF | " | A*2402 | 20 | 0,72 | 14 | " | " | " |
| 373 | 386 | 14 | WYWGPSLYSIVSPF | " | A*2902 | 15 | 0,72 | 11 | " | " | " |
| 374 | 386 | 13 | YWGPSLYSIVSPF | 1358 | A*2301 | 70 | 0,72 | 51 | " | " | " |
| 374 | 386 | 13 | YWGPSLYSIVSPF | " | A*2402 | 70 | 0,72 | 51 | " | " | " |
| 377 | 386 | 10 | PSLYSIVSPF | 1359 | A*3201 | 35 | 0,72 | 25 | " | " | " |
| 378 | 386 | 9 | SLYSIVSPF | 1360 | B*1525 | 95 | 0,72 | 69 | " | " | " |
| 378 | 386 | 9 | SLYSIVSPF | " | A*3201 | 90 | 0,72 | 65 | " | " | " |
| 378 | 386 | 9 | SLYSIVSPF | " | B*1501 | 85 | 0,72 | 61 | " | " | " |
| 378 | 386 | 9 | SLYSIVSPF | " | B*4601 | 20 | 0,72 | 14 | " | " | " |
| 378 | 386 | 9 | SLYSIVSPF | " | A*2601 | 10 | 0,72 | 7 | " | " | " |
| 374 | 387 | 14 | YWGPSLYSIVSPFI | 1361 | A*2402 | 15 | 1,16 | 17 | " | " | " |
| 378 | 387 | 10 | SLYSiVSPFI | 1362 | A*0201 | 3 | 1,16 | 3 | " | " | " |

TABLE 7a-continued

Predicted HLA class I-restricted CD8+ cytotoxic T cell epitopes
contained in SLP sequences from HBV large surface protein.

| | | | HLA class I binding peptides contained in SLP sequences derived from HBV Surface antigen | | | | | | Peptide of invention (SLP) | | |
|---|---|---|---|---|---|---|---|---|---|---|---|
| Start | End | Length | Sequence[A] | SEQ ID NO: | HLA class 1 molecule | Class I-B score[B] | C-score[C] | Class I-BCI score[D] | SLP# | SLP Start | SLP End |
| 376 | 389 | 14 | GPSLYSIVSPFIPL | 1363 | B*0702 | 65 | 0,42 | 27 | " | " | " |
| 378 | 389 | 12 | SLYSIVSPFIPL | 1364 | A*3201 | 75 | 0,42 | 32 | " | " | " |
| 378 | 389 | 12 | SLYSIVSPFIPL | " | A*0201 | 34 | 0,42 | 14 | " | " | " |
| 378 | 389 | 12 | SLYSIVSPFIPL | " | B*1502 | 30 | 0,42 | 13 | " | " | " |
| 378 | 389 | 12 | SLYSIVSPFIPL | " | B*1501 | 5 | 0,42 | 2 | " | " | " |
| 380 | 389 | 10 | YSIVSPFIPL | 1365 | B*3901 | 65 | 0,42 | 27 | " | " | " |
| 380 | 389 | 10 | YSIVSPFIPL | " | A*6802 | 45 | 0,42 | 19 | " | " | " |
| 380 | 389 | 10 | YSIVSPFIPL | " | B*4001 | 40 | 0,42 | 17 | " | " | " |
| 378 | 390 | 13 | SLYSIVSPFIPLL | 1366 | A*0201 | 17 | 1,76 | 30 | " | " | " |
| 379 | 392 | 14 | LYSIVSPFIPLLPI | 1367 | A*2402 | 60 | 1,07 | 64 | " | " | " |
| 380 | 392 | 13 | YSIVSPFIPLLPI | 1368 | B*4601 | 45 | 1,07 | 48 | " | " | " |
| 380 | 392 | 13 | YSIVSPFIPLLPI | " | B*5201 | 30 | 1,07 | 32 | " | " | " |
| 381 | 392 | 12 | SIVSPFIPLLPI | 1369 | A*6802 | 25 | 1,07 | 27 | " | " | " |
| 382 | 392 | 11 | IVSPFIPLLPI | 1370 | A*6802 | 30 | 1,07 | 32 | " | " | " |
| 384 | 392 | 9 | SPFIPLLPI | 1371 | B*5501 | 90 | 1,07 | 96 | " | " | " |
| 384 | 392 | 9 | SPFIPLLPI | " | B*5201 | 75 | 1,07 | 80 | " | " | " |
| 384 | 392 | 9 | SPFIPLLPI | " | B*5101 | 70 | 1,07 | 75 | " | " | " |
| 384 | 392 | 9 | SPFIPLLPI | " | B*5601 | 10 | 1,07 | 11 | " | " | " |
| 380 | 393 | 14 | YSIVSPFIPLLPIF | 1372 | B*4601 | 85 | 0,82 | 69 | " | " | " |
| 380 | 393 | 14 | YSIVSPFIPLLPIF | " | B*5801 | 55 | 0,82 | 45 | " | " | " |
| 380 | 393 | 14 | YSIVSPFIPLLPIF | " | A*2501 | 45 | 0,82 | 37 | " | " | " |
| 380 | 393 | 14 | YSIVSPFIPLLPIF | " | B*1525 | 30 | 0,82 | 25 | " | " | " |
| 380 | 393 | 14 | YSIVSPFIPLLPIF | " | B*1501 | 15 | 0,82 | 12 | " | " | " |
| 381 | 393 | 13 | SIVSPFIPLLPIF | 1373 | B*1525 | 40 | 0,82 | 33 | " | " | " |
| 381 | 393 | 13 | SIVSPFIPLLPIF | " | A*2601 | 5 | 0,82 | 4 | " | " | " |
| 384 | 393 | 10 | SPFIPLLPIF | 1374 | B*3501 | 65 | 0,82 | 53 | " | " | " |
| 384 | 393 | 10 | SPFIPLLPIF | " | B*3503 | 65 | 0,82 | 53 | " | " | " |
| 384 | 393 | 10 | SPFIPLLPIF | " | B*5101 | 45 | 0,82 | 37 | " | " | " |
| 385 | 393 | 9 | PFIPLLPIF | 1375 | A*2301 | 15 | 0,82 | 12 | " | " | " |
| 386 | 393 | 8 | FIPLLPIF | 1376 | A*2501 | 20 | 0,82 | 16 | " | " | " |
| 384 | 394 | 11 | SPFIPLLPIFF | 1377 | B*3503 | 100 | 1,11 | 111 | " | " | " |
| 387 | 394 | 8 | IPLLPIFF | 1378 | B*3503 | 70 | 1,11 | 78 | " | " | " |
| 386 | 395 | 10 | FIPLIPIFFC | 1379 | A*0201 | 9 | 0,98 | 8 | " | " | " |
| 384 | 396 | 13 | SPFIPLLPIFFCL | 1380 | B*3503 | 75 | 1,93 | 145 | " | " | " |
| 387 | 396 | 10 | IPLLPIFFCL | 1381 | B*5101 | 10 | 1,93 | 19 | " | " | " |

TABLE 7a-continued

Predicted HLA class I-restricted CD8+ cytotoxic T cell epitopes
contained in SLP sequences from HBV large surface protein.

| | | | HLA class I binding peptides contained in SLP sequences derived from HBV Surface antigen | | | | | Peptide of invention (SLP) | | |
|---|---|---|---|---|---|---|---|---|---|---|
| Start | End | Length | Sequence[A] | SEQ ID NO: | HLA class 1 molecule | Class I-B score[B] | C-score[C] | Class I-BCI score[D] | SLP# | SLP Start | SLP End |
| 384 | 397 | 14 | SPFIPLLPIFFCLW | 1382 | B*3503 | 60 | 1,67 | 100 | " | " | " |
| 384 | 397 | 14 | SPFIPLLPIFFCLW | " | B*5301 | 15 | 1,67 | 25 | " | " | " |
| 387 | 397 | 11 | IPLLPIFFCLW | 1383 | B*5101 | 55 | 1,67 | 92 | " | " | " |
| 387 | 398 | 12 | IPLLPIFFCLWV | 1384 | B*5101 | 100 | 1,51 | 151 | " | " | " |
| 389 | 398 | 10 | LLPIfFCLWV | 1385 | A*0201 | 89 | 1,51 | 134 | " | " | " |
| 390 | 398 | 9 | LPIFFCLWV | 1386 | B*5101 | 85 | 1,51 | 129 | " | " | " |
| 386 | 399 | 14 | FIPLLPIFFCLWVY | 1387 | A*2501 | 50 | 1,83 | 92 | " | " | " |
| 386 | 399 | 14 | FIPLLPIFFCLWVY | " | A*0101 | 35 | 1,83 | 64 | " | " | " |
| 386 | 399 | 14 | FIPLLPIFFCLWVY | " | A*2601 | 20 | 1,83 | 37 | " | " | " |
| 387 | 399 | 13 | IPLLPIFFCLWVY | 1388 | B*3501 | 60 | 1,83 | 110 | " | " | " |
| 388 | 399 | 12 | PLLPIFFCLWVY | 1389 | A*2902 | 25 | 1,83 | 46 | " | " | " |
| 388 | 399 | 12 | PLLPIFFCLWVY | " | A*3002 | 25 | 1,83 | 46 | " | " | " |
| 389 | 399 | 11 | LLPIFFCLWVY | 1390 | A*0101 | 60 | 1,83 | 110 | " | " | " |
| 390 | 399 | 10 | LPIFFCLWVY | 1391 | B*3501 | 95 | 1,83 | 174 | " | " | " |
| 390 | 399 | 10 | LPIFFCLWVY | " | B*5101 | 35 | 1,83 | 64 | " | " | " |
| 390 | 399 | 10 | LPIFFCLWVY | " | B*5301 | 35 | 1,83 | 64 | " | " | " |
| 391 | 399 | 9 | PIFFCLWVY | 1392 | A*3002 | 40 | 1,83 | 73 | " | " | " |
| 391 | 399 | 9 | PIFFCLWVY | " | A*2501 | 25 | 1,83 | 46 | " | " | " |
| 392 | 399 | 8 | IFFCLWVY | 1393 | A*3002 | 35 | 1,83 | 64 | " | " | " |
| 387 | 400 | 14 | IPLLPIFFCLWVYI | 1394 | B*5101 | 90 | 1,45 | 131 | " | " | " |
| 387 | 400 | 14 | IPLLPIFFCLWVYI | " | B*5201 | 20 | 1,45 | 29 | " | " | " |
| 390 | 400 | 11 | LPIFFCLWVYI | 1395 | B*3503 | 5 | 1,45 | 7 | " | " | " |
| | | | | | Cumulative Class I-BCI score: | | | 5389 | | | |
| 370 | 379 | 10 | WMMWYWGPSL | 1345 | B*0801 | 95 | 1,46 | 138 | 37 | 370 | 400 |
| 370 | 379 | 10 | WMMWYWGPSL | " | B*3801 | 95 | 1,46 | 138 | " | " | " |
| 370 | 379 | 10 | WMMWYWGPSL | " | B*3901 | 95 | 1,46 | 138 | " | " | " |
| 370 | 379 | 10 | WMMWYWGPSL | " | B*4801 | 80 | 1,46 | 117 | " | " | " |
| 370 | 379 | 10 | WMMWYWGPSL | " | B*3701 | 65 | 1,46 | 95 | " | " | " |
| 370 | 379 | 10 | WMMWYWGPSL | " | B*1301 | 40 | 1,46 | 58 | " | " | " |
| 370 | 379 | 10 | WMMWYWGPSL | " | B*1525 | 20 | 1,46 | 29 | " | " | " |
| 370 | 380 | 11 | WMMWYWGPSLY | 1349 | B*1502 | 100 | 1,93 | 193 | " | " | " |
| 370 | 380 | 11 | WMMWYWGPSLY | " | A*0101 | 95 | 1,93 | 183 | " | " | " |
| 370 | 380 | 11 | WMMWYWGPSLY | " | B*1501 | 75 | 1,93 | 145 | " | " | " |
| 371 | 380 | 10 | MMWYWGPSLY | 1350 | A*0301 | 100 | 1,93 | 193 | " | " | " |

TABLE 7a-continued

Predicted HLA class I-restricted CD8+ cytotoxic T cell epitopes
contained in SLP sequences from HBV large surface protein.

| | | | HLA class I binding peptides contained in SLP sequences derived from HBV Surface antigen | | | | | | Peptide of invention (SLP) | | |
|---|---|---|---|---|---|---|---|---|---|---|---|
| Start | End | Length | Sequence[A] | SEQ ID NO: | HLA class 1 molecule | Class I-B score[B] | C-score[C] | Class I-BCI score[D] | SLP# | SLP Start | SLP End |
| 371 | 380 | 10 | MMWYWGPSLY | " | A*3002 | 90 | 1,93 | 174 | " | " | " |
| 371 | 380 | 10 | MMWYWGPSLY | " | B*1525 | 90 | 1,93 | 174 | " | " | " |
| 371 | 380 | 10 | MMWYWGPSLY | " | A*7401 | 80 | 1,93 | 154 | " | " | " |
| 371 | 380 | 10 | MMWYWGPSLY | " | A*2902 | 65 | 1,93 | 125 | " | " | " |
| 372 | 380 | 9 | MWYWGPSLY | 1351 | A*2902 | 100 | 1,93 | 193 | " | " | " |
| 370 | 382 | 13 | WMMWYWGPSLYSI | 1353 | A*0206 | 100 | 0,77 | 77 | " | " | " |
| 370 | 382 | 13 | WMMWYWGPSLYSI | " | B*0801 | 85 | 0,77 | 65 | " | " | " |
| 370 | 382 | 13 | WMMWYWGPSLYSI | " | B*3801 | 75 | 0,77 | 58 | " | " | " |
| 370 | 382 | 13 | WMMWYWGPSLYSI | " | A*0201 | 74 | 0,77 | 57 | " | " | " |
| 371 | 382 | 12 | MMWYWGPSLYSI | 1354 | A*3201 | 100 | 0,77 | 77 | " | " | " |
| 371 | 382 | 12 | MMWYWGPSLYSI | " | B*5201 | 100 | 0,77 | 77 | " | " | " |
| 371 | 382 | 12 | MMWYWGPSLYSI | " | B*1302 | 95 | 0,77 | 73 | " | " | " |
| 371 | 382 | 12 | MMWYWGPSLYSI | " | A*0201 | 86 | 0,77 | 66 | " | " | " |
| 371 | 382 | 12 | MMWYWGPSLYSI | " | A*7401 | 75 | 0,77 | 58 | " | " | " |
| 371 | 382 | 12 | MMWYWGPSLYSI | " | B*4801 | 75 | 0,77 | 58 | " | " | " |
| 371 | 382 | 12 | MMWYWGPSLYSI | " | B*1301 | 70 | 0,77 | 54 | " | " | " |
| 370 | 383 | 14 | WMMWYWGPSLYSIV | 1355 | A*0206 | 70 | 0,79 | 55 | " | " | " |
| 370 | 383 | 14 | WMMWYWGPSLYSIV | " | A*0201 | 51 | 0,79 | 40 | " | " | " |
| 370 | 383 | 14 | WMMWYWGPSLYSIV | " | B*0801 | 45 | 0,79 | 35 | " | " | " |
| 370 | 383 | 14 | WMMWYWGPSLYSIV | " | B*3901 | 10 | 0,79 | 8 | " | " | " |
| 370 | 383 | 14 | WMMWYWGPSLYSIV | " | B*3801 | 5 | 0,79 | 4 | " | " | " |
| 371 | 383 | 13 | MMWYWGPSLYSIV | 1356 | A*0201 | 69 | 0,79 | 54 | " | " | " |
| 371 | 383 | 13 | MMWYWGPSLYSIV | " | B*1302 | 25 | 0,79 | 20 | " | " | " |
| 371 | 383 | 13 | MMWYWGPSLYSIV | " | B*4801 | 25 | 0,79 | 20 | " | " | " |
| 373 | 386 | 14 | WYWGPSLYSIVSPF | 1357 | B*1502 | 80 | 0,72 | 58 | " | " | " |
| 373 | 386 | 14 | WYWGPSLYSIVSPF | " | A*2301 | 55 | 0,72 | 40 | " | " | " |
| 373 | 386 | 14 | WYWGPSLYSIVSPF | " | A*2402 | 20 | 0,72 | 14 | " | " | " |
| 373 | 386 | 14 | WYWGPSLYSIVSPF | " | A*2902 | 15 | 0,72 | 11 | " | " | " |
| 374 | 386 | 13 | YWGPSLYSIVSPF | 1358 | A*2301 | 70 | 0,72 | 51 | " | " | " |
| 374 | 386 | 13 | YWGPSLYSIVSPF | " | A*2402 | 70 | 0,72 | 51 | " | " | " |
| 377 | 386 | 10 | PSLYSIVSPF | 1359 | A*3201 | 35 | 0,72 | 25 | " | " | " |
| 378 | 386 | 9 | SLYSIVSPF | 1360 | B*1525 | 95 | 0,72 | 69 | " | " | " |
| 378 | 386 | 9 | SLYSIVSPF | " | A*3201 | 90 | 0,72 | 65 | " | " | " |
| 378 | 386 | 9 | SLYSIVSPF | " | B*1501 | 85 | 0,72 | 61 | " | " | " |
| 378 | 386 | 9 | SLYSIVSPF | " | B*4601 | 20 | 0,72 | 14 | " | " | " |

TABLE 7a-continued

Predicted HLA class I-restricted CD8+ cytotoxic T cell epitopes
contained in SLP sequences from HBV large surface protein.

| | | | HLA class I binding peptides contained in SLP sequences derived from HBV Surface antigen | | | | | | Peptide of invention (SLP) | | |
|---|---|---|---|---|---|---|---|---|---|---|---|
| Start | End | Length | Sequence[A] | SEQ ID NO: | HLA class 1 molecule | Class I-B score[B] | C-score[C] | Class I-BCI score[D] | SLP# | SLP Start | SLP End |
| 378 | 386 | 9 | SLYSIVSPF | | A*2601 | 10 | 0,72 | 7 | " | " | " |
| 374 | 387 | 14 | YWGPSLYSIVSPFI | 1361 | A*2402 | 15 | 1,16 | 17 | " | " | " |
| 378 | 387 | 10 | SLYSiVSPFI | 1362 | A*0201 | 3 | 1,16 | 3 | " | " | " |
| 376 | 389 | 14 | GPSLYSIVSPFIPL | 1363 | B*0702 | 65 | 0,42 | 27 | " | " | " |
| 378 | 389 | 12 | SLYSIVSPFIPL | 1364 | A*3201 | 75 | 0,42 | 32 | " | " | " |
| 378 | 389 | 12 | SLYSIVSPFIPL | | A*0201 | 34 | 0,42 | 14 | " | " | " |
| 378 | 389 | 12 | SLYSIVSPFIPL | | B*1502 | 30 | 0,42 | 13 | " | " | " |
| 378 | 389 | 12 | SLYSIVSPFIPL | | B*1501 | 5 | 0,42 | 2 | " | " | " |
| 380 | 389 | 10 | YSIVSPFIPL | 1365 | B*3901 | 65 | 0,42 | 27 | " | " | " |
| 380 | 389 | 10 | YSIVSPFIPL | | A*6802 | 45 | 0,42 | 19 | " | " | " |
| 380 | 389 | 10 | YSIVSPFIPL | | B*4001 | 40 | 0,42 | 17 | " | " | " |
| 378 | 390 | 13 | SLYSIVSPFIPLL | 1366 | A*0201 | 17 | 1,76 | 30 | " | " | " |
| 379 | 392 | 14 | LYSIVSPFIPLLPI | 1367 | A*2402 | 60 | 1,07 | 64 | " | " | " |
| 380 | 392 | 13 | YSIVSPFIPLLPI | 1368 | B*4601 | 45 | 1,07 | 48 | " | " | " |
| 380 | 392 | 13 | YSIVSPFIPLLPI | | B*5201 | 30 | 1,07 | 32 | " | " | " |
| 381 | 392 | 12 | SIVSPFIPLLPI | 1369 | A*6802 | 25 | 1,07 | 27 | " | " | " |
| 382 | 392 | 11 | IVSPFIPLLPI | 1370 | A*6802 | 30 | 1,07 | 32 | " | " | " |
| 384 | 392 | 9 | SPFIPLLPI | 1371 | B*5501 | 90 | 1,07 | 96 | " | " | " |
| 384 | 392 | 9 | sPFIPLLPI | | B*5201 | 75 | 1,07 | 80 | " | " | " |
| 384 | 392 | 9 | sPFIPLLPI | | B*5101 | 70 | 1,07 | 75 | " | " | " |
| 384 | 392 | 9 | SPFIPLLPI | | B*5601 | 10 | 1,07 | 11 | " | " | " |
| 380 | 393 | 14 | YSIVSPFIPLLPIF | 1372 | B*4601 | 85 | 0,82 | 69 | " | " | " |
| 380 | 393 | 14 | YSIVSPFIPLLPIF | | B*5801 | 55 | 0,82 | 45 | " | " | " |
| 380 | 393 | 14 | YSIVSPFIPLLPIF | | A*2501 | 45 | 0,82 | 37 | " | " | " |
| 380 | 393 | 14 | YSIVSPFIPLLPIF | | B*1525 | 30 | 0,82 | 25 | " | " | " |
| 380 | 393 | 14 | YSIVSPFIPLLPIF | | B*1501 | 15 | 0,82 | 12 | " | " | " |
| 381 | 393 | 13 | SIVSPFIPLLPIF | 1373 | B*1525 | 40 | 0,82 | 33 | " | " | " |
| 381 | 393 | 13 | SIVSPFIPLLPIF | | A*2601 | 5 | 0,82 | 4 | " | " | " |
| 384 | 393 | 10 | SPFIPLLPIF | 1374 | B*3501 | 65 | 0,82 | 53 | " | " | " |
| 384 | 393 | 10 | SPFIPLLPIF | | B*3503 | 65 | 0,82 | 53 | " | " | " |
| 384 | 393 | 10 | SPFIPLLPIF | | B*5101 | 45 | 0,82 | 37 | " | " | " |
| 385 | 393 | 9 | PFIPLLPIF | 1375 | A*2301 | 15 | 0,82 | 12 | " | " | " |
| 386 | 393 | 8 | FIPLLPIF | 1376 | A*2501 | 20 | 0,82 | 16 | " | " | " |
| 384 | 394 | 11 | SPFIPLLPIFF | 1377 | B*3503 | 100 | 1,11 | 111 | " | " | " |
| 387 | 394 | 8 | IPLLPIFF | 1378 | B*3503 | 70 | 1,11 | 78 | " | " | " |

TABLE 7a-continued

Predicted HLA class I-restricted CD8+ cytotoxic T cell epitopes contained in SLP sequences from HBV large surface protein.

| | HLA class I binding peptides contained in SLP sequences derived from HBV Surface antigen | | | | | | | | Peptide of invention (SLP) | | |
|---|---|---|---|---|---|---|---|---|---|---|---|
| Start | End | Length | Sequence[A] | SEQ ID NO: | HLA class 1 molecule | Class I-B score[B] | C-score[C] | Class I-BCI score[D] | SLP# | SLP Start | SLP End |
| 386 | 395 | 10 | FIPLIPIFFC | 1379 | A*0201 | 9 | 0,98 | 8 | " | " | " |
| 384 | 396 | 13 | SPFIPLLPIFFCL | 1380 | B*3503 | 75 | 1,93 | 145 | " | " | " |
| 387 | 396 | 10 | IPLLPIFFCL | 1381 | B*5101 | 10 | 1,93 | 19 | " | " | " |
| 384 | 397 | 14 | SPFIPLLPIFFCLW | 1382 | B*3503 | 60 | 1,67 | 100 | " | " | " |
| 384 | 397 | 14 | SPFIPLLPIFFCLW | " | B*5301 | 15 | 1,67 | 25 | " | " | " |
| 387 | 397 | 11 | IPLLPIFFCLW | 1383 | B*5101 | 55 | 1,67 | 92 | " | " | " |
| 387 | 398 | 12 | IPLLPIFFCLWV | 1384 | B*5101 | 100 | 1,51 | 151 | " | " | " |
| 389 | 398 | 10 | LLPIfFCLWV | 1385 | A*0201 | 89 | 1,51 | 134 | " | " | " |
| 390 | 398 | 9 | LPIFFCLWV | 1386 | B*5101 | 85 | 1,51 | 129 | " | " | " |
| 386 | 399 | 14 | FIPLLPIFFCLWVY | 1387 | A*2501 | 50 | 1,83 | 92 | " | " | " |
| 386 | 399 | 14 | FIPLLPIFFCLWVY | " | A*0101 | 35 | 1,83 | 64 | " | " | " |
| 386 | 399 | 14 | FIPLLPIFFCLWVY | " | A*2601 | 20 | 1,83 | 37 | " | " | " |
| 387 | 399 | 13 | IPLLPIFFCLWVY | 1388 | B*3501 | 60 | 1,83 | 110 | " | " | " |
| 388 | 399 | 12 | PLLPIFFCLWVY | 1389 | A*2902 | 25 | 1,83 | 46 | " | " | " |
| 388 | 399 | 12 | PLLPIFFCLWVY | " | A*3002 | 25 | 1,83 | 46 | " | " | " |
| 389 | 399 | 11 | LLPIFFCLWVY | 1390 | A*0101 | 60 | 1,83 | 110 | " | " | " |
| 390 | 399 | 10 | LPIFFCLWVY | 1391 | B*3501 | 95 | 1,83 | 174 | " | " | " |
| 390 | 399 | 10 | LPIFFCLWVY | " | B*5101 | 35 | 1,83 | 64 | " | " | " |
| 390 | 399 | 10 | LPIFFCLWVY | " | B*5301 | 35 | 1,83 | 64 | " | " | " |
| 391 | 399 | 9 | PIFFCLWVY | 1392 | A*3002 | 40 | 1,83 | 73 | " | " | " |
| 391 | 399 | 9 | PIFFCLWVY | " | A*2501 | 25 | 1,83 | 46 | " | " | " |
| 392 | 399 | 8 | IFFCLWVY | 1393 | A*3002 | 35 | 1,83 | 64 | " | " | " |
| 387 | 400 | 14 | IPLLPIFFCLWVYI | 1394 | B*5101 | 90 | 1,45 | 131 | " | " | " |
| 387 | 400 | 14 | IPLLPIFFCLWVYI | " | B*5201 | 20 | 1,45 | 29 | " | " | " |
| 390 | 400 | 11 | LPIFFCLWVYI | 1395 | B*3503 | 5 | 1,45 | 7 | " | " | " |
| | | | | | Cumulative Class I-BCI score: | | | 6880 | | | |

"Start" and "End" are relative to the amino acid sequence of HBV large surface protein as depicted in SEQ ID NO: 1141
[A]Peptide amino acid sequence. Each HLA class I binding peptide of HBV large surface protein is listed separately for each HLA class I molecule to which it is predicted to bind, and can be listed multiple times for that reason.
[B]Class I-B score. See *Material and Methods* (Examples section).
[C]C-score. See *Material and Methods* (Examples section).
[D]Class I-BCI score. See *Material and Methods* (Examples section).
[E]Cumulative Class I-BCI score. See *Material and Methods* (Examples section).

TABLE 7b

Predicted HLA class II-restricted CD4+ T cell epitopes contained in SLP sequences from HBV large surface protein.

HLA class II binding peptides in SLP derived from HBV Surface antigen

| Start | End | Sequence[A] | SEQ ID NO: | HLA-DRB1 molecule | ClassII-B score[B] | Peptide of invention (SLP) | | |
|---|---|---|---|---|---|---|---|---|
| | | | | | | SLP# | SLP Start | SLP End |
| 181 | 195 | GFLGPLLVLQAGFFL | 1396 | *1501 | 85 | 30 | 175 | 210 |
| 181 | 195 | GFLGPLLVLQAGFFL | " | *0101 | 60 | " | " | " |
| 181 | 195 | GFLGPLLVLQAGFFL | " | *1301 | 53 | " | " | " |
| 181 | 195 | GFLGPLLVLQAGFFL | " | *0102 | 8 | " | " | " |
| 182 | 196 | FLGPLLVLQAGFFLL | 1397 | *0101 | 93 | " | " | " |
| 182 | 196 | FLGPLLVLQAGFFLL | " | *1501 | 83 | " | " | " |
| 182 | 196 | FLGPLLVLQAGFFLL | " | *1301 | 50 | " | " | " |
| 182 | 196 | FLGPLLVLQAGFFLL | " | *0102 | 35 | " | " | " |
| 182 | 196 | FLGPLLVLQAGFFLL | " | *0104 | 28 | " | " | " |
| 182 | 196 | FLGPLLVLQAGFFLL | " | *0106 | 20 | " | " | " |
| 183 | 197 | LGPLLVLQAGFFLLT | 1398 | *0101 | 90 | " | " | " |
| 183 | 197 | LGPLLVLQAGFFLLT | " | *1501 | 80 | " | " | " |
| 183 | 197 | LGPLLVLQAGFFLLT | " | *1301 | 48 | " | " | " |
| 183 | 197 | LGPLLVLQAGFFLLT | " | *0104 | 30 | " | " | " |
| 183 | 197 | LGPLLVLQAGFFLLT | " | *0102 | 13 | " | " | " |
| 183 | 197 | LGPLLVLQAGFFLLT | " | *0106 | 8 | " | " | " |
| 184 | 198 | GPLLVLQAGFFLLTR | 1399 | *1501 | 78 | " | " | " |
| 184 | 198 | GPLLVLQAGFFLLTR | " | *0101 | 58 | " | " | " |
| 184 | 198 | GPLLVLQAGFFLLTR | " | *1301 | 45 | " | " | " |
| 184 | 198 | GPLLVLQAGFFLLTR | " | *0104 | 33 | " | " | " |
| 184 | 198 | GPLLVLQAGFFLLTR | " | *0102 | 10 | " | " | " |
| 184 | 198 | GPLLVLQAGFFLLTR | " | *0106 | 3 | " | " | " |
| 185 | 199 | PLLVLQAGFFLLTRI | 1400 | *1501 | 75 | " | " | " |
| 185 | 199 | PLLVLQAGFFLLTRI | " | *1301 | 43 | " | " | " |
| 185 | 199 | PLLVLQAGFFLLTRI | " | *0101 | 13 | " | " | " |
| 186 | 200 | LLVLQAGFFLLTRIL | 1401 | *1301 | 40 | " | " | " |
| 186 | 200 | LLVLQAGFFLLTRIL | " | *1501 | 25 | " | " | " |
| 187 | 201 | LVLQAGFFLLTRILT | 1402 | *1101 | 83 | " | " | " |
| 187 | 201 | LVLQAGFFLLTRILT | " | *0101 | 40 | " | " | " |
| 187 | 201 | LVLQAGFFLLTRILT | " | *0701 | 40 | " | " | " |
| 187 | 201 | LVLQAGFFLLTRILT | " | *1301 | 38 | " | " | " |
| 187 | 201 | LVLQAGFFLLTRILT | " | *1501 | 15 | " | " | " |
| 187 | 201 | LVLQAGFFLLTRILT | " | *0301 | 10 | " | " | " |
| 188 | 202 | VLQAGFFLLTRILTI | 1403 | *0401 | 93 | " | " | " |
| 188 | 202 | VLQAGFFLLTRILTI | " | *0701 | 80 | " | " | " |

TABLE 7b-continued

Predicted HLA class II-restricted CD4+ T cell epitopes contained in SLP sequences from HBV large surface protein.

HLA class II binding peptides in SLP derived from HBV Surface antigen

| Start | End | Sequence[A] | SEQ ID NO: | HLA-DRB1 molecule | ClassII-B score[B] | Peptide of invention (SLP) SLP# | SLP Start | SLP End |
|---|---|---|---|---|---|---|---|---|
| 188 | 202 | VLQAGFFLLTRILTI | " | *1101 | 80 | " | " | " |
| 188 | 202 | VLQAGFFLLTRILTI | " | *0101 | 70 | " | " | " |
| 188 | 202 | VLQAGFFLLTRILTI | " | *0104 | 20 | " | " | " |
| 188 | 202 | VLQAGFFLLTRILTI | " | *0102 | 15 | " | " | " |
| 189 | 203 | LQAGFFLLTRILTIP | 1404 | *0401 | 90 | " | " | " |
| 189 | 203 | LQAGFFLLTRILTIP | " | *0701 | 78 | " | " | " |
| 189 | 203 | LQAGFFLLTRILTIP | " | *1101 | 78 | " | " | " |
| 189 | 203 | LQAGFFLLTRILTIP | " | *0101 | 50 | " | " | " |
| 189 | 203 | LQAGFFLLTRILTIP | " | *0104 | 35 | " | " | " |
| 189 | 203 | LQAGFFLLTRILTIP | " | *0102 | 33 | " | " | " |
| 190 | 204 | QAGFFLLTRILTIPQ | 1405 | *0401 | 100 | " | " | " |
| 190 | 204 | QAGFFLLTRILTIPQ | " | *0701 | 75 | " | " | " |
| 190 | 204 | QAGFFLLTRILTIPQ | " | *1101 | 75 | " | " | " |
| 190 | 204 | QAGFFLLTRILTIPQ | " | *0101 | 68 | " | " | " |
| 190 | 204 | QAGFFLLTRILTIPQ | " | *0102 | 63 | " | " | " |
| 190 | 204 | QAGFFLLTRILTIPQ | " | *0104 | 58 | " | " | " |
| 190 | 204 | QAGFFLLTRILTIPQ | " | *1501 | 20 | " | " | " |
| 190 | 204 | QAGFFLLTRILTIPQ | " | *0105 | 8 | " | " | " |
| 190 | 204 | QAGFFLLTRILTIPQ | " | *0107 | 8 | " | " | " |
| 191 | 205 | AGFFLLTRILTIPQS | 1406 | *0401 | 98 | " | " | " |
| 191 | 205 | AGFFLLTRILTIPQS | " | *0701 | 73 | " | " | " |
| 191 | 205 | AGFFLLTRILTIPQS | " | *1101 | 73 | " | " | " |
| 191 | 205 | AGFFLLTRILTIPQS | " | *0102 | 70 | " | " | " |
| 191 | 205 | AGFFLLTRILTIPQS | " | *0104 | 65 | " | " | " |
| 191 | 205 | AGFFLLTRILTIPQS | " | *0101 | 55 | " | " | " |
| 191 | 205 | AGFFLLTRILTIPQS | " | *0106 | 23 | " | " | " |
| 191 | 205 | AGFFLLTRILTIPQS | " | *0105 | 10 | " | " | " |
| 191 | 205 | AGFFLLTRILTIPQS | " | *0107 | 10 | " | " | " |
| 192 | 206 | GFFLLTRILTIPQSL | 1407 | *0401 | 95 | " | " | " |
| 192 | 206 | GFFLLTRILTIPQSL | " | *1301 | 85 | " | " | " |
| 192 | 206 | GFFLLTRILTIPQSL | " | *0102 | 83 | " | " | " |
| 192 | 206 | GFFLLTRILTIPQSL | " | *0104 | 80 | " | " | " |
| 192 | 206 | GFFLLTRILTIPQSL | " | *0701 | 70 | " | " | " |
| 192 | 206 | GFFLLTRILTIPQSL | " | *1101 | 70 | " | " | " |

TABLE 7b-continued

Predicted HLA class II-restricted CD4+ T cell epitopes contained in SLP sequences from HBV large surface protein.

HLA class II binding peptides in SLP derived from HBV Surface antigen

| Start | End | Sequence[A] | SEQ ID NO: | HLA-DRB1 molecule | ClassII-B score[B] | Peptide of invention (SLP) SLP# | SLP Start | SLP End |
|---|---|---|---|---|---|---|---|---|
| 192 | 206 | GFFLLTRILTIPQSL | " | *0106 | 50 | " | " | " |
| 192 | 206 | GFFLLTRILTIPQSL | " | *0105 | 28 | " | " | " |
| 192 | 206 | GFFLLTRILTIPQSL | " | *0107 | 28 | " | " | " |
| 192 | 206 | GFFLLTRILTIPQSL | " | *0101 | 18 | " | " | " |
| 192 | 206 | GFFLLTRILTIPQSL | " | *1501 | 10 | " | " | " |
| 193 | 207 | FFLLTRILTIPQSLD | 1408 | *0401 | 88 | " | " | " |
| 193 | 207 | FFLLTRILTIPQSLD | " | *0102 | 75 | " | " | " |
| 193 | 207 | FFLLTRILTIPQSLD | " | *1301 | 75 | " | " | " |
| 193 | 207 | FFLLTRILTIPQSLD | " | *0701 | 68 | " | " | " |
| 193 | 207 | FFLLTRILTIPQSLD | " | *1101 | 68 | " | " | " |
| 193 | 207 | FFLLTRILTIPQSLD | " | *0104 | 63 | " | " | " |
| 193 | 207 | FFLLTRILTIPQSLD | " | *0106 | 48 | " | " | " |
| 193 | 207 | FFLLTRILTIPQSLD | " | *0101 | 18 | " | " | " |
| 193 | 207 | FFLLTRILTIPQSLD | " | *0105 | 18 | " | " | " |
| 193 | 207 | FFLLTRILTIPQSLD | " | *0107 | 18 | " | " | " |
| 194 | 208 | FLLTRILTIPQSLDS | 1409 | *0401 | 85 | " | " | " |
| 194 | 208 | FLLTRILTIPQSLDS | " | *1301 | 65 | " | " | " |
| 194 | 208 | FLLTRILTIPQSLDS | " | *0102 | 58 | " | " | " |
| 194 | 208 | FLLTRILTIPQSLDS | " | *1101 | 53 | " | " | " |
| 194 | 208 | FLLTRILTIPQSLDS | " | *0106 | 43 | " | " | " |
| 194 | 208 | FLLTRILTIPQSLDS | " | *0104 | 40 | " | " | " |
| 194 | 208 | FLLTRILTIPQSLDS | " | *0701 | 3 | " | " | " |
| 195 | 209 | LLTRILTIPQSLDSW | " | *1301 | 70 | " | " | " |
| 195 | 209 | LLTRILTIPQSLDSW | " | *0102 | 45 | " | " | " |
| 195 | 209 | LLTRILTIPQSLDSW | " | *0106 | 35 | " | " | " |
| 195 | 209 | LLTRILTIPQSLDSW | 1410 | *0401 | 15 | " | " | " |
| 196 | 210 | LTRILTIPQSLDSWW | 1411 | *1301 | 45 | " | " | " |
| | | Cumulative Class 11-B score: | | | 4798 | | | |
| 240 | 254 | PPICPGYRWMCLRRF | 1412 | *1301 | 83 | 31 | 239 | 274 |
| 240 | 254 | PPICPGYRWMCLRRF | " | *1101 | 70 | " | " | " |
| 241 | 255 | PICPGYRWMCLRRFI | 1413 | *1301 | 80 | " | " | " |
| 241 | 255 | PICPGYRWMCLRRFI | " | *1101 | 80 | " | " | " |
| 241 | 255 | PICPGYRWMCLRRFI | " | *1501 | 60 | " | " | " |
| 241 | 255 | PICPGYRWMCLRRFI | " | *0701 | 35 | " | " | " |
| 242 | 256 | ICPGYRWMCLRRFII | 1414 | *1301 | 78 | " | " | " |

TABLE 7b-continued

Predicted HLA class II-restricted CD4+ T cell epitopes contained in SLP sequences from HBV large surface protein.

HLA class II binding peptides in SLP derived from HBV Surface antigen

| Start | End | Sequence[A] | SEQ ID NO: | HLA-DRB1 molecule | ClassII-B score[B] | SLP# | SLP Start | SLP End |
|---|---|---|---|---|---|---|---|---|
| 242 | 256 | ICPGYRWMCLRRFII | " | *1501 | 95 | " | " | " |
| 242 | 256 | ICPGYRWMCLRRFII | " | *1101 | 90 | " | " | " |
| 242 | 256 | ICPGYRWMCLRRFII | " | *0701 | 85 | " | " | " |
| 242 | 256 | ICPGYRWMCLRRFII | " | *0104 | 70 | " | " | " |
| 242 | 256 | ICPGYRWMCLRRFII | " | *0102 | 68 | " | " | " |
| 242 | 256 | ICPGYRWMCLRRFII | " | *0101 | 50 | " | " | " |
| 242 | 256 | ICPGYRWMCLRRFII | " | *0105 | 50 | " | " | " |
| 242 | 256 | ICPGYRWMCLRRFII | " | *0107 | 50 | " | " | " |
| 242 | 256 | ICPGYRWMCLRRFII | " | *0301 | 35 | " | " | " |
| 243 | 257 | CPGYRWMCLRRFIIF | 1415 | *1301 | 75 | " | " | " |
| 243 | 257 | CPGYRWMCLRRFIIF | " | *1101 | 5 | " | " | " |
| 243 | 257 | CPGYRWMCLRRFIIF | " | *1501 | 100 | " | " | " |
| 243 | 257 | CPGYRWMCLRRFIIF | " | *0701 | 95 | " | " | " |
| 243 | 257 | CPGYRWMCLRRFIIF | " | *0104 | 85 | " | " | " |
| 243 | 257 | CPGYRWMCLRRFIIF | " | *0102 | 80 | " | " | " |
| 243 | 257 | CPGYRWMCLRRFIIF | " | *0101 | 58 | " | " | " |
| 243 | 257 | CPGYRWMCLRRFIIF | " | *0105 | 58 | " | " | " |
| 243 | 257 | CPGYRWMCLRRFIIF | " | *0107 | 58 | " | " | " |
| 243 | 257 | CPGYRWMCLRRFIIF | " | *0301 | 40 | " | " | " |
| 244 | 258 | PGYRWMCLRRFIIFL | 1416 | *1301 | 73 | " | " | " |
| 244 | 258 | PGYRWMCLRRFIIFL | " | *1101 | 95 | " | " | " |
| 244 | 258 | PGYRWMCLRRFIIFL | " | *1501 | 90 | " | " | " |
| 244 | 258 | PGYRWMCLRRFIIFL | " | *0701 | 80 | " | " | " |
| 244 | 258 | PGYRWMCLRRFIIFL | " | *0104 | 75 | " | " | " |
| 244 | 258 | PGYRWMCLRRFIIFL | " | *0102 | 73 | " | " | " |
| 244 | 258 | PGYRWMCLRRFIIFL | " | *0101 | 45 | " | " | " |
| 244 | 258 | PGYRWMCLRRFIIFL | " | *0105 | 45 | " | " | " |
| 244 | 258 | PGYRWMCLRRFIIFL | " | *0107 | 45 | " | " | " |
| 244 | 258 | PGYRWMCLRRFIIFL | " | *0301 | 15 | " | " | " |
| 245 | 259 | GYRWMCLRRFIIFLF | 1417 | *1301 | 100 | " | " | " |
| 245 | 259 | GYRWMCLRRFIIFLF | " | *0701 | 48 | " | " | " |
| 245 | 259 | GYRWMCLRRFIIFLF | " | *1501 | 20 | " | " | " |
| 245 | 259 | GYRWMCLRRFIIFLF | " | *1101 | 85 | " | " | " |
| 245 | 259 | GYRWMCLRRFIIFLF | " | *0102 | 60 | " | " | " |

TABLE 7b-continued

Predicted HLA class II-restricted CD4+ T cell epitopes contained in SLP sequences from HBV large surface protein.

HLA class II binding peptides in SLP derived from HBV Surface antigen

| Start | End | Sequence[A] | SEQ ID NO: | HLA-DRB1 molecule | ClassII-B score[B] | Peptide of invention (SLP) | | |
|---|---|---|---|---|---|---|---|---|
| | | | | | | SLP# | SLP Start | SLP End |
| 245 | 259 | GYRWMCLRRFIIFLF | " | *0104 | 60 | " | " | " |
| 245 | 259 | GYRWMCLRRFIIFLF | " | *0101 | 30 | " | " | " |
| 245 | 259 | GYRWMCLRRFIIFLF | " | *0105 | 30 | " | " | " |
| 245 | 259 | GYRWMCLRRFIIFLF | " | *0107 | 30 | " | " | " |
| 246 | 260 | YRWMCLRRFIIFLFI | 1418 | *1301 | 98 | " | " | " |
| 246 | 260 | YRWMCLRRFIIFLFI | " | *0701 | 50 | " | " | " |
| 246 | 260 | YRWMCLRRFIIFLFI | " | *1501 | 23 | " | " | " |
| 246 | 260 | YRWMCLRRFIIFLFI | " | *1101 | 75 | " | " | " |
| 247 | 261 | RWMCLRRFIIFLFIL | 1419 | *1301 | 95 | " | " | " |
| 247 | 261 | RWMCLRRFIIFLFIL | " | *0701 | 30 | " | " | " |
| 247 | 261 | RWMCLRRFIIFLFIL | " | *1501 | 10 | " | " | " |
| 247 | 261 | RWMCLRRFIIFLFIL | " | *1101 | 45 | " | " | " |
| 248 | 262 | WMCLRRFIIFLFILL | 1420 | *1301 | 93 | " | " | " |
| 248 | 262 | WMCLRRFIIFLFILL | " | *1501 | 73 | " | " | " |
| 248 | 262 | WMCLRRFIIFLFILL | " | *0701 | 60 | " | " | " |
| 248 | 262 | WMCLRRFIIFLFILL | " | *0301 | 28 | " | " | " |
| 249 | 263 | MCLRRFIIFLFILLL | 1421 | *1501 | 95 | " | " | " |
| 249 | 263 | MCLRRFIIFLFILLL | " | *1301 | 90 | " | " | " |
| 249 | 263 | MCLRRFIIFLFILLL | " | *0301 | 80 | " | " | " |
| 249 | 263 | MCLRRFIIFLFILLL | " | *0701 | 58 | " | " | " |
| 249 | 263 | MCLRRFIIFLFILLL | " | *0101 | 53 | " | " | " |
| 249 | 263 | MCLRRFIIFLFILLL | " | *1101 | 50 | " | " | " |
| 249 | 263 | MCLRRFIIFLFILLL | " | *0401 | 3 | " | " | " |
| 250 | 264 | CLRRFIIFLFILLLC | 1422 | *1301 | 88 | " | " | " |
| 250 | 264 | CLRRFIIFLFILLLC | " | *0301 | 78 | " | " | " |
| 250 | 264 | CLRRFIIFLFILLLC | " | *1501 | 68 | " | " | " |
| 250 | 264 | CLRRFIIFLFILLLC | " | *0701 | 55 | " | " | " |
| 250 | 264 | CLRRFIIFLFILLLC | " | *0101 | 48 | " | " | " |
| 250 | 264 | CLRRFIIFLFILLLC | " | *1101 | 48 | " | " | " |
| 251 | 265 | LRRFIIFLFILLLCL | 1423 | *1501 | 100 | " | " | " |
| 251 | 265 | LRRFIIFLFILLLCL | " | *1301 | 85 | " | " | " |
| 251 | 265 | LRRFIIFLFILLLCL | " | *0101 | 83 | " | " | " |
| 251 | 265 | LRRFIIFLFILLLCL | " | *0301 | 83 | " | " | " |
| 251 | 265 | LRRFIIFLFILLLCL | " | *1101 | 58 | " | " | " |
| 251 | 265 | LRRFIIFLFILLLCL | " | *0701 | 53 | " | " | " |

TABLE 7b-continued

Predicted HLA class II-restricted CD4+ T cell epitopes contained in SLP sequences from HBV large surface protein.

HLA class II binding peptides in SLP derived from HBV Surface antigen

| Start | End | Sequence[A] | SEQ ID NO: | HLA-DRB1 molecule | ClassII-B score[B] | SLP# | SLP Start | SLP End |
|---|---|---|---|---|---|---|---|---|
| 252 | 266 | RRFIIFLFILLLCLI | 1424 | *1501 | 98 | " | " | " |
| 252 | 266 | RRFIIFLFILLLCLI | " | *0101 | 80 | " | " | " |
| 252 | 266 | RRFIIFLFILLLCLI | " | *1101 | 55 | " | " | " |
| 252 | 266 | RRFIIFLFILLLCLI | " | *0301 | 40 | " | " | " |
| 252 | 266 | RRFIIFLFILLLCLI | " | *0701 | 38 | " | " | " |
| 252 | 266 | RRFIIFLFILLLCLI | " | *1301 | 35 | " | " | " |
| 253 | 267 | RFIIFLFILLLCLIF | 1425 | *1101 | 100 | " | " | " |
| 253 | 267 | RFIIFLFILLLCLIF | " | *0101 | 78 | " | " | " |
| 253 | 267 | RFIIFLFILLLCLIF | " | *1501 | 60 | " | " | " |
| 253 | 267 | RFIIFLFILLLCLIF | " | *0301 | 38 | " | " | " |
| 253 | 267 | RFIIFLFILLLCLIF | " | *0701 | 35 | " | " | " |
| 253 | 267 | RFIIFLFILLLCLIF | " | *1301 | 33 | " | " | " |
| 253 | 267 | RFIIFLFILLLCLIF | " | *0401 | 8 | " | " | " |
| 254 | 268 | FIIFLFILLLCLIFL | 1426 | *1101 | 98 | " | " | " |
| 254 | 268 | FIIFLFILLLCLIFL | " | *1501 | 88 | " | " | " |
| 254 | 268 | FIIFLFILLLCLIFL | " | *0101 | 65 | " | " | " |
| 254 | 268 | FIIFLFILLLCLIFL | " | *0301 | 35 | " | " | " |
| 254 | 268 | FIIFLFILLLCLIFL | " | *1301 | 30 | " | " | " |
| 254 | 268 | FIIFLFILLLCLIFL | " | *0401 | 13 | " | " | " |
| 255 | 269 | IIFLFILLLCLIFLL | 1427 | *1101 | 95 | " | " | " |
| 255 | 269 | IIFLFILLLCLIFLL | " | *1501 | 93 | " | " | " |
| 255 | 269 | IIFLFILLLCLIFLL | " | *0301 | 70 | " | " | " |
| 255 | 269 | IIFLFILLLCLIFLL | " | *0101 | 35 | " | " | " |
| 255 | 269 | IIFLFILLLCLIFLL | " | *0401 | 35 | " | " | " |
| 255 | 269 | IIFLFILLLCLIFLL | " | *1301 | 28 | " | " | " |
| 256 | 270 | IFLFILLLCLIFLLV | 1428 | *1101 | 93 | " | " | " |
| 256 | 270 | IFLFILLLCLIFLLV | " | *0301 | 68 | " | " | " |
| 256 | 270 | IFLFILLLCLIFLLV | " | *1501 | 53 | " | " | " |
| 256 | 270 | IFLFILLLCLIFLLV | " | *0101 | 30 | " | " | " |
| 256 | 270 | IFLFILLLCLIFLLV | " | *1301 | 25 | " | " | " |
| 256 | 270 | IFLFILLLCLIFLLV | " | *0401 | 10 | " | " | " |
| 257 | 271 | FLFILLLCLIFLLVL | 1429 | *1101 | 90 | " | " | " |
| 257 | 271 | FLFILLLCLIFLLVL | " | *0301 | 65 | " | " | " |
| 257 | 271 | FLFILLLCLIFLLVL | " | *1501 | 58 | " | " | " |

TABLE 7b-continued

Predicted HLA class II-restricted CD4+ T cell epitopes contained in SLP sequences from HBV large surface protein.

HLA class II binding peptides in SLP derived from HBV Surface antigen

| Start | End | Sequence[A] | SEQ ID NO: | HLA-DRB1 molecule | ClassII-B score[B] | Peptide of invention (SLP) | | |
|---|---|---|---|---|---|---|---|---|
| | | | | | | SLP# | SLP Start | SLP End |
| 257 | 271 | FLFILLLCLIFLLVL | " | *0101 | 28 | " | " | " |
| 257 | 271 | FLFILLLCLIFLLVL | " | *1301 | 23 | " | " | " |
| 257 | 271 | FLFILLLCLIFLLVL | " | *0401 | 18 | " | " | " |
| 258 | 272 | LFILLLCLIFLLVLL | 1430 | *1101 | 88 | " | " | " |
| 258 | 272 | LFILLLCLIFLLVLL | " | *0301 | 63 | " | " | " |
| 258 | 272 | LFILLLCLIFLLVLL | " | *1501 | 50 | " | " | " |
| 258 | 272 | LFILLLCLIFLLVLL | " | *0101 | 25 | " | " | " |
| 258 | 272 | LFILLLCLIFLLVLL | " | *1301 | 20 | " | " | " |
| 259 | 273 | FILLLCLIFLLVLLD | 1431 | *1101 | 85 | " | " | " |
| 259 | 273 | FILLLCLIFLLVLLD | " | *0301 | 55 | " | " | " |
| 259 | 273 | FILLLCLIFLLVLLD | " | *1501 | 30 | " | " | " |
| 259 | 273 | FILLLCLIFLLVLLD | " | *0101 | 23 | " | " | " |
| 259 | 273 | FILLLCLIFLLVLLD | " | *1301 | 18 | " | " | " |
| 260 | 274 | ILLLCLIFLLVLLDY | 1432 | *1101 | 45 | " | " | " |
| 260 | 274 | ILLLCLIFLLVLLDY | " | *1301 | 15 | " | " | " |
| 260 | 274 | ILLLCLIFLLVLLDY | " | *1501 | 13 | " | " | " |
| | | Cumulative Class 11-B score: | | | 7238 | | | |
| 330 | 344 | WAFAKYLWEWASVRF | 1433 | *1501 | 5 | 32 | 323 | 358 |
| 331 | 345 | AFAKYLWEWASVRFS | 1434 | *0401 | 65 | " | " | " |
| 331 | 345 | AFAKYLWEWASVRFS | " | *0301 | 30 | " | " | " |
| 331 | 345 | AFAKYLWEWASVRFS | " | *1501 | 15 | " | " | " |
| 331 | 345 | AFAKYLWEWASVRFS | " | *1101 | 5 | " | " | " |
| 332 | 346 | FAKYLWEWASVRFSW | 1435 | *0401 | 80 | " | " | " |
| 332 | 346 | FAKYLWEWASVRFSW | " | *0301 | 55 | " | " | " |
| 332 | 346 | FAKYLWEWASVRFSW | " | *1501 | 50 | " | " | " |
| 332 | 346 | FAKYLWEWASVRFSW | " | *1101 | 40 | " | " | " |
| 332 | 346 | FAKYLWEWASVRFSW | " | *0104 | 25 | " | " | " |
| 332 | 346 | FAKYLWEWASVRFSW | " | *0101 | 23 | " | " | " |
| 332 | 346 | FAKYLWEWASVRFSW | " | *0105 | 23 | " | " | " |
| 332 | 346 | FAKYLWEWASVRFSW | " | *0107 | 23 | " | " | " |
| 332 | 346 | FAKYLWEWASVRFSW | " | *0701 | 15 | " | " | " |
| 333 | 347 | AKYLWEWASVRFSWL | 1436 | *0701 | 28 | " | " | " |
| 333 | 347 | AKYLWEWASVRFSWL | " | *0401 | 60 | " | " | " |
| 333 | 347 | AKYLWEWASVRFSWL | " | *0301 | 25 | " | " | " |
| 333 | 347 | AKYLWEWASVRFSWL | " | *1101 | 25 | " | " | " |

TABLE 7b-continued

Predicted HLA class II-restricted CD4+ T cell epitopes contained in SLP sequences from HBV large surface protein.

HLA class II binding peptides in SLP derived from HBV Surface antigen

| Start | End | Sequence[A] | SEQ ID NO: | HLA-DRB1 molecule | ClassII-B score[B] | SLP# | SLP Start | SLP End |
|---|---|---|---|---|---|---|---|---|
| 333 | 347 | AKYLWEWASVRFSWL | " | *0101 | 3 | " | " | " |
| 333 | 347 | AKYLWEWASVRFSWL | " | *0105 | 3 | " | " | " |
| 333 | 347 | AKYLWEWASVRFSWL | " | *0107 | 3 | " | " | " |
| 334 | 348 | KYLWEWASVRFSWLS | 1437 | *0701 | 25 | " | " | " |
| 334 | 348 | KYLWEWASVRFSWLS | " | *0401 | 5 | " | " | " |
| 336 | 350 | LWEWASVRFSWLSLL | 1438 | *0301 | 33 | " | " | " |
| 337 | 351 | WEWASVRFSWLSLLV | 1439 | *0301 | 73 | " | " | " |
| 337 | 351 | WEWASVRFSWLSLLV | " | *1501 | 45 | " | " | " |
| 337 | 351 | WEWASVRFSWLSLLV | " | *1301 | 25 | " | " | " |
| 338 | 352 | EWASVRFSWLSLLVP | 1440 | *0301 | 30 | " | " | " |
| 338 | 352 | EWASVRFSWLSLLVP | " | *1501 | 40 | " | " | " |
| 338 | 352 | EWASVRFSWLSLLVP | " | *1301 | 35 | " | " | " |
| 339 | 353 | WASVRFSWLSLLVPF | 1441 | *0301 | 58 | " | " | " |
| 339 | 353 | WASVRFSWLSLLVPF | " | *1501 | 55 | " | " | " |
| 339 | 353 | WASVRFSWLSLLVPF | " | *1301 | 50 | " | " | " |
| 339 | 353 | WASVRFSWLSLLVPF | " | *0104 | 38 | " | " | " |
| 339 | 353 | WASVRFSWLSLLVPF | " | *0102 | 5 | " | " | " |
| 340 | 354 | ASVRFSWLSLLVPFV | 1442 | *0301 | 75 | " | " | " |
| 340 | 354 | ASVRFSWLSLLVPFV | " | *0401 | 33 | " | " | " |
| 340 | 354 | ASVRFSWLSLLVPFV | " | *1101 | 18 | " | " | " |
| 340 | 354 | ASVRFSWLSLLVPFV | " | *0104 | 53 | " | " | " |
| 340 | 354 | ASVRFSWLSLLVPFV | " | *1501 | 30 | " | " | " |
| 340 | 354 | ASVRFSWLSLLVPFV | " | *0102 | 28 | " | " | " |
| 340 | 354 | ASVRFSWLSLLVPFV | " | *1301 | 20 | " | " | " |
| 340 | 354 | ASVRFSWLSLLVPFV | " | *0106 | 10 | " | " | " |
| 341 | 355 | SVRFSWLSLLVPFVQ | 1443 | *0401 | 30 | " | " | " |
| 341 | 355 | SVRFSWLSLLVPFVQ | " | *1101 | 15 | " | " | " |
| 341 | 355 | SVRFSWLSLLVPFVQ | " | *0104 | 50 | " | " | " |
| 341 | 355 | SVRFSWLSLLVPFVQ | " | *0102 | 23 | " | " | " |
| 341 | 355 | SVRFSWLSLLVPFVQ | " | *0106 | 5 | " | " | " |
| 342 | 356 | VRFSWLSLLVPFVQW | 1444 | *0401 | 28 | " | " | " |
| 342 | 356 | VRFSWLSLLVPFVQW | " | *0101 | 15 | " | " | " |
| 342 | 356 | VRFSWLSLLVPFVQW | " | *1101 | 13 | " | " | " |
| 342 | 356 | VRFSWLSLLVPFVQW | " | *0104 | 15 | " | " | " |

TABLE 7b-continued

Predicted HLA class II-restricted CD4+ T cell epitopes contained in SLP sequences from HBV large surface protein.

HLA class II binding peptides in SLP derived from HBV Surface antigen

| Start | End | Sequence[A] | SEQ ID NO: | HLA-DRB1 molecule | ClassII-B score[B] | Peptide of invention (SLP) SLP# | SLP Start | SLP End |
|---|---|---|---|---|---|---|---|---|
| 343 | 357 | RFSWLSLLVPFVQWF | 1445 | *0401 | 25 | " | " | " |
| 343 | 357 | RFSWLSLLVPFVQWF | " | *0101 | 20 | " | " | " |
| 343 | 357 | RFSWLSLLVPFVQWF | " | *1101 | 10 | " | " | " |
| 344 | 358 | FSWLSLLVPFVQWFV | 1446 | *1501 | 90 | " | " | " |
| 344 | 358 | FSWLSLLVPFVQWFV | " | *1301 | 70 | " | " | " |
| 344 | 358 | FSWLSLLVPFVQWFV | " | *0401 | 23 | " | " | " |
| 344 | 358 | FSWLSLLVPFVQWFV | " | *1101 | 8 | " | " | " |
| | | Cumulative Class 11-B score: | | | 1815 | | | " |
| 330 | 344 | WAFAKYLWEWASVRF | 1433 | *1501 | 5 | 33 | 327 | 358 |
| 331 | 345 | AFAKYLWEWASVRFS | 1434 | *0401 | 65 | " | " | " |
| 331 | 345 | AFAKYLWEWASVRFS | " | *0301 | 30 | " | " | " |
| 331 | 345 | AFAKYLWEWASVRFS | " | *1501 | 15 | " | " | " |
| 331 | 345 | AFAKYLWEWASVRFS | " | *1101 | 5 | " | " | " |
| 332 | 346 | FAKYLWEWASVRFSW | 1435 | *0401 | 80 | " | " | " |
| 332 | 346 | FAKYLWEWASVRFSW | " | *0301 | 55 | " | " | " |
| 332 | 346 | FAKYLWEWASVRFSW | " | *1501 | 50 | " | " | " |
| 332 | 346 | FAKYLWEWASVRFSW | " | *1101 | 40 | " | " | " |
| 332 | 346 | FAKYLWEWASVRFSW | " | *0104 | 25 | " | " | " |
| 332 | 346 | FAKYLWEWASVRFSW | " | *0101 | 23 | " | " | " |
| 332 | 346 | FAKYLWEWASVRFSW | " | *0105 | 23 | " | " | " |
| 332 | 346 | FAKYLWEWASVRFSW | " | *0107 | 23 | " | " | " |
| 332 | 346 | FAKYLWEWASVRFSW | " | *0701 | 15 | " | " | " |
| 333 | 347 | AKYLWEWASVRFSWL | 1436 | *0701 | 28 | " | " | " |
| 333 | 347 | AKYLWEWASVRFSWL | " | *0401 | 60 | " | " | " |
| 333 | 347 | AKYLWEWASVRFSWL | " | *0301 | 25 | " | " | " |
| 333 | 347 | AKYLWEWASVRFSWL | " | *1101 | 25 | " | " | " |
| 333 | 347 | AKYLWEWASVRFSWL | " | *0101 | 3 | " | " | " |
| 333 | 347 | AKYLWEWASVRFSWL | " | *0105 | 3 | " | " | " |
| 333 | 347 | AKYLWEWASVRFSWL | " | *0107 | 3 | " | " | " |
| 334 | 348 | KYLWEWASVRFSWLS | 1437 | *0701 | 25 | " | " | " |
| 334 | 348 | KYLWEWASVRFSWLS | " | *0401 | 5 | " | " | " |
| 336 | 350 | LWEWASVRFSWLSLL | 1438 | *0301 | 33 | " | " | " |
| 337 | 351 | WEWASVRFSWLSLLV | 1439 | *0301 | 73 | " | " | " |
| 337 | 351 | WEWASVRFSWLSLLV | " | *1501 | 45 | " | " | " |
| 337 | 351 | WEWASVRFSWLSLLV | " | *1301 | 25 | " | " | " |

TABLE 7b-continued

Predicted HLA class II-restricted CD4+ T cell epitopes contained in SLP sequences from HBV large surface protein.

HLA class II binding peptides in SLP derived from HBV Surface antigen

| Start | End | Sequence[A] | SEQ ID NO: | HLA-DRB1 molecule | ClassII-B score[B] | Peptide of invention (SLP) SLP# | SLP Start | SLP End |
|---|---|---|---|---|---|---|---|---|
| 338 | 352 | EWASVRFSWLSLLVP | 1440 | *0301 | 30 | " | " | " |
| 338 | 352 | EWASVRFSWLSLLVP | " | *1501 | 40 | " | " | " |
| 338 | 352 | EWASVRFSWLSLLVP | " | *1301 | 35 | " | " | " |
| 339 | 353 | WASVRFSWLSLLVPF | 1441 | *0301 | 58 | " | " | " |
| 339 | 353 | WASVRFSWLSLLVPF | " | *1501 | 55 | " | " | " |
| 339 | 353 | WASVRFSWLSLLVPF | " | *1301 | 50 | " | " | " |
| 339 | 353 | WASVRFSWLSLLVPF | " | *0104 | 38 | " | " | " |
| 339 | 353 | WASVRFSWLSLLVPF | " | *0102 | 5 | " | " | " |
| 340 | 354 | ASVRFSWLSLLVPFV | 1442 | *0301 | 75 | " | " | " |
| 340 | 354 | ASVRFSWLSLLVPFV | " | *0401 | 33 | " | " | " |
| 340 | 354 | ASVRFSWLSLLVPFV | " | *1101 | 18 | " | " | " |
| 340 | 354 | ASVRFSWLSLLVPFV | " | *0104 | 53 | " | " | " |
| 340 | 354 | ASVRFSWLSLLVPFV | " | *1501 | 30 | " | " | " |
| 340 | 354 | ASVRFSWLSLLVPFV | " | *0102 | 28 | " | " | " |
| 340 | 354 | ASVRFSWLSLLVPFV | " | *1301 | 20 | " | " | " |
| 340 | 354 | ASVRFSWLSLLVPFV | " | *0106 | 10 | " | " | " |
| 341 | 355 | SVRFSWLSLLVPFVQ | 1443 | *0401 | 30 | " | " | " |
| 341 | 355 | SVRFSWLSLLVPFVQ | " | *1101 | 15 | " | " | " |
| 341 | 355 | SVRFSWLSLLVPFVQ | " | *0104 | 50 | " | " | " |
| 341 | 355 | SVRFSWLSLLVPFVQ | " | *0102 | 23 | " | " | " |
| 341 | 355 | SVRFSWLSLLVPFVQ | " | *0106 | 5 | " | " | " |
| 342 | 356 | VRFSWLSLLVPFVQW | 1444 | *0401 | 28 | " | " | " |
| 342 | 356 | VRFSWLSLLVPFVQW | " | *0101 | 15 | " | " | " |
| 342 | 356 | VRFSWLSLLVPFVQW | " | *1101 | 13 | " | " | " |
| 342 | 356 | VRFSWLSLLVPFVQW | " | *0104 | 15 | " | " | " |
| 343 | 357 | RFSWLSLLVPFVQWF | 1445 | *0401 | 25 | " | " | " |
| 343 | 357 | RFSWLSLLVPFVQWF | " | *0101 | 20 | " | " | " |
| 343 | 357 | RFSWLSLLVPFVQWF | " | *1101 | 10 | " | " | " |
| 344 | 358 | FSWLSLLVPFVQWFV | 1446 | *1501 | 90 | " | " | " |
| 344 | 358 | FSWLSLLVPFVQWFV | " | *1301 | 70 | " | " | " |
| 344 | 358 | FSWLSLLVPFVQWFV | " | *0401 | 23 | " | " | " |
| 344 | 358 | FSWLSLLVPFVQWFV | " | *1101 | 8 | " | " | " |

Cumulative Class 11-B score: 1815

TABLE 7b-continued

Predicted HLA class II-restricted CD4+ T cell epitopes contained in SLP sequences from HBV large surface protein.

HLA class II binding peptides in SLP derived from HBV Surface antigen

| Start | End | Sequence[A] | SEQ ID NO: | HLA-DRB1 molecule | ClassII-B score[B] | Peptide of invention (SLP) | | |
|---|---|---|---|---|---|---|---|---|
| | | | | | | SLP# | SLP Start | SLP End |
| 330 | 344 | WAFAKYLWEWASVRF | 1433 | *1501 | 5 | 34 | 328 | 358 |
| 331 | 345 | AFAKYLWEWASVRFS | 1434 | *0401 | 65 | " | " | " |
| 331 | 345 | AFAKYLWEWASVRFS | " | *0301 | 30 | " | " | " |
| 331 | 345 | AFAKYLWEWASVRFS | " | *1501 | 15 | " | " | " |
| 331 | 345 | AFAKYLWEWASVRFS | " | *1101 | 5 | " | " | " |
| 332 | 346 | FAKYLWEWASVRFSW | 1435 | *0401 | 80 | " | " | " |
| 332 | 346 | FAKYLWEWASVRFSW | " | *0301 | 55 | " | " | " |
| 332 | 346 | FAKYLWEWASVRFSW | " | *1501 | 50 | " | " | " |
| 332 | 346 | FAKYLWEWASVRFSW | " | *1101 | 40 | " | " | " |
| 332 | 346 | FAKYLWEWASVRFSW | " | *0104 | 25 | " | " | " |
| 332 | 346 | FAKYLWEWASVRFSW | " | *0101 | 23 | " | " | " |
| 332 | 346 | FAKYLWEWASVRFSW | " | *0105 | 23 | " | " | " |
| 332 | 346 | FAKYLWEWASVRFSW | " | *0107 | 23 | " | " | " |
| 332 | 346 | FAKYLWEWASVRFSW | " | *0701 | 15 | " | " | " |
| 333 | 347 | AKYLWEWASVRFSWL | 1436 | *0701 | 28 | " | " | " |
| 333 | 347 | AKYLWEWASVRFSWL | " | *0401 | 60 | " | " | " |
| 333 | 347 | AKYLWEWASVRFSWL | " | *0301 | 25 | " | " | " |
| 333 | 347 | AKYLWEWASVRFSWL | " | *1101 | 25 | " | " | " |
| 333 | 347 | AKYLWEWASVRFSWL | " | *0101 | 3 | " | " | " |
| 333 | 347 | AKYLWEWASVRFSWL | " | *0105 | 3 | " | " | " |
| 333 | 347 | AKYLWEWASVRFSWL | " | *0107 | 3 | " | " | " |
| 334 | 348 | KYLWEWASVRFSWLS | 1437 | *0701 | 25 | " | " | " |
| 334 | 348 | KYLWEWASVRFSWLS | " | *0401 | 5 | " | " | " |
| 336 | 350 | LWEWASVRFSWLSLL | 1438 | *0301 | 33 | " | " | " |
| 337 | 351 | WEWASVRFSWLSLLV | 1439 | *0301 | 73 | " | " | " |
| 337 | 351 | WEWASVRFSWLSLLV | " | *1501 | 45 | " | " | " |
| 337 | 351 | WEWASVRFSWLSLLV | " | *1301 | 25 | " | " | " |
| 338 | 352 | EWASVRFSWLSLLVP | 1440 | *0301 | 30 | " | " | " |
| 338 | 352 | EWASVRFSWLSLLVP | " | *1501 | 40 | " | " | " |
| 338 | 352 | EWASVRFSWLSLLVP | " | *1301 | 35 | " | " | " |
| 339 | 353 | WASVRFSWLSLLVPF | 1441 | *0301 | 58 | " | " | " |
| 339 | 353 | WASVRFSWLSLLVPF | " | *1501 | 55 | " | " | " |
| 339 | 353 | WASVRFSWLSLLVPF | " | *1301 | 50 | " | " | " |
| 339 | 353 | WASVRFSWLSLLVPF | " | *0104 | 38 | " | " | " |

TABLE 7b-continued

Predicted HLA class II-restricted CD4+ T cell epitopes contained in SLP sequences from HBV large surface protein.

| HLA class II binding peptides in SLP derived from HBV Surface antigen | | | | | | | | |
|---|---|---|---|---|---|---|---|---|
| | | | SEQ | HLA- | | Peptide of invention (SLP) | | |
| Start | End | Sequence[A] | ID NO: | DRB1 molecule | ClassII-B score[B] | SLP# | SLP Start | SLP End |
| 339 | 353 | WASVRFSWLSLLVPF | " | *0102 | 5 | " | " | " |
| 340 | 354 | ASVRFSWLSLLVPFV | 1442 | *0301 | 75 | " | " | " |
| 340 | 354 | ASVRFSWLSLLVPFV | " | *0401 | 33 | " | " | " |
| 340 | 354 | ASVRFSWLSLLVPFV | " | *1101 | 18 | " | " | " |
| 340 | 354 | ASVRFSWLSLLVPFV | " | *0104 | 53 | " | " | " |
| 340 | 354 | ASVRFSWLSLLVPFV | " | *1501 | 30 | " | " | " |
| 340 | 354 | ASVRFSWLSLLVPFV | " | *0102 | 28 | " | " | " |
| 340 | 354 | ASVRFSWLSLLVPFV | " | *1301 | 20 | " | " | " |
| 340 | 354 | ASVRFSWLSLLVPFV | " | *0106 | 10 | " | " | " |
| 341 | 355 | SVRFSWLSLLVPFVQ | 1443 | *0401 | 30 | " | " | " |
| 341 | 355 | SVRFSWLSLLVPFVQ | " | *1101 | 15 | " | " | " |
| 341 | 355 | SVRFSWLSLLVPFVQ | " | *0104 | 50 | " | " | " |
| 341 | 355 | SVRFSWLSLLVPFVQ | " | *0102 | 23 | " | " | " |
| 341 | 355 | SVRFSWLSLLVPFVQ | " | *0106 | 5 | " | " | " |
| 342 | 356 | VRFSWLSLLVPFVQW | 1444 | *0401 | 28 | " | " | " |
| 342 | 356 | VRFSWLSLLVPFVQW | " | *0101 | 15 | " | " | " |
| 342 | 356 | VRFSWLSLLVPFVQW | " | *1101 | 13 | " | " | " |
| 342 | 356 | VRFSWLSLLVPFVQW | " | *0104 | 15 | " | " | " |
| 343 | 357 | RFSWLSLLVPFVQWF | 1445 | *0401 | 25 | " | " | " |
| 343 | 357 | RFSWLSLLVPFVQWF | " | *0101 | 20 | " | " | " |
| 343 | 357 | RFSWLSLLVPFVQWF | " | *1101 | 10 | " | " | " |
| 344 | 358 | FSWLSLLVPFVQWFV | 1446 | *1501 | 90 | " | " | " |
| 344 | 358 | FSWLSLLVPFVQWFV | " | *1301 | 70 | " | " | " |
| 344 | 358 | FSWLSLLVPFVQWFV | " | *0401 | 23 | " | " | " |
| 344 | 358 | FSWLSLLVPFVQWFV | " | *1101 | 8 | " | " | " |
| | | Cumulative Class 11-B score: | | | 1815 | | | |
| 365 | 379 | WLSAIWMMWYWGPSL | 1447 | *1501 | 35 | 35 | 365 | 400 |
| 366 | 380 | LSAIWMMWYWGPSLY | 1448 | *1501 | 48 | " | " | " |
| 367 | 381 | SAIWMMWYWGPSLYS | 1449 | *1501 | 40 | " | " | " |
| 368 | 382 | AIWMMWYWGPSLYSI | 1450 | *1501 | 45 | " | " | " |
| 369 | 383 | IWMMWYWGPSLYSIV | 1451 | *1501 | 38 | " | " | " |
| 369 | 383 | IWMMWYWGPSLYSIV | " | *0101 | 20 | " | " | " |
| 369 | 383 | IWMMWYWGPSLYSIV | " | *0105 | 20 | " | " | " |
| 369 | 383 | IWMMWYWGPSLYSIV | " | *0107 | 20 | " | " | " |
| 370 | 384 | WMMWYWGPSLYSIVS | 1452 | *1501 | 28 | " | " | " |

TABLE 7b-continued

Predicted HLA class II-restricted CD4+ T cell epitopes contained in SLP sequences from HBV large surface protein.

HLA class II binding peptides in SLP derived from HBV Surface antigen

| Start | End | Sequence[A] | SEQ ID NO: | HLA-DRB1 molecule | ClassII-B score[B] | Peptide of invention (SLP) SLP# | SLP Start | SLP End |
|---|---|---|---|---|---|---|---|---|
| 370 | 384 | WMMWYWGPSLYSIVS | " | *0101 | 33 | " | " | " |
| 370 | 384 | WMMWYWGPSLYSIVS | " | *0105 | 33 | " | " | " |
| 370 | 384 | WMMWYWGPSLYSIVS | " | *0107 | 33 | " | " | " |
| 371 | 385 | MMWYWGPSLYSIVSP | 1453 | *1501 | 8 | " | " | " |
| 373 | 387 | WYWGPSLYSIVSPFI | 1454 | *0701 | 90 | " | " | " |
| 373 | 387 | WYWGPSLYSIVSPFI | " | *0401 | 40 | " | " | " |
| 373 | 387 | WYWGPSLYSIVSPFI | " | *0106 | 45 | " | " | " |
| 373 | 387 | WYWGPSLYSIVSPFI | " | *0101 | 43 | " | " | " |
| 373 | 387 | WYWGPSLYSIVSPFI | " | *0105 | 43 | " | " | " |
| 373 | 387 | WYWGPSLYSIVSPFI | " | *0107 | 43 | " | " | " |
| 373 | 387 | WYWGPSLYSIVSPFI | " | *0102 | 18 | " | " | " |
| 374 | 388 | YWGPSLYSIVSPFIP | 1455 | *0701 | 65 | " | " | " |
| 374 | 388 | YWGPSLYSIVSPFIP | " | *0101 | 60 | " | " | " |
| 374 | 388 | YWGPSLYSIVSPFIP | " | *0105 | 60 | " | " | " |
| 374 | 388 | YWGPSLYSIVSPFIP | " | *0107 | 60 | " | " | " |
| 374 | 388 | YWGPSLYSIVSPFIP | " | *0401 | 55 | " | " | " |
| 374 | 388 | YWGPSLYSIVSPFIP | " | *0106 | 53 | " | " | " |
| 374 | 388 | YWGPSLYSIVSPFIP | " | *0102 | 48 | " | " | " |
| 374 | 388 | YWGPSLYSIVSPFIP | " | *0104 | 43 | " | " | " |
| 374 | 388 | YWGPSLYSIVSPFIP | " | *1501 | 25 | " | " | " |
| 375 | 389 | WGPSLYSIVSPFIPL | 1456 | *0701 | 85 | " | " | " |
| 375 | 389 | WGPSLYSIVSPFIPL | " | *0401 | 20 | " | " | " |
| 375 | 389 | WGPSLYSIVSPFIPL | " | *1501 | 18 | " | " | " |
| 375 | 389 | WGPSLYSIVSPFIPL | " | *0104 | 88 | " | " | " |
| 375 | 389 | WGPSLYSIVSPFIPL | " | *0102 | 85 | " | " | " |
| 375 | 389 | WGPSLYSIVSPFIPL | " | *0101 | 83 | " | " | " |
| 375 | 389 | WGPSLYSIVSPFIPL | " | *0105 | 83 | " | " | " |
| 375 | 389 | WGPSLYSIVSPFIPL | " | *0106 | 83 | " | " | " |
| 375 | 389 | WGPSLYSIVSPFIPL | " | *0107 | 83 | " | " | " |
| 375 | 389 | WGPSLYSIVSPFIPL | " | *0103 | 15 | " | " | " |
| 375 | 389 | WGPSLYSIVSPFIPL | " | *1101 | 15 | " | " | " |
| 376 | 390 | GPSLYSIVSPFIPLL | 1457 | *0701 | 83 | " | " | " |
| 376 | 390 | GPSLYSIVSPFIPLL | " | *0401 | 43 | " | " | " |
| 376 | 390 | GPSLYSIVSPFIPLL | " | *1501 | 43 | " | " | " |

TABLE 7b-continued

Predicted HLA class II-restricted CD4⁺ T cell epitopes contained in SLP sequences from HBV large surface protein.

HLA class II binding peptides in SLP derived from HBV Surface antigen

| Start | End | Sequence[A] | SEQ ID NO: | HLA-DRB1 molecule | ClassII-B score[B] | Peptide of invention (SLP) | | |
|---|---|---|---|---|---|---|---|---|
| | | | | | | SLP# | SLP Start | SLP End |
| 376 | 390 | GPSLYSIVSPFIPLL | " | *0101 | 33 | " | " | " |
| 376 | 390 | GPSLYSIVSPFIPLL | " | *0104 | 100 | " | " | " |
| 376 | 390 | GPSLYSIVSPFIPLL | " | *0102 | 98 | " | " | " |
| 376 | 390 | GPSLYSIVSPFIPLL | " | *0105 | 93 | " | " | " |
| 376 | 390 | GPSLYSIVSPFIPLL | " | *0107 | 93 | " | " | " |
| 376 | 390 | GPSLYSIVSPFIPLL | " | *0106 | 90 | " | " | " |
| 376 | 390 | GPSLYSIVSPFIPLL | " | *0103 | 50 | " | " | " |
| 376 | 390 | GPSLYSIVSPFIPLL | " | *1101 | 35 | " | " | " |
| 376 | 390 | GPSLYSIVSPFIPLL | " | *1301 | 15 | " | " | " |
| 377 | 391 | PSLYSIVSPFIPLLP | 1458 | *0701 | 63 | " | " | " |
| 377 | 391 | PSLYSIVSPFIPLLP | " | *1501 | 33 | " | " | " |
| 377 | 391 | PSLYSIVSPFIPLLP | " | *0101 | 10 | " | " | " |
| 377 | 391 | PSLYSIVSPFIPLLP | " | *0401 | 5 | " | " | " |
| 377 | 391 | PSLYSIVSPFIPLLP | " | *0104 | 93 | " | " | " |
| 377 | 391 | PSLYSIVSPFIPLLP | " | *0102 | 90 | " | " | " |
| 377 | 391 | PSLYSIVSPFIPLLP | " | *0106 | 85 | " | " | " |
| 377 | 391 | PSLYSIVSPFIPLLP | " | *0105 | 80 | " | " | " |
| 377 | 391 | PSLYSIVSPFIPLLP | " | *0107 | 80 | " | " | " |
| 377 | 391 | PSLYSIVSPFIPLLP | " | *0103 | 20 | " | " | " |
| 377 | 391 | PSLYSIVSPFIPLLP | " | *1101 | 20 | " | " | " |
| 377 | 391 | PSLYSIVSPFIPLLP | " | *1301 | 10 | " | " | " |
| 378 | 392 | SLYSIVSPFIPLLPI | 1459 | *0701 | 43 | " | " | " |
| 378 | 392 | SLYSIVSPFIPLLPI | " | *0104 | 83 | " | " | " |
| 378 | 392 | SLYSIVSPFIPLLPI | " | *0102 | 78 | " | " | " |
| 378 | 392 | SLYSIVSPFIPLLPI | " | *0106 | 73 | " | " | " |
| 378 | 392 | SLYSIVSPFIPLLPI | " | *0101 | 63 | " | " | " |
| 378 | 392 | SLYSIVSPFIPLLPI | " | *0105 | 63 | " | " | " |
| 378 | 392 | SLYSIVSPFIPLLPI | " | *0107 | 63 | " | " | " |
| 378 | 392 | SLYSIVSPFIPLLPI | " | *1501 | 35 | " | " | " |
| 378 | 392 | SLYSIVSPFIPLLPI | " | *0401 | 20 | " | " | " |
| 378 | 392 | SLYSIVSPFIPLLPI | " | *0103 | 5 | " | " | " |
| 379 | 393 | LYSIVSPFIPLLPIF | 1460 | *0701 | 33 | " | " | " |
| 379 | 393 | LYSIVSPFIPLLPIF | " | *0106 | 63 | " | " | " |
| 379 | 393 | LYSIVSPFIPLLPIF | " | *0102 | 55 | " | " | " |
| 379 | 393 | LYSIVSPFIPLLPIF | " | *0104 | 55 | " | " | " |

TABLE 7b-continued

Predicted HLA class II-restricted CD4+ T cell epitopes contained in SLP sequences from HBV large surface protein.

HLA class II binding peptides in SLP derived from HBV Surface antigen

| Start | End | Sequence[A] | SEQ ID NO: | HLA-DRB1 molecule | ClassII-B score[B] | Peptide of invention (SLP) SLP# | SLP Start | SLP End |
|---|---|---|---|---|---|---|---|---|
| 379 | 393 | LYSIVSPFIPLLPIF | " | *0101 | 53 | " | " | " |
| 379 | 393 | LYSIVSPFIPLLPIF | " | *0105 | 53 | " | " | " |
| 379 | 393 | LYSIVSPFIPLLPIF | " | *0107 | 53 | " | " | " |
| 380 | 394 | YSIVSPFIPLLPIFF | 1461 | *1101 | 35 | " | " | " |
| 380 | 394 | YSIVSPFIPLLPIFF | " | *0101 | 8 | " | " | " |
| 380 | 394 | YSIVSPFIPLLPIFF | " | *0104 | 23 | " | " | " |
| 380 | 394 | YSIVSPFIPLLPIFF | " | *0106 | 18 | " | " | " |
| 380 | 394 | YSIVSPFIPLLPIFF | " | *0105 | 5 | " | " | " |
| 380 | 394 | YSIVSPFIPLLPIFF | " | *0107 | 5 | " | " | " |
| 381 | 395 | SIVSPFIPLLPIFFC | 1462 | *1101 | 33 | " | " | " |
| 381 | 395 | SIVSPFIPLLPIFFC | " | *0101 | 5 | " | " | " |
| 382 | 396 | IVSPFIPLLPIFFCL | 1463 | *1101 | 30 | " | " | " |
| 382 | 396 | IVSPFIPLLPIFFCL | " | *0101 | 3 | " | " | " |
| 382 | 396 | IVSPFIPLLPIFFCL | " | *0104 | 18 | " | " | " |
| 382 | 396 | IVSPFIPLLPIFFCL | " | *0105 | 15 | " | " | " |
| 382 | 396 | IVSPFIPLLPIFFCL | " | *0107 | 15 | " | " | " |
| 382 | 396 | IVSPFIPLLPIFFCL | " | *0102 | 3 | " | " | " |
| 383 | 397 | VSPFIPLLPIFFCLW | 1464 | *1101 | 28 | " | " | " |
| 383 | 397 | VSPFIPLLPIFFCLW | " | *0101 | 13 | " | " | " |
| 383 | 397 | VSPFIPLLPIFFCLW | " | *0105 | 13 | " | " | " |
| 383 | 397 | VSPFIPLLPIFFCLW | " | *0107 | 13 | " | " | " |
| 383 | 397 | VSPFIPLLPIFFCLW | " | *0104 | 10 | " | " | " |
| 384 | 398 | SPFIPLLPIFFCLWV | 1465 | *1101 | 25 | " | " | " |
| 384 | 398 | SPFIPLLPIFFCLWV | " | *1501 | 5 | " | " | " |
| 386 | 400 | FIPLLPIFFCLWVYI | 1466 | *1101 | 23 | " | " | " |
| | | Cumulative Class 11-B score: | | | 4425 | | | |
| 371 | 385 | MMWYWGPSLYSIVSP | 1453 | *1501 | 8 | 36 | 371 | 400 |
| 373 | 387 | WYWGPSLYSIVSPFI | 1454 | *0701 | 90 | " | " | " |
| 373 | 387 | WYWGPSLYSIVSPFI | " | *0401 | 40 | " | " | " |
| 373 | 387 | WYWGPSLYSIVSPFI | " | *0106 | 45 | " | " | " |
| 373 | 387 | WYWGPSLYSIVSPFI | " | *0101 | 43 | " | " | " |
| 373 | 387 | WYWGPSLYSIVSPFI | " | *0105 | 43 | " | " | " |
| 373 | 387 | WYWGPSLYSIVSPFI | " | *0107 | 43 | " | " | " |
| 373 | 387 | WYWGPSLYSIVSPFI | " | *0102 | 18 | " | " | " |

TABLE 7b-continued

Predicted HLA class II-restricted CD4$^+$ T cell epitopes contained in SLP sequences from HBV large surface protein.

HLA class II binding peptides in SLP derived from HBV Surface antigen

| Start | End | Sequence$^A$ | SEQ ID NO: | HLA-DRB1 molecule | ClassII-B score$^B$ | SLP# | SLP Start | SLP End |
|---|---|---|---|---|---|---|---|---|
| 374 | 388 | YWGPSLYSIVSPFIP | 1455 | *0701 | 65 | " | " | " |
| 374 | 388 | YWGPSLYSIVSPFIP | " | *0101 | 60 | " | " | " |
| 374 | 388 | YWGPSLYSIVSPFIP | " | *0105 | 60 | " | " | " |
| 374 | 388 | YWGPSLYSIVSPFIP | " | *0107 | 60 | " | " | " |
| 374 | 388 | YWGPSLYSIVSPFIP | " | *0401 | 55 | " | " | " |
| 374 | 388 | YWGPSLYSIVSPFIP | " | *0106 | 53 | " | " | " |
| 374 | 388 | YWGPSLYSIVSPFIP | " | *0102 | 48 | " | " | " |
| 374 | 388 | YWGPSLYSIVSPFIP | " | *0104 | 43 | " | " | " |
| 374 | 388 | YWGPSLYSIVSPFIP | " | *1501 | 25 | " | " | " |
| 375 | 389 | WGPSLYSIVSPFIPL | 1456 | *0701 | 85 | " | " | " |
| 375 | 389 | WGPSLYSIVSPFIPL | " | *0401 | 20 | " | " | " |
| 375 | 389 | WGPSLYSIVSPFIPL | " | *1501 | 18 | " | " | " |
| 375 | 389 | WGPSLYSIVSPFIPL | " | *0104 | 88 | " | " | " |
| 375 | 389 | WGPSLYSIVSPFIPL | " | *0102 | 85 | " | " | " |
| 375 | 389 | WGPSLYSIVSPFIPL | " | *0101 | 83 | " | " | " |
| 375 | 389 | WGPSLYSIVSPFIPL | " | *0105 | 83 | " | " | " |
| 375 | 389 | WGPSLYSIVSPFIPL | " | *0106 | 83 | " | " | " |
| 375 | 389 | WGPSLYSIVSPFIPL | " | *0107 | 83 | " | " | " |
| 375 | 389 | WGPSLYSIVSPFIPL | " | *0103 | 15 | " | " | " |
| 375 | 389 | WGPSLYSIVSPFIPL | " | *1101 | 15 | " | " | " |
| 376 | 390 | GPSLYSIVSPFIPLL | 1457 | *0701 | 83 | " | " | " |
| 376 | 390 | GPSLYSIVSPFIPLL | " | *0401 | 43 | " | " | " |
| 376 | 390 | GPSLYSIVSPFIPLL | " | *1501 | 43 | " | " | " |
| 376 | 390 | GPSLYSIVSPFIPLL | " | *0101 | 33 | " | " | " |
| 376 | 390 | GPSLYSIVSPFIPLL | " | *0104 | 100 | " | " | " |
| 376 | 390 | GPSLYSIVSPFIPLL | " | *0102 | 98 | " | " | " |
| 376 | 390 | GPSLYSIVSPFIPLL | " | *0105 | 93 | " | " | " |
| 376 | 390 | GPSLYSIVSPFIPLL | " | *0107 | 93 | " | " | " |
| 376 | 390 | GPSLYSIVSPFIPLL | " | *0106 | 90 | " | " | " |
| 376 | 390 | GPSLYSIVSPFIPLL | " | *0103 | 50 | " | " | " |
| 376 | 390 | GPSLYSIVSPFIPLL | " | *1101 | 35 | " | " | " |
| 376 | 390 | GPSLYSIVSPFIPLL | " | *1301 | 15 | " | " | " |
| 377 | 391 | PSLYSIVSPFIPLLP | 1458 | *0701 | 63 | " | " | " |
| 377 | 391 | PSLYSIVSPFIPLLP | " | *1501 | 33 | " | " | " |
| 377 | 391 | PSLYSIVSPFIPLLP | " | *0101 | 10 | " | " | " |

TABLE 7b-continued

Predicted HLA class II-restricted CD4+ T cell epitopes contained in SLP sequences from HBV large surface protein.

HLA class II binding peptides in SLP derived from HBV Surface antigen

| Start | End | Sequence[A] | SEQ ID NO: | HLA-DRB1 molecule | ClassII-B score[B] | SLP# | SLP Start | SLP End |
|---|---|---|---|---|---|---|---|---|
| 377 | 391 | PSLYSIVSPFIPLLP | " | *0401 | 5 | " | " | " |
| 377 | 391 | PSLYSIVSPFIPLLP | " | *0104 | 93 | " | " | " |
| 377 | 391 | PSLYSIVSPFIPLLP | " | *0102 | 90 | " | " | " |
| 377 | 391 | PSLYSIVSPFIPLLP | " | *0106 | 85 | " | " | " |
| 377 | 391 | PSLYSIVSPFIPLLP | " | *0105 | 80 | " | " | " |
| 377 | 391 | PSLYSIVSPFIPLLP | " | *0107 | 80 | " | " | " |
| 377 | 391 | PSLYSIVSPFIPLLP | " | *0103 | 20 | " | " | " |
| 377 | 391 | PSLYSIVSPFIPLLP | " | *1101 | 20 | " | " | " |
| 377 | 391 | PSLYSIVSPFIPLLP | " | *1301 | 10 | " | " | " |
| 378 | 392 | SLYSIVSPFIPLLPI | 1459 | *0701 | 43 | " | " | " |
| 378 | 392 | SLYSIVSPFIPLLPI | " | *0104 | 83 | " | " | " |
| 378 | 392 | SLYSIVSPFIPLLPI | " | *0102 | 78 | " | " | " |
| 378 | 392 | SLYSIVSPFIPLLPI | " | *0106 | 73 | " | " | " |
| 378 | 392 | SLYSIVSPFIPLLPI | " | *0101 | 63 | " | " | " |
| 378 | 392 | SLYSIVSPFIPLLPI | " | *0105 | 63 | " | " | " |
| 378 | 392 | SLYSIVSPFIPLLPI | " | *0107 | 63 | " | " | " |
| 378 | 392 | SLYSIVSPFIPLLPI | " | *1501 | 35 | " | " | " |
| 378 | 392 | SLYSIVSPFIPLLPI | " | *0401 | 20 | " | " | " |
| 378 | 392 | SLYSIVSPFIPLLPI | " | *0103 | 5 | " | " | " |
| 379 | 393 | LYSIVSPFIPLLPIF | 1460 | *0701 | 33 | " | " | " |
| 379 | 393 | LYSIVSPFIPLLPIF | " | *0106 | 63 | " | " | " |
| 379 | 393 | LYSIVSPFIPLLPIF | " | *0102 | 55 | " | " | " |
| 379 | 393 | LYSIVSPFIPLLPIF | " | *0104 | 55 | " | " | " |
| 379 | 393 | LYSIVSPFIPLLPIF | " | *0101 | 53 | " | " | " |
| 379 | 393 | LYSIVSPFIPLLPIF | " | *0105 | 53 | " | " | " |
| 379 | 393 | LYSIVSPFIPLLPIF | " | *0107 | 53 | " | " | " |
| 380 | 394 | YSIVSPFIPLLPIFF | 1461 | *1101 | 35 | " | " | " |
| 380 | 394 | YSIVSPFIPLLPIFF | " | *0101 | 8 | " | " | " |
| 380 | 394 | YSIVSPFIPLLPIFF | " | *0104 | 23 | " | " | " |
| 380 | 394 | YSIVSPFIPLLPIFF | " | *0106 | 18 | " | " | " |
| 380 | 394 | YSIVSPFIPLLPIFF | " | *0105 | 5 | " | " | " |
| 380 | 394 | YSIVSPFIPLLPIFF | " | *0107 | 5 | " | " | " |
| 381 | 395 | SIVSPFIPLLPIFFC | 1462 | *1101 | 33 | " | " | " |
| 381 | 395 | SIVSPFIPLLPIFFC | " | *0101 | 5 | " | " | " |

TABLE 7b-continued

Predicted HLA class II-restricted CD4+ T cell epitopes contained in SLP sequences from HBV large surface protein.

HLA class II binding peptides in SLP derived from HBV Surface antigen

| Start | End | Sequence[A] | SEQ ID NO: | HLA-DRB1 molecule | ClassII-B score[B] | SLP# | SLP Start | SLP End |
|---|---|---|---|---|---|---|---|---|
| 382 | 396 | IVSPFIPLLPIFFCL | 1463 | *1101 | 30 | " | " | " |
| 382 | 396 | IVSPFIPLLPIFFCL | " | *0101 | 3 | " | " | " |
| 382 | 396 | IVSPFIPLLPIFFCL | " | *0104 | 18 | " | " | " |
| 382 | 396 | IVSPFIPLLPIFFCL | " | *0105 | 15 | " | " | " |
| 382 | 396 | IVSPFIPLLPIFFCL | " | *0107 | 15 | " | " | " |
| 382 | 396 | IVSPFIPLLPIFFCL | " | *0102 | 3 | " | " | " |
| 383 | 397 | VSPFIPLLPIFFCLW | 1464 | *1101 | 28 | " | " | " |
| 383 | 397 | VSPFIPLLPIFFCLW | " | *0101 | 13 | " | " | " |
| 383 | 397 | VSPFIPLLPIFFCLW | " | *0105 | 13 | " | " | " |
| 383 | 397 | VSPFIPLLPIFFCLW | " | *0107 | 13 | " | " | " |
| 383 | 397 | VSPFIPLLPIFFCLW | " | *0104 | 10 | " | " | " |
| 384 | 398 | SPFIPLLPIFFCLWV | 1465 | *1101 | 25 | " | " | " |
| 384 | 398 | SPFIPLLPIFFCLWV | " | *1501 | 5 | " | " | " |
| 386 | 400 | FIPLLPIFFCLWVYI | 1466 | *1101 | 23 | " | " | " |
| | | Cumulative Class 11-B score: | | | 4035 | | | |
| 370 | 384 | WMMWYWGPSLYSIVS | 1452 | *1501 | 28 | 37 | 370 | 400 |
| 370 | 384 | WMMWYWGPSLYSIVS | " | *0101 | 33 | " | " | " |
| 370 | 384 | WMMWYWGPSLYSIVS | " | *0105 | 33 | " | " | " |
| 370 | 384 | WMMWYWGPSLYSIVS | " | *0107 | 33 | " | " | " |
| 371 | 385 | MMWYWGPSLYSIVSP | 1453 | *1501 | 8 | " | " | " |
| 373 | 387 | WYWGPSLYSIVSPFI | 1454 | *0701 | 90 | " | " | " |
| 373 | 387 | WYWGPSLYSIVSPFI | " | *0401 | 40 | " | " | " |
| 373 | 387 | WYWGPSLYSIVSPFI | " | *0106 | 45 | " | " | " |
| 373 | 387 | WYWGPSLYSIVSPFI | " | *0101 | 43 | " | " | " |
| 373 | 387 | WYWGPSLYSIVSPFI | " | *0105 | 43 | " | " | " |
| 373 | 387 | WYWGPSLYSIVSPFI | " | *0107 | 43 | " | " | " |
| 373 | 387 | WYWGPSLYSIVSPFI | " | *0102 | 18 | " | " | " |
| 374 | 388 | YWGPSLYSIVSPFIP | 1455 | *0701 | 65 | " | " | " |
| 374 | 388 | YWGPSLYSIVSPFIP | " | *0101 | 60 | " | " | " |
| 374 | 388 | YWGPSLYSIVSPFIP | " | *0105 | 60 | " | " | " |
| 374 | 388 | YWGPSLYSIVSPFIP | " | *0107 | 60 | " | " | " |
| 374 | 388 | YWGPSLYSIVSPFIP | " | *0401 | 55 | " | " | " |
| 374 | 388 | YWGPSLYSIVSPFIP | " | *0106 | 53 | " | " | " |
| 374 | 388 | YWGPSLYSIVSPFIP | " | *0102 | 48 | " | " | " |
| 374 | 388 | YWGPSLYSIVSPFIP | " | *0104 | 43 | " | " | " |

TABLE 7b-continued

Predicted HLA class II-restricted CD4+ T cell epitopes contained in SLP sequences from HBV large surface protein.

HLA class II binding peptides in SLP derived from HBV Surface antigen

| Start | End | Sequence[A] | SEQ ID NO: | HLA-DRB1 molecule | ClassII-B score[B] | Peptide of invention (SLP) | | |
|---|---|---|---|---|---|---|---|---|
| | | | | | | SLP# | SLP Start | SLP End |
| 374 | 388 | YWGPSLYSIVSPFIP | " | *1501 | 25 | " | " | " |
| 375 | 389 | WGPSLYSIVSPFIPL | 1456 | *0701 | 85 | " | " | " |
| 375 | 389 | WGPSLYSIVSPFIPL | " | *0401 | 20 | " | " | " |
| 375 | 389 | WGPSLYSIVSPFIPL | " | *1501 | 18 | " | " | " |
| 375 | 389 | WGPSLYSIVSPFIPL | " | *0104 | 88 | " | " | " |
| 375 | 389 | WGPSLYSIVSPFIPL | " | *0102 | 85 | " | " | " |
| 375 | 389 | WGPSLYSIVSPFIPL | " | *0101 | 83 | " | " | " |
| 375 | 389 | WGPSLYSIVSPFIPL | " | *0105 | 83 | " | " | " |
| 375 | 389 | WGPSLYSIVSPFIPL | " | *0106 | 83 | " | " | " |
| 375 | 389 | WGPSLYSIVSPFIPL | " | *0107 | 83 | " | " | " |
| 375 | 389 | WGPSLYSIVSPFIPL | " | *0103 | 15 | " | " | " |
| 375 | 389 | WGPSLYSIVSPFIPL | " | *1101 | 15 | " | " | " |
| 376 | 390 | GPSLYSIVSPFIPLL | 1457 | *0701 | 83 | " | " | " |
| 376 | 390 | GPSLYSIVSPFIPLL | " | *0401 | 43 | " | " | " |
| 376 | 390 | GPSLYSIVSPFIPLL | " | *1501 | 43 | " | " | " |
| 376 | 390 | GPSLYSIVSPFIPLL | " | *0101 | 33 | " | " | " |
| 376 | 390 | GPSLYSIVSPFIPLL | " | *0104 | 100 | " | " | " |
| 376 | 390 | GPSLYSIVSPFIPLL | " | *0102 | 98 | " | " | " |
| 376 | 390 | GPSLYSIVSPFIPLL | " | *0105 | 93 | " | " | " |
| 376 | 390 | GPSLYSIVSPFIPLL | " | *0107 | 93 | " | " | " |
| 376 | 390 | GPSLYSIVSPFIPLL | " | *0106 | 90 | " | " | " |
| 376 | 390 | GPSLYSIVSPFIPLL | " | *0103 | 50 | " | " | " |
| 376 | 390 | GPSLYSIVSPFIPLL | " | *1101 | 35 | " | " | " |
| 376 | 390 | GPSLYSIVSPFIPLL | " | *1301 | 15 | " | " | " |
| 377 | 391 | PSLYSIVSPFIPLLP | 1458 | *0701 | 63 | " | " | " |
| 377 | 391 | PSLYSIVSPFIPLLP | " | *1501 | 33 | " | " | " |
| 377 | 391 | PSLYSIVSPFIPLLP | " | *0101 | 10 | " | " | " |
| 377 | 391 | PSLYSIVSPFIPLLP | " | *0401 | 5 | " | " | " |
| 377 | 391 | PSLYSIVSPFIPLLP | " | *0104 | 93 | " | " | " |
| 377 | 391 | PSLYSIVSPFIPLLP | " | *0102 | 90 | " | " | " |
| 377 | 391 | PSLYSIVSPFIPLLP | " | *0106 | 85 | " | " | " |
| 377 | 391 | PSLYSIVSPFIPLLP | " | *0105 | 80 | " | " | " |
| 377 | 391 | PSLYSIVSPFIPLLP | " | *0107 | 80 | " | " | " |
| 377 | 391 | PSLYSIVSPFIPLLP | " | *0103 | 20 | " | " | " |

TABLE 7b-continued

Predicted HLA class II-restricted CD4+ T cell epitopes contained in SLP sequences from HBV large surface protein.

HLA class II binding peptides in SLP derived from HBV Surface antigen

| Start | End | Sequence[A] | SEQ ID NO: | HLA-DRB1 molecule | ClassII-B score[B] | Peptide of invention (SLP) SLP# | SLP Start | SLP End |
|---|---|---|---|---|---|---|---|---|
| 377 | 391 | PSLYSIVSPFIPLLP | " | *1101 | 20 | " | " | " |
| 377 | 391 | PSLYSIVSPFIPLLP | " | *1301 | 10 | " | " | " |
| 378 | 392 | SLYSIVSPFIPLLPI | 1459 | *0701 | 43 | " | " | " |
| 378 | 392 | SLYSIVSPFIPLLPI | " | *0104 | 83 | " | " | " |
| 378 | 392 | SLYSIVSPFIPLLPI | " | *0102 | 78 | " | " | " |
| 378 | 392 | SLYSIVSPFIPLLPI | " | *0106 | 73 | " | " | " |
| 378 | 392 | SLYSIVSPFIPLLPI | " | *0101 | 63 | " | " | " |
| 378 | 392 | SLYSIVSPFIPLLPI | " | *0105 | 63 | " | " | " |
| 378 | 392 | SLYSIVSPFIPLLPI | " | *0107 | 63 | " | " | " |
| 378 | 392 | SLYSIVSPFIPLLPI | " | *1501 | 35 | " | " | " |
| 378 | 392 | SLYSIVSPFIPLLPI | " | *0401 | 20 | " | " | " |
| 378 | 392 | SLYSIVSPFIPLLPI | " | *0103 | 5 | " | " | " |
| 379 | 393 | LYSIVSPFIPLLPIF | 1460 | *0701 | 33 | " | " | " |
| 379 | 393 | LYSIVSPFIPLLPIF | " | *0106 | 63 | " | " | " |
| 379 | 393 | LYSIVSPFIPLLPIF | " | *0102 | 55 | " | " | " |
| 379 | 393 | LYSIVSPFIPLLPIF | " | *0104 | 55 | " | " | " |
| 379 | 393 | LYSIVSPFIPLLPIF | " | *0101 | 53 | " | " | " |
| 379 | 393 | LYSIVSPFIPLLPIF | " | *0105 | 53 | " | " | " |
| 379 | 393 | LYSIVSPFIPLLPIF | " | *0107 | 53 | " | " | " |
| 380 | 394 | YSIVSPFIPLLPIFF | 1461 | *1101 | 35 | " | " | " |
| 380 | 394 | YSIVSPFIPLLPIFF | " | *0101 | 8 | " | " | " |
| 380 | 394 | YSIVSPFIPLLPIFF | " | *0104 | 23 | " | " | " |
| 380 | 394 | YSIVSPFIPLLPIFF | " | *0106 | 18 | " | " | " |
| 380 | 394 | YSIVSPFIPLLPIFF | " | *0105 | 5 | " | " | " |
| 380 | 394 | YSIVSPFIPLLPIFF | " | *0107 | 5 | " | " | " |
| 381 | 395 | SIVSPFIPLLPIFFC | 1462 | *1101 | 33 | " | " | " |
| 381 | 395 | SIVSPFIPLLPIFFC | " | *0101 | 5 | " | " | " |
| 382 | 396 | IVSPFIPLLPIFFCL | 1463 | *1101 | 30 | " | " | " |
| 382 | 396 | IVSPFIPLLPIFFCL | " | *0101 | 3 | " | " | " |
| 382 | 396 | IVSPFIPLLPIFFCL | " | *0104 | 18 | " | " | " |
| 382 | 396 | IVSPFIPLLPIFFCL | " | *0105 | 15 | " | " | " |
| 382 | 396 | IVSPFIPLLPIFFCL | " | *0107 | 15 | " | " | " |
| 382 | 396 | IVSPFIPLLPIFFCL | " | *0102 | 3 | " | " | " |
| 383 | 397 | VSPFIPLLPIFFCLW | 1464 | *1101 | 28 | " | " | " |
| 383 | 397 | VSPFIPLLPIFFCLW | " | *0101 | 13 | " | " | " |

TABLE 7b-continued

Predicted HLA class II-restricted CD4+ T cell epitopes contained in SLP sequences from HBV large surface protein.

HLA class II binding peptides in SLP derived from HBV Surface antigen

| Start | End | Sequence[A] | SEQ ID NO: | HLA-DRB1 molecule | ClassII-B score[B] | Peptide of invention (SLP) | | |
|---|---|---|---|---|---|---|---|---|
| | | | | | | SLP# | SLP Start | SLP End |
| 383 | 397 | VSPFIPLLPIFFCLW | " | *0105 | 13 | " | " | " |
| 383 | 397 | VSPFIPLLPIFFCLW | " | *0107 | 13 | " | " | " |
| 383 | 397 | VSPFIPLLPIFFCLW | " | *0104 | 10 | " | " | " |
| 384 | 398 | SPFIPLLPIFFCLWV | 1465 | *1101 | 25 | " | " | " |
| 384 | 398 | SPFIPLLPIFFCLWV | " | *1501 | 5 | " | " | " |
| 386 | 400 | FIPLLPIFFCLWVYI | 1466 | *1101 | 23 | " | " | " |
| | | Cumulative Class 11-B score: | | | 4160 | | | |

"Start" and "End" are relative to the amino acid sequence of human HBV large surface protein as depicted in SEQ ID NO: 1141
[A]Peptide amino acid sequence. Each HLA-DRB1 binding peptide of HBV large surface protein is listed separately for each HLA class II molecule to which it is predicted to bind, and each peptide can be listed multiple times for that reason.
[B]B-score. See Material and Methods (Examples section).
[C]Cumulative B-score. See Material and Methods (Examples section).

REFERENCE LIST

Atherton, E. and Sheppard, R., 1989, Solid Phase Peptide Synthesis: A Practical Approach. IRL Press, Oxford.
Barany, G. and Merrifield, R., 1979. In The Peptides, Vol. 2 (E. Gross and J. Meienhofer, eds.) pp. 1-284. Academic Press, New York.
Buckanovich R J et al., 2008, Nature Medicine 14: 28.
Bui et al. 2006, BMC Bioinformatics 7:153.
Chapiro J et al., 2006; J Immunol 176:1053-1061.
Craiu A, et al., 1997, Proc Natl Acad Sci USA 94:10850-10855.
Fields, G. B., 1997, Methods Enzymol. Vol. 289.
Huang et al., 2011 Curr Opin Immunol 23:237-243.
Ganem et al., 2004, N Engl J Med 350:1118-1129.
Grimm et al., 2013 Clin Sci (Lond) 124:77-85.
Ishikawa K, 1994, PNAS 91: 4892.
Kato et al., 2005, Immunity, 1: 19-28.
Kessler J H et al., 2003, Hum Immunol 64: 245-255.
Lanzavecchia, 1998, Nature 393: 413.
Lok A S: 2002, N Engl J Med 346:1682-1683.
Lundegaard C, et al.—2010; Immunology 130: 309.
Michel M L et al, 2001, J. Hepatol 34: 917-921.
Michel M L, et al., 2011. J Hepatol 54: 1286-1296.
Morel S et al., 2000 Immunity 12:107-117, 2000.
Mo X Y et al., 1999 J Immunol 163:5851-5859.
Nielsen M, et al., 2005, Immunogenetics 57: 33
Nielsen M, et al., 2010, Immunome Res 6: 9
Rehermann et al., 2005, 5:215-229.
Remington; The Science and Practice of Pharmacy, 21st Edition 2005, University of Sciences in Philadelphia.
Ridge et al. 1998, Nature 393: 474.
Rock et al., 2004, Nat. Immunol. 5:670.
Rosalia et al., 2013, Eur J Immunol 43:2554-2565.
Schirle M et al., 2000, Eur J Immunol 30:2216-2225.
Schirle M et al., 2001 J Immunol Methods 257:1-16.
Schoenberger et al. 1998, Nature 393: 480.
Stoltze L et al., 1998 Eur J Immunol 28:4029-4036.
Sun et al. 2004, Nat. Immunol. 5: 927
Thimme et al: J Virol 77:68-76, 2003.
Toes et al., 1996a, J. Immunol. 156: 3911.
Toes et al., 1996b, Proc. Natl. Acad. Sci. U.S.A 93: 7855.
Van der Burg S H et al., 1995, Hum Immunol. 44:189.
Van der Burg S H et al., 1996, J. Immunol 156(9): 3308-14
Van der Burg S H et al., 2007, PNAS 104: 12087.
Viatte S, et al., 2006, Immunol Cell Biol 84:318-330.
Wang P, et al., 2008, PLoS Comput Biol 4: e1000048.
World Health Organization. Hepatitis B. World Health Organization. Fact Sheet 204 (Updated July 2013). Accessible at: http://www.who.int/mediacentre/factsheets/fs204/en/
Zeestraten et al, Int J Cancer. 2013 Apr. 1; 132 (7): 1581-91
Zwaveling et al., 2002, J. Immunol. 169: 350.13.
Zoulim et al., 2012, B. J Hepatol 56 Suppl 1:S112-S122.

The invention claimed is:

1. A method for the treatment of an HBV-related disease comprising administering to a subject suffering from the HBV-related disease an effective amount of a peptide of at least 30 and at most 40 amino acids in length and comprising an amino acid sequence selected from the group consisting of SEQ ID NOS: 51-79, 1142-1145 and 1468-1471, wherein the HBV-related disease is an acute HBV infection, a chronic HBV infection, conditions where the hepatitis virus is found in the blood or body fluids containing blood of a subject, liver cirrhosis, liver cancer, and a presence of the hepatitis virus in the body of the subject.

2. The method according to claim 1, wherein the peptide is in an immunogenic pharmaceutical composition.

3. The method according to claim 2, wherein the composition further comprises an immune-stimulating amount of at least one pharmaceutically acceptable adjuvant.

4. The method according to claim 3, wherein the pharmaceutically acceptable adjuvant is selected from the group consisting of a human toll-like receptor ligand and/or agonist, Montanide ISA-51, Montanide ISA-720, dsRNA, cyclic dinucleotides (CDNs), Muramyl dipeptide (MDP), a tetanus toxin derived peptide, Interferon alpha (INFα), and combinations thereof.

5. The method according to claim 1, wherein the peptide comprises an amino acid sequence of any of the proteins selected from the group consisting of HBV polymerase, HBV core protein, HBV X-protein and HBV large surface protein.

6. The method according to claim 1, wherein the peptide comprises an amino acid sequence selected from the group consisting of SEQ ID NOS: 51-53, 55, 57, 60, 63, 64, 66, 68, 71, 72, 74-78, 1142, 1145, 1468-1471.

7. The method according to claim 1, wherein the peptide further comprises a covalently linked functional group, an oligonucleotide conjugate, a sugar chain or glycan, or combinations thereof.

8. The method according to claim 4, wherein the human toll-like receptor ligand and/or agonist is selected from the group consisting of Gram positive bacterial glycolipid, LPS, LPA, LTA, fimbriae, an outer membrane protein, a heat shock protein, Mycobacterial lipoarabinomannans, dsRNA, poly(I:C), Gram negative bacterial glycolipid, a viral coat protein, a viral envelope protein, taxol and/or derivative thereof, hyaluronan containing oligosaccharides and fibronectins, bacterial flagellae, flagellin, Mycobacterial lipoproteins, group B Streptococcus heat labile soluble factor, a Staphylococcus modulin, imidazoquinolines, imiquimod and/or derivative thereof, resiquimod and/or derivative thereof, unmethylated CpG DNA, chromatin-IgG complexes, IC31, IMSAVAC, pam3cys and/or derivative thereof, poly-ICLC, and CpG oligodeoxynucleotides (CpG-ODNs).

9. The method according to claim 2, wherein the composition further comprises PSA, 2-aminoisobutyric acid (Abu), a DC pulse cassette, or combinations thereof.

10. A method for the treatment of an HBV-related disease comprising administering to a subject suffering from the HBV-related disease an effective amount of a polynucleotide encoding a peptide of at least 30 and at most 40 amino acids in length, the peptide comprising an amino acid sequence selected from the group consisting of SEQ ID NOS: 51-79, 1142-1145 and 1468-1471, wherein the HBV-related disease is selected from the group consisting of acute HBV infection, chronic HBV infection, conditions where the hepatitis virus is found in the blood or body fluids containing blood of a subject, liver cirrhosis, liver cancer, and presence of the virus in the body of a subject.

11. The method according to claim 10, wherein the polynucleotide is in an immunogenic pharmaceutical composition.

12. The method according to claim 11, wherein the composition further comprises an immune-stimulating amount of at least one pharmaceutically acceptable adjuvant.

13. The method according to claim 12, wherein the pharmaceutically acceptable adjuvant is selected from the group consisting of a human toll-like receptor ligand and/or agonist, Montanide ISA-51, Montanide ISA-720, dsRNA, cyclic dinucleotides (CDNs), Muramyl dipeptide (MDP), a tetanus toxin derived peptide, Interferon alpha (INFα), and combinations thereof.

14. The method according to claim 10, wherein the peptide comprises an amino acid sequence of any of the proteins selected from the group consisting of HBV polymerase, HBV core protein, HBV X-protein and HBV large surface protein.

15. The method according to claim 10, wherein the peptide comprises an amino acid sequence selected from the group consisting of SEQ ID NOS: 51-53, 55, 57, 60, 63, 64, 66, 68, 71, 72, 74-78, 1142, 1145, 1468-1471.

16. The method according to claim 10, wherein the polynucleotide further comprises a covalently linked functional group, an oligonucleotide conjugate, a sugar chain or glycan, or combinations thereof.

17. The method according to claim 13, wherein the human toll-like receptor ligand and/or agonist is selected from the group consisting of Gram positive bacterial glycolipid, LPS, LPA, LTA, fimbriae, an outer membrane protein, a heat shock protein, Mycobacterial lipoarabinomannans, dsRNA, poly(I:C), Gram negative bacterial glycolipid, a viral coat protein, a viral envelope protein, taxol and/or derivative thereof, hyaluronan containing oligosaccharides and fibronectins, bacterial flagellae, flagellin, Mycobacterial lipoproteins, group B Streptococcus heat labile soluble factor, a Staphylococcus modulin, imidazoquinolines, imiquimod and/or derivative thereof, resiquimod and/or derivative thereof, unmethylated CpG DNA, chromatin-IgG complexes, IC31, IMSAVAC, pam3cys and/or derivative thereof, poly-ICLC, and CpG oligodeoxynucleotides (CpG-ODNs).

18. The method according to claim 11, wherein the composition further comprises PSA, 2-aminoisobutyric acid (Abu), a DC pulse cassette, or combinations thereof.

19. The method according to claim 10, wherein the HBV-related disease is selected from the group consisting of acute HBV infection, chronic HBV infection, conditions where the hepatitis virus is found in the blood or body fluids containing blood of a subject, liver cirrhosis, liver cancer, and presence of the virus in the body of a subject.

* * * * *

SEQUENCE LISTING

<160> NUMBER OF SEQ ID NOS: 1471

<210> SEQ ID NO 1
<211> LENGTH: 845
<212> TYPE: PRT
<213> ORGANISM: Hepatitis B Virus

<400> SEQUENCE: 1

-continued

```
Met Pro Leu Ser Tyr Gln His Phe Arg Lys Leu Leu Leu Asp Asp
1               5                   10                  15

Gly Thr Glu Ala Gly Pro Leu Glu Glu Leu Pro Arg Leu Ala Asp
                20                  25                  30

Ala Asp Leu His Arg Arg Val Ala Glu Asp Leu Asn Leu Gly Asn Leu
            35                  40                  45

Asn Val Ser Ile Pro Trp Thr His Lys Val Gly Asn Phe Thr Gly Leu
50                      55                  60

Tyr Ser Ser Thr Val Pro Ile Phe Asn Pro Glu Trp Gln Thr Pro Ser
65                  70                  75                  80

Phe Pro Lys Ile His Leu Gln Glu Asp Ile Ile Asn Arg Cys Gln Gln
                85                  90                  95

Phe Val Gly Pro Leu Thr Val Asn Glu Lys Arg Leu Lys Leu Ile
                100                 105                 110

Met Pro Ala Arg Phe Tyr Pro Thr His Thr Lys Tyr Leu Pro Leu Asp
            115                 120                 125

Lys Gly Ile Lys Pro Tyr Tyr Pro Asp Gln Val Val Asn His Tyr Phe
130                 135                 140

Gln Thr Arg His Tyr Leu His Thr Leu Trp Lys Ala Gly Ile Leu Tyr
145                 150                 155                 160

Lys Arg Glu Thr Thr Arg Ser Ala Ser Phe Cys Gly Ser Pro Tyr Ser
                165                 170                 175

Trp Glu Gln Glu Leu Gln His Gly Arg Leu Val Ile Lys Thr Ser Gln
                180                 185                 190

Arg His Gly Asp Glu Ser Phe Cys Ser Gln Ser Ser Gly Ile Leu Ser
                195                 200                 205

Arg Ser Ser Val Gly Pro Cys Ile Arg Ser Gln Leu Lys Gln Ser Arg
210                 215                 220

Leu Gly Leu Gln Pro Arg Gln Gly Arg Leu Ala Ser Ser Gln Pro Ser
225                 230                 235                 240

Arg Ser Gly Ser Ile Arg Ala Lys Ala His Pro Ser Thr Arg Arg Tyr
                245                 250                 255

Phe Gly Val Glu Pro Ser Gly Ser Gly His Ile Asp His Ser Val Asn
                260                 265                 270

Asn Ser Ser Ser Cys Leu His Gln Ser Ala Val Arg Lys Ala Ala Tyr
                275                 280                 285

Ser His Leu Ser Thr Ser Lys Arg Gln Ser Ser Gly His Ala Val
                290                 295                 300

Glu Phe His Cys Leu Pro Pro Asn Ser Ala Gly Ser Gln Ser Gln Gly
305                 310                 315                 320

Ser Val Ser Ser Cys Trp Trp Leu Gln Phe Arg Asn Ser Lys Pro Cys
                325                 330                 335

Ser Glu Tyr Cys Leu Ser His Leu Val Asn Leu Arg Glu Asp Trp Gly
                340                 345                 350

Pro Cys Asp Glu His Gly Glu His Ile Arg Ile Pro Arg Thr Pro
            355                 360                 365

Ala Arg Val Thr Gly Gly Val Phe Leu Val Asp Lys Asn Pro His Asn
            370                 375                 380

Thr Ala Glu Ser Arg Leu Val Val Asp Phe Ser Gln Phe Ser Arg Gly
385                 390                 395                 400

Ile Ser Arg Val Ser Trp Pro Lys Phe Ala Val Pro Asn Leu Gln Ser
                405                 410                 415
```

```
Leu Thr Asn Leu Leu Ser Ser Asn Leu Ser Trp Leu Ser Leu Asp Val
            420                 425                 430

Ser Ala Ala Phe Tyr His Ile Pro Leu His Pro Ala Ala Met Pro His
            435                 440                 445

Leu Leu Ile Gly Ser Ser Gly Leu Ser Arg Tyr Val Ala Arg Leu Ser
            450                 455                 460

Ser Asn Ser Arg Ile Asn Asn Asn Gln Tyr Gly Thr Met Gln Asn Leu
465                 470                 475                 480

His Asp Ser Cys Ser Arg Gln Leu Tyr Val Ser Leu Met Leu Leu Tyr
                485                 490                 495

Lys Thr Tyr Gly Trp Lys Leu His Leu Tyr Ser His Pro Ile Val Leu
            500                 505                 510

Gly Phe Arg Lys Ile Pro Met Gly Val Gly Leu Ser Pro Phe Leu Leu
            515                 520                 525

Ala Gln Phe Thr Ser Ala Ile Cys Ser Val Val Arg Arg Ala Phe Pro
            530                 535                 540

His Cys Leu Ala Phe Ser Tyr Met Asp Asp Val Val Leu Gly Ala Lys
545                 550                 555                 560

Ser Val Gln His Arg Glu Ser Leu Tyr Thr Ala Val Thr Asn Phe Leu
                565                 570                 575

Leu Ser Leu Gly Ile His Leu Asn Pro Asn Lys Thr Lys Arg Trp Gly
            580                 585                 590

Tyr Ser Leu Asn Phe Met Gly Tyr Ile Ile Gly Ser Trp Gly Thr Leu
            595                 600                 605

Pro Gln Asp His Ile Val Gln Lys Ile Lys His Cys Phe Arg Lys Leu
            610                 615                 620

Pro Val Asn Arg Pro Ile Asp Trp Lys Val Cys Gln Arg Ile Val Gly
625                 630                 635                 640

Leu Leu Gly Phe Ala Ala Pro Phe Thr Gln Cys Gly Tyr Pro Ala Leu
                645                 650                 655

Met Pro Leu Tyr Ala Cys Ile Gln Ala Lys Gln Ala Phe Thr Phe Ser
            660                 665                 670

Pro Thr Tyr Lys Ala Phe Leu Ser Lys Gln Tyr Met Asn Leu Tyr Pro
            675                 680                 685

Val Ala Arg Gln Arg Pro Gly Leu Cys Gln Val Phe Ala Asp Ala Thr
            690                 695                 700

Pro Thr Gly Trp Gly Leu Ala Ile Gly His Gln Arg Met Arg Gly Thr
705                 710                 715                 720

Phe Val Ala Pro Leu Pro Ile His Thr Ala Glu Leu Leu Ala Ala Cys
                725                 730                 735

Phe Ala Arg Ser Arg Ser Gly Ala Lys Leu Ile Gly Thr Asp Asn Ser
            740                 745                 750

Val Val Leu Ser Arg Lys Tyr Thr Ser Phe Pro Trp Leu Leu Gly Cys
            755                 760                 765

Thr Ala Asn Trp Ile Leu Arg Gly Thr Ser Phe Val Tyr Val Pro Ser
            770                 775                 780

Ala Leu Asn Pro Ala Asp Asp Pro Ser Arg Gly Arg Leu Gly Leu Ser
785                 790                 795                 800

Arg Pro Leu Leu Arg Leu Pro Phe Gln Pro Thr Thr Gly Arg Thr Ser
                805                 810                 815

Leu Tyr Ala Val Ser Pro Ser Val Pro Ser His Leu Pro Val Arg Val
            820                 825                 830

His Phe Ala Ser Pro Leu His Val Ala Trp Arg Pro Pro
```

<210> SEQ ID NO 2
<211> LENGTH: 2538
<212> TYPE: DNA
<213> ORGANISM: Hepatitis B Virus

<400> SEQUENCE: 2

| | | | | | |
|---|---|---|---|---|---|
| atgcccctat | cttatcaaca | cttccggaaa | ctactgttgt | tagacgacgg | gaccgaggca | 60 |
| ggtcccctag | aagaagaact | ccctcgcctc | gcagacgcag | atctccatcg | ccgcgtcgca | 120 |
| gaagatctca | atctcgggaa | tctcaatgtt | agtattcctt | ggactcataa | ggtgggaaac | 180 |
| tttacggggc | tttattcctc | tacagtacct | atctttaatc | ctgaatggca | aactccttcc | 240 |
| tttcctaaga | ttcatttaca | agaggacatt | attaataggt | gtcaacaatt | tgtgggccct | 300 |
| ctcactgtaa | atgaaaagag | aagattgaaa | ttaattatgc | ctgctagatt | ctatcctacc | 360 |
| cacactaaat | atttgccctt | agacaaagga | attaaacctt | attatccaga | tcaggtagtt | 420 |
| aatcattact | tccaaaccag | acattattta | catactcttt | ggaaggctgg | tattctatat | 480 |
| aagcgggaaa | ccacacgtag | cgcatcattt | tgcgggtcac | catattcttg | ggaacaagag | 540 |
| ctacagcatg | ggaggttggt | catcaaaacc | tcgcaaaggc | atggggacga | atctttctgt | 600 |
| tcccaatcct | ctgggattct | ttcccgatca | tcagttggac | cctgcattcg | agccaactc | 660 |
| aaacaatcca | gattgggact | tcaaccccgt | caaggacgac | tggccagcag | ccaaccaagt | 720 |
| aggagtggga | gcattcgggc | caaggctcac | ccctccacac | ggcggtattt | tggggtggag | 780 |
| ccctcaggct | cagggcatat | tgaccacagt | gtcaacaatt | cctcctcctg | cctccaccaa | 840 |
| tcggcagtca | ggaaggcagc | ctactcccat | ctctccacct | ctaagagaca | gtcatcctca | 900 |
| ggccatgcag | tggaattcca | ctgccttcca | ccaaactctg | caggatccca | gagtcagggg | 960 |
| tctgtatctt | cctgctggtg | gctccagttc | aggaacagta | aaccctgctc | cgaatattgc | 1020 |
| ctctcacatc | tcgtcaatct | ccgcgaggac | tggggaccct | gtgacgaaca | tggagaacat | 1080 |
| cacatcagga | ttcctaggac | ccctgctcgt | gttacaggcg | gggtttttct | tgttgacaag | 1140 |
| aatcctcaca | ataccgcaga | gtctagactc | gtggtggact | tctctcaatt | ttctaggggg | 1200 |
| atctcccgtg | tgtcttggcc | aaaattcgca | gtccccaacc | tccaatcact | caccaacctc | 1260 |
| ctgtcctcca | atttgtcctg | gttatcgctg | gatgtgtctg | cggcgtttta | tcatattcct | 1320 |
| cttcatcctg | ctgctatgcc | tcatcttctt | attggttctt | ctggattatc | aaggtatgtt | 1380 |
| gcccgtttgt | cctctaattc | caggatcaac | aacaaccagt | acgggaccat | gcaaaacctg | 1440 |
| cacgactcct | gctcaaggca | actctatgtt | tccctcatgt | tgctgtacaa | aacctacgga | 1500 |
| tggaaattgc | acctgtattc | ccatcccatc | gtcctgggct | ttcgcaaaat | acctatggga | 1560 |
| gtgggcctca | gtccgtttct | cttggctcag | tttactagtg | ccatttgttc | agtggttcgt | 1620 |
| agggctttcc | cccactgttt | ggctttcagc | tatatggatg | atgtggtatt | ggggggccaag | 1680 |
| tctgtacagc | atcgtgagtc | cctttatacc | gctgttacca | attttctttt | gtctctgggt | 1740 |
| atacatttaa | accctaacaa | aacaaaaaga | tggggttatt | ccctaaactt | catgggctac | 1800 |
| ataattggaa | gttggggaac | tttgccacag | gatcatattg | tacaaaagat | caaacactgt | 1860 |
| tttagaaaac | ttcctgttaa | caggcctatt | gattggaaag | tatgtcaaag | aattgtgggt | 1920 |
| cttttgggct | ttgctgctcc | atttacacaa | tgtggatatc | ctgccttaat | gcctttgtat | 1980 |
| gcatgtatac | aagctaaaca | ggctttcact | ttctcgccaa | cttacaaggc | ctttctaagt | 2040 |
| aaacagtaca | tgaaccttta | ccccgttgct | cggcaacggc | ctggtctgtg | ccaagtgttt | 2100 |

-continued

| | |
|---|---|
| gctgacgcaa ccccactgg ctggggcttg gccataggcc atcagcgcat gcgtggaacc | 2160 |
| tttgtggctc ctctgccgat ccatactgcg gaactcctag ccgcttgttt tgctcgcagc | 2220 |
| cggtctggag caaagctcat cggaactgac aattctgtcg tcctctcgcg gaaatataca | 2280 |
| tcgtttccat ggctgctagg ctgtactgcc aactggatcc ttcgcgggac gtcctttgtt | 2340 |
| tacgtcccgt cggcgctgaa tcccgcggac gaccctctc ggggccgctt gggactctct | 2400 |
| cgtcccttc tccgtctgcc gttccagccg accacgggc gcacctctct ttacgcggtc | 2460 |
| tccccgtctg tgccttctca tctgccggtc cgtgtgcact tcgcttcacc tctgcacgtt | 2520 |
| gcatggagac caccgtga | 2538 |

<210> SEQ ID NO 3
<211> LENGTH: 3221
<212> TYPE: DNA
<213> ORGANISM: Hepatitis B virus

<400> SEQUENCE: 3

| | |
|---|---|
| catgcaactt tttcacctct gcctaatcat ctcttgtaca tgtcccactg ttcaagcctc | 60 |
| caagctgtgc cttgggtggc tttgggcat ggacattgac ccttataaag aatttggagc | 120 |
| tactgtggag ttactctcgt ttttgccttc tgacttcttt ccttccgtca gagatctcct | 180 |
| agacaccgcc tcagctctgt atcgagaagc cttagagtct cctgagcatt gctcacctca | 240 |
| ccatactgca ctcaggcaag ccattctctg ctgggggaa ttgatgactc tagctacctg | 300 |
| ggtgggtaat aatttggaag atccagcatc tagggatctt gtagtaaatt atgttaatac | 360 |
| taacgtgggt ttaaagatca ggcaactatt gtggtttcat atatcttgcc ttacttttgg | 420 |
| aagagagact gtacttgaat atttggtctc tttcggagtg tggattcgca ctcctccagc | 480 |
| ctatagacca ccaaatgccc ctatcttatc aacacttccg gaaactactg ttgttagacg | 540 |
| acggaccga gcaggtccc ctagaagaag aactccctcg cctcgcagac gcagatctcc | 600 |
| atcgccgcgt cgcagaagat ctcaatctcg ggaatctcaa tgttagtatt ccttggactc | 660 |
| ataaggtggg aaactttacg ggctttatt cctctacagt acctatcttt aatcctgaat | 720 |
| ggcaaactcc ttccttcct aagattcatt acaagagga cattattaat aggtgtcaac | 780 |
| aatttgtggg ccctctcact gtaaatgaaa agagaagatt gaaattaatt atgcctgcta | 840 |
| gattctatcc taccccacact aaatatttgc ccttagacaa aggaattaaa ccttattatc | 900 |
| cagatcaggt agttaatcat tacttccaaa ccagacatta tttacatact ctttggaagg | 960 |
| ctggtattct atataagcgg gaaaccacac gtagcgcatc attttgcggg tcaccatatt | 1020 |
| cttgggaaca agagctacag catgggaggt tggtcatcaa aacctcgcaa aggcatgggg | 1080 |
| acgaatcttt ctgttcccaa tcctctggga ttctttcccg atcatcagtt ggaccctgca | 1140 |
| ttcggagcca actcaaacaa tccagattgg gacttcaacc ccgtcaagga cgactggcca | 1200 |
| gcagccaacc aagtaggagt gggagcattc gggccaaggc tcacccctcc acacggcggt | 1260 |
| attttggggt ggagccctca ggctcagggc atattgacca cagtgtcaac aattcctcct | 1320 |
| cctgcctcca ccaatcggca gtcaggaagg cagcctactc ccatctctcc acctctaaga | 1380 |
| gacagtcatc ctcaggccat gcagtggaat tccactgcct tccaccaaac tctgcaggat | 1440 |
| cccagagtca gggtctgta tcttcctgct ggtggctcca gttcaggaac agtaaaccct | 1500 |
| gctccgaata ttgcctctca catctcgtca atctccgcga ggactgggga ccctgtgacg | 1560 |
| aacatggaga acatcacatc aggattccta ggacccctgc tcgtgttaca ggcggggttt | 1620 |

```
ttcttgttga caagaatcct cacaataccg cagagtctag actcgtggtg gacttctctc    1680
aattttctag ggggatctcc cgtgtgtctt ggccaaaatt cgcagtcccc aacctccaat    1740
cactcaccaa cctcctgtcc tccaatttgt cctggttatc gctggatgtg tctgcggcgt    1800
tttatcatat tcctcttcat cctgctgcta tgcctcatct tcttattggt tcttctggat    1860
tatcaaggta tgttgcccgt ttgtcctcta attccaggat caacaacaac cagtacggga    1920
ccatgcaaaa cctgcacgac tcctgctcaa ggcaactcta tgtttccctc atgttgctgt    1980
acaaaaccta cggatggaaa ttgcacctgt attcccatcc catcgtcctg ggctttcgca    2040
aaatacctat gggagtgggc ctcagtccgt ttctcttggc tcagtttact agtgccattt    2100
gttcagtggt tcgtagggct ttcccccact gtttggcttt cagctatatg gatgatgtgg    2160
tattgggggc caagtctgta cagcatcgtg agtcccttta taccgctgtt accaatttc     2220
ttttgtctct gggtatacat ttaaacccta acaaaacaaa agatggggt tattccctaa     2280
acttcatggg ctacataatt ggaagttggg aactttgcc acaggatcat attgtacaaa     2340
agatcaaaca ctgttttaga aaacttcctg ttaacaggcc tattgattgg aaagtatgtc    2400
aaagaattgt gggtcttttg gctttgctg ctccatttac acaatgtgga tatcctgcct     2460
taatgccttt gtatgcatgt atacaagcta acaggctttc actttctcg ccaacttaca     2520
aggcctttct aagtaaacag tacatgaacc tttacccgt tgctcggcaa cggcctggtc     2580
tgtgccaagt gtttgctgac gcaacccca ctggctgggg cttggccata ggccatcagc     2640
gcatgcgtgg aacctttgtg gctcctctgc cgatccatac tgcggaactc ctagccgctt    2700
gttttgctcg cagccggtct ggagcaaagc tcatcggaac tgacaattct gtcgtcctct    2760
cgcggaaata tacatcgttt ccatggctgc taggctgtac tgccaactgg atccttcgcg    2820
ggacgtcctt tgtttacgtc ccgtcggcgc tgaatcccgc ggacgacccc tctcggggcc    2880
gcttgggact ctctcgtccc cttctccgtc tgccgttcca gccgaccacg ggcgcacct     2940
ctctttacgc ggtctccccg tctgtgcctt ctcatctgcc ggtccgtgtg cacttcgctt    3000
cacctctgca cgttgcatgg agaccaccgt gaacgcccat cagatcctgc caaggtctt    3060
acataagagg actcttggac tcccagcaat gtcaacgacc gaccttgagg cctacttcaa    3120
agactgtgtg tttaaggact gggaggagct ggggggaggag attaggttaa aggtctttgt    3180
attaggaggc tgtaggcaca aattggtctg cgcaccagca c                        3221
```

<210> SEQ ID NO 4
<211> LENGTH: 214
<212> TYPE: PRT
<213> ORGANISM: Hepatitis B Virus

<400> SEQUENCE: 4

```
Met Gln Leu Phe His Leu Cys Leu Ile Ile Ser Cys Thr Cys Pro Thr
1               5                   10                  15

Val Gln Ala Ser Lys Leu Cys Leu Gly Trp Leu Trp Gly Met Asp Ile
            20                  25                  30

Asp Pro Tyr Lys Glu Phe Gly Ala Thr Val Glu Leu Leu Ser Phe Leu
        35                  40                  45

Pro Ser Asp Phe Phe Pro Ser Val Arg Asp Leu Leu Asp Thr Ala Ser
    50                  55                  60

Ala Leu Tyr Arg Glu Ala Leu Glu Ser Pro Glu His Cys Ser Pro His
65                  70                  75                  80

His Thr Ala Leu Arg Gln Ala Ile Leu Cys Trp Gly Glu Leu Met Thr
                85                  90                  95
```

Leu Ala Thr Trp Val Gly Asn Asn Leu Glu Asp Pro Ala Ser Arg Asp
            100                 105                 110

Leu Val Val Asn Tyr Val Asn Thr Asn Val Gly Leu Lys Ile Arg Gln
        115                 120                 125

Leu Leu Trp Phe His Ile Ser Cys Leu Thr Phe Gly Arg Glu Thr Val
    130                 135                 140

Leu Glu Tyr Leu Val Ser Phe Gly Val Trp Ile Arg Thr Pro Pro Ala
145                 150                 155                 160

Tyr Arg Pro Pro Asn Ala Pro Ile Leu Ser Thr Leu Pro Glu Thr Thr
                165                 170                 175

Val Val Arg Arg Arg Asp Arg Gly Arg Ser Pro Arg Arg Arg Thr Pro
            180                 185                 190

Ser Pro Arg Arg Arg Arg Ser Pro Ser Pro Arg Arg Arg Arg Ser Gln
        195                 200                 205

Ser Arg Glu Ser Gln Cys
        210

<210> SEQ ID NO 5
<211> LENGTH: 645
<212> TYPE: DNA
<213> ORGANISM: Hepatitis B Virus

<400> SEQUENCE: 5
atgcaacttt ttcacctctg cctaatcatc tcttgtacat gtcccactgt tcaagcctcc      60
aagctgtgcc ttgggtggct ttggggcatg gacattgacc cttataaaga atttggagct     120
actgtggagt tactctcgtt tttgccttct gacttctttc cttccgtcag agatctccta     180
gacaccgcct cagctctgta tcgagaagcc ttagagtctc ctgagcattg ctcacctcac     240
catactgcac tcaggcaagc cattctctgc tggggggaat gatgactct agctacctgg      300
gtgggtaata atttgaaga tccagcatct agggatcttg tagtaaatta tgttaatact     360
aacgtgggtt taaagatcag caactattg tggtttcata tatcttgcct tacttttgga     420
agagagactg tacttgaata tttggtctct ttcggagtgt ggattcgcac tcctccagcc     480
tatagaccac caaatgcccc tatcttatca acacttccgg aaactactgt tgttagacga     540
cgggaccgag gcaggtcccc tagaagaaga actccctcgc ctcgcagacg cagatctcca     600
tcgccgcgtc gcagaagatc tcaatctcgg gaatctcaat gttag                    645

<210> SEQ ID NO 6
<211> LENGTH: 154
<212> TYPE: PRT
<213> ORGANISM: Hepatitis B Virus

<400> SEQUENCE: 6

Met Ala Ala Arg Leu Tyr Cys Gln Leu Asp Ser Ser Arg Asp Val Leu
1               5                   10                  15

Cys Leu Arg Pro Val Gly Ala Glu Ser Arg Gly Arg Pro Leu Ala Gly
            20                  25                  30

Pro Leu Gly Ala Leu Ser Ser Pro Ser Pro Ser Ala Val Pro Ser Asp
        35                  40                  45

His Gly Ala His Leu Ser Leu Arg Gly Leu Pro Val Cys Ala Phe Ser
    50                  55                  60

Ser Ala Gly Pro Cys Ala Leu Arg Phe Thr Ser Ala Arg Cys Met Glu
65                  70                  75                  80

Thr Thr Val Asn Ala His Gln Ile Leu Pro Lys Val Leu His Lys Arg

```
                    85                  90                  95

Thr Leu Gly Leu Pro Ala Met Ser Thr Thr Asp Leu Glu Ala Tyr Phe
                100                 105                 110

Lys Asp Cys Val Phe Lys Asp Trp Glu Glu Leu Gly Glu Glu Ile Arg
            115                 120                 125

Leu Lys Val Phe Val Leu Gly Gly Cys Arg His Lys Leu Val Phe Ala
        130                 135                 140

Pro Ser Ser Cys Asn Phe Phe Thr Ser Ala
145                 150

<210> SEQ ID NO 7
<211> LENGTH: 154
<212> TYPE: PRT
<213> ORGANISM: Hepatitis B Virus

<400> SEQUENCE: 7

Met Ala Ala Arg Leu Cys Cys Gln Leu Asp Pro Ser Arg Asp Val Leu
1               5                   10                  15

Cys Leu Arg Pro Val Gly Ala Glu Ser Arg Gly Arg Pro Leu Ser Gly
            20                  25                  30

Pro Leu Gly Thr Leu Ser Ser Pro Ser Pro Ser Ala Val Pro Ala Asp
        35                  40                  45

His Gly Ala His Leu Ser Leu Arg Gly Leu Pro Val Cys Ala Phe Ser
    50                  55                  60

Ser Ala Gly Pro Cys Ala Leu Arg Phe Thr Ser Ala Arg Cys Met Glu
65                  70                  75                  80

Thr Thr Val Asn Ala His Gln Ser Leu Pro Lys Val Leu His Lys Arg
                85                  90                  95

Thr Leu Gly Leu Pro Ala Met Ser Thr Thr Asp Leu Glu Ala Tyr Phe
                100                 105                 110

Lys Asp Cys Val Phe Lys Asp Trp Glu Glu Leu Gly Glu Glu Ile Arg
            115                 120                 125

Leu Met Ile Phe Val Leu Gly Gly Cys Arg His Lys Leu Val Cys Ala
        130                 135                 140

Pro Ala Pro Cys Asn Phe Phe Thr Ser Ala
145                 150

<210> SEQ ID NO 8
<211> LENGTH: 154
<212> TYPE: PRT
<213> ORGANISM: Hepatitis B Virus

<400> SEQUENCE: 8

Met Ala Ala Arg Leu Tyr Cys Gln Leu Asp Pro Ser Arg Asp Val Leu
1               5                   10                  15

Cys Leu Arg Pro Val Gly Ala Glu Ser Arg Gly Arg Pro Leu Ser Gly
            20                  25                  30

Pro Leu Gly Thr Leu Ser Ser Pro Ser Pro Ser Ala Val Pro Ala Asp
        35                  40                  45

His Gly Ala His Leu Ser Leu Arg Gly Leu Pro Val Cys Ala Phe Ser
    50                  55                  60

Ser Ala Gly Pro Cys Ala Leu Arg Phe Thr Ser Ala Arg Cys Met Glu
65                  70                  75                  80

Thr Thr Val Asn Ala His Gln Ile Leu Pro Lys Val Leu His Lys Arg
                85                  90                  95

Thr Leu Gly Leu Pro Ala Met Ser Thr Thr Asp Leu Glu Ala Tyr Phe
```

```
            100                 105                 110
Lys Asp Ser Val Phe Lys Asp Trp Glu Glu Leu Gly Glu Glu Ile Arg
        115                 120                 125
Leu Lys Val Phe Val Leu Gly Gly Cys Arg His Lys Leu Val Cys Ala
        130                 135                 140
Pro Ala Pro Cys Asn Phe Phe Thr Ser Ala
145                 150

<210> SEQ ID NO 9
<211> LENGTH: 154
<212> TYPE: PRT
<213> ORGANISM: Hepatitis B Virus

<400> SEQUENCE: 9

Met Ala Thr Arg Leu Cys Cys Gln Leu Asp Pro Ser Arg Asp Val Leu
1               5                   10                  15
Cys Leu Arg Pro Val Gly Ala Glu Ser Arg Gly Arg Pro Leu Ser Gly
            20                  25                  30
Pro Leu Gly Thr Leu Ser Ser Pro Ser Pro Ser Ala Val Pro Ala Asp
        35                  40                  45
His Gly Ala His Leu Ser Leu Arg Gly Leu Pro Val Cys Ala Phe Ser
    50                  55                  60
Ser Ala Gly Pro Cys Ala Leu Arg Phe Thr Ser Ala Arg Cys Met Glu
65                  70                  75                  80
Thr Thr Val Asn Ala His Gln Ile Leu Pro Lys Val Leu His Lys Arg
                85                  90                  95
Thr Leu Gly Leu Pro Ala Met Ser Thr Thr Asp Leu Glu Ala Tyr Phe
            100                 105                 110
Lys Asp Cys Val Phe Lys Asp Trp Glu Glu Leu Gly Glu Glu Ile Arg
        115                 120                 125
Leu Lys Val Phe Val Leu Gly Gly Cys Arg His Lys Leu Val Cys Ala
        130                 135                 140
Pro Ala Pro Cys Asn Phe Phe Thr Ser Ala
145                 150

<210> SEQ ID NO 10
<211> LENGTH: 154
<212> TYPE: PRT
<213> ORGANISM: Hepatitis B Virus

<400> SEQUENCE: 10

Met Ala Ala Arg Leu Tyr Cys Gln Leu Asp Pro Ser Arg Asp Val Leu
1               5                   10                  15
Cys Leu Arg Pro Val Gly Ala Glu Ser Arg Gly Arg Pro Leu Ser Gly
            20                  25                  30
Pro Leu Gly Thr Leu Ser Ser Pro Ser Pro Ser Ala Val Pro Ala Asp
        35                  40                  45
His Gly Ala His Leu Ser Leu Arg Gly Leu Pro Val Cys Ala Phe Ser
    50                  55                  60
Ser Ala Gly Pro Cys Ala Leu Arg Phe Thr Ser Ala Arg Cys Met Glu
65                  70                  75                  80
Thr Thr Val Asn Ala His Gln Ile Leu Pro Lys Val Leu His Lys Arg
                85                  90                  95
Thr Leu Gly Leu Pro Ala Met Ser Thr Thr Asp Leu Glu Ala Tyr Phe
            100                 105                 110
Lys Asp Cys Val Phe Lys Asp Trp Glu Glu Leu Gly Glu Glu Ile Arg
```

```
            115                 120                 125
Leu Lys Val Phe Val Leu Gly Gly Cys Arg His Lys Leu Val Cys Ala
        130                 135                 140

Pro Ala Pro Cys Asn Phe Phe Thr Ser Ala
145                 150

<210> SEQ ID NO 11
<211> LENGTH: 154
<212> TYPE: PRT
<213> ORGANISM: Hepatitis B Virus

<400> SEQUENCE: 11

Met Ala Ala Arg Leu Tyr Cys Gln Leu Asp Ser Ser Arg Asn Val Leu
1               5                   10                  15

Cys Leu Arg Pro Val Gly Ala Glu Ser Cys Gly Arg Pro Leu Ser Gly
            20                  25                  30

Pro Val Gly Thr Leu Ser Ser Pro Ser Pro Ser Ala Val Pro Thr Asp
        35                  40                  45

His Gly Ala His Leu Ser Leu Arg Gly Leu Pro Val Cys Ala Phe Ser
    50                  55                  60

Ser Ala Gly Pro Cys Ala Leu Arg Phe Thr Ser Ala Arg Cys Met Glu
65                  70                  75                  80

Thr Thr Val Asn Ala His Gln Ile Leu Pro Lys Val Leu Tyr Lys Arg
                85                  90                  95

Thr Leu Gly Leu Pro Ala Met Ser Thr Thr Asp Leu Glu Ala Tyr Phe
            100                 105                 110

Lys Asp Cys Val Phe Lys Asp Trp Glu Glu Leu Gly Glu Glu Ile Arg
        115                 120                 125

Leu Lys Ile Phe Val Leu Gly Gly Cys Arg His Lys Leu Val Cys Ala
    130                 135                 140

Pro Phe Ser Cys Asn Phe Phe Thr Ser Ala
145                 150

<210> SEQ ID NO 12
<211> LENGTH: 154
<212> TYPE: PRT
<213> ORGANISM: Hepatitis B Virus

<400> SEQUENCE: 12

Met Ala Ala Arg Leu Tyr Cys Gln Leu Asp Ser Ser Arg Asp Val Leu
1               5                   10                  15

Cys Leu Arg Pro Val Gly Ala Glu Ser Arg Gly Arg Pro Phe Ser Gly
            20                  25                  30

Pro Leu Gly Thr Leu Ser Ser Pro Ser Pro Ser Ala Val Ser Ser Asp
        35                  40                  45

His Gly Ala His Leu Ser Leu Arg Gly Leu Pro Val Cys Ala Phe Ser
    50                  55                  60

Ser Ala Gly Pro Cys Ala Leu Arg Phe Thr Ser Ala Arg Cys Met Ala
65                  70                  75                  80

Thr Thr Val Asn Ala His Gln Ile Leu Pro Lys Val Leu His Lys Arg
                85                  90                  95

Thr Leu Gly Leu Pro Ala Met Ser Thr Thr Asp Leu Glu Ala Tyr Phe
            100                 105                 110

Lys Asp Cys Leu Phe Lys Asp Trp Glu Glu Leu Gly Glu Glu Ile Arg
        115                 120                 125

Leu Lys Val Phe Val Leu Gly Gly Cys Arg His Lys Leu Val Cys Ala
```

```
                130                 135                 140

Pro Ser Ser Cys Asn Phe Phe Thr Ser Ala
145                 150

<210> SEQ ID NO 13
<211> LENGTH: 154
<212> TYPE: PRT
<213> ORGANISM: Hepatitis B Virus

<400> SEQUENCE: 13

Met Ala Ala Arg Leu Cys Cys Gln Leu Asp Thr Ala Arg Asp Val Leu
1               5                   10                  15

Cys Leu Arg Pro Val Gly Ala Glu Ser Arg Gly Arg Pro Leu Pro Gly
                20                  25                  30

Pro Leu Gly Ala Leu Pro Pro Ala Ser Pro Ser Ala Val Pro Thr Asp
            35                  40                  45

His Gly Ala His Leu Ser Leu Arg Gly Leu Pro Val Cys Ala Phe Ser
    50                  55                  60

Ser Thr Gly Pro Cys Ala Leu Arg Phe Thr Ser Ala Arg Arg Met Glu
65                  70                  75                  80

Thr Thr Val Asn Ala His Arg Asn Leu Pro Lys Val Leu His Lys Arg
                85                  90                  95

Thr Leu Gly Leu Ser Ala Met Ser Thr Thr Asp Leu Glu Ala Tyr Phe
            100                 105                 110

Lys Asp Cys Val Phe Thr Glu Trp Glu Glu Leu Gly Glu Glu Met Arg
        115                 120                 125

Leu Lys Val Phe Val Leu Gly Gly Cys Arg His Lys Leu Val Cys Ser
    130                 135                 140

Pro Ala Pro Cys Asn Phe Phe Thr Ser Ala
145                 150

<210> SEQ ID NO 14
<211> LENGTH: 154
<212> TYPE: PRT
<213> ORGANISM: Hepatitis B Virus

<400> SEQUENCE: 14

Met Ala Ala Arg Leu Cys Cys Gln Leu Asp Pro Ala Arg Asp Val Leu
1               5                   10                  15

Cys Leu Arg Pro Val Gly Ala Glu Ser Arg Gly Arg Pro Leu Pro Gly
                20                  25                  30

Pro Leu Gly Ala Ile Pro Pro Ala Ser Pro Ser Thr Val Pro Thr Asp
            35                  40                  45

His Gly Ala His Leu Ser Leu Arg Gly Leu Pro Val Cys Ala Phe Ser
    50                  55                  60

Ser Ala Gly Pro Cys Ala Leu Arg Phe Thr Ser Ala Arg Arg Met Glu
65                  70                  75                  80

Thr Thr Val Asn Ala His Arg Asn Leu Pro Lys Val Leu His Lys Arg
                85                  90                  95

Thr Leu Gly Leu Ser Val Met Ser Thr Thr Asp Leu Glu Ala Tyr Phe
            100                 105                 110

Lys Asp Cys Val Phe Thr Glu Trp Glu Glu Leu Gly Glu Glu Met Arg
        115                 120                 125

Leu Lys Val Phe Val Leu Gly Gly Cys Arg His Lys Leu Val Cys Ser
    130                 135                 140

Pro Ala Pro Cys Asn Phe Phe Thr Ser Ala
```

<210> SEQ ID NO 15
<211> LENGTH: 154
<212> TYPE: PRT
<213> ORGANISM: Hepatitis B virus

<400> SEQUENCE: 15

Met Ala Ala Arg Leu Cys Cys Gln Leu Asp Pro Ala Arg Asp Val Leu
1               5                   10                  15

Cys Leu Arg Pro Val Gly Ala Glu Ser Arg Gly Arg Pro Leu Pro Gly
            20                  25                  30

Pro Leu Gly Ala Leu Pro Pro Ala Ser Pro Ser Ala Val Pro Ser Asp
        35                  40                  45

His Gly Ala His Leu Ser Leu Arg Gly Leu Pro Val Cys Ala Phe Ser
    50                  55                  60

Ser Ala Gly Pro Cys Ala Leu Arg Phe Thr Ser Ala Arg Arg Met Glu
65                  70                  75                  80

Thr Thr Val Asn Ala His Arg Asn Leu Pro Lys Val Leu His Lys Arg
                85                  90                  95

Thr Leu Gly Leu Ser Ala Met Ser Thr Thr Asp Leu Glu Ala Tyr Phe
            100                 105                 110

Lys Asp Cys Val Phe Asn Glu Trp Glu Glu Leu Gly Glu Glu Ile Arg
        115                 120                 125

Leu Lys Val Phe Val Leu Gly Gly Cys Arg His Lys Leu Val Cys Ser
    130                 135                 140

Pro Ala Pro Cys Asn Phe Phe Thr Ser Ala
145                 150

<210> SEQ ID NO 16
<211> LENGTH: 154
<212> TYPE: PRT
<213> ORGANISM: Hepatitis B Virus

<400> SEQUENCE: 16

Met Ala Ala Arg Leu Cys Cys Gln Leu Asp Pro Ala Arg Asp Val Leu
1               5                   10                  15

Cys Leu Arg Pro Val Gly Ala Glu Ser Arg Gly Arg Pro Leu Pro Gly
            20                  25                  30

Pro Leu Gly Ala Leu Pro Pro Ala Ser Pro Pro Ala Val Pro Ser Asp
        35                  40                  45

His Gly Ala His Leu Ser Leu Arg Gly Leu Pro Val Cys Ala Phe Ser
    50                  55                  60

Ser Ala Gly Pro Cys Ala Leu Arg Phe Thr Ser Ala Arg Arg Met Glu
65                  70                  75                  80

Thr Thr Val Asn Ala His Arg Asn Leu Pro Lys Val Leu His Lys Arg
                85                  90                  95

Thr Leu Gly Leu Ser Ala Met Ser Thr Thr Asp Leu Glu Ala His Phe
            100                 105                 110

Lys Asp Cys Val Phe Thr Glu Trp Glu Glu Leu Gly Glu Glu Ile Arg
        115                 120                 125

Leu Lys Val Phe Val Leu Gly Gly Cys Arg His Lys Leu Val Cys Ser
    130                 135                 140

Pro Ala Pro Cys Asn Phe Phe Thr Ser Ala
145                 150

```
<210> SEQ ID NO 17
<211> LENGTH: 154
<212> TYPE: PRT
<213> ORGANISM: Hepatitis B Virus

<400> SEQUENCE: 17

Met Ala Ala Arg Leu Cys Cys Gln Leu Asp Pro Ala Arg Asp Val Leu
1               5                   10                  15

Cys Leu Arg Pro Val Gly Ala Glu Ser Arg Gly Arg Pro Leu Pro Gly
            20                  25                  30

Pro Leu Gly Ala Ile Pro Pro Ala Ser Pro Val Val Pro Thr Asp
        35                  40                  45

His Gly Ala His Leu Ser Leu Arg Gly Leu Pro Val Cys Ala Phe Ser
    50                  55                  60

Ser Ala Gly Pro Cys Ala Leu Arg Phe Thr Ser Ala Arg Arg Met Glu
65                  70                  75                  80

Thr Thr Val Asn Ala Pro Gly Asn Leu Pro Lys Val Leu His Lys Arg
                85                  90                  95

Thr Leu Gly Leu Ser Val Met Ser Thr Thr Asp Leu Glu Ala Tyr Phe
            100                 105                 110

Lys Asp Cys Val Phe Thr Glu Trp Glu Glu Leu Gly Glu Glu Val Arg
        115                 120                 125

Leu Lys Val Phe Val Leu Gly Gly Cys Arg His Lys Leu Val Cys Pro
    130                 135                 140

Pro Ala Pro Cys Asn Phe Phe Thr Ser Ala
145                 150

<210> SEQ ID NO 18
<211> LENGTH: 154
<212> TYPE: PRT
<213> ORGANISM: Hepatitis B Virus

<400> SEQUENCE: 18

Met Ala Ala Arg Leu Cys Cys Gln Leu Asp Pro Ala Arg Asp Val Leu
1               5                   10                  15

Cys Leu Arg Pro Val Gly Ala Glu Ser Arg Gly Arg Pro Leu Pro Gly
            20                  25                  30

Pro Leu Gly Ala Leu Pro Pro Ala Ser Pro Pro Ile Val Pro Ser Asp
        35                  40                  45

His Gly Ala His Leu Ser Leu Arg Gly Leu Pro Val Cys Ala Phe Ser
    50                  55                  60

Ser Ala Gly Pro Cys Ala Leu Arg Phe Thr Ser Ala Arg Arg Met Glu
65                  70                  75                  80

Thr Thr Val Asn Ala His Trp Asn Leu Pro Lys Val Leu His Lys Arg
                85                  90                  95

Thr Leu Gly Leu Ser Ala Met Ser Thr Thr Asp Leu Glu Ala Tyr Phe
            100                 105                 110

Lys Asp Cys Val Phe Thr Glu Trp Glu Glu Leu Gly Glu Glu Phe Arg
        115                 120                 125

Leu Lys Val Phe Val Leu Gly Gly Cys Arg His Lys Leu Val Cys Ser
    130                 135                 140

Pro Ala Pro Cys Asn Phe Phe Thr Ser Ala
145                 150

<210> SEQ ID NO 19
<211> LENGTH: 154
<212> TYPE: PRT
```

<213> ORGANISM: Hepatitis B Virus

<400> SEQUENCE: 19

Met Ala Ala Arg Val Cys Cys Gln Leu Asp Pro Ala Arg Asp Val Leu
1               5                   10                  15

Cys Leu Arg Pro Val Gly Ala Glu Ser Arg Gly Arg Pro Leu Pro Gly
            20                  25                  30

Pro Leu Gly Thr Leu Pro Pro Ala Ser Pro Pro Ala Val Pro Thr Asp
        35                  40                  45

His Gly Ala His Leu Ser Leu Arg Gly Leu Pro Val Cys Ala Phe Ser
    50                  55                  60

Ser Ala Gly Pro Cys Ala Leu Arg Phe Thr Ser Ala Arg Arg Met Glu
65                  70                  75                  80

Thr Thr Val Asn Ala His Gly Asn Leu Pro Lys Val Leu His Lys Arg
                85                  90                  95

Thr Leu Gly Leu Ser Ala Met Ser Thr Thr Asp Leu Glu Ala Tyr Phe
            100                 105                 110

Lys Asp Cys Val Phe Asn Glu Trp Glu Glu Leu Gly Glu Glu Ile Arg
        115                 120                 125

Leu Lys Val Phe Val Leu Gly Cys Arg His Lys Leu Val Cys Ser
    130                 135                 140

Pro Ala Pro Cys Asn Phe Phe Thr Ser Ala
145                 150

<210> SEQ ID NO 20
<211> LENGTH: 154
<212> TYPE: PRT
<213> ORGANISM: Hepatitis B Virus

<400> SEQUENCE: 20

Met Ala Ala Arg Leu Cys Cys Gln Leu Asp Pro Ala Arg Asp Val Leu
1               5                   10                  15

Cys Leu Arg Pro Val Gly Ala Glu Ser Arg Gly Arg Pro Phe Pro Gly
            20                  25                  30

Pro Leu Gly Ala Leu Pro Pro Ala Ser Pro Pro Val Val Pro Thr Asp
        35                  40                  45

His Gly Ala His Leu Ser Leu Arg Gly Leu Pro Val Cys Ala Phe Ser
    50                  55                  60

Ser Ala Gly Pro Cys Ala Leu Arg Phe Thr Ser Ala Arg Arg Met Glu
65                  70                  75                  80

Thr Thr Val Asn Ala His Gly Asn Leu Pro Lys Val Leu His Lys Arg
                85                  90                  95

Thr Leu Gly Leu Ser Ala Met Ser Thr Thr Asp Leu Glu Ala Tyr Phe
            100                 105                 110

Lys Asp Cys Val Phe Asn Glu Trp Glu Glu Leu Gly Glu Glu Val Arg
        115                 120                 125

Leu Lys Val Phe Val Leu Gly Cys Arg His Lys Leu Val Cys Ser
    130                 135                 140

Pro Ala Pro Cys Asn Phe Phe Thr Ser Ala
145                 150

<210> SEQ ID NO 21
<211> LENGTH: 154
<212> TYPE: PRT
<213> ORGANISM: Hepatitis B Virus

<400> SEQUENCE: 21

```
Met Ala Ala Arg Leu Cys Cys Gln Leu Asp Pro Ala Arg Asp Val Leu
1               5                   10                  15

Cys Leu Arg Pro Val Gly Ala Glu Ser Arg Gly Arg Pro Val Ser Gly
                20                  25                  30

Ser Leu Gly Ala Leu Pro Ser Pro Ser Pro Ser Ala Val Pro Ala Asp
            35                  40                  45

His Gly Ala His Leu Ser Leu Arg Gly Leu Pro Val Cys Ala Phe Ser
        50                  55                  60

Ser Ala Gly Pro Cys Ala Leu Arg Phe Thr Ser Ala Arg Arg Met Glu
65                  70                  75                  80

Thr Thr Val Asn Ala Asn Gln Val Leu Pro Lys Val Leu His Lys Arg
                85                  90                  95

Thr Leu Gly Leu Ser Ala Leu Ser Thr Thr Asp Leu Glu Ala Tyr Phe
            100                 105                 110

Lys Asp Cys Val Phe Lys Asp Trp Glu Glu Leu Gly Glu Glu Ile Arg
            115                 120                 125

Leu Lys Val Phe Val Leu Gly Gly Cys Arg His Lys Leu Val Cys Val
        130                 135                 140

Pro Ala Pro Cys Asn Phe Phe Thr Ser Ala
145                 150

<210> SEQ ID NO 22
<211> LENGTH: 154
<212> TYPE: PRT
<213> ORGANISM: Hepatitis B Virus

<400> SEQUENCE: 22

Met Ala Ala Arg Val Cys Cys Gln Leu Asp Pro Ala Arg Asp Val Leu
1               5                   10                  15

Cys Leu Arg Pro Val Gly Ala Glu Ser Arg Gly Arg Pro Val Ser Gly
                20                  25                  30

Pro Phe Gly Pro Leu Pro Ser Pro Ser Ser Ala Val Pro Ala Asp
            35                  40                  45

His Gly Ala Arg Leu Ser Leu Arg Gly Leu Pro Val Cys Ala Phe Ser
        50                  55                  60

Ser Ala Gly Pro Cys Ala Leu Arg Phe Thr Ser Ala Arg Arg Met Glu
65                  70                  75                  80

Thr Thr Val Asn Ala His Gln Val Leu Pro Lys Val Leu His Lys Arg
                85                  90                  95

Thr Leu Gly Leu Ser Ala Met Ser Thr Thr Asp Leu Glu Ala Tyr Phe
            100                 105                 110

Lys Asp Cys Leu Phe Lys Asp Trp Glu Glu Leu Gly Glu Glu Ile Arg
            115                 120                 125

Leu Met Val Phe Val Leu Gly Gly Cys Arg His Lys Leu Val Cys Ser
        130                 135                 140

Pro Ala Pro Cys Asn Phe Phe Thr Ser Ala
145                 150

<210> SEQ ID NO 23
<211> LENGTH: 154
<212> TYPE: PRT
<213> ORGANISM: Hepatitis B Virus

<400> SEQUENCE: 23

Met Ala Ala Arg Val Cys Cys Gln Leu Asp Pro Ala Arg Asp Val Leu
1               5                   10                  15
```

```
Cys Leu Arg Pro Val Gly Ala Glu Ser Arg Gly Arg Pro Val Ser Gly
            20                  25                  30

Pro Phe Gly Thr Leu Pro Ser Pro Ser Ser Ala Val Pro Ala Asp
            35                  40                  45

His Gly Ala His Leu Ser Leu Arg Gly Leu Phe Val Cys Ala Phe Ser
     50                  55                  60

Ser Ala Gly Pro Cys Ala Leu Arg Phe Thr Ser Ala Arg Arg Met Glu
 65                  70                  75                  80

Thr Thr Val Asn Ala His Gln Val Leu Pro Lys Val Leu His Lys Arg
                 85                  90                  95

Thr Leu Gly Leu Ser Ala Met Ser Thr Thr Asp Leu Glu Ala Tyr Phe
            100                 105                 110

Lys Asp Cys Leu Phe Lys Asp Trp Glu Glu Leu Gly Glu Glu Ile Arg
                115                 120                 125

Leu Lys Val Phe Val Leu Gly Gly Cys Arg His Lys Leu Val Cys Ser
    130                 135                 140

Pro Ala Pro Cys Asn Phe Phe Thr Ser Ala
145                 150

<210> SEQ ID NO 24
<211> LENGTH: 154
<212> TYPE: PRT
<213> ORGANISM: Hepatitis B Virus

<400> SEQUENCE: 24

Met Ala Ala Arg Met Cys Cys Gln Leu Asp Pro Ala Arg Asp Val Leu
 1               5                  10                  15

Cys Leu Arg Pro Val Gly Ala Glu Ser Arg Gly Arg Pro Val Ser Gly
            20                  25                  30

Pro Phe Gly Pro Leu Pro Ser Pro Ser Ser Ala Val Pro Ala Asp
            35                  40                  45

His Gly Ala His Leu Ser Leu Arg Gly Leu Pro Val Cys Ala Phe Ser
     50                  55                  60

Ser Ala Gly Pro Cys Ala Leu Arg Phe Thr Ser Ala Arg Arg Met Glu
 65                  70                  75                  80

Thr Thr Val Asn Ala His Gln Val Leu Pro Lys Val Leu Tyr Lys Arg
                 85                  90                  95

Thr Leu Gly Leu Ser Ala Met Ser Thr Thr Asp Leu Glu Ala Tyr Phe
            100                 105                 110

Lys Asp Cys Leu Phe Lys Asp Trp Glu Glu Leu Gly Glu Glu Ile Arg
                115                 120                 125

Leu Met Ile Phe Val Leu Gly Gly Cys Arg His Lys Leu Val Cys Ser
    130                 135                 140

Pro Ala Pro Cys Asn Phe Phe Thr Ser Ala
145                 150

<210> SEQ ID NO 25
<211> LENGTH: 154
<212> TYPE: PRT
<213> ORGANISM: Hepatitis B Virus

<400> SEQUENCE: 25

Met Ala Ala Arg Leu Cys Cys Gln Leu Asp Pro Ala Arg Asp Val Leu
 1               5                  10                  15

Cys Leu Arg Pro Val Gly Ala Glu Ser Arg Gly Arg Pro Val Ser Gly
            20                  25                  30
```

```
Pro Phe Gly Pro Leu Pro Ser Pro Ser Ser Ala Val Pro Ala Asp
        35                  40                  45

His Gly Ala His Leu Ser Leu Arg Gly Leu Pro Val Cys Ala Phe Ser
    50                  55                  60

Ser Ala Gly Pro Cys Ala Leu Arg Phe Thr Ser Ala Arg Ser Met Glu
65                  70                  75                  80

Thr Thr Val Asn Ala His Gln Val Leu Pro Lys Val Leu His Lys Arg
                85                  90                  95

Thr Leu Gly Leu Ser Ala Met Ser Thr Thr Asp Leu Glu Ala Tyr Phe
            100                 105                 110

Lys Asp Cys Leu Phe Lys Asp Trp Glu Glu Leu Gly Glu Glu Ile Arg
            115                 120                 125

Leu Lys Val Phe Val Leu Gly Gly Cys Arg His Lys Leu Val Cys Ser
        130                 135                 140

Pro Ala Pro Cys Asn Phe Phe Pro Ser Ala
145                 150
```

<210> SEQ ID NO 26
<211> LENGTH: 154
<212> TYPE: PRT
<213> ORGANISM: Hepatitis B Virus

<400> SEQUENCE: 26

```
Met Ala Ala Arg Leu Cys Cys Gln Leu Asp Pro Thr Arg Asp Val Leu
1               5                   10                  15

Cys Leu Arg Pro Val Gly Ala Glu Ser Arg Gly Arg Pro Val Ser Gly
            20                  25                  30

Pro Leu Gly Asp Leu Pro Ser Pro Ser Ala Ser Pro Val Pro Thr Ile
        35                  40                  45

Asp Arg Ala His Leu Ser Leu Arg Gly Leu Pro Val Cys Ala Phe Ser
    50                  55                  60

Ser Ala Gly Pro Cys Ala Leu Arg Phe Thr Ser Ala Arg Arg Met Glu
65                  70                  75                  80

Thr Thr Val Asn Thr His Met Ile Leu Pro Lys Val Leu His Lys Arg
                85                  90                  95

Thr Leu Gly Leu Pro Ala Met Ser Thr Ile Asp Leu Glu Ala Tyr Phe
            100                 105                 110

Lys Asp Cys Leu Phe Lys Asp Trp Glu Glu Leu Gly Glu Glu Ile Arg
            115                 120                 125

Leu Lys Val Phe Val Leu Gly Gly Cys Arg His Lys Leu Val Cys Ser
        130                 135                 140

Pro Ala Pro Cys Asn Phe Phe Thr Ser Ala
145                 150
```

<210> SEQ ID NO 27
<211> LENGTH: 154
<212> TYPE: PRT
<213> ORGANISM: Hepatitis B Virus

<400> SEQUENCE: 27

```
Met Ala Ala Arg Leu Cys Cys Gln Leu Asp Pro Ala Arg Asp Val Leu
1               5                   10                  15

Cys Leu Arg Pro Val Gly Ala Glu Ser Arg Gly Arg Pro Phe Ser Gly
            20                  25                  30

Pro Leu Gly Thr Leu Pro Ser Pro Ser Ser Ala Val Pro Ala Asp
        35                  40                  45
```

-continued

His Gly Ala His Leu Ser Leu Arg Gly Leu Pro Val Cys Ala Phe Ser
        50                  55                  60

Ser Ala Gly Pro Cys Ala Leu Arg Phe Thr Phe Ala Arg Arg Met Glu
65                  70                  75                  80

Thr Thr Val Asn Ala His Gln Val Leu Pro Lys Val Leu His Lys Arg
                85                  90                  95

Thr Leu Gly Leu Ser Ala Met Ser Thr Thr Asp Leu Glu Ala Tyr Phe
                100                 105                 110

Lys Asp Cys Val Phe Lys Asp Trp Glu Glu Leu Gly Glu Glu Ile Arg
            115                 120                 125

Leu Lys Val Phe Val Leu Gly Gly Cys Arg His Lys Leu Val Cys Ser
        130                 135                 140

Pro Ala Pro Cys Asn Phe Phe Thr Ser Ala
145                 150

<210> SEQ ID NO 28
<211> LENGTH: 154
<212> TYPE: PRT
<213> ORGANISM: Hepatitis B Virus

<400> SEQUENCE: 28

Met Ala Ala Arg Leu Cys Cys Gln Leu Asp Pro Ala Arg Asp Val Leu
1               5                   10                  15

Cys Leu Arg Pro Val Gly Ala Glu Ser Arg Gly Arg Pro Phe Ser Gly
            20                  25                  30

Pro Leu Gly Thr Leu Ser Ser Pro Ser Pro Ser Ala Val Ser Thr Asp
        35                  40                  45

His Gly Ala His Leu Ser Leu Arg Gly Leu Pro Val Cys Ala Phe Ser
        50                  55                  60

Ser Ala Gly Pro Cys Ala Leu Arg Phe Thr Ser Ala Arg Arg Met Glu
65                  70                  75                  80

Thr Thr Val Asn Ala His Gln Phe Leu Pro Lys Val Leu His Lys Arg
                85                  90                  95

Thr Leu Gly Leu Ser Val Met Ser Thr Thr Asp Leu Glu Ala Tyr Phe
                100                 105                 110

Lys Asp Cys Leu Phe Lys Asp Trp Glu Glu Ser Gly Glu Glu Ile Arg
            115                 120                 125

Leu Met Ile Phe Val Leu Gly Gly Cys Arg His Lys Leu Val Cys Ala
        130                 135                 140

Pro Ala Pro Cys Asn Phe Phe Thr Ser Ala
145                 150

<210> SEQ ID NO 29
<211> LENGTH: 154
<212> TYPE: PRT
<213> ORGANISM: Hepatitis B Virus

<400> SEQUENCE: 29

Met Ala Ala Arg Leu Cys Cys Gln Leu Asp Pro Ala Arg Asp Val Leu
1               5                   10                  15

Cys Leu Arg Pro Val Gly Ala Glu Ser Arg Gly Arg Pro Phe Ser Gly
            20                  25                  30

Pro Phe Gly Thr Leu Ser Ser Pro Ser Pro Ser Ala Val Ser Thr Asp
        35                  40                  45

His Gly Ala His Leu Ser Leu Arg Gly Leu Pro Val Cys Ala Phe Ser
        50                  55                  60

```
Ser Ala Gly Pro Cys Ala Leu Arg Phe Thr Ser Ala Arg Arg Met Glu
 65                  70                  75                  80

Thr Thr Val Asn Ala His Gln Phe Leu Pro Lys Val Leu Tyr Lys Arg
                 85                  90                  95

Thr Leu Gly Leu Ser Val Met Ser Thr Thr Asp Leu Glu Ala Tyr Phe
            100                 105                 110

Lys Asp Cys Leu Phe Lys Asp Trp Glu Glu Leu Gly Glu Glu Thr Arg
            115                 120                 125

Leu Met Ile Phe Val Leu Gly Gly Cys Arg His Lys Leu Val Cys Ala
        130                 135                 140

Pro Ala Pro Cys Asn Phe Phe Thr Ser Ala
145                 150
```

<210> SEQ ID NO 30
<211> LENGTH: 154
<212> TYPE: PRT
<213> ORGANISM: Hepatitis B Virus

<400> SEQUENCE: 30

```
Met Ala Ala Arg Leu Cys Cys Gln Leu Asp Pro Ala Arg Asp Val Leu
 1               5                  10                  15

Cys Leu Arg Pro Val Gly Ala Glu Ser Arg Gly Arg Pro Phe Ser Gly
            20                  25                  30

Pro Leu Gly Ala Leu Ser Ser Ser Pro Pro Ala Val Pro Thr Asp
        35                  40                  45

His Gly Ala His Leu Ser Leu Arg Gly Leu Pro Val Cys Ala Phe Ser
    50                  55                  60

Ser Ala Gly Pro Cys Ala Leu Arg Phe Thr Ser Ala Arg Arg Met Glu
 65                  70                  75                  80

Thr Thr Val Asn Ala His Gln Phe Leu Pro Lys Val Leu His Lys Arg
                 85                  90                  95

Thr Leu Gly Leu Ser Ala Met Ser Thr Thr Asp Leu Glu Ala Tyr Phe
            100                 105                 110

Lys Asp Cys Leu Phe Lys Asp Trp Glu Glu Leu Gly Glu Glu Leu Arg
            115                 120                 125

Leu Lys Val Phe Val Leu Gly Gly Cys Arg His Lys Leu Val Cys Ala
        130                 135                 140

Pro Ala Pro Cys Asn Phe Phe Thr Ser Ala
145                 150
```

<210> SEQ ID NO 31
<211> LENGTH: 154
<212> TYPE: PRT
<213> ORGANISM: Hepatitis B Virus

<400> SEQUENCE: 31

```
Met Ala Ala Arg Leu Cys Cys Gln Leu Asp Pro Ala Arg Asp Val Leu
 1               5                  10                  15

Cys Leu Arg Pro Val Gly Ala Glu Ser Arg Gly Arg Pro Phe Ser Gly
            20                  25                  30

Ser Leu Gly Thr Leu Ser Ser Pro Ser Pro Ser Ala Val Pro Thr Asp
        35                  40                  45

His Gly Ala His Leu Ser Leu Arg Gly Leu Pro Val Cys Ala Phe Ser
    50                  55                  60

Ser Ala Gly Pro Cys Ala Leu Arg Phe Thr Ser Ala Arg Arg Met Glu
 65                  70                  75                  80
```

```
Thr Thr Val Asn Ala His Gln Ile Leu Pro Lys Val Leu His Lys Arg
                85                  90                  95

Thr Leu Gly Leu Ser Ala Met Ser Thr Thr Asp Leu Glu Ala Tyr Phe
            100                 105                 110

Lys Asp Cys Leu Phe Lys Asp Trp Glu Glu Leu Gly Glu Glu Ile Arg
        115                 120                 125

Leu Lys Val Phe Val Leu Gly Gly Cys Arg His Lys Leu Val Cys Ala
    130                 135                 140

Pro Ala Pro Cys Asn Phe Phe Thr Ser Ala
145                 150

<210> SEQ ID NO 32
<211> LENGTH: 154
<212> TYPE: PRT
<213> ORGANISM: Hepatitis B Virus

<400> SEQUENCE: 32

Met Ala Ala Arg Leu Cys Cys Gln Leu Asp Pro Ala Arg Asp Val Leu
1               5                   10                  15

Cys Leu Arg Pro Val Gly Ala Glu Ser Arg Gly Arg Pro Phe Ser Gly
            20                  25                  30

Pro Leu Gly Thr Leu Ser Ser Pro Ser Leu Ser Ala Val Ser Thr Asp
        35                  40                  45

His Gly Ala His Leu Ser Leu Arg Gly Leu Pro Val Cys Ala Phe Ser
    50                  55                  60

Ser Ala Gly Pro Cys Ala Leu Arg Phe Thr Ser Ala Arg Arg Met Glu
65                  70                  75                  80

Thr Thr Val Asn Ala His Gln Ile Leu Pro Lys Val Leu His Lys Arg
                85                  90                  95

Thr Leu Gly Leu Pro Ala Met Ser Thr Thr Asp Leu Glu Ala Tyr Phe
            100                 105                 110

Lys Asp Cys Val Phe Lys Asp Trp Glu Glu Leu Gly Glu Glu Ile Arg
        115                 120                 125

Leu Lys Val Phe Val Leu Gly Gly Cys Arg His Lys Leu Val Cys Ala
    130                 135                 140

Pro Ala Pro Cys Asn Phe Phe Thr Ser Ala
145                 150

<210> SEQ ID NO 33
<211> LENGTH: 154
<212> TYPE: PRT
<213> ORGANISM: Hepatitis B Virus

<400> SEQUENCE: 33

Met Ala Ala Arg Leu Cys Cys Gln Leu Asp Pro Ala Arg Asp Val Leu
1               5                   10                  15

Cys Leu Arg Pro Val Gly Ala Glu Ser Arg Gly Arg Pro Val Ser Gly
            20                  25                  30

Pro Leu Gly Ser Leu Ser Ser Ser Ser Pro Ser Ala Val Pro Thr Asp
        35                  40                  45

His Gly Ala His Leu Ser Leu Arg Gly Leu Pro Val Cys Ala Phe Ser
    50                  55                  60

Ser Ala Gly Pro Cys Ala Leu Arg Phe Thr Ser Ala Arg Arg Met Glu
65                  70                  75                  80

Thr Thr Val Asn Ala His Gln Ile Leu Pro Lys Ile Leu His Lys Arg
                85                  90                  95
```

```
Thr Leu Gly Leu Ser Thr Met Ser Thr Thr Asp Leu Glu Ala Tyr Phe
                100                 105                 110

Lys Asp Cys Leu Phe Lys Asp Trp Glu Glu Leu Gly Glu Glu Ile Arg
            115                 120                 125

Leu Lys Val Phe Val Leu Gly Gly Cys Arg His Lys Leu Val Cys Ala
        130                 135                 140

Pro Ala Pro Cys Asn Phe Phe Thr Ser Ala
145                 150

<210> SEQ ID NO 34
<211> LENGTH: 154
<212> TYPE: PRT
<213> ORGANISM: Hepatitis B Virus

<400> SEQUENCE: 34

Met Ala Ala Arg Leu Cys Cys Gln Leu Asp Pro Ala Arg Asp Val Leu
1               5                   10                  15

Cys Leu Arg Pro Val Ser Ala Glu Ser Cys Gly Arg Ser Val Ser Gly
            20                  25                  30

Ser Leu Gly Asp Leu Ser Ser Pro Ser Pro Ser Ala Val Pro Ala Asp
        35                  40                  45

His Gly Ala His Leu Ser Leu Arg Gly Leu Pro Val Cys Ala Phe Ser
    50                  55                  60

Ser Ala Gly Pro Cys Ala Leu Arg Phe Thr Ser Ala Arg Arg Met Glu
65                  70                  75                  80

Thr Thr Val Asn Ala His Gln Ile Leu Pro Lys Val Leu His Lys Arg
                85                  90                  95

Thr Leu Gly Leu Ser Ala Met Ser Thr Thr Asp Leu Glu Ala Tyr Phe
                100                 105                 110

Lys Ala Cys Leu Phe Lys Asp Trp Glu Glu Leu Gly Glu Glu Ile Arg
            115                 120                 125

Leu Lys Ile Phe Val Leu Gly Gly Cys Arg His Lys Leu Val Cys Ala
        130                 135                 140

Pro Ala Pro Cys Asn Phe Phe Thr Ser Ala
145                 150

<210> SEQ ID NO 35
<211> LENGTH: 154
<212> TYPE: PRT
<213> ORGANISM: Hepatitis B Virus

<400> SEQUENCE: 35

Met Ala Ala Arg Leu Cys Cys Gln Leu Asp Pro Ala Arg Asp Val Leu
1               5                   10                  15

Cys Leu Arg Pro Val Gly Ala Glu Ser Cys Gly Arg Pro Val Ser Gly
            20                  25                  30

Ser Leu Gly Gly Leu Ser Ser Pro Ser Pro Ser Ala Val Pro Ala Asp
        35                  40                  45

His Gly Ala His Leu Ser Leu Arg Gly Leu Pro Val Cys Ala Phe Ser
    50                  55                  60

Ser Ala Gly Pro Cys Ala Leu Arg Phe Thr Ser Ala Arg Arg Met Glu
65                  70                  75                  80

Thr Thr Val Asn Ala His Gln Ile Leu Pro Lys Val Leu His Lys Arg
                85                  90                  95

Thr Leu Gly Leu Ser Ala Met Ser Thr Thr Asp Leu Glu Ala Tyr Phe
                100                 105                 110
```

```
Lys Asp Cys Leu Phe Lys Asp Trp Glu Glu Leu Gly Glu Glu Ile Arg
        115                 120                 125

Leu Lys Val Phe Val Leu Gly Gly Cys Arg His Lys Leu Val Cys Val
    130                 135                 140

Pro Ala Pro Cys Asn Phe Phe Thr Ser Ala
145                 150

<210> SEQ ID NO 36
<211> LENGTH: 154
<212> TYPE: PRT
<213> ORGANISM: Hepatitis B Virus

<400> SEQUENCE: 36

Met Ala Ala Arg Leu Cys Cys Gln Leu Asp Pro Ala Arg Asp Val Leu
1               5                   10                  15

Cys Leu Arg Pro Val Ser Ala Glu Ser Cys Gly Arg Pro Val Ser Gly
            20                  25                  30

Ser Leu Gly Asp Leu Ser Ser Pro Ser Pro Ser Ala Val Pro Ala Asp
        35                  40                  45

His Gly Ala His Leu Ser Leu Arg Gly Leu Pro Val Cys Ala Phe Ser
50                  55                  60

Ser Ala Gly Pro Cys Ala Leu Arg Phe Thr Ser Ala Arg Arg Met Glu
65                  70                  75                  80

Thr Thr Val Asn Ala His Gln Ile Leu Pro Lys Val Leu His Lys Arg
                85                  90                  95

Thr Leu Gly Leu Ser Ala Met Ser Thr Thr Asp Leu Glu Ala Tyr Phe
            100                 105                 110

Lys Asp Cys Leu Phe Lys Asp Trp Glu Glu Leu Gly Glu Glu Ile Arg
        115                 120                 125

Leu Lys Val Phe Val Leu Gly Gly Cys Arg His Lys Leu Val Cys Ala
    130                 135                 140

Pro Ala Pro Cys Asn Phe Phe Thr Ser Ala
145                 150

<210> SEQ ID NO 37
<211> LENGTH: 154
<212> TYPE: PRT
<213> ORGANISM: Hepatitis B Virus

<400> SEQUENCE: 37

Met Ala Ala Arg Leu Cys Cys Gln Leu Asp Pro Ala Arg Asp Val Leu
1               5                   10                  15

Cys Leu Arg Pro Val Gly Ala Glu Ser Arg Gly Arg Ser Leu Ser Gly
            20                  25                  30

Ser Leu Gly Ala Val Ser Pro Pro Ser Pro Ser Ala Val Pro Ala Asn
        35                  40                  45

Asp Gly Ser His Leu Ser Leu Arg Gly Leu Pro Val Cys Ser Phe Ser
50                  55                  60

Ser Ala Gly Pro Cys Ala Leu Arg Phe Thr Ser Ala Arg Arg Met Glu
65                  70                  75                  80

Thr Thr Val Asn Ala Pro Arg Ser Leu Pro Thr Val Leu His Lys Arg
                85                  90                  95

Thr Leu Gly Leu Ser Gly Arg Ser Met Thr Trp Ile Glu Asp Tyr Ile
            100                 105                 110

Lys Asp Cys Val Phe Lys Asp Trp Glu Glu Leu Gly Glu Glu Ile Arg
        115                 120                 125
```

Leu Lys Val Phe Val Leu Gly Gly Cys Arg His Lys Leu Val Cys Ser
            130                 135                 140

Pro Ala Pro Cys Asn Phe Phe Thr Ser Ala
145                 150

<210> SEQ ID NO 38
<211> LENGTH: 154
<212> TYPE: PRT
<213> ORGANISM: Hepatitis B virus

<400> SEQUENCE: 38

Met Ala Ala Arg Met Cys Cys Gln Leu Asp Pro Ala Arg Asp Val Leu
1               5                   10                  15

Cys Leu Arg Pro Val Gly Ala Glu Ser Arg Gly Arg Pro Leu Pro Gly
            20                  25                  30

Pro Leu Gly Ala Leu Pro Pro Ser Ala Ser Ala Val Pro Ala Asp
        35                  40                  45

His Gly Ser His Leu Ser Leu Arg Gly Leu Pro Val Cys Ser Phe Ser
    50                  55                  60

Ser Ala Gly Pro Cys Ala Leu Arg Phe Thr Ser Ala Arg Arg Met Glu
65                  70                  75                  80

Thr Thr Val Asn Ala Pro Trp Ser Leu Pro Thr Val Leu His Lys Arg
                85                  90                  95

Thr Ile Gly Leu Ser Gly Arg Ser Met Thr Trp Ile Glu Glu Tyr Ile
            100                 105                 110

Lys Asp Cys Val Phe Lys Asp Trp Glu Glu Leu Gly Glu Glu Ile Arg
        115                 120                 125

Leu Lys Val Phe Val Leu Gly Gly Cys Arg His Lys Leu Val Cys Ser
    130                 135                 140

Pro Ala Pro Cys Asn Phe Phe Thr Ser Ala
145                 150

<210> SEQ ID NO 39
<211> LENGTH: 154
<212> TYPE: PRT
<213> ORGANISM: Hepatitis B Virus

<400> SEQUENCE: 39

Met Ala Ala Arg Met Cys Cys Lys Leu Asp Pro Ala Arg Asp Val Leu
1               5                   10                  15

Cys Leu Arg Pro Ile Gly Ala Glu Ser Arg Gly Arg Pro Leu Pro Gly
            20                  25                  30

Pro Leu Gly Ala Val Pro Pro Ser Pro Ser Ala Val Pro Ala Asp
        35                  40                  45

Asp Gly Ser His Leu Ser Leu Arg Gly Leu Pro Val Cys Ser Phe Ser
    50                  55                  60

Ser Ala Gly Pro Cys Ala Leu Arg Phe Thr Ser Ala Arg Arg Met Glu
65                  70                  75                  80

Thr Thr Val Asn Ala Pro Trp Ser Leu Pro Thr Val Leu His Lys Arg
                85                  90                  95

Thr Leu Gly Leu Ser Gly Trp Ser Met Thr Trp Ile Glu Glu Tyr Ile
            100                 105                 110

Lys Asp Cys Val Phe Lys Asp Trp Glu Glu Leu Gly Glu Glu Ile Arg
        115                 120                 125

Leu Lys Val Phe Val Leu Gly Gly Cys Arg His Lys Leu Val Cys Ser
    130                 135                 140

```
Pro Ala Pro Cys Asn Phe Phe Thr Ser Ala
145                 150

<210> SEQ ID NO 40
<211> LENGTH: 154
<212> TYPE: PRT
<213> ORGANISM: Hepatitis B Virus

<400> SEQUENCE: 40

Met Ala Ala Arg Leu Cys Cys Gln Leu Asp Pro Ala Arg Asp Val Leu
1               5                   10                  15

Cys Leu Arg Pro Val Gly Ala Glu Ser Ser Gly Arg Thr Leu Pro Gly
            20                  25                  30

Ser Leu Gly Ala Val Pro Pro Ser Ser Ser Ala Val Pro Ala Asp
        35                  40                  45

Asn Gly Ser His Leu Ser Leu Arg Gly Leu Pro Val Cys Ser Phe Ser
        50                  55                  60

Ser Ala Gly Pro Cys Ala Leu Arg Phe Thr Ser Ala Arg Arg Met Glu
65                  70                  75                  80

Thr Thr Val Asn Ala Pro Trp Ser Leu Pro Thr Val Leu His Lys Arg
                85                  90                  95

Thr Leu Gly Leu Ser Gly Arg Ser Met Thr Trp Ile Glu Asp Tyr Ile
            100                 105                 110

Lys Asp Cys Val Phe Lys Asp Trp Glu Glu Leu Gly Glu Glu Ile Arg
            115                 120                 125

Leu Lys Val Phe Val Leu Gly Gly Cys Arg His Lys Leu Val Cys Ser
    130                 135                 140

Pro Ala Pro Cys Asn Phe Phe Thr Ser Ala
145                 150

<210> SEQ ID NO 41
<211> LENGTH: 154
<212> TYPE: PRT
<213> ORGANISM: Hepatitis B Virus

<400> SEQUENCE: 41

Met Ala Ala Arg Leu Cys Cys Gln Leu Asp Pro Ser Arg Asp Val Leu
1               5                   10                  15

Cys Leu Arg Pro Val Ser Ala Glu Ser Ser Gly Arg Pro Leu Pro Gly
            20                  25                  30

Pro Phe Gly Ala Leu Ser Pro Ser Pro Ser Ala Val Pro Ala Asp
        35                  40                  45

His Gly Ala His Leu Ser Leu Arg Gly Leu Pro Val Cys Ser Phe Ser
        50                  55                  60

Ser Ala Gly Pro Cys Ala Leu Arg Phe Thr Ser Ala Arg Tyr Met Glu
65                  70                  75                  80

Thr Ala Met Asn Thr Ser His His Leu Pro Arg Gln Leu Tyr Lys Trp
                85                  90                  95

Thr Leu Gly Leu Phe Val Met Ser Thr Thr Gly Val Glu Lys Tyr Phe
            100                 105                 110

Lys Asp Cys Val Phe Ala Glu Trp Glu Glu Leu Gly Asn Glu Ser Arg
            115                 120                 125

Leu Met Thr Phe Val Leu Gly Gly Cys Arg His Lys Leu Val Cys Ala
    130                 135                 140

Pro Ala Pro Cys Asn Phe Phe Thr Ser Ala
145                 150
```

<210> SEQ ID NO 42
<211> LENGTH: 154
<212> TYPE: PRT
<213> ORGANISM: Hepatitis B Virus

<400> SEQUENCE: 42

```
Met Ala Ala Arg Leu Cys Cys Gln Leu Asp Pro Ala Arg Asp Val Leu
1               5                   10                  15

Cys Leu Arg Pro Val Gly Ala Glu Ser Cys Gly Arg Pro Leu Ser Trp
            20                  25                  30

Ser Leu Gly Ala Leu Pro Pro Ser Ser Pro Ala Val Pro Ala Asp
        35                  40                  45

Asp Gly Ser His Leu Ser Leu Arg Gly Leu Pro Ala Cys Ala Phe Ser
        50                  55                  60

Ser Ala Gly Pro Cys Ala Leu Arg Phe Thr Ser Ala Arg Arg Met Glu
65                  70                  75                  80

Thr Thr Val Asn Ala Pro Trp Asn Leu Pro Thr Thr Leu His Lys Arg
                85                  90                  95

Thr Leu Gly Leu Ser Pro Arg Ser Thr Thr Trp Ile Glu Glu Tyr Ile
            100                 105                 110

Lys Asp Cys Val Phe Lys Asp Trp Glu Glu Ser Gly Glu Glu Leu Arg
            115                 120                 125

Leu Lys Val Phe Val Leu Gly Gly Cys Arg His Lys Leu Val Cys Ser
        130                 135                 140

Pro Ala Pro Cys Asn Phe Phe Thr Ser Ala
145                 150
```

<210> SEQ ID NO 43
<211> LENGTH: 154
<212> TYPE: PRT
<213> ORGANISM: Hepatitis B Virus

<400> SEQUENCE: 43

```
Met Ala Ala Arg Leu Cys Cys Gln Leu Asp Pro Ala Arg Asp Val Leu
1               5                   10                  15

Cys Leu Arg Pro Val Gly Ala Glu Ser Cys Gly Arg Pro Leu Ser Trp
            20                  25                  30

Ser Pro Gly Ala Leu Pro Pro Ser Pro Ser Val Pro Ala Asp
        35                  40                  45

Asp Arg Ala His Leu Ser Leu Arg Gly Leu Pro Ala Cys Ala Phe Ser
        50                  55                  60

Ser Ala Gly Pro Cys Ala Leu Arg Phe Thr Ser Ala Arg Arg Met Glu
65                  70                  75                  80

Thr Thr Val Asn Ala Pro Gln Ser Leu Pro Thr Pro Leu His Lys Arg
                85                  90                  95

Thr Leu Gly Leu Ser Pro Arg Ser Thr Thr Trp Ile Glu Glu Tyr Ile
            100                 105                 110

Lys Asp Cys Val Phe Lys Asp Trp Glu Glu Ser Gly Glu Glu Leu Arg
            115                 120                 125

Leu Lys Val Phe Val Leu Gly Gly Cys Arg His Lys Leu Val Cys Ser
        130                 135                 140

Pro Ala Pro Cys Asn Phe Phe Thr Ser Ala
145                 150
```

<210> SEQ ID NO 44

```
<211> LENGTH: 154
<212> TYPE: PRT
<213> ORGANISM: Hepatitis B Virus

<400> SEQUENCE: 44

Met Ala Ala Arg Leu Cys Cys Gln Leu Asp Pro Ala Arg Asp Val Leu
1               5                   10                  15

Cys Leu Arg Pro Val Gly Ala Glu Ser Cys Gly Arg Pro Leu Ser Trp
                20                  25                  30

Ser Pro Gly Ala Leu Pro Pro Ser Pro Pro Ser Val Pro Ala Asp
                35                  40                  45

Asp Gly Ser His Leu Ser Leu Arg Gly Leu Pro Ala Cys Ala Phe Ser
    50                  55                  60

Ser Ala Gly Pro Cys Ala Leu Arg Phe Thr Ser Ala Arg Arg Met Glu
65                  70                  75                  80

Thr Thr Val Asn Ala Pro Gln Ser Leu Pro Thr Thr Leu His Lys Arg
                    85                  90                  95

Thr Leu Gly Leu Ser Pro Arg Ser Thr Thr Trp Ile Glu Glu Tyr Ile
                100                 105                 110

Lys Asp Cys Val Phe Lys Asp Trp Glu Glu Ser Gly Glu Glu Leu Arg
                115                 120                 125

Leu Lys Val Phe Val Leu Gly Gly Cys Arg His Lys Leu Val Cys Ser
    130                 135                 140

Pro Ala Pro Cys Asn Phe Phe Thr Ser Ala
145                 150

<210> SEQ ID NO 45
<211> LENGTH: 154
<212> TYPE: PRT
<213> ORGANISM: Artificial sequence Sequence
<220> FEATURE:
<223> OTHER INFORMATION: Consensus aa sequence of Hepatitis B virus X
      protein

<400> SEQUENCE: 45

Met Ala Ala Arg Leu Cys Cys Gln Leu Asp Pro Ala Arg Asp Val Leu
1               5                   10                  15

Cys Leu Arg Pro Val Gly Ala Glu Ser Arg Gly Arg Pro Leu Ser Gly
                20                  25                  30

Pro Leu Gly Ala Leu Pro Ser Pro Ser Pro Ser Ala Val Pro Ala Asp
                35                  40                  45

His Gly Ala His Leu Ser Leu Arg Gly Leu Pro Val Cys Ala Phe Ser
    50                  55                  60

Ser Ala Gly Pro Cys Ala Leu Arg Phe Thr Ser Ala Arg Arg Met Glu
65                  70                  75                  80

Thr Thr Val Asn Ala His Gln Ile Leu Pro Lys Val Leu His Lys Arg
                    85                  90                  95

Thr Leu Gly Leu Ser Ala Met Ser Thr Thr Asp Leu Glu Ala Tyr Phe
                100                 105                 110

Lys Asp Cys Val Phe Lys Asp Trp Glu Glu Leu Gly Glu Glu Ile Arg
                115                 120                 125

Leu Lys Val Phe Val Leu Gly Gly Cys Arg His Lys Leu Val Cys Ser
    130                 135                 140

Pro Ala Pro Cys Asn Phe Phe Thr Ser Ala
145                 150

<210> SEQ ID NO 46
```

```
<400> SEQUENCE: 46

000

<210> SEQ ID NO 47

<400> SEQUENCE: 47

000

<210> SEQ ID NO 48

<400> SEQUENCE: 48

000

<210> SEQ ID NO 49

<400> SEQUENCE: 49

000

<210> SEQ ID NO 50

<400> SEQUENCE: 50

000

<210> SEQ ID NO 51
<211> LENGTH: 30
<212> TYPE: PRT
<213> ORGANISM: Artificial sequence
<220> FEATURE:
<223> OTHER INFORMATION: HBV Polymerase aa 1 - 30  (SLP No. 1)

<400> SEQUENCE: 51

Met Pro Leu Ser Tyr Gln His Phe Arg Lys Leu Leu Leu Leu Asp Asp
1               5                   10                  15

Gly Thr Glu Ala Gly Pro Leu Glu Glu Glu Leu Pro Arg Leu
            20                  25                  30

<210> SEQ ID NO 52
<211> LENGTH: 35
<212> TYPE: PRT
<213> ORGANISM: Artificial sequence
<220> FEATURE:
<223> OTHER INFORMATION: HBV Polymerase aa 52 - 86  (SLP No. 2)

<400> SEQUENCE: 52

Ile Pro Trp Thr His Lys Val Gly Asn Phe Thr Gly Leu Tyr Ser Ser
1               5                   10                  15

Thr Val Pro Ile Phe Asn Pro Glu Trp Gln Thr Pro Ser Phe Pro Lys
            20                  25                  30

Ile His Leu
        35

<210> SEQ ID NO 53
<211> LENGTH: 33
<212> TYPE: PRT
<213> ORGANISM: Artificial sequence
<220> FEATURE:
<223> OTHER INFORMATION: HBV Polymerase aa 103 - 135  (SLP No. 3)

<400> SEQUENCE: 53

Val Asn Glu Lys Arg Arg Leu Lys Leu Ile Met Pro Ala Arg Phe Tyr
```

```
1               5                   10                  15
Pro Thr His Thr Lys Tyr Leu Pro Leu Asp Lys Gly Ile Lys Pro Tyr
            20                  25                  30
Tyr

<210> SEQ ID NO 54
<211> LENGTH: 33
<212> TYPE: PRT
<213> ORGANISM: Artificial sequence
<220> FEATURE:
<223> OTHER INFORMATION: HBV Polymerase aa 118 - 150  (SLP No. 4)

<400> SEQUENCE: 54

Tyr Pro Thr His Thr Lys Tyr Leu Pro Leu Asp Lys Gly Ile Lys Pro
1               5                   10                  15
Tyr Tyr Pro Asp Gln Val Val Asn His Tyr Phe Gln Thr Arg His Tyr
            20                  25                  30
Leu

<210> SEQ ID NO 55
<211> LENGTH: 39
<212> TYPE: PRT
<213> ORGANISM: Artificial sequence
<220> FEATURE:
<223> OTHER INFORMATION: HBV Polymerase aa 139 - 177  (SLP No. 5)

<400> SEQUENCE: 55

Val Val Asn His Tyr Phe Gln Thr Arg His Tyr Leu His Thr Leu Trp
1               5                   10                  15
Lys Ala Gly Ile Leu Tyr Lys Arg Glu Thr Thr Arg Ser Ala Ser Phe
            20                  25                  30
Cys Gly Ser Pro Tyr Ser Trp
        35

<210> SEQ ID NO 56
<211> LENGTH: 35
<212> TYPE: PRT
<213> ORGANISM: Artificial sequence
<220> FEATURE:
<223> OTHER INFORMATION: HBV Polymerase aa 143 - 177  (SLP No. 6)

<400> SEQUENCE: 56

Tyr Phe Gln Thr Arg His Tyr Leu His Thr Leu Trp Lys Ala Gly Ile
1               5                   10                  15
Leu Tyr Lys Arg Glu Thr Thr Arg Ser Ala Ser Phe Cys Gly Ser Pro
            20                  25                  30
Tyr Ser Trp
        35

<210> SEQ ID NO 57
<211> LENGTH: 34
<212> TYPE: PRT
<213> ORGANISM: Artificial sequence
<220> FEATURE:
<223> OTHER INFORMATION: HBV Polymerase aa 137 - 170  (SLP No. 7)

<400> SEQUENCE: 57

Asp Gln Val Val Asn His Tyr Phe Gln Thr Arg His Tyr Leu His Thr
1               5                   10                  15
Leu Trp Lys Ala Gly Ile Leu Tyr Lys Arg Glu Thr Thr Arg Ser Ala
            20                  25                  30
```

Ser Phe

<210> SEQ ID NO 58
<211> LENGTH: 32
<212> TYPE: PRT
<213> ORGANISM: Artificial sequence
<220> FEATURE:
<223> OTHER INFORMATION: HBV Polymerase aa 316 - 347  (SLP No. 8)

<400> SEQUENCE: 58

Ser Gln Ser Gln Gly Ser Val Ser Ser Cys Trp Trp Leu Gln Phe Arg
1               5                   10                  15

Asn Ser Lys Pro Cys Ser Glu Tyr Cys Leu Ser His Leu Val Asn Leu
            20                  25                  30

<210> SEQ ID NO 59
<211> LENGTH: 33
<212> TYPE: PRT
<213> ORGANISM: Artificial sequence
<220> FEATURE:
<223> OTHER INFORMATION: HBV Polymerase aa 385 - 417  (SLP No. 9)

<400> SEQUENCE: 59

Thr Ala Glu Ser Arg Leu Val Val Asp Phe Ser Gln Phe Ser Arg Gly
1               5                   10                  15

Ile Ser Arg Val Ser Trp Pro Lys Phe Ala Val Pro Asn Leu Gln Ser
            20                  25                  30

Leu

<210> SEQ ID NO 60
<211> LENGTH: 38
<212> TYPE: PRT
<213> ORGANISM: Artificial sequence
<220> FEATURE:
<223> OTHER INFORMATION: HBV Polymerase aa 419 - 456  (SLP No. 10)

<400> SEQUENCE: 60

Asn Leu Leu Ser Ser Asn Leu Ser Trp Leu Ser Leu Asp Val Ser Ala
1               5                   10                  15

Ala Phe Tyr His Ile Pro Leu His Pro Ala Ala Met Pro His Leu Leu
            20                  25                  30

Ile Gly Ser Ser Gly Leu
        35

<210> SEQ ID NO 61
<211> LENGTH: 38
<212> TYPE: PRT
<213> ORGANISM: Artificial sequence
<220> FEATURE:
<223> OTHER INFORMATION: HBV Polymerase aa 422 - 459  (SLP No. 11)

<400> SEQUENCE: 61

Ser Ser Asn Leu Ser Trp Leu Ser Leu Asp Val Ser Ala Ala Phe Tyr
1               5                   10                  15

His Ile Pro Leu His Pro Ala Ala Met Pro His Leu Leu Ile Gly Ser
            20                  25                  30

Ser Gly Leu Ser Arg Tyr
        35

<210> SEQ ID NO 62
<211> LENGTH: 33
<212> TYPE: PRT
<213> ORGANISM: Artificial sequence -continued

```
<220> FEATURE:
<223> OTHER INFORMATION: HBV Polymerase aa 427 - 459  (SLP No. 12)

<400> SEQUENCE: 62

Trp Leu Ser Leu Asp Val Ser Ala Ala Phe Tyr His Ile Pro Leu His
1               5                   10                  15

Pro Ala Ala Met Pro His Leu Leu Ile Gly Ser Ser Gly Leu Ser Arg
            20                  25                  30

Tyr

<210> SEQ ID NO 63
<211> LENGTH: 34
<212> TYPE: PRT
<213> ORGANISM: Artificial sequence
<220> FEATURE:
<223> OTHER INFORMATION: HBV Polymerase aa 481 - 514  (SLP No. 13)

<400> SEQUENCE: 63

His Asp Ser Cys Ser Arg Gln Leu Tyr Val Ser Leu Met Leu Leu Tyr
1               5                   10                  15

Lys Thr Tyr Gly Trp Lys Leu His Leu Tyr Ser His Pro Ile Val Leu
            20                  25                  30

Gly Phe

<210> SEQ ID NO 64
<211> LENGTH: 36
<212> TYPE: PRT
<213> ORGANISM: Artificial sequence
<220> FEATURE:
<223> OTHER INFORMATION: HBV Polymerase aa 524 - 559  (SLP No. 14)

<400> SEQUENCE: 64

Ser Pro Phe Leu Leu Ala Gln Phe Thr Ser Ala Ile Cys Ser Val Val
1               5                   10                  15

Arg Arg Ala Phe Pro His Cys Leu Ala Phe Ser Tyr Met Asp Asp Val
            20                  25                  30

Val Leu Gly Ala
        35

<210> SEQ ID NO 65
<211> LENGTH: 34
<212> TYPE: PRT
<213> ORGANISM: Artificial sequence
<220> FEATURE:
<223> OTHER INFORMATION: HBV Polymerase aa 526 - 559  (SLP No. 15)

<400> SEQUENCE: 65

Phe Leu Leu Ala Gln Phe Thr Ser Ala Ile Cys Ser Val Val Arg Arg
1               5                   10                  15

Ala Phe Pro His Cys Leu Ala Phe Ser Tyr Met Asp Asp Val Val Leu
            20                  25                  30

Gly Ala

<210> SEQ ID NO 66
<211> LENGTH: 34
<212> TYPE: PRT
<213> ORGANISM: Artificial sequence
<220> FEATURE:
<223> OTHER INFORMATION: HBV Polymerase aa 565 - 598  (SLP No. 16)

<400> SEQUENCE: 66

Arg Glu Ser Leu Tyr Thr Ala Val Thr Asn Phe Leu Leu Ser Leu Gly
```

```
                1               5                  10                  15
Ile His Leu Asn Pro Asn Lys Thr Lys Arg Trp Gly Tyr Ser Leu Asn
            20                  25                  30

Phe Met

<210> SEQ ID NO 67
<211> LENGTH: 34
<212> TYPE: PRT
<213> ORGANISM: Artificial sequence
<220> FEATURE:
<223> OTHER INFORMATION: HBV Polymerase aa 584 - 617  (SLP No. 17)

<400> SEQUENCE: 67

Asn Pro Asn Lys Thr Lys Arg Trp Gly Tyr Ser Leu Asn Phe Met Gly
1               5                   10                  15

Tyr Ile Ile Gly Ser Trp Gly Thr Leu Pro Gln Asp His Ile Val Gln
            20                  25                  30

Lys Ile

<210> SEQ ID NO 68
<211> LENGTH: 39
<212> TYPE: PRT
<213> ORGANISM: Artificial sequence
<220> FEATURE:
<223> OTHER INFORMATION: HBV Polymerase aa 653 - 691  (SLP No. 18)

<400> SEQUENCE: 68

Tyr Pro Ala Leu Met Pro Leu Tyr Ala Cys Ile Gln Ala Lys Gln Ala
1               5                   10                  15

Phe Thr Phe Ser Pro Thr Tyr Lys Ala Phe Leu Ser Lys Gln Tyr Met
            20                  25                  30

Asn Leu Tyr Pro Val Ala Arg
            35

<210> SEQ ID NO 69
<211> LENGTH: 35
<212> TYPE: PRT
<213> ORGANISM: Artificial sequence
<220> FEATURE:
<223> OTHER INFORMATION: HBV Polymerase aa 657 - 691  (SLP No. 19)

<400> SEQUENCE: 69

Met Pro Leu Tyr Ala Cys Ile Gln Ala Lys Gln Ala Phe Thr Phe Ser
1               5                   10                  15

Pro Thr Tyr Lys Ala Phe Leu Ser Lys Gln Tyr Met Asn Leu Tyr Pro
            20                  25                  30

Val Ala Arg
        35

<210> SEQ ID NO 70
<211> LENGTH: 32
<212> TYPE: PRT
<213> ORGANISM: Artificial sequence
<220> FEATURE:
<223> OTHER INFORMATION: HBV Polymerase aa 715 - 746  (SLP No. 20)

<400> SEQUENCE: 70

Gln Arg Met Arg Gly Thr Phe Val Ala Pro Leu Pro Ile His Thr Ala
1               5                   10                  15

Glu Leu Leu Ala Ala Cys Phe Ala Arg Ser Arg Ser Gly Ala Lys Leu
            20                  25                  30
```

-continued

```
<210> SEQ ID NO 71
<211> LENGTH: 38
<212> TYPE: PRT
<213> ORGANISM: Artificial sequence
<220> FEATURE:
<223> OTHER INFORMATION: HBV Polymerase aa 754 - 791  (SLP No. 21)

<400> SEQUENCE: 71

Val Leu Ser Arg Lys Tyr Thr Ser Phe Pro Trp Leu Leu Gly Cys Thr
1               5                   10                  15

Ala Asn Trp Ile Leu Arg Gly Thr Ser Phe Val Tyr Val Pro Ser Ala
            20                  25                  30

Leu Asn Pro Ala Asp Asp
        35

<210> SEQ ID NO 72
<211> LENGTH: 36
<212> TYPE: PRT
<213> ORGANISM: Artificial sequence
<220> FEATURE:
<223> OTHER INFORMATION: HBV Polymerase aa 757 - 792  (SLP No. 22)

<400> SEQUENCE: 72

Arg Lys Tyr Thr Ser Phe Pro Trp Leu Leu Gly Cys Thr Ala Asn Trp
1               5                   10                  15

Ile Leu Arg Gly Thr Ser Phe Val Tyr Val Pro Ser Ala Leu Asn Pro
            20                  25                  30

Ala Asp Asp Pro
        35

<210> SEQ ID NO 73
<211> LENGTH: 36
<212> TYPE: PRT
<213> ORGANISM: Artificial sequence
<220> FEATURE:
<223> OTHER INFORMATION: HBV Polymerase aa 754 - 789  (SLP No. 23)

<400> SEQUENCE: 73

Val Leu Ser Arg Lys Tyr Thr Ser Phe Pro Trp Leu Leu Gly Cys Thr
1               5                   10                  15

Ala Asn Trp Ile Leu Arg Gly Thr Ser Phe Val Tyr Val Pro Ser Ala
            20                  25                  30

Leu Asn Pro Ala
        35

<210> SEQ ID NO 74
<211> LENGTH: 35
<212> TYPE: PRT
<213> ORGANISM: Artificial sequence
<220> FEATURE:
<223> OTHER INFORMATION: HBV Core aa 107 - 141  (SLP No. 24)

<400> SEQUENCE: 74

Asp Pro Ala Ser Arg Asp Leu Val Val Asn Tyr Val Asn Thr Asn Val
1               5                   10                  15

Gly Leu Lys Ile Arg Gln Leu Leu Trp Phe His Ile Ser Cys Leu Thr
            20                  25                  30

Phe Gly Arg
        35

<210> SEQ ID NO 75
<211> LENGTH: 34
```

```
-continued

<212> TYPE: PRT
<213> ORGANISM: Artificial sequence
<220> FEATURE:
<223> OTHER INFORMATION: HBV Core aa 136 - 169  (SLP No. 25)

<400> SEQUENCE: 75

Cys Leu Thr Phe Gly Arg Glu Thr Val Leu Glu Tyr Leu Val Ser Phe
1               5                   10                  15

Gly Val Trp Ile Arg Thr Pro Pro Ala Tyr Arg Pro Pro Asn Ala Pro
            20                  25                  30

Ile Leu

<210> SEQ ID NO 76
<211> LENGTH: 33
<212> TYPE: PRT
<213> ORGANISM: Artificial sequence
<220> FEATURE:
<223> OTHER INFORMATION: consensus sequence HBV X protein aa 36 - 68
      (SLP No. 26)

<400> SEQUENCE: 76

Ala Leu Pro Ser Pro Ser Pro Ser Ala Val Pro Ala Asp His Gly Ala
1               5                   10                  15

His Leu Ser Leu Arg Gly Leu Pro Val Cys Ala Phe Ser Ser Ala Gly
            20                  25                  30

Pro

<210> SEQ ID NO 77
<211> LENGTH: 35
<212> TYPE: PRT
<213> ORGANISM: Artificial sequence
<220> FEATURE:
<223> OTHER INFORMATION: consensus sequence HBV X protein aa 61 - 95
      (SLP No. 27)

<400> SEQUENCE: 77

Cys Ala Phe Ser Ser Ala Gly Pro Cys Ala Leu Arg Phe Thr Ser Ala
1               5                   10                  15

Arg Arg Met Glu Thr Thr Val Asn Ala His Gln Ile Leu Pro Lys Val
            20                  25                  30

Leu His Lys
        35

<210> SEQ ID NO 78
<211> LENGTH: 35
<212> TYPE: PRT
<213> ORGANISM: Artificial sequence
<220> FEATURE:
<223> OTHER INFORMATION: consensus sequence HBV X protein aa 86 - 120
      (SLP No. 28)

<400> SEQUENCE: 78

His Gln Ile Leu Pro Lys Val Leu His Lys Arg Thr Leu Gly Leu Ser
1               5                   10                  15

Ala Met Ser Thr Thr Asp Leu Glu Ala Tyr Phe Lys Asp Cys Val Phe
            20                  25                  30

Lys Asp Trp
        35

<210> SEQ ID NO 79
<211> LENGTH: 34
<212> TYPE: PRT
<213> ORGANISM: Artificial sequence
```

```
<220> FEATURE:
<223> OTHER INFORMATION: consensus sequence HBV X protein aa 108 - 141
      (SLP No. 29)

<400> SEQUENCE: 79

Leu Glu Ala Tyr Phe Lys Asp Cys Val Phe Lys Asp Trp Glu Glu Leu
1               5                   10                  15

Gly Glu Glu Ile Arg Leu Lys Val Phe Val Leu Gly Gly Cys Arg His
            20                  25                  30

Lys Leu

<210> SEQ ID NO 80
<211> LENGTH: 8
<212> TYPE: PRT
<213> ORGANISM: Artificial sequence
<220> FEATURE:
<223> OTHER INFORMATION: Peptide derived from HBV Polymerase protein

<400> SEQUENCE: 80

Met Pro Leu Ser Tyr Gln His Phe
1               5

<210> SEQ ID NO 81
<211> LENGTH: 9
<212> TYPE: PRT
<213> ORGANISM: Artificial sequence
<220> FEATURE:
<223> OTHER INFORMATION: Peptide derived from HBV Polymerase protein

<400> SEQUENCE: 81

Met Pro Leu Ser Tyr Gln His Phe Arg
1               5

<210> SEQ ID NO 82
<211> LENGTH: 8
<212> TYPE: PRT
<213> ORGANISM: Artificial sequence
<220> FEATURE:
<223> OTHER INFORMATION: Peptide derived from HBV Polymerase protein

<400> SEQUENCE: 82

Pro Leu Ser Tyr Gln His Phe Arg
1               5

<210> SEQ ID NO 83
<211> LENGTH: 10
<212> TYPE: PRT
<213> ORGANISM: Artificial sequence
<220> FEATURE:
<223> OTHER INFORMATION: Peptide derived from HBV Polymerase protein

<400> SEQUENCE: 83

Met Pro Leu Ser Tyr Gln His Phe Arg Lys
1               5                   10

<210> SEQ ID NO 84
<211> LENGTH: 8
<212> TYPE: PRT
<213> ORGANISM: Artificial sequence
<220> FEATURE:
<223> OTHER INFORMATION: Peptide derived from HBV Polymerase protein

<400> SEQUENCE: 84

Leu Ser Tyr Gln His Phe Arg Lys
1               5
```

<210> SEQ ID NO 85
<211> LENGTH: 11
<212> TYPE: PRT
<213> ORGANISM: Artificial sequence
<220> FEATURE:
<223> OTHER INFORMATION: Peptide derived from HBV Polymerase protein

<400> SEQUENCE: 85

Met Pro Leu Ser Tyr Gln His Phe Arg Lys Leu
1               5                   10

<210> SEQ ID NO 86
<211> LENGTH: 9
<212> TYPE: PRT
<213> ORGANISM: Artificial sequence
<220> FEATURE:
<223> OTHER INFORMATION: Peptide derived from HBV Polymerase protein

<400> SEQUENCE: 86

Leu Ser Tyr Gln His Phe Arg Lys Leu
1               5

<210> SEQ ID NO 87
<211> LENGTH: 8
<212> TYPE: PRT
<213> ORGANISM: Artificial sequence
<220> FEATURE:
<223> OTHER INFORMATION: Peptide derived from HBV Polymerase protein

<400> SEQUENCE: 87

Ser Tyr Gln His Phe Arg Lys Leu
1               5

<210> SEQ ID NO 88
<211> LENGTH: 10
<212> TYPE: PRT
<213> ORGANISM: Artificial sequence
<220> FEATURE:
<223> OTHER INFORMATION: Peptide derived from HBV Polymerase protein

<400> SEQUENCE: 88

Leu Ser Tyr Gln His Phe Arg Lys Leu Leu
1               5                   10

<210> SEQ ID NO 89
<211> LENGTH: 9
<212> TYPE: PRT
<213> ORGANISM: Artificial sequence
<220> FEATURE:
<223> OTHER INFORMATION: Peptide derived from HBV Polymerase protein

<400> SEQUENCE: 89

Ser Tyr Gln His Phe Arg Lys Leu Leu
1               5

<210> SEQ ID NO 90
<211> LENGTH: 8
<212> TYPE: PRT
<213> ORGANISM: Artificial sequence
<220> FEATURE:
<223> OTHER INFORMATION: Peptide derived from HBV Polymerase protein

<400> SEQUENCE: 90

Tyr Gln His Phe Arg Lys Leu Leu
1               5

```
<210> SEQ ID NO 91
<211> LENGTH: 11
<212> TYPE: PRT
<213> ORGANISM: Artificial sequence
<220> FEATURE:
<223> OTHER INFORMATION: Peptide derived from HBV Polymerase protein

<400> SEQUENCE: 91

Leu Ser Tyr Gln His Phe Arg Lys Leu Leu Leu
1               5                   10

<210> SEQ ID NO 92
<211> LENGTH: 10
<212> TYPE: PRT
<213> ORGANISM: Artificial sequence
<220> FEATURE:
<223> OTHER INFORMATION: Peptide derived from HBV Polymerase protein

<400> SEQUENCE: 92

Ser Tyr Gln His Phe Arg Lys Leu Leu Leu
1               5                   10

<210> SEQ ID NO 93
<211> LENGTH: 9
<212> TYPE: PRT
<213> ORGANISM: Artificial sequence
<220> FEATURE:
<223> OTHER INFORMATION: Peptide derived from HBV Polymerase protein

<400> SEQUENCE: 93

Tyr Gln His Phe Arg Lys Leu Leu Leu
1               5

<210> SEQ ID NO 94
<211> LENGTH: 8
<212> TYPE: PRT
<213> ORGANISM: Artificial sequence
<220> FEATURE:
<223> OTHER INFORMATION: Peptide derived from HBV Polymerase protein

<400> SEQUENCE: 94

Gln His Phe Arg Lys Leu Leu Leu
1               5

<210> SEQ ID NO 95
<211> LENGTH: 11
<212> TYPE: PRT
<213> ORGANISM: Artificial sequence
<220> FEATURE:
<223> OTHER INFORMATION: Peptide derived from HBV Polymerase protein

<400> SEQUENCE: 95

Ser Tyr Gln His Phe Arg Lys Leu Leu Leu Leu
1               5                   10

<210> SEQ ID NO 96
<211> LENGTH: 10
<212> TYPE: PRT
<213> ORGANISM: Artificial sequence
<220> FEATURE:
<223> OTHER INFORMATION: Peptide derived from HBV Polymerase protein

<400> SEQUENCE: 96

Tyr Gln His Phe Arg Lys Leu Leu Leu Leu
1               5                   10

<210> SEQ ID NO 97
```

-continued

```
<211> LENGTH: 9
<212> TYPE: PRT
<213> ORGANISM: Artificial sequence
<220> FEATURE:
<223> OTHER INFORMATION: Peptide derived from HBV Polymerase protein

<400> SEQUENCE: 97

Gln His Phe Arg Lys Leu Leu Leu Leu
1               5

<210> SEQ ID NO 98
<211> LENGTH: 8
<212> TYPE: PRT
<213> ORGANISM: Artificial sequence
<220> FEATURE:
<223> OTHER INFORMATION: Peptide derived from HBV Polymerase protein

<400> SEQUENCE: 98

His Phe Arg Lys Leu Leu Leu Leu
1               5

<210> SEQ ID NO 99
<211> LENGTH: 11
<212> TYPE: PRT
<213> ORGANISM: Artificial sequence
<220> FEATURE:
<223> OTHER INFORMATION: Peptide derived from HBV Polymerase protein

<400> SEQUENCE: 99

Tyr Gln His Phe Arg Lys Leu Leu Leu Leu Asp
1               5                   10

<210> SEQ ID NO 100
<211> LENGTH: 11
<212> TYPE: PRT
<213> ORGANISM: Artificial sequence
<220> FEATURE:
<223> OTHER INFORMATION: Peptide derived from HBV Polymerase protein

<400> SEQUENCE: 100

Gln His Phe Arg Lys Leu Leu Leu Leu Asp Asp
1               5                   10

<210> SEQ ID NO 101
<211> LENGTH: 11
<212> TYPE: PRT
<213> ORGANISM: Artificial sequence
<220> FEATURE:
<223> OTHER INFORMATION: Peptide derived from HBV Polymerase protein

<400> SEQUENCE: 101

Phe Arg Lys Leu Leu Leu Leu Asp Asp Gly Thr
1               5                   10

<210> SEQ ID NO 102
<211> LENGTH: 9
<212> TYPE: PRT
<213> ORGANISM: Artificial sequence
<220> FEATURE:
<223> OTHER INFORMATION: Peptide derived from HBV Polymerase protein

<400> SEQUENCE: 102

Leu Leu Leu Asp Asp Gly Thr Glu Ala
1               5

<210> SEQ ID NO 103
<211> LENGTH: 11
```

```
<212> TYPE: PRT
<213> ORGANISM: Artificial sequence
<220> FEATURE:
<223> OTHER INFORMATION: Peptide derived from HBV Polymerase protein

<400> SEQUENCE: 103

Leu Leu Asp Asp Gly Thr Glu Ala Gly Pro Leu
1               5                   10

<210> SEQ ID NO 104
<211> LENGTH: 10
<212> TYPE: PRT
<213> ORGANISM: Artificial sequence
<220> FEATURE:
<223> OTHER INFORMATION: Peptide derived from HBV Polymerase protein

<400> SEQUENCE: 104

Thr Glu Ala Gly Pro Leu Glu Glu Glu Leu
1               5                   10

<210> SEQ ID NO 105
<211> LENGTH: 8
<212> TYPE: PRT
<213> ORGANISM: Artificial sequence
<220> FEATURE:
<223> OTHER INFORMATION: Peptide derived from HBV Polymerase protein

<400> SEQUENCE: 105

Leu Glu Glu Glu Leu Pro Arg Leu
1               5

<210> SEQ ID NO 106
<211> LENGTH: 10
<212> TYPE: PRT
<213> ORGANISM: Artificial sequence
<220> FEATURE:
<223> OTHER INFORMATION: Peptide derived from HBV Polymerase protein

<400> SEQUENCE: 106

Ile Pro Trp Thr His Lys Val Gly Asn Phe
1               5                   10

<210> SEQ ID NO 107
<211> LENGTH: 8
<212> TYPE: PRT
<213> ORGANISM: Artificial sequence
<220> FEATURE:
<223> OTHER INFORMATION: Peptide derived from HBV Polymerase protein

<400> SEQUENCE: 107

Trp Thr His Lys Val Gly Asn Phe
1               5

<210> SEQ ID NO 108
<211> LENGTH: 11
<212> TYPE: PRT
<213> ORGANISM: Artificial sequence
<220> FEATURE:
<223> OTHER INFORMATION: Peptide derived from HBV Polymerase protein

<400> SEQUENCE: 108

Ile Pro Trp Thr His Lys Val Gly Asn Phe Thr
1               5                   10

<210> SEQ ID NO 109
<211> LENGTH: 11
<212> TYPE: PRT
```

```
<213> ORGANISM: Artificial sequence
<220> FEATURE:
<223> OTHER INFORMATION: Peptide derived from HBV Polymerase protein

<400> SEQUENCE: 109

Trp Thr His Lys Val Gly Asn Phe Thr Gly Leu
1               5                   10

<210> SEQ ID NO 110
<211> LENGTH: 9
<212> TYPE: PRT
<213> ORGANISM: Artificial sequence
<220> FEATURE:
<223> OTHER INFORMATION: Peptide derived from HBV Polymerase protein

<400> SEQUENCE: 110

His Lys Val Gly Asn Phe Thr Gly Leu
1               5

<210> SEQ ID NO 111
<211> LENGTH: 8
<212> TYPE: PRT
<213> ORGANISM: Artificial sequence
<220> FEATURE:
<223> OTHER INFORMATION: Peptide derived from HBV Polymerase protein

<400> SEQUENCE: 111

Lys Val Gly Asn Phe Thr Gly Leu
1               5

<210> SEQ ID NO 112
<211> LENGTH: 11
<212> TYPE: PRT
<213> ORGANISM: Artificial sequence
<220> FEATURE:
<223> OTHER INFORMATION: Peptide derived from HBV Polymerase protein

<400> SEQUENCE: 112

Thr His Lys Val Gly Asn Phe Thr Gly Leu Tyr
1               5                   10

<210> SEQ ID NO 113
<211> LENGTH: 10
<212> TYPE: PRT
<213> ORGANISM: Artificial sequence
<220> FEATURE:
<223> OTHER INFORMATION: Peptide derived from HBV Polymerase protein

<400> SEQUENCE: 113

His Lys Val Gly Asn Phe Thr Gly Leu Tyr
1               5                   10

<210> SEQ ID NO 114
<211> LENGTH: 9
<212> TYPE: PRT
<213> ORGANISM: Artificial sequence
<220> FEATURE:
<223> OTHER INFORMATION: Peptide derived from HBV Polymerase protein

<400> SEQUENCE: 114

Lys Val Gly Asn Phe Thr Gly Leu Tyr
1               5

<210> SEQ ID NO 115
<211> LENGTH: 8
<212> TYPE: PRT
<213> ORGANISM: Artificial sequence
```

```
<220> FEATURE:
<223> OTHER INFORMATION: Peptide derived from HBV Polymerase protein

<400> SEQUENCE: 115

Val Gly Asn Phe Thr Gly Leu Tyr
1               5

<210> SEQ ID NO 116
<211> LENGTH: 11
<212> TYPE: PRT
<213> ORGANISM: Artificial sequence
<220> FEATURE:
<223> OTHER INFORMATION: Peptide derived from HBV Polymerase protein

<400> SEQUENCE: 116

Phe Thr Gly Leu Tyr Ser Ser Thr Val Pro Ile
1               5                   10

<210> SEQ ID NO 117
<211> LENGTH: 10
<212> TYPE: PRT
<213> ORGANISM: Artificial sequence
<220> FEATURE:
<223> OTHER INFORMATION: Peptide derived from HBV Polymerase protein

<400> SEQUENCE: 117

Thr Gly Leu Tyr Ser Ser Thr Val Pro Ile
1               5                   10

<210> SEQ ID NO 118
<211> LENGTH: 9
<212> TYPE: PRT
<213> ORGANISM: Artificial sequence
<220> FEATURE:
<223> OTHER INFORMATION: Peptide derived from HBV Polymerase protein

<400> SEQUENCE: 118

Gly Leu Tyr Ser Ser Thr Val Pro Ile
1               5

<210> SEQ ID NO 119
<211> LENGTH: 8
<212> TYPE: PRT
<213> ORGANISM: Artificial sequence
<220> FEATURE:
<223> OTHER INFORMATION: Peptide derived from HBV Polymerase protein

<400> SEQUENCE: 119

Leu Tyr Ser Ser Thr Val Pro Ile
1               5

<210> SEQ ID NO 120
<211> LENGTH: 10
<212> TYPE: PRT
<213> ORGANISM: Artificial sequence
<220> FEATURE:
<223> OTHER INFORMATION: Peptide derived from HBV Polymerase protein

<400> SEQUENCE: 120

Gly Leu Tyr Ser Ser Thr Val Pro Ile Phe
1               5                   10

<210> SEQ ID NO 121
<211> LENGTH: 9
<212> TYPE: PRT
<213> ORGANISM: Artificial sequence
<220> FEATURE:
```

<223> OTHER INFORMATION: Peptide derived from HBV Polymerase protein

<400> SEQUENCE: 121

Leu Tyr Ser Ser Thr Val Pro Ile Phe
1               5

<210> SEQ ID NO 122
<211> LENGTH: 8
<212> TYPE: PRT
<213> ORGANISM: Artificial sequence
<220> FEATURE:
<223> OTHER INFORMATION: Peptide derived from HBV Polymerase protein

<400> SEQUENCE: 122

Tyr Ser Ser Thr Val Pro Ile Phe
1               5

<210> SEQ ID NO 123
<211> LENGTH: 10
<212> TYPE: PRT
<213> ORGANISM: Artificial sequence
<220> FEATURE:
<223> OTHER INFORMATION: Peptide derived from HBV Polymerase protein

<400> SEQUENCE: 123

Tyr Ser Ser Thr Val Pro Ile Phe Asn Pro
1               5                   10

<210> SEQ ID NO 124
<211> LENGTH: 11
<212> TYPE: PRT
<213> ORGANISM: Artificial sequence
<220> FEATURE:
<223> OTHER INFORMATION: Peptide derived from HBV Polymerase protein

<400> SEQUENCE: 124

Ser Ser Thr Val Pro Ile Phe Asn Pro Glu Trp
1               5                   10

<210> SEQ ID NO 125
<211> LENGTH: 10
<212> TYPE: PRT
<213> ORGANISM: Artificial sequence
<220> FEATURE:
<223> OTHER INFORMATION: Peptide derived from HBV Polymerase protein

<400> SEQUENCE: 125

Ser Thr Val Pro Ile Phe Asn Pro Glu Trp
1               5                   10

<210> SEQ ID NO 126
<211> LENGTH: 8
<212> TYPE: PRT
<213> ORGANISM: Artificial sequence
<220> FEATURE:
<223> OTHER INFORMATION: Peptide derived from HBV Polymerase protein

<400> SEQUENCE: 126

Val Pro Ile Phe Asn Pro Glu Trp
1               5

<210> SEQ ID NO 127
<211> LENGTH: 10
<212> TYPE: PRT
<213> ORGANISM: Artificial sequence
<220> FEATURE:
<223> OTHER INFORMATION: Peptide derived from HBV Polymerase protein

```
<400> SEQUENCE: 127

Pro Ile Phe Asn Pro Glu Trp Gln Thr Pro
1               5                   10

<210> SEQ ID NO 128
<211> LENGTH: 11
<212> TYPE: PRT
<213> ORGANISM: Artificial sequence
<220> FEATURE:
<223> OTHER INFORMATION: Peptide derived from HBV Polymerase protein

<400> SEQUENCE: 128

Ile Phe Asn Pro Glu Trp Gln Thr Pro Ser Phe
1               5                   10

<210> SEQ ID NO 129
<211> LENGTH: 9
<212> TYPE: PRT
<213> ORGANISM: Artificial sequence
<220> FEATURE:
<223> OTHER INFORMATION: Peptide derived from HBV Polymerase protein

<400> SEQUENCE: 129

Asn Pro Glu Trp Gln Thr Pro Ser Phe
1               5

<210> SEQ ID NO 130
<211> LENGTH: 8
<212> TYPE: PRT
<213> ORGANISM: Artificial sequence
<220> FEATURE:
<223> OTHER INFORMATION: Peptide derived from HBV Polymerase protein

<400> SEQUENCE: 130

Pro Glu Trp Gln Thr Pro Ser Phe
1               5

<210> SEQ ID NO 131
<211> LENGTH: 8
<212> TYPE: PRT
<213> ORGANISM: Artificial sequence
<220> FEATURE:
<223> OTHER INFORMATION: Peptide derived from HBV Polymerase protein

<400> SEQUENCE: 131

Trp Gln Thr Pro Ser Phe Pro Lys
1               5

<210> SEQ ID NO 132
<211> LENGTH: 11
<212> TYPE: PRT
<213> ORGANISM: Artificial sequence
<220> FEATURE:
<223> OTHER INFORMATION: Peptide derived from HBV Polymerase protein

<400> SEQUENCE: 132

Pro Glu Trp Gln Thr Pro Ser Phe Pro Lys Ile
1               5                   10

<210> SEQ ID NO 133
<211> LENGTH: 9
<212> TYPE: PRT
<213> ORGANISM: Artificial sequence
<220> FEATURE:
<223> OTHER INFORMATION: Peptide derived from HBV Polymerase protein
```

```
<400> SEQUENCE: 133

Trp Gln Thr Pro Ser Phe Pro Lys Ile
1               5

<210> SEQ ID NO 134
<211> LENGTH: 11
<212> TYPE: PRT
<213> ORGANISM: Artificial sequence
<220> FEATURE:
<223> OTHER INFORMATION: Peptide derived from HBV Polymerase protein

<400> SEQUENCE: 134

Trp Gln Thr Pro Ser Phe Pro Lys Ile His Leu
1               5                   10

<210> SEQ ID NO 135
<211> LENGTH: 9
<212> TYPE: PRT
<213> ORGANISM: Artificial sequence
<220> FEATURE:
<223> OTHER INFORMATION: Peptide derived from HBV Polymerase protein

<400> SEQUENCE: 135

Thr Pro Ser Phe Pro Lys Ile His Leu
1               5

<210> SEQ ID NO 136
<211> LENGTH: 8
<212> TYPE: PRT
<213> ORGANISM: Artificial sequence
<220> FEATURE:
<223> OTHER INFORMATION: Peptide derived from HBV Polymerase protein

<400> SEQUENCE: 136

Asn Glu Lys Arg Arg Leu Lys Leu
1               5

<210> SEQ ID NO 137
<211> LENGTH: 9
<212> TYPE: PRT
<213> ORGANISM: Artificial sequence
<220> FEATURE:
<223> OTHER INFORMATION: Peptide derived from HBV Polymerase protein

<400> SEQUENCE: 137

Asn Glu Lys Arg Arg Leu Lys Leu Ile
1               5

<210> SEQ ID NO 138
<211> LENGTH: 8
<212> TYPE: PRT
<213> ORGANISM: Artificial sequence
<220> FEATURE:
<223> OTHER INFORMATION: Peptide derived from HBV Polymerase protein

<400> SEQUENCE: 138

Lys Arg Arg Leu Lys Leu Ile Met
1               5

<210> SEQ ID NO 139
<211> LENGTH: 8
<212> TYPE: PRT
<213> ORGANISM: Artificial sequence
<220> FEATURE:
<223> OTHER INFORMATION: Peptide derived from HBV Polymerase protein

<400> SEQUENCE: 139
```

Arg Arg Leu Lys Leu Ile Met Pro
1               5

<210> SEQ ID NO 140
<211> LENGTH: 10
<212> TYPE: PRT
<213> ORGANISM: Artificial sequence
<220> FEATURE:
<223> OTHER INFORMATION: Peptide derived from HBV Polymerase protein

<400> SEQUENCE: 140

Lys Arg Arg Leu Lys Leu Ile Met Pro Ala
1               5                   10

<210> SEQ ID NO 141
<211> LENGTH: 9
<212> TYPE: PRT
<213> ORGANISM: Artificial sequence
<220> FEATURE:
<223> OTHER INFORMATION: Peptide derived from HBV Polymerase protein

<400> SEQUENCE: 141

Arg Arg Leu Lys Leu Ile Met Pro Ala
1               5

<210> SEQ ID NO 142
<211> LENGTH: 8
<212> TYPE: PRT
<213> ORGANISM: Artificial sequence
<220> FEATURE:
<223> OTHER INFORMATION: Peptide derived from HBV Polymerase protein

<400> SEQUENCE: 142

Arg Leu Lys Leu Ile Met Pro Ala
1               5

<210> SEQ ID NO 143
<211> LENGTH: 11
<212> TYPE: PRT
<213> ORGANISM: Artificial sequence
<220> FEATURE:
<223> OTHER INFORMATION: Peptide derived from HBV Polymerase protein

<400> SEQUENCE: 143

Lys Arg Arg Leu Lys Leu Ile Met Pro Ala Arg
1               5                   10

<210> SEQ ID NO 144
<211> LENGTH: 10
<212> TYPE: PRT
<213> ORGANISM: Artificial sequence
<220> FEATURE:
<223> OTHER INFORMATION: Peptide derived from HBV Polymerase protein

<400> SEQUENCE: 144

Arg Arg Leu Lys Leu Ile Met Pro Ala Arg
1               5                   10

<210> SEQ ID NO 145
<211> LENGTH: 9
<212> TYPE: PRT
<213> ORGANISM: Artificial sequence
<220> FEATURE:
<223> OTHER INFORMATION: Peptide derived from HBV Polymerase protein

<400> SEQUENCE: 145

```
Arg Leu Lys Leu Ile Met Pro Ala Arg
1               5

<210> SEQ ID NO 146
<211> LENGTH: 11
<212> TYPE: PRT
<213> ORGANISM: Artificial sequence
<220> FEATURE:
<223> OTHER INFORMATION: Peptide derived from HBV Polymerase protein

<400> SEQUENCE: 146

Arg Arg Leu Lys Leu Ile Met Pro Ala Arg Phe
1               5                   10

<210> SEQ ID NO 147
<211> LENGTH: 10
<212> TYPE: PRT
<213> ORGANISM: Artificial sequence
<220> FEATURE:
<223> OTHER INFORMATION: Peptide derived from HBV Polymerase protein

<400> SEQUENCE: 147

Arg Leu Lys Leu Ile Met Pro Ala Arg Phe
1               5                   10

<210> SEQ ID NO 148
<211> LENGTH: 8
<212> TYPE: PRT
<213> ORGANISM: Artificial sequence
<220> FEATURE:
<223> OTHER INFORMATION: Peptide derived from HBV Polymerase protein

<400> SEQUENCE: 148

Lys Leu Ile Met Pro Ala Arg Phe
1               5

<210> SEQ ID NO 149
<211> LENGTH: 11
<212> TYPE: PRT
<213> ORGANISM: Artificial sequence
<220> FEATURE:
<223> OTHER INFORMATION: Peptide derived from HBV Polymerase protein

<400> SEQUENCE: 149

Arg Leu Lys Leu Ile Met Pro Ala Arg Phe Tyr
1               5                   10

<210> SEQ ID NO 150
<211> LENGTH: 10
<212> TYPE: PRT
<213> ORGANISM: Artificial sequence
<220> FEATURE:
<223> OTHER INFORMATION: Peptide derived from HBV Polymerase protein

<400> SEQUENCE: 150

Leu Lys Leu Ile Met Pro Ala Arg Phe Tyr
1               5                   10

<210> SEQ ID NO 151
<211> LENGTH: 9
<212> TYPE: PRT
<213> ORGANISM: Artificial sequence
<220> FEATURE:
<223> OTHER INFORMATION: Peptide derived from HBV Polymerase protein

<400> SEQUENCE: 151

Lys Leu Ile Met Pro Ala Arg Phe Tyr
```

```
1               5
```

<210> SEQ ID NO 152
<211> LENGTH: 8
<212> TYPE: PRT
<213> ORGANISM: Artificial sequence
<220> FEATURE:
<223> OTHER INFORMATION: Peptide derived from HBV Polymerase protein

<400> SEQUENCE: 152

```
Leu Ile Met Pro Ala Arg Phe Tyr
1               5
```

<210> SEQ ID NO 153
<211> LENGTH: 10
<212> TYPE: PRT
<213> ORGANISM: Artificial sequence
<220> FEATURE:
<223> OTHER INFORMATION: Peptide derived from HBV Polymerase protein

<400> SEQUENCE: 153

```
Leu Ile Met Pro Ala Arg Phe Tyr Pro Thr
1               5                   10
```

<210> SEQ ID NO 154
<211> LENGTH: 8
<212> TYPE: PRT
<213> ORGANISM: Artificial sequence
<220> FEATURE:
<223> OTHER INFORMATION: Peptide derived from HBV Polymerase protein

<400> SEQUENCE: 154

```
Met Pro Ala Arg Phe Tyr Pro Thr
1               5
```

<210> SEQ ID NO 155
<211> LENGTH: 9
<212> TYPE: PRT
<213> ORGANISM: Artificial sequence
<220> FEATURE:
<223> OTHER INFORMATION: Peptide derived from HBV Polymerase protein

<400> SEQUENCE: 155

```
Met Pro Ala Arg Phe Tyr Pro Thr His
1               5
```

<210> SEQ ID NO 156
<211> LENGTH: 10
<212> TYPE: PRT
<213> ORGANISM: Artificial sequence
<220> FEATURE:
<223> OTHER INFORMATION: Peptide derived from HBV Polymerase protein

<400> SEQUENCE: 156

```
Met Pro Ala Arg Phe Tyr Pro Thr His Thr
1               5                   10
```

<210> SEQ ID NO 157
<211> LENGTH: 8
<212> TYPE: PRT
<213> ORGANISM: Artificial sequence
<220> FEATURE:
<223> OTHER INFORMATION: Peptide derived from HBV Polymerase protein

<400> SEQUENCE: 157

```
Ala Arg Phe Tyr Pro Thr His Thr
1               5
```

<210> SEQ ID NO 158
<211> LENGTH: 11
<212> TYPE: PRT
<213> ORGANISM: Artificial sequence
<220> FEATURE:
<223> OTHER INFORMATION: Peptide derived from HBV Polymerase protein

<400> SEQUENCE: 158

Met Pro Ala Arg Phe Tyr Pro Thr His Thr Lys
1               5                   10

<210> SEQ ID NO 159
<211> LENGTH: 9
<212> TYPE: PRT
<213> ORGANISM: Artificial sequence
<220> FEATURE:
<223> OTHER INFORMATION: Peptide derived from HBV Polymerase protein

<400> SEQUENCE: 159

Ala Arg Phe Tyr Pro Thr His Thr Lys
1               5

<210> SEQ ID NO 160
<211> LENGTH: 8
<212> TYPE: PRT
<213> ORGANISM: Artificial sequence
<220> FEATURE:
<223> OTHER INFORMATION: Peptide derived from HBV Polymerase protein

<400> SEQUENCE: 160

Arg Phe Tyr Pro Thr His Thr Lys
1               5

<210> SEQ ID NO 161
<211> LENGTH: 10
<212> TYPE: PRT
<213> ORGANISM: Artificial sequence
<220> FEATURE:
<223> OTHER INFORMATION: Peptide derived from HBV Polymerase protein

<400> SEQUENCE: 161

Ala Arg Phe Tyr Pro Thr His Thr Lys Tyr
1               5                   10

<210> SEQ ID NO 162
<211> LENGTH: 9
<212> TYPE: PRT
<213> ORGANISM: Artificial sequence
<220> FEATURE:
<223> OTHER INFORMATION: Peptide derived from HBV Polymerase protein

<400> SEQUENCE: 162

Arg Phe Tyr Pro Thr His Thr Lys Tyr
1               5

<210> SEQ ID NO 163
<211> LENGTH: 8
<212> TYPE: PRT
<213> ORGANISM: Artificial sequence
<220> FEATURE:
<223> OTHER INFORMATION: Peptide derived from HBV Polymerase protein

<400> SEQUENCE: 163

Phe Tyr Pro Thr His Thr Lys Tyr
1               5

```
<210> SEQ ID NO 164
<211> LENGTH: 11
<212> TYPE: PRT
<213> ORGANISM: Artificial sequence
<220> FEATURE:
<223> OTHER INFORMATION: Peptide derived from HBV Polymerase protein

<400> SEQUENCE: 164

Ala Arg Phe Tyr Pro Thr His Thr Lys Tyr Leu
1               5                   10

<210> SEQ ID NO 165
<211> LENGTH: 10
<212> TYPE: PRT
<213> ORGANISM: Artificial sequence
<220> FEATURE:
<223> OTHER INFORMATION: Peptide derived from HBV Polymerase protein

<400> SEQUENCE: 165

Arg Phe Tyr Pro Thr His Thr Lys Tyr Leu
1               5                   10

<210> SEQ ID NO 166
<211> LENGTH: 9
<212> TYPE: PRT
<213> ORGANISM: Artificial sequence
<220> FEATURE:
<223> OTHER INFORMATION: Peptide derived from HBV Polymerase protein

<400> SEQUENCE: 166

Phe Tyr Pro Thr His Thr Lys Tyr Leu
1               5

<210> SEQ ID NO 167
<211> LENGTH: 8
<212> TYPE: PRT
<213> ORGANISM: Artificial sequence
<220> FEATURE:
<223> OTHER INFORMATION: Peptide derived from HBV Polymerase protein

<400> SEQUENCE: 167

Tyr Pro Thr His Thr Lys Tyr Leu
1               5

<210> SEQ ID NO 168
<211> LENGTH: 10
<212> TYPE: PRT
<213> ORGANISM: Artificial sequence
<220> FEATURE:
<223> OTHER INFORMATION: Peptide derived from HBV Polymerase protein

<400> SEQUENCE: 168

Phe Tyr Pro Thr His Thr Lys Tyr Leu Pro
1               5                   10

<210> SEQ ID NO 169
<211> LENGTH: 9
<212> TYPE: PRT
<213> ORGANISM: Artificial sequence
<220> FEATURE:
<223> OTHER INFORMATION: Peptide derived from HBV Polymerase protein

<400> SEQUENCE: 169

Tyr Pro Thr His Thr Lys Tyr Leu Pro
1               5
```

```
<210> SEQ ID NO 170
<211> LENGTH: 11
<212> TYPE: PRT
<213> ORGANISM: Artificial sequence
<220> FEATURE:
<223> OTHER INFORMATION: Peptide derived from HBV Polymerase protein

<400> SEQUENCE: 170

Phe Tyr Pro Thr His Thr Lys Tyr Leu Pro Leu
1               5                   10

<210> SEQ ID NO 171
<211> LENGTH: 10
<212> TYPE: PRT
<213> ORGANISM: Artificial sequence
<220> FEATURE:
<223> OTHER INFORMATION: Peptide derived from HBV Polymerase protein

<400> SEQUENCE: 171

Tyr Pro Thr His Thr Lys Tyr Leu Pro Leu
1               5                   10

<210> SEQ ID NO 172
<211> LENGTH: 8
<212> TYPE: PRT
<213> ORGANISM: Artificial sequence
<220> FEATURE:
<223> OTHER INFORMATION: Peptide derived from HBV Polymerase protein

<400> SEQUENCE: 172

Thr His Thr Lys Tyr Leu Pro Leu
1               5

<210> SEQ ID NO 173
<211> LENGTH: 10
<212> TYPE: PRT
<213> ORGANISM: Artificial sequence
<220> FEATURE:
<223> OTHER INFORMATION: Peptide derived from HBV Polymerase protein

<400> SEQUENCE: 173

Pro Thr His Thr Lys Tyr Leu Pro Leu Asp
1               5                   10

<210> SEQ ID NO 174
<211> LENGTH: 9
<212> TYPE: PRT
<213> ORGANISM: Artificial sequence
<220> FEATURE:
<223> OTHER INFORMATION: Peptide derived from HBV Polymerase protein

<400> SEQUENCE: 174

His Thr Lys Tyr Leu Pro Leu Asp Lys
1               5

<210> SEQ ID NO 175
<211> LENGTH: 9
<212> TYPE: PRT
<213> ORGANISM: Artificial sequence
<220> FEATURE:
<223> OTHER INFORMATION: Peptide derived from HBV Polymerase protein

<400> SEQUENCE: 175

Lys Tyr Leu Pro Leu Asp Lys Gly Ile
1               5

<210> SEQ ID NO 176
```

```
<211> LENGTH: 8
<212> TYPE: PRT
<213> ORGANISM: Artificial sequence
<220> FEATURE:
<223> OTHER INFORMATION: Peptide derived from HBV Polymerase protein

<400> SEQUENCE: 176

Leu Pro Leu Asp Lys Gly Ile Lys
1               5

<210> SEQ ID NO 177
<211> LENGTH: 10
<212> TYPE: PRT
<213> ORGANISM: Artificial sequence
<220> FEATURE:
<223> OTHER INFORMATION: Peptide derived from HBV Polymerase protein

<400> SEQUENCE: 177

Leu Pro Leu Asp Lys Gly Ile Lys Pro Tyr
1               5                   10

<210> SEQ ID NO 178
<211> LENGTH: 9
<212> TYPE: PRT
<213> ORGANISM: Artificial sequence
<220> FEATURE:
<223> OTHER INFORMATION: Peptide derived from HBV Polymerase protein

<400> SEQUENCE: 178

Pro Leu Asp Lys Gly Ile Lys Pro Tyr
1               5

<210> SEQ ID NO 179
<211> LENGTH: 8
<212> TYPE: PRT
<213> ORGANISM: Artificial sequence
<220> FEATURE:
<223> OTHER INFORMATION: Peptide derived from HBV Polymerase protein

<400> SEQUENCE: 179

Leu Asp Lys Gly Ile Lys Pro Tyr
1               5

<210> SEQ ID NO 180
<211> LENGTH: 11
<212> TYPE: PRT
<213> ORGANISM: Artificial sequence
<220> FEATURE:
<223> OTHER INFORMATION: Peptide derived from HBV Polymerase protein

<400> SEQUENCE: 180

Leu Pro Leu Asp Lys Gly Ile Lys Pro Tyr Tyr
1               5                   10

<210> SEQ ID NO 181
<211> LENGTH: 10
<212> TYPE: PRT
<213> ORGANISM: Artificial sequence
<220> FEATURE:
<223> OTHER INFORMATION: Peptide derived from HBV Polymerase protein

<400> SEQUENCE: 181

Pro Leu Asp Lys Gly Ile Lys Pro Tyr Tyr
1               5                   10

<210> SEQ ID NO 182
<211> LENGTH: 8
```

```
<212> TYPE: PRT
<213> ORGANISM: Artificial sequence
<220> FEATURE:
<223> OTHER INFORMATION: Peptide derived from HBV Polymerase protein

<400> SEQUENCE: 182

Lys Pro Tyr Tyr Pro Asp Gln Val
1               5

<210> SEQ ID NO 183
<211> LENGTH: 9
<212> TYPE: PRT
<213> ORGANISM: Artificial sequence
<220> FEATURE:
<223> OTHER INFORMATION: Peptide derived from HBV Polymerase protein

<400> SEQUENCE: 183

Lys Pro Tyr Tyr Pro Asp Gln Val Val
1               5

<210> SEQ ID NO 184
<211> LENGTH: 8
<212> TYPE: PRT
<213> ORGANISM: Artificial sequence
<220> FEATURE:
<223> OTHER INFORMATION: Peptide derived from HBV Polymerase protein

<400> SEQUENCE: 184

Tyr Pro Asp Gln Val Val Asn His
1               5

<210> SEQ ID NO 185
<211> LENGTH: 10
<212> TYPE: PRT
<213> ORGANISM: Artificial sequence
<220> FEATURE:
<223> OTHER INFORMATION: Peptide derived from HBV Polymerase protein

<400> SEQUENCE: 185

Tyr Tyr Pro Asp Gln Val Val Asn His Tyr
1               5                   10

<210> SEQ ID NO 186
<211> LENGTH: 9
<212> TYPE: PRT
<213> ORGANISM: Artificial sequence
<220> FEATURE:
<223> OTHER INFORMATION: Peptide derived from HBV Polymerase protein

<400> SEQUENCE: 186

Tyr Pro Asp Gln Val Val Asn His Tyr
1               5

<210> SEQ ID NO 187
<211> LENGTH: 8
<212> TYPE: PRT
<213> ORGANISM: Artificial sequence
<220> FEATURE:
<223> OTHER INFORMATION: Peptide derived from HBV Polymerase protein

<400> SEQUENCE: 187

Pro Asp Gln Val Val Asn His Tyr
1               5

<210> SEQ ID NO 188
<211> LENGTH: 11
<212> TYPE: PRT
```

```
<213> ORGANISM: Artificial sequence
<220> FEATURE:
<223> OTHER INFORMATION: Peptide derived from HBV Polymerase protein

<400> SEQUENCE: 188

Tyr Tyr Pro Asp Gln Val Val Asn His Tyr Phe
1               5                   10

<210> SEQ ID NO 189
<211> LENGTH: 10
<212> TYPE: PRT
<213> ORGANISM: Artificial sequence
<220> FEATURE:
<223> OTHER INFORMATION: Peptide derived from HBV Polymerase protein

<400> SEQUENCE: 189

Tyr Pro Asp Gln Val Val Asn His Tyr Phe
1               5                   10

<210> SEQ ID NO 190
<211> LENGTH: 8
<212> TYPE: PRT
<213> ORGANISM: Artificial sequence
<220> FEATURE:
<223> OTHER INFORMATION: Peptide derived from HBV Polymerase protein

<400> SEQUENCE: 190

Asp Gln Val Val Asn His Tyr Phe
1               5

<210> SEQ ID NO 191
<211> LENGTH: 11
<212> TYPE: PRT
<213> ORGANISM: Artificial sequence
<220> FEATURE:
<223> OTHER INFORMATION: Peptide derived from HBV Polymerase protein

<400> SEQUENCE: 191

Asp Gln Val Val Asn His Tyr Phe Gln Thr Arg
1               5                   10

<210> SEQ ID NO 192
<211> LENGTH: 10
<212> TYPE: PRT
<213> ORGANISM: Artificial sequence
<220> FEATURE:
<223> OTHER INFORMATION: Peptide derived from HBV Polymerase protein

<400> SEQUENCE: 192

Gln Val Val Asn His Tyr Phe Gln Thr Arg
1               5                   10

<210> SEQ ID NO 193
<211> LENGTH: 9
<212> TYPE: PRT
<213> ORGANISM: Artificial sequence
<220> FEATURE:
<223> OTHER INFORMATION: Peptide derived from HBV Polymerase protein

<400> SEQUENCE: 193

Val Val Asn His Tyr Phe Gln Thr Arg
1               5

<210> SEQ ID NO 194
<211> LENGTH: 11
<212> TYPE: PRT
<213> ORGANISM: Artificial sequence
```

```
<220> FEATURE:
<223> OTHER INFORMATION: Peptide derived from HBV Polymerase protein

<400> SEQUENCE: 194

Val Val Asn His Tyr Phe Gln Thr Arg His Tyr
1               5                   10

<210> SEQ ID NO 195
<211> LENGTH: 9
<212> TYPE: PRT
<213> ORGANISM: Artificial sequence
<220> FEATURE:
<223> OTHER INFORMATION: Peptide derived from HBV Polymerase protein

<400> SEQUENCE: 195

Asn His Tyr Phe Gln Thr Arg His Tyr
1               5

<210> SEQ ID NO 196
<211> LENGTH: 8
<212> TYPE: PRT
<213> ORGANISM: Artificial sequence
<220> FEATURE:
<223> OTHER INFORMATION: Peptide derived from HBV Polymerase protein

<400> SEQUENCE: 196

His Tyr Phe Gln Thr Arg His Tyr
1               5

<210> SEQ ID NO 197
<211> LENGTH: 10
<212> TYPE: PRT
<213> ORGANISM: Artificial sequence
<220> FEATURE:
<223> OTHER INFORMATION: Peptide derived from HBV Polymerase protein

<400> SEQUENCE: 197

Asn His Tyr Phe Gln Thr Arg His Tyr Leu
1               5                   10

<210> SEQ ID NO 198
<211> LENGTH: 9
<212> TYPE: PRT
<213> ORGANISM: Artificial sequence
<220> FEATURE:
<223> OTHER INFORMATION: Peptide derived from HBV Polymerase protein

<400> SEQUENCE: 198

His Tyr Phe Gln Thr Arg His Tyr Leu
1               5

<210> SEQ ID NO 199
<211> LENGTH: 8
<212> TYPE: PRT
<213> ORGANISM: Artificial sequence
<220> FEATURE:
<223> OTHER INFORMATION: Peptide derived from HBV Polymerase protein

<400> SEQUENCE: 199

Tyr Phe Gln Thr Arg His Tyr Leu
1               5

<210> SEQ ID NO 200
<211> LENGTH: 10
<212> TYPE: PRT
<213> ORGANISM: Artificial sequence
<220> FEATURE:
```

<223> OTHER INFORMATION: Peptide derived from HBV Polymerase protein

<400> SEQUENCE: 200

His Tyr Phe Gln Thr Arg His Tyr Leu His
1               5                   10

<210> SEQ ID NO 201
<211> LENGTH: 9
<212> TYPE: PRT
<213> ORGANISM: Artificial sequence
<220> FEATURE:
<223> OTHER INFORMATION: Peptide derived from HBV Polymerase protein

<400> SEQUENCE: 201

Tyr Phe Gln Thr Arg His Tyr Leu His
1               5

<210> SEQ ID NO 202
<211> LENGTH: 11
<212> TYPE: PRT
<213> ORGANISM: Artificial sequence
<220> FEATURE:
<223> OTHER INFORMATION: Peptide derived from HBV Polymerase protein

<400> SEQUENCE: 202

Tyr Phe Gln Thr Arg His Tyr Leu His Thr Leu
1               5                   10

<210> SEQ ID NO 203
<211> LENGTH: 10
<212> TYPE: PRT
<213> ORGANISM: Artificial sequence
<220> FEATURE:
<223> OTHER INFORMATION: Peptide derived from HBV Polymerase protein

<400> SEQUENCE: 203

Phe Gln Thr Arg His Tyr Leu His Thr Leu
1               5                   10

<210> SEQ ID NO 204
<211> LENGTH: 9
<212> TYPE: PRT
<213> ORGANISM: Artificial sequence
<220> FEATURE:
<223> OTHER INFORMATION: Peptide derived from HBV Polymerase protein

<400> SEQUENCE: 204

Gln Thr Arg His Tyr Leu His Thr Leu
1               5

<210> SEQ ID NO 205
<211> LENGTH: 8
<212> TYPE: PRT
<213> ORGANISM: Artificial sequence
<220> FEATURE:
<223> OTHER INFORMATION: Peptide derived from HBV Polymerase protein

<400> SEQUENCE: 205

Thr Arg His Tyr Leu His Thr Leu
1               5

<210> SEQ ID NO 206
<211> LENGTH: 11
<212> TYPE: PRT
<213> ORGANISM: Artificial sequence
<220> FEATURE:
<223> OTHER INFORMATION: Peptide derived from HBV Polymerase protein

```
<400> SEQUENCE: 206

Phe Gln Thr Arg His Tyr Leu His Thr Leu Trp
1               5                   10

<210> SEQ ID NO 207
<211> LENGTH: 10
<212> TYPE: PRT
<213> ORGANISM: Artificial sequence
<220> FEATURE:
<223> OTHER INFORMATION: Peptide derived from HBV Polymerase protein

<400> SEQUENCE: 207

Gln Thr Arg His Tyr Leu His Thr Leu Trp
1               5                   10

<210> SEQ ID NO 208
<211> LENGTH: 9
<212> TYPE: PRT
<213> ORGANISM: Artificial sequence
<220> FEATURE:
<223> OTHER INFORMATION: Peptide derived from HBV Polymerase protein

<400> SEQUENCE: 208

Thr Arg His Tyr Leu His Thr Leu Trp
1               5

<210> SEQ ID NO 209
<211> LENGTH: 8
<212> TYPE: PRT
<213> ORGANISM: Artificial sequence
<220> FEATURE:
<223> OTHER INFORMATION: Peptide derived from HBV Polymerase protein

<400> SEQUENCE: 209

Arg His Tyr Leu His Thr Leu Trp
1               5

<210> SEQ ID NO 210
<211> LENGTH: 11
<212> TYPE: PRT
<213> ORGANISM: Artificial sequence
<220> FEATURE:
<223> OTHER INFORMATION: Peptide derived from HBV Polymerase protein

<400> SEQUENCE: 210

Gln Thr Arg His Tyr Leu His Thr Leu Trp Lys
1               5                   10

<210> SEQ ID NO 211
<211> LENGTH: 10
<212> TYPE: PRT
<213> ORGANISM: Artificial sequence
<220> FEATURE:
<223> OTHER INFORMATION: Peptide derived from HBV Polymerase protein

<400> SEQUENCE: 211

Thr Arg His Tyr Leu His Thr Leu Trp Lys
1               5                   10

<210> SEQ ID NO 212
<211> LENGTH: 9
<212> TYPE: PRT
<213> ORGANISM: Artificial sequence
<220> FEATURE:
<223> OTHER INFORMATION: Peptide derived from HBV Polymerase protein
```

```
<400> SEQUENCE: 212

Arg His Tyr Leu His Thr Leu Trp Lys
1               5

<210> SEQ ID NO 213
<211> LENGTH: 8
<212> TYPE: PRT
<213> ORGANISM: Artificial sequence
<220> FEATURE:
<223> OTHER INFORMATION: Peptide derived from HBV Polymerase protein

<400> SEQUENCE: 213

His Tyr Leu His Thr Leu Trp Lys
1               5

<210> SEQ ID NO 214
<211> LENGTH: 11
<212> TYPE: PRT
<213> ORGANISM: Artificial sequence
<220> FEATURE:
<223> OTHER INFORMATION: Peptide derived from HBV Polymerase protein

<400> SEQUENCE: 214

Thr Arg His Tyr Leu His Thr Leu Trp Lys Ala
1               5                   10

<210> SEQ ID NO 215
<211> LENGTH: 9
<212> TYPE: PRT
<213> ORGANISM: Artificial sequence
<220> FEATURE:
<223> OTHER INFORMATION: Peptide derived from HBV Polymerase protein

<400> SEQUENCE: 215

His Tyr Leu His Thr Leu Trp Lys Ala
1               5

<210> SEQ ID NO 216
<211> LENGTH: 11
<212> TYPE: PRT
<213> ORGANISM: Artificial sequence
<220> FEATURE:
<223> OTHER INFORMATION: Peptide derived from HBV Polymerase protein

<400> SEQUENCE: 216

Arg His Tyr Leu His Thr Leu Trp Lys Ala Gly
1               5                   10

<210> SEQ ID NO 217
<211> LENGTH: 10
<212> TYPE: PRT
<213> ORGANISM: Artificial sequence
<220> FEATURE:
<223> OTHER INFORMATION: Peptide derived from HBV Polymerase protein

<400> SEQUENCE: 217

His Tyr Leu His Thr Leu Trp Lys Ala Gly
1               5                   10

<210> SEQ ID NO 218
<211> LENGTH: 11
<212> TYPE: PRT
<213> ORGANISM: Artificial sequence
<220> FEATURE:
<223> OTHER INFORMATION: Peptide derived from HBV Polymerase protein

<400> SEQUENCE: 218
```

```
His Tyr Leu His Thr Leu Trp Lys Ala Gly Ile
1               5                   10

<210> SEQ ID NO 219
<211> LENGTH: 10
<212> TYPE: PRT
<213> ORGANISM: Artificial sequence
<220> FEATURE:
<223> OTHER INFORMATION: Peptide derived from HBV Polymerase protein

<400> SEQUENCE: 219

Tyr Leu His Thr Leu Trp Lys Ala Gly Ile
1               5                   10

<210> SEQ ID NO 220
<211> LENGTH: 8
<212> TYPE: PRT
<213> ORGANISM: Artificial sequence
<220> FEATURE:
<223> OTHER INFORMATION: Peptide derived from HBV Polymerase protein

<400> SEQUENCE: 220

His Thr Leu Trp Lys Ala Gly Ile
1               5

<210> SEQ ID NO 221
<211> LENGTH: 11
<212> TYPE: PRT
<213> ORGANISM: Artificial sequence
<220> FEATURE:
<223> OTHER INFORMATION: Peptide derived from HBV Polymerase protein

<400> SEQUENCE: 221

Tyr Leu His Thr Leu Trp Lys Ala Gly Ile Leu
1               5                   10

<210> SEQ ID NO 222
<211> LENGTH: 10
<212> TYPE: PRT
<213> ORGANISM: Artificial sequence
<220> FEATURE:
<223> OTHER INFORMATION: Peptide derived from HBV Polymerase protein

<400> SEQUENCE: 222

Leu His Thr Leu Trp Lys Ala Gly Ile Leu
1               5                   10

<210> SEQ ID NO 223
<211> LENGTH: 9
<212> TYPE: PRT
<213> ORGANISM: Artificial sequence
<220> FEATURE:
<223> OTHER INFORMATION: Peptide derived from HBV Polymerase protein

<400> SEQUENCE: 223

His Thr Leu Trp Lys Ala Gly Ile Leu
1               5

<210> SEQ ID NO 224
<211> LENGTH: 10
<212> TYPE: PRT
<213> ORGANISM: Artificial sequence
<220> FEATURE:
<223> OTHER INFORMATION: Peptide derived from HBV Polymerase protein

<400> SEQUENCE: 224
```

His Thr Leu Trp Lys Ala Gly Ile Leu Tyr
1               5                   10

<210> SEQ ID NO 225
<211> LENGTH: 9
<212> TYPE: PRT
<213> ORGANISM: Artificial sequence
<220> FEATURE:
<223> OTHER INFORMATION: Peptide derived from HBV Polymerase protein

<400> SEQUENCE: 225

Thr Leu Trp Lys Ala Gly Ile Leu Tyr
1               5

<210> SEQ ID NO 226
<211> LENGTH: 8
<212> TYPE: PRT
<213> ORGANISM: Artificial sequence
<220> FEATURE:
<223> OTHER INFORMATION: Peptide derived from HBV Polymerase protein

<400> SEQUENCE: 226

Leu Trp Lys Ala Gly Ile Leu Tyr
1               5

<210> SEQ ID NO 227
<211> LENGTH: 11
<212> TYPE: PRT
<213> ORGANISM: Artificial sequence
<220> FEATURE:
<223> OTHER INFORMATION: Peptide derived from HBV Polymerase protein

<400> SEQUENCE: 227

His Thr Leu Trp Lys Ala Gly Ile Leu Tyr Lys
1               5                   10

<210> SEQ ID NO 228
<211> LENGTH: 10
<212> TYPE: PRT
<213> ORGANISM: Artificial sequence
<220> FEATURE:
<223> OTHER INFORMATION: Peptide derived from HBV Polymerase protein

<400> SEQUENCE: 228

Thr Leu Trp Lys Ala Gly Ile Leu Tyr Lys
1               5                   10

<210> SEQ ID NO 229
<211> LENGTH: 9
<212> TYPE: PRT
<213> ORGANISM: Artificial sequence
<220> FEATURE:
<223> OTHER INFORMATION: Peptide derived from HBV Polymerase protein

<400> SEQUENCE: 229

Leu Trp Lys Ala Gly Ile Leu Tyr Lys
1               5

<210> SEQ ID NO 230
<211> LENGTH: 11
<212> TYPE: PRT
<213> ORGANISM: Artificial sequence
<220> FEATURE:
<223> OTHER INFORMATION: Peptide derived from HBV Polymerase protein

<400> SEQUENCE: 230

Thr Leu Trp Lys Ala Gly Ile Leu Tyr Lys Arg

```
1               5              10
```

```
<210> SEQ ID NO 231
<211> LENGTH: 10
<212> TYPE: PRT
<213> ORGANISM: Artificial sequence
<220> FEATURE:
<223> OTHER INFORMATION: Peptide derived from HBV Polymerase protein

<400> SEQUENCE: 231

Leu Trp Lys Ala Gly Ile Leu Tyr Lys Arg
1               5                  10

<210> SEQ ID NO 232
<211> LENGTH: 8
<212> TYPE: PRT
<213> ORGANISM: Artificial sequence
<220> FEATURE:
<223> OTHER INFORMATION: Peptide derived from HBV Polymerase protein

<400> SEQUENCE: 232

Lys Ala Gly Ile Leu Tyr Lys Arg
1               5

<210> SEQ ID NO 233
<211> LENGTH: 9
<212> TYPE: PRT
<213> ORGANISM: Artificial sequence
<220> FEATURE:
<223> OTHER INFORMATION: Peptide derived from HBV Polymerase protein

<400> SEQUENCE: 233

Ile Leu Tyr Lys Arg Glu Thr Thr Arg
1               5

<210> SEQ ID NO 234
<211> LENGTH: 11
<212> TYPE: PRT
<213> ORGANISM: Artificial sequence
<220> FEATURE:
<223> OTHER INFORMATION: Peptide derived from HBV Polymerase protein

<400> SEQUENCE: 234

Ile Leu Tyr Lys Arg Glu Thr Thr Arg Ser Ala
1               5                  10

<210> SEQ ID NO 235
<211> LENGTH: 11
<212> TYPE: PRT
<213> ORGANISM: Artificial sequence
<220> FEATURE:
<223> OTHER INFORMATION: Peptide derived from HBV Polymerase protein

<400> SEQUENCE: 235

Tyr Lys Arg Glu Thr Thr Arg Ser Ala Ser Phe
1               5                  10

<210> SEQ ID NO 236
<211> LENGTH: 10
<212> TYPE: PRT
<213> ORGANISM: Artificial sequence
<220> FEATURE:
<223> OTHER INFORMATION: Peptide derived from HBV Polymerase protein

<400> SEQUENCE: 236

Lys Arg Glu Thr Thr Arg Ser Ala Ser Phe
1               5                  10
```

<210> SEQ ID NO 237
<211> LENGTH: 9
<212> TYPE: PRT
<213> ORGANISM: Artificial sequence
<220> FEATURE:
<223> OTHER INFORMATION: Peptide derived from HBV Polymerase protein

<400> SEQUENCE: 237

Arg Glu Thr Thr Arg Ser Ala Ser Phe
1               5

<210> SEQ ID NO 238
<211> LENGTH: 8
<212> TYPE: PRT
<213> ORGANISM: Artificial sequence
<220> FEATURE:
<223> OTHER INFORMATION: Peptide derived from HBV Polymerase protein

<400> SEQUENCE: 238

Glu Thr Thr Arg Ser Ala Ser Phe
1               5

<210> SEQ ID NO 239
<211> LENGTH: 10
<212> TYPE: PRT
<213> ORGANISM: Artificial sequence
<220> FEATURE:
<223> OTHER INFORMATION: Peptide derived from HBV Polymerase protein

<400> SEQUENCE: 239

Arg Ser Ala Ser Phe Cys Gly Ser Pro Tyr
1               5                   10

<210> SEQ ID NO 240
<211> LENGTH: 9
<212> TYPE: PRT
<213> ORGANISM: Artificial sequence
<220> FEATURE:
<223> OTHER INFORMATION: Peptide derived from HBV Polymerase protein

<400> SEQUENCE: 240

Ser Ala Ser Phe Cys Gly Ser Pro Tyr
1               5

<210> SEQ ID NO 241
<211> LENGTH: 8
<212> TYPE: PRT
<213> ORGANISM: Artificial sequence
<220> FEATURE:
<223> OTHER INFORMATION: Peptide derived from HBV Polymerase protein

<400> SEQUENCE: 241

Ala Ser Phe Cys Gly Ser Pro Tyr
1               5

<210> SEQ ID NO 242
<211> LENGTH: 10
<212> TYPE: PRT
<213> ORGANISM: Artificial sequence
<220> FEATURE:
<223> OTHER INFORMATION: Peptide derived from HBV Polymerase protein

<400> SEQUENCE: 242

Ser Ala Ser Phe Cys Gly Ser Pro Tyr Ser
1               5                   10

<210> SEQ ID NO 243
<211> LENGTH: 9
<212> TYPE: PRT
<213> ORGANISM: Artificial sequence
<220> FEATURE:
<223> OTHER INFORMATION: Peptide derived from HBV Polymerase protein

<400> SEQUENCE: 243

Ala Ser Phe Cys Gly Ser Pro Tyr Ser
1               5

<210> SEQ ID NO 244
<211> LENGTH: 11
<212> TYPE: PRT
<213> ORGANISM: Artificial sequence
<220> FEATURE:
<223> OTHER INFORMATION: Peptide derived from HBV Polymerase protein

<400> SEQUENCE: 244

Ser Ala Ser Phe Cys Gly Ser Pro Tyr Ser Trp
1               5                   10

<210> SEQ ID NO 245
<211> LENGTH: 10
<212> TYPE: PRT
<213> ORGANISM: Artificial sequence
<220> FEATURE:
<223> OTHER INFORMATION: Peptide derived from HBV Polymerase protein

<400> SEQUENCE: 245

Ala Ser Phe Cys Gly Ser Pro Tyr Ser Trp
1               5                   10

<210> SEQ ID NO 246
<211> LENGTH: 9
<212> TYPE: PRT
<213> ORGANISM: Artificial sequence
<220> FEATURE:
<223> OTHER INFORMATION: Peptide derived from HBV Polymerase protein

<400> SEQUENCE: 246

Ser Phe Cys Gly Ser Pro Tyr Ser Trp
1               5

<210> SEQ ID NO 247
<211> LENGTH: 11
<212> TYPE: PRT
<213> ORGANISM: Artificial sequence
<220> FEATURE:
<223> OTHER INFORMATION: Peptide derived from HBV Polymerase protein

<400> SEQUENCE: 247

Ser Gln Ser Gln Gly Ser Val Ser Ser Cys Trp
1               5                   10

<210> SEQ ID NO 248
<211> LENGTH: 10
<212> TYPE: PRT
<213> ORGANISM: Artificial sequence
<220> FEATURE:
<223> OTHER INFORMATION: Peptide derived from HBV Polymerase protein

<400> SEQUENCE: 248

Gln Ser Gln Gly Ser Val Ser Ser Cys Trp
1               5                   10

```
<210> SEQ ID NO 249
<211> LENGTH: 8
<212> TYPE: PRT
<213> ORGANISM: Artificial sequence
<220> FEATURE:
<223> OTHER INFORMATION: Peptide derived from HBV Polymerase protein

<400> SEQUENCE: 249

Gln Gly Ser Val Ser Ser Cys Trp
1               5

<210> SEQ ID NO 250
<211> LENGTH: 11
<212> TYPE: PRT
<213> ORGANISM: Artificial sequence
<220> FEATURE:
<223> OTHER INFORMATION: Peptide derived from HBV Polymerase protein

<400> SEQUENCE: 250

Gln Ser Gln Gly Ser Val Ser Ser Cys Trp Trp
1               5                   10

<210> SEQ ID NO 251
<211> LENGTH: 9
<212> TYPE: PRT
<213> ORGANISM: Artificial sequence
<220> FEATURE:
<223> OTHER INFORMATION: Peptide derived from HBV Polymerase protein

<400> SEQUENCE: 251

Gln Gly Ser Val Ser Ser Cys Trp Trp
1               5

<210> SEQ ID NO 252
<211> LENGTH: 8
<212> TYPE: PRT
<213> ORGANISM: Artificial sequence
<220> FEATURE:
<223> OTHER INFORMATION: Peptide derived from HBV Polymerase protein

<400> SEQUENCE: 252

Gly Ser Val Ser Ser Cys Trp Trp
1               5

<210> SEQ ID NO 253
<211> LENGTH: 11
<212> TYPE: PRT
<213> ORGANISM: Artificial sequence
<220> FEATURE:
<223> OTHER INFORMATION: Peptide derived from HBV Polymerase protein

<400> SEQUENCE: 253

Ser Gln Gly Ser Val Ser Ser Cys Trp Trp Leu
1               5                   10

<210> SEQ ID NO 254
<211> LENGTH: 10
<212> TYPE: PRT
<213> ORGANISM: Artificial sequence
<220> FEATURE:
<223> OTHER INFORMATION: Peptide derived from HBV Polymerase protein

<400> SEQUENCE: 254

Gly Ser Val Ser Ser Cys Trp Trp Leu Gln
1               5                   10

<210> SEQ ID NO 255
```

```
<211> LENGTH: 11
<212> TYPE: PRT
<213> ORGANISM: Artificial sequence
<220> FEATURE:
<223> OTHER INFORMATION: Peptide derived from HBV Polymerase protein

<400> SEQUENCE: 255

Gly Ser Val Ser Ser Cys Trp Trp Leu Gln Phe
1               5                   10

<210> SEQ ID NO 256
<211> LENGTH: 10
<212> TYPE: PRT
<213> ORGANISM: Artificial sequence
<220> FEATURE:
<223> OTHER INFORMATION: Peptide derived from HBV Polymerase protein

<400> SEQUENCE: 256

Ser Val Ser Ser Cys Trp Trp Leu Gln Phe
1               5                   10

<210> SEQ ID NO 257
<211> LENGTH: 9
<212> TYPE: PRT
<213> ORGANISM: Artificial sequence
<220> FEATURE:
<223> OTHER INFORMATION: Peptide derived from HBV Polymerase protein

<400> SEQUENCE: 257

Val Ser Ser Cys Trp Trp Leu Gln Phe
1               5

<210> SEQ ID NO 258
<211> LENGTH: 8
<212> TYPE: PRT
<213> ORGANISM: Artificial sequence
<220> FEATURE:
<223> OTHER INFORMATION: Peptide derived from HBV Polymerase protein

<400> SEQUENCE: 258

Ser Ser Cys Trp Trp Leu Gln Phe
1               5

<210> SEQ ID NO 259
<211> LENGTH: 11
<212> TYPE: PRT
<213> ORGANISM: Artificial sequence
<220> FEATURE:
<223> OTHER INFORMATION: Peptide derived from HBV Polymerase protein

<400> SEQUENCE: 259

Ser Val Ser Ser Cys Trp Trp Leu Gln Phe Arg
1               5                   10

<210> SEQ ID NO 260
<211> LENGTH: 10
<212> TYPE: PRT
<213> ORGANISM: Artificial sequence
<220> FEATURE:
<223> OTHER INFORMATION: Peptide derived from HBV Polymerase protein

<400> SEQUENCE: 260

Val Ser Ser Cys Trp Trp Leu Gln Phe Arg
1               5                   10

<210> SEQ ID NO 261
<211> LENGTH: 9
```

```
<212> TYPE: PRT
<213> ORGANISM: Artificial sequence
<220> FEATURE:
<223> OTHER INFORMATION: Peptide derived from HBV Polymerase protein

<400> SEQUENCE: 261

Ser Ser Cys Trp Trp Leu Gln Phe Arg
1               5

<210> SEQ ID NO 262
<211> LENGTH: 8
<212> TYPE: PRT
<213> ORGANISM: Artificial sequence
<220> FEATURE:
<223> OTHER INFORMATION: Peptide derived from HBV Polymerase protein

<400> SEQUENCE: 262

Ser Cys Trp Trp Leu Gln Phe Arg
1               5

<210> SEQ ID NO 263
<211> LENGTH: 8
<212> TYPE: PRT
<213> ORGANISM: Artificial sequence
<220> FEATURE:
<223> OTHER INFORMATION: Peptide derived from HBV Polymerase protein

<400> SEQUENCE: 263

Trp Leu Gln Phe Arg Asn Ser Lys
1               5

<210> SEQ ID NO 264
<211> LENGTH: 8
<212> TYPE: PRT
<213> ORGANISM: Artificial sequence
<220> FEATURE:
<223> OTHER INFORMATION: Peptide derived from HBV Polymerase protein

<400> SEQUENCE: 264

Leu Gln Phe Arg Asn Ser Lys Pro
1               5

<210> SEQ ID NO 265
<211> LENGTH: 10
<212> TYPE: PRT
<213> ORGANISM: Artificial sequence
<220> FEATURE:
<223> OTHER INFORMATION: Peptide derived from HBV Polymerase protein

<400> SEQUENCE: 265

Trp Leu Gln Phe Arg Asn Ser Lys Pro Cys
1               5                   10

<210> SEQ ID NO 266
<211> LENGTH: 10
<212> TYPE: PRT
<213> ORGANISM: Artificial sequence
<220> FEATURE:
<223> OTHER INFORMATION: Peptide derived from HBV Polymerase protein

<400> SEQUENCE: 266

Leu Gln Phe Arg Asn Ser Lys Pro Cys Ser
1               5                   10

<210> SEQ ID NO 267
<211> LENGTH: 11
<212> TYPE: PRT
```

```
<213> ORGANISM: Artificial sequence
<220> FEATURE:
<223> OTHER INFORMATION: Peptide derived from HBV Polymerase protein

<400> SEQUENCE: 267

Gln Phe Arg Asn Ser Lys Pro Cys Ser Glu Tyr
1               5                   10

<210> SEQ ID NO 268
<211> LENGTH: 9
<212> TYPE: PRT
<213> ORGANISM: Artificial sequence
<220> FEATURE:
<223> OTHER INFORMATION: Peptide derived from HBV Polymerase protein

<400> SEQUENCE: 268

Arg Asn Ser Lys Pro Cys Ser Glu Tyr
1               5

<210> SEQ ID NO 269
<211> LENGTH: 8
<212> TYPE: PRT
<213> ORGANISM: Artificial sequence
<220> FEATURE:
<223> OTHER INFORMATION: Peptide derived from HBV Polymerase protein

<400> SEQUENCE: 269

Asn Ser Lys Pro Cys Ser Glu Tyr
1               5

<210> SEQ ID NO 270
<211> LENGTH: 8
<212> TYPE: PRT
<213> ORGANISM: Artificial sequence
<220> FEATURE:
<223> OTHER INFORMATION: Peptide derived from HBV Polymerase protein

<400> SEQUENCE: 270

Cys Ser Glu Tyr Cys Leu Ser His
1               5

<210> SEQ ID NO 271
<211> LENGTH: 8
<212> TYPE: PRT
<213> ORGANISM: Artificial sequence
<220> FEATURE:
<223> OTHER INFORMATION: Peptide derived from HBV Polymerase protein

<400> SEQUENCE: 271

Ser Glu Tyr Cys Leu Ser His Leu
1               5

<210> SEQ ID NO 272
<211> LENGTH: 11
<212> TYPE: PRT
<213> ORGANISM: Artificial sequence
<220> FEATURE:
<223> OTHER INFORMATION: Peptide derived from HBV Polymerase protein

<400> SEQUENCE: 272

Pro Cys Ser Glu Tyr Cys Leu Ser His Leu Val
1               5                   10

<210> SEQ ID NO 273
<211> LENGTH: 9
<212> TYPE: PRT
<213> ORGANISM: Artificial sequence
```

```
<220> FEATURE:
<223> OTHER INFORMATION: Peptide derived from HBV Polymerase protein

<400> SEQUENCE: 273

Ser Glu Tyr Cys Leu Ser His Leu Val
1               5

<210> SEQ ID NO 274
<211> LENGTH: 10
<212> TYPE: PRT
<213> ORGANISM: Artificial sequence
<220> FEATURE:
<223> OTHER INFORMATION: Peptide derived from HBV Polymerase protein

<400> SEQUENCE: 274

Ser Glu Tyr Cys Leu Ser His Leu Val Asn
1               5                   10

<210> SEQ ID NO 275
<211> LENGTH: 11
<212> TYPE: PRT
<213> ORGANISM: Artificial sequence
<220> FEATURE:
<223> OTHER INFORMATION: Peptide derived from HBV Polymerase protein

<400> SEQUENCE: 275

Ser Glu Tyr Cys Leu Ser His Leu Val Asn Leu
1               5                   10

<210> SEQ ID NO 276
<211> LENGTH: 10
<212> TYPE: PRT
<213> ORGANISM: Artificial sequence
<220> FEATURE:
<223> OTHER INFORMATION: Peptide derived from HBV Polymerase protein

<400> SEQUENCE: 276

Glu Tyr Cys Leu Ser His Leu Val Asn Leu
1               5                   10

<210> SEQ ID NO 277

<400> SEQUENCE: 277

000

<210> SEQ ID NO 278
<211> LENGTH: 9
<212> TYPE: PRT
<213> ORGANISM: Artificial sequence
<220> FEATURE:
<223> OTHER INFORMATION: Peptide derived from HBV Polymerase protein

<400> SEQUENCE: 278

Ala Glu Ser Arg Leu Val Val Asp Phe
1               5

<210> SEQ ID NO 279
<211> LENGTH: 11
<212> TYPE: PRT
<213> ORGANISM: Artificial sequence
<220> FEATURE:
<223> OTHER INFORMATION: Peptide derived from HBV Polymerase protein

<400> SEQUENCE: 279

Ala Glu Ser Arg Leu Val Val Asp Phe Ser Gln
1               5                   10
```

<210> SEQ ID NO 280
<211> LENGTH: 11
<212> TYPE: PRT
<213> ORGANISM: Artificial sequence
<220> FEATURE:
<223> OTHER INFORMATION: Peptide derived from HBV Polymerase protein

<400> SEQUENCE: 280

Glu Ser Arg Leu Val Val Asp Phe Ser Gln Phe
1               5                   10

<210> SEQ ID NO 281
<211> LENGTH: 10
<212> TYPE: PRT
<213> ORGANISM: Artificial sequence
<220> FEATURE:
<223> OTHER INFORMATION: Peptide derived from HBV Polymerase protein

<400> SEQUENCE: 281

Ser Arg Leu Val Val Asp Phe Ser Gln Phe
1               5                   10

<210> SEQ ID NO 282
<211> LENGTH: 9
<212> TYPE: PRT
<213> ORGANISM: Artificial sequence
<220> FEATURE:
<223> OTHER INFORMATION: Peptide derived from HBV Polymerase protein

<400> SEQUENCE: 282

Arg Leu Val Val Asp Phe Ser Gln Phe
1               5

<210> SEQ ID NO 283
<211> LENGTH: 8
<212> TYPE: PRT
<213> ORGANISM: Artificial sequence
<220> FEATURE:
<223> OTHER INFORMATION: Peptide derived from HBV Polymerase protein

<400> SEQUENCE: 283

Leu Val Val Asp Phe Ser Gln Phe
1               5

<210> SEQ ID NO 284
<211> LENGTH: 11
<212> TYPE: PRT
<213> ORGANISM: Artificial sequence
<220> FEATURE:
<223> OTHER INFORMATION: Peptide derived from HBV Polymerase protein

<400> SEQUENCE: 284

Arg Leu Val Val Asp Phe Ser Gln Phe Ser Arg
1               5                   10

<210> SEQ ID NO 285
<211> LENGTH: 10
<212> TYPE: PRT
<213> ORGANISM: Artificial sequence
<220> FEATURE:
<223> OTHER INFORMATION: Peptide derived from HBV Polymerase protein

<400> SEQUENCE: 285

Leu Val Val Asp Phe Ser Gln Phe Ser Arg
1               5                   10

<210> SEQ ID NO 286
<211> LENGTH: 9
<212> TYPE: PRT
<213> ORGANISM: Artificial sequence
<220> FEATURE:
<223> OTHER INFORMATION: Peptide derived from HBV Polymerase protein

<400> SEQUENCE: 286

Val Val Asp Phe Ser Gln Phe Ser Arg
1               5

<210> SEQ ID NO 287
<211> LENGTH: 11
<212> TYPE: PRT
<213> ORGANISM: Artificial sequence
<220> FEATURE:
<223> OTHER INFORMATION: Peptide derived from HBV Polymerase protein

<400> SEQUENCE: 287

Leu Val Val Asp Phe Ser Gln Phe Ser Arg Gly
1               5                   10

<210> SEQ ID NO 288
<211> LENGTH: 10
<212> TYPE: PRT
<213> ORGANISM: Artificial sequence
<220> FEATURE:
<223> OTHER INFORMATION: Peptide derived from HBV Polymerase protein

<400> SEQUENCE: 288

Val Asp Phe Ser Gln Phe Ser Arg Gly Ile
1               5                   10

<210> SEQ ID NO 289
<211> LENGTH: 11
<212> TYPE: PRT
<213> ORGANISM: Artificial sequence
<220> FEATURE:
<223> OTHER INFORMATION: Peptide derived from HBV Polymerase protein

<400> SEQUENCE: 289

Asp Phe Ser Gln Phe Ser Arg Gly Ile Ser Arg
1               5                   10

<210> SEQ ID NO 290
<211> LENGTH: 10
<212> TYPE: PRT
<213> ORGANISM: Artificial sequence
<220> FEATURE:
<223> OTHER INFORMATION: Peptide derived from HBV Polymerase protein

<400> SEQUENCE: 290

Phe Ser Gln Phe Ser Arg Gly Ile Ser Arg
1               5                   10

<210> SEQ ID NO 291
<211> LENGTH: 9
<212> TYPE: PRT
<213> ORGANISM: Artificial sequence
<220> FEATURE:
<223> OTHER INFORMATION: Peptide derived from HBV Polymerase protein

<400> SEQUENCE: 291

Ser Gln Phe Ser Arg Gly Ile Ser Arg
1               5

```
<210> SEQ ID NO 292
<211> LENGTH: 8
<212> TYPE: PRT
<213> ORGANISM: Artificial sequence
<220> FEATURE:
<223> OTHER INFORMATION: Peptide derived from HBV Polymerase protein

<400> SEQUENCE: 292

Gln Phe Ser Arg Gly Ile Ser Arg
1               5

<210> SEQ ID NO 293
<211> LENGTH: 10
<212> TYPE: PRT
<213> ORGANISM: Artificial sequence
<220> FEATURE:
<223> OTHER INFORMATION: Peptide derived from HBV Polymerase protein

<400> SEQUENCE: 293

Ser Gln Phe Ser Arg Gly Ile Ser Arg Val
1               5                   10

<210> SEQ ID NO 294
<211> LENGTH: 8
<212> TYPE: PRT
<213> ORGANISM: Artificial sequence
<220> FEATURE:
<223> OTHER INFORMATION: Peptide derived from HBV Polymerase protein

<400> SEQUENCE: 294

Ser Arg Gly Ile Ser Arg Val Ser
1               5

<210> SEQ ID NO 295
<211> LENGTH: 10
<212> TYPE: PRT
<213> ORGANISM: Artificial sequence
<220> FEATURE:
<223> OTHER INFORMATION: Peptide derived from HBV Polymerase protein

<400> SEQUENCE: 295

Phe Ser Arg Gly Ile Ser Arg Val Ser Trp
1               5                   10

<210> SEQ ID NO 296
<211> LENGTH: 9
<212> TYPE: PRT
<213> ORGANISM: Artificial sequence
<220> FEATURE:
<223> OTHER INFORMATION: Peptide derived from HBV Polymerase protein

<400> SEQUENCE: 296

Ser Arg Gly Ile Ser Arg Val Ser Trp
1               5

<210> SEQ ID NO 297
<211> LENGTH: 8
<212> TYPE: PRT
<213> ORGANISM: Artificial sequence
<220> FEATURE:
<223> OTHER INFORMATION: Peptide derived from HBV Polymerase protein

<400> SEQUENCE: 297

Arg Gly Ile Ser Arg Val Ser Trp
1               5

<210> SEQ ID NO 298
```

```
<211> LENGTH: 9
<212> TYPE: PRT
<213> ORGANISM: Artificial sequence
<220> FEATURE:
<223> OTHER INFORMATION: Peptide derived from HBV Polymerase protein

<400> SEQUENCE: 298

Gly Ile Ser Arg Val Ser Trp Pro Lys
1               5

<210> SEQ ID NO 299
<211> LENGTH: 8
<212> TYPE: PRT
<213> ORGANISM: Artificial sequence
<220> FEATURE:
<223> OTHER INFORMATION: Peptide derived from HBV Polymerase protein

<400> SEQUENCE: 299

Ile Ser Arg Val Ser Trp Pro Lys
1               5

<210> SEQ ID NO 300
<211> LENGTH: 11
<212> TYPE: PRT
<213> ORGANISM: Artificial sequence
<220> FEATURE:
<223> OTHER INFORMATION: Peptide derived from HBV Polymerase protein

<400> SEQUENCE: 300

Arg Gly Ile Ser Arg Val Ser Trp Pro Lys Phe
1               5                   10

<210> SEQ ID NO 301
<211> LENGTH: 10
<212> TYPE: PRT
<213> ORGANISM: Artificial sequence
<220> FEATURE:
<223> OTHER INFORMATION: Peptide derived from HBV Polymerase protein

<400> SEQUENCE: 301

Gly Ile Ser Arg Val Ser Trp Pro Lys Phe
1               5                   10

<210> SEQ ID NO 302
<211> LENGTH: 9
<212> TYPE: PRT
<213> ORGANISM: Artificial sequence
<220> FEATURE:
<223> OTHER INFORMATION: Peptide derived from HBV Polymerase protein

<400> SEQUENCE: 302

Ile Ser Arg Val Ser Trp Pro Lys Phe
1               5

<210> SEQ ID NO 303
<211> LENGTH: 8
<212> TYPE: PRT
<213> ORGANISM: Artificial sequence
<220> FEATURE:
<223> OTHER INFORMATION: Peptide derived from HBV Polymerase protein

<400> SEQUENCE: 303

Ser Arg Val Ser Trp Pro Lys Phe
1               5

<210> SEQ ID NO 304
<211> LENGTH: 8
```

```
<212> TYPE: PRT
<213> ORGANISM: Artificial sequence
<220> FEATURE:
<223> OTHER INFORMATION: Peptide derived from HBV Polymerase protein

<400> SEQUENCE: 304

Arg Val Ser Trp Pro Lys Phe Ala
1               5

<210> SEQ ID NO 305
<211> LENGTH: 11
<212> TYPE: PRT
<213> ORGANISM: Artificial sequence
<220> FEATURE:
<223> OTHER INFORMATION: Peptide derived from HBV Polymerase protein

<400> SEQUENCE: 305

Ile Ser Arg Val Ser Trp Pro Lys Phe Ala Val
1               5                   10

<210> SEQ ID NO 306
<211> LENGTH: 10
<212> TYPE: PRT
<213> ORGANISM: Artificial sequence
<220> FEATURE:
<223> OTHER INFORMATION: Peptide derived from HBV Polymerase protein

<400> SEQUENCE: 306

Ser Arg Val Ser Trp Pro Lys Phe Ala Val
1               5                   10

<210> SEQ ID NO 307
<211> LENGTH: 9
<212> TYPE: PRT
<213> ORGANISM: Artificial sequence
<220> FEATURE:
<223> OTHER INFORMATION: Peptide derived from HBV Polymerase protein

<400> SEQUENCE: 307

Arg Val Ser Trp Pro Lys Phe Ala Val
1               5

<210> SEQ ID NO 308
<211> LENGTH: 8
<212> TYPE: PRT
<213> ORGANISM: Artificial sequence
<220> FEATURE:
<223> OTHER INFORMATION: Peptide derived from HBV Polymerase protein

<400> SEQUENCE: 308

Val Ser Trp Pro Lys Phe Ala Val
1               5

<210> SEQ ID NO 309
<211> LENGTH: 8
<212> TYPE: PRT
<213> ORGANISM: Artificial sequence
<220> FEATURE:
<223> OTHER INFORMATION: Peptide derived from HBV Polymerase protein

<400> SEQUENCE: 309

Ser Trp Pro Lys Phe Ala Val Pro
1               5

<210> SEQ ID NO 310
<211> LENGTH: 11
<212> TYPE: PRT
```

```
<213> ORGANISM: Artificial sequence
<220> FEATURE:
<223> OTHER INFORMATION: Peptide derived from HBV Polymerase protein

<400> SEQUENCE: 310

Val Ser Trp Pro Lys Phe Ala Val Pro Asn Leu
1               5                   10

<210> SEQ ID NO 311
<211> LENGTH: 10
<212> TYPE: PRT
<213> ORGANISM: Artificial sequence
<220> FEATURE:
<223> OTHER INFORMATION: Peptide derived from HBV Polymerase protein

<400> SEQUENCE: 311

Ser Trp Pro Lys Phe Ala Val Pro Asn Leu
1               5                   10

<210> SEQ ID NO 312
<211> LENGTH: 9
<212> TYPE: PRT
<213> ORGANISM: Artificial sequence
<220> FEATURE:
<223> OTHER INFORMATION: Peptide derived from HBV Polymerase protein

<400> SEQUENCE: 312

Trp Pro Lys Phe Ala Val Pro Asn Leu
1               5

<210> SEQ ID NO 313
<211> LENGTH: 9
<212> TYPE: PRT
<213> ORGANISM: Artificial sequence
<220> FEATURE:
<223> OTHER INFORMATION: Peptide derived from HBV Polymerase protein

<400> SEQUENCE: 313

Phe Ala Val Pro Asn Leu Gln Ser Leu
1               5

<210> SEQ ID NO 314
<211> LENGTH: 8
<212> TYPE: PRT
<213> ORGANISM: Artificial sequence
<220> FEATURE:
<223> OTHER INFORMATION: Peptide derived from HBV Polymerase protein

<400> SEQUENCE: 314

Ala Val Pro Asn Leu Gln Ser Leu
1               5

<210> SEQ ID NO 315

<400> SEQUENCE: 315

000

<210> SEQ ID NO 316
<211> LENGTH: 8
<212> TYPE: PRT
<213> ORGANISM: Artificial sequence
<220> FEATURE:
<223> OTHER INFORMATION: Peptide derived from HBV Polymerase protein

<400> SEQUENCE: 316

Leu Leu Ser Ser Asn Leu Ser Trp
```

```
1               5
```

<210> SEQ ID NO 317
<211> LENGTH: 10
<212> TYPE: PRT
<213> ORGANISM: Artificial sequence
<220> FEATURE:
<223> OTHER INFORMATION: Peptide derived from HBV Polymerase protein

<400> SEQUENCE: 317

```
Asn Leu Leu Ser Ser Asn Leu Ser Trp Leu
1               5                   10
```

<210> SEQ ID NO 318
<211> LENGTH: 9
<212> TYPE: PRT
<213> ORGANISM: Artificial sequence
<220> FEATURE:
<223> OTHER INFORMATION: Peptide derived from HBV Polymerase protein

<400> SEQUENCE: 318

```
Leu Leu Ser Ser Asn Leu Ser Trp Leu
1               5
```

<210> SEQ ID NO 319
<211> LENGTH: 8
<212> TYPE: PRT
<213> ORGANISM: Artificial sequence
<220> FEATURE:
<223> OTHER INFORMATION: Peptide derived from HBV Polymerase protein

<400> SEQUENCE: 319

```
Leu Ser Ser Asn Leu Ser Trp Leu
1               5
```

<210> SEQ ID NO 320
<211> LENGTH: 9
<212> TYPE: PRT
<213> ORGANISM: Artificial sequence
<220> FEATURE:
<223> OTHER INFORMATION: Peptide derived from HBV Polymerase protein

<400> SEQUENCE: 320

```
Leu Ser Ser Asn Leu Ser Trp Leu Ser
1               5
```

<210> SEQ ID NO 321
<211> LENGTH: 11
<212> TYPE: PRT
<213> ORGANISM: Artificial sequence
<220> FEATURE:
<223> OTHER INFORMATION: Peptide derived from HBV Polymerase protein

<400> SEQUENCE: 321

```
Leu Leu Ser Ser Asn Leu Ser Trp Leu Ser Leu
1               5                   10
```

<210> SEQ ID NO 322
<211> LENGTH: 10
<212> TYPE: PRT
<213> ORGANISM: Artificial sequence
<220> FEATURE:
<223> OTHER INFORMATION: Peptide derived from HBV Polymerase protein

<400> SEQUENCE: 322

```
Leu Ser Ser Asn Leu Ser Trp Leu Ser Leu
1               5                   10
```

```
<210> SEQ ID NO 323
<211> LENGTH: 10
<212> TYPE: PRT
<213> ORGANISM: Artificial sequence
<220> FEATURE:
<223> OTHER INFORMATION: Peptide derived from HBV Polymerase protein

<400> SEQUENCE: 323

Ser Ser Asn Leu Ser Trp Leu Ser Leu Asp
1               5                   10

<210> SEQ ID NO 324
<211> LENGTH: 11
<212> TYPE: PRT
<213> ORGANISM: Artificial sequence
<220> FEATURE:
<223> OTHER INFORMATION: Peptide derived from HBV Polymerase protein

<400> SEQUENCE: 324

Ser Ser Asn Leu Ser Trp Leu Ser Leu Asp Val
1               5                   10

<210> SEQ ID NO 325
<211> LENGTH: 9
<212> TYPE: PRT
<213> ORGANISM: Artificial sequence
<220> FEATURE:
<223> OTHER INFORMATION: Peptide derived from HBV Polymerase protein

<400> SEQUENCE: 325

Asn Leu Ser Trp Leu Ser Leu Asp Val
1               5

<210> SEQ ID NO 326
<211> LENGTH: 8
<212> TYPE: PRT
<213> ORGANISM: Artificial sequence
<220> FEATURE:
<223> OTHER INFORMATION: Peptide derived from HBV Polymerase protein

<400> SEQUENCE: 326

Leu Ser Trp Leu Ser Leu Asp Val
1               5

<210> SEQ ID NO 327
<211> LENGTH: 11
<212> TYPE: PRT
<213> ORGANISM: Artificial sequence
<220> FEATURE:
<223> OTHER INFORMATION: Peptide derived from HBV Polymerase protein

<400> SEQUENCE: 327

Leu Ser Trp Leu Ser Leu Asp Val Ser Ala Ala
1               5                   10

<210> SEQ ID NO 328
<211> LENGTH: 9
<212> TYPE: PRT
<213> ORGANISM: Artificial sequence
<220> FEATURE:
<223> OTHER INFORMATION: Peptide derived from HBV Polymerase protein

<400> SEQUENCE: 328

Trp Leu Ser Leu Asp Val Ser Ala Ala
1               5
```

<210> SEQ ID NO 329
<211> LENGTH: 11
<212> TYPE: PRT
<213> ORGANISM: Artificial sequence
<220> FEATURE:
<223> OTHER INFORMATION: Peptide derived from HBV Polymerase protein

<400> SEQUENCE: 329

Ser Trp Leu Ser Leu Asp Val Ser Ala Ala Phe
1               5                   10

<210> SEQ ID NO 330
<211> LENGTH: 10
<212> TYPE: PRT
<213> ORGANISM: Artificial sequence
<220> FEATURE:
<223> OTHER INFORMATION: Peptide derived from HBV Polymerase protein

<400> SEQUENCE: 330

Trp Leu Ser Leu Asp Val Ser Ala Ala Phe
1               5                   10

<210> SEQ ID NO 331
<211> LENGTH: 9
<212> TYPE: PRT
<213> ORGANISM: Artificial sequence
<220> FEATURE:
<223> OTHER INFORMATION: Peptide derived from HBV Polymerase protein

<400> SEQUENCE: 331

Leu Ser Leu Asp Val Ser Ala Ala Phe
1               5

<210> SEQ ID NO 332
<211> LENGTH: 11
<212> TYPE: PRT
<213> ORGANISM: Artificial sequence
<220> FEATURE:
<223> OTHER INFORMATION: Peptide derived from HBV Polymerase protein

<400> SEQUENCE: 332

Trp Leu Ser Leu Asp Val Ser Ala Ala Phe Tyr
1               5                   10

<210> SEQ ID NO 333
<211> LENGTH: 10
<212> TYPE: PRT
<213> ORGANISM: Artificial sequence
<220> FEATURE:
<223> OTHER INFORMATION: Peptide derived from HBV Polymerase protein

<400> SEQUENCE: 333

Leu Ser Leu Asp Val Ser Ala Ala Phe Tyr
1               5                   10

<210> SEQ ID NO 334
<211> LENGTH: 9
<212> TYPE: PRT
<213> ORGANISM: Artificial sequence
<220> FEATURE:
<223> OTHER INFORMATION: Peptide derived from HBV Polymerase protein

<400> SEQUENCE: 334

Ser Leu Asp Val Ser Ala Ala Phe Tyr
1               5

```
<210> SEQ ID NO 335
<211> LENGTH: 8
<212> TYPE: PRT
<213> ORGANISM: Artificial sequence
<220> FEATURE:
<223> OTHER INFORMATION: Peptide derived from HBV Polymerase protein

<400> SEQUENCE: 335

Leu Asp Val Ser Ala Ala Phe Tyr
1               5

<210> SEQ ID NO 336
<211> LENGTH: 10
<212> TYPE: PRT
<213> ORGANISM: Artificial sequence
<220> FEATURE:
<223> OTHER INFORMATION: Peptide derived from HBV Polymerase protein

<400> SEQUENCE: 336

Leu Asp Val Ser Ala Ala Phe Tyr His Ile
1               5                   10

<210> SEQ ID NO 337
<211> LENGTH: 9
<212> TYPE: PRT
<213> ORGANISM: Artificial sequence
<220> FEATURE:
<223> OTHER INFORMATION: Peptide derived from HBV Polymerase protein

<400> SEQUENCE: 337

Asp Val Ser Ala Ala Phe Tyr His Ile
1               5

<210> SEQ ID NO 338
<211> LENGTH: 8
<212> TYPE: PRT
<213> ORGANISM: Artificial sequence
<220> FEATURE:
<223> OTHER INFORMATION: Peptide derived from HBV Polymerase protein

<400> SEQUENCE: 338

Val Ser Ala Ala Phe Tyr His Ile
1               5

<210> SEQ ID NO 339
<211> LENGTH: 11
<212> TYPE: PRT
<213> ORGANISM: Artificial sequence
<220> FEATURE:
<223> OTHER INFORMATION: Peptide derived from HBV Polymerase protein

<400> SEQUENCE: 339

Asp Val Ser Ala Ala Phe Tyr His Ile Pro Leu
1               5                   10

<210> SEQ ID NO 340
<211> LENGTH: 10
<212> TYPE: PRT
<213> ORGANISM: Artificial sequence
<220> FEATURE:
<223> OTHER INFORMATION: Peptide derived from HBV Polymerase protein

<400> SEQUENCE: 340

Val Ser Ala Ala Phe Tyr His Ile Pro Leu
1               5                   10

<210> SEQ ID NO 341
```

```
<211> LENGTH: 9
<212> TYPE: PRT
<213> ORGANISM: Artificial sequence
<220> FEATURE:
<223> OTHER INFORMATION: Peptide derived from HBV Polymerase protein

<400> SEQUENCE: 341

Ser Ala Ala Phe Tyr His Ile Pro Leu
1               5

<210> SEQ ID NO 342
<211> LENGTH: 8
<212> TYPE: PRT
<213> ORGANISM: Artificial sequence
<220> FEATURE:
<223> OTHER INFORMATION: Peptide derived from HBV Polymerase protein

<400> SEQUENCE: 342

Ala Ala Phe Tyr His Ile Pro Leu
1               5

<210> SEQ ID NO 343
<211> LENGTH: 10
<212> TYPE: PRT
<213> ORGANISM: Artificial sequence
<220> FEATURE:
<223> OTHER INFORMATION: Peptide derived from HBV Polymerase protein

<400> SEQUENCE: 343

Ser Ala Ala Phe Tyr His Ile Pro Leu His
1               5                   10

<210> SEQ ID NO 344
<211> LENGTH: 11
<212> TYPE: PRT
<213> ORGANISM: Artificial sequence
<220> FEATURE:
<223> OTHER INFORMATION: Peptide derived from HBV Polymerase protein

<400> SEQUENCE: 344

Ala Ala Phe Tyr His Ile Pro Leu His Pro Ala
1               5                   10

<210> SEQ ID NO 345
<211> LENGTH: 8
<212> TYPE: PRT
<213> ORGANISM: Artificial sequence
<220> FEATURE:
<223> OTHER INFORMATION: Peptide derived from HBV Polymerase protein

<400> SEQUENCE: 345

Tyr His Ile Pro Leu His Pro Ala
1               5

<210> SEQ ID NO 346
<211> LENGTH: 9
<212> TYPE: PRT
<213> ORGANISM: Artificial sequence
<220> FEATURE:
<223> OTHER INFORMATION: Peptide derived from HBV Polymerase protein

<400> SEQUENCE: 346

Tyr His Ile Pro Leu His Pro Ala Ala
1               5

<210> SEQ ID NO 347
<211> LENGTH: 11
```

```
<212> TYPE: PRT
<213> ORGANISM: Artificial sequence
<220> FEATURE:
<223> OTHER INFORMATION: Peptide derived from HBV Polymerase protein

<400> SEQUENCE: 347

Phe Tyr His Ile Pro Leu His Pro Ala Ala Met
1               5                   10

<210> SEQ ID NO 348
<211> LENGTH: 10
<212> TYPE: PRT
<213> ORGANISM: Artificial sequence
<220> FEATURE:
<223> OTHER INFORMATION: Peptide derived from HBV Polymerase protein

<400> SEQUENCE: 348

Tyr His Ile Pro Leu His Pro Ala Ala Met
1               5                   10

<210> SEQ ID NO 349
<211> LENGTH: 9
<212> TYPE: PRT
<213> ORGANISM: Artificial sequence
<220> FEATURE:
<223> OTHER INFORMATION: Peptide derived from HBV Polymerase protein

<400> SEQUENCE: 349

His Ile Pro Leu His Pro Ala Ala Met
1               5

<210> SEQ ID NO 350
<211> LENGTH: 8
<212> TYPE: PRT
<213> ORGANISM: Artificial sequence
<220> FEATURE:
<223> OTHER INFORMATION: Peptide derived from HBV Polymerase protein

<400> SEQUENCE: 350

Ile Pro Leu His Pro Ala Ala Met
1               5

<210> SEQ ID NO 351
<211> LENGTH: 11
<212> TYPE: PRT
<213> ORGANISM: Artificial sequence
<220> FEATURE:
<223> OTHER INFORMATION: Peptide derived from HBV Polymerase protein

<400> SEQUENCE: 351

Ile Pro Leu His Pro Ala Ala Met Pro His Leu
1               5                   10

<210> SEQ ID NO 352
<211> LENGTH: 9
<212> TYPE: PRT
<213> ORGANISM: Artificial sequence
<220> FEATURE:
<223> OTHER INFORMATION: Peptide derived from HBV Polymerase protein

<400> SEQUENCE: 352

Leu His Pro Ala Ala Met Pro His Leu
1               5

<210> SEQ ID NO 353
<211> LENGTH: 8
<212> TYPE: PRT
```

```
<213> ORGANISM: Artificial sequence
<220> FEATURE:
<223> OTHER INFORMATION: Peptide derived from HBV Polymerase protein

<400> SEQUENCE: 353

His Pro Ala Ala Met Pro His Leu
1               5

<210> SEQ ID NO 354
<211> LENGTH: 10
<212> TYPE: PRT
<213> ORGANISM: Artificial sequence
<220> FEATURE:
<223> OTHER INFORMATION: Peptide derived from HBV Polymerase protein

<400> SEQUENCE: 354

Leu His Pro Ala Ala Met Pro His Leu Leu
1               5                   10

<210> SEQ ID NO 355
<211> LENGTH: 9
<212> TYPE: PRT
<213> ORGANISM: Artificial sequence
<220> FEATURE:
<223> OTHER INFORMATION: Peptide derived from HBV Polymerase protein

<400> SEQUENCE: 355

His Pro Ala Ala Met Pro His Leu Leu
1               5

<210> SEQ ID NO 356
<211> LENGTH: 11
<212> TYPE: PRT
<213> ORGANISM: Artificial sequence
<220> FEATURE:
<223> OTHER INFORMATION: Peptide derived from HBV Polymerase protein

<400> SEQUENCE: 356

Leu His Pro Ala Ala Met Pro His Leu Leu Ile
1               5                   10

<210> SEQ ID NO 357
<211> LENGTH: 10
<212> TYPE: PRT
<213> ORGANISM: Artificial sequence
<220> FEATURE:
<223> OTHER INFORMATION: Peptide derived from HBV Polymerase protein

<400> SEQUENCE: 357

His Pro Ala Ala Met Pro His Leu Leu Ile
1               5                   10

<210> SEQ ID NO 358
<211> LENGTH: 8
<212> TYPE: PRT
<213> ORGANISM: Artificial sequence
<220> FEATURE:
<223> OTHER INFORMATION: Peptide derived from HBV Polymerase protein

<400> SEQUENCE: 358

Ala Ala Met Pro His Leu Leu Ile
1               5

<210> SEQ ID NO 359
<211> LENGTH: 11
<212> TYPE: PRT
<213> ORGANISM: Artificial sequence
```

```
<220> FEATURE:
<223> OTHER INFORMATION: Peptide derived from HBV Polymerase protein

<400> SEQUENCE: 359

His Pro Ala Ala Met Pro His Leu Leu Ile Gly
1               5                   10

<210> SEQ ID NO 360
<211> LENGTH: 8
<212> TYPE: PRT
<213> ORGANISM: Artificial sequence
<220> FEATURE:
<223> OTHER INFORMATION: Peptide derived from HBV Polymerase protein

<400> SEQUENCE: 360

Met Pro His Leu Leu Ile Gly Ser
1               5

<210> SEQ ID NO 361
<211> LENGTH: 9
<212> TYPE: PRT
<213> ORGANISM: Artificial sequence
<220> FEATURE:
<223> OTHER INFORMATION: Peptide derived from HBV Polymerase protein

<400> SEQUENCE: 361

Met Pro His Leu Leu Ile Gly Ser Ser
1               5

<210> SEQ ID NO 362
<211> LENGTH: 10
<212> TYPE: PRT
<213> ORGANISM: Artificial sequence
<220> FEATURE:
<223> OTHER INFORMATION: Peptide derived from HBV Polymerase protein

<400> SEQUENCE: 362

Met Pro His Leu Leu Ile Gly Ser Ser Gly
1               5                   10

<210> SEQ ID NO 363
<211> LENGTH: 11
<212> TYPE: PRT
<213> ORGANISM: Artificial sequence
<220> FEATURE:
<223> OTHER INFORMATION: Peptide derived from HBV Polymerase protein

<400> SEQUENCE: 363

Met Pro His Leu Leu Ile Gly Ser Ser Gly Leu
1               5                   10

<210> SEQ ID NO 364
<211> LENGTH: 9
<212> TYPE: PRT
<213> ORGANISM: Artificial sequence
<220> FEATURE:
<223> OTHER INFORMATION: Peptide derived from HBV Polymerase protein

<400> SEQUENCE: 364

His Leu Leu Ile Gly Ser Ser Gly Leu
1               5

<210> SEQ ID NO 365
<211> LENGTH: 8
<212> TYPE: PRT
<213> ORGANISM: Artificial sequence
<220> FEATURE:
```

-continued

<223> OTHER INFORMATION: Peptide derived from HBV Polymerase protein

<400> SEQUENCE: 365

Leu Leu Ile Gly Ser Ser Gly Leu
1               5

<210> SEQ ID NO 366
<211> LENGTH: 11
<212> TYPE: PRT
<213> ORGANISM: Artificial sequence
<220> FEATURE:
<223> OTHER INFORMATION: Peptide derived from HBV Polymerase protein

<400> SEQUENCE: 366

His Leu Leu Ile Gly Ser Ser Gly Leu Ser Arg
1               5                   10

<210> SEQ ID NO 367
<211> LENGTH: 10
<212> TYPE: PRT
<213> ORGANISM: Artificial sequence
<220> FEATURE:
<223> OTHER INFORMATION: Peptide derived from HBV Polymerase protein

<400> SEQUENCE: 367

Leu Leu Ile Gly Ser Ser Gly Leu Ser Arg
1               5                   10

<210> SEQ ID NO 368
<211> LENGTH: 11
<212> TYPE: PRT
<213> ORGANISM: Artificial sequence
<220> FEATURE:
<223> OTHER INFORMATION: Peptide derived from HBV Polymerase protein

<400> SEQUENCE: 368

Leu Leu Ile Gly Ser Ser Gly Leu Ser Arg Tyr
1               5                   10

<210> SEQ ID NO 369
<211> LENGTH: 10
<212> TYPE: PRT
<213> ORGANISM: Artificial sequence
<220> FEATURE:
<223> OTHER INFORMATION: Peptide derived from HBV Polymerase protein

<400> SEQUENCE: 369

Leu Ile Gly Ser Ser Gly Leu Ser Arg Tyr
1               5                   10

<210> SEQ ID NO 370
<211> LENGTH: 9
<212> TYPE: PRT
<213> ORGANISM: Artificial sequence
<220> FEATURE:
<223> OTHER INFORMATION: Peptide derived from HBV Polymerase protein

<400> SEQUENCE: 370

Ile Gly Ser Ser Gly Leu Ser Arg Tyr
1               5

<210> SEQ ID NO 371
<211> LENGTH: 8
<212> TYPE: PRT
<213> ORGANISM: Artificial sequence
<220> FEATURE:
<223> OTHER INFORMATION: Peptide derived from HBV Polymerase protein

<400> SEQUENCE: 371

Gly Ser Ser Gly Leu Ser Arg Tyr
1               5

<210> SEQ ID NO 372
<211> LENGTH: 8
<212> TYPE: PRT
<213> ORGANISM: Artificial sequence
<220> FEATURE:
<223> OTHER INFORMATION: Peptide derived from HBV Polymerase protein

<400> SEQUENCE: 372

Ser Arg Gln Leu Tyr Val Ser Leu
1               5

<210> SEQ ID NO 373
<211> LENGTH: 10
<212> TYPE: PRT
<213> ORGANISM: Artificial sequence
<220> FEATURE:
<223> OTHER INFORMATION: Peptide derived from HBV Polymerase protein

<400> SEQUENCE: 373

Cys Ser Arg Gln Leu Tyr Val Ser Leu Met
1               5                   10

<210> SEQ ID NO 374
<211> LENGTH: 9
<212> TYPE: PRT
<213> ORGANISM: Artificial sequence
<220> FEATURE:
<223> OTHER INFORMATION: Peptide derived from HBV Polymerase protein

<400> SEQUENCE: 374

Ser Arg Gln Leu Tyr Val Ser Leu Met
1               5

<210> SEQ ID NO 375
<211> LENGTH: 8
<212> TYPE: PRT
<213> ORGANISM: Artificial sequence
<220> FEATURE:
<223> OTHER INFORMATION: Peptide derived from HBV Polymerase protein

<400> SEQUENCE: 375

Arg Gln Leu Tyr Val Ser Leu Met
1               5

<210> SEQ ID NO 376
<211> LENGTH: 10
<212> TYPE: PRT
<213> ORGANISM: Artificial sequence
<220> FEATURE:
<223> OTHER INFORMATION: Peptide derived from HBV Polymerase protein

<400> SEQUENCE: 376

Ser Arg Gln Leu Tyr Val Ser Leu Met Leu
1               5                   10

<210> SEQ ID NO 377
<211> LENGTH: 9
<212> TYPE: PRT
<213> ORGANISM: Artificial sequence
<220> FEATURE:
<223> OTHER INFORMATION: Peptide derived from HBV Polymerase protein

```
<400> SEQUENCE: 377

Arg Gln Leu Tyr Val Ser Leu Met Leu
 1               5

<210> SEQ ID NO 378
<211> LENGTH: 8
<212> TYPE: PRT
<213> ORGANISM: Artificial sequence
<220> FEATURE:
<223> OTHER INFORMATION: Peptide derived from HBV Polymerase protein

<400> SEQUENCE: 378

Gln Leu Tyr Val Ser Leu Met Leu
 1               5

<210> SEQ ID NO 379
<211> LENGTH: 11
<212> TYPE: PRT
<213> ORGANISM: Artificial sequence
<220> FEATURE:
<223> OTHER INFORMATION: Peptide derived from HBV Polymerase protein

<400> SEQUENCE: 379

Ser Arg Gln Leu Tyr Val Ser Leu Met Leu Leu
 1               5                   10

<210> SEQ ID NO 380
<211> LENGTH: 10
<212> TYPE: PRT
<213> ORGANISM: Artificial sequence
<220> FEATURE:
<223> OTHER INFORMATION: Peptide derived from HBV Polymerase protein

<400> SEQUENCE: 380

Arg Gln Leu Tyr Val Ser Leu Met Leu Leu
 1               5                   10

<210> SEQ ID NO 381
<211> LENGTH: 8
<212> TYPE: PRT
<213> ORGANISM: Artificial sequence
<220> FEATURE:
<223> OTHER INFORMATION: Peptide derived from HBV Polymerase protein

<400> SEQUENCE: 381

Leu Tyr Val Ser Leu Met Leu Leu
 1               5

<210> SEQ ID NO 382
<211> LENGTH: 11
<212> TYPE: PRT
<213> ORGANISM: Artificial sequence
<220> FEATURE:
<223> OTHER INFORMATION: Peptide derived from HBV Polymerase protein

<400> SEQUENCE: 382

Arg Gln Leu Tyr Val Ser Leu Met Leu Leu Tyr
 1               5                   10

<210> SEQ ID NO 383
<211> LENGTH: 10
<212> TYPE: PRT
<213> ORGANISM: Artificial sequence
<220> FEATURE:
<223> OTHER INFORMATION: Peptide derived from HBV Polymerase protein

<400> SEQUENCE: 383
```

```
Gln Leu Tyr Val Ser Leu Met Leu Leu Tyr
1               5                   10

<210> SEQ ID NO 384
<211> LENGTH: 9
<212> TYPE: PRT
<213> ORGANISM: Artificial sequence
<220> FEATURE:
<223> OTHER INFORMATION: Peptide derived from HBV Polymerase protein

<400> SEQUENCE: 384

Leu Tyr Val Ser Leu Met Leu Leu Tyr
1               5

<210> SEQ ID NO 385
<211> LENGTH: 8
<212> TYPE: PRT
<213> ORGANISM: Artificial sequence
<220> FEATURE:
<223> OTHER INFORMATION: Peptide derived from HBV Polymerase protein

<400> SEQUENCE: 385

Tyr Val Ser Leu Met Leu Leu Tyr
1               5

<210> SEQ ID NO 386
<211> LENGTH: 11
<212> TYPE: PRT
<213> ORGANISM: Artificial sequence
<220> FEATURE:
<223> OTHER INFORMATION: Peptide derived from HBV Polymerase protein

<400> SEQUENCE: 386

Gln Leu Tyr Val Ser Leu Met Leu Leu Tyr Lys
1               5                   10

<210> SEQ ID NO 387
<211> LENGTH: 10
<212> TYPE: PRT
<213> ORGANISM: Artificial sequence
<220> FEATURE:
<223> OTHER INFORMATION: Peptide derived from HBV Polymerase protein

<400> SEQUENCE: 387

Leu Tyr Val Ser Leu Met Leu Leu Tyr Lys
1               5                   10

<210> SEQ ID NO 388
<211> LENGTH: 9
<212> TYPE: PRT
<213> ORGANISM: Artificial sequence
<220> FEATURE:
<223> OTHER INFORMATION: Peptide derived from HBV Polymerase protein

<400> SEQUENCE: 388

Tyr Val Ser Leu Met Leu Leu Tyr Lys
1               5

<210> SEQ ID NO 389
<211> LENGTH: 8
<212> TYPE: PRT
<213> ORGANISM: Artificial sequence
<220> FEATURE:
<223> OTHER INFORMATION: Peptide derived from HBV Polymerase protein

<400> SEQUENCE: 389
```

```
Val Ser Leu Met Leu Leu Tyr Lys
1               5
```

<210> SEQ ID NO 390
<211> LENGTH: 11
<212> TYPE: PRT
<213> ORGANISM: Artificial sequence
<220> FEATURE:
<223> OTHER INFORMATION: Peptide derived from HBV Polymerase protein

<400> SEQUENCE: 390

```
Tyr Val Ser Leu Met Leu Leu Tyr Lys Thr Tyr
1               5                   10
```

<210> SEQ ID NO 391
<211> LENGTH: 10
<212> TYPE: PRT
<213> ORGANISM: Artificial sequence
<220> FEATURE:
<223> OTHER INFORMATION: Peptide derived from HBV Polymerase protein

<400> SEQUENCE: 391

```
Val Ser Leu Met Leu Leu Tyr Lys Thr Tyr
1               5                   10
```

<210> SEQ ID NO 392
<211> LENGTH: 8
<212> TYPE: PRT
<213> ORGANISM: Artificial sequence
<220> FEATURE:
<223> OTHER INFORMATION: Peptide derived from HBV Polymerase protein

<400> SEQUENCE: 392

```
Leu Met Leu Leu Tyr Lys Thr Tyr
1               5
```

<210> SEQ ID NO 393
<211> LENGTH: 10
<212> TYPE: PRT
<213> ORGANISM: Artificial sequence
<220> FEATURE:
<223> OTHER INFORMATION: Peptide derived from HBV Polymerase protein

<400> SEQUENCE: 393

```
Ser Leu Met Leu Leu Tyr Lys Thr Tyr Gly
1               5                   10
```

<210> SEQ ID NO 394
<211> LENGTH: 11
<212> TYPE: PRT
<213> ORGANISM: Artificial sequence
<220> FEATURE:
<223> OTHER INFORMATION: Peptide derived from HBV Polymerase protein

<400> SEQUENCE: 394

```
Ser Leu Met Leu Leu Tyr Lys Thr Tyr Gly Trp
1               5                   10
```

<210> SEQ ID NO 395
<211> LENGTH: 10
<212> TYPE: PRT
<213> ORGANISM: Artificial sequence
<220> FEATURE:
<223> OTHER INFORMATION: Peptide derived from HBV Polymerase protein

<400> SEQUENCE: 395

Leu Met Leu Leu Tyr Lys Thr Tyr Gly Trp

```
1               5                  10
```

<210> SEQ ID NO 396
<211> LENGTH: 9
<212> TYPE: PRT
<213> ORGANISM: Artificial sequence
<220> FEATURE:
<223> OTHER INFORMATION: Peptide derived from HBV Polymerase protein

<400> SEQUENCE: 396

```
Met Leu Leu Tyr Lys Thr Tyr Gly Trp
1               5
```

<210> SEQ ID NO 397
<211> LENGTH: 8
<212> TYPE: PRT
<213> ORGANISM: Artificial sequence
<220> FEATURE:
<223> OTHER INFORMATION: Peptide derived from HBV Polymerase protein

<400> SEQUENCE: 397

```
Leu Leu Tyr Lys Thr Tyr Gly Trp
1               5
```

<210> SEQ ID NO 398
<211> LENGTH: 11
<212> TYPE: PRT
<213> ORGANISM: Artificial sequence
<220> FEATURE:
<223> OTHER INFORMATION: Peptide derived from HBV Polymerase protein

<400> SEQUENCE: 398

```
Leu Met Leu Leu Tyr Lys Thr Tyr Gly Trp Lys
1               5                  10
```

<210> SEQ ID NO 399
<211> LENGTH: 10
<212> TYPE: PRT
<213> ORGANISM: Artificial sequence
<220> FEATURE:
<223> OTHER INFORMATION: Peptide derived from HBV Polymerase protein

<400> SEQUENCE: 399

```
Met Leu Leu Tyr Lys Thr Tyr Gly Trp Lys
1               5                  10
```

<210> SEQ ID NO 400
<211> LENGTH: 9
<212> TYPE: PRT
<213> ORGANISM: Artificial sequence
<220> FEATURE:
<223> OTHER INFORMATION: Peptide derived from HBV Polymerase protein

<400> SEQUENCE: 400

```
Leu Leu Tyr Lys Thr Tyr Gly Trp Lys
1               5
```

<210> SEQ ID NO 401
<211> LENGTH: 8
<212> TYPE: PRT
<213> ORGANISM: Artificial sequence
<220> FEATURE:
<223> OTHER INFORMATION: Peptide derived from HBV Polymerase protein

<400> SEQUENCE: 401

```
Leu Tyr Lys Thr Tyr Gly Trp Lys
1               5
```

<210> SEQ ID NO 402
<211> LENGTH: 11
<212> TYPE: PRT
<213> ORGANISM: Artificial sequence
<220> FEATURE:
<223> OTHER INFORMATION: Peptide derived from HBV Polymerase protein

<400> SEQUENCE: 402

Met Leu Leu Tyr Lys Thr Tyr Gly Trp Lys Leu
1               5                   10

<210> SEQ ID NO 403
<211> LENGTH: 10
<212> TYPE: PRT
<213> ORGANISM: Artificial sequence
<220> FEATURE:
<223> OTHER INFORMATION: Peptide derived from HBV Polymerase protein

<400> SEQUENCE: 403

Leu Leu Tyr Lys Thr Tyr Gly Trp Lys Leu
1               5                   10

<210> SEQ ID NO 404
<211> LENGTH: 9
<212> TYPE: PRT
<213> ORGANISM: Artificial sequence
<220> FEATURE:
<223> OTHER INFORMATION: Peptide derived from HBV Polymerase protein

<400> SEQUENCE: 404

Leu Tyr Lys Thr Tyr Gly Trp Lys Leu
1               5

<210> SEQ ID NO 405
<211> LENGTH: 8
<212> TYPE: PRT
<213> ORGANISM: Artificial sequence
<220> FEATURE:
<223> OTHER INFORMATION: Peptide derived from HBV Polymerase protein

<400> SEQUENCE: 405

Tyr Lys Thr Tyr Gly Trp Lys Leu
1               5

<210> SEQ ID NO 406
<211> LENGTH: 10
<212> TYPE: PRT
<213> ORGANISM: Artificial sequence
<220> FEATURE:
<223> OTHER INFORMATION: Peptide derived from HBV Polymerase protein

<400> SEQUENCE: 406

Leu Tyr Lys Thr Tyr Gly Trp Lys Leu His
1               5                   10

<210> SEQ ID NO 407
<211> LENGTH: 8
<212> TYPE: PRT
<213> ORGANISM: Artificial sequence
<220> FEATURE:
<223> OTHER INFORMATION: Peptide derived from HBV Polymerase protein

<400> SEQUENCE: 407

Lys Thr Tyr Gly Trp Lys Leu His
1               5

```
<210> SEQ ID NO 408
<211> LENGTH: 11
<212> TYPE: PRT
<213> ORGANISM: Artificial sequence
<220> FEATURE:
<223> OTHER INFORMATION: Peptide derived from HBV Polymerase protein

<400> SEQUENCE: 408

Leu Tyr Lys Thr Tyr Gly Trp Lys Leu His Leu
1               5                   10

<210> SEQ ID NO 409
<211> LENGTH: 10
<212> TYPE: PRT
<213> ORGANISM: Artificial sequence
<220> FEATURE:
<223> OTHER INFORMATION: Peptide derived from HBV Polymerase protein

<400> SEQUENCE: 409

Tyr Lys Thr Tyr Gly Trp Lys Leu His Leu
1               5                   10

<210> SEQ ID NO 410
<211> LENGTH: 9
<212> TYPE: PRT
<213> ORGANISM: Artificial sequence
<220> FEATURE:
<223> OTHER INFORMATION: Peptide derived from HBV Polymerase protein

<400> SEQUENCE: 410

Lys Thr Tyr Gly Trp Lys Leu His Leu
1               5

<210> SEQ ID NO 411
<211> LENGTH: 8
<212> TYPE: PRT
<213> ORGANISM: Artificial sequence
<220> FEATURE:
<223> OTHER INFORMATION: Peptide derived from HBV Polymerase protein

<400> SEQUENCE: 411

Thr Tyr Gly Trp Lys Leu His Leu
1               5

<210> SEQ ID NO 412
<211> LENGTH: 11
<212> TYPE: PRT
<213> ORGANISM: Artificial sequence
<220> FEATURE:
<223> OTHER INFORMATION: Peptide derived from HBV Polymerase protein

<400> SEQUENCE: 412

Tyr Lys Thr Tyr Gly Trp Lys Leu His Leu Tyr
1               5                   10

<210> SEQ ID NO 413
<211> LENGTH: 10
<212> TYPE: PRT
<213> ORGANISM: Artificial sequence
<220> FEATURE:
<223> OTHER INFORMATION: Peptide derived from HBV Polymerase protein

<400> SEQUENCE: 413

Lys Thr Tyr Gly Trp Lys Leu His Leu Tyr
1               5                   10
```

-continued

```
<210> SEQ ID NO 414
<211> LENGTH: 9
<212> TYPE: PRT
<213> ORGANISM: Artificial sequence
<220> FEATURE:
<223> OTHER INFORMATION: Peptide derived from HBV Polymerase protein

<400> SEQUENCE: 414

Thr Tyr Gly Trp Lys Leu His Leu Tyr
1               5

<210> SEQ ID NO 415
<211> LENGTH: 8
<212> TYPE: PRT
<213> ORGANISM: Artificial sequence
<220> FEATURE:
<223> OTHER INFORMATION: Peptide derived from HBV Polymerase protein

<400> SEQUENCE: 415

Tyr Gly Trp Lys Leu His Leu Tyr
1               5

<210> SEQ ID NO 416
<211> LENGTH: 11
<212> TYPE: PRT
<213> ORGANISM: Artificial sequence
<220> FEATURE:
<223> OTHER INFORMATION: Peptide derived from HBV Polymerase protein

<400> SEQUENCE: 416

Gly Trp Lys Leu His Leu Tyr Ser His Pro Ile
1               5                   10

<210> SEQ ID NO 417
<211> LENGTH: 10
<212> TYPE: PRT
<213> ORGANISM: Artificial sequence
<220> FEATURE:
<223> OTHER INFORMATION: Peptide derived from HBV Polymerase protein

<400> SEQUENCE: 417

Trp Lys Leu His Leu Tyr Ser His Pro Ile
1               5                   10

<210> SEQ ID NO 418
<211> LENGTH: 9
<212> TYPE: PRT
<213> ORGANISM: Artificial sequence
<220> FEATURE:
<223> OTHER INFORMATION: Peptide derived from HBV Polymerase protein

<400> SEQUENCE: 418

Lys Leu His Leu Tyr Ser His Pro Ile
1               5

<210> SEQ ID NO 419
<211> LENGTH: 8
<212> TYPE: PRT
<213> ORGANISM: Artificial sequence
<220> FEATURE:
<223> OTHER INFORMATION: Peptide derived from HBV Polymerase protein

<400> SEQUENCE: 419

Leu His Leu Tyr Ser His Pro Ile
1               5

<210> SEQ ID NO 420
```

```
<211> LENGTH: 10
<212> TYPE: PRT
<213> ORGANISM: Artificial sequence
<220> FEATURE:
<223> OTHER INFORMATION: Peptide derived from HBV Polymerase protein

<400> SEQUENCE: 420

Lys Leu His Leu Tyr Ser His Pro Ile Val
1               5                   10

<210> SEQ ID NO 421
<211> LENGTH: 9
<212> TYPE: PRT
<213> ORGANISM: Artificial sequence
<220> FEATURE:
<223> OTHER INFORMATION: Peptide derived from HBV Polymerase protein

<400> SEQUENCE: 421

Leu His Leu Tyr Ser His Pro Ile Val
1               5

<210> SEQ ID NO 422
<211> LENGTH: 8
<212> TYPE: PRT
<213> ORGANISM: Artificial sequence
<220> FEATURE:
<223> OTHER INFORMATION: Peptide derived from HBV Polymerase protein

<400> SEQUENCE: 422

His Leu Tyr Ser His Pro Ile Val
1               5

<210> SEQ ID NO 423
<211> LENGTH: 11
<212> TYPE: PRT
<213> ORGANISM: Artificial sequence
<220> FEATURE:
<223> OTHER INFORMATION: Peptide derived from HBV Polymerase protein

<400> SEQUENCE: 423

Lys Leu His Leu Tyr Ser His Pro Ile Val Leu
1               5                   10

<210> SEQ ID NO 424
<211> LENGTH: 10
<212> TYPE: PRT
<213> ORGANISM: Artificial sequence
<220> FEATURE:
<223> OTHER INFORMATION: Peptide derived from HBV Polymerase protein

<400> SEQUENCE: 424

Leu His Leu Tyr Ser His Pro Ile Val Leu
1               5                   10

<210> SEQ ID NO 425
<211> LENGTH: 9
<212> TYPE: PRT
<213> ORGANISM: Artificial sequence
<220> FEATURE:
<223> OTHER INFORMATION: Peptide derived from HBV Polymerase protein

<400> SEQUENCE: 425

His Leu Tyr Ser His Pro Ile Val Leu
1               5

<210> SEQ ID NO 426
<211> LENGTH: 8
```

```
<212> TYPE: PRT
<213> ORGANISM: Artificial sequence
<220> FEATURE:
<223> OTHER INFORMATION: Peptide derived from HBV Polymerase protein

<400> SEQUENCE: 426

Leu Tyr Ser His Pro Ile Val Leu
1               5

<210> SEQ ID NO 427
<211> LENGTH: 11
<212> TYPE: PRT
<213> ORGANISM: Artificial sequence
<220> FEATURE:
<223> OTHER INFORMATION: Peptide derived from HBV Polymerase protein

<400> SEQUENCE: 427

His Leu Tyr Ser His Pro Ile Val Leu Gly Phe
1               5                   10

<210> SEQ ID NO 428
<211> LENGTH: 10
<212> TYPE: PRT
<213> ORGANISM: Artificial sequence
<220> FEATURE:
<223> OTHER INFORMATION: Peptide derived from HBV Polymerase protein

<400> SEQUENCE: 428

Leu Tyr Ser His Pro Ile Val Leu Gly Phe
1               5                   10

<210> SEQ ID NO 429
<211> LENGTH: 9
<212> TYPE: PRT
<213> ORGANISM: Artificial sequence
<220> FEATURE:
<223> OTHER INFORMATION: Peptide derived from HBV Polymerase protein

<400> SEQUENCE: 429

Tyr Ser His Pro Ile Val Leu Gly Phe
1               5

<210> SEQ ID NO 430

<400> SEQUENCE: 430

000

<210> SEQ ID NO 431

<400> SEQUENCE: 431

000

<210> SEQ ID NO 432
<211> LENGTH: 8
<212> TYPE: PRT
<213> ORGANISM: Artificial sequence
<220> FEATURE:
<223> OTHER INFORMATION: Peptide derived from HBV Polymerase protein

<400> SEQUENCE: 432

Ser Pro Phe Leu Leu Ala Gln Phe
1               5

<210> SEQ ID NO 433
<211> LENGTH: 9
```

```
<212> TYPE: PRT
<213> ORGANISM: Artificial sequence
<220> FEATURE:
<223> OTHER INFORMATION: Peptide derived from HBV Polymerase protein

<400> SEQUENCE: 433

Ser Pro Phe Leu Leu Ala Gln Phe Thr
1               5

<210> SEQ ID NO 434
<211> LENGTH: 10
<212> TYPE: PRT
<213> ORGANISM: Artificial sequence
<220> FEATURE:
<223> OTHER INFORMATION: Peptide derived from HBV Polymerase protein

<400> SEQUENCE: 434

Ser Pro Phe Leu Leu Ala Gln Phe Thr Ser
1               5                   10

<210> SEQ ID NO 435
<211> LENGTH: 8
<212> TYPE: PRT
<213> ORGANISM: Artificial sequence
<220> FEATURE:
<223> OTHER INFORMATION: Peptide derived from HBV Polymerase protein

<400> SEQUENCE: 435

Phe Leu Leu Ala Gln Phe Thr Ser
1               5

<210> SEQ ID NO 436
<211> LENGTH: 11
<212> TYPE: PRT
<213> ORGANISM: Artificial sequence
<220> FEATURE:
<223> OTHER INFORMATION: Peptide derived from HBV Polymerase protein

<400> SEQUENCE: 436

Ser Pro Phe Leu Leu Ala Gln Phe Thr Ser Ala
1               5                   10

<210> SEQ ID NO 437
<211> LENGTH: 9
<212> TYPE: PRT
<213> ORGANISM: Artificial sequence
<220> FEATURE:
<223> OTHER INFORMATION: Peptide derived from HBV Polymerase protein

<400> SEQUENCE: 437

Phe Leu Leu Ala Gln Phe Thr Ser Ala
1               5

<210> SEQ ID NO 438
<211> LENGTH: 10
<212> TYPE: PRT
<213> ORGANISM: Artificial sequence
<220> FEATURE:
<223> OTHER INFORMATION: Peptide derived from HBV Polymerase protein

<400> SEQUENCE: 438

Phe Leu Leu Ala Gln Phe Thr Ser Ala Ile
1               5                   10

<210> SEQ ID NO 439
<211> LENGTH: 9
<212> TYPE: PRT
```

```
<213> ORGANISM: Artificial sequence
<220> FEATURE:
<223> OTHER INFORMATION: Peptide derived from HBV Polymerase protein

<400> SEQUENCE: 439

Leu Leu Ala Gln Phe Thr Ser Ala Ile
1               5

<210> SEQ ID NO 440
<211> LENGTH: 8
<212> TYPE: PRT
<213> ORGANISM: Artificial sequence
<220> FEATURE:
<223> OTHER INFORMATION: Peptide derived from HBV Polymerase protein

<400> SEQUENCE: 440

Leu Ala Gln Phe Thr Ser Ala Ile
1               5

<210> SEQ ID NO 441
<211> LENGTH: 11
<212> TYPE: PRT
<213> ORGANISM: Artificial sequence
<220> FEATURE:
<223> OTHER INFORMATION: Peptide derived from HBV Polymerase protein

<400> SEQUENCE: 441

Leu Leu Ala Gln Phe Thr Ser Ala Ile Cys Ser
1               5                   10

<210> SEQ ID NO 442
<211> LENGTH: 11
<212> TYPE: PRT
<213> ORGANISM: Artificial sequence
<220> FEATURE:
<223> OTHER INFORMATION: Peptide derived from HBV Polymerase protein

<400> SEQUENCE: 442

Leu Ala Gln Phe Thr Ser Ala Ile Cys Ser Val
1               5                   10

<210> SEQ ID NO 443
<211> LENGTH: 10
<212> TYPE: PRT
<213> ORGANISM: Artificial sequence
<220> FEATURE:
<223> OTHER INFORMATION: Peptide derived from HBV Polymerase protein

<400> SEQUENCE: 443

Ala Gln Phe Thr Ser Ala Ile Cys Ser Val
1               5                   10

<210> SEQ ID NO 444
<211> LENGTH: 8
<212> TYPE: PRT
<213> ORGANISM: Artificial sequence
<220> FEATURE:
<223> OTHER INFORMATION: Peptide derived from HBV Polymerase protein

<400> SEQUENCE: 444

Phe Thr Ser Ala Ile Cys Ser Val
1               5

<210> SEQ ID NO 445
<211> LENGTH: 11
<212> TYPE: PRT
<213> ORGANISM: Artificial sequence
```

<220> FEATURE:
<223> OTHER INFORMATION: Peptide derived from HBV Polymerase protein

<400> SEQUENCE: 445

Ala Gln Phe Thr Ser Ala Ile Cys Ser Val Val
1               5                   10

<210> SEQ ID NO 446
<211> LENGTH: 9
<212> TYPE: PRT
<213> ORGANISM: Artificial sequence
<220> FEATURE:
<223> OTHER INFORMATION: Peptide derived from HBV Polymerase protein

<400> SEQUENCE: 446

Phe Thr Ser Ala Ile Cys Ser Val Val
1               5

<210> SEQ ID NO 447
<211> LENGTH: 11
<212> TYPE: PRT
<213> ORGANISM: Artificial sequence
<220> FEATURE:
<223> OTHER INFORMATION: Peptide derived from HBV Polymerase protein

<400> SEQUENCE: 447

Gln Phe Thr Ser Ala Ile Cys Ser Val Val Arg
1               5                   10

<210> SEQ ID NO 448
<211> LENGTH: 10
<212> TYPE: PRT
<213> ORGANISM: Artificial sequence
<220> FEATURE:
<223> OTHER INFORMATION: Peptide derived from HBV Polymerase protein

<400> SEQUENCE: 448

Phe Thr Ser Ala Ile Cys Ser Val Val Arg
1               5                   10

<210> SEQ ID NO 449
<211> LENGTH: 9
<212> TYPE: PRT
<213> ORGANISM: Artificial sequence
<220> FEATURE:
<223> OTHER INFORMATION: Peptide derived from HBV Polymerase protein

<400> SEQUENCE: 449

Thr Ser Ala Ile Cys Ser Val Val Arg
1               5

<210> SEQ ID NO 450
<211> LENGTH: 8
<212> TYPE: PRT
<213> ORGANISM: Artificial sequence
<220> FEATURE:
<223> OTHER INFORMATION: Peptide derived from HBV Polymerase protein

<400> SEQUENCE: 450

Ser Ala Ile Cys Ser Val Val Arg
1               5

<210> SEQ ID NO 451
<211> LENGTH: 11
<212> TYPE: PRT
<213> ORGANISM: Artificial sequence
<220> FEATURE:

<223> OTHER INFORMATION: Peptide derived from HBV Polymerase protein

<400> SEQUENCE: 451

Phe Thr Ser Ala Ile Cys Ser Val Val Arg Arg
1               5                   10

<210> SEQ ID NO 452
<211> LENGTH: 10
<212> TYPE: PRT
<213> ORGANISM: Artificial sequence
<220> FEATURE:
<223> OTHER INFORMATION: Peptide derived from HBV Polymerase protein

<400> SEQUENCE: 452

Thr Ser Ala Ile Cys Ser Val Val Arg Arg
1               5                   10

<210> SEQ ID NO 453
<211> LENGTH: 9
<212> TYPE: PRT
<213> ORGANISM: Artificial sequence
<220> FEATURE:
<223> OTHER INFORMATION: Peptide derived from HBV Polymerase protein

<400> SEQUENCE: 453

Ser Ala Ile Cys Ser Val Val Arg Arg
1               5

<210> SEQ ID NO 454
<211> LENGTH: 8
<212> TYPE: PRT
<213> ORGANISM: Artificial sequence
<220> FEATURE:
<223> OTHER INFORMATION: Peptide derived from HBV Polymerase protein

<400> SEQUENCE: 454

Ala Ile Cys Ser Val Val Arg Arg
1               5

<210> SEQ ID NO 455
<211> LENGTH: 11
<212> TYPE: PRT
<213> ORGANISM: Artificial sequence
<220> FEATURE:
<223> OTHER INFORMATION: Peptide derived from HBV Polymerase protein

<400> SEQUENCE: 455

Ser Ala Ile Cys Ser Val Val Arg Arg Ala Phe
1               5                   10

<210> SEQ ID NO 456
<211> LENGTH: 8
<212> TYPE: PRT
<213> ORGANISM: Artificial sequence
<220> FEATURE:
<223> OTHER INFORMATION: Peptide derived from HBV Polymerase protein

<400> SEQUENCE: 456

Cys Ser Val Val Arg Arg Ala Phe
1               5

<210> SEQ ID NO 457
<211> LENGTH: 10
<212> TYPE: PRT
<213> ORGANISM: Artificial sequence
<220> FEATURE:
<223> OTHER INFORMATION: Peptide derived from HBV Polymerase protein

```
<400> SEQUENCE: 457

Cys Ser Val Val Arg Arg Ala Phe Pro His
1               5                   10

<210> SEQ ID NO 458
<211> LENGTH: 8
<212> TYPE: PRT
<213> ORGANISM: Artificial sequence
<220> FEATURE:
<223> OTHER INFORMATION: Peptide derived from HBV Polymerase protein

<400> SEQUENCE: 458

Val Val Arg Arg Ala Phe Pro His
1               5

<210> SEQ ID NO 459
<211> LENGTH: 10
<212> TYPE: PRT
<213> ORGANISM: Artificial sequence
<220> FEATURE:
<223> OTHER INFORMATION: Peptide derived from HBV Polymerase protein

<400> SEQUENCE: 459

Ser Val Val Arg Arg Ala Phe Pro His Cys
1               5                   10

<210> SEQ ID NO 460
<211> LENGTH: 11
<212> TYPE: PRT
<213> ORGANISM: Artificial sequence
<220> FEATURE:
<223> OTHER INFORMATION: Peptide derived from HBV Polymerase protein

<400> SEQUENCE: 460

Ser Val Val Arg Arg Ala Phe Pro His Cys Leu
1               5                   10

<210> SEQ ID NO 461
<211> LENGTH: 9
<212> TYPE: PRT
<213> ORGANISM: Artificial sequence
<220> FEATURE:
<223> OTHER INFORMATION: Peptide derived from HBV Polymerase protein

<400> SEQUENCE: 461

Val Arg Arg Ala Phe Pro His Cys Leu
1               5

<210> SEQ ID NO 462
<211> LENGTH: 8
<212> TYPE: PRT
<213> ORGANISM: Artificial sequence
<220> FEATURE:
<223> OTHER INFORMATION: Peptide derived from HBV Polymerase protein

<400> SEQUENCE: 462

Arg Arg Ala Phe Pro His Cys Leu
1               5

<210> SEQ ID NO 463
<211> LENGTH: 11
<212> TYPE: PRT
<213> ORGANISM: Artificial sequence
<220> FEATURE:
<223> OTHER INFORMATION: Peptide derived from HBV Polymerase protein
```

```
<400> SEQUENCE: 463

Val Val Arg Arg Ala Phe Pro His Cys Leu Ala
1               5                   10

<210> SEQ ID NO 464
<211> LENGTH: 9
<212> TYPE: PRT
<213> ORGANISM: Artificial sequence
<220> FEATURE:
<223> OTHER INFORMATION: Peptide derived from HBV Polymerase protein

<400> SEQUENCE: 464

Arg Arg Ala Phe Pro His Cys Leu Ala
1               5

<210> SEQ ID NO 465
<211> LENGTH: 8
<212> TYPE: PRT
<213> ORGANISM: Artificial sequence
<220> FEATURE:
<223> OTHER INFORMATION: Peptide derived from HBV Polymerase protein

<400> SEQUENCE: 465

Arg Ala Phe Pro His Cys Leu Ala
1               5

<210> SEQ ID NO 466
<211> LENGTH: 10
<212> TYPE: PRT
<213> ORGANISM: Artificial sequence
<220> FEATURE:
<223> OTHER INFORMATION: Peptide derived from HBV Polymerase protein

<400> SEQUENCE: 466

Arg Arg Ala Phe Pro His Cys Leu Ala Phe
1               5                   10

<210> SEQ ID NO 467
<211> LENGTH: 9
<212> TYPE: PRT
<213> ORGANISM: Artificial sequence
<220> FEATURE:
<223> OTHER INFORMATION: Peptide derived from HBV Polymerase protein

<400> SEQUENCE: 467

Arg Ala Phe Pro His Cys Leu Ala Phe
1               5

<210> SEQ ID NO 468
<211> LENGTH: 8
<212> TYPE: PRT
<213> ORGANISM: Artificial sequence
<220> FEATURE:
<223> OTHER INFORMATION: Peptide derived from HBV Polymerase protein

<400> SEQUENCE: 468

Ala Phe Pro His Cys Leu Ala Phe
1               5

<210> SEQ ID NO 469
<211> LENGTH: 8
<212> TYPE: PRT
<213> ORGANISM: Artificial sequence
<220> FEATURE:
<223> OTHER INFORMATION: Peptide derived from HBV Polymerase protein

<400> SEQUENCE: 469
```

```
Phe Pro His Cys Leu Ala Phe Ser
1               5

<210> SEQ ID NO 470
<211> LENGTH: 11
<212> TYPE: PRT
<213> ORGANISM: Artificial sequence
<220> FEATURE:
<223> OTHER INFORMATION: Peptide derived from HBV Polymerase protein

<400> SEQUENCE: 470

Arg Ala Phe Pro His Cys Leu Ala Phe Ser Tyr
1               5                   10

<210> SEQ ID NO 471
<211> LENGTH: 10
<212> TYPE: PRT
<213> ORGANISM: Artificial sequence
<220> FEATURE:
<223> OTHER INFORMATION: Peptide derived from HBV Polymerase protein

<400> SEQUENCE: 471

Ala Phe Pro His Cys Leu Ala Phe Ser Tyr
1               5                   10

<210> SEQ ID NO 472
<211> LENGTH: 9
<212> TYPE: PRT
<213> ORGANISM: Artificial sequence
<220> FEATURE:
<223> OTHER INFORMATION: Peptide derived from HBV Polymerase protein

<400> SEQUENCE: 472

Phe Pro His Cys Leu Ala Phe Ser Tyr
1               5

<210> SEQ ID NO 473
<211> LENGTH: 11
<212> TYPE: PRT
<213> ORGANISM: Artificial sequence
<220> FEATURE:
<223> OTHER INFORMATION: Peptide derived from HBV Polymerase protein

<400> SEQUENCE: 473

Ala Phe Pro His Cys Leu Ala Phe Ser Tyr Met
1               5                   10

<210> SEQ ID NO 474
<211> LENGTH: 10
<212> TYPE: PRT
<213> ORGANISM: Artificial sequence
<220> FEATURE:
<223> OTHER INFORMATION: Peptide derived from HBV Polymerase protein

<400> SEQUENCE: 474

Phe Pro His Cys Leu Ala Phe Ser Tyr Met
1               5                   10

<210> SEQ ID NO 475
<211> LENGTH: 11
<212> TYPE: PRT
<213> ORGANISM: Artificial sequence
<220> FEATURE:
<223> OTHER INFORMATION: Peptide derived from HBV Polymerase protein

<400> SEQUENCE: 475
```

His Cys Leu Ala Phe Ser Tyr Met Asp Asp Val
1               5                   10

<210> SEQ ID NO 476
<211> LENGTH: 9
<212> TYPE: PRT
<213> ORGANISM: Artificial sequence
<220> FEATURE:
<223> OTHER INFORMATION: Peptide derived from HBV Polymerase protein

<400> SEQUENCE: 476

Leu Ala Phe Ser Tyr Met Asp Asp Val
1               5

<210> SEQ ID NO 477
<211> LENGTH: 10
<212> TYPE: PRT
<213> ORGANISM: Artificial sequence
<220> FEATURE:
<223> OTHER INFORMATION: Peptide derived from HBV Polymerase protein

<400> SEQUENCE: 477

Leu Ala Phe Ser Tyr Met Asp Asp Val Val
1               5                   10

<210> SEQ ID NO 478
<211> LENGTH: 8
<212> TYPE: PRT
<213> ORGANISM: Artificial sequence
<220> FEATURE:
<223> OTHER INFORMATION: Peptide derived from HBV Polymerase protein

<400> SEQUENCE: 478

Phe Ser Tyr Met Asp Asp Val Val
1               5

<210> SEQ ID NO 479
<211> LENGTH: 11
<212> TYPE: PRT
<213> ORGANISM: Artificial sequence
<220> FEATURE:
<223> OTHER INFORMATION: Peptide derived from HBV Polymerase protein

<400> SEQUENCE: 479

Leu Ala Phe Ser Tyr Met Asp Asp Val Val Leu
1               5                   10

<210> SEQ ID NO 480
<211> LENGTH: 9
<212> TYPE: PRT
<213> ORGANISM: Artificial sequence
<220> FEATURE:
<223> OTHER INFORMATION: Peptide derived from HBV Polymerase protein

<400> SEQUENCE: 480

Phe Ser Tyr Met Asp Asp Val Val Leu
1               5

<210> SEQ ID NO 481
<211> LENGTH: 8
<212> TYPE: PRT
<213> ORGANISM: Artificial sequence
<220> FEATURE:
<223> OTHER INFORMATION: Peptide derived from HBV Polymerase protein

<400> SEQUENCE: 481

Ser Tyr Met Asp Asp Val Val Leu

```
<210> SEQ ID NO 482
<211> LENGTH: 9
<212> TYPE: PRT
<213> ORGANISM: Artificial sequence
<220> FEATURE:
<223> OTHER INFORMATION: Peptide derived from HBV Polymerase protein

<400> SEQUENCE: 482

Tyr Met Asp Asp Val Val Leu Gly Ala
1               5

<210> SEQ ID NO 483
<211> LENGTH: 8
<212> TYPE: PRT
<213> ORGANISM: Artificial sequence
<220> FEATURE:
<223> OTHER INFORMATION: Peptide derived from HBV Polymerase protein

<400> SEQUENCE: 483

Met Asp Asp Val Val Leu Gly Ala
1               5

<210> SEQ ID NO 484

<400> SEQUENCE: 484

000

<210> SEQ ID NO 485

<400> SEQUENCE: 485

000

<210> SEQ ID NO 486
<211> LENGTH: 8
<212> TYPE: PRT
<213> ORGANISM: Artificial sequence
<220> FEATURE:
<223> OTHER INFORMATION: Peptide derived from HBV Polymerase protein

<400> SEQUENCE: 486

Arg Glu Ser Leu Tyr Thr Ala Val
1               5

<210> SEQ ID NO 487
<211> LENGTH: 9
<212> TYPE: PRT
<213> ORGANISM: Artificial sequence
<220> FEATURE:
<223> OTHER INFORMATION: Peptide derived from HBV Polymerase protein

<400> SEQUENCE: 487

Arg Glu Ser Leu Tyr Thr Ala Val Thr
1               5

<210> SEQ ID NO 488
<211> LENGTH: 10
<212> TYPE: PRT
<213> ORGANISM: Artificial sequence
<220> FEATURE:
<223> OTHER INFORMATION: Peptide derived from HBV Polymerase protein

<400> SEQUENCE: 488

Arg Glu Ser Leu Tyr Thr Ala Val Thr Asn
```

```
1               5                    10
```

<210> SEQ ID NO 489
<211> LENGTH: 11
<212> TYPE: PRT
<213> ORGANISM: Artificial sequence
<220> FEATURE:
<223> OTHER INFORMATION: Peptide derived from HBV Polymerase protein

<400> SEQUENCE: 489

```
Arg Glu Ser Leu Tyr Thr Ala Val Thr Asn Phe
1               5                   10
```

<210> SEQ ID NO 490
<211> LENGTH: 10
<212> TYPE: PRT
<213> ORGANISM: Artificial sequence
<220> FEATURE:
<223> OTHER INFORMATION: Peptide derived from HBV Polymerase protein

<400> SEQUENCE: 490

```
Glu Ser Leu Tyr Thr Ala Val Thr Asn Phe
1               5                   10
```

<210> SEQ ID NO 491
<211> LENGTH: 9
<212> TYPE: PRT
<213> ORGANISM: Artificial sequence
<220> FEATURE:
<223> OTHER INFORMATION: Peptide derived from HBV Polymerase protein

<400> SEQUENCE: 491

```
Ser Leu Tyr Thr Ala Val Thr Asn Phe
1               5
```

<210> SEQ ID NO 492
<211> LENGTH: 8
<212> TYPE: PRT
<213> ORGANISM: Artificial sequence
<220> FEATURE:
<223> OTHER INFORMATION: Peptide derived from HBV Polymerase protein

<400> SEQUENCE: 492

```
Leu Tyr Thr Ala Val Thr Asn Phe
1               5
```

<210> SEQ ID NO 493
<211> LENGTH: 10
<212> TYPE: PRT
<213> ORGANISM: Artificial sequence
<220> FEATURE:
<223> OTHER INFORMATION: Peptide derived from HBV Polymerase protein

<400> SEQUENCE: 493

```
Ser Leu Tyr Thr Ala Val Thr Asn Phe Leu
1               5                   10
```

<210> SEQ ID NO 494
<211> LENGTH: 9
<212> TYPE: PRT
<213> ORGANISM: Artificial sequence
<220> FEATURE:
<223> OTHER INFORMATION: Peptide derived from HBV Polymerase protein

<400> SEQUENCE: 494

```
Leu Tyr Thr Ala Val Thr Asn Phe Leu
1               5
```

```
<210> SEQ ID NO 495
<211> LENGTH: 8
<212> TYPE: PRT
<213> ORGANISM: Artificial sequence
<220> FEATURE:
<223> OTHER INFORMATION: Peptide derived from HBV Polymerase protein

<400> SEQUENCE: 495

Tyr Thr Ala Val Thr Asn Phe Leu
1               5

<210> SEQ ID NO 496
<211> LENGTH: 11
<212> TYPE: PRT
<213> ORGANISM: Artificial sequence
<220> FEATURE:
<223> OTHER INFORMATION: Peptide derived from HBV Polymerase protein

<400> SEQUENCE: 496

Ser Leu Tyr Thr Ala Val Thr Asn Phe Leu Leu
1               5                   10

<210> SEQ ID NO 497
<211> LENGTH: 10
<212> TYPE: PRT
<213> ORGANISM: Artificial sequence
<220> FEATURE:
<223> OTHER INFORMATION: Peptide derived from HBV Polymerase protein

<400> SEQUENCE: 497

Leu Tyr Thr Ala Val Thr Asn Phe Leu Leu
1               5                   10

<210> SEQ ID NO 498
<211> LENGTH: 9
<212> TYPE: PRT
<213> ORGANISM: Artificial sequence
<220> FEATURE:
<223> OTHER INFORMATION: Peptide derived from HBV Polymerase protein

<400> SEQUENCE: 498

Tyr Thr Ala Val Thr Asn Phe Leu Leu
1               5

<210> SEQ ID NO 499
<211> LENGTH: 11
<212> TYPE: PRT
<213> ORGANISM: Artificial sequence
<220> FEATURE:
<223> OTHER INFORMATION: Peptide derived from HBV Polymerase protein

<400> SEQUENCE: 499

Tyr Thr Ala Val Thr Asn Phe Leu Leu Ser Leu
1               5                   10

<210> SEQ ID NO 500
<211> LENGTH: 8
<212> TYPE: PRT
<213> ORGANISM: Artificial sequence
<220> FEATURE:
<223> OTHER INFORMATION: Peptide derived from HBV Polymerase protein

<400> SEQUENCE: 500

Val Thr Asn Phe Leu Leu Ser Leu
1               5
```

```
<210> SEQ ID NO 501
<211> LENGTH: 11
<212> TYPE: PRT
<213> ORGANISM: Artificial sequence
<220> FEATURE:
<223> OTHER INFORMATION: Peptide derived from HBV Polymerase protein

<400> SEQUENCE: 501

Ala Val Thr Asn Phe Leu Leu Ser Leu Gly Ile
1               5                   10

<210> SEQ ID NO 502
<211> LENGTH: 9
<212> TYPE: PRT
<213> ORGANISM: Artificial sequence
<220> FEATURE:
<223> OTHER INFORMATION: Peptide derived from HBV Polymerase protein

<400> SEQUENCE: 502

Thr Asn Phe Leu Leu Ser Leu Gly Ile
1               5

<210> SEQ ID NO 503
<211> LENGTH: 9
<212> TYPE: PRT
<213> ORGANISM: Artificial sequence
<220> FEATURE:
<223> OTHER INFORMATION: Peptide derived from HBV Polymerase protein

<400> SEQUENCE: 503

Phe Leu Leu Ser Leu Gly Ile His Leu
1               5

<210> SEQ ID NO 504
<211> LENGTH: 8
<212> TYPE: PRT
<213> ORGANISM: Artificial sequence
<220> FEATURE:
<223> OTHER INFORMATION: Peptide derived from HBV Polymerase protein

<400> SEQUENCE: 504

Leu Leu Ser Leu Gly Ile His Leu
1               5

<210> SEQ ID NO 505
<211> LENGTH: 8
<212> TYPE: PRT
<213> ORGANISM: Artificial sequence
<220> FEATURE:
<223> OTHER INFORMATION: Peptide derived from HBV Polymerase protein

<400> SEQUENCE: 505

Ser Leu Gly Ile His Leu Asn Pro
1               5

<210> SEQ ID NO 506
<211> LENGTH: 11
<212> TYPE: PRT
<213> ORGANISM: Artificial sequence
<220> FEATURE:
<223> OTHER INFORMATION: Peptide derived from HBV Polymerase protein

<400> SEQUENCE: 506

Leu Leu Ser Leu Gly Ile His Leu Asn Pro Asn
1               5                   10
```

```
<210> SEQ ID NO 507
<211> LENGTH: 11
<212> TYPE: PRT
<213> ORGANISM: Artificial sequence
<220> FEATURE:
<223> OTHER INFORMATION: Peptide derived from HBV Polymerase protein

<400> SEQUENCE: 507

Leu Ser Leu Gly Ile His Leu Asn Pro Asn Lys
1               5                   10

<210> SEQ ID NO 508
<211> LENGTH: 10
<212> TYPE: PRT
<213> ORGANISM: Artificial sequence
<220> FEATURE:
<223> OTHER INFORMATION: Peptide derived from HBV Polymerase protein

<400> SEQUENCE: 508

Ser Leu Gly Ile His Leu Asn Pro Asn Lys
1               5                   10

<210> SEQ ID NO 509
<211> LENGTH: 8
<212> TYPE: PRT
<213> ORGANISM: Artificial sequence
<220> FEATURE:
<223> OTHER INFORMATION: Peptide derived from HBV Polymerase protein

<400> SEQUENCE: 509

Gly Ile His Leu Asn Pro Asn Lys
1               5

<210> SEQ ID NO 510
<211> LENGTH: 8
<212> TYPE: PRT
<213> ORGANISM: Artificial sequence
<220> FEATURE:
<223> OTHER INFORMATION: Peptide derived from HBV Polymerase protein

<400> SEQUENCE: 510

His Leu Asn Pro Asn Lys Thr Lys
1               5

<210> SEQ ID NO 511
<211> LENGTH: 9
<212> TYPE: PRT
<213> ORGANISM: Artificial sequence
<220> FEATURE:
<223> OTHER INFORMATION: Peptide derived from HBV Polymerase protein

<400> SEQUENCE: 511

His Leu Asn Pro Asn Lys Thr Lys Arg
1               5

<210> SEQ ID NO 512
<211> LENGTH: 8
<212> TYPE: PRT
<213> ORGANISM: Artificial sequence
<220> FEATURE:
<223> OTHER INFORMATION: Peptide derived from HBV Polymerase protein

<400> SEQUENCE: 512

Asn Pro Asn Lys Thr Lys Arg Trp
1               5

<210> SEQ ID NO 513
```

-continued

```
<211> LENGTH: 10
<212> TYPE: PRT
<213> ORGANISM: Artificial sequence
<220> FEATURE:
<223> OTHER INFORMATION: Peptide derived from HBV Polymerase protein

<400> SEQUENCE: 513

Pro Asn Lys Thr Lys Arg Trp Gly Tyr Ser
1               5                   10

<210> SEQ ID NO 514
<211> LENGTH: 8
<212> TYPE: PRT
<213> ORGANISM: Artificial sequence
<220> FEATURE:
<223> OTHER INFORMATION: Peptide derived from HBV Polymerase protein

<400> SEQUENCE: 514

Lys Thr Lys Arg Trp Gly Tyr Ser
1               5

<210> SEQ ID NO 515
<211> LENGTH: 10
<212> TYPE: PRT
<213> ORGANISM: Artificial sequence
<220> FEATURE:
<223> OTHER INFORMATION: Peptide derived from HBV Polymerase protein

<400> SEQUENCE: 515

Asn Lys Thr Lys Arg Trp Gly Tyr Ser Leu
1               5                   10

<210> SEQ ID NO 516
<211> LENGTH: 9
<212> TYPE: PRT
<213> ORGANISM: Artificial sequence
<220> FEATURE:
<223> OTHER INFORMATION: Peptide derived from HBV Polymerase protein

<400> SEQUENCE: 516

Lys Thr Lys Arg Trp Gly Tyr Ser Leu
1               5

<210> SEQ ID NO 517
<211> LENGTH: 8
<212> TYPE: PRT
<213> ORGANISM: Artificial sequence
<220> FEATURE:
<223> OTHER INFORMATION: Peptide derived from HBV Polymerase protein

<400> SEQUENCE: 517

Thr Lys Arg Trp Gly Tyr Ser Leu
1               5

<210> SEQ ID NO 518
<211> LENGTH: 8
<212> TYPE: PRT
<213> ORGANISM: Artificial sequence
<220> FEATURE:
<223> OTHER INFORMATION: Peptide derived from HBV Polymerase protein

<400> SEQUENCE: 518

Lys Arg Trp Gly Tyr Ser Leu Asn
1               5

<210> SEQ ID NO 519
<211> LENGTH: 11
```

```
<212> TYPE: PRT
<213> ORGANISM: Artificial sequence
<220> FEATURE:
<223> OTHER INFORMATION: Peptide derived from HBV Polymerase protein

<400> SEQUENCE: 519

Lys Thr Lys Arg Trp Gly Tyr Ser Leu Asn Phe
1               5                   10

<210> SEQ ID NO 520
<211> LENGTH: 9
<212> TYPE: PRT
<213> ORGANISM: Artificial sequence
<220> FEATURE:
<223> OTHER INFORMATION: Peptide derived from HBV Polymerase protein

<400> SEQUENCE: 520

Lys Arg Trp Gly Tyr Ser Leu Asn Phe
1               5

<210> SEQ ID NO 521
<211> LENGTH: 8
<212> TYPE: PRT
<213> ORGANISM: Artificial sequence
<220> FEATURE:
<223> OTHER INFORMATION: Peptide derived from HBV Polymerase protein

<400> SEQUENCE: 521

Arg Trp Gly Tyr Ser Leu Asn Phe
1               5

<210> SEQ ID NO 522
<211> LENGTH: 10
<212> TYPE: PRT
<213> ORGANISM: Artificial sequence
<220> FEATURE:
<223> OTHER INFORMATION: Peptide derived from HBV Polymerase protein

<400> SEQUENCE: 522

Lys Arg Trp Gly Tyr Ser Leu Asn Phe Met
1               5                   10

<210> SEQ ID NO 523
<211> LENGTH: 9
<212> TYPE: PRT
<213> ORGANISM: Artificial sequence
<220> FEATURE:
<223> OTHER INFORMATION: Peptide derived from HBV Polymerase protein

<400> SEQUENCE: 523

Arg Trp Gly Tyr Ser Leu Asn Phe Met
1               5

<210> SEQ ID NO 524
<211> LENGTH: 11
<212> TYPE: PRT
<213> ORGANISM: Artificial sequence
<220> FEATURE:
<223> OTHER INFORMATION: Peptide derived from HBV Polymerase protein

<400> SEQUENCE: 524

Lys Arg Trp Gly Tyr Ser Leu Asn Phe Met Gly
1               5                   10

<210> SEQ ID NO 525
<211> LENGTH: 11
<212> TYPE: PRT
```

<213> ORGANISM: Artificial sequence
<220> FEATURE:
<223> OTHER INFORMATION: Peptide derived from HBV Polymerase protein

<400> SEQUENCE: 525

Arg Trp Gly Tyr Ser Leu Asn Phe Met Gly Tyr
1               5                   10

<210> SEQ ID NO 526
<211> LENGTH: 9
<212> TYPE: PRT
<213> ORGANISM: Artificial sequence
<220> FEATURE:
<223> OTHER INFORMATION: Peptide derived from HBV Polymerase protein

<400> SEQUENCE: 526

Gly Tyr Ser Leu Asn Phe Met Gly Tyr
1               5

<210> SEQ ID NO 527
<211> LENGTH: 8
<212> TYPE: PRT
<213> ORGANISM: Artificial sequence
<220> FEATURE:
<223> OTHER INFORMATION: Peptide derived from HBV Polymerase protein

<400> SEQUENCE: 527

Tyr Ser Leu Asn Phe Met Gly Tyr
1               5

<210> SEQ ID NO 528
<211> LENGTH: 11
<212> TYPE: PRT
<213> ORGANISM: Artificial sequence
<220> FEATURE:
<223> OTHER INFORMATION: Peptide derived from HBV Polymerase protein

<400> SEQUENCE: 528

Trp Gly Tyr Ser Leu Asn Phe Met Gly Tyr Ile
1               5                   10

<210> SEQ ID NO 529
<211> LENGTH: 9
<212> TYPE: PRT
<213> ORGANISM: Artificial sequence
<220> FEATURE:
<223> OTHER INFORMATION: Peptide derived from HBV Polymerase protein

<400> SEQUENCE: 529

Tyr Ser Leu Asn Phe Met Gly Tyr Ile
1               5

<210> SEQ ID NO 530
<211> LENGTH: 8
<212> TYPE: PRT
<213> ORGANISM: Artificial sequence
<220> FEATURE:
<223> OTHER INFORMATION: Peptide derived from HBV Polymerase protein

<400> SEQUENCE: 530

Ser Leu Asn Phe Met Gly Tyr Ile
1               5

<210> SEQ ID NO 531
<211> LENGTH: 11
<212> TYPE: PRT
<213> ORGANISM: Artificial sequence
<220> FEATURE:
<223> OTHER INFORMATION: Peptide derived from HBV Polymerase protein

<400> SEQUENCE: 531

Gly Tyr Ser Leu Asn Phe Met Gly Tyr Ile Ile
1               5                   10

<210> SEQ ID NO 532
<211> LENGTH: 10
<212> TYPE: PRT
<213> ORGANISM: Artificial sequence
<220> FEATURE:
<223> OTHER INFORMATION: Peptide derived from HBV Polymerase protein

<400> SEQUENCE: 532

Tyr Ser Leu Asn Phe Met Gly Tyr Ile Ile
1               5                   10

<210> SEQ ID NO 533
<211> LENGTH: 9
<212> TYPE: PRT
<213> ORGANISM: Artificial sequence
<220> FEATURE:
<223> OTHER INFORMATION: Peptide derived from HBV Polymerase protein

<400> SEQUENCE: 533

Ser Leu Asn Phe Met Gly Tyr Ile Ile
1               5

<210> SEQ ID NO 534
<211> LENGTH: 8
<212> TYPE: PRT
<213> ORGANISM: Artificial sequence
<220> FEATURE:
<223> OTHER INFORMATION: Peptide derived from HBV Polymerase protein

<400> SEQUENCE: 534

Leu Asn Phe Met Gly Tyr Ile Ile
1               5

<210> SEQ ID NO 535
<211> LENGTH: 8
<212> TYPE: PRT
<213> ORGANISM: Artificial sequence
<220> FEATURE:
<223> OTHER INFORMATION: Peptide derived from HBV Polymerase protein

<400> SEQUENCE: 535

Phe Met Gly Tyr Ile Ile Gly Ser
1               5

<210> SEQ ID NO 536
<211> LENGTH: 11
<212> TYPE: PRT
<213> ORGANISM: Artificial sequence
<220> FEATURE:
<223> OTHER INFORMATION: Peptide derived from HBV Polymerase protein

<400> SEQUENCE: 536

Leu Asn Phe Met Gly Tyr Ile Ile Gly Ser Trp
1               5                   10

<210> SEQ ID NO 537
<211> LENGTH: 10
<212> TYPE: PRT
<213> ORGANISM: Artificial sequence
<220> FEATURE:

<223> OTHER INFORMATION: Peptide derived from HBV Polymerase protein

<400> SEQUENCE: 537

Asn Phe Met Gly Tyr Ile Ile Gly Ser Trp
1               5                   10

<210> SEQ ID NO 538
<211> LENGTH: 9
<212> TYPE: PRT
<213> ORGANISM: Artificial sequence
<220> FEATURE:
<223> OTHER INFORMATION: Peptide derived from HBV Polymerase protein

<400> SEQUENCE: 538

Phe Met Gly Tyr Ile Ile Gly Ser Trp
1               5

<210> SEQ ID NO 539
<211> LENGTH: 8
<212> TYPE: PRT
<213> ORGANISM: Artificial sequence
<220> FEATURE:
<223> OTHER INFORMATION: Peptide derived from HBV Polymerase protein

<400> SEQUENCE: 539

Met Gly Tyr Ile Ile Gly Ser Trp
1               5

<210> SEQ ID NO 540
<211> LENGTH: 11
<212> TYPE: PRT
<213> ORGANISM: Artificial sequence
<220> FEATURE:
<223> OTHER INFORMATION: Peptide derived from HBV Polymerase protein

<400> SEQUENCE: 540

Met Gly Tyr Ile Ile Gly Ser Trp Gly Thr Leu
1               5                   10

<210> SEQ ID NO 541
<211> LENGTH: 10
<212> TYPE: PRT
<213> ORGANISM: Artificial sequence
<220> FEATURE:
<223> OTHER INFORMATION: Peptide derived from HBV Polymerase protein

<400> SEQUENCE: 541

Gly Tyr Ile Ile Gly Ser Trp Gly Thr Leu
1               5                   10

<210> SEQ ID NO 542
<211> LENGTH: 9
<212> TYPE: PRT
<213> ORGANISM: Artificial sequence
<220> FEATURE:
<223> OTHER INFORMATION: Peptide derived from HBV Polymerase protein

<400> SEQUENCE: 542

Tyr Ile Ile Gly Ser Trp Gly Thr Leu
1               5

<210> SEQ ID NO 543
<211> LENGTH: 8
<212> TYPE: PRT
<213> ORGANISM: Artificial sequence
<220> FEATURE:
<223> OTHER INFORMATION: Peptide derived from HBV Polymerase protein

<400> SEQUENCE: 543

Thr Leu Pro Gln Asp His Ile Val
1               5

<210> SEQ ID NO 544
<211> LENGTH: 11
<212> TYPE: PRT
<213> ORGANISM: Artificial sequence
<220> FEATURE:
<223> OTHER INFORMATION: Peptide derived from HBV Polymerase protein

<400> SEQUENCE: 544

Gly Thr Leu Pro Gln Asp His Ile Val Gln Lys
1               5                   10

<210> SEQ ID NO 545
<211> LENGTH: 10
<212> TYPE: PRT
<213> ORGANISM: Artificial sequence
<220> FEATURE:
<223> OTHER INFORMATION: Peptide derived from HBV Polymerase protein

<400> SEQUENCE: 545

Leu Pro Gln Asp His Ile Val Gln Lys Ile
1               5                   10

<210> SEQ ID NO 546

<400> SEQUENCE: 546

000

<210> SEQ ID NO 547

<400> SEQUENCE: 547

000

<210> SEQ ID NO 548
<211> LENGTH: 8
<212> TYPE: PRT
<213> ORGANISM: Artificial sequence
<220> FEATURE:
<223> OTHER INFORMATION: Peptide derived from HBV Polymerase protein

<400> SEQUENCE: 548

Tyr Pro Ala Leu Met Pro Leu Tyr
1               5

<210> SEQ ID NO 549
<211> LENGTH: 10
<212> TYPE: PRT
<213> ORGANISM: Artificial sequence
<220> FEATURE:
<223> OTHER INFORMATION: Peptide derived from HBV Polymerase protein

<400> SEQUENCE: 549

Gly Tyr Pro Ala Leu Met Pro Leu Tyr Ala
1               5                   10

<210> SEQ ID NO 550
<211> LENGTH: 9
<212> TYPE: PRT
<213> ORGANISM: Artificial sequence
<220> FEATURE:
<223> OTHER INFORMATION: Peptide derived from HBV Polymerase protein

```
<400> SEQUENCE: 550

Tyr Pro Ala Leu Met Pro Leu Tyr Ala
1               5

<210> SEQ ID NO 551
<211> LENGTH: 10
<212> TYPE: PRT
<213> ORGANISM: Artificial sequence
<220> FEATURE:
<223> OTHER INFORMATION: Peptide derived from HBV Polymerase protein

<400> SEQUENCE: 551

Tyr Pro Ala Leu Met Pro Leu Tyr Ala Cys
1               5                   10

<210> SEQ ID NO 552
<211> LENGTH: 8
<212> TYPE: PRT
<213> ORGANISM: Artificial sequence
<220> FEATURE:
<223> OTHER INFORMATION: Peptide derived from HBV Polymerase protein

<400> SEQUENCE: 552

Ala Leu Met Pro Leu Tyr Ala Cys
1               5

<210> SEQ ID NO 553
<211> LENGTH: 11
<212> TYPE: PRT
<213> ORGANISM: Artificial sequence
<220> FEATURE:
<223> OTHER INFORMATION: Peptide derived from HBV Polymerase protein

<400> SEQUENCE: 553

Tyr Pro Ala Leu Met Pro Leu Tyr Ala Cys Ile
1               5                   10

<210> SEQ ID NO 554
<211> LENGTH: 9
<212> TYPE: PRT
<213> ORGANISM: Artificial sequence
<220> FEATURE:
<223> OTHER INFORMATION: Peptide derived from HBV Polymerase protein

<400> SEQUENCE: 554

Ala Leu Met Pro Leu Tyr Ala Cys Ile
1               5

<210> SEQ ID NO 555
<211> LENGTH: 8
<212> TYPE: PRT
<213> ORGANISM: Artificial sequence
<220> FEATURE:
<223> OTHER INFORMATION: Peptide derived from HBV Polymerase protein

<400> SEQUENCE: 555

Met Pro Leu Tyr Ala Cys Ile Gln
1               5

<210> SEQ ID NO 556
<211> LENGTH: 9
<212> TYPE: PRT
<213> ORGANISM: Artificial sequence
<220> FEATURE:
<223> OTHER INFORMATION: Peptide derived from HBV Polymerase protein
```

```
<400> SEQUENCE: 556

Met Pro Leu Tyr Ala Cys Ile Gln Ala
1               5

<210> SEQ ID NO 557
<211> LENGTH: 10
<212> TYPE: PRT
<213> ORGANISM: Artificial sequence
<220> FEATURE:
<223> OTHER INFORMATION: Peptide derived from HBV Polymerase protein

<400> SEQUENCE: 557

Met Pro Leu Tyr Ala Cys Ile Gln Ala Lys
1               5                   10

<210> SEQ ID NO 558
<211> LENGTH: 9
<212> TYPE: PRT
<213> ORGANISM: Artificial sequence
<220> FEATURE:
<223> OTHER INFORMATION: Peptide derived from HBV Polymerase protein

<400> SEQUENCE: 558

Pro Leu Tyr Ala Cys Ile Gln Ala Lys
1               5

<210> SEQ ID NO 559
<211> LENGTH: 11
<212> TYPE: PRT
<213> ORGANISM: Artificial sequence
<220> FEATURE:
<223> OTHER INFORMATION: Peptide derived from HBV Polymerase protein

<400> SEQUENCE: 559

Leu Tyr Ala Cys Ile Gln Ala Lys Gln Ala Phe
1               5                   10

<210> SEQ ID NO 560
<211> LENGTH: 10
<212> TYPE: PRT
<213> ORGANISM: Artificial sequence
<220> FEATURE:
<223> OTHER INFORMATION: Peptide derived from HBV Polymerase protein

<400> SEQUENCE: 560

Tyr Ala Cys Ile Gln Ala Lys Gln Ala Phe
1               5                   10

<210> SEQ ID NO 561
<211> LENGTH: 9
<212> TYPE: PRT
<213> ORGANISM: Artificial sequence
<220> FEATURE:
<223> OTHER INFORMATION: Peptide derived from HBV Polymerase protein

<400> SEQUENCE: 561

Ile Gln Ala Lys Gln Ala Phe Thr Phe
1               5

<210> SEQ ID NO 562
<211> LENGTH: 8
<212> TYPE: PRT
<213> ORGANISM: Artificial sequence
<220> FEATURE:
<223> OTHER INFORMATION: Peptide derived from HBV Polymerase protein

<400> SEQUENCE: 562
```

Gln Ala Lys Gln Ala Phe Thr Phe
1               5

<210> SEQ ID NO 563
<211> LENGTH: 10
<212> TYPE: PRT
<213> ORGANISM: Artificial sequence
<220> FEATURE:
<223> OTHER INFORMATION: Peptide derived from HBV Polymerase protein

<400> SEQUENCE: 563

Lys Gln Ala Phe Thr Phe Ser Pro Thr Tyr
1               5                   10

<210> SEQ ID NO 564
<211> LENGTH: 9
<212> TYPE: PRT
<213> ORGANISM: Artificial sequence
<220> FEATURE:
<223> OTHER INFORMATION: Peptide derived from HBV Polymerase protein

<400> SEQUENCE: 564

Gln Ala Phe Thr Phe Ser Pro Thr Tyr
1               5

<210> SEQ ID NO 565
<211> LENGTH: 8
<212> TYPE: PRT
<213> ORGANISM: Artificial sequence
<220> FEATURE:
<223> OTHER INFORMATION: Peptide derived from HBV Polymerase protein

<400> SEQUENCE: 565

Ala Phe Thr Phe Ser Pro Thr Tyr
1               5

<210> SEQ ID NO 566
<211> LENGTH: 11
<212> TYPE: PRT
<213> ORGANISM: Artificial sequence
<220> FEATURE:
<223> OTHER INFORMATION: Peptide derived from HBV Polymerase protein

<400> SEQUENCE: 566

Lys Gln Ala Phe Thr Phe Ser Pro Thr Tyr Lys
1               5                   10

<210> SEQ ID NO 567
<211> LENGTH: 10
<212> TYPE: PRT
<213> ORGANISM: Artificial sequence
<220> FEATURE:
<223> OTHER INFORMATION: Peptide derived from HBV Polymerase protein

<400> SEQUENCE: 567

Gln Ala Phe Thr Phe Ser Pro Thr Tyr Lys
1               5                   10

<210> SEQ ID NO 568
<211> LENGTH: 8
<212> TYPE: PRT
<213> ORGANISM: Artificial sequence
<220> FEATURE:
<223> OTHER INFORMATION: Peptide derived from HBV Polymerase protein

<400> SEQUENCE: 568

Phe Thr Phe Ser Pro Thr Tyr Lys
1               5

<210> SEQ ID NO 569
<211> LENGTH: 9
<212> TYPE: PRT
<213> ORGANISM: Artificial sequence
<220> FEATURE:
<223> OTHER INFORMATION: Peptide derived from HBV Polymerase protein

<400> SEQUENCE: 569

Phe Thr Phe Ser Pro Thr Tyr Lys Ala
1               5

<210> SEQ ID NO 570
<211> LENGTH: 11
<212> TYPE: PRT
<213> ORGANISM: Artificial sequence
<220> FEATURE:
<223> OTHER INFORMATION: Peptide derived from HBV Polymerase protein

<400> SEQUENCE: 570

Ala Phe Thr Phe Ser Pro Thr Tyr Lys Ala Phe
1               5                   10

<210> SEQ ID NO 571
<211> LENGTH: 10
<212> TYPE: PRT
<213> ORGANISM: Artificial sequence
<220> FEATURE:
<223> OTHER INFORMATION: Peptide derived from HBV Polymerase protein

<400> SEQUENCE: 571

Phe Thr Phe Ser Pro Thr Tyr Lys Ala Phe
1               5                   10

<210> SEQ ID NO 572
<211> LENGTH: 9
<212> TYPE: PRT
<213> ORGANISM: Artificial sequence
<220> FEATURE:
<223> OTHER INFORMATION: Peptide derived from HBV Polymerase protein

<400> SEQUENCE: 572

Thr Phe Ser Pro Thr Tyr Lys Ala Phe
1               5

<210> SEQ ID NO 573
<211> LENGTH: 11
<212> TYPE: PRT
<213> ORGANISM: Artificial sequence
<220> FEATURE:
<223> OTHER INFORMATION: Peptide derived from HBV Polymerase protein

<400> SEQUENCE: 573

Phe Thr Phe Ser Pro Thr Tyr Lys Ala Phe Leu
1               5                   10

<210> SEQ ID NO 574
<211> LENGTH: 8
<212> TYPE: PRT
<213> ORGANISM: Artificial sequence
<220> FEATURE:
<223> OTHER INFORMATION: Peptide derived from HBV Polymerase protein

<400> SEQUENCE: 574

Ser Pro Thr Tyr Lys Ala Phe Leu

-continued

```
1               5

<210> SEQ ID NO 575
<211> LENGTH: 9
<212> TYPE: PRT
<213> ORGANISM: Artificial sequence
<220> FEATURE:
<223> OTHER INFORMATION: Peptide derived from HBV Polymerase protein

<400> SEQUENCE: 575

Pro Thr Tyr Lys Ala Phe Leu Ser Lys
1               5

<210> SEQ ID NO 576
<211> LENGTH: 8
<212> TYPE: PRT
<213> ORGANISM: Artificial sequence
<220> FEATURE:
<223> OTHER INFORMATION: Peptide derived from HBV Polymerase protein

<400> SEQUENCE: 576

Thr Tyr Lys Ala Phe Leu Ser Lys
1               5

<210> SEQ ID NO 577
<211> LENGTH: 11
<212> TYPE: PRT
<213> ORGANISM: Artificial sequence
<220> FEATURE:
<223> OTHER INFORMATION: Peptide derived from HBV Polymerase protein

<400> SEQUENCE: 577

Pro Thr Tyr Lys Ala Phe Leu Ser Lys Gln Tyr
1               5                   10

<210> SEQ ID NO 578
<211> LENGTH: 10
<212> TYPE: PRT
<213> ORGANISM: Artificial sequence
<220> FEATURE:
<223> OTHER INFORMATION: Peptide derived from HBV Polymerase protein

<400> SEQUENCE: 578

Thr Tyr Lys Ala Phe Leu Ser Lys Gln Tyr
1               5                   10

<210> SEQ ID NO 579
<211> LENGTH: 8
<212> TYPE: PRT
<213> ORGANISM: Artificial sequence
<220> FEATURE:
<223> OTHER INFORMATION: Peptide derived from HBV Polymerase protein

<400> SEQUENCE: 579

Lys Ala Phe Leu Ser Lys Gln Tyr
1               5

<210> SEQ ID NO 580
<211> LENGTH: 9
<212> TYPE: PRT
<213> ORGANISM: Artificial sequence
<220> FEATURE:
<223> OTHER INFORMATION: Peptide derived from HBV Polymerase protein

<400> SEQUENCE: 580

Lys Ala Phe Leu Ser Lys Gln Tyr Met
1               5
```

<210> SEQ ID NO 581
<211> LENGTH: 10
<212> TYPE: PRT
<213> ORGANISM: Artificial sequence
<220> FEATURE:
<223> OTHER INFORMATION: Peptide derived from HBV Polymerase protein

<400> SEQUENCE: 581

Lys Ala Phe Leu Ser Lys Gln Tyr Met Asn
1               5                   10

<210> SEQ ID NO 582
<211> LENGTH: 11
<212> TYPE: PRT
<213> ORGANISM: Artificial sequence
<220> FEATURE:
<223> OTHER INFORMATION: Peptide derived from HBV Polymerase protein

<400> SEQUENCE: 582

Lys Ala Phe Leu Ser Lys Gln Tyr Met Asn Leu
1               5                   10

<210> SEQ ID NO 583
<211> LENGTH: 9
<212> TYPE: PRT
<213> ORGANISM: Artificial sequence
<220> FEATURE:
<223> OTHER INFORMATION: Peptide derived from HBV Polymerase protein

<400> SEQUENCE: 583

Phe Leu Ser Lys Gln Tyr Met Asn Leu
1               5

<210> SEQ ID NO 584
<211> LENGTH: 11
<212> TYPE: PRT
<213> ORGANISM: Artificial sequence
<220> FEATURE:
<223> OTHER INFORMATION: Peptide derived from HBV Polymerase protein

<400> SEQUENCE: 584

Ala Phe Leu Ser Lys Gln Tyr Met Asn Leu Tyr
1               5                   10

<210> SEQ ID NO 585
<211> LENGTH: 10
<212> TYPE: PRT
<213> ORGANISM: Artificial sequence
<220> FEATURE:
<223> OTHER INFORMATION: Peptide derived from HBV Polymerase protein

<400> SEQUENCE: 585

Phe Leu Ser Lys Gln Tyr Met Asn Leu Tyr
1               5                   10

<210> SEQ ID NO 586
<211> LENGTH: 9
<212> TYPE: PRT
<213> ORGANISM: Artificial sequence
<220> FEATURE:
<223> OTHER INFORMATION: Peptide derived from HBV Polymerase protein

<400> SEQUENCE: 586

Leu Ser Lys Gln Tyr Met Asn Leu Tyr
1               5

```
<210> SEQ ID NO 587
<211> LENGTH: 8
<212> TYPE: PRT
<213> ORGANISM: Artificial sequence
<220> FEATURE:
<223> OTHER INFORMATION: Peptide derived from HBV Polymerase protein

<400> SEQUENCE: 587

Ser Lys Gln Tyr Met Asn Leu Tyr
1               5

<210> SEQ ID NO 588
<211> LENGTH: 11
<212> TYPE: PRT
<213> ORGANISM: Artificial sequence
<220> FEATURE:
<223> OTHER INFORMATION: Peptide derived from HBV Polymerase protein

<400> SEQUENCE: 588

Leu Ser Lys Gln Tyr Met Asn Leu Tyr Pro Val
1               5                   10

<210> SEQ ID NO 589
<211> LENGTH: 9
<212> TYPE: PRT
<213> ORGANISM: Artificial sequence
<220> FEATURE:
<223> OTHER INFORMATION: Peptide derived from HBV Polymerase protein

<400> SEQUENCE: 589

Lys Gln Tyr Met Asn Leu Tyr Pro Val
1               5

<210> SEQ ID NO 590
<211> LENGTH: 8
<212> TYPE: PRT
<213> ORGANISM: Artificial sequence
<220> FEATURE:
<223> OTHER INFORMATION: Peptide derived from HBV Polymerase protein

<400> SEQUENCE: 590

Gln Tyr Met Asn Leu Tyr Pro Val
1               5

<210> SEQ ID NO 591
<211> LENGTH: 10
<212> TYPE: PRT
<213> ORGANISM: Artificial sequence
<220> FEATURE:
<223> OTHER INFORMATION: Peptide derived from HBV Polymerase protein

<400> SEQUENCE: 591

Lys Gln Tyr Met Asn Leu Tyr Pro Val Ala
1               5                   10

<210> SEQ ID NO 592
<211> LENGTH: 11
<212> TYPE: PRT
<213> ORGANISM: Artificial sequence
<220> FEATURE:
<223> OTHER INFORMATION: Peptide derived from HBV Polymerase protein

<400> SEQUENCE: 592

Lys Gln Tyr Met Asn Leu Tyr Pro Val Ala Arg
1               5                   10
```

```
<210> SEQ ID NO 593
<211> LENGTH: 10
<212> TYPE: PRT
<213> ORGANISM: Artificial sequence
<220> FEATURE:
<223> OTHER INFORMATION: Peptide derived from HBV Polymerase protein

<400> SEQUENCE: 593

Gln Tyr Met Asn Leu Tyr Pro Val Ala Arg
1               5                   10

<210> SEQ ID NO 594
<211> LENGTH: 9
<212> TYPE: PRT
<213> ORGANISM: Artificial sequence
<220> FEATURE:
<223> OTHER INFORMATION: Peptide derived from HBV Polymerase protein

<400> SEQUENCE: 594

Tyr Met Asn Leu Tyr Pro Val Ala Arg
1               5

<210> SEQ ID NO 595
<211> LENGTH: 8
<212> TYPE: PRT
<213> ORGANISM: Artificial sequence
<220> FEATURE:
<223> OTHER INFORMATION: Peptide derived from HBV Polymerase protein

<400> SEQUENCE: 595

Met Asn Leu Tyr Pro Val Ala Arg
1               5

<210> SEQ ID NO 596
<211> LENGTH: 8
<212> TYPE: PRT
<213> ORGANISM: Artificial sequence
<220> FEATURE:
<223> OTHER INFORMATION: Peptide derived from HBV Polymerase protein

<400> SEQUENCE: 596

Arg Met Arg Gly Thr Phe Val Ala
1               5

<210> SEQ ID NO 597
<211> LENGTH: 9
<212> TYPE: PRT
<213> ORGANISM: Artificial sequence
<220> FEATURE:
<223> OTHER INFORMATION: Peptide derived from HBV Polymerase protein

<400> SEQUENCE: 597

Arg Met Arg Gly Thr Phe Val Ala Pro
1               5

<210> SEQ ID NO 598
<211> LENGTH: 8
<212> TYPE: PRT
<213> ORGANISM: Artificial sequence
<220> FEATURE:
<223> OTHER INFORMATION: Peptide derived from HBV Polymerase protein

<400> SEQUENCE: 598

Met Arg Gly Thr Phe Val Ala Pro
1               5

<210> SEQ ID NO 599
```

```
<211> LENGTH: 11
<212> TYPE: PRT
<213> ORGANISM: Artificial sequence
<220> FEATURE:
<223> OTHER INFORMATION: Peptide derived from HBV Polymerase protein

<400> SEQUENCE: 599

Gln Arg Met Arg Gly Thr Phe Val Ala Pro Leu
1               5                   10

<210> SEQ ID NO 600
<211> LENGTH: 10
<212> TYPE: PRT
<213> ORGANISM: Artificial sequence
<220> FEATURE:
<223> OTHER INFORMATION: Peptide derived from HBV Polymerase protein

<400> SEQUENCE: 600

Arg Met Arg Gly Thr Phe Val Ala Pro Leu
1               5                   10

<210> SEQ ID NO 601
<211> LENGTH: 9
<212> TYPE: PRT
<213> ORGANISM: Artificial sequence
<220> FEATURE:
<223> OTHER INFORMATION: Peptide derived from HBV Polymerase protein

<400> SEQUENCE: 601

Met Arg Gly Thr Phe Val Ala Pro Leu
1               5

<210> SEQ ID NO 602
<211> LENGTH: 11
<212> TYPE: PRT
<213> ORGANISM: Artificial sequence
<220> FEATURE:
<223> OTHER INFORMATION: Peptide derived from HBV Polymerase protein

<400> SEQUENCE: 602

Arg Met Arg Gly Thr Phe Val Ala Pro Leu Pro
1               5                   10

<210> SEQ ID NO 603
<211> LENGTH: 9
<212> TYPE: PRT
<213> ORGANISM: Artificial sequence
<220> FEATURE:
<223> OTHER INFORMATION: Peptide derived from HBV Polymerase protein

<400> SEQUENCE: 603

Arg Gly Thr Phe Val Ala Pro Leu Pro
1               5

<210> SEQ ID NO 604
<211> LENGTH: 11
<212> TYPE: PRT
<213> ORGANISM: Artificial sequence
<220> FEATURE:
<223> OTHER INFORMATION: Peptide derived from HBV Polymerase protein

<400> SEQUENCE: 604

Met Arg Gly Thr Phe Val Ala Pro Leu Pro Ile
1               5                   10

<210> SEQ ID NO 605
<211> LENGTH: 9
```

```
<212> TYPE: PRT
<213> ORGANISM: Artificial sequence
<220> FEATURE:
<223> OTHER INFORMATION: Peptide derived from HBV Polymerase protein

<400> SEQUENCE: 605

Gly Thr Phe Val Ala Pro Leu Pro Ile
1               5

<210> SEQ ID NO 606
<211> LENGTH: 8
<212> TYPE: PRT
<213> ORGANISM: Artificial sequence
<220> FEATURE:
<223> OTHER INFORMATION: Peptide derived from HBV Polymerase protein

<400> SEQUENCE: 606

Thr Phe Val Ala Pro Leu Pro Ile
1               5

<210> SEQ ID NO 607
<211> LENGTH: 10
<212> TYPE: PRT
<213> ORGANISM: Artificial sequence
<220> FEATURE:
<223> OTHER INFORMATION: Peptide derived from HBV Polymerase protein

<400> SEQUENCE: 607

Gly Thr Phe Val Ala Pro Leu Pro Ile His
1               5                   10

<210> SEQ ID NO 608
<211> LENGTH: 10
<212> TYPE: PRT
<213> ORGANISM: Artificial sequence
<220> FEATURE:
<223> OTHER INFORMATION: Peptide derived from HBV Polymerase protein

<400> SEQUENCE: 608

Phe Val Ala Pro Leu Pro Ile His Thr Ala
1               5                   10

<210> SEQ ID NO 609
<211> LENGTH: 8
<212> TYPE: PRT
<213> ORGANISM: Artificial sequence
<220> FEATURE:
<223> OTHER INFORMATION: Peptide derived from HBV Polymerase protein

<400> SEQUENCE: 609

Ala Pro Leu Pro Ile His Thr Ala
1               5

<210> SEQ ID NO 610
<211> LENGTH: 10
<212> TYPE: PRT
<213> ORGANISM: Artificial sequence
<220> FEATURE:
<223> OTHER INFORMATION: Peptide derived from HBV Polymerase protein

<400> SEQUENCE: 610

Ala Pro Leu Pro Ile His Thr Ala Glu Leu
1               5                   10

<210> SEQ ID NO 611
<211> LENGTH: 8
<212> TYPE: PRT
```

```
<213> ORGANISM: Artificial sequence
<220> FEATURE:
<223> OTHER INFORMATION: Peptide derived from HBV Polymerase protein

<400> SEQUENCE: 611

Leu Pro Ile His Thr Ala Glu Leu
1               5

<210> SEQ ID NO 612
<211> LENGTH: 11
<212> TYPE: PRT
<213> ORGANISM: Artificial sequence
<220> FEATURE:
<223> OTHER INFORMATION: Peptide derived from HBV Polymerase protein

<400> SEQUENCE: 612

Ala Pro Leu Pro Ile His Thr Ala Glu Leu Leu
1               5                   10

<210> SEQ ID NO 613
<211> LENGTH: 9
<212> TYPE: PRT
<213> ORGANISM: Artificial sequence
<220> FEATURE:
<223> OTHER INFORMATION: Peptide derived from HBV Polymerase protein

<400> SEQUENCE: 613

Leu Pro Ile His Thr Ala Glu Leu Leu
1               5

<210> SEQ ID NO 614
<211> LENGTH: 10
<212> TYPE: PRT
<213> ORGANISM: Artificial sequence
<220> FEATURE:
<223> OTHER INFORMATION: Peptide derived from HBV Polymerase protein

<400> SEQUENCE: 614

Leu Pro Ile His Thr Ala Glu Leu Leu Ala
1               5                   10

<210> SEQ ID NO 615
<211> LENGTH: 11
<212> TYPE: PRT
<213> ORGANISM: Artificial sequence
<220> FEATURE:
<223> OTHER INFORMATION: Peptide derived from HBV Polymerase protein

<400> SEQUENCE: 615

Leu Pro Ile His Thr Ala Glu Leu Leu Ala Ala
1               5                   10

<210> SEQ ID NO 616
<211> LENGTH: 8
<212> TYPE: PRT
<213> ORGANISM: Artificial sequence
<220> FEATURE:
<223> OTHER INFORMATION: Peptide derived from HBV Polymerase protein

<400> SEQUENCE: 616

His Thr Ala Glu Leu Leu Ala Ala
1               5

<210> SEQ ID NO 617
<211> LENGTH: 9
<212> TYPE: PRT
<213> ORGANISM: Artificial sequence
```

```
<220> FEATURE:
<223> OTHER INFORMATION: Peptide derived from HBV Polymerase protein

<400> SEQUENCE: 617

His Thr Ala Glu Leu Leu Ala Ala Cys
1               5

<210> SEQ ID NO 618
<211> LENGTH: 10
<212> TYPE: PRT
<213> ORGANISM: Artificial sequence
<220> FEATURE:
<223> OTHER INFORMATION: Peptide derived from HBV Polymerase protein

<400> SEQUENCE: 618

His Thr Ala Glu Leu Leu Ala Ala Cys Phe
1               5                   10

<210> SEQ ID NO 619
<211> LENGTH: 8
<212> TYPE: PRT
<213> ORGANISM: Artificial sequence
<220> FEATURE:
<223> OTHER INFORMATION: Peptide derived from HBV Polymerase protein

<400> SEQUENCE: 619

Ala Glu Leu Leu Ala Ala Cys Phe
1               5

<210> SEQ ID NO 620
<211> LENGTH: 11
<212> TYPE: PRT
<213> ORGANISM: Artificial sequence
<220> FEATURE:
<223> OTHER INFORMATION: Peptide derived from HBV Polymerase protein

<400> SEQUENCE: 620

His Thr Ala Glu Leu Leu Ala Ala Cys Phe Ala
1               5                   10

<210> SEQ ID NO 621
<211> LENGTH: 9
<212> TYPE: PRT
<213> ORGANISM: Artificial sequence
<220> FEATURE:
<223> OTHER INFORMATION: Peptide derived from HBV Polymerase protein

<400> SEQUENCE: 621

Ala Glu Leu Leu Ala Ala Cys Phe Ala
1               5

<210> SEQ ID NO 622
<211> LENGTH: 11
<212> TYPE: PRT
<213> ORGANISM: Artificial sequence
<220> FEATURE:
<223> OTHER INFORMATION: Peptide derived from HBV Polymerase protein

<400> SEQUENCE: 622

Thr Ala Glu Leu Leu Ala Ala Cys Phe Ala Arg
1               5                   10

<210> SEQ ID NO 623
<211> LENGTH: 10
<212> TYPE: PRT
<213> ORGANISM: Artificial sequence
<220> FEATURE:
```

<223> OTHER INFORMATION: Peptide derived from HBV Polymerase protein

<400> SEQUENCE: 623

Ala Glu Leu Leu Ala Ala Cys Phe Ala Arg
1               5                   10

<210> SEQ ID NO 624
<211> LENGTH: 9
<212> TYPE: PRT
<213> ORGANISM: Artificial sequence
<220> FEATURE:
<223> OTHER INFORMATION: Peptide derived from HBV Polymerase protein

<400> SEQUENCE: 624

Glu Leu Leu Ala Ala Cys Phe Ala Arg
1               5

<210> SEQ ID NO 625
<211> LENGTH: 8
<212> TYPE: PRT
<213> ORGANISM: Artificial sequence
<220> FEATURE:
<223> OTHER INFORMATION: Peptide derived from HBV Polymerase protein

<400> SEQUENCE: 625

Leu Leu Ala Ala Cys Phe Ala Arg
1               5

<210> SEQ ID NO 626
<211> LENGTH: 11
<212> TYPE: PRT
<213> ORGANISM: Artificial sequence
<220> FEATURE:
<223> OTHER INFORMATION: Peptide derived from HBV Polymerase protein

<400> SEQUENCE: 626

Ala Glu Leu Leu Ala Ala Cys Phe Ala Arg Ser
1               5                   10

<210> SEQ ID NO 627
<211> LENGTH: 8
<212> TYPE: PRT
<213> ORGANISM: Artificial sequence
<220> FEATURE:
<223> OTHER INFORMATION: Peptide derived from HBV Polymerase protein

<400> SEQUENCE: 627

Leu Ala Ala Cys Phe Ala Arg Ser
1               5

<210> SEQ ID NO 628
<211> LENGTH: 11
<212> TYPE: PRT
<213> ORGANISM: Artificial sequence
<220> FEATURE:
<223> OTHER INFORMATION: Peptide derived from HBV Polymerase protein

<400> SEQUENCE: 628

Glu Leu Leu Ala Ala Cys Phe Ala Arg Ser Arg
1               5                   10

<210> SEQ ID NO 629
<211> LENGTH: 10
<212> TYPE: PRT
<213> ORGANISM: Artificial sequence
<220> FEATURE:
<223> OTHER INFORMATION: Peptide derived from HBV Polymerase protein

```
<400> SEQUENCE: 629

Leu Leu Ala Ala Cys Phe Ala Arg Ser Arg
1               5                   10

<210> SEQ ID NO 630
<211> LENGTH: 9
<212> TYPE: PRT
<213> ORGANISM: Artificial sequence
<220> FEATURE:
<223> OTHER INFORMATION: Peptide derived from HBV Polymerase protein

<400> SEQUENCE: 630

Leu Ala Ala Cys Phe Ala Arg Ser Arg
1               5

<210> SEQ ID NO 631
<211> LENGTH: 8
<212> TYPE: PRT
<213> ORGANISM: Artificial sequence
<220> FEATURE:
<223> OTHER INFORMATION: Peptide derived from HBV Polymerase protein

<400> SEQUENCE: 631

Ala Ala Cys Phe Ala Arg Ser Arg
1               5

<210> SEQ ID NO 632
<211> LENGTH: 8
<212> TYPE: PRT
<213> ORGANISM: Artificial sequence
<220> FEATURE:
<223> OTHER INFORMATION: Peptide derived from HBV Polymerase protein

<400> SEQUENCE: 632

Phe Ala Arg Ser Arg Ser Gly Ala
1               5

<210> SEQ ID NO 633
<211> LENGTH: 9
<212> TYPE: PRT
<213> ORGANISM: Artificial sequence
<220> FEATURE:
<223> OTHER INFORMATION: Peptide derived from HBV Polymerase protein

<400> SEQUENCE: 633

Phe Ala Arg Ser Arg Ser Gly Ala Lys
1               5

<210> SEQ ID NO 634
<211> LENGTH: 10
<212> TYPE: PRT
<213> ORGANISM: Artificial sequence
<220> FEATURE:
<223> OTHER INFORMATION: Peptide derived from HBV Polymerase protein

<400> SEQUENCE: 634

Phe Ala Arg Ser Arg Ser Gly Ala Lys Leu
1               5                   10

<210> SEQ ID NO 635
<211> LENGTH: 9
<212> TYPE: PRT
<213> ORGANISM: Artificial sequence
<220> FEATURE:
<223> OTHER INFORMATION: Peptide derived from HBV Polymerase protein
```

```
<400> SEQUENCE: 635

Ala Arg Ser Arg Ser Gly Ala Lys Leu
1               5

<210> SEQ ID NO 636
<211> LENGTH: 8
<212> TYPE: PRT
<213> ORGANISM: Artificial sequence
<220> FEATURE:
<223> OTHER INFORMATION: Peptide derived from HBV Polymerase protein

<400> SEQUENCE: 636

Arg Ser Arg Ser Gly Ala Lys Leu
1               5

<210> SEQ ID NO 637

<400> SEQUENCE: 637

000

<210> SEQ ID NO 638
<211> LENGTH: 9
<212> TYPE: PRT
<213> ORGANISM: Artificial sequence
<220> FEATURE:
<223> OTHER INFORMATION: Peptide derived from HBV Polymerase protein

<400> SEQUENCE: 638

Val Leu Ser Arg Lys Tyr Thr Ser Phe
1               5

<210> SEQ ID NO 639
<211> LENGTH: 8
<212> TYPE: PRT
<213> ORGANISM: Artificial sequence
<220> FEATURE:
<223> OTHER INFORMATION: Peptide derived from HBV Polymerase protein

<400> SEQUENCE: 639

Leu Ser Arg Lys Tyr Thr Ser Phe
1               5

<210> SEQ ID NO 640
<211> LENGTH: 11
<212> TYPE: PRT
<213> ORGANISM: Artificial sequence
<220> FEATURE:
<223> OTHER INFORMATION: Peptide derived from HBV Polymerase protein

<400> SEQUENCE: 640

Val Leu Ser Arg Lys Tyr Thr Ser Phe Pro Trp
1               5                   10

<210> SEQ ID NO 641
<211> LENGTH: 10
<212> TYPE: PRT
<213> ORGANISM: Artificial sequence
<220> FEATURE:
<223> OTHER INFORMATION: Peptide derived from HBV Polymerase protein

<400> SEQUENCE: 641

Leu Ser Arg Lys Tyr Thr Ser Phe Pro Trp
1               5                   10

<210> SEQ ID NO 642
```

```
<211> LENGTH: 9
<212> TYPE: PRT
<213> ORGANISM: Artificial sequence
<220> FEATURE:
<223> OTHER INFORMATION: Peptide derived from HBV Polymerase protein

<400> SEQUENCE: 642

Ser Arg Lys Tyr Thr Ser Phe Pro Trp
1               5

<210> SEQ ID NO 643
<211> LENGTH: 8
<212> TYPE: PRT
<213> ORGANISM: Artificial sequence
<220> FEATURE:
<223> OTHER INFORMATION: Peptide derived from HBV Polymerase protein

<400> SEQUENCE: 643

Arg Lys Tyr Thr Ser Phe Pro Trp
1               5

<210> SEQ ID NO 644
<211> LENGTH: 11
<212> TYPE: PRT
<213> ORGANISM: Artificial sequence
<220> FEATURE:
<223> OTHER INFORMATION: Peptide derived from HBV Polymerase protein

<400> SEQUENCE: 644

Leu Ser Arg Lys Tyr Thr Ser Phe Pro Trp Leu
1               5                   10

<210> SEQ ID NO 645
<211> LENGTH: 10
<212> TYPE: PRT
<213> ORGANISM: Artificial sequence
<220> FEATURE:
<223> OTHER INFORMATION: Peptide derived from HBV Polymerase protein

<400> SEQUENCE: 645

Ser Arg Lys Tyr Thr Ser Phe Pro Trp Leu
1               5                   10

<210> SEQ ID NO 646
<211> LENGTH: 9
<212> TYPE: PRT
<213> ORGANISM: Artificial sequence
<220> FEATURE:
<223> OTHER INFORMATION: Peptide derived from HBV Polymerase protein

<400> SEQUENCE: 646

Arg Lys Tyr Thr Ser Phe Pro Trp Leu
1               5

<210> SEQ ID NO 647
<211> LENGTH: 8
<212> TYPE: PRT
<213> ORGANISM: Artificial sequence
<220> FEATURE:
<223> OTHER INFORMATION: Peptide derived from HBV Polymerase protein

<400> SEQUENCE: 647

Lys Tyr Thr Ser Phe Pro Trp Leu
1               5

<210> SEQ ID NO 648
<211> LENGTH: 11
```

```
<212> TYPE: PRT
<213> ORGANISM: Artificial sequence
<220> FEATURE:
<223> OTHER INFORMATION: Peptide derived from HBV Polymerase protein

<400> SEQUENCE: 648

Ser Arg Lys Tyr Thr Ser Phe Pro Trp Leu Leu
1               5                   10

<210> SEQ ID NO 649
<211> LENGTH: 10
<212> TYPE: PRT
<213> ORGANISM: Artificial sequence
<220> FEATURE:
<223> OTHER INFORMATION: Peptide derived from HBV Polymerase protein

<400> SEQUENCE: 649

Arg Lys Tyr Thr Ser Phe Pro Trp Leu Leu
1               5                   10

<210> SEQ ID NO 650
<211> LENGTH: 9
<212> TYPE: PRT
<213> ORGANISM: Artificial sequence
<220> FEATURE:
<223> OTHER INFORMATION: Peptide derived from HBV Polymerase protein

<400> SEQUENCE: 650

Lys Tyr Thr Ser Phe Pro Trp Leu Leu
1               5

<210> SEQ ID NO 651
<211> LENGTH: 8
<212> TYPE: PRT
<213> ORGANISM: Artificial sequence
<220> FEATURE:
<223> OTHER INFORMATION: Peptide derived from HBV Polymerase protein

<400> SEQUENCE: 651

Tyr Thr Ser Phe Pro Trp Leu Leu
1               5

<210> SEQ ID NO 652
<211> LENGTH: 11
<212> TYPE: PRT
<213> ORGANISM: Artificial sequence
<220> FEATURE:
<223> OTHER INFORMATION: Peptide derived from HBV Polymerase protein

<400> SEQUENCE: 652

Arg Lys Tyr Thr Ser Phe Pro Trp Leu Leu Gly
1               5                   10

<210> SEQ ID NO 653
<211> LENGTH: 10
<212> TYPE: PRT
<213> ORGANISM: Artificial sequence
<220> FEATURE:
<223> OTHER INFORMATION: Peptide derived from HBV Polymerase protein

<400> SEQUENCE: 653

Lys Tyr Thr Ser Phe Pro Trp Leu Leu Gly
1               5                   10

<210> SEQ ID NO 654
<211> LENGTH: 9
<212> TYPE: PRT
```

```
<213> ORGANISM: Artificial sequence
<220> FEATURE:
<223> OTHER INFORMATION: Peptide derived from HBV Polymerase protein

<400

```
<220> FEATURE:
<223> OTHER INFORMATION: Peptide derived from HBV Polymerase protein

<400> SEQUENCE: 660

Trp Leu Leu Gly Cys Thr Ala Asn Trp
1               5

<210> SEQ ID NO 661
<211> LENGTH: 10
<212> TYPE: PRT
<213> ORGANISM: Artificial sequence
<220> FEATURE:
<223> OTHER INFORMATION: Peptide derived from HBV Polymerase protein

<400> SEQUENCE: 661

Trp Leu Leu Gly Cys Thr Ala Asn Trp Ile
1               5                   10

<210> SEQ ID NO 662
<211> LENGTH: 9
<212> TYPE: PRT
<213> ORGANISM: Artificial sequence
<220> FEATURE:
<223> OTHER INFORMATION: Peptide derived from HBV Polymerase protein

<400> SEQUENCE: 662

Leu Leu Gly Cys Thr Ala Asn Trp Ile
1               5

<210> SEQ ID NO 663
<211> LENGTH: 11
<212> TYPE: PRT
<213> ORGANISM: Artificial sequence
<220> FEATURE:
<223> OTHER INFORMATION: Peptide derived from HBV Polymerase protein

<400> SEQUENCE: 663

Trp Leu Leu Gly Cys Thr Ala Asn Trp Ile Leu
1               5                   10

<210> SEQ ID NO 664
<211> LENGTH: 10
<212> TYPE: PRT
<213> ORGANISM: Artificial sequence
<220> FEATURE:
<223> OTHER INFORMATION: Peptide derived from HBV Polymerase protein

<400> SEQUENCE: 664

Leu Leu Gly Cys Thr Ala Asn Trp Ile Leu
1               5                   10

<210> SEQ ID NO 665
<211> LENGTH: 11
<212> TYPE: PRT
<213> ORGANISM: Artificial sequence
<220> FEATURE:
<223> OTHER INFORMATION: Peptide derived from HBV Polymerase protein

<400> SEQUENCE: 665

Leu Leu Gly Cys Thr Ala Asn Trp Ile Leu Arg
1               5                   10

<210> SEQ ID NO 666
<211> LENGTH: 10
<212> TYPE: PRT
<213> ORGANISM: Artificial sequence
<220> FEATURE:
```

<223> OTHER INFORMATION: Peptide derived from HBV Polymerase protein

<400> SEQUENCE: 666

Leu Gly Cys Thr Ala Asn Trp Ile Leu Arg
1               5                   10

<210> SEQ ID NO 667
<211> LENGTH: 8
<212> TYPE: PRT
<213> ORGANISM: Artificial sequence
<220> FEATURE:
<223> OTHER INFORMATION: Peptide derived from HBV Polymerase protein

<400> SEQUENCE: 667

Cys Thr Ala Asn Trp Ile Leu Arg
1               5

<210> SEQ ID NO 668
<211> LENGTH: 11
<212> TYPE: PRT
<213> ORGANISM: Artificial sequence
<220> FEATURE:
<223> OTHER INFORMATION: Peptide derived from HBV Polymerase protein

<400> SEQUENCE: 668

Thr Ala Asn Trp Ile Leu Arg Gly Thr Ser Phe
1               5                   10

<210> SEQ ID NO 669
<211> LENGTH: 10
<212> TYPE: PRT
<213> ORGANISM: Artificial sequence
<220> FEATURE:
<223> OTHER INFORMATION: Peptide derived from HBV Polymerase protein

<400> SEQUENCE: 669

Ala Asn Trp Ile Leu Arg Gly Thr Ser Phe
1               5                   10

<210> SEQ ID NO 670
<211> LENGTH: 9
<212> TYPE: PRT
<213> ORGANISM: Artificial sequence
<220> FEATURE:
<223> OTHER INFORMATION: Peptide derived from HBV Polymerase protein

<400> SEQUENCE: 670

Asn Trp Ile Leu Arg Gly Thr Ser Phe
1               5

<210> SEQ ID NO 671
<211> LENGTH: 8
<212> TYPE: PRT
<213> ORGANISM: Artificial sequence
<220> FEATURE:
<223> OTHER INFORMATION: Peptide derived from HBV Polymerase protein

<400> SEQUENCE: 671

Trp Ile Leu Arg Gly Thr Ser Phe
1               5

<210> SEQ ID NO 672
<211> LENGTH: 9
<212> TYPE: PRT
<213> ORGANISM: Artificial sequence
<220> FEATURE:
<223> OTHER INFORMATION: Peptide derived from HBV Polymerase protein

```
<400> SEQUENCE: 672

Trp Ile Leu Arg Gly Thr Ser Phe Val
1               5

<210> SEQ ID NO 673
<211> LENGTH: 11
<212> TYPE: PRT
<213> ORGANISM: Artificial sequence
<220> FEATURE:
<223> OTHER INFORMATION: Peptide derived from HBV Polymerase protein

<400> SEQUENCE: 673

Asn Trp Ile Leu Arg Gly Thr Ser Phe Val Tyr
1               5                   10

<210> SEQ ID NO 674
<211> LENGTH: 10
<212> TYPE: PRT
<213> ORGANISM: Artificial sequence
<220> FEATURE:
<223> OTHER INFORMATION: Peptide derived from HBV Polymerase protein

<400> SEQUENCE: 674

Trp Ile Leu Arg Gly Thr Ser Phe Val Tyr
1               5                   10

<210> SEQ ID NO 675
<211> LENGTH: 9
<212> TYPE: PRT
<213> ORGANISM: Artificial sequence
<220> FEATURE:
<223> OTHER INFORMATION: Peptide derived from HBV Polymerase protein

<400> SEQUENCE: 675

Ile Leu Arg Gly Thr Ser Phe Val Tyr
1               5

<210> SEQ ID NO 676
<211> LENGTH: 8
<212> TYPE: PRT
<213> ORGANISM: Artificial sequence
<220> FEATURE:
<223> OTHER INFORMATION: Peptide derived from HBV Polymerase protein

<400> SEQUENCE: 676

Leu Arg Gly Thr Ser Phe Val Tyr
1               5

<210> SEQ ID NO 677
<211> LENGTH: 10
<212> TYPE: PRT
<213> ORGANISM: Artificial sequence
<220> FEATURE:
<223> OTHER INFORMATION: Peptide derived from HBV Polymerase protein

<400> SEQUENCE: 677

Ile Leu Arg Gly Thr Ser Phe Val Tyr Val
1               5                   10

<210> SEQ ID NO 678
<211> LENGTH: 10
<212> TYPE: PRT
<213> ORGANISM: Artificial sequence
<220> FEATURE:
<223> OTHER INFORMATION: Peptide derived from HBV Polymerase protein
```

```
<400> SEQUENCE: 678

Gly Thr Ser Phe Val Tyr Val Pro Ser Ala
1               5                   10

<210> SEQ ID NO 679
<211> LENGTH: 9
<212> TYPE: PRT
<213> ORGANISM: Artificial sequence
<220> FEATURE:
<223> OTHER INFORMATION: Peptide derived from HBV Polymerase protein

<400> SEQUENCE: 679

Ser Phe Val Tyr Val Pro Ser Ala Leu
1               5

<210> SEQ ID NO 680
<211> LENGTH: 8
<212> TYPE: PRT
<213> ORGANISM: Artificial sequence
<220> FEATURE:
<223> OTHER INFORMATION: Peptide derived from HBV Polymerase protein

<400> SEQUENCE: 680

Phe Val Tyr Val Pro Ser Ala Leu
1               5

<210> SEQ ID NO 681
<211> LENGTH: 8
<212> TYPE: PRT
<213> ORGANISM: Artificial sequence
<220> FEATURE:
<223> OTHER INFORMATION: Peptide derived from HBV Polymerase protein

<400> SEQUENCE: 681

Tyr Val Pro Ser Ala Leu Asn Pro
1               5

<210> SEQ ID NO 682
<211> LENGTH: 11
<212> TYPE: PRT
<213> ORGANISM: Artificial sequence
<220> FEATURE:
<223> OTHER INFORMATION: Peptide derived from HBV Polymerase protein

<400> SEQUENCE: 682

Phe Val Tyr Val Pro Ser Ala Leu Asn Pro Ala
1               5                   10

<210> SEQ ID NO 683
<211> LENGTH: 9
<212> TYPE: PRT
<213> ORGANISM: Artificial sequence
<220> FEATURE:
<223> OTHER INFORMATION: Peptide derived from HBV Polymerase protein

<400> SEQUENCE: 683

Tyr Val Pro Ser Ala Leu Asn Pro Ala
1               5

<210> SEQ ID NO 684
<211> LENGTH: 8
<212> TYPE: PRT
<213> ORGANISM: Artificial sequence
<220> FEATURE:
<223> OTHER INFORMATION: Peptide derived from HBV Polymerase protein

<400> SEQUENCE: 684
```

Val Pro Ser Ala Leu Asn Pro Ala
1               5

<210> SEQ ID NO 685
<211> LENGTH: 10
<212> TYPE: PRT
<213> ORGANISM: Artificial sequence
<220> FEATURE:
<223> OTHER INFORMATION: Peptide derived from HBV Polymerase protein

<400> SEQUENCE: 685

Tyr Val Pro Ser Ala Leu Asn Pro Ala Asp
1               5                   10

<210> SEQ ID NO 686
<211> LENGTH: 15
<212> TYPE: PRT
<213> ORGANISM: Artificial sequence
<220> FEATURE:
<223> OTHER INFORMATION: Peptide derived from HBV Polymerase protein

<400> SEQUENCE: 686

Met Pro Leu Ser Tyr Gln His Phe Arg Lys Leu Leu Leu Leu Asp
1               5                   10                  15

<210> SEQ ID NO 687
<211> LENGTH: 15
<212> TYPE: PRT
<213> ORGANISM: Artificial sequence
<220> FEATURE:
<223> OTHER INFORMATION: Peptide derived from HBV Polymerase protein

<400> SEQUENCE: 687

Pro Leu Ser Tyr Gln His Phe Arg Lys Leu Leu Leu Leu Asp Asp
1               5                   10                  15

<210> SEQ ID NO 688
<211> LENGTH: 15
<212> TYPE: PRT
<213> ORGANISM: Artificial sequence
<220> FEATURE:
<223> OTHER INFORMATION: Peptide derived from HBV Polymerase protein

<400> SEQUENCE: 688

Leu Ser Tyr Gln His Phe Arg Lys Leu Leu Leu Leu Asp Asp Gly
1               5                   10                  15

<210> SEQ ID NO 689
<211> LENGTH: 15
<212> TYPE: PRT
<213> ORGANISM: Artificial sequence
<220> FEATURE:
<223> OTHER INFORMATION: Peptide derived from HBV Polymerase protein

<400> SEQUENCE: 689

Ser Tyr Gln His Phe Arg Lys Leu Leu Leu Leu Asp Asp Gly Thr
1               5                   10                  15

<210> SEQ ID NO 690
<211> LENGTH: 15
<212> TYPE: PRT
<213> ORGANISM: Artificial sequence
<220> FEATURE:
<223> OTHER INFORMATION: Peptide derived from HBV Polymerase protein

<400> SEQUENCE: 690

Tyr Gln His Phe Arg Lys Leu Leu Leu Leu Asp Asp Gly Thr Glu
1               5                   10                  15

<210> SEQ ID NO 691
<211> LENGTH: 15
<212> TYPE: PRT
<213> ORGANISM: Artificial sequence
<220> FEATURE:
<223> OTHER INFORMATION: Peptide derived from HBV Polymerase protein

<400> SEQUENCE: 691

Gln His Phe Arg Lys Leu Leu Leu Leu Asp Asp Gly Thr Glu Ala
1               5                   10                  15

<210> SEQ ID NO 692
<211> LENGTH: 15
<212> TYPE: PRT
<213> ORGANISM: Artificial sequence
<220> FEATURE:
<223> OTHER INFORMATION: Peptide derived from HBV Polymerase protein

<400> SEQUENCE: 692

His Phe Arg Lys Leu Leu Leu Leu Asp Asp Gly Thr Glu Ala Gly
1               5                   10                  15

<210> SEQ ID NO 693
<211> LENGTH: 15
<212> TYPE: PRT
<213> ORGANISM: Artificial sequence
<220> FEATURE:
<223> OTHER INFORMATION: Peptide derived from HBV Polymerase protein

<400> SEQUENCE: 693

Phe Arg Lys Leu Leu Leu Leu Asp Asp Gly Thr Glu Ala Gly Pro
1               5                   10                  15

<210> SEQ ID NO 694
<211> LENGTH: 15
<212> TYPE: PRT
<213> ORGANISM: Artificial sequence
<220> FEATURE:
<223> OTHER INFORMATION: Peptide derived from HBV Polymerase protein

<400> SEQUENCE: 694

Arg Lys Leu Leu Leu Leu Asp Asp Gly Thr Glu Ala Gly Pro Leu
1               5                   10                  15

<210> SEQ ID NO 695
<211> LENGTH: 15
<212> TYPE: PRT
<213> ORGANISM: Artificial sequence
<220> FEATURE:
<223> OTHER INFORMATION: Peptide derived from HBV Polymerase protein

<400> SEQUENCE: 695

Lys Leu Leu Leu Leu Asp Asp Gly Thr Glu Ala Gly Pro Leu Glu
1               5                   10                  15

<210> SEQ ID NO 696
<211> LENGTH: 15
<212> TYPE: PRT
<213> ORGANISM: Artificial sequence
<220> FEATURE:
<223> OTHER INFORMATION: Peptide derived from HBV Polymerase protein

<400> SEQUENCE: 696

Leu Leu Leu Leu Asp Asp Gly Thr Glu Ala Gly Pro Leu Glu Glu

```
                1               5              10              15
```

<210> SEQ ID NO 697
<211> LENGTH: 15
<212> TYPE: PRT
<213> ORGANISM: Artificial sequence
<220> FEATURE:
<223> OTHER INFORMATION: Peptide derived from HBV Polymerase protein

<400> SEQUENCE: 697

```
Thr His Lys Val Gly Asn Phe Thr Gly Leu Tyr Ser Ser Thr Val
1               5                  10                  15
```

<210> SEQ ID NO 698
<211> LENGTH: 15
<212> TYPE: PRT
<213> ORGANISM: Artificial sequence
<220> FEATURE:
<223> OTHER INFORMATION: Peptide derived from HBV Polymerase protein

<400> SEQUENCE: 698

```
His Lys Val Gly Asn Phe Thr Gly Leu Tyr Ser Ser Thr Val Pro
1               5                  10                  15
```

<210> SEQ ID NO 699
<211> LENGTH: 15
<212> TYPE: PRT
<213> ORGANISM: Artificial sequence
<220> FEATURE:
<223> OTHER INFORMATION: Peptide derived from HBV Polymerase protein

<400> SEQUENCE: 699

```
Lys Val Gly Asn Phe Thr Gly Leu Tyr Ser Ser Thr Val Pro Ile
1               5                  10                  15
```

<210> SEQ ID NO 700
<211> LENGTH: 15
<212> TYPE: PRT
<213> ORGANISM: Artificial sequence
<220> FEATURE:
<223> OTHER INFORMATION: Peptide derived from HBV Polymerase protein

<400> SEQUENCE: 700

```
Val Gly Asn Phe Thr Gly Leu Tyr Ser Ser Thr Val Pro Ile Phe
1               5                  10                  15
```

<210> SEQ ID NO 701
<211> LENGTH: 15
<212> TYPE: PRT
<213> ORGANISM: Artificial sequence
<220> FEATURE:
<223> OTHER INFORMATION: Peptide derived from HBV Polymerase protein

<400> SEQUENCE: 701

```
Gly Asn Phe Thr Gly Leu Tyr Ser Ser Thr Val Pro Ile Phe Asn
1               5                  10                  15
```

<210> SEQ ID NO 702
<211> LENGTH: 15
<212> TYPE: PRT
<213> ORGANISM: Artificial sequence
<220> FEATURE:
<223> OTHER INFORMATION: Peptide derived from HBV Polymerase protein

<400> SEQUENCE: 702

```
Asn Phe Thr Gly Leu Tyr Ser Ser Thr Val Pro Ile Phe Asn Pro
1               5                  10                  15
```

```
<210> SEQ ID NO 703
<211> LENGTH: 15
<212> TYPE: PRT
<213> ORGANISM: Artificial sequence
<220> FEATURE:
<223> OTHER INFORMATION: Peptide derived from HBV Polymerase protein

<400> SEQUENCE: 703

Phe Thr Gly Leu Tyr Ser Ser Thr Val Pro Ile Phe Asn Pro Glu
1               5                   10                  15

<210> SEQ ID NO 704
<211> LENGTH: 15
<212> TYPE: PRT
<213> ORGANISM: Artificial sequence
<220> FEATURE:
<223> OTHER INFORMATION: Peptide derived from HBV Polymerase protein

<400> SEQUENCE: 704

Thr Gly Leu Tyr Ser Ser Thr Val Pro Ile Phe Asn Pro Glu Trp
1               5                   10                  15

<210> SEQ ID NO 705
<211> LENGTH: 15
<212> TYPE: PRT
<213> ORGANISM: Artificial sequence
<220> FEATURE:
<223> OTHER INFORMATION: Peptide derived from HBV Polymerase protein

<400> SEQUENCE: 705

Val Asn Glu Lys Arg Arg Leu Lys Leu Ile Met Pro Ala Arg Phe
1               5                   10                  15

<210> SEQ ID NO 706
<211> LENGTH: 15
<212> TYPE: PRT
<213> ORGANISM: Artificial sequence
<220> FEATURE:
<223> OTHER INFORMATION: Peptide derived from HBV Polymerase protein

<400> SEQUENCE: 706

Asn Glu Lys Arg Arg Leu Lys Leu Ile Met Pro Ala Arg Phe Tyr
1               5                   10                  15

<210> SEQ ID NO 707
<211> LENGTH: 15
<212> TYPE: PRT
<213> ORGANISM: Artificial sequence
<220> FEATURE:
<223> OTHER INFORMATION: Peptide derived from HBV Polymerase protein

<400> SEQUENCE: 707

Glu Lys Arg Arg Leu Lys Leu Ile Met Pro Ala Arg Phe Tyr Pro
1               5                   10                  15

<210> SEQ ID NO 708
<211> LENGTH: 15
<212> TYPE: PRT
<213> ORGANISM: Artificial sequence
<220> FEATURE:
<223> OTHER INFORMATION: Peptide derived from HBV Polymerase protein

<400> SEQUENCE: 708

Lys Arg Arg Leu Lys Leu Ile Met Pro Ala Arg Phe Tyr Pro Thr
1               5                   10                  15
```

<210> SEQ ID NO 709
<211> LENGTH: 15
<212> TYPE: PRT
<213> ORGANISM: Artificial sequence
<220> FEATURE:
<223> OTHER INFORMATION: Peptide derived from HBV Polymerase protein

<400> SEQUENCE: 709

Arg Arg Leu Lys Leu Ile Met Pro Ala Arg Phe Tyr Pro Thr His
1               5                   10                  15

<210> SEQ ID NO 710
<211> LENGTH: 15
<212> TYPE: PRT
<213> ORGANISM: Artificial sequence
<220> FEATURE:
<223> OTHER INFORMATION: Peptide derived from HBV Polymerase protein

<400> SEQUENCE: 710

Arg Leu Lys Leu Ile Met Pro Ala Arg Phe Tyr Pro Thr His Thr
1               5                   10                  15

<210> SEQ ID NO 711
<211> LENGTH: 15
<212> TYPE: PRT
<213> ORGANISM: Artificial sequence
<220> FEATURE:
<223> OTHER INFORMATION: Peptide derived from HBV Polymerase protein

<400> SEQUENCE: 711

Leu Lys Leu Ile Met Pro Ala Arg Phe Tyr Pro Thr His Thr Lys
1               5                   10                  15

<210> SEQ ID NO 712
<211> LENGTH: 15
<212> TYPE: PRT
<213> ORGANISM: Artificial sequence
<220> FEATURE:
<223> OTHER INFORMATION: Peptide derived from HBV Polymerase protein

<400> SEQUENCE: 712

Leu Ile Met Pro Ala Arg Phe Tyr Pro Thr His Thr Lys Tyr Leu
1               5                   10                  15

<210> SEQ ID NO 713
<211> LENGTH: 15
<212> TYPE: PRT
<213> ORGANISM: Artificial sequence
<220> FEATURE:
<223> OTHER INFORMATION: Peptide derived from HBV Polymerase protein

<400> SEQUENCE: 713

Ile Met Pro Ala Arg Phe Tyr Pro Thr His Thr Lys Tyr Leu Pro
1               5                   10                  15

<210> SEQ ID NO 714
<211> LENGTH: 15
<212> TYPE: PRT
<213> ORGANISM: Artificial sequence
<220> FEATURE:
<223> OTHER INFORMATION: Peptide derived from HBV Polymerase protein

<400> SEQUENCE: 714

Met Pro Ala Arg Phe Tyr Pro Thr His Thr Lys Tyr Leu Pro Leu
1               5                   10                  15

```
<210> SEQ ID NO 715
<211> LENGTH: 15
<212> TYPE: PRT
<213> ORGANISM: Artificial sequence
<220> FEATURE:
<223> OTHER INFORMATION: Peptide derived from HBV Polymerase protein

<400> SEQUENCE: 715

Pro Ala Arg Phe Tyr Pro Thr His Thr Lys Tyr Leu Pro Leu Asp
1               5                   10                  15

<210> SEQ ID NO 716
<211> LENGTH: 15
<212> TYPE: PRT
<213> ORGANISM: Artificial sequence
<220> FEATURE:
<223> OTHER INFORMATION: Peptide derived from HBV Polymerase protein

<400> SEQUENCE: 716

Ala Arg Phe Tyr Pro Thr His Thr Lys Tyr Leu Pro Leu Asp Lys
1               5                   10                  15

<210> SEQ ID NO 717
<211> LENGTH: 15
<212> TYPE: PRT
<213> ORGANISM: Artificial sequence
<220> FEATURE:
<223> OTHER INFORMATION: Peptide derived from HBV Polymerase protein

<400> SEQUENCE: 717

Arg Phe Tyr Pro Thr His Thr Lys Tyr Leu Pro Leu Asp Lys Gly
1               5                   10                  15

<210> SEQ ID NO 718
<211> LENGTH: 15
<212> TYPE: PRT
<213> ORGANISM: Artificial sequence
<220> FEATURE:
<223> OTHER INFORMATION: Peptide derived from HBV Polymerase protein

<400> SEQUENCE: 718

Phe Tyr Pro Thr His Thr Lys Tyr Leu Pro Leu Asp Lys Gly Ile
1               5                   10                  15

<210> SEQ ID NO 719
<211> LENGTH: 15
<212> TYPE: PRT
<213> ORGANISM: Artificial sequence
<220> FEATURE:
<223> OTHER INFORMATION: Peptide derived from HBV Polymerase protein

<400> SEQUENCE: 719

His Thr Lys Tyr Leu Pro Leu Asp Lys Gly Ile Lys Pro Tyr Tyr
1               5                   10                  15

<210> SEQ ID NO 720
<211> LENGTH: 15
<212> TYPE: PRT
<213> ORGANISM: Artificial sequence
<220> FEATURE:
<223> OTHER INFORMATION: Peptide derived from HBV Polymerase protein

<400> SEQUENCE: 720

Thr Lys Tyr Leu Pro Leu Asp Lys Gly Ile Lys Pro Tyr Tyr Pro
1               5                   10                  15

<210> SEQ ID NO 721
```

```
<211> LENGTH: 15
<212> TYPE: PRT
<213> ORGANISM: Artificial sequence
<220> FEATURE:
<223> OTHER INFORMATION: Peptide derived from HBV Polymerase protein

<400> SEQUENCE: 721

Gly Ile Lys Pro Tyr Tyr Pro Asp Gln Val Val Asn His Tyr Phe
1               5                   10                  15

<210> SEQ ID NO 722
<211> LENGTH: 15
<212> TYPE: PRT
<213> ORGANISM: Artificial sequence
<220> FEATURE:
<223> OTHER INFORMATION: Peptide derived from HBV Polymerase protein

<400> SEQUENCE: 722

Ile Lys Pro Tyr Tyr Pro Asp Gln Val Val Asn His Tyr Phe Gln
1               5                   10                  15

<210> SEQ ID NO 723
<211> LENGTH: 15
<212> TYPE: PRT
<213> ORGANISM: Artificial sequence
<220> FEATURE:
<223> OTHER INFORMATION: Peptide derived from HBV Polymerase protein

<400> SEQUENCE: 723

Lys Pro Tyr Tyr Pro Asp Gln Val Val Asn His Tyr Phe Gln Thr
1               5                   10                  15

<210> SEQ ID NO 724
<211> LENGTH: 15
<212> TYPE: PRT
<213> ORGANISM: Artificial sequence
<220> FEATURE:
<223> OTHER INFORMATION: Peptide derived from HBV Polymerase protein

<400> SEQUENCE: 724

Asp Gln Val Val Asn His Tyr Phe Gln Thr Arg His Tyr Leu His
1               5                   10                  15

<210> SEQ ID NO 725
<211> LENGTH: 15
<212> TYPE: PRT
<213> ORGANISM: Artificial sequence
<220> FEATURE:
<223> OTHER INFORMATION: Peptide derived from HBV Polymerase protein

<400> SEQUENCE: 725

Gln Val Val Asn His Tyr Phe Gln Thr Arg His Tyr Leu His Thr
1               5                   10                  15

<210> SEQ ID NO 726
<211> LENGTH: 15
<212> TYPE: PRT
<213> ORGANISM: Artificial sequence
<220> FEATURE:
<223> OTHER INFORMATION: Peptide derived from HBV Polymerase protein

<400> SEQUENCE: 726

Val Val Asn His Tyr Phe Gln Thr Arg His Tyr Leu His Thr Leu
1               5                   10                  15

<210> SEQ ID NO 727
<211> LENGTH: 15
```

```
<212> TYPE: PRT
<213> ORGANISM: Artificial sequence
<220> FEATURE:
<223> OTHER INFORMATION: Peptide derived from HBV Polymerase protein

<400> SEQUENCE: 727

Val Asn His Tyr Phe Gln Thr Arg His Tyr Leu His Thr Leu Trp
1               5                   10                  15

<210> SEQ ID NO 728
<211> LENGTH: 15
<212> TYPE: PRT
<213> ORGANISM: Artificial sequence
<220> FEATURE:
<223> OTHER INFORMATION: Peptide derived from HBV Polymerase protein

<400> SEQUENCE: 728

Asn His Tyr Phe Gln Thr Arg His Tyr Leu His Thr Leu Trp Lys
1               5                   10                  15

<210> SEQ ID NO 729
<211> LENGTH: 15
<212> TYPE: PRT
<213> ORGANISM: Artificial sequence
<220> FEATURE:
<223> OTHER INFORMATION: Peptide derived from HBV Polymerase protein

<400> SEQUENCE: 729

His Tyr Phe Gln Thr Arg His Tyr Leu His Thr Leu Trp Lys Ala
1               5                   10                  15

<210> SEQ ID NO 730
<211> LENGTH: 15
<212> TYPE: PRT
<213> ORGANISM: Artificial sequence
<220> FEATURE:
<223> OTHER INFORMATION: Peptide derived from HBV Polymerase protein

<400> SEQUENCE: 730

Tyr Phe Gln Thr Arg His Tyr Leu His Thr Leu Trp Lys Ala Gly
1               5                   10                  15

<210> SEQ ID NO 731
<211> LENGTH: 15
<212> TYPE: PRT
<213> ORGANISM: Artificial sequence
<220> FEATURE:
<223> OTHER INFORMATION: Peptide derived from HBV Polymerase protein

<400> SEQUENCE: 731

Phe Gln Thr Arg His Tyr Leu His Thr Leu Trp Lys Ala Gly Ile
1               5                   10                  15

<210> SEQ ID NO 732
<211> LENGTH: 15
<212> TYPE: PRT
<213> ORGANISM: Artificial sequence
<220> FEATURE:
<223> OTHER INFORMATION: Peptide derived from HBV Polymerase protein

<400> SEQUENCE: 732

Gln Thr Arg His Tyr Leu His Thr Leu Trp Lys Ala Gly Ile Leu
1               5                   10                  15

<210> SEQ ID NO 733
<211> LENGTH: 15
<212> TYPE: PRT
```

```
<213> ORGANISM: Artificial sequence
<220> FEATURE:
<223> OTHER INFORMATION: Peptide derived from HBV Polymerase protein

<400> SEQUENCE: 733

Thr Arg His Tyr Leu His Thr Leu Trp Lys Ala Gly Ile Leu Tyr
1               5                   10                  15

<210> SEQ ID NO 734
<211> LENGTH: 15
<212> TYPE: PRT
<213> ORGANISM: Artificial sequence
<220> FEATURE:
<223> OTHER INFORMATION: Peptide derived from HBV Polymerase protein

<400> SEQUENCE: 734

Arg His Tyr Leu His Thr Leu Trp Lys Ala Gly Ile Leu Tyr Lys
1               5                   10                  15

<210> SEQ ID NO 735
<211> LENGTH: 15
<212> TYPE: PRT
<213> ORGANISM: Artificial sequence
<220> FEATURE:
<223> OTHER INFORMATION: Peptide derived from HBV Polymerase protein

<400> SEQUENCE: 735

His Tyr Leu His Thr Leu Trp Lys Ala Gly Ile Leu Tyr Lys Arg
1               5                   10                  15

<210> SEQ ID NO 736
<211> LENGTH: 15
<212> TYPE: PRT
<213> ORGANISM: Artificial sequence
<220> FEATURE:
<223> OTHER INFORMATION: Peptide derived from HBV Polymerase protein

<400> SEQUENCE: 736

Trp Lys Ala Gly Ile Leu Tyr Lys Arg Glu Thr Thr Arg Ser Ala
1               5                   10                  15

<210> SEQ ID NO 737
<211> LENGTH: 15
<212> TYPE: PRT
<213> ORGANISM: Artificial sequence
<220> FEATURE:
<223> OTHER INFORMATION: Peptide derived from HBV Polymerase protein

<400> SEQUENCE: 737

Lys Ala Gly Ile Leu Tyr Lys Arg Glu Thr Thr Arg Ser Ala Ser
1               5                   10                  15

<210> SEQ ID NO 738
<211> LENGTH: 15
<212> TYPE: PRT
<213> ORGANISM: Artificial sequence
<220> FEATURE:
<223> OTHER INFORMATION: Peptide derived from HBV Polymerase protein

<400> SEQUENCE: 738

Ala Gly Ile Leu Tyr Lys Arg Glu Thr Thr Arg Ser Ala Ser Phe
1               5                   10                  15

<210> SEQ ID NO 739
<211> LENGTH: 15
<212> TYPE: PRT
<213> ORGANISM: Artificial sequence
```

```
<220> FEATURE:
<223> OTHER INFORMATION: Peptide derived from HBV Polymerase protein

<400> SEQUENCE: 739

Gly Ile Leu Tyr Lys Arg Glu Thr Thr Arg Ser Ala Ser Phe Cys
1               5                   10                  15

<210> SEQ ID NO 740
<211> LENGTH: 15
<212> TYPE: PRT
<213> ORGANISM: Artificial sequence
<220> FEATURE:
<223> OTHER INFORMATION: Peptide derived from HBV Polymerase protein

<400> SEQUENCE: 740

Ile Leu Tyr Lys Arg Glu Thr Thr Arg Ser Ala Ser Phe Cys Gly
1               5                   10                  15

<210> SEQ ID NO 741
<211> LENGTH: 15
<212> TYPE: PRT
<213> ORGANISM: Artificial sequence
<220> FEATURE:
<223> OTHER INFORMATION: Peptide derived from HBV Polymerase protein

<400> SEQUENCE: 741

Leu Tyr Lys Arg Glu Thr Thr Arg Ser Ala Ser Phe Cys Gly Ser
1               5                   10                  15

<210> SEQ ID NO 742
<211> LENGTH: 15
<212> TYPE: PRT
<213> ORGANISM: Artificial sequence
<220> FEATURE:
<223> OTHER INFORMATION: Peptide derived from HBV Polymerase protein

<400> SEQUENCE: 742

Ser Cys Trp Trp Leu Gln Phe Arg Asn Ser Lys Pro Cys Ser Glu
1               5                   10                  15

<210> SEQ ID NO 743
<211> LENGTH: 15
<212> TYPE: PRT
<213> ORGANISM: Artificial sequence
<220> FEATURE:
<223> OTHER INFORMATION: Peptide derived from HBV Polymerase protein

<400> SEQUENCE: 743

Thr Ala Glu Ser Arg Leu Val Val Asp Phe Ser Gln Phe Ser Arg
1               5                   10                  15

<210> SEQ ID NO 744
<211> LENGTH: 15
<212> TYPE: PRT
<213> ORGANISM: Artificial sequence
<220> FEATURE:
<223> OTHER INFORMATION: Peptide derived from HBV Polymerase protein

<400> SEQUENCE: 744

Ala Glu Ser Arg Leu Val Val Asp Phe Ser Gln Phe Ser Arg Gly
1               5                   10                  15

<210> SEQ ID NO 745
<211> LENGTH: 15
<212> TYPE: PRT
<213> ORGANISM: Artificial sequence
<220> FEATURE:
```

<223> OTHER INFORMATION: Peptide derived from HBV Polymerase protein

<400> SEQUENCE: 745

Glu Ser Arg Leu Val Val Asp Phe Ser Gln Phe Ser Arg Gly Ile
1               5                   10                  15

<210> SEQ ID NO 746
<211> LENGTH: 15
<212> TYPE: PRT
<213> ORGANISM: Artificial sequence
<220> FEATURE:
<223> OTHER INFORMATION: Peptide derived from HBV Polymerase protein

<400> SEQUENCE: 746

Ser Arg Leu Val Val Asp Phe Ser Gln Phe Ser Arg Gly Ile Ser
1               5                   10                  15

<210> SEQ ID NO 747
<211> LENGTH: 15
<212> TYPE: PRT
<213> ORGANISM: Artificial sequence
<220> FEATURE:
<223> OTHER INFORMATION: Peptide derived from HBV Polymerase protein

<400> SEQUENCE: 747

Arg Leu Val Val Asp Phe Ser Gln Phe Ser Arg Gly Ile Ser Arg
1               5                   10                  15

<210> SEQ ID NO 748
<211> LENGTH: 15
<212> TYPE: PRT
<213> ORGANISM: Artificial sequence
<220> FEATURE:
<223> OTHER INFORMATION: Peptide derived from HBV Polymerase protein

<400> SEQUENCE: 748

Leu Val Val Asp Phe Ser Gln Phe Ser Arg Gly Ile Ser Arg Val
1               5                   10                  15

<210> SEQ ID NO 749
<211> LENGTH: 15
<212> TYPE: PRT
<213> ORGANISM: Artificial sequence
<220> FEATURE:
<223> OTHER INFORMATION: Peptide derived from HBV Polymerase protein

<400> SEQUENCE: 749

Leu Ser Ser Asn Leu Ser Trp Leu Ser Leu Asp Val Ser Ala Ala
1               5                   10                  15

<210> SEQ ID NO 750
<211> LENGTH: 15
<212> TYPE: PRT
<213> ORGANISM: Artificial sequence
<220> FEATURE:
<223> OTHER INFORMATION: Peptide derived from HBV Polymerase protein

<400> SEQUENCE: 750

Ser Ser Asn Leu Ser Trp Leu Ser Leu Asp Val Ser Ala Ala Phe
1               5                   10                  15

<210> SEQ ID NO 751
<211> LENGTH: 15
<212> TYPE: PRT
<213> ORGANISM: Artificial sequence
<220> FEATURE:
<223> OTHER INFORMATION: Peptide derived from HBV Polymerase protein

```
<400> SEQUENCE: 751

Ser Asn Leu Ser Trp Leu Ser Leu Asp Val Ser Ala Ala Phe Tyr
1               5                   10                  15

<210> SEQ ID NO 752
<211> LENGTH: 15
<212> TYPE: PRT
<213> ORGANISM: Artificial sequence
<220> FEATURE:
<223> OTHER INFORMATION: Peptide derived from HBV Polymerase protein

<400> SEQUENCE: 752

Asn Leu Ser Trp Leu Ser Leu Asp Val Ser Ala Ala Phe Tyr His
1               5                   10                  15

<210> SEQ ID NO 753
<211> LENGTH: 15
<212> TYPE: PRT
<213> ORGANISM: Artificial sequence
<220> FEATURE:
<223> OTHER INFORMATION: Peptide derived from HBV Polymerase protein

<400> SEQUENCE: 753

Leu Ser Trp Leu Ser Leu Asp Val Ser Ala Ala Phe Tyr His Ile
1               5                   10                  15

<210> SEQ ID NO 754
<211> LENGTH: 15
<212> TYPE: PRT
<213> ORGANISM: Artificial sequence
<220> FEATURE:
<223> OTHER INFORMATION: Peptide derived from HBV Polymerase protein

<400> SEQUENCE: 754

Ser Trp Leu Ser Leu Asp Val Ser Ala Ala Phe Tyr His Ile Pro
1               5                   10                  15

<210> SEQ ID NO 755
<211> LENGTH: 15
<212> TYPE: PRT
<213> ORGANISM: Artificial sequence
<220> FEATURE:
<223> OTHER INFORMATION: Peptide derived from HBV Polymerase protein

<400> SEQUENCE: 755

Trp Leu Ser Leu Asp Val Ser Ala Ala Phe Tyr His Ile Pro Leu
1               5                   10                  15

<210> SEQ ID NO 756
<211> LENGTH: 15
<212> TYPE: PRT
<213> ORGANISM: Artificial sequence
<220> FEATURE:
<223> OTHER INFORMATION: Peptide derived from HBV Polymerase protein

<400> SEQUENCE: 756

Leu Ser Leu Asp Val Ser Ala Ala Phe Tyr His Ile Pro Leu His
1               5                   10                  15

<210> SEQ ID NO 757
<211> LENGTH: 15
<212> TYPE: PRT
<213> ORGANISM: Artificial sequence
<220> FEATURE:
<223> OTHER INFORMATION: Peptide derived from HBV Polymerase protein
```

```
<400> SEQUENCE: 757

Val Ser Ala Ala Phe Tyr His Ile Pro Leu His Pro Ala Ala Met
1               5                   10                  15

<210> SEQ ID NO 758
<211> LENGTH: 15
<212> TYPE: PRT
<213> ORGANISM: Artificial sequence
<220> FEATURE:
<223> OTHER INFORMATION: Peptide derived from HBV Polymerase protein

<400> SEQUENCE: 758

Ser Ala Ala Phe Tyr His Ile Pro Leu His Pro Ala Ala Met Pro
1               5                   10                  15

<210> SEQ ID NO 759
<211> LENGTH: 15
<212> TYPE: PRT
<213> ORGANISM: Artificial sequence
<220> FEATURE:
<223> OTHER INFORMATION: Peptide derived from HBV Polymerase protein

<400> SEQUENCE: 759

Ala Ala Phe Tyr His Ile Pro Leu His Pro Ala Ala Met Pro His
1               5                   10                  15

<210> SEQ ID NO 760
<211> LENGTH: 15
<212> TYPE: PRT
<213> ORGANISM: Artificial sequence
<220> FEATURE:
<223> OTHER INFORMATION: Peptide derived from HBV Polymerase protein

<400> SEQUENCE: 760

Ala Ala Met Pro His Leu Leu Ile Gly Ser Ser Gly Leu Ser Arg
1               5                   10                  15

<210> SEQ ID NO 761
<211> LENGTH: 15
<212> TYPE: PRT
<213> ORGANISM: Artificial sequence
<220> FEATURE:
<223> OTHER INFORMATION: Peptide derived from HBV Polymerase protein

<400> SEQUENCE: 761

Ala Met Pro His Leu Leu Ile Gly Ser Ser Gly Leu Ser Arg Tyr
1               5                   10                  15

<210> SEQ ID NO 762
<211> LENGTH: 15
<212> TYPE: PRT
<213> ORGANISM: Artificial sequence
<220> FEATURE:
<223> OTHER INFORMATION: Peptide derived from HBV Polymerase protein

<400> SEQUENCE: 762

Ser Cys Ser Arg Gln Leu Tyr Val Ser Leu Met Leu Leu Tyr Lys
1               5                   10                  15

<210> SEQ ID NO 763
<211> LENGTH: 15
<212> TYPE: PRT
<213> ORGANISM: Artificial sequence
<220> FEATURE:
<223> OTHER INFORMATION: Peptide derived from HBV Polymerase protein

<400> SEQUENCE: 763
```

```
Cys Ser Arg Gln Leu Tyr Val Ser Leu Met Leu Leu Tyr Lys Thr
1               5                   10                  15

<210> SEQ ID NO 764
<211> LENGTH: 15
<212> TYPE: PRT
<213> ORGANISM: Artificial sequence
<220> FEATURE:
<223> OTHER INFORMATION: Peptide derived from HBV Polymerase protein

<400> SEQUENCE: 764

Ser Arg Gln Leu Tyr Val Ser Leu Met Leu Leu Tyr Lys Thr Tyr
1               5                   10                  15

<210> SEQ ID NO 765
<211> LENGTH: 15
<212> TYPE: PRT
<213> ORGANISM: Artificial sequence
<220> FEATURE:
<223> OTHER INFORMATION: Peptide derived from HBV Polymerase protein

<400> SEQUENCE: 765

Arg Gln Leu Tyr Val Ser Leu Met Leu Leu Tyr Lys Thr Tyr Gly
1               5                   10                  15

<210> SEQ ID NO 766
<211> LENGTH: 15
<212> TYPE: PRT
<213> ORGANISM: Artificial sequence
<220> FEATURE:
<223> OTHER INFORMATION: Peptide derived from HBV Polymerase protein

<400> SEQUENCE: 766

Gln Leu Tyr Val Ser Leu Met Leu Leu Tyr Lys Thr Tyr Gly Trp
1               5                   10                  15

<210> SEQ ID NO 767
<211> LENGTH: 15
<212> TYPE: PRT
<213> ORGANISM: Artificial sequence
<220> FEATURE:
<223> OTHER INFORMATION: Peptide derived from HBV Polymerase protein

<400> SEQUENCE: 767

Leu Tyr Val Ser Leu Met Leu Leu Tyr Lys Thr Tyr Gly Trp Lys
1               5                   10                  15

<210> SEQ ID NO 768
<211> LENGTH: 15
<212> TYPE: PRT
<213> ORGANISM: Artificial sequence
<220> FEATURE:
<223> OTHER INFORMATION: Peptide derived from HBV Polymerase protein

<400> SEQUENCE: 768

Tyr Val Ser Leu Met Leu Leu Tyr Lys Thr Tyr Gly Trp Lys Leu
1               5                   10                  15

<210> SEQ ID NO 769
<211> LENGTH: 15
<212> TYPE: PRT
<213> ORGANISM: Artificial sequence
<220> FEATURE:
<223> OTHER INFORMATION: Peptide derived from HBV Polymerase protein

<400> SEQUENCE: 769
```

```
Val Ser Leu Met Leu Leu Tyr Lys Thr Tyr Gly Trp Lys Leu His
1               5                   10                  15
```

<210> SEQ ID NO 770
<211> LENGTH: 15
<212> TYPE: PRT
<213> ORGANISM: Artificial sequence
<220> FEATURE:
<223> OTHER INFORMATION: Peptide derived from HBV Polymerase protein

<400> SEQUENCE: 770

```
Ser Leu Met Leu Leu Tyr Lys Thr Tyr Gly Trp Lys Leu His Leu
1               5                   10                  15
```

<210> SEQ ID NO 771
<211> LENGTH: 15
<212> TYPE: PRT
<213> ORGANISM: Artificial sequence
<220> FEATURE:
<223> OTHER INFORMATION: Peptide derived from HBV Polymerase protein

<400> SEQUENCE: 771

```
Leu Met Leu Leu Tyr Lys Thr Tyr Gly Trp Lys Leu His Leu Tyr
1               5                   10                  15
```

<210> SEQ ID NO 772
<211> LENGTH: 15
<212> TYPE: PRT
<213> ORGANISM: Artificial sequence
<220> FEATURE:
<223> OTHER INFORMATION: Peptide derived from HBV Polymerase protein

<400> SEQUENCE: 772

```
Met Leu Leu Tyr Lys Thr Tyr Gly Trp Lys Leu His Leu Tyr Ser
1               5                   10                  15
```

<210> SEQ ID NO 773
<211> LENGTH: 15
<212> TYPE: PRT
<213> ORGANISM: Artificial sequence
<220> FEATURE:
<223> OTHER INFORMATION: Peptide derived from HBV Polymerase protein

<400> SEQUENCE: 773

```
Leu Leu Tyr Lys Thr Tyr Gly Trp Lys Leu His Leu Tyr Ser His
1               5                   10                  15
```

<210> SEQ ID NO 774
<211> LENGTH: 15
<212> TYPE: PRT
<213> ORGANISM: Artificial sequence
<220> FEATURE:
<223> OTHER INFORMATION: Peptide derived from HBV Polymerase protein

<400> SEQUENCE: 774

```
Leu Tyr Lys Thr Tyr Gly Trp Lys Leu His Leu Tyr Ser His Pro
1               5                   10                  15
```

<210> SEQ ID NO 775
<211> LENGTH: 15
<212> TYPE: PRT
<213> ORGANISM: Artificial sequence
<220> FEATURE:
<223> OTHER INFORMATION: Peptide derived from HBV Polymerase protein

<400> SEQUENCE: 775

Tyr Lys Thr Tyr Gly Trp Lys Leu His Leu Tyr Ser His Pro Ile

-continued

```
1               5                   10                  15
```

<210> SEQ ID NO 776
<211> LENGTH: 15
<212> TYPE: PRT
<213> ORGANISM: Artificial sequence
<220> FEATURE:
<223> OTHER INFORMATION: Peptide derived from HBV Polymerase protein

<400> SEQUENCE: 776

```
Lys Thr Tyr Gly Trp Lys Leu His Leu Tyr Ser His Pro Ile Val
1               5                   10                  15
```

<210> SEQ ID NO 777
<211> LENGTH: 15
<212> TYPE: PRT
<213> ORGANISM: Artificial sequence
<220> FEATURE:
<223> OTHER INFORMATION: Peptide derived from HBV Polymerase protein

<400> SEQUENCE: 777

```
Thr Tyr Gly Trp Lys Leu His Leu Tyr Ser His Pro Ile Val Leu
1               5                   10                  15
```

<210> SEQ ID NO 778
<211> LENGTH: 15
<212> TYPE: PRT
<213> ORGANISM: Artificial sequence
<220> FEATURE:
<223> OTHER INFORMATION: Peptide derived from HBV Polymerase protein

<400> SEQUENCE: 778

```
Tyr Gly Trp Lys Leu His Leu Tyr Ser His Pro Ile Val Leu Gly
1               5                   10                  15
```

<210> SEQ ID NO 779
<211> LENGTH: 15
<212> TYPE: PRT
<213> ORGANISM: Artificial sequence
<220> FEATURE:
<223> OTHER INFORMATION: Peptide derived from HBV Polymerase protein

<400> SEQUENCE: 779

```
Gly Trp Lys Leu His Leu Tyr Ser His Pro Ile Val Leu Gly Phe
1               5                   10                  15
```

<210> SEQ ID NO 780
<211> LENGTH: 15
<212> TYPE: PRT
<213> ORGANISM: Artificial sequence
<220> FEATURE:
<223> OTHER INFORMATION: Peptide derived from HBV Polymerase protein

<400> SEQUENCE: 780

```
Ser Pro Phe Leu Leu Ala Gln Phe Thr Ser Ala Ile Cys Ser Val
1               5                   10                  15
```

<210> SEQ ID NO 781
<211> LENGTH: 15
<212> TYPE: PRT
<213> ORGANISM: Artificial sequence
<220> FEATURE:
<223> OTHER INFORMATION: Peptide derived from HBV Polymerase protein

<400> SEQUENCE: 781

```
Pro Phe Leu Leu Ala Gln Phe Thr Ser Ala Ile Cys Ser Val Val
1               5                   10                  15
```

```
<210> SEQ ID NO 782
<211> LENGTH: 15
<212> TYPE: PRT
<213> ORGANISM: Artificial sequence
<220> FEATURE:
<223> OTHER INFORMATION: Peptide derived from HBV Polymerase protein

<400> SEQUENCE: 782

Phe Leu Leu Ala Gln Phe Thr Ser Ala Ile Cys Ser Val Val Arg
1               5                   10                  15

<210> SEQ ID NO 783
<211> LENGTH: 15
<212> TYPE: PRT
<213> ORGANISM: Artificial sequence
<220> FEATURE:
<223> OTHER INFORMATION: Peptide derived from HBV Polymerase protein

<400> SEQUENCE: 783

Leu Leu Ala Gln Phe Thr Ser Ala Ile Cys Ser Val Val Arg Arg
1               5                   10                  15

<210> SEQ ID NO 784
<211> LENGTH: 15
<212> TYPE: PRT
<213> ORGANISM: Artificial sequence
<220> FEATURE:
<223> OTHER INFORMATION: Peptide derived from HBV Polymerase protein

<400> SEQUENCE: 784

Leu Ala Gln Phe Thr Ser Ala Ile Cys Ser Val Val Arg Arg Ala
1               5                   10                  15

<210> SEQ ID NO 785
<211> LENGTH: 15
<212> TYPE: PRT
<213> ORGANISM: Artificial sequence
<220> FEATURE:
<223> OTHER INFORMATION: Peptide derived from HBV Polymerase protein

<400> SEQUENCE: 785

Ala Gln Phe Thr Ser Ala Ile Cys Ser Val Val Arg Arg Ala Phe
1               5                   10                  15

<210> SEQ ID NO 786
<211> LENGTH: 15
<212> TYPE: PRT
<213> ORGANISM: Artificial sequence
<220> FEATURE:
<223> OTHER INFORMATION: Peptide derived from HBV Polymerase protein

<400> SEQUENCE: 786

Ser Ala Ile Cys Ser Val Val Arg Arg Ala Phe Pro His Cys Leu
1               5                   10                  15

<210> SEQ ID NO 787
<211> LENGTH: 15
<212> TYPE: PRT
<213> ORGANISM: Artificial sequence
<220> FEATURE:
<223> OTHER INFORMATION: Peptide derived from HBV Polymerase protein

<400> SEQUENCE: 787

Ala Ile Cys Ser Val Val Arg Arg Ala Phe Pro His Cys Leu Ala
1               5                   10                  15
```

```
<210> SEQ ID NO 788
<211> LENGTH: 15
<212> TYPE: PRT
<213> ORGANISM: Artificial sequence
<220> FEATURE:
<223> OTHER INFORMATION: Peptide derived from HBV Polymerase protein

<400> SEQUENCE: 788

Ile Cys Ser Val Val Arg Arg Ala Phe Pro His Cys Leu Ala Phe
1               5                   10                  15

<210> SEQ ID NO 789
<211> LENGTH: 15
<212> TYPE: PRT
<213> ORGANISM: Artificial sequence
<220> FEATURE:
<223> OTHER INFORMATION: Peptide derived from HBV Polymerase protein

<400> SEQUENCE: 789

Cys Ser Val Val Arg Arg Ala Phe Pro His Cys Leu Ala Phe Ser
1               5                   10                  15

<210> SEQ ID NO 790
<211> LENGTH: 15
<212> TYPE: PRT
<213> ORGANISM: Artificial sequence
<220> FEATURE:
<223> OTHER INFORMATION: Peptide derived from HBV Polymerase protein

<400> SEQUENCE: 790

Ser Val Val Arg Arg Ala Phe Pro His Cys Leu Ala Phe Ser Tyr
1               5                   10                  15

<210> SEQ ID NO 791
<211> LENGTH: 15
<212> TYPE: PRT
<213> ORGANISM: Artificial sequence
<220> FEATURE:
<223> OTHER INFORMATION: Peptide derived from HBV Polymerase protein

<400> SEQUENCE: 791

Val Val Arg Arg Ala Phe Pro His Cys Leu Ala Phe Ser Tyr Met
1               5                   10                  15

<210> SEQ ID NO 792
<211> LENGTH: 15
<212> TYPE: PRT
<213> ORGANISM: Artificial sequence
<220> FEATURE:
<223> OTHER INFORMATION: Peptide derived from HBV Polymerase protein

<400> SEQUENCE: 792

Val Arg Arg Ala Phe Pro His Cys Leu Ala Phe Ser Tyr Met Asp
1               5                   10                  15

<210> SEQ ID NO 793
<211> LENGTH: 15
<212> TYPE: PRT
<213> ORGANISM: Artificial sequence
<220> FEATURE:
<223> OTHER INFORMATION: Peptide derived from HBV Polymerase protein

<400> SEQUENCE: 793

His Cys Leu Ala Phe Ser Tyr Met Asp Asp Val Val Leu Gly Ala
1               5                   10                  15
```

```
<210> SEQ ID NO 794
<211> LENGTH: 15
<212> TYPE: PRT
<213> ORGANISM: Artificial sequence
<220> FEATURE:
<223> OTHER INFORMATION: Peptide derived from HBV Polymerase protein

<400> SEQUENCE: 794

Arg Glu Ser Leu Tyr Thr Ala Val Thr Asn Phe Leu Leu Ser Leu
1               5                   10                  15

<210> SEQ ID NO 795
<211> LENGTH: 15
<212> TYPE: PRT
<213> ORGANISM: Artificial sequence
<220> FEATURE:
<223> OTHER INFORMATION: Peptide derived from HBV Polymerase protein

<400> SEQUENCE: 795

Glu Ser Leu Tyr Thr Ala Val Thr Asn Phe Leu Leu Ser Leu Gly
1               5                   10                  15

<210> SEQ ID NO 796
<211> LENGTH: 15
<212> TYPE: PRT
<213> ORGANISM: Artificial sequence
<220> FEATURE:
<223> OTHER INFORMATION: Peptide derived from HBV Polymerase protein

<400> SEQUENCE: 796

Ser Leu Tyr Thr Ala Val Thr Asn Phe Leu Leu Ser Leu Gly Ile
1               5                   10                  15

<210> SEQ ID NO 797
<211> LENGTH: 15
<212> TYPE: PRT
<213> ORGANISM: Artificial sequence
<220> FEATURE:
<223> OTHER INFORMATION: Peptide derived from HBV Polymerase protein

<400> SEQUENCE: 797

Leu Tyr Thr Ala Val Thr Asn Phe Leu Leu Ser Leu Gly Ile His
1               5                   10                  15

<210> SEQ ID NO 798
<211> LENGTH: 15
<212> TYPE: PRT
<213> ORGANISM: Artificial sequence
<220> FEATURE:
<223> OTHER INFORMATION: Peptide derived from HBV Polymerase protein

<400> SEQUENCE: 798

Tyr Thr Ala Val Thr Asn Phe Leu Leu Ser Leu Gly Ile His Leu
1               5                   10                  15

<210> SEQ ID NO 799
<211> LENGTH: 15
<212> TYPE: PRT
<213> ORGANISM: Artificial sequence
<220> FEATURE:
<223> OTHER INFORMATION: Peptide derived from HBV Polymerase protein

<400> SEQUENCE: 799

Thr Ala Val Thr Asn Phe Leu Leu Ser Leu Gly Ile His Leu Asn
1               5                   10                  15

<210> SEQ ID NO 800
```

```
<211> LENGTH: 15
<212> TYPE: PRT
<213> ORGANISM: Artificial sequence
<220> FEATURE:
<223> OTHER INFORMATION: Peptide derived from HBV Polymerase protein

<400> SEQUENCE: 800

Ala Val Thr Asn Phe Leu Leu Ser Leu Gly Ile His Leu Asn Pro
1               5                   10                  15

<210> SEQ ID NO 801
<211> LENGTH: 15
<212> TYPE: PRT
<213> ORGANISM: Artificial sequence
<220> FEATURE:
<223> OTHER INFORMATION: Peptide derived from HBV Polymerase protein

<400> SEQUENCE: 801

Val Thr Asn Phe Leu Leu Ser Leu Gly Ile His Leu Asn Pro Asn
1               5                   10                  15

<210> SEQ ID NO 802
<211> LENGTH: 15
<212> TYPE: PRT
<213> ORGANISM: Artificial sequence
<220> FEATURE:
<223> OTHER INFORMATION: Peptide derived from HBV Polymerase protein

<400> SEQUENCE: 802

Thr Asn Phe Leu Leu Ser Leu Gly Ile His Leu Asn Pro Asn Lys
1               5                   10                  15

<210> SEQ ID NO 803
<211> LENGTH: 15
<212> TYPE: PRT
<213> ORGANISM: Artificial sequence
<220> FEATURE:
<223> OTHER INFORMATION: Peptide derived from HBV Polymerase protein

<400> SEQUENCE: 803

Asn Phe Leu Leu Ser Leu Gly Ile His Leu Asn Pro Asn Lys Thr
1               5                   10                  15

<210> SEQ ID NO 804
<211> LENGTH: 15
<212> TYPE: PRT
<213> ORGANISM: Artificial sequence
<220> FEATURE:
<223> OTHER INFORMATION: Peptide derived from HBV Polymerase protein

<400> SEQUENCE: 804

Phe Leu Leu Ser Leu Gly Ile His Leu Asn Pro Asn Lys Thr Lys
1               5                   10                  15

<210> SEQ ID NO 805
<211> LENGTH: 15
<212> TYPE: PRT
<213> ORGANISM: Artificial sequence
<220> FEATURE:
<223> OTHER INFORMATION: Peptide derived from HBV Polymerase protein

<400> SEQUENCE: 805

Leu Leu Ser Leu Gly Ile His Leu Asn Pro Asn Lys Thr Lys Arg
1               5                   10                  15

<210> SEQ ID NO 806
<211> LENGTH: 15
```

```
<212> TYPE: PRT
<213> ORGANISM: Artificial sequence
<220> FEATURE:
<223> OTHER INFORMATION: Peptide derived from HBV Polymerase protein

<400> SEQUENCE: 806

Leu Ser Leu Gly Ile His Leu Asn Pro Asn Lys Thr Lys Arg Trp
1               5                   10                  15

<210> SEQ ID NO 807
<211> LENGTH: 15
<212> TYPE: PRT
<213> ORGANISM: Artificial sequence
<220> FEATURE:
<223> OTHER INFORMATION: Peptide derived from HBV Polymerase protein

<400> SEQUENCE: 807

Ser Leu Gly Ile His Leu Asn Pro Asn Lys Thr Lys Arg Trp Gly
1               5                   10                  15

<210> SEQ ID NO 808
<211> LENGTH: 15
<212> TYPE: PRT
<213> ORGANISM: Artificial sequence
<220> FEATURE:
<223> OTHER INFORMATION: Peptide derived from HBV Polymerase protein

<400> SEQUENCE: 808

Leu Gly Ile His Leu Asn Pro Asn Lys Thr Lys Arg Trp Gly Tyr
1               5                   10                  15

<210> SEQ ID NO 809
<211> LENGTH: 15
<212> TYPE: PRT
<213> ORGANISM: Artificial sequence
<220> FEATURE:
<223> OTHER INFORMATION: Peptide derived from HBV Polymerase protein

<400> SEQUENCE: 809

Lys Arg Trp Gly Tyr Ser Leu Asn Phe Met Gly Tyr Ile Ile Gly
1               5                   10                  15

<210> SEQ ID NO 810
<211> LENGTH: 15
<212> TYPE: PRT
<213> ORGANISM: Artificial sequence
<220> FEATURE:
<223> OTHER INFORMATION: Peptide derived from HBV Polymerase protein

<400> SEQUENCE: 810

Arg Trp Gly Tyr Ser Leu Asn Phe Met Gly Tyr Ile Ile Gly Ser
1               5                   10                  15

<210> SEQ ID NO 811
<211> LENGTH: 15
<212> TYPE: PRT
<213> ORGANISM: Artificial sequence
<220> FEATURE:
<223> OTHER INFORMATION: Peptide derived from HBV Polymerase protein

<400> SEQUENCE: 811

Trp Gly Tyr Ser Leu Asn Phe Met Gly Tyr Ile Ile Gly Ser Trp
1               5                   10                  15

<210> SEQ ID NO 812
<211> LENGTH: 15
<212> TYPE: PRT
```

<213> ORGANISM: Artificial sequence
<220> FEATURE:
<223> OTHER INFORMATION: Peptide derived from HBV Polymerase protein

<400> SEQUENCE: 812

Gly Tyr Ser Leu Asn Phe Met Gly Tyr Ile Ile Gly Ser Trp Gly
1               5                   10                  15

<210> SEQ ID NO 813
<211> LENGTH: 15
<212> TYPE: PRT
<213> ORGANISM: Artificial sequence
<220> FEATURE:
<223> OTHER INFORMATION: Peptide derived from HBV Polymerase protein

<400> SEQUENCE: 813

Tyr Ser Leu Asn Phe Met Gly Tyr Ile Ile Gly Ser Trp Gly Thr
1               5                   10                  15

<210> SEQ ID NO 814
<211> LENGTH: 15
<212> TYPE: PRT
<213> ORGANISM: Artificial sequence
<220> FEATURE:
<223> OTHER INFORMATION: Peptide derived from HBV Polymerase protein

<400> SEQUENCE: 814

Ser Leu Asn Phe Met Gly Tyr Ile Ile Gly Ser Trp Gly Thr Leu
1               5                   10                  15

<210> SEQ ID NO 815
<211> LENGTH: 15
<212> TYPE: PRT
<213> ORGANISM: Artificial sequence
<220> FEATURE:
<223> OTHER INFORMATION: Peptide derived from HBV Polymerase protein

<400> SEQUENCE: 815

Leu Asn Phe Met Gly Tyr Ile Ile Gly Ser Trp Gly Thr Leu Pro
1               5                   10                  15

<210> SEQ ID NO 816
<211> LENGTH: 15
<212> TYPE: PRT
<213> ORGANISM: Artificial sequence
<220> FEATURE:
<223> OTHER INFORMATION: Peptide derived from HBV Polymerase protein

<400> SEQUENCE: 816

Tyr Pro Ala Leu Met Pro Leu Tyr Ala Cys Ile Gln Ala Lys Gln
1               5                   10                  15

<210> SEQ ID NO 817
<211> LENGTH: 15
<212> TYPE: PRT
<213> ORGANISM: Artificial sequence
<220> FEATURE:
<223> OTHER INFORMATION: Peptide derived from HBV Polymerase protein

<400> SEQUENCE: 817

Leu Met Pro Leu Tyr Ala Cys Ile Gln Ala Lys Gln Ala Phe Thr
1               5                   10                  15

<210> SEQ ID NO 818
<211> LENGTH: 15
<212> TYPE: PRT
<213> ORGANISM: Artificial sequence

```
<220> FEATURE:
<223> OTHER INFORMATION: Peptide derived from HBV Polymerase protein

<400> SEQUENCE: 818

Met Pro Leu Tyr Ala Cys Ile Gln Ala Lys Gln Ala Phe Thr Phe
1               5                   10                  15

<210> SEQ ID NO 819
<211> LENGTH: 15
<212> TYPE: PRT
<213> ORGANISM: Artificial sequence
<220> FEATURE:
<223> OTHER INFORMATION: Peptide derived from HBV Polymerase protein

<400> SEQUENCE: 819

Pro Leu Tyr Ala Cys Ile Gln Ala Lys Gln Ala Phe Thr Phe Ser
1               5                   10                  15

<210> SEQ ID NO 820
<211> LENGTH: 15
<212> TYPE: PRT
<213> ORGANISM: Artificial sequence
<220> FEATURE:
<223> OTHER INFORMATION: Peptide derived from HBV Polymerase protein

<400> SEQUENCE: 820

Leu Tyr Ala Cys Ile Gln Ala Lys Gln Ala Phe Thr Phe Ser Pro
1               5                   10                  15

<210> SEQ ID NO 821
<211> LENGTH: 15
<212> TYPE: PRT
<213> ORGANISM: Artificial sequence
<220> FEATURE:
<223> OTHER INFORMATION: Peptide derived from HBV Polymerase protein

<400> SEQUENCE: 821

Tyr Ala Cys Ile Gln Ala Lys Gln Ala Phe Thr Phe Ser Pro Thr
1               5                   10                  15

<210> SEQ ID NO 822
<211> LENGTH: 15
<212> TYPE: PRT
<213> ORGANISM: Artificial sequence
<220> FEATURE:
<223> OTHER INFORMATION: Peptide derived from HBV Polymerase protein

<400> SEQUENCE: 822

Ala Cys Ile Gln Ala Lys Gln Ala Phe Thr Phe Ser Pro Thr Tyr
1               5                   10                  15

<210> SEQ ID NO 823
<211> LENGTH: 15
<212> TYPE: PRT
<213> ORGANISM: Artificial sequence
<220> FEATURE:
<223> OTHER INFORMATION: Peptide derived from HBV Polymerase protein

<400> SEQUENCE: 823

Cys Ile Gln Ala Lys Gln Ala Phe Thr Phe Ser Pro Thr Tyr Lys
1               5                   10                  15

<210> SEQ ID NO 824
<211> LENGTH: 15
<212> TYPE: PRT
<213> ORGANISM: Artificial sequence
<220> FEATURE:
```

<223> OTHER INFORMATION: Peptide derived from HBV Polymerase protein

<400> SEQUENCE: 824

Ile Gln Ala Lys Gln Ala Phe Thr Phe Ser Pro Thr Tyr Lys Ala
1               5                   10                  15

<210> SEQ ID NO 825
<211> LENGTH: 15
<212> TYPE: PRT
<213> ORGANISM: Artificial sequence
<220> FEATURE:
<223> OTHER INFORMATION: Peptide derived from HBV Polymerase protein

<400> SEQUENCE: 825

Gln Ala Lys Gln Ala Phe Thr Phe Ser Pro Thr Tyr Lys Ala Phe
1               5                   10                  15

<210> SEQ ID NO 826
<211> LENGTH: 15
<212> TYPE: PRT
<213> ORGANISM: Artificial sequence
<220> FEATURE:
<223> OTHER INFORMATION: Peptide derived from HBV Polymerase protein

<400> SEQUENCE: 826

Ala Lys Gln Ala Phe Thr Phe Ser Pro Thr Tyr Lys Ala Phe Leu
1               5                   10                  15

<210> SEQ ID NO 827
<211> LENGTH: 15
<212> TYPE: PRT
<213> ORGANISM: Artificial sequence
<220> FEATURE:
<223> OTHER INFORMATION: Peptide derived from HBV Polymerase protein

<400> SEQUENCE: 827

Lys Gln Ala Phe Thr Phe Ser Pro Thr Tyr Lys Ala Phe Leu Ser
1               5                   10                  15

<210> SEQ ID NO 828
<211> LENGTH: 15
<212> TYPE: PRT
<213> ORGANISM: Artificial sequence
<220> FEATURE:
<223> OTHER INFORMATION: Peptide derived from HBV Polymerase protein

<400> SEQUENCE: 828

Gln Ala Phe Thr Phe Ser Pro Thr Tyr Lys Ala Phe Leu Ser Lys
1               5                   10                  15

<210> SEQ ID NO 829
<211> LENGTH: 15
<212> TYPE: PRT
<213> ORGANISM: Artificial sequence
<220> FEATURE:
<223> OTHER INFORMATION: Peptide derived from HBV Polymerase protein

<400> SEQUENCE: 829

Ala Phe Thr Phe Ser Pro Thr Tyr Lys Ala Phe Leu Ser Lys Gln
1               5                   10                  15

<210> SEQ ID NO 830
<211> LENGTH: 15
<212> TYPE: PRT
<213> ORGANISM: Artificial sequence
<220> FEATURE:
<223> OTHER INFORMATION: Peptide derived from HBV Polymerase protein

<400> SEQUENCE: 830

Phe Thr Phe Ser Pro Thr Tyr Lys Ala Phe Leu Ser Lys Gln Tyr
1               5                   10                  15

<210> SEQ ID NO 831
<211> LENGTH: 15
<212> TYPE: PRT
<213> ORGANISM: Artificial sequence
<220> FEATURE:
<223> OTHER INFORMATION: Peptide derived from HBV Polymerase protein

<400> SEQUENCE: 831

Ser Pro Thr Tyr Lys Ala Phe Leu Ser Lys Gln Tyr Met Asn Leu
1               5                   10                  15

<210> SEQ ID NO 832
<211> LENGTH: 15
<212> TYPE: PRT
<213> ORGANISM: Artificial sequence
<220> FEATURE:
<223> OTHER INFORMATION: Peptide derived from HBV Polymerase protein

<400> SEQUENCE: 832

Pro Thr Tyr Lys Ala Phe Leu Ser Lys Gln Tyr Met Asn Leu Tyr
1               5                   10                  15

<210> SEQ ID NO 833
<211> LENGTH: 15
<212> TYPE: PRT
<213> ORGANISM: Artificial sequence
<220> FEATURE:
<223> OTHER INFORMATION: Peptide derived from HBV Polymerase protein

<400> SEQUENCE: 833

Ala Phe Leu Ser Lys Gln Tyr Met Asn Leu Tyr Pro Val Ala Arg
1               5                   10                  15

<210> SEQ ID NO 834
<211> LENGTH: 15
<212> TYPE: PRT
<213> ORGANISM: Artificial sequence
<220> FEATURE:
<223> OTHER INFORMATION: Peptide derived from HBV Polymerase protein

<400> SEQUENCE: 834

Met Arg Gly Thr Phe Val Ala Pro Leu Pro Ile His Thr Ala Glu
1               5                   10                  15

<210> SEQ ID NO 835
<211> LENGTH: 15
<212> TYPE: PRT
<213> ORGANISM: Artificial sequence
<220> FEATURE:
<223> OTHER INFORMATION: Peptide derived from HBV Polymerase protein

<400> SEQUENCE: 835

Arg Gly Thr Phe Val Ala Pro Leu Pro Ile His Thr Ala Glu Leu
1               5                   10                  15

<210> SEQ ID NO 836
<211> LENGTH: 15
<212> TYPE: PRT
<213> ORGANISM: Artificial sequence
<220> FEATURE:
<223> OTHER INFORMATION: Peptide derived from HBV Polymerase protein

```
<400> SEQUENCE: 836

Gly Thr Phe Val Ala Pro Leu Pro Ile His Thr Ala Glu Leu Leu
1               5                   10                  15

<210> SEQ ID NO 837
<211> LENGTH: 15
<212> TYPE: PRT
<213> ORGANISM: Artificial sequence
<220> FEATURE:
<223> OTHER INFORMATION: Peptide derived from HBV Polymerase protein

<400> SEQUENCE: 837

Leu Leu Ala Ala Cys Phe Ala Arg Ser Arg Ser Gly Ala Lys Leu
1               5                   10                  15

<210> SEQ ID NO 838
<211> LENGTH: 15
<212> TYPE: PRT
<213> ORGANISM: Artificial sequence
<220> FEATURE:
<223> OTHER INFORMATION: Peptide derived from HBV Polymerase protein

<400> SEQUENCE: 838

Gly Cys Thr Ala Asn Trp Ile Leu Arg Gly Thr Ser Phe Val Tyr
1               5                   10                  15

<210> SEQ ID NO 839
<211> LENGTH: 15
<212> TYPE: PRT
<213> ORGANISM: Artificial sequence
<220> FEATURE:
<223> OTHER INFORMATION: Peptide derived from HBV Polymerase protein

<400> SEQUENCE: 839

Cys Thr Ala Asn Trp Ile Leu Arg Gly Thr Ser Phe Val Tyr Val
1               5                   10                  15

<210> SEQ ID NO 840
<211> LENGTH: 15
<212> TYPE: PRT
<213> ORGANISM: Artificial sequence
<220> FEATURE:
<223> OTHER INFORMATION: Peptide derived from HBV Polymerase protein

<400> SEQUENCE: 840

Ile Leu Arg Gly Thr Ser Phe Val Tyr Val Pro Ser Ala Leu Asn
1               5                   10                  15

<210> SEQ ID NO 841
<211> LENGTH: 15
<212> TYPE: PRT
<213> ORGANISM: Artificial sequence
<220> FEATURE:
<223> OTHER INFORMATION: Peptide derived from HBV Polymerase protein

<400> SEQUENCE: 841

Leu Arg Gly Thr Ser Phe Val Tyr Val Pro Ser Ala Leu Asn Pro
1               5                   10                  15

<210> SEQ ID NO 842
<211> LENGTH: 15
<212> TYPE: PRT
<213> ORGANISM: Artificial sequence
<220> FEATURE:
<223> OTHER INFORMATION: Peptide derived from HBV Polymerase protein

<400> SEQUENCE: 842
```

Arg Gly Thr Ser Phe Val Tyr Val Pro Ser Ala Leu Asn Pro Ala
1               5                   10                  15

<210> SEQ ID NO 843
<211> LENGTH: 15
<212> TYPE: PRT
<213> ORGANISM: Artificial sequence
<220> FEATURE:
<223> OTHER INFORMATION: Peptide derived from HBV Polymerase protein

<400> SEQUENCE: 843

Gly Thr Ser Phe Val Tyr Val Pro Ser Ala Leu Asn Pro Ala Asp
1               5                   10                  15

<210> SEQ ID NO 844
<211> LENGTH: 15
<212> TYPE: PRT
<213> ORGANISM: Artificial sequence
<220> FEATURE:
<223> OTHER INFORMATION: Peptide derived from HBV Polymerase protein

<400> SEQUENCE: 844

Thr Ser Phe Val Tyr Val Pro Ser Ala Leu Asn Pro Ala Asp Asp
1               5                   10                  15

<210> SEQ ID NO 845
<211> LENGTH: 15
<212> TYPE: PRT
<213> ORGANISM: Artificial sequence
<220> FEATURE:
<223> OTHER INFORMATION: Peptide derived from HBV Polymerase protein

<400> SEQUENCE: 845

Ser Phe Val Tyr Val Pro Ser Ala Leu Asn Pro Ala Asp Asp Pro
1               5                   10                  15

<210> SEQ ID NO 846
<211> LENGTH: 11
<212> TYPE: PRT
<213> ORGANISM: Artificial sequence
<220> FEATURE:
<223> OTHER INFORMATION: Peptide derived from HBV Core protein

<400> SEQUENCE: 846

Asp Pro Ala Ser Arg Asp Leu Val Val Asn Tyr
1               5                   10

<210> SEQ ID NO 847
<211> LENGTH: 10
<212> TYPE: PRT
<213> ORGANISM: Artificial sequence
<220> FEATURE:
<223> OTHER INFORMATION: Peptide derived from HBV Core protein

<400> SEQUENCE: 847

Pro Ala Ser Arg Asp Leu Val Val Asn Tyr
1               5                   10

<210> SEQ ID NO 848
<211> LENGTH: 9
<212> TYPE: PRT
<213> ORGANISM: Artificial sequence
<220> FEATURE:
<223> OTHER INFORMATION: Peptide derived from HBV Core protein

<400> SEQUENCE: 848

```
Ala Ser Arg Asp Leu Val Val Asn Tyr
1               5

<210> SEQ ID NO 849
<211> LENGTH: 8
<212> TYPE: PRT
<213> ORGANISM: Artificial sequence
<220> FEATURE:
<223> OTHER INFORMATION: Peptide derived from HBV Core protein

<400> SEQUENCE: 849

Arg Asp Leu Val Val Asn Tyr Val
1               5

<210> SEQ ID NO 850
<211> LENGTH: 10
<212> TYPE: PRT
<213> ORGANISM: Artificial sequence
<220> FEATURE:
<223> OTHER INFORMATION: Peptide derived from HBV Core protein

<400> SEQUENCE: 850

Leu Val Val Asn Tyr Val Asn Thr Asn Val
1               5                   10

<210> SEQ ID NO 851
<211> LENGTH: 9
<212> TYPE: PRT
<213> ORGANISM: Artificial sequence
<220> FEATURE:
<223> OTHER INFORMATION: Peptide derived from HBV Core protein

<400> SEQUENCE: 851

Val Val Asn Tyr Val Asn Thr Asn Val
1               5

<210> SEQ ID NO 852
<211> LENGTH: 11
<212> TYPE: PRT
<213> ORGANISM: Artificial sequence
<220> FEATURE:
<223> OTHER INFORMATION: Peptide derived from HBV Core protein

<400> SEQUENCE: 852

Leu Val Val Asn Tyr Val Asn Thr Asn Val Gly
1               5                   10

<210> SEQ ID NO 853
<211> LENGTH: 9
<212> TYPE: PRT
<213> ORGANISM: Artificial sequence
<220> FEATURE:
<223> OTHER INFORMATION: Peptide derived from HBV Core protein

<400> SEQUENCE: 853

Asn Tyr Val Asn Thr Asn Val Gly Leu
1               5

<210> SEQ ID NO 854
<211> LENGTH: 9
<212> TYPE: PRT
<213> ORGANISM: Artificial sequence
<220> FEATURE:
<223> OTHER INFORMATION: Peptide derived from HBV Core protein

<400> SEQUENCE: 854

Tyr Val Asn Thr Asn Val Gly Leu Lys
```

<210> SEQ ID NO 855
<211> LENGTH: 11
<212> TYPE: PRT
<213> ORGANISM: Artificial sequence
<220> FEATURE:
<223> OTHER INFORMATION: Peptide derived from HBV Core protein

<400> SEQUENCE: 855

Asn Tyr Val Asn Thr Asn Val Gly Leu Lys Ile
1               5                   10

<210> SEQ ID NO 856
<211> LENGTH: 10
<212> TYPE: PRT
<213> ORGANISM: Artificial sequence
<220> FEATURE:
<223> OTHER INFORMATION: Peptide derived from HBV Core protein

<400> SEQUENCE: 856

Thr Asn Val Gly Leu Lys Ile Arg Gln Leu
1               5                   10

<210> SEQ ID NO 857
<211> LENGTH: 9
<212> TYPE: PRT
<213> ORGANISM: Artificial sequence
<220> FEATURE:
<223> OTHER INFORMATION: Peptide derived from HBV Core protein

<400> SEQUENCE: 857

Asn Val Gly Leu Lys Ile Arg Gln Leu
1               5

<210> SEQ ID NO 858
<211> LENGTH: 10
<212> TYPE: PRT
<213> ORGANISM: Artificial sequence
<220> FEATURE:
<223> OTHER INFORMATION: Peptide derived from HBV Core protein

<400> SEQUENCE: 858

Asn Val Gly Leu Lys Ile Arg Gln Leu Leu
1               5                   10

<210> SEQ ID NO 859
<211> LENGTH: 8
<212> TYPE: PRT
<213> ORGANISM: Artificial sequence
<220> FEATURE:
<223> OTHER INFORMATION: Peptide derived from HBV Core protein

<400> SEQUENCE: 859

Gly Leu Lys Ile Arg Gln Leu Leu
1               5

<210> SEQ ID NO 860
<211> LENGTH: 10
<212> TYPE: PRT
<213> ORGANISM: Artificial sequence
<220> FEATURE:
<223> OTHER INFORMATION: Peptide derived from HBV Core protein

<400> SEQUENCE: 860

Val Gly Leu Lys Ile Arg Gln Leu Leu Trp
1               5                   10

```
<210> SEQ ID NO 861
<211> LENGTH: 10
<212> TYPE: PRT
<213> ORGANISM: Artificial sequence
<220> FEATURE:
<223> OTHER INFORMATION: Peptide derived from HBV Core protein

<400> SEQUENCE: 861

Gly Leu Lys Ile Arg Gln Leu Leu Trp Phe
1               5                   10

<210> SEQ ID NO 862
<211> LENGTH: 8
<212> TYPE: PRT
<213> ORGANISM: Artificial sequence
<220> FEATURE:
<223> OTHER INFORMATION: Peptide derived from HBV Core protein

<400> SEQUENCE: 862

Lys Ile Arg Gln Leu Leu Trp Phe
1               5

<210> SEQ ID NO 863
<211> LENGTH: 9
<212> TYPE: PRT
<213> ORGANISM: Artificial sequence
<220> FEATURE:
<223> OTHER INFORMATION: Peptide derived from HBV Core protein

<400> SEQUENCE: 863

Ile Arg Gln Leu Leu Trp Phe His Ile
1               5

<210> SEQ ID NO 864
<211> LENGTH: 8
<212> TYPE: PRT
<213> ORGANISM: Artificial sequence
<220> FEATURE:
<223> OTHER INFORMATION: Peptide derived from HBV Core protein

<400> SEQUENCE: 864

Arg Gln Leu Leu Trp Phe His Ile
1               5

<210> SEQ ID NO 865
<211> LENGTH: 10
<212> TYPE: PRT
<213> ORGANISM: Artificial sequence
<220> FEATURE:
<223> OTHER INFORMATION: Peptide derived from HBV Core protein

<400> SEQUENCE: 865

Ile Arg Gln Leu Leu Trp Phe His Ile Ser
1               5                   10

<210> SEQ ID NO 866
<211> LENGTH: 9
<212> TYPE: PRT
<213> ORGANISM: Artificial sequence
<220> FEATURE:
<223> OTHER INFORMATION: Peptide derived from HBV Core protein

<400> SEQUENCE: 866

Arg Gln Leu Leu Trp Phe His Ile Ser
1               5
```

<210> SEQ ID NO 867
<211> LENGTH: 10
<212> TYPE: PRT
<213> ORGANISM: Artificial sequence
<220> FEATURE:
<223> OTHER INFORMATION: Peptide derived from HBV Core protein

<400> SEQUENCE: 867

Arg Gln Leu Leu Trp Phe His Ile Ser Cys
1               5                   10

<210> SEQ ID NO 868
<211> LENGTH: 9
<212> TYPE: PRT
<213> ORGANISM: Artificial sequence
<220> FEATURE:
<223> OTHER INFORMATION: Peptide derived from HBV Core protein

<400> SEQUENCE: 868

Gln Leu Leu Trp Phe His Ile Ser Cys
1               5

<210> SEQ ID NO 869
<211> LENGTH: 8
<212> TYPE: PRT
<213> ORGANISM: Artificial sequence
<220> FEATURE:
<223> OTHER INFORMATION: Peptide derived from HBV Core protein

<400> SEQUENCE: 869

Leu Leu Trp Phe His Ile Ser Cys
1               5

<210> SEQ ID NO 870
<211> LENGTH: 11
<212> TYPE: PRT
<213> ORGANISM: Artificial sequence
<220> FEATURE:
<223> OTHER INFORMATION: Peptide derived from HBV Core protein

<400> SEQUENCE: 870

Arg Gln Leu Leu Trp Phe His Ile Ser Cys Leu
1               5                   10

<210> SEQ ID NO 871
<211> LENGTH: 10
<212> TYPE: PRT
<213> ORGANISM: Artificial sequence
<220> FEATURE:
<223> OTHER INFORMATION: Peptide derived from HBV Core protein

<400> SEQUENCE: 871

Gln Leu Leu Trp Phe His Ile Ser Cys Leu
1               5                   10

<210> SEQ ID NO 872
<211> LENGTH: 9
<212> TYPE: PRT
<213> ORGANISM: Artificial sequence
<220> FEATURE:
<223> OTHER INFORMATION: Peptide derived from HBV Core protein

<400> SEQUENCE: 872

Leu Leu Trp Phe His Ile Ser Cys Leu
1               5

<210> SEQ ID NO 873
<211> LENGTH: 8
<212> TYPE: PRT
<213> ORGANISM: Artificial sequence
<220> FEATURE:
<223> OTHER INFORMATION: Peptide derived from HBV Core protein

<400> SEQUENCE: 873

Leu Trp Phe His Ile Ser Cys Leu
1               5

<210> SEQ ID NO 874
<211> LENGTH: 10
<212> TYPE: PRT
<213> ORGANISM: Artificial sequence
<220> FEATURE:
<223> OTHER INFORMATION: Peptide derived from HBV Core protein

<400> SEQUENCE: 874

Leu Leu Trp Phe His Ile Ser Cys Leu Thr
1               5                   10

<210> SEQ ID NO 875
<211> LENGTH: 11
<212> TYPE: PRT
<213> ORGANISM: Artificial sequence
<220> FEATURE:
<223> OTHER INFORMATION: Peptide derived from HBV Core protein

<400> SEQUENCE: 875

Leu Leu Trp Phe His Ile Ser Cys Leu Thr Phe
1               5                   10

<210> SEQ ID NO 876
<211> LENGTH: 10
<212> TYPE: PRT
<213> ORGANISM: Artificial sequence
<220> FEATURE:
<223> OTHER INFORMATION: Peptide derived from HBV Core protein

<400> SEQUENCE: 876

Leu Trp Phe His Ile Ser Cys Leu Thr Phe
1               5                   10

<210> SEQ ID NO 877
<211> LENGTH: 8
<212> TYPE: PRT
<213> ORGANISM: Artificial sequence
<220> FEATURE:
<223> OTHER INFORMATION: Peptide derived from HBV Core protein

<400> SEQUENCE: 877

Phe His Ile Ser Cys Leu Thr Phe
1               5

<210> SEQ ID NO 878
<211> LENGTH: 11
<212> TYPE: PRT
<213> ORGANISM: Artificial sequence
<220> FEATURE:
<223> OTHER INFORMATION: Peptide derived from HBV Core protein

<400> SEQUENCE: 878

Trp Phe His Ile Ser Cys Leu Thr Phe Gly Arg
1               5                   10

<210> SEQ ID NO 879

```
<211> LENGTH: 10
<212> TYPE: PRT
<213> ORGANISM: Artificial sequence
<220> FEATURE:
<223> OTHER INFORMATION: Peptide derived from HBV Core protein

<400> SEQUENCE: 879

Phe His Ile Ser Cys Leu Thr Phe Gly Arg
1               5                   10

<210> SEQ ID NO 880
<211> LENGTH: 9
<212> TYPE: PRT
<213> ORGANISM: Artificial sequence
<220> FEATURE:
<223> OTHER INFORMATION: Peptide derived from HBV Core protein

<400> SEQUENCE: 880

His Ile Ser Cys Leu Thr Phe Gly Arg
1               5

<210> SEQ ID NO 881
<211> LENGTH: 8
<212> TYPE: PRT
<213> ORGANISM: Artificial sequence
<220> FEATURE:
<223> OTHER INFORMATION: Peptide derived from HBV Core protein

<400> SEQUENCE: 881

Ile Ser Cys Leu Thr Phe Gly Arg
1               5

<210> SEQ ID NO 882
<211> LENGTH: 10
<212> TYPE: PRT
<213> ORGANISM: Artificial sequence
<220> FEATURE:
<223> OTHER INFORMATION: Peptide derived from HBV Core protein

<400> SEQUENCE: 882

Cys Leu Thr Phe Gly Arg Glu Thr Val Leu
1               5                   10

<210> SEQ ID NO 883
<211> LENGTH: 11
<212> TYPE: PRT
<213> ORGANISM: Artificial sequence
<220> FEATURE:
<223> OTHER INFORMATION: Peptide derived from HBV Core protein

<400> SEQUENCE: 883

Leu Thr Phe Gly Arg Glu Thr Val Leu Glu Tyr
1               5                   10

<210> SEQ ID NO 884
<211> LENGTH: 9
<212> TYPE: PRT
<213> ORGANISM: Artificial sequence
<220> FEATURE:
<223> OTHER INFORMATION: Peptide derived from HBV Core protein

<400> SEQUENCE: 884

Phe Gly Arg Glu Thr Val Leu Glu Tyr
1               5

<210> SEQ ID NO 885
<211> LENGTH: 11
```

```
<212> TYPE: PRT
<213> ORGANISM: Artificial sequence
<220> FEATURE:
<223> OTHER INFORMATION: Peptide derived from HBV Core protein

<400> SEQUENCE: 885

Thr Phe Gly Arg Glu Thr Val Leu Glu Tyr Leu
1               5                   10

<210> SEQ ID NO 886
<211> LENGTH: 10
<212> TYPE: PRT
<213> ORGANISM: Artificial sequence
<220> FEATURE:
<223> OTHER INFORMATION: Peptide derived from HBV Core protein

<400> SEQUENCE: 886

Phe Gly Arg Glu Thr Val Leu Glu Tyr Leu
1               5                   10

<210> SEQ ID NO 887
<211> LENGTH: 9
<212> TYPE: PRT
<213> ORGANISM: Artificial sequence
<220> FEATURE:
<223> OTHER INFORMATION: Peptide derived from HBV Core protein

<400> SEQUENCE: 887

Gly Arg Glu Thr Val Leu Glu Tyr Leu
1               5

<210> SEQ ID NO 888
<211> LENGTH: 8
<212> TYPE: PRT
<213> ORGANISM: Artificial sequence
<220> FEATURE:
<223> OTHER INFORMATION: Peptide derived from HBV Core protein

<400> SEQUENCE: 888

Arg Glu Thr Val Leu Glu Tyr Leu
1               5

<210> SEQ ID NO 889
<211> LENGTH: 11
<212> TYPE: PRT
<213> ORGANISM: Artificial sequence
<220> FEATURE:
<223> OTHER INFORMATION: Peptide derived from HBV Core protein

<400> SEQUENCE: 889

Phe Gly Arg Glu Thr Val Leu Glu Tyr Leu Val
1               5                   10

<210> SEQ ID NO 890
<211> LENGTH: 9
<212> TYPE: PRT
<213> ORGANISM: Artificial sequence
<220> FEATURE:
<223> OTHER INFORMATION: Peptide derived from HBV Core protein

<400> SEQUENCE: 890

Arg Glu Thr Val Leu Glu Tyr Leu Val
1               5

<210> SEQ ID NO 891
<211> LENGTH: 8
<212> TYPE: PRT
```

```
<213> ORGANISM: Artificial sequence
<220> FEATURE:
<223> OTHER INFORMATION: Peptide derived from HBV Core protein

<400> SEQUENCE: 891

Glu Thr Val Leu Glu Tyr Leu Val
1               5

<210> SEQ ID NO 892
<211> LENGTH: 10
<212> TYPE: PRT
<213> ORGANISM: Artificial sequence
<220> FEATURE:
<223> OTHER INFORMATION: Peptide derived from HBV Core protein

<400> SEQUENCE: 892

Arg Glu Thr Val Leu Glu Tyr Leu Val Ser
1               5                   10

<210> SEQ ID NO 893
<211> LENGTH: 11
<212> TYPE: PRT
<213> ORGANISM: Artificial sequence
<220> FEATURE:
<223> OTHER INFORMATION: Peptide derived from HBV Core protein

<400> SEQUENCE: 893

Arg Glu Thr Val Leu Glu Tyr Leu Val Ser Phe
1               5                   10

<210> SEQ ID NO 894
<211> LENGTH: 10
<212> TYPE: PRT
<213> ORGANISM: Artificial sequence
<220> FEATURE:
<223> OTHER INFORMATION: Peptide derived from HBV Core protein

<400> SEQUENCE: 894

Glu Thr Val Leu Glu Tyr Leu Val Ser Phe
1               5                   10

<210> SEQ ID NO 895
<211> LENGTH: 9
<212> TYPE: PRT
<213> ORGANISM: Artificial sequence
<220> FEATURE:
<223> OTHER INFORMATION: Peptide derived from HBV Core protein

<400> SEQUENCE: 895

Thr Val Leu Glu Tyr Leu Val Ser Phe
1               5

<210> SEQ ID NO 896
<211> LENGTH: 8
<212> TYPE: PRT
<213> ORGANISM: Artificial sequence
<220> FEATURE:
<223> OTHER INFORMATION: Peptide derived from HBV Core protein

<400> SEQUENCE: 896

Leu Glu Tyr Leu Val Ser Phe Gly
1               5

<210> SEQ ID NO 897
<211> LENGTH: 11
<212> TYPE: PRT
<213> ORGANISM: Artificial sequence
```

```
<220> FEATURE:
<223> OTHER INFORMATION: Peptide derived from HBV Core protein

<400> SEQUENCE: 897

Thr Val Leu Glu Tyr Leu Val Ser Phe Gly Val
1               5                   10

<210> SEQ ID NO 898
<211> LENGTH: 10
<212> TYPE: PRT
<213> ORGANISM: Artificial sequence
<220> FEATURE:
<223> OTHER INFORMATION: Peptide derived from HBV Core protein

<400> SEQUENCE: 898

Val Leu Glu Tyr Leu Val Ser Phe Gly Val
1               5                   10

<210> SEQ ID NO 899
<211> LENGTH: 9
<212> TYPE: PRT
<213> ORGANISM: Artificial sequence
<220> FEATURE:
<223> OTHER INFORMATION: Peptide derived from HBV Core protein

<400> SEQUENCE: 899

Leu Glu Tyr Leu Val Ser Phe Gly Val
1               5

<210> SEQ ID NO 900
<211> LENGTH: 10
<212> TYPE: PRT
<213> ORGANISM: Artificial sequence
<220> FEATURE:
<223> OTHER INFORMATION: Peptide derived from HBV Core protein

<400> SEQUENCE: 900

Leu Glu Tyr Leu Val Ser Phe Gly Val Trp
1               5                   10

<210> SEQ ID NO 901
<211> LENGTH: 9
<212> TYPE: PRT
<213> ORGANISM: Artificial sequence
<220> FEATURE:
<223> OTHER INFORMATION: Peptide derived from HBV Core protein

<400> SEQUENCE: 901

Glu Tyr Leu Val Ser Phe Gly Val Trp
1               5

<210> SEQ ID NO 902
<211> LENGTH: 8
<212> TYPE: PRT
<213> ORGANISM: Artificial sequence
<220> FEATURE:
<223> OTHER INFORMATION: Peptide derived from HBV Core protein

<400> SEQUENCE: 902

Tyr Leu Val Ser Phe Gly Val Trp
1               5

<210> SEQ ID NO 903
<211> LENGTH: 11
<212> TYPE: PRT
<213> ORGANISM: Artificial sequence
<220> FEATURE:
```

<223> OTHER INFORMATION: Peptide derived from HBV Core protein

<400> SEQUENCE: 903

Leu Glu Tyr Leu Val Ser Phe Gly Val Trp Ile
1               5                   10

<210> SEQ ID NO 904
<211> LENGTH: 9
<212> TYPE: PRT
<213> ORGANISM: Artificial sequence
<220> FEATURE:
<223> OTHER INFORMATION: Peptide derived from HBV Core protein

<400> SEQUENCE: 904

Tyr Leu Val Ser Phe Gly Val Trp Ile
1               5

<210> SEQ ID NO 905
<211> LENGTH: 11
<212> TYPE: PRT
<213> ORGANISM: Artificial sequence
<220> FEATURE:
<223> OTHER INFORMATION: Peptide derived from HBV Core protein

<400> SEQUENCE: 905

Glu Tyr Leu Val Ser Phe Gly Val Trp Ile Arg
1               5                   10

<210> SEQ ID NO 906
<211> LENGTH: 10
<212> TYPE: PRT
<213> ORGANISM: Artificial sequence
<220> FEATURE:
<223> OTHER INFORMATION: Peptide derived from HBV Core protein

<400> SEQUENCE: 906

Tyr Leu Val Ser Phe Gly Val Trp Ile Arg
1               5                   10

<210> SEQ ID NO 907
<211> LENGTH: 9
<212> TYPE: PRT
<213> ORGANISM: Artificial sequence
<220> FEATURE:
<223> OTHER INFORMATION: Peptide derived from HBV Core protein

<400> SEQUENCE: 907

Leu Val Ser Phe Gly Val Trp Ile Arg
1               5

<210> SEQ ID NO 908
<211> LENGTH: 8
<212> TYPE: PRT
<213> ORGANISM: Artificial sequence
<220> FEATURE:
<223> OTHER INFORMATION: Peptide derived from HBV Core protein

<400> SEQUENCE: 908

Val Ser Phe Gly Val Trp Ile Arg
1               5

<210> SEQ ID NO 909
<211> LENGTH: 10
<212> TYPE: PRT
<213> ORGANISM: Artificial sequence
<220> FEATURE:
<223> OTHER INFORMATION: Peptide derived from HBV Core protein

```
<400> SEQUENCE: 909

Leu Val Ser Phe Gly Val Trp Ile Arg Thr
1               5                   10

<210> SEQ ID NO 910
<211> LENGTH: 11
<212> TYPE: PRT
<213> ORGANISM: Artificial sequence
<220> FEATURE:
<223> OTHER INFORMATION: Peptide derived from HBV Core protein

<400> SEQUENCE: 910

Leu Val Ser Phe Gly Val Trp Ile Arg Thr Pro
1               5                   10

<210> SEQ ID NO 911
<211> LENGTH: 10
<212> TYPE: PRT
<213> ORGANISM: Artificial sequence
<220> FEATURE:
<223> OTHER INFORMATION: Peptide derived from HBV Core protein

<400> SEQUENCE: 911

Phe Gly Val Trp Ile Arg Thr Pro Pro Ala
1               5                   10

<210> SEQ ID NO 912
<211> LENGTH: 11
<212> TYPE: PRT
<213> ORGANISM: Artificial sequence
<220> FEATURE:
<223> OTHER INFORMATION: Peptide derived from HBV Core protein

<400> SEQUENCE: 912

Phe Gly Val Trp Ile Arg Thr Pro Pro Ala Tyr
1               5                   10

<210> SEQ ID NO 913
<211> LENGTH: 10
<212> TYPE: PRT
<213> ORGANISM: Artificial sequence
<220> FEATURE:
<223> OTHER INFORMATION: Peptide derived from HBV Core protein

<400> SEQUENCE: 913

Gly Val Trp Ile Arg Thr Pro Pro Ala Tyr
1               5                   10

<210> SEQ ID NO 914
<211> LENGTH: 9
<212> TYPE: PRT
<213> ORGANISM: Artificial sequence
<220> FEATURE:
<223> OTHER INFORMATION: Peptide derived from HBV Core protein

<400> SEQUENCE: 914

Val Trp Ile Arg Thr Pro Pro Ala Tyr
1               5

<210> SEQ ID NO 915
<211> LENGTH: 8
<212> TYPE: PRT
<213> ORGANISM: Artificial sequence
<220> FEATURE:
<223> OTHER INFORMATION: Peptide derived from HBV Core protein
```

```
<400> SEQUENCE: 915

Trp Ile Arg Thr Pro Pro Ala Tyr
1               5

<210> SEQ ID NO 916
<211> LENGTH: 11
<212> TYPE: PRT
<213> ORGANISM: Artificial sequence
<220> FEATURE:
<223> OTHER INFORMATION: Peptide derived from HBV Core protein

<400> SEQUENCE: 916

Gly Val Trp Ile Arg Thr Pro Pro Ala Tyr Arg
1               5                   10

<210> SEQ ID NO 917
<211> LENGTH: 10
<212> TYPE: PRT
<213> ORGANISM: Artificial sequence
<220> FEATURE:
<223> OTHER INFORMATION: Peptide derived from HBV Core protein

<400> SEQUENCE: 917

Val Trp Ile Arg Thr Pro Pro Ala Tyr Arg
1               5                   10

<210> SEQ ID NO 918
<211> LENGTH: 9
<212> TYPE: PRT
<213> ORGANISM: Artificial sequence
<220> FEATURE:
<223> OTHER INFORMATION: Peptide derived from HBV Core protein

<400> SEQUENCE: 918

Trp Ile Arg Thr Pro Pro Ala Tyr Arg
1               5

<210> SEQ ID NO 919
<211> LENGTH: 10
<212> TYPE: PRT
<213> ORGANISM: Artificial sequence
<220> FEATURE:
<223> OTHER INFORMATION: Peptide derived from HBV Core protein

<400> SEQUENCE: 919

Arg Thr Pro Pro Ala Tyr Arg Pro Pro Asn
1               5                   10

<210> SEQ ID NO 920
<211> LENGTH: 11
<212> TYPE: PRT
<213> ORGANISM: Artificial sequence
<220> FEATURE:
<223> OTHER INFORMATION: Peptide derived from HBV Core protein

<400> SEQUENCE: 920

Pro Pro Ala Tyr Arg Pro Pro Asn Ala Pro Ile
1               5                   10

<210> SEQ ID NO 921
<211> LENGTH: 9
<212> TYPE: PRT
<213> ORGANISM: Artificial sequence
<220> FEATURE:
<223> OTHER INFORMATION: Peptide derived from HBV Core protein

<400> SEQUENCE: 921
```

```
Ala Tyr Arg Pro Pro Asn Ala Pro Ile
1               5

<210> SEQ ID NO 922
<211> LENGTH: 10
<212> TYPE: PRT
<213> ORGANISM: Artificial sequence
<220> FEATURE:
<223> OTHER INFORMATION: Peptide derived from HBV Core protein

<400> SEQUENCE: 922

Ala Tyr Arg Pro Pro Asn Ala Pro Ile Leu
1               5                   10

<210> SEQ ID NO 923
<211> LENGTH: 9
<212> TYPE: PRT
<213> ORGANISM: Artificial sequence
<220> FEATURE:
<223> OTHER INFORMATION: Peptide derived from HBV Core protein

<400> SEQUENCE: 923

Tyr Arg Pro Pro Asn Ala Pro Ile Leu
1               5

<210> SEQ ID NO 924
<211> LENGTH: 15
<212> TYPE: PRT
<213> ORGANISM: Artificial sequence
<220> FEATURE:
<223> OTHER INFORMATION: Peptide derived from HBV Core protein

<400> SEQUENCE: 924

Asp Pro Ala Ser Arg Asp Leu Val Val Asn Tyr Val Asn Thr Asn
1               5                   10                  15

<210> SEQ ID NO 925
<211> LENGTH: 15
<212> TYPE: PRT
<213> ORGANISM: Artificial sequence
<220> FEATURE:
<223> OTHER INFORMATION: Peptide derived from HBV Core protein

<400> SEQUENCE: 925

Pro Ala Ser Arg Asp Leu Val Val Asn Tyr Val Asn Thr Asn Val
1               5                   10                  15

<210> SEQ ID NO 926
<211> LENGTH: 15
<212> TYPE: PRT
<213> ORGANISM: Artificial sequence
<220> FEATURE:
<223> OTHER INFORMATION: Peptide derived from HBV Core protein

<400> SEQUENCE: 926

Ala Ser Arg Asp Leu Val Val Asn Tyr Val Asn Thr Asn Val Gly
1               5                   10                  15

<210> SEQ ID NO 927
<211> LENGTH: 15
<212> TYPE: PRT
<213> ORGANISM: Artificial sequence
<220> FEATURE:
<223> OTHER INFORMATION: Peptide derived from HBV Core protein

<400> SEQUENCE: 927
```

Ser Arg Asp Leu Val Val Asn Tyr Val Asn Thr Asn Val Gly Leu
1               5                   10                  15

<210> SEQ ID NO 928
<211> LENGTH: 15
<212> TYPE: PRT
<213> ORGANISM: Artificial sequence
<220> FEATURE:
<223> OTHER INFORMATION: Peptide derived from HBV Core protein

<400> SEQUENCE: 928

Arg Asp Leu Val Val Asn Tyr Val Asn Thr Asn Val Gly Leu Lys
1               5                   10                  15

<210> SEQ ID NO 929
<211> LENGTH: 15
<212> TYPE: PRT
<213> ORGANISM: Artificial sequence
<220> FEATURE:
<223> OTHER INFORMATION: Peptide derived from HBV Core protein

<400> SEQUENCE: 929

Asp Leu Val Val Asn Tyr Val Asn Thr Asn Val Gly Leu Lys Ile
1               5                   10                  15

<210> SEQ ID NO 930
<211> LENGTH: 15
<212> TYPE: PRT
<213> ORGANISM: Artificial sequence
<220> FEATURE:
<223> OTHER INFORMATION: Peptide derived from HBV Core protein

<400> SEQUENCE: 930

Leu Val Val Asn Tyr Val Asn Thr Asn Val Gly Leu Lys Ile Arg
1               5                   10                  15

<210> SEQ ID NO 931
<211> LENGTH: 15
<212> TYPE: PRT
<213> ORGANISM: Artificial sequence
<220> FEATURE:
<223> OTHER INFORMATION: Peptide derived from HBV Core protein

<400> SEQUENCE: 931

Val Val Asn Tyr Val Asn Thr Asn Val Gly Leu Lys Ile Arg Gln
1               5                   10                  15

<210> SEQ ID NO 932
<211> LENGTH: 15
<212> TYPE: PRT
<213> ORGANISM: Artificial sequence
<220> FEATURE:
<223> OTHER INFORMATION: Peptide derived from HBV Core protein

<400> SEQUENCE: 932

Val Asn Tyr Val Asn Thr Asn Val Gly Leu Lys Ile Arg Gln Leu
1               5                   10                  15

<210> SEQ ID NO 933
<211> LENGTH: 15
<212> TYPE: PRT
<213> ORGANISM: Artificial sequence
<220> FEATURE:
<223> OTHER INFORMATION: Peptide derived from HBV Core protein

<400> SEQUENCE: 933

Asn Tyr Val Asn Thr Asn Val Gly Leu Lys Ile Arg Gln Leu Leu

<210> SEQ ID NO 934
<211> LENGTH: 15
<212> TYPE: PRT
<213> ORGANISM: Artificial sequence
<220> FEATURE:
<223> OTHER INFORMATION: Peptide derived from HBV Core protein

<400> SEQUENCE: 934

Tyr Val Asn Thr Asn Val Gly Leu Lys Ile Arg Gln Leu Leu Trp
1               5                   10                  15

<210> SEQ ID NO 935
<211> LENGTH: 15
<212> TYPE: PRT
<213> ORGANISM: Artificial sequence
<220> FEATURE:
<223> OTHER INFORMATION: Peptide derived from HBV Core protein

<400> SEQUENCE: 935

Val Asn Thr Asn Val Gly Leu Lys Ile Arg Gln Leu Leu Trp Phe
1               5                   10                  15

<210> SEQ ID NO 936
<211> LENGTH: 15
<212> TYPE: PRT
<213> ORGANISM: Artificial sequence
<220> FEATURE:
<223> OTHER INFORMATION: Peptide derived from HBV Core protein

<400> SEQUENCE: 936

Asn Thr Asn Val Gly Leu Lys Ile Arg Gln Leu Leu Trp Phe His
1               5                   10                  15

<210> SEQ ID NO 937
<211> LENGTH: 15
<212> TYPE: PRT
<213> ORGANISM: Artificial sequence
<220> FEATURE:
<223> OTHER INFORMATION: Peptide derived from HBV Core protein

<400> SEQUENCE: 937

Thr Asn Val Gly Leu Lys Ile Arg Gln Leu Leu Trp Phe His Ile
1               5                   10                  15

<210> SEQ ID NO 938
<211> LENGTH: 15
<212> TYPE: PRT
<213> ORGANISM: Artificial sequence
<220> FEATURE:
<223> OTHER INFORMATION: Peptide derived from HBV Core protein

<400> SEQUENCE: 938

Asn Val Gly Leu Lys Ile Arg Gln Leu Leu Trp Phe His Ile Ser
1               5                   10                  15

<210> SEQ ID NO 939
<211> LENGTH: 15
<212> TYPE: PRT
<213> ORGANISM: Artificial sequence
<220> FEATURE:
<223> OTHER INFORMATION: Peptide derived from HBV Core protein

<400> SEQUENCE: 939

Val Gly Leu Lys Ile Arg Gln Leu Leu Trp Phe His Ile Ser Cys
1               5                   10                  15

<210> SEQ ID NO 940
<211> LENGTH: 15
<212> TYPE: PRT
<213> ORGANISM: Artificial sequence
<220> FEATURE:
<223> OTHER INFORMATION: Peptide derived from HBV Core protein

<400> SEQUENCE: 940

Gly Leu Lys Ile Arg Gln Leu Leu Trp Phe His Ile Ser Cys Leu
1               5                   10                  15

<210> SEQ ID NO 941
<211> LENGTH: 15
<212> TYPE: PRT
<213> ORGANISM: Artificial sequence
<220> FEATURE:
<223> OTHER INFORMATION: Peptide derived from HBV Core protein

<400> SEQUENCE: 941

Leu Lys Ile Arg Gln Leu Leu Trp Phe His Ile Ser Cys Leu Thr
1               5                   10                  15

<210> SEQ ID NO 942
<211> LENGTH: 15
<212> TYPE: PRT
<213> ORGANISM: Artificial sequence
<220> FEATURE:
<223> OTHER INFORMATION: Peptide derived from HBV Core protein

<400> SEQUENCE: 942

Lys Ile Arg Gln Leu Leu Trp Phe His Ile Ser Cys Leu Thr Phe
1               5                   10                  15

<210> SEQ ID NO 943
<211> LENGTH: 15
<212> TYPE: PRT
<213> ORGANISM: Artificial sequence
<220> FEATURE:
<223> OTHER INFORMATION: Peptide derived from HBV Core protein

<400> SEQUENCE: 943

Ile Arg Gln Leu Leu Trp Phe His Ile Ser Cys Leu Thr Phe Gly
1               5                   10                  15

<210> SEQ ID NO 944
<211> LENGTH: 15
<212> TYPE: PRT
<213> ORGANISM: Artificial sequence
<220> FEATURE:
<223> OTHER INFORMATION: Peptide derived from HBV Core protein

<400> SEQUENCE: 944

Arg Gln Leu Leu Trp Phe His Ile Ser Cys Leu Thr Phe Gly Arg
1               5                   10                  15

<210> SEQ ID NO 945
<211> LENGTH: 15
<212> TYPE: PRT
<213> ORGANISM: Artificial sequence
<220> FEATURE:
<223> OTHER INFORMATION: Peptide derived from HBV Core protein

<400> SEQUENCE: 945

Phe Gly Arg Glu Thr Val Leu Glu Tyr Leu Val Ser Phe Gly Val
1               5                   10                  15

<210> SEQ ID NO 946
<211> LENGTH: 15
<212> TYPE: PRT
<213> ORGANISM: Artificial sequence
<220> FEATURE:
<223> OTHER INFORMATION: Peptide derived from HBV Core protein

<400> SEQUENCE: 946

Gly Arg Glu Thr Val Leu Glu Tyr Leu Val Ser Phe Gly Val Trp
1               5                   10                  15

<210> SEQ ID NO 947
<211> LENGTH: 15
<212> TYPE: PRT
<213> ORGANISM: Artificial sequence
<220> FEATURE:
<223> OTHER INFORMATION: Peptide derived from HBV Core protein

<400> SEQUENCE: 947

Arg Glu Thr Val Leu Glu Tyr Leu Val Ser Phe Gly Val Trp Ile
1               5                   10                  15

<210> SEQ ID NO 948
<211> LENGTH: 15
<212> TYPE: PRT
<213> ORGANISM: Artificial sequence
<220> FEATURE:
<223> OTHER INFORMATION: Peptide derived from HBV Core protein

<400> SEQUENCE: 948

Glu Thr Val Leu Glu Tyr Leu Val Ser Phe Gly Val Trp Ile Arg
1               5                   10                  15

<210> SEQ ID NO 949
<211> LENGTH: 15
<212> TYPE: PRT
<213> ORGANISM: Artificial sequence
<220> FEATURE:
<223> OTHER INFORMATION: Peptide derived from HBV Core protein

<400> SEQUENCE: 949

Thr Val Leu Glu Tyr Leu Val Ser Phe Gly Val Trp Ile Arg Thr
1               5                   10                  15

<210> SEQ ID NO 950
<211> LENGTH: 15
<212> TYPE: PRT
<213> ORGANISM: Artificial sequence
<220> FEATURE:
<223> OTHER INFORMATION: Peptide derived from HBV Core protein

<400> SEQUENCE: 950

Val Leu Glu Tyr Leu Val Ser Phe Gly Val Trp Ile Arg Thr Pro
1               5                   10                  15

<210> SEQ ID NO 951
<211> LENGTH: 15
<212> TYPE: PRT
<213> ORGANISM: Artificial sequence
<220> FEATURE:
<223> OTHER INFORMATION: Peptide derived from HBV Core protein

<400> SEQUENCE: 951

Leu Glu Tyr Leu Val Ser Phe Gly Val Trp Ile Arg Thr Pro Pro
1               5                   10                  15

-continued

<210> SEQ ID NO 952
<211> LENGTH: 15
<212> TYPE: PRT
<213> ORGANISM: Artificial sequence
<220> FEATURE:
<223> OTHER INFORMATION: Peptide derived from HBV Core protein

<400> SEQUENCE: 952

Glu Tyr Leu Val Ser Phe Gly Val Trp Ile Arg Thr Pro Pro Ala
1               5                   10                  15

<210> SEQ ID NO 953
<211> LENGTH: 15
<212> TYPE: PRT
<213> ORGANISM: Artificial sequence
<220> FEATURE:
<223> OTHER INFORMATION: Peptide derived from HBV Core protein

<400> SEQUENCE: 953

Tyr Leu Val Ser Phe Gly Val Trp Ile Arg Thr Pro Pro Ala Tyr
1               5                   10                  15

<210> SEQ ID NO 954
<211> LENGTH: 15
<212> TYPE: PRT
<213> ORGANISM: Artificial sequence
<220> FEATURE:
<223> OTHER INFORMATION: Peptide derived from HBV Core protein

<400> SEQUENCE: 954

Leu Val Ser Phe Gly Val Trp Ile Arg Thr Pro Pro Ala Tyr Arg
1               5                   10                  15

<210> SEQ ID NO 955
<211> LENGTH: 15
<212> TYPE: PRT
<213> ORGANISM: Artificial sequence
<220> FEATURE:
<223> OTHER INFORMATION: Peptide derived from HBV Core protein

<400> SEQUENCE: 955

Val Ser Phe Gly Val Trp Ile Arg Thr Pro Pro Ala Tyr Arg Pro
1               5                   10                  15

<210> SEQ ID NO 956
<211> LENGTH: 15
<212> TYPE: PRT
<213> ORGANISM: Artificial sequence
<220> FEATURE:
<223> OTHER INFORMATION: Peptide derived from HBV Core protein

<400> SEQUENCE: 956

Ser Phe Gly Val Trp Ile Arg Thr Pro Pro Ala Tyr Arg Pro Pro
1               5                   10                  15

<210> SEQ ID NO 957
<211> LENGTH: 15
<212> TYPE: PRT
<213> ORGANISM: Artificial sequence
<220> FEATURE:
<223> OTHER INFORMATION: Peptide derived from HBV Core protein

<400> SEQUENCE: 957

Phe Gly Val Trp Ile Arg Thr Pro Pro Ala Tyr Arg Pro Pro Asn
1               5                   10                  15

<210> SEQ ID NO 958

```
<211> LENGTH: 15
<212> TYPE: PRT
<213> ORGANISM: Artificial sequence
<220> FEATURE:
<223> OTHER INFORMATION: Peptide derived from HBV Core protein

<400> SEQUENCE: 958

Gly Val Trp Ile Arg Thr Pro Pro Ala Tyr Arg Pro Pro Asn Ala
1               5                   10                  15

<210> SEQ ID NO 959
<211> LENGTH: 9
<212> TYPE: PRT
<213> ORGANISM: Artificial sequence
<220> FEATURE:
<223> OTHER INFORMATION: Peptide derived from HBV X protein

<400> SEQUENCE: 959

Ala Leu Pro Ser Pro Ser Pro Ser Ala
1               5

<210> SEQ ID NO 960
<211> LENGTH: 8
<212> TYPE: PRT
<213> ORGANISM: Artificial sequence
<220> FEATURE:
<223> OTHER INFORMATION: Peptide derived from HBV X protein

<400> SEQUENCE: 960

Leu Pro Ser Pro Ser Pro Ser Ala
1               5

<210> SEQ ID NO 961
<211> LENGTH: 10
<212> TYPE: PRT
<213> ORGANISM: Artificial sequence
<220> FEATURE:
<223> OTHER INFORMATION: Peptide derived from HBV X protein

<400> SEQUENCE: 961

Ala Leu Pro Ser Pro Ser Pro Ser Ala Val
1               5                   10

<210> SEQ ID NO 962
<211> LENGTH: 9
<212> TYPE: PRT
<213> ORGANISM: Artificial sequence
<220> FEATURE:
<223> OTHER INFORMATION: Peptide derived from HBV X protein

<400> SEQUENCE: 962

Leu Pro Ser Pro Ser Pro Ser Ala Val
1               5

<210> SEQ ID NO 963
<211> LENGTH: 11
<212> TYPE: PRT
<213> ORGANISM: Artificial sequence
<220> FEATURE:
<223> OTHER INFORMATION: Peptide derived from HBV X protein

<400> SEQUENCE: 963

Leu Pro Ser Pro Ser Pro Ser Ala Val Pro Ala
1               5                   10

<210> SEQ ID NO 964
<211> LENGTH: 9
```

```
<212> TYPE: PRT
<213> ORGANISM: Artificial sequence
<220> FEATURE:
<223> OTHER INFORMATION: Peptide derived from HBV X protein

<400> SEQUENCE: 964

Ser Pro Ser Pro Ser Ala Val Pro Ala
1               5

<210> SEQ ID NO 965
<211> LENGTH: 11
<212> TYPE: PRT
<213> ORGANISM: Artificial sequence
<220> FEATURE:
<223> OTHER INFORMATION: Peptide derived from HBV X protein

<400> SEQUENCE: 965

Ser Pro Ser Ala Val Pro Ala Asp His Gly Ala
1               5                   10

<210> SEQ ID NO 966
<211> LENGTH: 10
<212> TYPE: PRT
<213> ORGANISM: Artificial sequence
<220> FEATURE:
<223> OTHER INFORMATION: Peptide derived from HBV X protein

<400> SEQUENCE: 966

Ala Val Pro Ala Asp His Gly Ala His Leu
1               5                   10

<210> SEQ ID NO 967
<211> LENGTH: 9
<212> TYPE: PRT
<213> ORGANISM: Artificial sequence
<220> FEATURE:
<223> OTHER INFORMATION: Peptide derived from HBV X protein

<400> SEQUENCE: 967

Val Pro Ala Asp His Gly Ala His Leu
1               5

<210> SEQ ID NO 968
<211> LENGTH: 11
<212> TYPE: PRT
<213> ORGANISM: Artificial sequence
<220> FEATURE:
<223> OTHER INFORMATION: Peptide derived from HBV X protein

<400> SEQUENCE: 968

Val Pro Ala Asp His Gly Ala His Leu Ser Leu
1               5                   10

<210> SEQ ID NO 969
<211> LENGTH: 9
<212> TYPE: PRT
<213> ORGANISM: Artificial sequence
<220> FEATURE:
<223> OTHER INFORMATION: Peptide derived from HBV X protein

<400> SEQUENCE: 969

Ala Asp His Gly Ala His Leu Ser Leu
1               5

<210> SEQ ID NO 970
<211> LENGTH: 8
<212> TYPE: PRT
```

```
<213> ORGANISM: Artificial sequence
<220> FEATURE:
<223> OTHER INFORMATION: Peptide derived from HBV X protein

<400> SEQUENCE: 970

Asp His Gly Ala His Leu Ser Leu
1               5

<210> SEQ ID NO 971
<211> LENGTH: 8
<212> TYPE: PRT
<213> ORGANISM: Artificial sequence
<220> FEATURE:
<223> OTHER INFORMATION: Peptide derived from HBV X protein

<400> SEQUENCE: 971

His Gly Ala His Leu Ser Leu Arg
1               5

<210> SEQ ID NO 972
<211> LENGTH: 9
<212> TYPE: PRT
<213> ORGANISM: Artificial sequence
<220> FEATURE:
<223> OTHER INFORMATION: Peptide derived from HBV X protein

<400> SEQUENCE: 972

Gly Ala His Leu Ser Leu Arg Gly Leu
1               5

<210> SEQ ID NO 973
<211> LENGTH: 8
<212> TYPE: PRT
<213> ORGANISM: Artificial sequence
<220> FEATURE:
<223> OTHER INFORMATION: Peptide derived from HBV X protein

<400> SEQUENCE: 973

Ala His Leu Ser Leu Arg Gly Leu
1               5

<210> SEQ ID NO 974
<211> LENGTH: 10
<212> TYPE: PRT
<213> ORGANISM: Artificial sequence
<220> FEATURE:
<223> OTHER INFORMATION: Peptide derived from HBV X protein

<400> SEQUENCE: 974

Ala His Leu Ser Leu Arg Gly Leu Pro Val
1               5                   10

<210> SEQ ID NO 975
<211> LENGTH: 9
<212> TYPE: PRT
<213> ORGANISM: Artificial sequence
<220> FEATURE:
<223> OTHER INFORMATION: Peptide derived from HBV X protein

<400> SEQUENCE: 975

His Leu Ser Leu Arg Gly Leu Pro Val
1               5

<210> SEQ ID NO 976
<211> LENGTH: 8
<212> TYPE: PRT
<213> ORGANISM: Artificial sequence
```

<220> FEATURE:
<223> OTHER INFORMATION: Peptide derived from HBV X protein

<400> SEQUENCE: 976

Leu Ser Leu Arg Gly Leu Pro Val
1               5

<210> SEQ ID NO 977
<211> LENGTH: 10
<212> TYPE: PRT
<213> ORGANISM: Artificial sequence
<220> FEATURE:
<223> OTHER INFORMATION: Peptide derived from HBV X protein

<400> SEQUENCE: 977

His Leu Ser Leu Arg Gly Leu Pro Val Cys
1               5                   10

<210> SEQ ID NO 978
<211> LENGTH: 9
<212> TYPE: PRT
<213> ORGANISM: Artificial sequence
<220> FEATURE:
<223> OTHER INFORMATION: Peptide derived from HBV X protein

<400> SEQUENCE: 978

Leu Ser Leu Arg Gly Leu Pro Val Cys
1               5

<210> SEQ ID NO 979
<211> LENGTH: 11
<212> TYPE: PRT
<213> ORGANISM: Artificial sequence
<220> FEATURE:
<223> OTHER INFORMATION: Peptide derived from HBV X protein

<400> SEQUENCE: 979

Leu Ser Leu Arg Gly Leu Pro Val Cys Ala Phe
1               5                   10

<210> SEQ ID NO 980
<211> LENGTH: 10
<212> TYPE: PRT
<213> ORGANISM: Artificial sequence
<220> FEATURE:
<223> OTHER INFORMATION: Peptide derived from HBV X protein

<400> SEQUENCE: 980

Ser Leu Arg Gly Ile Pro Val Cys Ala Phe
1               5                   10

<210> SEQ ID NO 981
<211> LENGTH: 10
<212> TYPE: PRT
<213> ORGANISM: Artificial sequence
<220> FEATURE:
<223> OTHER INFORMATION: Peptide derived from HBV X protein

<400> SEQUENCE: 981

Ser Leu Arg Gly Leu Pro Val Cys Ala Phe
1               5                   10

<210> SEQ ID NO 982
<211> LENGTH: 8
<212> TYPE: PRT
<213> ORGANISM: Artificial sequence
<220> FEATURE:

<223> OTHER INFORMATION: Peptide derived from HBV X protein

<400> SEQUENCE: 982

Arg Gly Leu Pro Val Cys Ala Phe
1               5

<210> SEQ ID NO 983
<211> LENGTH: 8
<212> TYPE: PRT
<213> ORGANISM: Artificial sequence
<220> FEATURE:
<223> OTHER INFORMATION: Peptide derived from HBV X protein

<400> SEQUENCE: 983

Leu Pro Val Cys Ala Phe Ser Ser
1               5

<210> SEQ ID NO 984
<211> LENGTH: 11
<212> TYPE: PRT
<213> ORGANISM: Artificial sequence
<220> FEATURE:
<223> OTHER INFORMATION: Peptide derived from HBV X protein

<400> SEQUENCE: 984

Arg Gly Leu Pro Val Cys Ala Phe Ser Ser Ala
1               5                   10

<210> SEQ ID NO 985
<211> LENGTH: 10
<212> TYPE: PRT
<213> ORGANISM: Artificial sequence
<220> FEATURE:
<223> OTHER INFORMATION: Peptide derived from HBV X protein

<400> SEQUENCE: 985

Gly Leu Pro Val Cys Ala Phe Ser Ser Ala
1               5                   10

<210> SEQ ID NO 986
<211> LENGTH: 9
<212> TYPE: PRT
<213> ORGANISM: Artificial sequence
<220> FEATURE:
<223> OTHER INFORMATION: Peptide derived from HBV X protein

<400> SEQUENCE: 986

Leu Pro Val Cys Ala Phe Ser Ser Ala
1               5

<210> SEQ ID NO 987
<211> LENGTH: 10
<212> TYPE: PRT
<213> ORGANISM: Artificial sequence
<220> FEATURE:
<223> OTHER INFORMATION: Peptide derived from HBV X protein

<400> SEQUENCE: 987

Leu Pro Val Cys Ala Phe Ser Ser Ala Gly
1               5                   10

<210> SEQ ID NO 988
<211> LENGTH: 10
<212> TYPE: PRT
<213> ORGANISM: Artificial sequence
<220> FEATURE:
<223> OTHER INFORMATION: Peptide derived from HBV X protein

<400> SEQUENCE: 988

Cys Ala Phe Ser Ser Ala Gly Pro Cys Ala
1               5                   10

<210> SEQ ID NO 989
<211> LENGTH: 11
<212> TYPE: PRT
<213> ORGANISM: Artificial sequence
<220> FEATURE:
<223> OTHER INFORMATION: Peptide derived from HBV X protein

<400> SEQUENCE: 989

Cys Ala Phe Ser Ser Ala Gly Pro Cys Ala Leu
1               5                   10

<210> SEQ ID NO 990
<211> LENGTH: 9
<212> TYPE: PRT
<213> ORGANISM: Artificial sequence
<220> FEATURE:
<223> OTHER INFORMATION: Peptide derived from HBV X protein

<400> SEQUENCE: 990

Phe Ser Ser Ala Gly Pro Cys Ala Leu
1               5

<210> SEQ ID NO 991
<211> LENGTH: 11
<212> TYPE: PRT
<213> ORGANISM: Artificial sequence
<220> FEATURE:
<223> OTHER INFORMATION: Peptide derived from HBV X protein

<400> SEQUENCE: 991

Ala Phe Ser Ser Ala Gly Pro Cys Ala Leu Arg
1               5                   10

<210> SEQ ID NO 992
<211> LENGTH: 10
<212> TYPE: PRT
<213> ORGANISM: Artificial sequence
<220> FEATURE:
<223> OTHER INFORMATION: Peptide derived from HBV X protein

<400> SEQUENCE: 992

Phe Ser Ser Ala Gly Pro Cys Ala Leu Arg
1               5                   10

<210> SEQ ID NO 993
<211> LENGTH: 9
<212> TYPE: PRT
<213> ORGANISM: Artificial sequence
<220> FEATURE:
<223> OTHER INFORMATION: Peptide derived from HBV X protein

<400> SEQUENCE: 993

Ser Ser Ala Gly Pro Cys Ala Leu Arg
1               5

<210> SEQ ID NO 994
<211> LENGTH: 11
<212> TYPE: PRT
<213> ORGANISM: Artificial sequence
<220> FEATURE:
<223> OTHER INFORMATION: Peptide derived from HBV X protein

```
<400> SEQUENCE: 994

Phe Ser Ser Ala Gly Pro Cys Ala Leu Arg Phe
1               5                   10

<210> SEQ ID NO 995
<211> LENGTH: 10
<212> TYPE: PRT
<213> ORGANISM: Artificial sequence
<220> FEATURE:
<223> OTHER INFORMATION: Peptide derived from HBV X protein

<400> SEQUENCE: 995

Ser Ser Ala Gly Pro Cys Ala Leu Arg Phe
1               5                   10

<210> SEQ ID NO 996
<211> LENGTH: 9
<212> TYPE: PRT
<213> ORGANISM: Artificial sequence
<220> FEATURE:
<223> OTHER INFORMATION: Peptide derived from HBV X protein

<400> SEQUENCE: 996

Ser Ala Gly Pro Cys Ala Leu Arg Phe
1               5

<210> SEQ ID NO 997
<211> LENGTH: 9
<212> TYPE: PRT
<213> ORGANISM: Artificial sequence
<220> FEATURE:
<223> OTHER INFORMATION: Peptide derived from HBV X protein

<400> SEQUENCE: 997

Cys Ala Leu Arg Phe Thr Ser Ala Arg
1               5

<210> SEQ ID NO 998
<211> LENGTH: 8
<212> TYPE: PRT
<213> ORGANISM: Artificial sequence
<220> FEATURE:
<223> OTHER INFORMATION: Peptide derived from HBV X protein

<400> SEQUENCE: 998

Ala Leu Arg Phe Thr Ser Ala Arg
1               5

<210> SEQ ID NO 999
<211> LENGTH: 10
<212> TYPE: PRT
<213> ORGANISM: Artificial sequence
<220> FEATURE:
<223> OTHER INFORMATION: Peptide derived from HBV X protein

<400> SEQUENCE: 999

Cys Ala Leu Arg Phe Thr Ser Ala Arg Arg
1               5                   10

<210> SEQ ID NO 1000
<211> LENGTH: 9
<212> TYPE: PRT
<213> ORGANISM: Artificial sequence
<220> FEATURE:
<223> OTHER INFORMATION: Peptide derived from HBV X protein

<400> SEQUENCE: 1000
```

Ala Leu Arg Phe Thr Ser Ala Arg Arg
1               5

<210> SEQ ID NO 1001
<211> LENGTH: 8
<212> TYPE: PRT
<213> ORGANISM: Artificial sequence
<220> FEATURE:
<223> OTHER INFORMATION: Peptide derived from HBV X protein

<400> SEQUENCE: 1001

Leu Arg Phe Thr Ser Ala Arg Arg
1               5

<210> SEQ ID NO 1002
<211> LENGTH: 10
<212> TYPE: PRT
<213> ORGANISM: Artificial sequence
<220> FEATURE:
<223> OTHER INFORMATION: Peptide derived from HBV X protein

<400> SEQUENCE: 1002

Ala Leu Arg Phe Thr Ser Ala Arg Arg Met
1               5                   10

<210> SEQ ID NO 1003
<211> LENGTH: 9
<212> TYPE: PRT
<213> ORGANISM: Artificial sequence
<220> FEATURE:
<223> OTHER INFORMATION: Peptide derived from HBV X protein

<400> SEQUENCE: 1003

Leu Arg Phe Thr Ser Ala Arg Arg Met
1               5

<210> SEQ ID NO 1004
<211> LENGTH: 8
<212> TYPE: PRT
<213> ORGANISM: Artificial sequence
<220> FEATURE:
<223> OTHER INFORMATION: Peptide derived from HBV X protein

<400> SEQUENCE: 1004

Arg Arg Met Glu Thr Thr Val Asn
1               5

<210> SEQ ID NO 1005
<211> LENGTH: 11
<212> TYPE: PRT
<213> ORGANISM: Artificial sequence
<220> FEATURE:
<223> OTHER INFORMATION: Peptide derived from HBV X protein

<400> SEQUENCE: 1005

Ser Ala Arg Arg Met Glu Thr Thr Val Asn Ala
1               5                   10

<210> SEQ ID NO 1006
<211> LENGTH: 9
<212> TYPE: PRT
<213> ORGANISM: Artificial sequence
<220> FEATURE:
<223> OTHER INFORMATION: Peptide derived from HBV X protein

<400> SEQUENCE: 1006

Arg Arg Met Glu Thr Thr Val Asn Ala
1               5

<210> SEQ ID NO 1007
<211> LENGTH: 10
<212> TYPE: PRT
<213> ORGANISM: Artificial sequence
<220> FEATURE:
<223> OTHER INFORMATION: Peptide derived from HBV X protein

<400> SEQUENCE: 1007

Arg Arg Met Glu Thr Thr Val Asn Ala His
1               5                   10

<210> SEQ ID NO 1008
<211> LENGTH: 8
<212> TYPE: PRT
<213> ORGANISM: Artificial sequence
<220> FEATURE:
<223> OTHER INFORMATION: Peptide derived from HBV X protein

<400> SEQUENCE: 1008

Met Glu Thr Thr Val Asn Ala His
1               5

<210> SEQ ID NO 1009
<211> LENGTH: 11
<212> TYPE: PRT
<213> ORGANISM: Artificial sequence
<220> FEATURE:
<223> OTHER INFORMATION: Peptide derived from HBV X protein

<400> SEQUENCE: 1009

Arg Arg Met Glu Thr Thr Val Asn Ala His Gln
1               5                   10

<210> SEQ ID NO 1010
<211> LENGTH: 9
<212> TYPE: PRT
<213> ORGANISM: Artificial sequence
<220> FEATURE:
<223> OTHER INFORMATION: Peptide derived from HBV X protein

<400> SEQUENCE: 1010

Met Glu Thr Thr Val Asn Ala His Gln
1               5

<210> SEQ ID NO 1011
<211> LENGTH: 11
<212> TYPE: PRT
<213> ORGANISM: Artificial sequence
<220> FEATURE:
<223> OTHER INFORMATION: Peptide derived from HBV X protein

<400> SEQUENCE: 1011

Arg Met Glu Thr Thr Val Asn Ala His Gln Ile
1               5                   10

<210> SEQ ID NO 1012
<211> LENGTH: 10
<212> TYPE: PRT
<213> ORGANISM: Artificial sequence
<220> FEATURE:
<223> OTHER INFORMATION: Peptide derived from HBV X protein

<400> SEQUENCE: 1012

Met Glu Thr Thr Val Asn Ala His Gln Ile

```
<210> SEQ ID NO 1013
<211> LENGTH: 9
<212> TYPE: PRT
<213> ORGANISM: Artificial sequence
<220> FEATURE:
<223> OTHER INFORMATION: Peptide derived from HBV X protein

<400> SEQUENCE: 1013

Glu Thr Thr Val Asn Ala His Gln Ile
1               5

<210> SEQ ID NO 1014
<211> LENGTH: 11
<212> TYPE: PRT
<213> ORGANISM: Artificial sequence
<220> FEATURE:
<223> OTHER INFORMATION: Peptide derived from HBV X protein

<400> SEQUENCE: 1014

Met Glu Thr Thr Val Asn Ala His Gln Ile Leu
1               5                   10

<210> SEQ ID NO 1015
<211> LENGTH: 10
<212> TYPE: PRT
<213> ORGANISM: Artificial sequence
<220> FEATURE:
<223> OTHER INFORMATION: Peptide derived from HBV X protein

<400> SEQUENCE: 1015

Glu Thr Thr Val Asn Ala His Gln Ile Leu
1               5                   10

<210> SEQ ID NO 1016
<211> LENGTH: 11
<212> TYPE: PRT
<213> ORGANISM: Artificial sequence
<220> FEATURE:
<223> OTHER INFORMATION: Peptide derived from HBV X protein

<400> SEQUENCE: 1016

Thr Thr Val Asn Ala His Gln Ile Leu Pro Lys
1               5                   10

<210> SEQ ID NO 1017
<211> LENGTH: 10
<212> TYPE: PRT
<213> ORGANISM: Artificial sequence
<220> FEATURE:
<223> OTHER INFORMATION: Peptide derived from HBV X protein

<400> SEQUENCE: 1017

Thr Val Asn Ala His Gln Ile Leu Pro Lys
1               5                   10

<210> SEQ ID NO 1018
<211> LENGTH: 11
<212> TYPE: PRT
<213> ORGANISM: Artificial sequence
<220> FEATURE:
<223> OTHER INFORMATION: Peptide derived from HBV X protein

<400> SEQUENCE: 1018

Thr Val Asn Ala His Gln Ile Leu Pro Lys Val
1               5                   10
```

```
<210> SEQ ID NO 1019
<211> LENGTH: 10
<212> TYPE: PRT
<213> ORGANISM: Artificial sequence
<220> FEATURE:
<223> OTHER INFORMATION: Peptide derived from HBV X protein

<400> SEQUENCE: 1019

Asn Ala His Gln Ile Leu Pro Lys Val Leu
1               5                   10

<210> SEQ ID NO 1020
<211> LENGTH: 9
<212> TYPE: PRT
<213> ORGANISM: Artificial sequence
<220> FEATURE:
<223> OTHER INFORMATION: Peptide derived from HBV X protein

<400> SEQUENCE: 1020

Ala His Gln Ile Leu Pro Lys Val Leu
1               5

<210> SEQ ID NO 1021
<211> LENGTH: 8
<212> TYPE: PRT
<213> ORGANISM: Artificial sequence
<220> FEATURE:
<223> OTHER INFORMATION: Peptide derived from HBV X protein

<400> SEQUENCE: 1021

His Gln Ile Leu Pro Lys Val Leu
1               5

<210> SEQ ID NO 1022
<211> LENGTH: 10
<212> TYPE: PRT
<213> ORGANISM: Artificial sequence
<220> FEATURE:
<223> OTHER INFORMATION: Peptide derived from HBV X protein

<400> SEQUENCE: 1022

His Gln Ile Leu Pro Lys Val Leu His Lys
1               5                   10

<210> SEQ ID NO 1023
<211> LENGTH: 9
<212> TYPE: PRT
<213> ORGANISM: Artificial sequence
<220> FEATURE:
<223> OTHER INFORMATION: Peptide derived from HBV X protein

<400> SEQUENCE: 1023

Gln Ile Leu Pro Lys Val Leu His Lys
1               5

<210> SEQ ID NO 1024
<211> LENGTH: 8
<212> TYPE: PRT
<213> ORGANISM: Artificial sequence
<220> FEATURE:
<223> OTHER INFORMATION: Peptide derived from HBV X protein

<400> SEQUENCE: 1024

Ile Leu Pro Lys Val Leu His Lys
1               5
```

<210> SEQ ID NO 1025
<211> LENGTH: 11
<212> TYPE: PRT
<213> ORGANISM: Artificial sequence
<220> FEATURE:
<223> OTHER INFORMATION: Peptide derived from HBV X protein

<400> SEQUENCE: 1025

His Gln Ile Leu Pro Lys Val Leu His Lys Arg
1               5                   10

<210> SEQ ID NO 1026
<211> LENGTH: 10
<212> TYPE: PRT
<213> ORGANISM: Artificial sequence
<220> FEATURE:
<223> OTHER INFORMATION: Peptide derived from HBV X protein

<400> SEQUENCE: 1026

Gln Ile Leu Pro Lys Val Leu His Lys Arg
1               5                   10

<210> SEQ ID NO 1027
<211> LENGTH: 9
<212> TYPE: PRT
<213> ORGANISM: Artificial sequence
<220> FEATURE:
<223> OTHER INFORMATION: Peptide derived from HBV X protein

<400> SEQUENCE: 1027

Ile Leu Pro Lys Val Leu His Lys Arg
1               5

<210> SEQ ID NO 1028
<211> LENGTH: 8
<212> TYPE: PRT
<213> ORGANISM: Artificial sequence
<220> FEATURE:
<223> OTHER INFORMATION: Peptide derived from HBV X protein

<400> SEQUENCE: 1028

Leu Pro Lys Val Leu His Lys Arg
1               5

<210> SEQ ID NO 1029
<211> LENGTH: 10
<212> TYPE: PRT
<213> ORGANISM: Artificial sequence
<220> FEATURE:
<223> OTHER INFORMATION: Peptide derived from HBV X protein

<400> SEQUENCE: 1029

Ile Leu Pro Lys Val Leu His Lys Arg Thr
1               5                   10

<210> SEQ ID NO 1030
<211> LENGTH: 10
<212> TYPE: PRT
<213> ORGANISM: Artificial sequence
<220> FEATURE:
<223> OTHER INFORMATION: Peptide derived from HBV X protein

<400> SEQUENCE: 1030

Leu Pro Lys Val Leu His Lys Arg Thr Leu
1               5                   10

```
<210> SEQ ID NO 1031
<211> LENGTH: 8
<212> TYPE: PRT
<213> ORGANISM: Artificial sequence
<220> FEATURE:
<223> OTHER INFORMATION: Peptide derived from HBV X protein

<400> SEQUENCE: 1031

Lys Val Leu His Lys Arg Thr Leu
1               5

<210> SEQ ID NO 1032
<211> LENGTH: 10
<212> TYPE: PRT
<213> ORGANISM: Artificial sequence
<220> FEATURE:
<223> OTHER INFORMATION: Peptide derived from HBV X protein

<400> SEQUENCE: 1032

Lys Val Leu His Lys Arg Thr Leu Gly Leu
1               5                   10

<210> SEQ ID NO 1033
<211> LENGTH: 9
<212> TYPE: PRT
<213> ORGANISM: Artificial sequence
<220> FEATURE:
<223> OTHER INFORMATION: Peptide derived from HBV X protein

<400> SEQUENCE: 1033

Val Leu His Lys Arg Thr Leu Gly Leu
1               5

<210> SEQ ID NO 1034
<211> LENGTH: 11
<212> TYPE: PRT
<213> ORGANISM: Artificial sequence
<220> FEATURE:
<223> OTHER INFORMATION: Peptide derived from HBV X protein

<400> SEQUENCE: 1034

Val Leu His Lys Arg Thr Leu Gly Leu Ser Ala
1               5                   10

<210> SEQ ID NO 1035
<211> LENGTH: 8
<212> TYPE: PRT
<213> ORGANISM: Artificial sequence
<220> FEATURE:
<223> OTHER INFORMATION: Peptide derived from HBV X protein

<400> SEQUENCE: 1035

Lys Arg Thr Leu Gly Leu Ser Ala
1               5

<210> SEQ ID NO 1036
<211> LENGTH: 11
<212> TYPE: PRT
<213> ORGANISM: Artificial sequence
<220> FEATURE:
<223> OTHER INFORMATION: Peptide derived from HBV X protein

<400> SEQUENCE: 1036

Leu His Lys Arg Thr Leu Gly Leu Ser Ala Met
1               5                   10

<210> SEQ ID NO 1037
```

```
<211> LENGTH: 10
<212> TYPE: PRT
<213> ORGANISM: Artificial sequence
<220> FEATURE:
<223> OTHER INFORMATION: Peptide derived from HBV X protein

<400> SEQUENCE: 1037

His Lys Arg Thr Leu Gly Leu Ser Ala Met
1               5                   10

<210> SEQ ID NO 1038
<211> LENGTH: 9
<212> TYPE: PRT
<213> ORGANISM: Artificial sequence
<220> FEATURE:
<223> OTHER INFORMATION: Peptide derived from HBV X protein

<400> SEQUENCE: 1038

Lys Arg Thr Leu Gly Leu Ser Ala Met
1               5

<210> SEQ ID NO 1039
<211> LENGTH: 8
<212> TYPE: PRT
<213> ORGANISM: Artificial sequence
<220> FEATURE:
<223> OTHER INFORMATION: Peptide derived from HBV X protein

<400> SEQUENCE: 1039

Arg Thr Leu Gly Leu Ser Ala Met
1               5

<210> SEQ ID NO 1040
<211> LENGTH: 8
<212> TYPE: PRT
<213> ORGANISM: Artificial sequence
<220> FEATURE:
<223> OTHER INFORMATION: Peptide derived from HBV X protein

<400> SEQUENCE: 1040

Thr Leu Gly Leu Ser Ala Met Ser
1               5

<210> SEQ ID NO 1041
<211> LENGTH: 9
<212> TYPE: PRT
<213> ORGANISM: Artificial sequence
<220> FEATURE:
<223> OTHER INFORMATION: Peptide derived from HBV X protein

<400> SEQUENCE: 1041

Thr Leu Gly Leu Ser Ala Met Ser Thr
1               5

<210> SEQ ID NO 1042
<211> LENGTH: 10
<212> TYPE: PRT
<213> ORGANISM: Artificial sequence
<220> FEATURE:
<223> OTHER INFORMATION: Peptide derived from HBV X protein

<400> SEQUENCE: 1042

Thr Leu Gly Leu Ser Ala Met Ser Thr Thr
1               5                   10

<210> SEQ ID NO 1043
<211> LENGTH: 10
```

```
<212> TYPE: PRT
<213> ORGANISM: Artificial sequence
<220> FEATURE:
<223> OTHER INFORMATION: Peptide derived from HBV X protein

<400> SEQUENCE: 1043

Gly Leu Ser Ala Met Ser Thr Thr Asp Leu
1               5                   10

<210> SEQ ID NO 1044
<211> LENGTH: 11
<212> TYPE: PRT
<213> ORGANISM: Artificial sequence
<220> FEATURE:
<223> OTHER INFORMATION: Peptide derived from HBV X protein

<400> SEQUENCE: 1044

Leu Ser Ala Met Ser Thr Thr Asp Leu Glu Ala
1               5                   10

<210> SEQ ID NO 1045
<211> LENGTH: 11
<212> TYPE: PRT
<213> ORGANISM: Artificial sequence
<220> FEATURE:
<223> OTHER INFORMATION: Peptide derived from HBV X protein

<400> SEQUENCE: 1045

Ser Ala Met Ser Thr Thr Asp Leu Glu Ala Tyr
1               5                   10

<210> SEQ ID NO 1046
<211> LENGTH: 10
<212> TYPE: PRT
<213> ORGANISM: Artificial sequence
<220> FEATURE:
<223> OTHER INFORMATION: Peptide derived from HBV X protein

<400> SEQUENCE: 1046

Ala Met Ser Thr Thr Asp Leu Glu Ala Tyr
1               5                   10

<210> SEQ ID NO 1047
<211> LENGTH: 9
<212> TYPE: PRT
<213> ORGANISM: Artificial sequence
<220> FEATURE:
<223> OTHER INFORMATION: Peptide derived from HBV X protein

<400> SEQUENCE: 1047

Met Ser Thr Thr Asp Leu Glu Ala Tyr
1               5

<210> SEQ ID NO 1048
<211> LENGTH: 8
<212> TYPE: PRT
<213> ORGANISM: Artificial sequence
<220> FEATURE:
<223> OTHER INFORMATION: Peptide derived from HBV X protein

<400> SEQUENCE: 1048

Ser Thr Thr Asp Leu Glu Ala Tyr
1               5

<210> SEQ ID NO 1049
<211> LENGTH: 11
<212> TYPE: PRT
```

<213> ORGANISM: Artificial sequence
<220> FEATURE:
<223> OTHER INFORMATION: Peptide derived from HBV X protein

<400> SEQUENCE: 1049

Ala Met Ser Thr Thr Asp Leu Glu Ala Tyr Phe
1               5                   10

<210> SEQ ID NO 1050
<211> LENGTH: 10
<212> TYPE: PRT
<213> ORGANISM: Artificial sequence
<220> FEATURE:
<223> OTHER INFORMATION: Peptide derived from HBV X protein

<400> SEQUENCE: 1050

Met Ser Thr Thr Asp Leu Glu Ala Tyr Phe
1               5                   10

<210> SEQ ID NO 1051
<211> LENGTH: 9
<212> TYPE: PRT
<213> ORGANISM: Artificial sequence
<220> FEATURE:
<223> OTHER INFORMATION: Peptide derived from HBV X protein

<400> SEQUENCE: 1051

Ser Thr Thr Asp Leu Glu Ala Tyr Phe
1               5

<210> SEQ ID NO 1052
<211> LENGTH: 8
<212> TYPE: PRT
<213> ORGANISM: Artificial sequence
<220> FEATURE:
<223> OTHER INFORMATION: Peptide derived from HBV X protein

<400> SEQUENCE: 1052

Thr Thr Asp Leu Glu Ala Tyr Phe
1               5

<210> SEQ ID NO 1053
<211> LENGTH: 11
<212> TYPE: PRT
<213> ORGANISM: Artificial sequence
<220> FEATURE:
<223> OTHER INFORMATION: Peptide derived from HBV X protein

<400> SEQUENCE: 1053

Met Ser Thr Thr Asp Leu Glu Ala Tyr Phe Lys
1               5                   10

<210> SEQ ID NO 1054
<211> LENGTH: 10
<212> TYPE: PRT
<213> ORGANISM: Artificial sequence
<220> FEATURE:
<223> OTHER INFORMATION: Peptide derived from HBV X protein

<400> SEQUENCE: 1054

Ser Thr Thr Asp Leu Glu Ala Tyr Phe Lys
1               5                   10

<210> SEQ ID NO 1055
<211> LENGTH: 9
<212> TYPE: PRT
<213> ORGANISM: Artificial sequence

```
<220> FEATURE:
<223> OTHER INFORMATION: Peptide derived from HBV X protein

<400> SEQUENCE: 1055

Thr Thr Asp Leu Glu Ala Tyr Phe Lys
1               5

<210> SEQ ID NO 1056
<211> LENGTH: 11
<212> TYPE: PRT
<213> ORGANISM: Artificial sequence
<220> FEATURE:
<223> OTHER INFORMATION: Peptide derived from HBV X protein

<400> SEQUENCE: 1056

Thr Asp Leu Glu Ala Tyr Phe Lys Asp Cys Val
1               5                   10

<210> SEQ ID NO 1057
<211> LENGTH: 9
<212> TYPE: PRT
<213> ORGANISM: Artificial sequence
<220> FEATURE:
<223> OTHER INFORMATION: Peptide derived from HBV X protein

<400> SEQUENCE: 1057

Leu Glu Ala Tyr Phe Lys Asp Cys Val
1               5

<210> SEQ ID NO 1058
<211> LENGTH: 8
<212> TYPE: PRT
<213> ORGANISM: Artificial sequence
<220> FEATURE:
<223> OTHER INFORMATION: Peptide derived from HBV X protein

<400> SEQUENCE: 1058

Glu Ala Tyr Phe Lys Asp Cys Val
1               5

<210> SEQ ID NO 1059
<211> LENGTH: 10
<212> TYPE: PRT
<213> ORGANISM: Artificial sequence
<220> FEATURE:
<223> OTHER INFORMATION: Peptide derived from HBV X protein

<400> SEQUENCE: 1059

Leu Glu Ala Tyr Phe Lys Asp Cys Val Phe
1               5                   10

<210> SEQ ID NO 1060
<211> LENGTH: 8
<212> TYPE: PRT
<213> ORGANISM: Artificial sequence
<220> FEATURE:
<223> OTHER INFORMATION: Peptide derived from HBV X protein

<400> SEQUENCE: 1060

Ala Tyr Phe Lys Asp Cys Val Phe
1               5

<210> SEQ ID NO 1061
<211> LENGTH: 10
<212> TYPE: PRT
<213> ORGANISM: Artificial sequence
<220> FEATURE:
```

<223> OTHER INFORMATION: Peptide derived from HBV X protein

<400> SEQUENCE: 1061

Glu Ala Tyr Phe Lys Asp Cys Val Phe Lys
1               5                   10

<210> SEQ ID NO 1062
<211> LENGTH: 9
<212> TYPE: PRT
<213> ORGANISM: Artificial sequence
<220> FEATURE:
<223> OTHER INFORMATION: Peptide derived from HBV X protein

<400> SEQUENCE: 1062

Ala Tyr Phe Lys Asp Cys Val Phe Lys
1               5

<210> SEQ ID NO 1063
<211> LENGTH: 8
<212> TYPE: PRT
<213> ORGANISM: Artificial sequence
<220> FEATURE:
<223> OTHER INFORMATION: Peptide derived from HBV X protein

<400> SEQUENCE: 1063

Tyr Phe Lys Asp Cys Val Phe Lys
1               5

<210> SEQ ID NO 1064
<211> LENGTH: 11
<212> TYPE: PRT
<213> ORGANISM: Artificial sequence
<220> FEATURE:
<223> OTHER INFORMATION: Peptide derived from HBV X protein

<400> SEQUENCE: 1064

Ala Tyr Phe Lys Asp Cys Val Phe Lys Asp Trp
1               5                   10

<210> SEQ ID NO 1065
<211> LENGTH: 10
<212> TYPE: PRT
<213> ORGANISM: Artificial sequence
<220> FEATURE:
<223> OTHER INFORMATION: Peptide derived from HBV X protein

<400> SEQUENCE: 1065

Asp Cys Val Phe Lys Asp Trp Glu Glu Leu
1               5                   10

<210> SEQ ID NO 1066
<211> LENGTH: 9
<212> TYPE: PRT
<213> ORGANISM: Artificial sequence
<220> FEATURE:
<223> OTHER INFORMATION: Peptide derived from HBV X protein

<400> SEQUENCE: 1066

Cys Val Phe Lys Asp Trp Glu Glu Leu
1               5

<210> SEQ ID NO 1067
<211> LENGTH: 10
<212> TYPE: PRT
<213> ORGANISM: Artificial sequence
<220> FEATURE:
<223> OTHER INFORMATION: Peptide derived from HBV X protein

<400> SEQUENCE: 1067

Lys Asp Trp Glu Glu Leu Gly Glu Glu Ile
1               5                   10

<210> SEQ ID NO 1068
<211> LENGTH: 8
<212> TYPE: PRT
<213> ORGANISM: Artificial sequence
<220> FEATURE:
<223> OTHER INFORMATION: Peptide derived from HBV X protein

<400> SEQUENCE: 1068

Trp Glu Glu Leu Gly Glu Glu Ile
1               5

<210> SEQ ID NO 1069
<211> LENGTH: 11
<212> TYPE: PRT
<213> ORGANISM: Artificial sequence
<220> FEATURE:
<223> OTHER INFORMATION: Peptide derived from HBV X protein

<400> SEQUENCE: 1069

Asp Trp Glu Glu Leu Gly Glu Glu Ile Arg Leu
1               5                   10

<210> SEQ ID NO 1070
<211> LENGTH: 10
<212> TYPE: PRT
<213> ORGANISM: Artificial sequence
<220> FEATURE:
<223> OTHER INFORMATION: Peptide derived from HBV X protein

<400> SEQUENCE: 1070

Trp Glu Glu Leu Gly Glu Glu Ile Arg Leu
1               5                   10

<210> SEQ ID NO 1071
<211> LENGTH: 9
<212> TYPE: PRT
<213> ORGANISM: Artificial sequence
<220> FEATURE:
<223> OTHER INFORMATION: Peptide derived from HBV X protein

<400> SEQUENCE: 1071

Glu Glu Leu Gly Glu Glu Ile Arg Leu
1               5

<210> SEQ ID NO 1072
<211> LENGTH: 11
<212> TYPE: PRT
<213> ORGANISM: Artificial sequence
<220> FEATURE:
<223> OTHER INFORMATION: Peptide derived from HBV X protein

<400> SEQUENCE: 1072

Glu Glu Leu Gly Glu Glu Ile Arg Leu Lys Val
1               5                   10

<210> SEQ ID NO 1073
<211> LENGTH: 10
<212> TYPE: PRT
<213> ORGANISM: Artificial sequence
<220> FEATURE:
<223> OTHER INFORMATION: Peptide derived from HBV X protein

```
<400> SEQUENCE: 1073

Glu Leu Gly Glu Glu Ile Arg Leu Lys Val
1               5                   10

<210> SEQ ID NO 1074
<211> LENGTH: 8
<212> TYPE: PRT
<213> ORGANISM: Artificial sequence
<220> FEATURE:
<223> OTHER INFORMATION: Peptide derived from HBV X protein

<400> SEQUENCE: 1074

Gly Glu Glu Ile Arg Leu Lys Val
1               5

<210> SEQ ID NO 1075
<211> LENGTH: 10
<212> TYPE: PRT
<213> ORGANISM: Artificial sequence
<220> FEATURE:
<223> OTHER INFORMATION: Peptide derived from HBV X protein

<400> SEQUENCE: 1075

Leu Gly Glu Glu Ile Arg Leu Lys Val Phe
1               5                   10

<210> SEQ ID NO 1076
<211> LENGTH: 9
<212> TYPE: PRT
<213> ORGANISM: Artificial sequence
<220> FEATURE:
<223> OTHER INFORMATION: Peptide derived from HBV X protein

<400> SEQUENCE: 1076

Gly Glu Glu Ile Arg Leu Lys Val Phe
1               5

<210> SEQ ID NO 1077
<211> LENGTH: 8
<212> TYPE: PRT
<213> ORGANISM: Artificial sequence
<220> FEATURE:
<223> OTHER INFORMATION: Peptide derived from HBV X protein

<400> SEQUENCE: 1077

Glu Glu Ile Arg Leu Lys Val Phe
1               5

<210> SEQ ID NO 1078
<211> LENGTH: 11
<212> TYPE: PRT
<213> ORGANISM: Artificial sequence
<220> FEATURE:
<223> OTHER INFORMATION: Peptide derived from HBV X protein

<400> SEQUENCE: 1078

Leu Gly Glu Glu Ile Arg Leu Lys Val Phe Val
1               5                   10

<210> SEQ ID NO 1079
<211> LENGTH: 9
<212> TYPE: PRT
<213> ORGANISM: Artificial sequence
<220> FEATURE:
<223> OTHER INFORMATION: Peptide derived from HBV X protein

<400> SEQUENCE: 1079
```

Glu Glu Ile Arg Leu Lys Val Phe Val
1               5

<210> SEQ ID NO 1080
<211> LENGTH: 8
<212> TYPE: PRT
<213> ORGANISM: Artificial sequence
<220> FEATURE:
<223> OTHER INFORMATION: Peptide derived from HBV X protein

<400> SEQUENCE: 1080

Glu Ile Arg Leu Lys Val Phe Val
1               5

<210> SEQ ID NO 1081
<211> LENGTH: 10
<212> TYPE: PRT
<213> ORGANISM: Artificial sequence
<220> FEATURE:
<223> OTHER INFORMATION: Peptide derived from HBV X protein

<400> SEQUENCE: 1081

Glu Glu Ile Arg Leu Lys Val Phe Val Leu
1               5                   10

<210> SEQ ID NO 1082
<211> LENGTH: 9
<212> TYPE: PRT
<213> ORGANISM: Artificial sequence
<220> FEATURE:
<223> OTHER INFORMATION: Peptide derived from HBV X protein

<400> SEQUENCE: 1082

Glu Ile Arg Leu Lys Val Phe Val Leu
1               5

<210> SEQ ID NO 1083
<211> LENGTH: 8
<212> TYPE: PRT
<213> ORGANISM: Artificial sequence
<220> FEATURE:
<223> OTHER INFORMATION: Peptide derived from HBV X protein

<400> SEQUENCE: 1083

Ile Arg Leu Lys Val Phe Val Leu
1               5

<210> SEQ ID NO 1084
<211> LENGTH: 8
<212> TYPE: PRT
<213> ORGANISM: Artificial sequence
<220> FEATURE:
<223> OTHER INFORMATION: Peptide derived from HBV X protein

<400> SEQUENCE: 1084

Leu Lys Val Phe Val Leu Gly Gly
1               5

<210> SEQ ID NO 1085
<211> LENGTH: 11
<212> TYPE: PRT
<213> ORGANISM: Artificial sequence
<220> FEATURE:
<223> OTHER INFORMATION: Peptide derived from HBV X protein

<400> SEQUENCE: 1085

```
Arg Leu Lys Val Phe Val Leu Gly Gly Cys Arg
1               5                   10
```

<210> SEQ ID NO 1086
<211> LENGTH: 9
<212> TYPE: PRT
<213> ORGANISM: Artificial sequence
<220> FEATURE:
<223> OTHER INFORMATION: Peptide derived from HBV X protein

<400> SEQUENCE: 1086

```
Lys Val Phe Val Leu Gly Gly Cys Arg
1               5
```

<210> SEQ ID NO 1087
<211> LENGTH: 11
<212> TYPE: PRT
<213> ORGANISM: Artificial sequence
<220> FEATURE:
<223> OTHER INFORMATION: Peptide derived from HBV X protein

<400> SEQUENCE: 1087

```
Lys Val Phe Val Leu Gly Gly Cys Arg His Lys
1               5                   10
```

<210> SEQ ID NO 1088
<211> LENGTH: 8
<212> TYPE: PRT
<213> ORGANISM: Artificial sequence
<220> FEATURE:
<223> OTHER INFORMATION: Peptide derived from HBV X protein

<400> SEQUENCE: 1088

```
Val Leu Gly Gly Cys Arg His Lys
1               5
```

<210> SEQ ID NO 1089
<211> LENGTH: 10
<212> TYPE: PRT
<213> ORGANISM: Artificial sequence
<220> FEATURE:
<223> OTHER INFORMATION: Peptide derived from HBV X protein

<400> SEQUENCE: 1089

```
Phe Val Leu Gly Gly Cys Arg His Lys Leu
1               5                   10
```

<210> SEQ ID NO 1090
<211> LENGTH: 9
<212> TYPE: PRT
<213> ORGANISM: Artificial sequence
<220> FEATURE:
<223> OTHER INFORMATION: Peptide derived from HBV X protein

<400> SEQUENCE: 1090

```
Val Leu Gly Gly Cys Arg His Lys Leu
1               5
```

<210> SEQ ID NO 1091
<211> LENGTH: 15
<212> TYPE: PRT
<213> ORGANISM: Artificial sequence
<220> FEATURE:
<223> OTHER INFORMATION: Peptide derived from HBV X protein

<400> SEQUENCE: 1091

```
Pro Ala Asp His Gly Ala His Leu Ser Leu Arg Gly Leu Pro Val
```

```
1               5                   10                  15

<210> SEQ ID NO 1092
<211> LENGTH: 15
<212> TYPE: PRT
<213> ORGANISM: Artificial sequence
<220> FEATURE:
<223> OTHER INFORMATION: Peptide derived from HBV X protein

<400> SEQUENCE: 1092

Ala Asp His Gly Ala His Leu Ser Leu Arg Gly Leu Pro Val Cys
1               5                   10                  15

<210> SEQ ID NO 1093
<211> LENGTH: 15
<212> TYPE: PRT
<213> ORGANISM: Artificial sequence
<220> FEATURE:
<223> OTHER INFORMATION: Peptide derived from HBV X protein

<400> SEQUENCE: 1093

Asp His Gly Ala His Leu Ser Leu Arg Gly Leu Pro Val Cys Ala
1               5                   10                  15

<210> SEQ ID NO 1094
<211> LENGTH: 15
<212> TYPE: PRT
<213> ORGANISM: Artificial sequence
<220> FEATURE:
<223> OTHER INFORMATION: Peptide derived from HBV X protein

<400> SEQUENCE: 1094

His Gly Ala His Leu Ser Leu Arg Gly Leu Pro Val Cys Ala Phe
1               5                   10                  15

<210> SEQ ID NO 1095
<211> LENGTH: 15
<212> TYPE: PRT
<213> ORGANISM: Artificial sequence
<220> FEATURE:
<223> OTHER INFORMATION: Peptide derived from HBV X protein

<400> SEQUENCE: 1095

Gly Ala His Leu Ser Leu Arg Gly Leu Pro Val Cys Ala Phe Ser
1               5                   10                  15

<210> SEQ ID NO 1096
<211> LENGTH: 15
<212> TYPE: PRT
<213> ORGANISM: Artificial sequence
<220> FEATURE:
<223> OTHER INFORMATION: Peptide derived from HBV X protein

<400> SEQUENCE: 1096

Ala His Leu Ser Leu Arg Gly Leu Pro Val Cys Ala Phe Ser Ser
1               5                   10                  15

<210> SEQ ID NO 1097
<211> LENGTH: 15
<212> TYPE: PRT
<213> ORGANISM: Artificial sequence
<220> FEATURE:
<223> OTHER INFORMATION: Peptide derived from HBV X protein

<400> SEQUENCE: 1097

His Leu Ser Leu Arg Gly Leu Pro Val Cys Ala Phe Ser Ser Ala
1               5                   10                  15
```

<210> SEQ ID NO 1098
<211> LENGTH: 15
<212> TYPE: PRT
<213> ORGANISM: Artificial sequence
<220> FEATURE:
<223> OTHER INFORMATION: Peptide derived from HBV X protein

<400> SEQUENCE: 1098

Leu Ser Leu Arg Gly Leu Pro Val Cys Ala Phe Ser Ser Ala Gly
1               5                   10                  15

<210> SEQ ID NO 1099
<211> LENGTH: 15
<212> TYPE: PRT
<213> ORGANISM: Artificial sequence
<220> FEATURE:
<223> OTHER INFORMATION: Peptide derived from HBV X protein

<400> SEQUENCE: 1099

Ser Leu Arg Gly Leu Pro Val Cys Ala Phe Ser Ser Ala Gly Pro
1               5                   10                  15

<210> SEQ ID NO 1100
<211> LENGTH: 15
<212> TYPE: PRT
<213> ORGANISM: Artificial sequence
<220> FEATURE:
<223> OTHER INFORMATION: Peptide derived from HBV X protein

<400> SEQUENCE: 1100

Cys Ala Phe Ser Ser Ala Gly Pro Cys Ala Leu Arg Phe Thr Ser
1               5                   10                  15

<210> SEQ ID NO 1101
<211> LENGTH: 15
<212> TYPE: PRT
<213> ORGANISM: Artificial sequence
<220> FEATURE:
<223> OTHER INFORMATION: Peptide derived from HBV X protein

<400> SEQUENCE: 1101

Ser Ser Ala Gly Pro Cys Ala Leu Arg Phe Thr Ser Ala Arg Arg
1               5                   10                  15

<210> SEQ ID NO 1102
<211> LENGTH: 15
<212> TYPE: PRT
<213> ORGANISM: Artificial sequence
<220> FEATURE:
<223> OTHER INFORMATION: Peptide derived from HBV X protein

<400> SEQUENCE: 1102

Ser Ala Gly Pro Cys Ala Leu Arg Phe Thr Ser Ala Arg Arg Met
1               5                   10                  15

<210> SEQ ID NO 1103
<211> LENGTH: 15
<212> TYPE: PRT
<213> ORGANISM: Artificial sequence
<220> FEATURE:
<223> OTHER INFORMATION: Peptide derived from HBV X protein

<400> SEQUENCE: 1103

Ala Gly Pro Cys Ala Leu Arg Phe Thr Ser Ala Arg Arg Met Glu
1               5                   10                  15

-continued

<210> SEQ ID NO 1104
<211> LENGTH: 15
<212> TYPE: PRT
<213> ORGANISM: Artificial sequence
<220> FEATURE:
<223> OTHER INFORMATION: Peptide derived from HBV X protein

<400> SEQUENCE: 1104

Gly Pro Cys Ala Leu Arg Phe Thr Ser Ala Arg Arg Met Glu Thr
1               5                   10                  15

<210> SEQ ID NO 1105
<211> LENGTH: 15
<212> TYPE: PRT
<213> ORGANISM: Artificial sequence
<220> FEATURE:
<223> OTHER INFORMATION: Peptide derived from HBV X protein

<400> SEQUENCE: 1105

Pro Cys Ala Leu Arg Phe Thr Ser Ala Arg Arg Met Glu Thr Thr
1               5                   10                  15

<210> SEQ ID NO 1106
<211> LENGTH: 15
<212> TYPE: PRT
<213> ORGANISM: Artificial sequence
<220> FEATURE:
<223> OTHER INFORMATION: Peptide derived from HBV X protein

<400> SEQUENCE: 1106

Cys Ala Leu Arg Phe Thr Ser Ala Arg Arg Met Glu Thr Thr Val
1               5                   10                  15

<210> SEQ ID NO 1107
<211> LENGTH: 15
<212> TYPE: PRT
<213> ORGANISM: Artificial sequence
<220> FEATURE:
<223> OTHER INFORMATION: Peptide derived from HBV X protein

<400> SEQUENCE: 1107

Ala Leu Arg Phe Thr Ser Ala Arg Arg Met Glu Thr Thr Val Asn
1               5                   10                  15

<210> SEQ ID NO 1108
<211> LENGTH: 15
<212> TYPE: PRT
<213> ORGANISM: Artificial sequence
<220> FEATURE:
<223> OTHER INFORMATION: Peptide derived from HBV X protein

<400> SEQUENCE: 1108

Leu Arg Phe Thr Ser Ala Arg Arg Met Glu Thr Thr Val Asn Ala
1               5                   10                  15

<210> SEQ ID NO 1109
<211> LENGTH: 15
<212> TYPE: PRT
<213> ORGANISM: Artificial sequence
<220> FEATURE:
<223> OTHER INFORMATION: Peptide derived from HBV X protein

<400> SEQUENCE: 1109

Phe Thr Ser Ala Arg Arg Met Glu Thr Thr Val Asn Ala His Gln
1               5                   10                  15

```
<210> SEQ ID NO 1110
<211> LENGTH: 15
<212> TYPE: PRT
<213> ORGANISM: Artificial sequence
<220> FEATURE:
<223> OTHER INFORMATION: Peptide derived from HBV X protein

<400> SEQUENCE: 1110

Thr Ser Ala Arg Arg Met Glu Thr Thr Val Asn Ala His Gln Ile
1               5                   10                  15

<210> SEQ ID NO 1111
<211> LENGTH: 15
<212> TYPE: PRT
<213> ORGANISM: Artificial sequence
<220> FEATURE:
<223> OTHER INFORMATION: Peptide derived from HBV X protein

<400> SEQUENCE: 1111

Ser Ala Arg Arg Met Glu Thr Thr Val Asn Ala His Gln Ile Leu
1               5                   10                  15

<210> SEQ ID NO 1112
<211> LENGTH: 15
<212> TYPE: PRT
<213> ORGANISM: Artificial sequence
<220> FEATURE:
<223> OTHER INFORMATION: Peptide derived from HBV X protein

<400> SEQUENCE: 1112

Ala Arg Arg Met Glu Thr Thr Val Asn Ala His Gln Ile Leu Pro
1               5                   10                  15

<210> SEQ ID NO 1113
<211> LENGTH: 15
<212> TYPE: PRT
<213> ORGANISM: Artificial sequence
<220> FEATURE:
<223> OTHER INFORMATION: Peptide derived from HBV X protein

<400> SEQUENCE: 1113

Arg Arg Met Glu Thr Thr Val Asn Ala His Gln Ile Leu Pro Lys
1               5                   10                  15

<210> SEQ ID NO 1114
<211> LENGTH: 15
<212> TYPE: PRT
<213> ORGANISM: Artificial sequence
<220> FEATURE:
<223> OTHER INFORMATION: Peptide derived from HBV X protein

<400> SEQUENCE: 1114

Arg Met Glu Thr Thr Val Asn Ala His Gln Ile Leu Pro Lys Val
1               5                   10                  15

<210> SEQ ID NO 1115
<211> LENGTH: 15
<212> TYPE: PRT
<213> ORGANISM: Artificial sequence
<220> FEATURE:
<223> OTHER INFORMATION: Peptide derived from HBV X protein

<400> SEQUENCE: 1115

Thr Thr Val Asn Ala His Gln Ile Leu Pro Lys Val Leu His Lys
1               5                   10                  15

<210> SEQ ID NO 1116
```

```
<211> LENGTH: 15
<212> TYPE: PRT
<213> ORGANISM: Artificial sequence
<220> FEATURE:
<223> OTHER INFORMATION: Peptide derived from HBV X protein

<400> SEQUENCE: 1116

His Gln Ile Leu Pro Lys Val Leu His Lys Arg Thr Leu Gly Leu
1               5                   10                  15

<210> SEQ ID NO 1117
<211> LENGTH: 15
<212> TYPE: PRT
<213> ORGANISM: Artificial sequence
<220> FEATURE:
<223> OTHER INFORMATION: Peptide derived from HBV X protein

<400> SEQUENCE: 1117

Gln Ile Leu Pro Lys Val Leu His Lys Arg Thr Leu Gly Leu Ser
1               5                   10                  15

<210> SEQ ID NO 1118
<211> LENGTH: 15
<212> TYPE: PRT
<213> ORGANISM: Artificial sequence
<220> FEATURE:
<223> OTHER INFORMATION: Peptide derived from HBV X protein

<400> SEQUENCE: 1118

Ile Leu Pro Lys Val Leu His Lys Arg Thr Leu Gly Leu Ser Ala
1               5                   10                  15

<210> SEQ ID NO 1119
<211> LENGTH: 15
<212> TYPE: PRT
<213> ORGANISM: Artificial sequence
<220> FEATURE:
<223> OTHER INFORMATION: Peptide derived from HBV X protein

<400> SEQUENCE: 1119

Leu Pro Lys Val Leu His Lys Arg Thr Leu Gly Leu Ser Ala Met
1               5                   10                  15

<210> SEQ ID NO 1120
<211> LENGTH: 15
<212> TYPE: PRT
<213> ORGANISM: Artificial sequence
<220> FEATURE:
<223> OTHER INFORMATION: Peptide derived from HBV X protein

<400> SEQUENCE: 1120

Pro Lys Val Leu His Lys Arg Thr Leu Gly Leu Ser Ala Met Ser
1               5                   10                  15

<210> SEQ ID NO 1121
<211> LENGTH: 15
<212> TYPE: PRT
<213> ORGANISM: Artificial sequence
<220> FEATURE:
<223> OTHER INFORMATION: Peptide derived from HBV X protein

<400> SEQUENCE: 1121

Lys Val Leu His Lys Arg Thr Leu Gly Leu Ser Ala Met Ser Thr
1               5                   10                  15

<210> SEQ ID NO 1122
<211> LENGTH: 15
```

<212> TYPE: PRT
<213> ORGANISM: Artificial sequence
<220> FEATURE:
<223> OTHER INFORMATION: Peptide derived from HBV X protein

<400> SEQUENCE: 1122

```
Val Leu His Lys Arg Thr Leu Gly Leu Ser Ala Met Ser Thr Thr
1               5                   10                  15
```

<210> SEQ ID NO 1123
<211> LENGTH: 15
<212> TYPE: PRT
<213> ORGANISM: Artificial sequence
<220> FEATURE:
<223> OTHER INFORMATION: Peptide derived from HBV X protein

<400> SEQUENCE: 1123

```
Leu His Lys Arg Thr Leu Gly Leu Ser Ala Met Ser Thr Thr Asp
1               5                   10                  15
```

<210> SEQ ID NO 1124
<211> LENGTH: 15
<212> TYPE: PRT
<213> ORGANISM: Artificial sequence
<220> FEATURE:
<223> OTHER INFORMATION: Peptide derived from HBV X protein

<400> SEQUENCE: 1124

```
His Lys Arg Thr Leu Gly Leu Ser Ala Met Ser Thr Thr Asp Leu
1               5                   10                  15
```

<210> SEQ ID NO 1125
<211> LENGTH: 15
<212> TYPE: PRT
<213> ORGANISM: Artificial sequence
<220> FEATURE:
<223> OTHER INFORMATION: Peptide derived from HBV X protein

<400> SEQUENCE: 1125

```
Lys Arg Thr Leu Gly Leu Ser Ala Met Ser Thr Thr Asp Leu Glu
1               5                   10                  15
```

<210> SEQ ID NO 1126
<211> LENGTH: 15
<212> TYPE: PRT
<213> ORGANISM: Artificial sequence
<220> FEATURE:
<223> OTHER INFORMATION: Peptide derived from HBV X protein

<400> SEQUENCE: 1126

```
Arg Thr Leu Gly Leu Ser Ala Met Ser Thr Thr Asp Leu Glu Ala
1               5                   10                  15
```

<210> SEQ ID NO 1127
<211> LENGTH: 15
<212> TYPE: PRT
<213> ORGANISM: Artificial sequence
<220> FEATURE:
<223> OTHER INFORMATION: Peptide derived from HBV X protein

<400> SEQUENCE: 1127

```
Thr Leu Gly Leu Ser Ala Met Ser Thr Thr Asp Leu Glu Ala Tyr
1               5                   10                  15
```

<210> SEQ ID NO 1128
<211> LENGTH: 15
<212> TYPE: PRT

```
<213> ORGANISM: Artificial sequence
<220> FEATURE:
<223> OTHER INFORMATION: Peptide derived from HBV X protein

<400> SEQUENCE: 1128

Thr Thr Asp Leu Glu Ala Tyr Phe Lys Asp Cys Val Phe Lys Asp
1               5                   10                  15

<210> SEQ ID NO 1129
<211> LENGTH: 15
<212> TYPE: PRT
<213> ORGANISM: Artificial sequence
<220> FEATURE:
<223> OTHER INFORMATION: Peptide derived from HBV X protein

<400> SEQUENCE: 1129

Thr Asp Leu Glu Ala Tyr Phe Lys Asp Cys Val Phe Lys Asp Trp
1               5                   10                  15

<210> SEQ ID NO 1130
<211> LENGTH: 15
<212> TYPE: PRT
<213> ORGANISM: Artificial sequence
<220> FEATURE:
<223> OTHER INFORMATION: Peptide derived from HBV X protein

<400> SEQUENCE: 1130

Leu Glu Ala Tyr Phe Lys Asp Cys Val Phe Lys Asp Trp Glu Glu
1               5                   10                  15

<210> SEQ ID NO 1131
<211> LENGTH: 15
<212> TYPE: PRT
<213> ORGANISM: Artificial sequence
<220> FEATURE:
<223> OTHER INFORMATION: Peptide derived from HBV X protein

<400> SEQUENCE: 1131

Ala Tyr Phe Lys Asp Cys Val Phe Lys Asp Trp Glu Glu Leu Gly
1               5                   10                  15

<210> SEQ ID NO 1132
<211> LENGTH: 15
<212> TYPE: PRT
<213> ORGANISM: Artificial sequence
<220> FEATURE:
<223> OTHER INFORMATION: Peptide derived from HBV X protein

<400> SEQUENCE: 1132

Tyr Phe Lys Asp Cys Val Phe Lys Asp Trp Glu Glu Leu Gly Glu
1               5                   10                  15

<210> SEQ ID NO 1133
<211> LENGTH: 15
<212> TYPE: PRT
<213> ORGANISM: Artificial sequence
<220> FEATURE:
<223> OTHER INFORMATION: Peptide derived from HBV X protein

<400> SEQUENCE: 1133

Asp Trp Glu Glu Leu Gly Glu Glu Ile Arg Leu Lys Val Phe Val
1               5                   10                  15

<210> SEQ ID NO 1134
<211> LENGTH: 15
<212> TYPE: PRT
<213> ORGANISM: Artificial sequence
```

```
<220> FEATURE:
<223> OTHER INFORMATION: Peptide derived from HBV X protein

<400> SEQUENCE: 1134

Trp Glu Glu Leu Gly Glu Glu Ile Arg Leu Lys Val Phe Val Leu
1               5                   10                  15

<210> SEQ ID NO 1135
<211> LENGTH: 15
<212> TYPE: PRT
<213> ORGANISM: Artificial sequence
<220> FEATURE:
<223> OTHER INFORMATION: Peptide derived from HBV X protein

<400> SEQUENCE: 1135

Glu Glu Leu Gly Glu Glu Ile Arg Leu Lys Val Phe Val Leu Gly
1               5                   10                  15

<210> SEQ ID NO 1136
<211> LENGTH: 15
<212> TYPE: PRT
<213> ORGANISM: Artificial sequence
<220> FEATURE:
<223> OTHER INFORMATION: Peptide derived from HBV X protein

<400> SEQUENCE: 1136

Leu Gly Glu Glu Ile Arg Leu Lys Val Phe Val Leu Gly Gly Cys
1               5                   10                  15

<210> SEQ ID NO 1137
<211> LENGTH: 15
<212> TYPE: PRT
<213> ORGANISM: Artificial sequence
<220> FEATURE:
<223> OTHER INFORMATION: Peptide derived from HBV X protein

<400> SEQUENCE: 1137

Gly Glu Glu Ile Arg Leu Lys Val Phe Val Leu Gly Gly Cys Arg
1               5                   10                  15

<210> SEQ ID NO 1138
<211> LENGTH: 15
<212> TYPE: PRT
<213> ORGANISM: Artificial sequence
<220> FEATURE:
<223> OTHER INFORMATION: Peptide derived from HBV X protein

<400> SEQUENCE: 1138

Glu Glu Ile Arg Leu Lys Val Phe Val Leu Gly Gly Cys Arg His
1               5                   10                  15

<210> SEQ ID NO 1139
<211> LENGTH: 15
<212> TYPE: PRT
<213> ORGANISM: Artificial sequence
<220> FEATURE:
<223> OTHER INFORMATION: Peptide derived from HBV X protein

<400> SEQUENCE: 1139

Glu Ile Arg Leu Lys Val Phe Val Leu Gly Gly Cys Arg His Lys
1               5                   10                  15

<210> SEQ ID NO 1140
<211> LENGTH: 15
<212> TYPE: PRT
<213> ORGANISM: Artificial sequence
<220> FEATURE:
```

-continued

<223> OTHER INFORMATION: Peptide derived from HBV X protein

<400> SEQUENCE: 1140

Ile Arg Leu Lys Val Phe Val Leu Gly Gly Cys Arg His Lys Leu
1               5                   10                  15

<210> SEQ ID NO 1141
<211> LENGTH: 400
<212> TYPE: PRT
<213> ORGANISM: Hepatitis B Virus

<400> SEQUENCE: 1141

Met Gly Gly Trp Ser Ser Lys Pro Arg Lys Gly Met Gly Thr Asn Leu
1               5                   10                  15

Ser Val Pro Asn Pro Leu Gly Phe Phe Pro Asp His Gln Leu Asp Pro
                20                  25                  30

Ala Phe Gly Ala Asn Ser Asn Asn Pro Asp Trp Asp Phe Asn Pro Val
            35                  40                  45

Lys Asp Asp Trp Pro Ala Ala Asn Gln Val Gly Val Gly Ala Phe Gly
        50                  55                  60

Pro Arg Leu Thr Pro Pro His Gly Gly Ile Leu Gly Trp Ser Pro Gln
65                  70                  75                  80

Ala Gln Gly Ile Leu Thr Thr Val Ser Thr Ile Pro Pro Pro Ala Ser
                85                  90                  95

Thr Asn Arg Gln Ser Gly Arg Gln Pro Thr Pro Ile Ser Pro Pro Leu
            100                 105                 110

Arg Asp Ser His Pro Gln Ala Met Gln Trp Asn Ser Thr Ala Phe His
        115                 120                 125

Gln Thr Leu Gln Asp Pro Arg Val Arg Gly Leu Tyr Leu Pro Ala Gly
    130                 135                 140

Gly Ser Ser Ser Gly Thr Val Asn Pro Ala Pro Asn Ile Ala Ser His
145                 150                 155                 160

Ile Ser Ser Ile Ser Ala Arg Thr Gly Asp Pro Val Thr Asn Met Glu
                165                 170                 175

Asn Ile Thr Ser Gly Phe Leu Gly Pro Leu Leu Val Leu Gln Ala Gly
            180                 185                 190

Phe Phe Leu Leu Thr Arg Ile Leu Thr Ile Pro Gln Ser Leu Asp Ser
        195                 200                 205

Trp Trp Thr Ser Leu Asn Phe Leu Gly Gly Ser Pro Val Cys Leu Gly
    210                 215                 220

Gln Asn Ser Gln Ser Pro Thr Ser Asn His Ser Pro Thr Ser Cys Pro
225                 230                 235                 240

Pro Ile Cys Pro Gly Tyr Arg Trp Met Cys Leu Arg Arg Phe Ile Ile
                245                 250                 255

Phe Leu Phe Ile Leu Leu Leu Cys Leu Ile Phe Leu Leu Val Leu Leu
            260                 265                 270

Asp Tyr Gln Gly Met Leu Pro Val Cys Pro Leu Ile Pro Gly Ser Thr
        275                 280                 285

Thr Thr Ser Thr Gly Pro Cys Lys Thr Cys Thr Thr Pro Ala Gln Gly
    290                 295                 300

Asn Ser Met Phe Pro Ser Cys Cys Cys Thr Lys Pro Thr Asp Gly Asn
305                 310                 315                 320

Cys Thr Cys Ile Pro Ile Pro Ser Ser Trp Ala Phe Ala Lys Tyr Leu
                325                 330                 335

Trp Glu Trp Ala Ser Val Arg Phe Ser Trp Leu Ser Leu Leu Val Pro

```
                    340                 345                 350
Phe Val Gln Trp Phe Val Gly Leu Ser Pro Thr Val Trp Leu Ser Ala
            355                 360                 365

Ile Trp Met Met Trp Tyr Trp Gly Pro Ser Leu Tyr Ser Ile Val Ser
    370                 375                 380

Pro Phe Ile Pro Leu Leu Pro Ile Phe Phe Cys Leu Trp Val Tyr Ile
385                 390                 395                 400

<210> SEQ ID NO 1142
<211> LENGTH: 36
<212> TYPE: PRT
<213> ORGANISM: Artificial sequence
<220> FEATURE:
<223> OTHER INFORMATION: HBV Large surface protein aa 175 - 210  (SLP
      No. 30)

<400> SEQUENCE: 1142

Met Glu Asn Ile Thr Ser Gly Phe Leu Gly Pro Leu Leu Val Leu Gln
1               5                   10                  15

Ala Gly Phe Phe Leu Leu Thr Arg Ile Leu Thr Ile Pro Gln Ser Leu
            20                  25                  30

Asp Ser Trp Trp
        35

<210> SEQ ID NO 1143
<211> LENGTH: 36
<212> TYPE: PRT
<213> ORGANISM: Artificial sequence
<220> FEATURE:
<223> OTHER INFORMATION: HBV Large surface protein aa 239 - 274  (SLP
      No. 31)

<400> SEQUENCE: 1143

Cys Pro Pro Ile Cys Pro Gly Tyr Arg Trp Met Cys Leu Arg Arg Phe
1               5                   10                  15

Ile Ile Phe Leu Phe Ile Leu Leu Leu Cys Leu Ile Phe Leu Leu Val
            20                  25                  30

Leu Leu Asp Tyr
        35

<210> SEQ ID NO 1144
<211> LENGTH: 36
<212> TYPE: PRT
<213> ORGANISM: Artificial sequence
<220> FEATURE:
<223> OTHER INFORMATION: HBV Large surface protein aa 323 - 358  (SLP
      No. 32)

<400> SEQUENCE: 1144

Cys Ile Pro Ile Pro Ser Ser Trp Ala Phe Ala Lys Tyr Leu Trp Glu
1               5                   10                  15

Trp Ala Ser Val Arg Phe Ser Trp Leu Ser Leu Leu Val Pro Phe Val
            20                  25                  30

Gln Trp Phe Val
        35

<210> SEQ ID NO 1145
<211> LENGTH: 36
<212> TYPE: PRT
<213> ORGANISM: Artificial sequence
<220> FEATURE:
<223> OTHER INFORMATION: HBV Large surface protein aa 365 - 400  (SLP
      No. 33)
```

<400> SEQUENCE: 1145

Trp Leu Ser Ala Ile Trp Met Met Trp Tyr Trp Gly Pro Ser Leu Tyr
1               5                   10                  15

Ser Ile Val Ser Pro Phe Ile Pro Leu Leu Pro Ile Phe Phe Cys Leu
            20                  25                  30

Trp Val Tyr Ile
        35

<210> SEQ ID NO 1146
<211> LENGTH: 8
<212> TYPE: PRT
<213> ORGANISM: Artificial sequence
<220> FEATURE:
<223> OTHER INFORMATION: Peptide derived from HBV Large surface protein

<400> SEQUENCE: 1146

Met Glu Asn Ile Thr Ser Gly Phe
1               5

<210> SEQ ID NO 1147
<211> LENGTH: 9
<212> TYPE: PRT
<213> ORGANISM: Artificial sequence
<220> FEATURE:
<223> OTHER INFORMATION: Peptide derived from HBV Large surface protein

<400> SEQUENCE: 1147

Met Glu Asn Ile Thr Ser Gly Phe Leu
1               5

<210> SEQ ID NO 1148
<211> LENGTH: 10
<212> TYPE: PRT
<213> ORGANISM: Artificial sequence
<220> FEATURE:
<223> OTHER INFORMATION: Peptide derived from HBV Large surface protein

<400> SEQUENCE: 1148

Met Glu Asn Ile Thr Ser Gly Phe Leu Gly
1               5                   10

<210> SEQ ID NO 1149
<211> LENGTH: 11
<212> TYPE: PRT
<213> ORGANISM: Artificial sequence
<220> FEATURE:
<223> OTHER INFORMATION: Peptide derived from HBV Large surface protein

<400> SEQUENCE: 1149

Met Glu Asn Ile Thr Ser Gly Phe Leu Gly Pro
1               5                   10

<210> SEQ ID NO 1150
<211> LENGTH: 12
<212> TYPE: PRT
<213> ORGANISM: Artificial sequence
<220> FEATURE:
<223> OTHER INFORMATION: Peptide derived from HBV Large surface protein

<400> SEQUENCE: 1150

Met Glu Asn Ile Thr Ser Gly Phe Leu Gly Pro Leu
1               5                   10

<210> SEQ ID NO 1151

```
<211> LENGTH: 11
<212> TYPE: PRT
<213> ORGANISM: Artificial sequence
<220> FEATURE:
<223> OTHER INFORMATION: Peptide derived from HBV Large surface protein

<400> SEQUENCE: 1151

Glu Asn Ile Thr Ser Gly Phe Leu Gly Pro Leu
1               5                   10

<210> SEQ ID NO 1152
<211> LENGTH: 13
<212> TYPE: PRT
<213> ORGANISM: Artificial sequence
<220> FEATURE:
<223> OTHER INFORMATION: Peptide derived from HBV Large surface protein

<400> SEQUENCE: 1152

Met Glu Asn Ile Thr Ser Gly Phe Leu Gly Pro Leu Leu
1               5                   10

<210> SEQ ID NO 1153
<211> LENGTH: 10
<212> TYPE: PRT
<213> ORGANISM: Artificial sequence
<220> FEATURE:
<223> OTHER INFORMATION: Peptide derived from HBV Large surface protein

<400> SEQUENCE: 1153

Ile Thr Ser Gly Phe Leu Gly Pro Leu Leu
1               5                   10

<210> SEQ ID NO 1154
<211> LENGTH: 14
<212> TYPE: PRT
<213> ORGANISM: Artificial sequence
<220> FEATURE:
<223> OTHER INFORMATION: Peptide derived from HBV Large surface protein

<400> SEQUENCE: 1154

Met Glu Asn Ile Thr Ser Gly Phe Leu Gly Pro Leu Leu Val
1               5                   10

<210> SEQ ID NO 1155
<211> LENGTH: 12
<212> TYPE: PRT
<213> ORGANISM: Artificial sequence
<220> FEATURE:
<223> OTHER INFORMATION: Peptide derived from HBV Large surface protein

<400> SEQUENCE: 1155

Phe Leu Gly Pro Leu Leu Val Leu Gln Ala Gly Phe
1               5                   10

<210> SEQ ID NO 1156
<211> LENGTH: 8
<212> TYPE: PRT
<213> ORGANISM: Artificial sequence
<220> FEATURE:
<223> OTHER INFORMATION: Peptide derived from HBV Large surface protein

<400> SEQUENCE: 1156

Leu Leu Val Leu Gln Ala Gly Phe
1               5

<210> SEQ ID NO 1157
<211> LENGTH: 8
```

```
<212> TYPE: PRT
<213> ORGANISM: Artificial sequence
<220> FEATURE:
<223> OTHER INFORMATION: Peptide derived from HBV Large surface protein

<400> SEQUENCE: 1157

Leu Val Leu Gln Ala Gly Phe Phe
1               5

<210> SEQ ID NO 1158
<211> LENGTH: 14
<212> TYPE: PRT
<213> ORGANISM: Artificial sequence
<220> FEATURE:
<223> OTHER INFORMATION: Peptide derived from HBV Large surface protein

<400> SEQUENCE: 1158

Phe Leu Gly Pro Leu Leu Val Leu Gln Ala Gly Phe Phe Leu
1               5                   10

<210> SEQ ID NO 1159
<211> LENGTH: 10
<212> TYPE: PRT
<213> ORGANISM: Artificial sequence
<220> FEATURE:
<223> OTHER INFORMATION: Peptide derived from HBV Large surface protein

<400> SEQUENCE: 1159

Leu Leu Val Leu Gln Ala Gly Phe Phe Leu
1               5                   10

<210> SEQ ID NO 1160
<211> LENGTH: 9
<212> TYPE: PRT
<213> ORGANISM: Artificial sequence
<220> FEATURE:
<223> OTHER INFORMATION: Peptide derived from HBV Large surface protein

<400> SEQUENCE: 1160

Leu Val Leu Gln Ala Gly Phe Phe Leu
1               5

<210> SEQ ID NO 1161
<211> LENGTH: 10
<212> TYPE: PRT
<213> ORGANISM: Artificial sequence
<220> FEATURE:
<223> OTHER INFORMATION: Peptide derived from HBV Large surface protein

<400> SEQUENCE: 1161

Leu Val Leu Gln Ala Gly Phe Phe Leu Leu
1               5                   10

<210> SEQ ID NO 1162
<211> LENGTH: 9
<212> TYPE: PRT
<213> ORGANISM: Artificial sequence
<220> FEATURE:
<223> OTHER INFORMATION: Peptide derived from HBV Large surface protein

<400> SEQUENCE: 1162

Val Leu Gln Ala Gly Phe Phe Leu Leu
1               5

<210> SEQ ID NO 1163
<211> LENGTH: 8
<212> TYPE: PRT
```

```
<213> ORGANISM: Artificial sequence
<220> FEATURE:
<223> OTHER INFORMATION: Peptide derived from HBV Large surface protein

<400> SEQUENCE: 1163

Leu Gln Ala Gly Phe Phe Leu Leu
1               5

<210> SEQ ID NO 1164
<211> LENGTH: 12
<212> TYPE: PRT
<213> ORGANISM: Artificial sequence
<220> FEATURE:
<223> OTHER INFORMATION: Peptide derived from HBV Large surface protein

<400> SEQUENCE: 1164

Leu Val Leu Gln Ala Gly Phe Phe Leu Leu Thr Arg
1               5                   10

<210> SEQ ID NO 1165
<211> LENGTH: 11
<212> TYPE: PRT
<213> ORGANISM: Artificial sequence
<220> FEATURE:
<223> OTHER INFORMATION: Peptide derived from HBV Large surface protein

<400> SEQUENCE: 1165

Val Leu Gln Ala Gly Phe Phe Leu Leu Thr Arg
1               5                   10

<210> SEQ ID NO 1166
<211> LENGTH: 10
<212> TYPE: PRT
<213> ORGANISM: Artificial sequence
<220> FEATURE:
<223> OTHER INFORMATION: Peptide derived from HBV Large surface protein

<400> SEQUENCE: 1166

Leu Gln Ala Gly Phe Phe Leu Leu Thr Arg
1               5                   10

<210> SEQ ID NO 1167
<211> LENGTH: 9
<212> TYPE: PRT
<213> ORGANISM: Artificial sequence
<220> FEATURE:
<223> OTHER INFORMATION: Peptide derived from HBV Large surface protein

<400> SEQUENCE: 1167

Gln Ala Gly Phe Phe Leu Leu Thr Arg
1               5

<210> SEQ ID NO 1168
<211> LENGTH: 8
<212> TYPE: PRT
<213> ORGANISM: Artificial sequence
<220> FEATURE:
<223> OTHER INFORMATION: Peptide derived from HBV Large surface protein

<400> SEQUENCE: 1168

Ala Gly Phe Phe Leu Leu Thr Arg
1               5

<210> SEQ ID NO 1169
<211> LENGTH: 11
<212> TYPE: PRT
<213> ORGANISM: Artificial sequence
```

<220> FEATURE:
<223> OTHER INFORMATION: Peptide derived from HBV Large surface protein

<400> SEQUENCE: 1169

Leu Gln Ala Gly Phe Phe Leu Leu Thr Arg Ile
1               5                   10

<210> SEQ ID NO 1170
<211> LENGTH: 12
<212> TYPE: PRT
<213> ORGANISM: Artificial sequence
<220> FEATURE:
<223> OTHER INFORMATION: Peptide derived from HBV Large surface protein

<400> SEQUENCE: 1170

Leu Gln Ala Gly Phe Phe Leu Leu Thr Arg Ile Leu
1               5                   10

<210> SEQ ID NO 1171
<211> LENGTH: 14
<212> TYPE: PRT
<213> ORGANISM: Artificial sequence
<220> FEATURE:
<223> OTHER INFORMATION: Peptide derived from HBV Large surface protein

<400> SEQUENCE: 1171

Leu Gln Ala Gly Phe Phe Leu Leu Thr Arg Ile Leu Thr Ile
1               5                   10

<210> SEQ ID NO 1172
<211> LENGTH: 12
<212> TYPE: PRT
<213> ORGANISM: Artificial sequence
<220> FEATURE:
<223> OTHER INFORMATION: Peptide derived from HBV Large surface protein

<400> SEQUENCE: 1172

Ala Gly Phe Phe Leu Leu Thr Arg Ile Leu Thr Ile
1               5                   10

<210> SEQ ID NO 1173
<211> LENGTH: 9
<212> TYPE: PRT
<213> ORGANISM: Artificial sequence
<220> FEATURE:
<223> OTHER INFORMATION: Peptide derived from HBV Large surface protein

<400> SEQUENCE: 1173

Phe Leu Leu Thr Arg Ile Leu Thr Ile
1               5

<210> SEQ ID NO 1174
<211> LENGTH: 13
<212> TYPE: PRT
<213> ORGANISM: Artificial sequence
<220> FEATURE:
<223> OTHER INFORMATION: Peptide derived from HBV Large surface protein

<400> SEQUENCE: 1174

Phe Leu Leu Thr Arg Ile Leu Thr Ile Pro Gln Ser Leu
1               5                   10

<210> SEQ ID NO 1175
<211> LENGTH: 12
<212> TYPE: PRT
<213> ORGANISM: Artificial sequence
<220> FEATURE:

<223> OTHER INFORMATION: Peptide derived from HBV Large surface protein

<400> SEQUENCE: 1175

Leu Leu Thr Arg Ile Leu Thr Ile Pro Gln Ser Leu
1               5                   10

<210> SEQ ID NO 1176
<211> LENGTH: 11
<212> TYPE: PRT
<213> ORGANISM: Artificial sequence
<220> FEATURE:
<223> OTHER INFORMATION: Peptide derived from HBV Large surface protein

<400> SEQUENCE: 1176

Leu Thr Arg Ile Leu Thr Ile Pro Gln Ser Leu
1               5                   10

<210> SEQ ID NO 1177
<211> LENGTH: 10
<212> TYPE: PRT
<213> ORGANISM: Artificial sequence
<220> FEATURE:
<223> OTHER INFORMATION: Peptide derived from HBV Large surface protein

<400> SEQUENCE: 1177

Thr Arg Ile Leu Thr Ile Pro Gln Ser Leu
1               5                   10

<210> SEQ ID NO 1178
<211> LENGTH: 14
<212> TYPE: PRT
<213> ORGANISM: Artificial sequence
<220> FEATURE:
<223> OTHER INFORMATION: Peptide derived from HBV Large surface protein

<400> SEQUENCE: 1178

Leu Thr Arg Ile Leu Thr Ile Pro Gln Ser Leu Asp Ser Trp
1               5                   10

<210> SEQ ID NO 1179
<211> LENGTH: 12
<212> TYPE: PRT
<213> ORGANISM: Artificial sequence
<220> FEATURE:
<223> OTHER INFORMATION: Peptide derived from HBV Large surface protein

<400> SEQUENCE: 1179

Arg Ile Leu Thr Ile Pro Gln Ser Leu Asp Ser Trp
1               5                   10

<210> SEQ ID NO 1180
<211> LENGTH: 10
<212> TYPE: PRT
<213> ORGANISM: Artificial sequence
<220> FEATURE:
<223> OTHER INFORMATION: Peptide derived from HBV Large surface protein

<400> SEQUENCE: 1180

Leu Thr Ile Pro Gln Ser Leu Asp Ser Trp
1               5                   10

<210> SEQ ID NO 1181
<211> LENGTH: 14
<212> TYPE: PRT
<213> ORGANISM: Artificial sequence
<220> FEATURE:
<223> OTHER INFORMATION: Peptide derived from HBV Large surface protein

<400> SEQUENCE: 1181

Thr Arg Ile Leu Thr Ile Pro Gln Ser Leu Asp Ser Trp Trp
1               5                   10

<210> SEQ ID NO 1182
<211> LENGTH: 13
<212> TYPE: PRT
<213> ORGANISM: Artificial sequence
<220> FEATURE:
<223> OTHER INFORMATION: Peptide derived from HBV Large surface protein

<400> SEQUENCE: 1182

Arg Ile Leu Thr Ile Pro Gln Ser Leu Asp Ser Trp Trp
1               5                   10

<210> SEQ ID NO 1183
<211> LENGTH: 11
<212> TYPE: PRT
<213> ORGANISM: Artificial sequence
<220> FEATURE:
<223> OTHER INFORMATION: Peptide derived from HBV Large surface protein

<400> SEQUENCE: 1183

Leu Thr Ile Pro Gln Ser Leu Asp Ser Trp Trp
1               5                   10

<210> SEQ ID NO 1184
<211> LENGTH: 9
<212> TYPE: PRT
<213> ORGANISM: Artificial sequence
<220> FEATURE:
<223> OTHER INFORMATION: Peptide derived from HBV Large surface protein

<400> SEQUENCE: 1184

Ile Pro Gln Ser Leu Asp Ser Trp Trp
1               5

<210> SEQ ID NO 1185
<211> LENGTH: 8
<212> TYPE: PRT
<213> ORGANISM: Artificial sequence
<220> FEATURE:
<223> OTHER INFORMATION: Peptide derived from HBV Large surface protein

<400> SEQUENCE: 1185

Cys Pro Pro Ile Cys Pro Gly Tyr
1               5

<210> SEQ ID NO 1186
<211> LENGTH: 10
<212> TYPE: PRT
<213> ORGANISM: Artificial sequence
<220> FEATURE:
<223> OTHER INFORMATION: Peptide derived from HBV Large surface protein

<400> SEQUENCE: 1186

Cys Pro Pro Ile Cys Pro Gly Tyr Arg Trp
1               5                   10

<210> SEQ ID NO 1187
<211> LENGTH: 12
<212> TYPE: PRT
<213> ORGANISM: Artificial sequence
<220> FEATURE:
<223> OTHER INFORMATION: Peptide derived from HBV Large surface protein

```
<400> SEQUENCE: 1187

Pro Pro Ile Cys Pro Gly Tyr Arg Trp Met Cys Leu
1               5                   10

<210> SEQ ID NO 1188
<211> LENGTH: 9
<212> TYPE: PRT
<213> ORGANISM: Artificial sequence
<220> FEATURE:
<223> OTHER INFORMATION: Peptide derived from HBV Large surface protein

<400> SEQUENCE: 1188

Cys Pro Gly Tyr Arg Trp Met Cys Leu
1               5

<210> SEQ ID NO 1189
<211> LENGTH: 10
<212> TYPE: PRT
<213> ORGANISM: Artificial sequence
<220> FEATURE:
<223> OTHER INFORMATION: Peptide derived from HBV Large surface protein

<400> SEQUENCE: 1189

Cys Pro Gly Tyr Arg Trp Met Cys Leu Arg
1               5                   10

<210> SEQ ID NO 1190
<211> LENGTH: 9
<212> TYPE: PRT
<213> ORGANISM: Artificial sequence
<220> FEATURE:
<223> OTHER INFORMATION: Peptide derived from HBV Large surface protein

<400> SEQUENCE: 1190

Pro Gly Tyr Arg Trp Met Cys Leu Arg
1               5

<210> SEQ ID NO 1191
<211> LENGTH: 8
<212> TYPE: PRT
<213> ORGANISM: Artificial sequence
<220> FEATURE:
<223> OTHER INFORMATION: Peptide derived from HBV Large surface protein

<400> SEQUENCE: 1191

Gly Tyr Arg Trp Met Cys Leu Arg
1               5

<210> SEQ ID NO 1192
<211> LENGTH: 9
<212> TYPE: PRT
<213> ORGANISM: Artificial sequence
<220> FEATURE:
<223> OTHER INFORMATION: Peptide derived from HBV Large surface protein

<400> SEQUENCE: 1192

Gly Tyr Arg Trp Met Cys Leu Arg Arg
1               5

<210> SEQ ID NO 1193
<211> LENGTH: 10
<212> TYPE: PRT
<213> ORGANISM: Artificial sequence
<220> FEATURE:
<223> OTHER INFORMATION: Peptide derived from HBV Large surface protein

<400> SEQUENCE: 1193
```

```
Gly Tyr Arg Trp Met Cys Leu Arg Arg Phe
1               5                   10

<210> SEQ ID NO 1194
<211> LENGTH: 9
<212> TYPE: PRT
<213> ORGANISM: Artificial sequence
<220> FEATURE:
<223> OTHER INFORMATION: Peptide derived from HBV Large surface protein

<400> SEQUENCE: 1194

Tyr Arg Trp Met Cys Leu Arg Arg Phe
1               5

<210> SEQ ID NO 1195
<211> LENGTH: 11
<212> TYPE: PRT
<213> ORGANISM: Artificial sequence
<220> FEATURE:
<223> OTHER INFORMATION: Peptide derived from HBV Large surface protein

<400> SEQUENCE: 1195

Gly Tyr Arg Trp Met Cys Leu Arg Arg Phe Ile
1               5                   10

<210> SEQ ID NO 1196
<211> LENGTH: 10
<212> TYPE: PRT
<213> ORGANISM: Artificial sequence
<220> FEATURE:
<223> OTHER INFORMATION: Peptide derived from HBV Large surface protein

<400> SEQUENCE: 1196

Tyr Arg Trp Met Cys Leu Arg Arg Phe Ile
1               5                   10

<210> SEQ ID NO 1197
<211> LENGTH: 14
<212> TYPE: PRT
<213> ORGANISM: Artificial sequence
<220> FEATURE:
<223> OTHER INFORMATION: Peptide derived from HBV Large surface protein

<400> SEQUENCE: 1197

Cys Pro Gly Tyr Arg Trp Met Cys Leu Arg Arg Phe Ile Ile
1               5                   10

<210> SEQ ID NO 1198
<211> LENGTH: 11
<212> TYPE: PRT
<213> ORGANISM: Artificial sequence
<220> FEATURE:
<223> OTHER INFORMATION: Peptide derived from HBV Large surface protein

<400> SEQUENCE: 1198

Tyr Arg Trp Met Cys Leu Arg Arg Phe Ile Ile
1               5                   10

<210> SEQ ID NO 1199
<211> LENGTH: 10
<212> TYPE: PRT
<213> ORGANISM: Artificial sequence
<220> FEATURE:
<223> OTHER INFORMATION: Peptide derived from HBV Large surface protein

<400> SEQUENCE: 1199
```

Arg Trp Met Cys Leu Arg Arg Phe Ile Ile
1               5                   10

<210> SEQ ID NO 1200
<211> LENGTH: 13
<212> TYPE: PRT
<213> ORGANISM: Artificial sequence
<220> FEATURE:
<223> OTHER INFORMATION: Peptide derived from HBV Large surface protein

<400> SEQUENCE: 1200

Gly Tyr Arg Trp Met Cys Leu Arg Arg Phe Ile Ile Phe
1               5                   10

<210> SEQ ID NO 1201
<211> LENGTH: 12
<212> TYPE: PRT
<213> ORGANISM: Artificial sequence
<220> FEATURE:
<223> OTHER INFORMATION: Peptide derived from HBV Large surface protein

<400> SEQUENCE: 1201

Tyr Arg Trp Met Cys Leu Arg Arg Phe Ile Ile Phe
1               5                   10

<210> SEQ ID NO 1202
<211> LENGTH: 11
<212> TYPE: PRT
<213> ORGANISM: Artificial sequence
<220> FEATURE:
<223> OTHER INFORMATION: Peptide derived from HBV Large surface protein

<400> SEQUENCE: 1202

Arg Trp Met Cys Leu Arg Arg Phe Ile Ile Phe
1               5                   10

<210> SEQ ID NO 1203
<211> LENGTH: 9
<212> TYPE: PRT
<213> ORGANISM: Artificial sequence
<220> FEATURE:
<223> OTHER INFORMATION: Peptide derived from HBV Large surface protein

<400> SEQUENCE: 1203

Met Cys Leu Arg Arg Phe Ile Ile Phe
1               5

<210> SEQ ID NO 1204
<211> LENGTH: 14
<212> TYPE: PRT
<213> ORGANISM: Artificial sequence
<220> FEATURE:
<223> OTHER INFORMATION: Peptide derived from HBV Large surface protein

<400> SEQUENCE: 1204

Gly Tyr Arg Trp Met Cys Leu Arg Arg Phe Ile Ile Phe Leu
1               5                   10

<210> SEQ ID NO 1205
<211> LENGTH: 13
<212> TYPE: PRT
<213> ORGANISM: Artificial sequence
<220> FEATURE:
<223> OTHER INFORMATION: Peptide derived from HBV Large surface protein

<400> SEQUENCE: 1205

Tyr Arg Trp Met Cys Leu Arg Arg Phe Ile Ile Phe Leu

```
1               5                   10
```

<210> SEQ ID NO 1206
<211> LENGTH: 10
<212> TYPE: PRT
<213> ORGANISM: Artificial sequence
<220> FEATURE:
<223> OTHER INFORMATION: Peptide derived from HBV Large surface protein

<400> SEQUENCE: 1206

```
Met Cys Leu Arg Arg Phe Ile Ile Phe Leu
1               5                   10
```

<210> SEQ ID NO 1207
<211> LENGTH: 8
<212> TYPE: PRT
<213> ORGANISM: Artificial sequence
<220> FEATURE:
<223> OTHER INFORMATION: Peptide derived from HBV Large surface protein

<400> SEQUENCE: 1207

```
Leu Arg Arg Phe Ile Ile Phe Leu
1               5
```

<210> SEQ ID NO 1208
<211> LENGTH: 14
<212> TYPE: PRT
<213> ORGANISM: Artificial sequence
<220> FEATURE:
<223> OTHER INFORMATION: Peptide derived from HBV Large surface protein

<400> SEQUENCE: 1208

```
Tyr Arg Trp Met Cys Leu Arg Arg Phe Ile Ile Phe Leu Phe
1               5                   10
```

<210> SEQ ID NO 1209
<211> LENGTH: 13
<212> TYPE: PRT
<213> ORGANISM: Artificial sequence
<220> FEATURE:
<223> OTHER INFORMATION: Peptide derived from HBV Large surface protein

<400> SEQUENCE: 1209

```
Arg Trp Met Cys Leu Arg Arg Phe Ile Ile Phe Leu Phe
1               5                   10
```

<210> SEQ ID NO 1210
<211> LENGTH: 11
<212> TYPE: PRT
<213> ORGANISM: Artificial sequence
<220> FEATURE:
<223> OTHER INFORMATION: Peptide derived from HBV Large surface protein

<400> SEQUENCE: 1210

```
Met Cys Leu Arg Arg Phe Ile Ile Phe Leu Phe
1               5                   10
```

<210> SEQ ID NO 1211
<211> LENGTH: 9
<212> TYPE: PRT
<213> ORGANISM: Artificial sequence
<220> FEATURE:
<223> OTHER INFORMATION: Peptide derived from HBV Large surface protein

<400> SEQUENCE: 1211

```
Leu Arg Arg Phe Ile Ile Phe Leu Phe
1               5
```

<210> SEQ ID NO 1212
<211> LENGTH: 8
<212> TYPE: PRT
<213> ORGANISM: Artificial sequence
<220> FEATURE:
<223> OTHER INFORMATION: Peptide derived from HBV Large surface protein

<400> SEQUENCE: 1212

Arg Arg Phe Ile Ile Phe Leu Phe
1               5

<210> SEQ ID NO 1213
<211> LENGTH: 14
<212> TYPE: PRT
<213> ORGANISM: Artificial sequence
<220> FEATURE:
<223> OTHER INFORMATION: Peptide derived from HBV Large surface protein

<400> SEQUENCE: 1213

Arg Trp Met Cys Leu Arg Arg Phe Ile Ile Phe Leu Phe Ile
1               5                   10

<210> SEQ ID NO 1214
<211> LENGTH: 13
<212> TYPE: PRT
<213> ORGANISM: Artificial sequence
<220> FEATURE:
<223> OTHER INFORMATION: Peptide derived from HBV Large surface protein

<400> SEQUENCE: 1214

Trp Met Cys Leu Arg Arg Phe Ile Ile Phe Leu Phe Ile
1               5                   10

<210> SEQ ID NO 1215
<211> LENGTH: 12
<212> TYPE: PRT
<213> ORGANISM: Artificial sequence
<220> FEATURE:
<223> OTHER INFORMATION: Peptide derived from HBV Large surface protein

<400> SEQUENCE: 1215

Met Cys Leu Arg Arg Phe Ile Ile Phe Leu Phe Ile
1               5                   10

<210> SEQ ID NO 1216
<211> LENGTH: 11
<212> TYPE: PRT
<213> ORGANISM: Artificial sequence
<220> FEATURE:
<223> OTHER INFORMATION: Peptide derived from HBV Large surface protein

<400> SEQUENCE: 1216

Cys Leu Arg Arg Phe Ile Ile Phe Leu Phe Ile
1               5                   10

<210> SEQ ID NO 1217
<211> LENGTH: 10
<212> TYPE: PRT
<213> ORGANISM: Artificial sequence
<220> FEATURE:
<223> OTHER INFORMATION: Peptide derived from HBV Large surface protein

<400> SEQUENCE: 1217

Leu Arg Arg Phe Ile Ile Phe Leu Phe Ile
1               5                   10

```
<210> SEQ ID NO 1218
<211> LENGTH: 9
<212> TYPE: PRT
<213> ORGANISM: Artificial sequence
<220> FEATURE:
<223> OTHER INFORMATION: Peptide derived from HBV Large surface protein

<400> SEQUENCE: 1218

Arg Arg Phe Ile Ile Phe Leu Phe Ile
1               5

<210> SEQ ID NO 1219
<211> LENGTH: 14
<212> TYPE: PRT
<213> ORGANISM: Artificial sequence
<220> FEATURE:
<223> OTHER INFORMATION: Peptide derived from HBV Large surface protein

<400> SEQUENCE: 1219

Trp Met Cys Leu Arg Arg Phe Ile Ile Phe Leu Phe Ile Leu
1               5                   10

<210> SEQ ID NO 1220
<211> LENGTH: 13
<212> TYPE: PRT
<213> ORGANISM: Artificial sequence
<220> FEATURE:
<223> OTHER INFORMATION: Peptide derived from HBV Large surface protein

<400> SEQUENCE: 1220

Met Cys Leu Arg Arg Phe Ile Ile Phe Leu Phe Ile Leu
1               5                   10

<210> SEQ ID NO 1221
<211> LENGTH: 12
<212> TYPE: PRT
<213> ORGANISM: Artificial sequence
<220> FEATURE:
<223> OTHER INFORMATION: Peptide derived from HBV Large surface protein

<400> SEQUENCE: 1221

Cys Leu Arg Arg Phe Ile Ile Phe Leu Phe Ile Leu
1               5                   10

<210> SEQ ID NO 1222
<211> LENGTH: 11
<212> TYPE: PRT
<213> ORGANISM: Artificial sequence
<220> FEATURE:
<223> OTHER INFORMATION: Peptide derived from HBV Large surface protein

<400> SEQUENCE: 1222

Leu Arg Arg Phe Ile Ile Phe Leu Phe Ile Leu
1               5                   10

<210> SEQ ID NO 1223
<211> LENGTH: 10
<212> TYPE: PRT
<213> ORGANISM: Artificial sequence
<220> FEATURE:
<223> OTHER INFORMATION: Peptide derived from HBV Large surface protein

<400> SEQUENCE: 1223

Arg Arg Phe Ile Ile Phe Leu Phe Ile Leu
1               5                   10
```

```
<210> SEQ ID NO 1224
<211> LENGTH: 9
<212> TYPE: PRT
<213> ORGANISM: Artificial sequence
<220> FEATURE:
<223> OTHER INFORMATION: Peptide derived from HBV Large surface protein

<400> SEQUENCE: 1224

Arg Phe Ile Ile Phe Leu Phe Ile Leu
1               5

<210> SEQ ID NO 1225
<211> LENGTH: 8
<212> TYPE: PRT
<213> ORGANISM: Artificial sequence
<220> FEATURE:
<223> OTHER INFORMATION: Peptide derived from HBV Large surface protein

<400> SEQUENCE: 1225

Phe Ile Ile Phe Leu Phe Ile Leu
1               5

<210> SEQ ID NO 1226
<211> LENGTH: 14
<212> TYPE: PRT
<213> ORGANISM: Artificial sequence
<220> FEATURE:
<223> OTHER INFORMATION: Peptide derived from HBV Large surface protein

<400> SEQUENCE: 1226

Met Cys Leu Arg Arg Phe Ile Ile Phe Leu Phe Ile Leu Leu
1               5                   10

<210> SEQ ID NO 1227
<211> LENGTH: 13
<212> TYPE: PRT
<213> ORGANISM: Artificial sequence
<220> FEATURE:
<223> OTHER INFORMATION: Peptide derived from HBV Large surface protein

<400> SEQUENCE: 1227

Cys Leu Arg Arg Phe Ile Ile Phe Leu Phe Ile Leu Leu
1               5                   10

<210> SEQ ID NO 1228
<211> LENGTH: 12
<212> TYPE: PRT
<213> ORGANISM: Artificial sequence
<220> FEATURE:
<223> OTHER INFORMATION: Peptide derived from HBV Large surface protein

<400> SEQUENCE: 1228

Leu Arg Arg Phe Ile Ile Phe Leu Phe Ile Leu Leu
1               5                   10

<210> SEQ ID NO 1229
<211> LENGTH: 11
<212> TYPE: PRT
<213> ORGANISM: Artificial sequence
<220> FEATURE:
<223> OTHER INFORMATION: Peptide derived from HBV Large surface protein

<400> SEQUENCE: 1229

Arg Arg Phe Ile Ile Phe Leu Phe Ile Leu Leu
1               5                   10

<210> SEQ ID NO 1230
```

```
<211> LENGTH: 10
<212> TYPE: PRT
<213> ORGANISM: Artificial sequence
<220> FEATURE:
<223> OTHER INFORMATION: Peptide derived from HBV Large surface protein

<400> SEQUENCE: 1230

Arg Phe Ile Ile Phe Leu Phe Ile Leu Leu
1               5                   10

<210> SEQ ID NO 1231
<211> LENGTH: 9
<212> TYPE: PRT
<213> ORGANISM: Artificial sequence
<220> FEATURE:
<223> OTHER INFORMATION: Peptide derived from HBV Large surface protein

<400> SEQUENCE: 1231

Phe Ile Ile Phe Leu Phe Ile Leu Leu
1               5

<210> SEQ ID NO 1232
<211> LENGTH: 13
<212> TYPE: PRT
<213> ORGANISM: Artificial sequence
<220> FEATURE:
<223> OTHER INFORMATION: Peptide derived from HBV Large surface protein

<400> SEQUENCE: 1232

Leu Arg Arg Phe Ile Ile Phe Leu Phe Ile Leu Leu Leu
1               5                   10

<210> SEQ ID NO 1233
<211> LENGTH: 12
<212> TYPE: PRT
<213> ORGANISM: Artificial sequence
<220> FEATURE:
<223> OTHER INFORMATION: Peptide derived from HBV Large surface protein

<400> SEQUENCE: 1233

Arg Arg Phe Ile Ile Phe Leu Phe Ile Leu Leu Leu
1               5                   10

<210> SEQ ID NO 1234
<211> LENGTH: 10
<212> TYPE: PRT
<213> ORGANISM: Artificial sequence
<220> FEATURE:
<223> OTHER INFORMATION: Peptide derived from HBV Large surface protein

<400> SEQUENCE: 1234

Phe Ile Ile Phe Leu Phe Ile Leu Leu Leu
1               5                   10

<210> SEQ ID NO 1235
<211> LENGTH: 13
<212> TYPE: PRT
<213> ORGANISM: Artificial sequence
<220> FEATURE:
<223> OTHER INFORMATION: Peptide derived from HBV Large surface protein

<400> SEQUENCE: 1235

Arg Arg Phe Ile Ile Phe Leu Phe Ile Leu Leu Leu Cys
1               5                   10

<210> SEQ ID NO 1236
<211> LENGTH: 14
```

```
<212> TYPE: PRT
<213> ORGANISM: Artificial sequence
<220> FEATURE:
<223> OTHER INFORMATION: Peptide derived from HBV Large surface protein

<400> SEQUENCE: 1236

Arg Arg Phe Ile Ile Phe Leu Phe Ile Leu Leu Leu Cys Leu
1               5                   10

<210> SEQ ID NO 1237
<211> LENGTH: 9
<212> TYPE: PRT
<213> ORGANISM: Artificial sequence
<220> FEATURE:
<223> OTHER INFORMATION: Peptide derived from HBV Large surface protein

<400> SEQUENCE: 1237

Phe Leu Phe Ile Leu Leu Leu Cys Leu
1               5

<210> SEQ ID NO 1238
<211> LENGTH: 13
<212> TYPE: PRT
<213> ORGANISM: Artificial sequence
<220> FEATURE:
<223> OTHER INFORMATION: Peptide derived from HBV Large surface protein

<400> SEQUENCE: 1238

Phe Ile Ile Phe Leu Phe Ile Leu Leu Leu Cys Leu Ile
1               5                   10

<210> SEQ ID NO 1239
<211> LENGTH: 10
<212> TYPE: PRT
<213> ORGANISM: Artificial sequence
<220> FEATURE:
<223> OTHER INFORMATION: Peptide derived from HBV Large surface protein

<400> SEQUENCE: 1239

Phe Leu Phe Ile Leu Leu Leu Cys Leu Ile
1               5                   10

<210> SEQ ID NO 1240
<211> LENGTH: 14
<212> TYPE: PRT
<213> ORGANISM: Artificial sequence
<220> FEATURE:
<223> OTHER INFORMATION: Peptide derived from HBV Large surface protein

<400> SEQUENCE: 1240

Phe Ile Ile Phe Leu Phe Ile Leu Leu Leu Cys Leu Ile Phe
1               5                   10

<210> SEQ ID NO 1241
<211> LENGTH: 13
<212> TYPE: PRT
<213> ORGANISM: Artificial sequence
<220> FEATURE:
<223> OTHER INFORMATION: Peptide derived from HBV Large surface protein

<400> SEQUENCE: 1241

Ile Ile Phe Leu Phe Ile Leu Leu Leu Cys Leu Ile Phe
1               5                   10

<210> SEQ ID NO 1242
<211> LENGTH: 12
<212> TYPE: PRT
```

```
<213> ORGANISM: Artificial sequence
<220> FEATURE:
<223> OTHER INFORMATION: Peptide derived from HBV Large surface protein

<400> SEQUENCE: 1242

Ile Phe Leu Phe Ile Leu Leu Leu Cys Leu Ile Phe
1               5                   10

<210> SEQ ID NO 1243
<211> LENGTH: 11
<212> TYPE: PRT
<213> ORGANISM: Artificial sequence
<220> FEATURE:
<223> OTHER INFORMATION: Peptide derived from HBV Large surface protein

<400> SEQUENCE: 1243

Phe Leu Phe Ile Leu Leu Leu Cys Leu Ile Phe
1               5                   10

<210> SEQ ID NO 1244
<211> LENGTH: 10
<212> TYPE: PRT
<213> ORGANISM: Artificial sequence
<220> FEATURE:
<223> OTHER INFORMATION: Peptide derived from HBV Large surface protein

<400> SEQUENCE: 1244

Leu Phe Ile Leu Leu Leu Cys Leu Ile Phe
1               5                   10

<210> SEQ ID NO 1245
<211> LENGTH: 13
<212> TYPE: PRT
<213> ORGANISM: Artificial sequence
<220> FEATURE:
<223> OTHER INFORMATION: Peptide derived from HBV Large surface protein

<400> SEQUENCE: 1245

Ile Phe Leu Phe Ile Leu Leu Leu Cys Leu Ile Phe Leu
1               5                   10

<210> SEQ ID NO 1246
<211> LENGTH: 12
<212> TYPE: PRT
<213> ORGANISM: Artificial sequence
<220> FEATURE:
<223> OTHER INFORMATION: Peptide derived from HBV Large surface protein

<400> SEQUENCE: 1246

Phe Leu Phe Ile Leu Leu Leu Cys Leu Ile Phe Leu
1               5                   10

<210> SEQ ID NO 1247
<211> LENGTH: 10
<212> TYPE: PRT
<213> ORGANISM: Artificial sequence
<220> FEATURE:
<223> OTHER INFORMATION: Peptide derived from HBV Large surface protein

<400> SEQUENCE: 1247

Phe Ile Leu Leu Leu Cys Leu Ile Phe Leu
1               5                   10

<210> SEQ ID NO 1248
<211> LENGTH: 9
<212> TYPE: PRT
<213> ORGANISM: Artificial sequence
```

```
<220> FEATURE:
<223> OTHER INFORMATION: Peptide derived from HBV Large surface protein

<400> SEQUENCE: 1248

Ile Leu Leu Leu Cys Leu Ile Phe Leu
1               5

<210> SEQ ID NO 1249
<211> LENGTH: 14
<212> TYPE: PRT
<213> ORGANISM: Artificial sequence
<220> FEATURE:
<223> OTHER INFORMATION: Peptide derived from HBV Large surface protein

<400> SEQUENCE: 1249

Ile Phe Leu Phe Ile Leu Leu Leu Cys Leu Ile Phe Leu Leu
1               5                   10

<210> SEQ ID NO 1250
<211> LENGTH: 13
<212> TYPE: PRT
<213> ORGANISM: Artificial sequence
<220> FEATURE:
<223> OTHER INFORMATION: Peptide derived from HBV Large surface protein

<400> SEQUENCE: 1250

Phe Leu Phe Ile Leu Leu Leu Cys Leu Ile Phe Leu Leu
1               5                   10

<210> SEQ ID NO 1251
<211> LENGTH: 10
<212> TYPE: PRT
<213> ORGANISM: Artificial sequence
<220> FEATURE:
<223> OTHER INFORMATION: Peptide derived from HBV Large surface protein

<400> SEQUENCE: 1251

Ile Leu Leu Leu Cys Leu Ile Phe Leu Leu
1               5                   10

<210> SEQ ID NO 1252
<211> LENGTH: 9
<212> TYPE: PRT
<213> ORGANISM: Artificial sequence
<220> FEATURE:
<223> OTHER INFORMATION: Peptide derived from HBV Large surface protein

<400> SEQUENCE: 1252

Leu Leu Leu Cys Leu Ile Phe Leu Leu
1               5

<210> SEQ ID NO 1253
<211> LENGTH: 12
<212> TYPE: PRT
<213> ORGANISM: Artificial sequence
<220> FEATURE:
<223> OTHER INFORMATION: Peptide derived from HBV Large surface protein

<400> SEQUENCE: 1253

Phe Ile Leu Leu Leu Cys Leu Ile Phe Leu Leu Val
1               5                   10

<210> SEQ ID NO 1254
<211> LENGTH: 11
<212> TYPE: PRT
<213> ORGANISM: Artificial sequence
<220> FEATURE:
```

<223> OTHER INFORMATION: Peptide derived from HBV Large surface protein

<400> SEQUENCE: 1254

Ile Leu Leu Leu Cys Leu Ile Phe Leu Leu Val
1               5                   10

<210> SEQ ID NO 1255
<211> LENGTH: 10
<212> TYPE: PRT
<213> ORGANISM: Artificial sequence
<220> FEATURE:
<223> OTHER INFORMATION: Peptide derived from HBV Large surface protein

<400> SEQUENCE: 1255

Leu Leu Leu Cys Leu Ile Phe Leu Leu Val
1               5                   10

<210> SEQ ID NO 1256
<211> LENGTH: 9
<212> TYPE: PRT
<213> ORGANISM: Artificial sequence
<220> FEATURE:
<223> OTHER INFORMATION: Peptide derived from HBV Large surface protein

<400> SEQUENCE: 1256

Leu Leu Cys Leu Ile Phe Leu Leu Val
1               5

<210> SEQ ID NO 1257
<211> LENGTH: 11
<212> TYPE: PRT
<213> ORGANISM: Artificial sequence
<220> FEATURE:
<223> OTHER INFORMATION: Peptide derived from HBV Large surface protein

<400> SEQUENCE: 1257

Leu Leu Leu Cys Leu Ile Phe Leu Leu Val Leu
1               5                   10

<210> SEQ ID NO 1258
<211> LENGTH: 14
<212> TYPE: PRT
<213> ORGANISM: Artificial sequence
<220> FEATURE:
<223> OTHER INFORMATION: Peptide derived from HBV Large surface protein

<400> SEQUENCE: 1258

Leu Leu Leu Cys Leu Ile Phe Leu Leu Val Leu Leu Asp Tyr
1               5                   10

<210> SEQ ID NO 1259
<211> LENGTH: 13
<212> TYPE: PRT
<213> ORGANISM: Artificial sequence
<220> FEATURE:
<223> OTHER INFORMATION: Peptide derived from HBV Large surface protein

<400> SEQUENCE: 1259

Leu Leu Cys Leu Ile Phe Leu Leu Val Leu Leu Asp Tyr
1               5                   10

<210> SEQ ID NO 1260
<211> LENGTH: 11
<212> TYPE: PRT
<213> ORGANISM: Artificial sequence
<220> FEATURE:
<223> OTHER INFORMATION: Peptide derived from HBV Large surface protein

<400> SEQUENCE: 1260

Cys Leu Ile Phe Leu Leu Val Leu Leu Asp Tyr
1               5                   10

<210> SEQ ID NO 1261
<211> LENGTH: 10
<212> TYPE: PRT
<213> ORGANISM: Artificial sequence
<220> FEATURE:
<223> OTHER INFORMATION: Peptide derived from HBV Large surface protein

<400> SEQUENCE: 1261

Leu Ile Phe Leu Leu Val Leu Leu Asp Tyr
1               5                   10

<210> SEQ ID NO 1262
<211> LENGTH: 9
<212> TYPE: PRT
<213> ORGANISM: Artificial sequence
<220> FEATURE:
<223> OTHER INFORMATION: Peptide derived from HBV Large surface protein

<400> SEQUENCE: 1262

Ile Phe Leu Leu Val Leu Leu Asp Tyr
1               5

<210> SEQ ID NO 1263
<211> LENGTH: 8
<212> TYPE: PRT
<213> ORGANISM: Artificial sequence
<220> FEATURE:
<223> OTHER INFORMATION: Peptide derived from HBV Large surface protein

<400> SEQUENCE: 1263

Phe Leu Leu Val Leu Leu Asp Tyr
1               5

<210> SEQ ID NO 1264
<211> LENGTH: 8
<212> TYPE: PRT
<213> ORGANISM: Artificial sequence
<220> FEATURE:
<223> OTHER INFORMATION: Peptide derived from HBV Large surface protein

<400> SEQUENCE: 1264

Ile Pro Ile Pro Ser Ser Trp Ala
1               5

<210> SEQ ID NO 1265
<211> LENGTH: 9
<212> TYPE: PRT
<213> ORGANISM: Artificial sequence
<220> FEATURE:
<223> OTHER INFORMATION: Peptide derived from HBV Large surface protein

<400> SEQUENCE: 1265

Ile Pro Ile Pro Ser Ser Trp Ala Phe
1               5

<210> SEQ ID NO 1266
<211> LENGTH: 10
<212> TYPE: PRT
<213> ORGANISM: Artificial sequence
<220> FEATURE:
<223> OTHER INFORMATION: Peptide derived from HBV Large surface protein

<400> SEQUENCE: 1266

Ile Pro Ile Pro Ser Ser Trp Ala Phe Ala
1               5                   10

<210> SEQ ID NO 1267
<211> LENGTH: 8
<212> TYPE: PRT
<213> ORGANISM: Artificial sequence
<220> FEATURE:
<223> OTHER INFORMATION: Peptide derived from HBV Large surface protein

<400> SEQUENCE: 1267

Ile Pro Ser Ser Trp Ala Phe Ala
1               5

<210> SEQ ID NO 1268
<211> LENGTH: 12
<212> TYPE: PRT
<213> ORGANISM: Artificial sequence
<220> FEATURE:
<223> OTHER INFORMATION: Peptide derived from HBV Large surface protein

<400> SEQUENCE: 1268

Cys Ile Pro Ile Pro Ser Ser Trp Ala Phe Ala Lys
1               5                   10

<210> SEQ ID NO 1269
<211> LENGTH: 11
<212> TYPE: PRT
<213> ORGANISM: Artificial sequence
<220> FEATURE:
<223> OTHER INFORMATION: Peptide derived from HBV Large surface protein

<400> SEQUENCE: 1269

Ile Pro Ile Pro Ser Ser Trp Ala Phe Ala Lys
1               5                   10

<210> SEQ ID NO 1270
<211> LENGTH: 9
<212> TYPE: PRT
<213> ORGANISM: Artificial sequence
<220> FEATURE:
<223> OTHER INFORMATION: Peptide derived from HBV Large surface protein

<400> SEQUENCE: 1270

Ile Pro Ser Ser Trp Ala Phe Ala Lys
1               5

<210> SEQ ID NO 1271
<211> LENGTH: 8
<212> TYPE: PRT
<213> ORGANISM: Artificial sequence
<220> FEATURE:
<223> OTHER INFORMATION: Peptide derived from HBV Large surface protein

<400> SEQUENCE: 1271

Pro Ser Ser Trp Ala Phe Ala Lys
1               5

<210> SEQ ID NO 1272
<211> LENGTH: 12
<212> TYPE: PRT
<213> ORGANISM: Artificial sequence
<220> FEATURE:
<223> OTHER INFORMATION: Peptide derived from HBV Large surface protein

<400> SEQUENCE: 1272

```
Ile Pro Ile Pro Ser Ser Trp Ala Phe Ala Lys Tyr
1               5                   10
```

<210> SEQ ID NO 1273
<211> LENGTH: 11
<212> TYPE: PRT
<213> ORGANISM: Artificial sequence
<220> FEATURE:
<223> OTHER INFORMATION: Peptide derived from HBV Large surface protein

<400> SEQUENCE: 1273

```
Pro Ile Pro Ser Ser Trp Ala Phe Ala Lys Tyr
1               5                   10
```

<210> SEQ ID NO 1274
<211> LENGTH: 10
<212> TYPE: PRT
<213> ORGANISM: Artificial sequence
<220> FEATURE:
<223> OTHER INFORMATION: Peptide derived from HBV Large surface protein

<400> SEQUENCE: 1274

```
Ile Pro Ser Ser Trp Ala Phe Ala Lys Tyr
1               5                   10
```

<210> SEQ ID NO 1275
<211> LENGTH: 9
<212> TYPE: PRT
<213> ORGANISM: Artificial sequence
<220> FEATURE:
<223> OTHER INFORMATION: Peptide derived from HBV Large surface protein

<400> SEQUENCE: 1275

```
Pro Ser Ser Trp Ala Phe Ala Lys Tyr
1               5
```

<210> SEQ ID NO 1276
<211> LENGTH: 8
<212> TYPE: PRT
<213> ORGANISM: Artificial sequence
<220> FEATURE:
<223> OTHER INFORMATION: Peptide derived from HBV Large surface protein

<400> SEQUENCE: 1276

```
Ser Ser Trp Ala Phe Ala Lys Tyr
1               5
```

<210> SEQ ID NO 1277
<211> LENGTH: 13
<212> TYPE: PRT
<213> ORGANISM: Artificial sequence
<220> FEATURE:
<223> OTHER INFORMATION: Peptide derived from HBV Large surface protein

<400> SEQUENCE: 1277

```
Ile Pro Ile Pro Ser Ser Trp Ala Phe Ala Lys Tyr Leu
1               5                   10
```

<210> SEQ ID NO 1278
<211> LENGTH: 14
<212> TYPE: PRT
<213> ORGANISM: Artificial sequence
<220> FEATURE:
<223> OTHER INFORMATION: Peptide derived from HBV Large surface protein

<400> SEQUENCE: 1278

Ile Pro Ile Pro Ser Ser Trp Ala Phe Ala Lys Tyr Leu Trp
1               5                   10

<210> SEQ ID NO 1279
<211> LENGTH: 12
<212> TYPE: PRT
<213> ORGANISM: Artificial sequence
<220> FEATURE:
<223> OTHER INFORMATION: Peptide derived from HBV Large surface protein

<400> SEQUENCE: 1279

Ile Pro Ser Ser Trp Ala Phe Ala Lys Tyr Leu Trp
1               5                   10

<210> SEQ ID NO 1280
<211> LENGTH: 10
<212> TYPE: PRT
<213> ORGANISM: Artificial sequence
<220> FEATURE:
<223> OTHER INFORMATION: Peptide derived from HBV Large surface protein

<400> SEQUENCE: 1280

Ser Ser Trp Ala Phe Ala Lys Tyr Leu Trp
1               5                   10

<210> SEQ ID NO 1281
<211> LENGTH: 8
<212> TYPE: PRT
<213> ORGANISM: Artificial sequence
<220> FEATURE:
<223> OTHER INFORMATION: Peptide derived from HBV Large surface protein

<400> SEQUENCE: 1281

Trp Ala Phe Ala Lys Tyr Leu Trp
1               5

<210> SEQ ID NO 1282
<211> LENGTH: 14
<212> TYPE: PRT
<213> ORGANISM: Artificial sequence
<220> FEATURE:
<223> OTHER INFORMATION: Peptide derived from HBV Large surface protein

<400> SEQUENCE: 1282

Ile Pro Ser Ser Trp Ala Phe Ala Lys Tyr Leu Trp Glu Trp
1               5                   10

<210> SEQ ID NO 1283
<211> LENGTH: 12
<212> TYPE: PRT
<213> ORGANISM: Artificial sequence
<220> FEATURE:
<223> OTHER INFORMATION: Peptide derived from HBV Large surface protein

<400> SEQUENCE: 1283

Ser Ser Trp Ala Phe Ala Lys Tyr Leu Trp Glu Trp
1               5                   10

<210> SEQ ID NO 1284
<211> LENGTH: 10
<212> TYPE: PRT
<213> ORGANISM: Artificial sequence
<220> FEATURE:
<223> OTHER INFORMATION: Peptide derived from HBV Large surface protein

<400> SEQUENCE: 1284

Trp Ala Phe Ala Lys Tyr Leu Trp Glu Trp

```
1               5                  10
```

<210> SEQ ID NO 1285
<211> LENGTH: 9
<212> TYPE: PRT
<213> ORGANISM: Artificial sequence
<220> FEATURE:
<223> OTHER INFORMATION: Peptide derived from HBV Large surface protein

<400> SEQUENCE: 1285

```
Ala Phe Ala Lys Tyr Leu Trp Glu Trp
1               5
```

<210> SEQ ID NO 1286
<211> LENGTH: 8
<212> TYPE: PRT
<213> ORGANISM: Artificial sequence
<220> FEATURE:
<223> OTHER INFORMATION: Peptide derived from HBV Large surface protein

<400> SEQUENCE: 1286

```
Phe Ala Lys Tyr Leu Trp Glu Trp
1               5
```

<210> SEQ ID NO 1287
<211> LENGTH: 13
<212> TYPE: PRT
<213> ORGANISM: Artificial sequence
<220> FEATURE:
<223> OTHER INFORMATION: Peptide derived from HBV Large surface protein

<400> SEQUENCE: 1287

```
Trp Ala Phe Ala Lys Tyr Leu Trp Glu Trp Ala Ser Val
1               5                  10
```

<210> SEQ ID NO 1288
<211> LENGTH: 11
<212> TYPE: PRT
<213> ORGANISM: Artificial sequence
<220> FEATURE:
<223> OTHER INFORMATION: Peptide derived from HBV Large surface protein

<400> SEQUENCE: 1288

```
Phe Ala Lys Tyr Leu Trp Glu Trp Ala Ser Val
1               5                  10
```

<210> SEQ ID NO 1289
<211> LENGTH: 14
<212> TYPE: PRT
<213> ORGANISM: Artificial sequence
<220> FEATURE:
<223> OTHER INFORMATION: Peptide derived from HBV Large surface protein

<400> SEQUENCE: 1289

```
Trp Ala Phe Ala Lys Tyr Leu Trp Glu Trp Ala Ser Val Arg
1               5                  10
```

<210> SEQ ID NO 1290
<211> LENGTH: 13
<212> TYPE: PRT
<213> ORGANISM: Artificial sequence
<220> FEATURE:
<223> OTHER INFORMATION: Peptide derived from HBV Large surface protein

<400> SEQUENCE: 1290

```
Ala Phe Ala Lys Tyr Leu Trp Glu Trp Ala Ser Val Arg
1               5                  10
```

<210> SEQ ID NO 1291
<211> LENGTH: 12
<212> TYPE: PRT
<213> ORGANISM: Artificial sequence
<220> FEATURE:
<223> OTHER INFORMATION: Peptide derived from HBV Large surface protein

<400> SEQUENCE: 1291

Phe Ala Lys Tyr Leu Trp Glu Trp Ala Ser Val Arg
1               5                   10

<210> SEQ ID NO 1292
<211> LENGTH: 10
<212> TYPE: PRT
<213> ORGANISM: Artificial sequence
<220> FEATURE:
<223> OTHER INFORMATION: Peptide derived from HBV Large surface protein

<400> SEQUENCE: 1292

Lys Tyr Leu Trp Glu Trp Ala Ser Val Arg
1               5                   10

<210> SEQ ID NO 1293
<211> LENGTH: 9
<212> TYPE: PRT
<213> ORGANISM: Artificial sequence
<220> FEATURE:
<223> OTHER INFORMATION: Peptide derived from HBV Large surface protein

<400> SEQUENCE: 1293

Tyr Leu Trp Glu Trp Ala Ser Val Arg
1               5

<210> SEQ ID NO 1294
<211> LENGTH: 14
<212> TYPE: PRT
<213> ORGANISM: Artificial sequence
<220> FEATURE:
<223> OTHER INFORMATION: Peptide derived from HBV Large surface protein

<400> SEQUENCE: 1294

Ala Phe Ala Lys Tyr Leu Trp Glu Trp Ala Ser Val Arg Phe
1               5                   10

<210> SEQ ID NO 1295
<211> LENGTH: 13
<212> TYPE: PRT
<213> ORGANISM: Artificial sequence
<220> FEATURE:
<223> OTHER INFORMATION: Peptide derived from HBV Large surface protein

<400> SEQUENCE: 1295

Phe Ala Lys Tyr Leu Trp Glu Trp Ala Ser Val Arg Phe
1               5                   10

<210> SEQ ID NO 1296
<211> LENGTH: 10
<212> TYPE: PRT
<213> ORGANISM: Artificial sequence
<220> FEATURE:
<223> OTHER INFORMATION: Peptide derived from HBV Large surface protein

<400> SEQUENCE: 1296

Tyr Leu Trp Glu Trp Ala Ser Val Arg Phe
1               5                   10

<210> SEQ ID NO 1297
<211> LENGTH: 8
<212> TYPE: PRT
<213> ORGANISM: Artificial sequence
<220> FEATURE:
<223> OTHER INFORMATION: Peptide derived from HBV Large surface protein

<400> SEQUENCE: 1297

Trp Glu Trp Ala Ser Val Arg Phe
1               5

<210> SEQ ID NO 1298
<211> LENGTH: 9
<212> TYPE: PRT
<213> ORGANISM: Artificial sequence
<220> FEATURE:
<223> OTHER INFORMATION: Peptide derived from HBV Large surface protein

<400> SEQUENCE: 1298

Trp Glu Trp Ala Ser Val Arg Phe Ser
1               5

<210> SEQ ID NO 1299
<211> LENGTH: 14
<212> TYPE: PRT
<213> ORGANISM: Artificial sequence
<220> FEATURE:
<223> OTHER INFORMATION: Peptide derived from HBV Large surface protein

<400> SEQUENCE: 1299

Ala Lys Tyr Leu Trp Glu Trp Ala Ser Val Arg Phe Ser Trp
1               5                   10

<210> SEQ ID NO 1300
<211> LENGTH: 13
<212> TYPE: PRT
<213> ORGANISM: Artificial sequence
<220> FEATURE:
<223> OTHER INFORMATION: Peptide derived from HBV Large surface protein

<400> SEQUENCE: 1300

Lys Tyr Leu Trp Glu Trp Ala Ser Val Arg Phe Ser Trp
1               5                   10

<210> SEQ ID NO 1301
<211> LENGTH: 12
<212> TYPE: PRT
<213> ORGANISM: Artificial sequence
<220> FEATURE:
<223> OTHER INFORMATION: Peptide derived from HBV Large surface protein

<400> SEQUENCE: 1301

Tyr Leu Trp Glu Trp Ala Ser Val Arg Phe Ser Trp
1               5                   10

<210> SEQ ID NO 1302
<211> LENGTH: 10
<212> TYPE: PRT
<213> ORGANISM: Artificial sequence
<220> FEATURE:
<223> OTHER INFORMATION: Peptide derived from HBV Large surface protein

<400> SEQUENCE: 1302

Trp Glu Trp Ala Ser Val Arg Phe Ser Trp
1               5                   10

```
<210> SEQ ID NO 1303
<211> LENGTH: 8
<212> TYPE: PRT
<213> ORGANISM: Artificial sequence
<220> FEATURE:
<223> OTHER INFORMATION: Peptide derived from HBV Large surface protein

<400> SEQUENCE: 1303

Trp Ala Ser Val Arg Phe Ser Trp
1               5

<210> SEQ ID NO 1304
<211> LENGTH: 14
<212> TYPE: PRT
<213> ORGANISM: Artificial sequence
<220> FEATURE:
<223> OTHER INFORMATION: Peptide derived from HBV Large surface protein

<400> SEQUENCE: 1304

Lys Tyr Leu Trp Glu Trp Ala Ser Val Arg Phe Ser Trp Leu
1               5                   10

<210> SEQ ID NO 1305
<211> LENGTH: 13
<212> TYPE: PRT
<213> ORGANISM: Artificial sequence
<220> FEATURE:
<223> OTHER INFORMATION: Peptide derived from HBV Large surface protein

<400> SEQUENCE: 1305

Tyr Leu Trp Glu Trp Ala Ser Val Arg Phe Ser Trp Leu
1               5                   10

<210> SEQ ID NO 1306
<211> LENGTH: 11
<212> TYPE: PRT
<213> ORGANISM: Artificial sequence
<220> FEATURE:
<223> OTHER INFORMATION: Peptide derived from HBV Large surface protein

<400> SEQUENCE: 1306

Trp Glu Trp Ala Ser Val Arg Phe Ser Trp Leu
1               5                   10

<210> SEQ ID NO 1307
<211> LENGTH: 9
<212> TYPE: PRT
<213> ORGANISM: Artificial sequence
<220> FEATURE:
<223> OTHER INFORMATION: Peptide derived from HBV Large surface protein

<400> SEQUENCE: 1307

Trp Ala Ser Val Arg Phe Ser Trp Leu
1               5

<210> SEQ ID NO 1308
<211> LENGTH: 12
<212> TYPE: PRT
<213> ORGANISM: Artificial sequence
<220> FEATURE:
<223> OTHER INFORMATION: Peptide derived from HBV Large surface protein

<400> SEQUENCE: 1308

Trp Glu Trp Ala Ser Val Arg Phe Ser Trp Leu Ser
1               5                   10

<210> SEQ ID NO 1309
```

```
<211> LENGTH: 8
<212> TYPE: PRT
<213> ORGANISM: Artificial sequence
<220> FEATURE:
<223> OTHER INFORMATION: Peptide derived from HBV Large surface protein

<400> SEQUENCE: 1309

Ser Val Arg Phe Ser Trp Leu Ser
1               5

<210> SEQ ID NO 1310
<211> LENGTH: 13
<212> TYPE: PRT
<213> ORGANISM: Artificial sequence
<220> FEATURE:
<223> OTHER INFORMATION: Peptide derived from HBV Large surface protein

<400> SEQUENCE: 1310

Trp Glu Trp Ala Ser Val Arg Phe Ser Trp Leu Ser Leu
1               5                   10

<210> SEQ ID NO 1311
<211> LENGTH: 11
<212> TYPE: PRT
<213> ORGANISM: Artificial sequence
<220> FEATURE:
<223> OTHER INFORMATION: Peptide derived from HBV Large surface protein

<400> SEQUENCE: 1311

Trp Ala Ser Val Arg Phe Ser Trp Leu Ser Leu
1               5                   10

<210> SEQ ID NO 1312
<211> LENGTH: 9
<212> TYPE: PRT
<213> ORGANISM: Artificial sequence
<220> FEATURE:
<223> OTHER INFORMATION: Peptide derived from HBV Large surface protein

<400> SEQUENCE: 1312

Ser Val Arg Phe Ser Trp Leu Ser Leu
1               5

<210> SEQ ID NO 1313
<211> LENGTH: 8
<212> TYPE: PRT
<213> ORGANISM: Artificial sequence
<220> FEATURE:
<223> OTHER INFORMATION: Peptide derived from HBV Large surface protein

<400> SEQUENCE: 1313

Val Arg Phe Ser Trp Leu Ser Leu
1               5

<210> SEQ ID NO 1314
<211> LENGTH: 14
<212> TYPE: PRT
<213> ORGANISM: Artificial sequence
<220> FEATURE:
<223> OTHER INFORMATION: Peptide derived from HBV Large surface protein

<400> SEQUENCE: 1314

Trp Glu Trp Ala Ser Val Arg Phe Ser Trp Leu Ser Leu Leu
1               5                   10

<210> SEQ ID NO 1315
<211> LENGTH: 9
```

```
<212> TYPE: PRT
<213> ORGANISM: Artificial sequence
<220> FEATURE:
<223> OTHER INFORMATION: Peptide derived from HBV Large surface protein

<400> SEQUENCE: 1315

Val Arg Phe Ser Trp Leu Ser Leu Leu
1               5

<210> SEQ ID NO 1316
<211> LENGTH: 13
<212> TYPE: PRT
<213> ORGANISM: Artificial sequence
<220> FEATURE:
<223> OTHER INFORMATION: Peptide derived from HBV Large surface protein

<400> SEQUENCE: 1316

Trp Ala Ser Val Arg Phe Ser Trp Leu Ser Leu Leu Val
1               5                   10

<210> SEQ ID NO 1317
<211> LENGTH: 11
<212> TYPE: PRT
<213> ORGANISM: Artificial sequence
<220> FEATURE:
<223> OTHER INFORMATION: Peptide derived from HBV Large surface protein

<400> SEQUENCE: 1317

Ser Val Arg Phe Ser Trp Leu Ser Leu Leu Val
1               5                   10

<210> SEQ ID NO 1318
<211> LENGTH: 14
<212> TYPE: PRT
<213> ORGANISM: Artificial sequence
<220> FEATURE:
<223> OTHER INFORMATION: Peptide derived from HBV Large surface protein

<400> SEQUENCE: 1318

Ala Ser Val Arg Phe Ser Trp Leu Ser Leu Leu Val Pro Phe
1               5                   10

<210> SEQ ID NO 1319
<211> LENGTH: 13
<212> TYPE: PRT
<213> ORGANISM: Artificial sequence
<220> FEATURE:
<223> OTHER INFORMATION: Peptide derived from HBV Large surface protein

<400> SEQUENCE: 1319

Ser Val Arg Phe Ser Trp Leu Ser Leu Leu Val Pro Phe
1               5                   10

<210> SEQ ID NO 1320
<211> LENGTH: 12
<212> TYPE: PRT
<213> ORGANISM: Artificial sequence
<220> FEATURE:
<223> OTHER INFORMATION: Peptide derived from HBV Large surface protein

<400> SEQUENCE: 1320

Val Arg Phe Ser Trp Leu Ser Leu Leu Val Pro Phe
1               5                   10

<210> SEQ ID NO 1321
<211> LENGTH: 11
<212> TYPE: PRT
```

```
<213> ORGANISM: Artificial sequence
<220> FEATURE:
<223> OTHER INFORMATION: Peptide derived from HBV Large surface protein

<400> SEQUENCE: 1321

Arg Phe Ser Trp Leu Ser Leu Leu Val Pro Phe
1               5                   10

<210> SEQ ID NO 1322
<211> LENGTH: 10
<212> TYPE: PRT
<213> ORGANISM: Artificial sequence
<220> FEATURE:
<223> OTHER INFORMATION: Peptide derived from HBV Large surface protein

<400> SEQUENCE: 1322

Phe Ser Trp Leu Ser Leu Leu Val Pro Phe
1               5                   10

<210> SEQ ID NO 1323
<211> LENGTH: 8
<212> TYPE: PRT
<213> ORGANISM: Artificial sequence
<220> FEATURE:
<223> OTHER INFORMATION: Peptide derived from HBV Large surface protein

<400> SEQUENCE: 1323

Trp Leu Ser Leu Leu Val Pro Phe
1               5

<210> SEQ ID NO 1324
<211> LENGTH: 14
<212> TYPE: PRT
<213> ORGANISM: Artificial sequence
<220> FEATURE:
<223> OTHER INFORMATION: Peptide derived from HBV Large surface protein

<400> SEQUENCE: 1324

Ser Val Arg Phe Ser Trp Leu Ser Leu Leu Val Pro Phe Val
1               5                   10

<210> SEQ ID NO 1325
<211> LENGTH: 13
<212> TYPE: PRT
<213> ORGANISM: Artificial sequence
<220> FEATURE:
<223> OTHER INFORMATION: Peptide derived from HBV Large surface protein

<400> SEQUENCE: 1325

Val Arg Phe Ser Trp Leu Ser Leu Leu Val Pro Phe Val
1               5                   10

<210> SEQ ID NO 1326
<211> LENGTH: 9
<212> TYPE: PRT
<213> ORGANISM: Artificial sequence
<220> FEATURE:
<223> OTHER INFORMATION: Peptide derived from HBV Large surface protein

<400> SEQUENCE: 1326

Trp Leu Ser Leu Leu Val Pro Phe Val
1               5

<210> SEQ ID NO 1327
<211> LENGTH: 14
<212> TYPE: PRT
<213> ORGANISM: Artificial sequence
```

<220> FEATURE:
<223> OTHER INFORMATION: Peptide derived from HBV Large surface protein

<400> SEQUENCE: 1327

Arg Phe Ser Trp Leu Ser Leu Leu Val Pro Phe Val Gln Trp
1               5                   10

<210> SEQ ID NO 1328
<211> LENGTH: 13
<212> TYPE: PRT
<213> ORGANISM: Artificial sequence
<220> FEATURE:
<223> OTHER INFORMATION: Peptide derived from HBV Large surface protein

<400> SEQUENCE: 1328

Phe Ser Trp Leu Ser Leu Leu Val Pro Phe Val Gln Trp
1               5                   10

<210> SEQ ID NO 1329
<211> LENGTH: 10
<212> TYPE: PRT
<213> ORGANISM: Artificial sequence
<220> FEATURE:
<223> OTHER INFORMATION: Peptide derived from HBV Large surface protein

<400> SEQUENCE: 1329

Leu Ser Leu Leu Val Pro Phe Val Gln Trp
1               5                   10

<210> SEQ ID NO 1330
<211> LENGTH: 14
<212> TYPE: PRT
<213> ORGANISM: Artificial sequence
<220> FEATURE:
<223> OTHER INFORMATION: Peptide derived from HBV Large surface protein

<400> SEQUENCE: 1330

Phe Ser Trp Leu Ser Leu Leu Val Pro Phe Val Gln Trp Phe
1               5                   10

<210> SEQ ID NO 1331
<211> LENGTH: 13
<212> TYPE: PRT
<213> ORGANISM: Artificial sequence
<220> FEATURE:
<223> OTHER INFORMATION: Peptide derived from HBV Large surface protein

<400> SEQUENCE: 1331

Ser Trp Leu Ser Leu Leu Val Pro Phe Val Gln Trp Phe
1               5                   10

<210> SEQ ID NO 1332
<211> LENGTH: 11
<212> TYPE: PRT
<213> ORGANISM: Artificial sequence
<220> FEATURE:
<223> OTHER INFORMATION: Peptide derived from HBV Large surface protein

<400> SEQUENCE: 1332

Leu Ser Leu Leu Val Pro Phe Val Gln Trp Phe
1               5                   10

<210> SEQ ID NO 1333
<211> LENGTH: 10
<212> TYPE: PRT
<213> ORGANISM: Artificial sequence
<220> FEATURE:

<223> OTHER INFORMATION: Peptide derived from HBV Large surface protein

<400> SEQUENCE: 1333

Ser Leu Leu Val Pro Phe Val Gln Trp Phe
1               5                   10

<210> SEQ ID NO 1334
<211> LENGTH: 9
<212> TYPE: PRT
<213> ORGANISM: Artificial sequence
<220> FEATURE:
<223> OTHER INFORMATION: Peptide derived from HBV Large surface protein

<400> SEQUENCE: 1334

Leu Leu Val Pro Phe Val Gln Trp Phe
1               5

<210> SEQ ID NO 1335
<211> LENGTH: 13
<212> TYPE: PRT
<213> ORGANISM: Artificial sequence
<220> FEATURE:
<223> OTHER INFORMATION: Peptide derived from HBV Large surface protein

<400> SEQUENCE: 1335

Trp Leu Ser Leu Leu Val Pro Phe Val Gln Trp Phe Val
1               5                   10

<210> SEQ ID NO 1336
<211> LENGTH: 10
<212> TYPE: PRT
<213> ORGANISM: Artificial sequence
<220> FEATURE:
<223> OTHER INFORMATION: Peptide derived from HBV Large surface protein

<400> SEQUENCE: 1336

Leu Leu Val Pro Phe Val Gln Trp Phe Val
1               5                   10

<210> SEQ ID NO 1337
<211> LENGTH: 9
<212> TYPE: PRT
<213> ORGANISM: Artificial sequence
<220> FEATURE:
<223> OTHER INFORMATION: Peptide derived from HBV Large surface protein

<400> SEQUENCE: 1337

Leu Val Pro Phe Val Gln Trp Phe Val
1               5

<210> SEQ ID NO 1338
<211> LENGTH: 8
<212> TYPE: PRT
<213> ORGANISM: Artificial sequence
<220> FEATURE:
<223> OTHER INFORMATION: Peptide derived from HBV Large surface protein

<400> SEQUENCE: 1338

Leu Ser Ala Ile Trp Met Met Trp
1               5

<210> SEQ ID NO 1339
<211> LENGTH: 10
<212> TYPE: PRT
<213> ORGANISM: Artificial sequence
<220> FEATURE:
<223> OTHER INFORMATION: Peptide derived from HBV Large surface protein

```
<400> SEQUENCE: 1339

Trp Leu Ser Ala Ile Trp Met Met Trp Tyr
1               5                   10

<210> SEQ ID NO 1340
<211> LENGTH: 9
<212> TYPE: PRT
<213> ORGANISM: Artificial sequence
<220> FEATURE:
<223> OTHER INFORMATION: Peptide derived from HBV Large surface protein

<400> SEQUENCE: 1340

Leu Ser Ala Ile Trp Met Met Trp Tyr
1               5

<210> SEQ ID NO 1341
<211> LENGTH: 8
<212> TYPE: PRT
<213> ORGANISM: Artificial sequence
<220> FEATURE:
<223> OTHER INFORMATION: Peptide derived from HBV Large surface protein

<400> SEQUENCE: 1341

Ser Ala Ile Trp Met Met Trp Tyr
1               5

<210> SEQ ID NO 1342
<211> LENGTH: 10
<212> TYPE: PRT
<213> ORGANISM: Artificial sequence
<220> FEATURE:
<223> OTHER INFORMATION: Peptide derived from HBV Large surface protein

<400> SEQUENCE: 1342

Leu Ser Ala Ile Trp Met Met Trp Tyr Trp
1               5                   10

<210> SEQ ID NO 1343
<211> LENGTH: 9
<212> TYPE: PRT
<213> ORGANISM: Artificial sequence
<220> FEATURE:
<223> OTHER INFORMATION: Peptide derived from HBV Large surface protein

<400> SEQUENCE: 1343

Ser Ala Ile Trp Met Met Trp Tyr Trp
1               5

<210> SEQ ID NO 1344
<211> LENGTH: 8
<212> TYPE: PRT
<213> ORGANISM: Artificial sequence
<220> FEATURE:
<223> OTHER INFORMATION: Peptide derived from HBV Large surface protein

<400> SEQUENCE: 1344

Ala Ile Trp Met Met Trp Tyr Trp
1               5

<210> SEQ ID NO 1345
<211> LENGTH: 10
<212> TYPE: PRT
<213> ORGANISM: Artificial sequence
<220> FEATURE:
<223> OTHER INFORMATION: Peptide derived from HBV Large surface protein
```

```
<400> SEQUENCE: 1345

Trp Met Met Trp Tyr Trp Gly Pro Ser Leu
1               5                   10

<210> SEQ ID NO 1346
<211> LENGTH: 9
<212> TYPE: PRT
<213> ORGANISM: Artificial sequence
<220> FEATURE:
<223> OTHER INFORMATION: Peptide derived from HBV Large surface protein

<400> SEQUENCE: 1346

Met Met Trp Tyr Trp Gly Pro Ser Leu
1               5

<210> SEQ ID NO 1347
<211> LENGTH: 14
<212> TYPE: PRT
<213> ORGANISM: Artificial sequence
<220> FEATURE:
<223> OTHER INFORMATION: Peptide derived from HBV Large surface protein

<400> SEQUENCE: 1347

Ser Ala Ile Trp Met Met Trp Tyr Trp Gly Pro Ser Leu Tyr
1               5                   10

<210> SEQ ID NO 1348
<211> LENGTH: 13
<212> TYPE: PRT
<213> ORGANISM: Artificial sequence
<220> FEATURE:
<223> OTHER INFORMATION: Peptide derived from HBV Large surface protein

<400> SEQUENCE: 1348

Ala Ile Trp Met Met Trp Tyr Trp Gly Pro Ser Leu Tyr
1               5                   10

<210> SEQ ID NO 1349
<211> LENGTH: 11
<212> TYPE: PRT
<213> ORGANISM: Artificial sequence
<220> FEATURE:
<223> OTHER INFORMATION: Peptide derived from HBV Large surface protein

<400> SEQUENCE: 1349

Trp Met Met Trp Tyr Trp Gly Pro Ser Leu Tyr
1               5                   10

<210> SEQ ID NO 1350
<211> LENGTH: 10
<212> TYPE: PRT
<213> ORGANISM: Artificial sequence
<220> FEATURE:
<223> OTHER INFORMATION: Peptide derived from HBV Large surface protein

<400> SEQUENCE: 1350

Met Met Trp Tyr Trp Gly Pro Ser Leu Tyr
1               5                   10

<210> SEQ ID NO 1351
<211> LENGTH: 9
<212> TYPE: PRT
<213> ORGANISM: Artificial sequence
<220> FEATURE:
<223> OTHER INFORMATION: Peptide derived from HBV Large surface protein

<400> SEQUENCE: 1351
```

```
Met Trp Tyr Trp Gly Pro Ser Leu Tyr
1               5
```

<210> SEQ ID NO 1352
<211> LENGTH: 14
<212> TYPE: PRT
<213> ORGANISM: Artificial sequence
<220> FEATURE:
<223> OTHER INFORMATION: Peptide derived from HBV Large surface protein

<400> SEQUENCE: 1352

```
Ile Trp Met Met Trp Tyr Trp Gly Pro Ser Leu Tyr Ser Ile
1               5                   10
```

<210> SEQ ID NO 1353
<211> LENGTH: 13
<212> TYPE: PRT
<213> ORGANISM: Artificial sequence
<220> FEATURE:
<223> OTHER INFORMATION: Peptide derived from HBV Large surface protein

<400> SEQUENCE: 1353

```
Trp Met Met Trp Tyr Trp Gly Pro Ser Leu Tyr Ser Ile
1               5                   10
```

<210> SEQ ID NO 1354
<211> LENGTH: 12
<212> TYPE: PRT
<213> ORGANISM: Artificial sequence
<220> FEATURE:
<223> OTHER INFORMATION: Peptide derived from HBV Large surface protein

<400> SEQUENCE: 1354

```
Met Met Trp Tyr Trp Gly Pro Ser Leu Tyr Ser Ile
1               5                   10
```

<210> SEQ ID NO 1355
<211> LENGTH: 14
<212> TYPE: PRT
<213> ORGANISM: Artificial sequence
<220> FEATURE:
<223> OTHER INFORMATION: Peptide derived from HBV Large surface protein

<400> SEQUENCE: 1355

```
Trp Met Met Trp Tyr Trp Gly Pro Ser Leu Tyr Ser Ile Val
1               5                   10
```

<210> SEQ ID NO 1356
<211> LENGTH: 13
<212> TYPE: PRT
<213> ORGANISM: Artificial sequence
<220> FEATURE:
<223> OTHER INFORMATION: Peptide derived from HBV Large surface protein

<400> SEQUENCE: 1356

```
Met Met Trp Tyr Trp Gly Pro Ser Leu Tyr Ser Ile Val
1               5                   10
```

<210> SEQ ID NO 1357
<211> LENGTH: 14
<212> TYPE: PRT
<213> ORGANISM: Artificial sequence
<220> FEATURE:
<223> OTHER INFORMATION: Peptide derived from HBV Large surface protein

<400> SEQUENCE: 1357

Trp Tyr Trp Gly Pro Ser Leu Tyr Ser Ile Val Ser Pro Phe
1               5                   10

<210> SEQ ID NO 1358
<211> LENGTH: 13
<212> TYPE: PRT
<213> ORGANISM: Artificial sequence
<220> FEATURE:
<223> OTHER INFORMATION: Peptide derived from HBV Large surface protein

<400> SEQUENCE: 1358

Tyr Trp Gly Pro Ser Leu Tyr Ser Ile Val Ser Pro Phe
1               5                   10

<210> SEQ ID NO 1359
<211> LENGTH: 10
<212> TYPE: PRT
<213> ORGANISM: Artificial sequence
<220> FEATURE:
<223> OTHER INFORMATION: Peptide derived from HBV Large surface protein

<400> SEQUENCE: 1359

Pro Ser Leu Tyr Ser Ile Val Ser Pro Phe
1               5                   10

<210> SEQ ID NO 1360
<211> LENGTH: 9
<212> TYPE: PRT
<213> ORGANISM: Artificial sequence
<220> FEATURE:
<223> OTHER INFORMATION: Peptide derived from HBV Large surface protein

<400> SEQUENCE: 1360

Ser Leu Tyr Ser Ile Val Ser Pro Phe
1               5

<210> SEQ ID NO 1361
<211> LENGTH: 14
<212> TYPE: PRT
<213> ORGANISM: Artificial sequence
<220> FEATURE:
<223> OTHER INFORMATION: Peptide derived from HBV Large surface protein

<400> SEQUENCE: 1361

Tyr Trp Gly Pro Ser Leu Tyr Ser Ile Val Ser Pro Phe Ile
1               5                   10

<210> SEQ ID NO 1362
<211> LENGTH: 10
<212> TYPE: PRT
<213> ORGANISM: Artificial sequence
<220> FEATURE:
<223> OTHER INFORMATION: Peptide derived from HBV Large surface protein

<400> SEQUENCE: 1362

Ser Leu Tyr Ser Ile Val Ser Pro Phe Ile
1               5                   10

<210> SEQ ID NO 1363
<211> LENGTH: 14
<212> TYPE: PRT
<213> ORGANISM: Artificial sequence
<220> FEATURE:
<223> OTHER INFORMATION: Peptide derived from HBV Large surface protein

<400> SEQUENCE: 1363

Gly Pro Ser Leu Tyr Ser Ile Val Ser Pro Phe Ile Pro Leu

```
1               5                   10
```

<210> SEQ ID NO 1364
<211> LENGTH: 12
<212> TYPE: PRT
<213> ORGANISM: Artificial sequence
<220> FEATURE:
<223> OTHER INFORMATION: Peptide derived from HBV Large surface protein

<400> SEQUENCE: 1364

```
Ser Leu Tyr Ser Ile Val Ser Pro Phe Ile Pro Leu
1               5                   10
```

<210> SEQ ID NO 1365
<211> LENGTH: 10
<212> TYPE: PRT
<213> ORGANISM: Artificial sequence
<220> FEATURE:
<223> OTHER INFORMATION: Peptide derived from HBV Large surface protein

<400> SEQUENCE: 1365

```
Tyr Ser Ile Val Ser Pro Phe Ile Pro Leu
1               5                   10
```

<210> SEQ ID NO 1366
<211> LENGTH: 13
<212> TYPE: PRT
<213> ORGANISM: Artificial sequence
<220> FEATURE:
<223> OTHER INFORMATION: Peptide derived from HBV Large surface protein

<400> SEQUENCE: 1366

```
Ser Leu Tyr Ser Ile Val Ser Pro Phe Ile Pro Leu Leu
1               5                   10
```

<210> SEQ ID NO 1367
<211> LENGTH: 14
<212> TYPE: PRT
<213> ORGANISM: Artificial sequence
<220> FEATURE:
<223> OTHER INFORMATION: Peptide derived from HBV Large surface protein

<400> SEQUENCE: 1367

```
Leu Tyr Ser Ile Val Ser Pro Phe Ile Pro Leu Leu Pro Ile
1               5                   10
```

<210> SEQ ID NO 1368
<211> LENGTH: 13
<212> TYPE: PRT
<213> ORGANISM: Artificial sequence
<220> FEATURE:
<223> OTHER INFORMATION: Peptide derived from HBV Large surface protein

<400> SEQUENCE: 1368

```
Tyr Ser Ile Val Ser Pro Phe Ile Pro Leu Leu Pro Ile
1               5                   10
```

<210> SEQ ID NO 1369
<211> LENGTH: 12
<212> TYPE: PRT
<213> ORGANISM: Artificial sequence
<220> FEATURE:
<223> OTHER INFORMATION: Peptide derived from HBV Large surface protein

<400> SEQUENCE: 1369

```
Ser Ile Val Ser Pro Phe Ile Pro Leu Leu Pro Ile
1               5                   10
```

```
<210> SEQ ID NO 1370
<211> LENGTH: 11
<212> TYPE: PRT
<213> ORGANISM: Artificial sequence
<220> FEATURE:
<223> OTHER INFORMATION: Peptide derived from HBV Large surface protein

<400> SEQUENCE: 1370

Ile Val Ser Pro Phe Ile Pro Leu Leu Pro Ile
1               5                   10

<210> SEQ ID NO 1371
<211> LENGTH: 9
<212> TYPE: PRT
<213> ORGANISM: Artificial sequence
<220> FEATURE:
<223> OTHER INFORMATION: Peptide derived from HBV Large surface protein

<400> SEQUENCE: 1371

Ser Pro Phe Ile Pro Leu Leu Pro Ile
1               5

<210> SEQ ID NO 1372
<211> LENGTH: 14
<212> TYPE: PRT
<213> ORGANISM: Artificial sequence
<220> FEATURE:
<223> OTHER INFORMATION: Peptide derived from HBV Large surface protein

<400> SEQUENCE: 1372

Tyr Ser Ile Val Ser Pro Phe Ile Pro Leu Leu Pro Ile Phe
1               5                   10

<210> SEQ ID NO 1373
<211> LENGTH: 13
<212> TYPE: PRT
<213> ORGANISM: Artificial sequence
<220> FEATURE:
<223> OTHER INFORMATION: Peptide derived from HBV Large surface protein

<400> SEQUENCE: 1373

Ser Ile Val Ser Pro Phe Ile Pro Leu Leu Pro Ile Phe
1               5                   10

<210> SEQ ID NO 1374
<211> LENGTH: 10
<212> TYPE: PRT
<213> ORGANISM: Artificial sequence
<220> FEATURE:
<223> OTHER INFORMATION: Peptide derived from HBV Large surface protein

<400> SEQUENCE: 1374

Ser Pro Phe Ile Pro Leu Leu Pro Ile Phe
1               5                   10

<210> SEQ ID NO 1375
<211> LENGTH: 9
<212> TYPE: PRT
<213> ORGANISM: Artificial sequence
<220> FEATURE:
<223> OTHER INFORMATION: Peptide derived from HBV Large surface protein

<400> SEQUENCE: 1375

Pro Phe Ile Pro Leu Leu Pro Ile Phe
1               5
```

<210> SEQ ID NO 1376
<211> LENGTH: 8
<212> TYPE: PRT
<213> ORGANISM: Artificial sequence
<220> FEATURE:
<223> OTHER INFORMATION: Peptide derived from HBV Large surface protein

<400> SEQUENCE: 1376

Phe Ile Pro Leu Leu Pro Ile Phe
1               5

<210> SEQ ID NO 1377
<211> LENGTH: 11
<212> TYPE: PRT
<213> ORGANISM: Artificial sequence
<220> FEATURE:
<223> OTHER INFORMATION: Peptide derived from HBV Large surface protein

<400> SEQUENCE: 1377

Ser Pro Phe Ile Pro Leu Leu Pro Ile Phe Phe
1               5                   10

<210> SEQ ID NO 1378
<211> LENGTH: 8
<212> TYPE: PRT
<213> ORGANISM: Artificial sequence
<220> FEATURE:
<223> OTHER INFORMATION: Peptide derived from HBV Large surface protein

<400> SEQUENCE: 1378

Ile Pro Leu Leu Pro Ile Phe Phe
1               5

<210> SEQ ID NO 1379
<211> LENGTH: 10
<212> TYPE: PRT
<213> ORGANISM: Artificial sequence
<220> FEATURE:
<223> OTHER INFORMATION: Peptide derived from HBV Large surface protein

<400> SEQUENCE: 1379

Phe Ile Pro Leu Leu Pro Ile Phe Phe Cys
1               5                   10

<210> SEQ ID NO 1380
<211> LENGTH: 13
<212> TYPE: PRT
<213> ORGANISM: Artificial sequence
<220> FEATURE:
<223> OTHER INFORMATION: Peptide derived from HBV Large surface protein

<400> SEQUENCE: 1380

Ser Pro Phe Ile Pro Leu Leu Pro Ile Phe Phe Cys Leu
1               5                   10

<210> SEQ ID NO 1381
<211> LENGTH: 10
<212> TYPE: PRT
<213> ORGANISM: Artificial sequence
<220> FEATURE:
<223> OTHER INFORMATION: Peptide derived from HBV Large surface protein

<400> SEQUENCE: 1381

Ile Pro Leu Leu Pro Ile Phe Phe Cys Leu
1               5                   10

-continued

```
<210> SEQ ID NO 1382
<211> LENGTH: 14
<212> TYPE: PRT
<213> ORGANISM: Artificial sequence
<220> FEATURE:
<223> OTHER INFORMATION: Peptide derived from HBV Large surface protein

<400> SEQUENCE: 1382

Ser Pro Phe Ile Pro Leu Leu Pro Ile Phe Phe Cys Leu Trp
1               5                   10

<210> SEQ ID NO 1383
<211> LENGTH: 11
<212> TYPE: PRT
<213> ORGANISM: Artificial sequence
<220> FEATURE:
<223> OTHER INFORMATION: Peptide derived from HBV Large surface protein

<400> SEQUENCE: 1383

Ile Pro Leu Leu Pro Ile Phe Phe Cys Leu Trp
1               5                   10

<210> SEQ ID NO 1384
<211> LENGTH: 12
<212> TYPE: PRT
<213> ORGANISM: Artificial sequence
<220> FEATURE:
<223> OTHER INFORMATION: Peptide derived from HBV Large surface protein

<400> SEQUENCE: 1384

Ile Pro Leu Leu Pro Ile Phe Phe Cys Leu Trp Val
1               5                   10

<210> SEQ ID NO 1385
<211> LENGTH: 10
<212> TYPE: PRT
<213> ORGANISM: Artificial sequence
<220> FEATURE:
<223> OTHER INFORMATION: Peptide derived from HBV Large surface protein

<400> SEQUENCE: 1385

Leu Leu Pro Ile Phe Phe Cys Leu Trp Val
1               5                   10

<210> SEQ ID NO 1386
<211> LENGTH: 9
<212> TYPE: PRT
<213> ORGANISM: Artificial sequence
<220> FEATURE:
<223> OTHER INFORMATION: Peptide derived from HBV Large surface protein

<400> SEQUENCE: 1386

Leu Pro Ile Phe Phe Cys Leu Trp Val
1               5

<210> SEQ ID NO 1387
<211> LENGTH: 14
<212> TYPE: PRT
<213> ORGANISM: Artificial sequence
<220> FEATURE:
<223> OTHER INFORMATION: Peptide derived from HBV Large surface protein

<400> SEQUENCE: 1387

Phe Ile Pro Leu Leu Pro Ile Phe Phe Cys Leu Trp Val Tyr
1               5                   10

<210> SEQ ID NO 1388
```

<211> LENGTH: 13
<212> TYPE: PRT
<213> ORGANISM: Artificial sequence
<220> FEATURE:
<223> OTHER INFORMATION: Peptide derived from HBV Large surface protein

<400> SEQUENCE: 1388

Ile Pro Leu Leu Pro Ile Phe Phe Cys Leu Trp Val Tyr
1               5                   10

<210> SEQ ID NO 1389
<211> LENGTH: 12
<212> TYPE: PRT
<213> ORGANISM: Artificial sequence
<220> FEATURE:
<223> OTHER INFORMATION: Peptide derived from HBV Large surface protein

<400> SEQUENCE: 1389

Pro Leu Leu Pro Ile Phe Phe Cys Leu Trp Val Tyr
1               5                   10

<210> SEQ ID NO 1390
<211> LENGTH: 11
<212> TYPE: PRT
<213> ORGANISM: Artificial sequence
<220> FEATURE:
<223> OTHER INFORMATION: Peptide derived from HBV Large surface protein

<400> SEQUENCE: 1390

Leu Leu Pro Ile Phe Phe Cys Leu Trp Val Tyr
1               5                   10

<210> SEQ ID NO 1391
<211> LENGTH: 10
<212> TYPE: PRT
<213> ORGANISM: Artificial sequence
<220> FEATURE:
<223> OTHER INFORMATION: Peptide derived from HBV Large surface protein

<400> SEQUENCE: 1391

Leu Pro Ile Phe Phe Cys Leu Trp Val Tyr
1               5                   10

<210> SEQ ID NO 1392
<211> LENGTH: 9
<212> TYPE: PRT
<213> ORGANISM: Artificial sequence
<220> FEATURE:
<223> OTHER INFORMATION: Peptide derived from HBV Large surface protein

<400> SEQUENCE: 1392

Pro Ile Phe Phe Cys Leu Trp Val Tyr
1               5

<210> SEQ ID NO 1393
<211> LENGTH: 8
<212> TYPE: PRT
<213> ORGANISM: Artificial sequence
<220> FEATURE:
<223> OTHER INFORMATION: Peptide derived from HBV Large surface protein

<400> SEQUENCE: 1393

Ile Phe Phe Cys Leu Trp Val Tyr
1               5

<210> SEQ ID NO 1394
<211> LENGTH: 14

```
<212> TYPE: PRT
<213> ORGANISM: Artificial sequence
<220> FEATURE:
<223> OTHER INFORMATION: Peptide derived from HBV Large surface protein

<400> SEQUENCE: 1394

Ile Pro Leu Leu Pro Ile Phe Phe Cys Leu Trp Val Tyr Ile
1               5                   10

<210> SEQ ID NO 1395
<211> LENGTH: 11
<212> TYPE: PRT
<213> ORGANISM: Artificial sequence
<220> FEATURE:
<223> OTHER INFORMATION: Peptide derived from HBV Large surface protein

<400> SEQUENCE: 1395

Leu Pro Ile Phe Phe Cys Leu Trp Val Tyr Ile
1               5                   10

<210> SEQ ID NO 1396
<211> LENGTH: 15
<212> TYPE: PRT
<213> ORGANISM: Artificial sequence
<220> FEATURE:
<223> OTHER INFORMATION: Peptide derived from HBV Large surface protein

<400> SEQUENCE: 1396

Gly Phe Leu Gly Pro Leu Leu Val Leu Gln Ala Gly Phe Phe Leu
1               5                   10                  15

<210> SEQ ID NO 1397
<211> LENGTH: 15
<212> TYPE: PRT
<213> ORGANISM: Artificial sequence
<220> FEATURE:
<223> OTHER INFORMATION: Peptide derived from HBV Large surface protein

<400> SEQUENCE: 1397

Phe Leu Gly Pro Leu Leu Val Leu Gln Ala Gly Phe Phe Leu Leu
1               5                   10                  15

<210> SEQ ID NO 1398
<211> LENGTH: 15
<212> TYPE: PRT
<213> ORGANISM: Artificial sequence
<220> FEATURE:
<223> OTHER INFORMATION: Peptide derived from HBV Large surface protein

<400> SEQUENCE: 1398

Leu Gly Pro Leu Leu Val Leu Gln Ala Gly Phe Phe Leu Leu Thr
1               5                   10                  15

<210> SEQ ID NO 1399
<211> LENGTH: 15
<212> TYPE: PRT
<213> ORGANISM: Artificial sequence
<220> FEATURE:
<223> OTHER INFORMATION: Peptide derived from HBV Large surface protein

<400> SEQUENCE: 1399

Gly Pro Leu Leu Val Leu Gln Ala Gly Phe Phe Leu Leu Thr Arg
1               5                   10                  15

<210> SEQ ID NO 1400
<211> LENGTH: 15
<212> TYPE: PRT
```

<213> ORGANISM: Artificial sequence
<220> FEATURE:
<223> OTHER INFORMATION: Peptide derived from HBV Large surface protein

<400> SEQUENCE: 1400

Pro Leu Leu Val Leu Gln Ala Gly Phe Phe Leu Leu Thr Arg Ile
1               5                   10                  15

<210> SEQ ID NO 1401
<211> LENGTH: 15
<212> TYPE: PRT
<213> ORGANISM: Artificial sequence
<220> FEATURE:
<223> OTHER INFORMATION: Peptide derived from HBV Large surface protein

<400> SEQUENCE: 1401

Leu Leu Val Leu Gln Ala Gly Phe Phe Leu Leu Thr Arg Ile Leu
1               5                   10                  15

<210> SEQ ID NO 1402
<211> LENGTH: 15
<212> TYPE: PRT
<213> ORGANISM: Artificial sequence
<220> FEATURE:
<223> OTHER INFORMATION: Peptide derived from HBV Large surface protein

<400> SEQUENCE: 1402

Leu Val Leu Gln Ala Gly Phe Phe Leu Leu Thr Arg Ile Leu Thr
1               5                   10                  15

<210> SEQ ID NO 1403
<211> LENGTH: 15
<212> TYPE: PRT
<213> ORGANISM: Artificial sequence
<220> FEATURE:
<223> OTHER INFORMATION: Peptide derived from HBV Large surface protein

<400> SEQUENCE: 1403

Val Leu Gln Ala Gly Phe Phe Leu Leu Thr Arg Ile Leu Thr Ile
1               5                   10                  15

<210> SEQ ID NO 1404
<211> LENGTH: 15
<212> TYPE: PRT
<213> ORGANISM: Artificial sequence
<220> FEATURE:
<223> OTHER INFORMATION: Peptide derived from HBV Large surface protein

<400> SEQUENCE: 1404

Leu Gln Ala Gly Phe Phe Leu Leu Thr Arg Ile Leu Thr Ile Pro
1               5                   10                  15

<210> SEQ ID NO 1405
<211> LENGTH: 15
<212> TYPE: PRT
<213> ORGANISM: Artificial sequence
<220> FEATURE:
<223> OTHER INFORMATION: Peptide derived from HBV Large surface protein

<400> SEQUENCE: 1405

Gln Ala Gly Phe Phe Leu Leu Thr Arg Ile Leu Thr Ile Pro Gln
1               5                   10                  15

<210> SEQ ID NO 1406
<211> LENGTH: 15
<212> TYPE: PRT
<213> ORGANISM: Artificial sequence

```
<220> FEATURE:
<223> OTHER INFORMATION: Peptide derived from HBV Large surface protein

<400> SEQUENCE: 1406

Ala Gly Phe Phe Leu Leu Thr Arg Ile Leu Thr Ile Pro Gln Ser
1               5                   10                  15

<210> SEQ ID NO 1407
<211> LENGTH: 15
<212> TYPE: PRT
<213> ORGANISM: Artificial sequence
<220> FEATURE:
<223> OTHER INFORMATION: Peptide derived from HBV Large surface protein

<400> SEQUENCE: 1407

Gly Phe Phe Leu Leu Thr Arg Ile Leu Thr Ile Pro Gln Ser Leu
1               5                   10                  15

<210> SEQ ID NO 1408
<211> LENGTH: 15
<212> TYPE: PRT
<213> ORGANISM: Artificial sequence
<220> FEATURE:
<223> OTHER INFORMATION: Peptide derived from HBV Large surface protein

<400> SEQUENCE: 1408

Phe Phe Leu Leu Thr Arg Ile Leu Thr Ile Pro Gln Ser Leu Asp
1               5                   10                  15

<210> SEQ ID NO 1409
<211> LENGTH: 15
<212> TYPE: PRT
<213> ORGANISM: Artificial sequence
<220> FEATURE:
<223> OTHER INFORMATION: Peptide derived from HBV Large surface protein

<400> SEQUENCE: 1409

Phe Leu Leu Thr Arg Ile Leu Thr Ile Pro Gln Ser Leu Asp Ser
1               5                   10                  15

<210> SEQ ID NO 1410
<211> LENGTH: 15
<212> TYPE: PRT
<213> ORGANISM: Artificial sequence
<220> FEATURE:
<223> OTHER INFORMATION: Peptide derived from HBV Large surface protein

<400> SEQUENCE: 1410

Leu Leu Thr Arg Ile Leu Thr Ile Pro Gln Ser Leu Asp Ser Trp
1               5                   10                  15

<210> SEQ ID NO 1411
<211> LENGTH: 15
<212> TYPE: PRT
<213> ORGANISM: Artificial sequence
<220> FEATURE:
<223> OTHER INFORMATION: Peptide derived from HBV Large surface protein

<400> SEQUENCE: 1411

Leu Thr Arg Ile Leu Thr Ile Pro Gln Ser Leu Asp Ser Trp Trp
1               5                   10                  15

<210> SEQ ID NO 1412
<211> LENGTH: 15
<212> TYPE: PRT
<213> ORGANISM: Artificial sequence
<220> FEATURE:
```

<223> OTHER INFORMATION: Peptide derived from HBV Large surface protein

<400> SEQUENCE: 1412

Pro Pro Ile Cys Pro Gly Tyr Arg Trp Met Cys Leu Arg Arg Phe
1               5                   10                  15

<210> SEQ ID NO 1413
<211> LENGTH: 15
<212> TYPE: PRT
<213> ORGANISM: Artificial sequence
<220> FEATURE:
<223> OTHER INFORMATION: Peptide derived from HBV Large surface protein

<400> SEQUENCE: 1413

Pro Ile Cys Pro Gly Tyr Arg Trp Met Cys Leu Arg Arg Phe Ile
1               5                   10                  15

<210> SEQ ID NO 1414
<211> LENGTH: 15
<212> TYPE: PRT
<213> ORGANISM: Artificial sequence
<220> FEATURE:
<223> OTHER INFORMATION: Peptide derived from HBV Large surface protein

<400> SEQUENCE: 1414

Ile Cys Pro Gly Tyr Arg Trp Met Cys Leu Arg Arg Phe Ile Ile
1               5                   10                  15

<210> SEQ ID NO 1415
<211> LENGTH: 15
<212> TYPE: PRT
<213> ORGANISM: Artificial sequence
<220> FEATURE:
<223> OTHER INFORMATION: Peptide derived from HBV Large surface protein

<400> SEQUENCE: 1415

Cys Pro Gly Tyr Arg Trp Met Cys Leu Arg Arg Phe Ile Ile Phe
1               5                   10                  15

<210> SEQ ID NO 1416
<211> LENGTH: 15
<212> TYPE: PRT
<213> ORGANISM: Artificial sequence
<220> FEATURE:
<223> OTHER INFORMATION: Peptide derived from HBV Large surface protein

<400> SEQUENCE: 1416

Pro Gly Tyr Arg Trp Met Cys Leu Arg Arg Phe Ile Ile Phe Leu
1               5                   10                  15

<210> SEQ ID NO 1417
<211> LENGTH: 15
<212> TYPE: PRT
<213> ORGANISM: Artificial sequence
<220> FEATURE:
<223> OTHER INFORMATION: Peptide derived from HBV Large surface protein

<400> SEQUENCE: 1417

Gly Tyr Arg Trp Met Cys Leu Arg Arg Phe Ile Ile Phe Leu Phe
1               5                   10                  15

<210> SEQ ID NO 1418
<211> LENGTH: 15
<212> TYPE: PRT
<213> ORGANISM: Artificial sequence
<220> FEATURE:
<223> OTHER INFORMATION: Peptide derived from HBV Large surface protein

<400> SEQUENCE: 1418

Tyr Arg Trp Met Cys Leu Arg Arg Phe Ile Ile Phe Leu Phe Ile
1               5                   10                  15

<210> SEQ ID NO 1419
<211> LENGTH: 15
<212> TYPE: PRT
<213> ORGANISM: Artificial sequence
<220> FEATURE:
<223> OTHER INFORMATION: Peptide derived from HBV Large surface protein

<400> SEQUENCE: 1419

Arg Trp Met Cys Leu Arg Arg Phe Ile Ile Phe Leu Phe Ile Leu
1               5                   10                  15

<210> SEQ ID NO 1420
<211> LENGTH: 15
<212> TYPE: PRT
<213> ORGANISM: Artificial sequence
<220> FEATURE:
<223> OTHER INFORMATION: Peptide derived from HBV Large surface protein

<400> SEQUENCE: 1420

Trp Met Cys Leu Arg Arg Phe Ile Ile Phe Leu Phe Ile Leu Leu
1               5                   10                  15

<210> SEQ ID NO 1421
<211> LENGTH: 15
<212> TYPE: PRT
<213> ORGANISM: Artificial sequence
<220> FEATURE:
<223> OTHER INFORMATION: Peptide derived from HBV Large surface protein

<400> SEQUENCE: 1421

Met Cys Leu Arg Arg Phe Ile Ile Phe Leu Phe Ile Leu Leu Leu
1               5                   10                  15

<210> SEQ ID NO 1422
<211> LENGTH: 15
<212> TYPE: PRT
<213> ORGANISM: Artificial sequence
<220> FEATURE:
<223> OTHER INFORMATION: Peptide derived from HBV Large surface protein

<400> SEQUENCE: 1422

Cys Leu Arg Arg Phe Ile Ile Phe Leu Phe Ile Leu Leu Leu Cys
1               5                   10                  15

<210> SEQ ID NO 1423
<211> LENGTH: 15
<212> TYPE: PRT
<213> ORGANISM: Artificial sequence
<220> FEATURE:
<223> OTHER INFORMATION: Peptide derived from HBV Large surface protein

<400> SEQUENCE: 1423

Leu Arg Arg Phe Ile Ile Phe Leu Phe Ile Leu Leu Leu Cys Leu
1               5                   10                  15

<210> SEQ ID NO 1424
<211> LENGTH: 15
<212> TYPE: PRT
<213> ORGANISM: Artificial sequence
<220> FEATURE:
<223> OTHER INFORMATION: Peptide derived from HBV Large surface protein

```
<400> SEQUENCE: 1424

Arg Arg Phe Ile Ile Phe Leu Phe Ile Leu Leu Leu Cys Leu Ile
1               5                   10                  15

<210> SEQ ID NO 1425
<211> LENGTH: 15
<212> TYPE: PRT
<213> ORGANISM: Artificial sequence
<220> FEATURE:
<223> OTHER INFORMATION: Peptide derived from HBV Large surface protein

<400> SEQUENCE: 1425

Arg Phe Ile Ile Phe Leu Phe Ile Leu Leu Leu Cys Leu Ile Phe
1               5                   10                  15

<210> SEQ ID NO 1426
<211> LENGTH: 15
<212> TYPE: PRT
<213> ORGANISM: Artificial sequence
<220> FEATURE:
<223> OTHER INFORMATION: Peptide derived from HBV Large surface protein

<400> SEQUENCE: 1426

Phe Ile Ile Phe Leu Phe Ile Leu Leu Leu Cys Leu Ile Phe Leu
1               5                   10                  15

<210> SEQ ID NO 1427
<211> LENGTH: 15
<212> TYPE: PRT
<213> ORGANISM: Artificial sequence
<220> FEATURE:
<223> OTHER INFORMATION: Peptide derived from HBV Large surface protein

<400> SEQUENCE: 1427

Ile Ile Phe Leu Phe Ile Leu Leu Leu Cys Leu Ile Phe Leu Leu
1               5                   10                  15

<210> SEQ ID NO 1428
<211> LENGTH: 15
<212> TYPE: PRT
<213> ORGANISM: Artificial sequence
<220> FEATURE:
<223> OTHER INFORMATION: Peptide derived from HBV Large surface protein

<400> SEQUENCE: 1428

Ile Phe Leu Phe Ile Leu Leu Leu Cys Leu Ile Phe Leu Leu Val
1               5                   10                  15

<210> SEQ ID NO 1429
<211> LENGTH: 15
<212> TYPE: PRT
<213> ORGANISM: Artificial sequence
<220> FEATURE:
<223> OTHER INFORMATION: Peptide derived from HBV Large surface protein

<400> SEQUENCE: 1429

Phe Leu Phe Ile Leu Leu Leu Cys Leu Ile Phe Leu Leu Val Leu
1               5                   10                  15

<210> SEQ ID NO 1430
<211> LENGTH: 15
<212> TYPE: PRT
<213> ORGANISM: Artificial sequence
<220> FEATURE:
<223> OTHER INFORMATION: Peptide derived from HBV Large surface protein

<400> SEQUENCE: 1430
```

```
Leu Phe Ile Leu Leu Leu Cys Leu Ile Phe Leu Leu Val Leu Leu
1               5                   10                  15
```

<210> SEQ ID NO 1431
<211> LENGTH: 15
<212> TYPE: PRT
<213> ORGANISM: Artificial sequence
<220> FEATURE:
<223> OTHER INFORMATION: Peptide derived from HBV Large surface protein

<400> SEQUENCE: 1431

```
Phe Ile Leu Leu Leu Cys Leu Ile Phe Leu Leu Val Leu Leu Asp
1               5                   10                  15
```

<210> SEQ ID NO 1432
<211> LENGTH: 15
<212> TYPE: PRT
<213> ORGANISM: Artificial sequence
<220> FEATURE:
<223> OTHER INFORMATION: Peptide derived from HBV Large surface protein

<400> SEQUENCE: 1432

```
Ile Leu Leu Leu Cys Leu Ile Phe Leu Leu Val Leu Leu Asp Tyr
1               5                   10                  15
```

<210> SEQ ID NO 1433
<211> LENGTH: 15
<212> TYPE: PRT
<213> ORGANISM: Artificial sequence
<220> FEATURE:
<223> OTHER INFORMATION: Peptide derived from HBV Large surface protein

<400> SEQUENCE: 1433

```
Trp Ala Phe Ala Lys Tyr Leu Trp Glu Trp Ala Ser Val Arg Phe
1               5                   10                  15
```

<210> SEQ ID NO 1434
<211> LENGTH: 15
<212> TYPE: PRT
<213> ORGANISM: Artificial sequence
<220> FEATURE:
<223> OTHER INFORMATION: Peptide derived from HBV Large surface protein

<400> SEQUENCE: 1434

```
Ala Phe Ala Lys Tyr Leu Trp Glu Trp Ala Ser Val Arg Phe Ser
1               5                   10                  15
```

<210> SEQ ID NO 1435
<211> LENGTH: 15
<212> TYPE: PRT
<213> ORGANISM: Artificial sequence
<220> FEATURE:
<223> OTHER INFORMATION: Peptide derived from HBV Large surface protein

<400> SEQUENCE: 1435

```
Phe Ala Lys Tyr Leu Trp Glu Trp Ala Ser Val Arg Phe Ser Trp
1               5                   10                  15
```

<210> SEQ ID NO 1436
<211> LENGTH: 15
<212> TYPE: PRT
<213> ORGANISM: Artificial sequence
<220> FEATURE:
<223> OTHER INFORMATION: Peptide derived from HBV Large surface protein

<400> SEQUENCE: 1436

Ala Lys Tyr Leu Trp Glu Trp Ala Ser Val Arg Phe Ser Trp Leu
1               5                   10                  15

<210> SEQ ID NO 1437
<211> LENGTH: 15
<212> TYPE: PRT
<213> ORGANISM: Artificial sequence
<220> FEATURE:
<223> OTHER INFORMATION: Peptide derived from HBV Large surface protein

<400> SEQUENCE: 1437

Lys Tyr Leu Trp Glu Trp Ala Ser Val Arg Phe Ser Trp Leu Ser
1               5                   10                  15

<210> SEQ ID NO 1438
<211> LENGTH: 15
<212> TYPE: PRT
<213> ORGANISM: Artificial sequence
<220> FEATURE:
<223> OTHER INFORMATION: Peptide derived from HBV Large surface protein

<400> SEQUENCE: 1438

Leu Trp Glu Trp Ala Ser Val Arg Phe Ser Trp Leu Ser Leu Leu
1               5                   10                  15

<210> SEQ ID NO 1439
<211> LENGTH: 15
<212> TYPE: PRT
<213> ORGANISM: Artificial sequence
<220> FEATURE:
<223> OTHER INFORMATION: Peptide derived from HBV Large surface protein

<400> SEQUENCE: 1439

Trp Glu Trp Ala Ser Val Arg Phe Ser Trp Leu Ser Leu Leu Val
1               5                   10                  15

<210> SEQ ID NO 1440
<211> LENGTH: 15
<212> TYPE: PRT
<213> ORGANISM: Artificial sequence
<220> FEATURE:
<223> OTHER INFORMATION: Peptide derived from HBV Large surface protein

<400> SEQUENCE: 1440

Glu Trp Ala Ser Val Arg Phe Ser Trp Leu Ser Leu Leu Val Pro
1               5                   10                  15

<210> SEQ ID NO 1441
<211> LENGTH: 15
<212> TYPE: PRT
<213> ORGANISM: Artificial sequence
<220> FEATURE:
<223> OTHER INFORMATION: Peptide derived from HBV Large surface protein

<400> SEQUENCE: 1441

Trp Ala Ser Val Arg Phe Ser Trp Leu Ser Leu Leu Val Pro Phe
1               5                   10                  15

<210> SEQ ID NO 1442
<211> LENGTH: 15
<212> TYPE: PRT
<213> ORGANISM: Artificial sequence
<220> FEATURE:
<223> OTHER INFORMATION: Peptide derived from HBV Large surface protein

<400> SEQUENCE: 1442

Ala Ser Val Arg Phe Ser Trp Leu Ser Leu Leu Val Pro Phe Val

```
<210> SEQ ID NO 1443
<211> LENGTH: 15
<212> TYPE: PRT
<213> ORGANISM: Artificial sequence
<220> FEATURE:
<223> OTHER INFORMATION: Peptide derived from HBV Large surface protein

<400> SEQUENCE: 1443

Ser Val Arg Phe Ser Trp Leu Ser Leu Leu Val Pro Phe Val Gln
1               5                   10                  15

<210> SEQ ID NO 1444
<211> LENGTH: 15
<212> TYPE: PRT
<213> ORGANISM: Artificial sequence
<220> FEATURE:
<223> OTHER INFORMATION: Peptide derived from HBV Large surface protein

<400> SEQUENCE: 1444

Val Arg Phe Ser Trp Leu Ser Leu Leu Val Pro Phe Val Gln Trp
1               5                   10                  15

<210> SEQ ID NO 1445
<211> LENGTH: 15
<212> TYPE: PRT
<213> ORGANISM: Artificial sequence
<220> FEATURE:
<223> OTHER INFORMATION: Peptide derived from HBV Large surface protein

<400> SEQUENCE: 1445

Arg Phe Ser Trp Leu Ser Leu Leu Val Pro Phe Val Gln Trp Phe
1               5                   10                  15

<210> SEQ ID NO 1446
<211> LENGTH: 15
<212> TYPE: PRT
<213> ORGANISM: Artificial sequence
<220> FEATURE:
<223> OTHER INFORMATION: Peptide derived from HBV Large surface protein

<400> SEQUENCE: 1446

Phe Ser Trp Leu Ser Leu Leu Val Pro Phe Val Gln Trp Phe Val
1               5                   10                  15

<210> SEQ ID NO 1447
<211> LENGTH: 15
<212> TYPE: PRT
<213> ORGANISM: Artificial sequence
<220> FEATURE:
<223> OTHER INFORMATION: Peptide derived from HBV Large surface protein

<400> SEQUENCE: 1447

Trp Leu Ser Ala Ile Trp Met Met Trp Tyr Trp Gly Pro Ser Leu
1               5                   10                  15

<210> SEQ ID NO 1448
<211> LENGTH: 15
<212> TYPE: PRT
<213> ORGANISM: Artificial sequence
<220> FEATURE:
<223> OTHER INFORMATION: Peptide derived from HBV Large surface protein

<400> SEQUENCE: 1448

Leu Ser Ala Ile Trp Met Met Trp Tyr Trp Gly Pro Ser Leu Tyr
1               5                   10                  15
```

<210> SEQ ID NO 1449
<211> LENGTH: 15
<212> TYPE: PRT
<213> ORGANISM: Artificial sequence
<220> FEATURE:
<223> OTHER INFORMATION: Peptide derived from HBV Large surface protein

<400> SEQUENCE: 1449

Ser Ala Ile Trp Met Met Trp Tyr Trp Gly Pro Ser Leu Tyr Ser
1               5                   10                  15

<210> SEQ ID NO 1450
<211> LENGTH: 15
<212> TYPE: PRT
<213> ORGANISM: Artificial sequence
<220> FEATURE:
<223> OTHER INFORMATION: Peptide derived from HBV Large surface protein

<400> SEQUENCE: 1450

Ala Ile Trp Met Met Trp Tyr Trp Gly Pro Ser Leu Tyr Ser Ile
1               5                   10                  15

<210> SEQ ID NO 1451
<211> LENGTH: 15
<212> TYPE: PRT
<213> ORGANISM: Artificial sequence
<220> FEATURE:
<223> OTHER INFORMATION: Peptide derived from HBV Large surface protein

<400> SEQUENCE: 1451

Ile Trp Met Met Trp Tyr Trp Gly Pro Ser Leu Tyr Ser Ile Val
1               5                   10                  15

<210> SEQ ID NO 1452
<211> LENGTH: 15
<212> TYPE: PRT
<213> ORGANISM: Artificial sequence
<220> FEATURE:
<223> OTHER INFORMATION: Peptide derived from HBV Large surface protein

<400> SEQUENCE: 1452

Trp Met Met Trp Tyr Trp Gly Pro Ser Leu Tyr Ser Ile Val Ser
1               5                   10                  15

<210> SEQ ID NO 1453
<211> LENGTH: 15
<212> TYPE: PRT
<213> ORGANISM: Artificial sequence
<220> FEATURE:
<223> OTHER INFORMATION: Peptide derived from HBV Large surface protein

<400> SEQUENCE: 1453

Met Met Trp Tyr Trp Gly Pro Ser Leu Tyr Ser Ile Val Ser Pro
1               5                   10                  15

<210> SEQ ID NO 1454
<211> LENGTH: 15
<212> TYPE: PRT
<213> ORGANISM: Artificial sequence
<220> FEATURE:
<223> OTHER INFORMATION: Peptide derived from HBV Large surface protein

<400> SEQUENCE: 1454

Trp Tyr Trp Gly Pro Ser Leu Tyr Ser Ile Val Ser Pro Phe Ile
1               5                   10                  15

<210> SEQ ID NO 1455
<211> LENGTH: 15
<212> TYPE: PRT
<213> ORGANISM: Artificial sequence
<220> FEATURE:
<223> OTHER INFORMATION: Peptide derived from HBV Large surface protein

<400> SEQUENCE: 1455

Tyr Trp Gly Pro Ser Leu Tyr Ser Ile Val Ser Pro Phe Ile Pro
1               5                   10                  15

<210> SEQ ID NO 1456
<211> LENGTH: 15
<212> TYPE: PRT
<213> ORGANISM: Artificial sequence
<220> FEATURE:
<223> OTHER INFORMATION: Peptide derived from HBV Large surface protein

<400> SEQUENCE: 1456

Trp Gly Pro Ser Leu Tyr Ser Ile Val Ser Pro Phe Ile Pro Leu
1               5                   10                  15

<210> SEQ ID NO 1457
<211> LENGTH: 15
<212> TYPE: PRT
<213> ORGANISM: Artificial sequence
<220> FEATURE:
<223> OTHER INFORMATION: Peptide derived from HBV Large surface protein

<400> SEQUENCE: 1457

Gly Pro Ser Leu Tyr Ser Ile Val Ser Pro Phe Ile Pro Leu Leu
1               5                   10                  15

<210> SEQ ID NO 1458
<211> LENGTH: 15
<212> TYPE: PRT
<213> ORGANISM: Artificial sequence
<220> FEATURE:
<223> OTHER INFORMATION: Peptide derived from HBV Large surface protein

<400> SEQUENCE: 1458

Pro Ser Leu Tyr Ser Ile Val Ser Pro Phe Ile Pro Leu Leu Pro
1               5                   10                  15

<210> SEQ ID NO 1459
<211> LENGTH: 15
<212> TYPE: PRT
<213> ORGANISM: Artificial sequence
<220> FEATURE:
<223> OTHER INFORMATION: Peptide derived from HBV Large surface protein

<400> SEQUENCE: 1459

Ser Leu Tyr Ser Ile Val Ser Pro Phe Ile Pro Leu Leu Pro Ile
1               5                   10                  15

<210> SEQ ID NO 1460
<211> LENGTH: 15
<212> TYPE: PRT
<213> ORGANISM: Artificial sequence
<220> FEATURE:
<223> OTHER INFORMATION: Peptide derived from HBV Large surface protein

<400> SEQUENCE: 1460

Leu Tyr Ser Ile Val Ser Pro Phe Ile Pro Leu Leu Pro Ile Phe
1               5                   10                  15

```
<210> SEQ ID NO 1461
<211> LENGTH: 15
<212> TYPE: PRT
<213> ORGANISM: Artificial sequence
<220> FEATURE:
<223> OTHER INFORMATION: Peptide derived from HBV Large surface protein

<400> SEQUENCE: 1461

Tyr Ser Ile Val Ser Pro Phe Ile Pro Leu Leu Pro Ile Phe Phe
1               5                   10                  15

<210> SEQ ID NO 1462
<211> LENGTH: 15
<212> TYPE: PRT
<213> ORGANISM: Artificial sequence
<220> FEATURE:
<223> OTHER INFORMATION: Peptide derived from HBV Large surface protein

<400> SEQUENCE: 1462

Ser Ile Val Ser Pro Phe Ile Pro Leu Leu Pro Ile Phe Phe Cys
1               5                   10                  15

<210> SEQ ID NO 1463
<211> LENGTH: 15
<212> TYPE: PRT
<213> ORGANISM: Artificial sequence
<220> FEATURE:
<223> OTHER INFORMATION: Peptide derived from HBV Large surface protein

<400> SEQUENCE: 1463

Ile Val Ser Pro Phe Ile Pro Leu Leu Pro Ile Phe Phe Cys Leu
1               5                   10                  15

<210> SEQ ID NO 1464
<211> LENGTH: 15
<212> TYPE: PRT
<213> ORGANISM: Artificial sequence
<220> FEATURE:
<223> OTHER INFORMATION: Peptide derived from HBV Large surface protein

<400> SEQUENCE: 1464

Val Ser Pro Phe Ile Pro Leu Leu Pro Ile Phe Phe Cys Leu Trp
1               5                   10                  15

<210> SEQ ID NO 1465
<211> LENGTH: 15
<212> TYPE: PRT
<213> ORGANISM: Artificial sequence
<220> FEATURE:
<223> OTHER INFORMATION: Peptide derived from HBV Large surface protein

<400> SEQUENCE: 1465

Ser Pro Phe Ile Pro Leu Leu Pro Ile Phe Phe Cys Leu Trp Val
1               5                   10                  15

<210> SEQ ID NO 1466
<211> LENGTH: 15
<212> TYPE: PRT
<213> ORGANISM: Artificial sequence
<220> FEATURE:
<223> OTHER INFORMATION: Peptide derived from HBV Large surface protein

<400> SEQUENCE: 1466

Phe Ile Pro Leu Leu Pro Ile Phe Phe Cys Leu Trp Val Tyr Ile
1               5                   10                  15

<210> SEQ ID NO 1467
```

```
<211> LENGTH: 1203
<212> TYPE: DNA
<213> ORGANISM: Hepatitis B virus

<400> SEQUENCE: 1467
atgggaggtt ggtcatcaaa acctcgcaaa ggcatgggga cgaatctttc tgttcccaat     60
cctctgggat tctttcccga tcatcagttg gaccctgcat tcggagccaa ctcaaacaat    120
ccagattggg acttcaaccc cgtcaaggac gactggccag cagccaacca agtaggagtg    180
ggagcattcg ggccaaggct cacccctcca cacggcggta ttttgggggtg gagccctcag    240
gctcagggca tattgaccac agtgtcaaca attcctcctc ctgcctccac caatcggcag    300
tcaggaaggc agcctactcc catctctcca cctctaagag acagtcatcc tcaggccatg    360
cagtggaatt ccactgcctt ccaccaaact ctgcaggatc ccagagtcag ggtctgtat    420
cttcctgctg gtggctccag ttcaggaaca gtaaaccctg ctccgaatat tgcctctcac    480
atctcgtcaa tctccgcgag gactggggac cctgtgacga acatggagaa catcacatca    540
ggattcctag gacccctgct cgtgttacag gcggggtttt tcttgttgac aagaatcctc    600
acaataccgc agagtctaga ctcgtggtgg acttctctca attttctagg gggatctccc    660
gtgtgtcttg gccaaaattc gcagtcccca acctccaatc actcaccaac ctcctgtcct    720
ccaatttgtc ctggttatcg ctggatgtgt ctgcggcgtt ttatcatatt cctcttcatc    780
ctgctgctat gcctcatctt cttattggtt cttctggatt atcaaggtat gttgcccgtt    840
tgtcctctaa ttccaggatc aacaacaacc agtacgggac catgcaaaac ctgcacgact    900
cctgctcaag caactctat gtttccctca tgttgctgta caaaacctac ggatggaaat    960
tgcacctgta ttcccatccc atcgtcctgg gctttcgcaa atacctatg ggagtgggcc   1020
tcagtccgtt tctcttggct cagtttacta gtgccatttg ttcagtggtt cgtagggctt   1080
tcccccactg tttggctttc agctatatgg atgatgtggt attgggggcc aagtctgtac   1140
agcatcgtga gtcccttat accgctgtta ccaattttct tttgtctctg ggtatacatt   1200
taa                                                                 1203

<210> SEQ ID NO 1468
<211> LENGTH: 32
<212> TYPE: PRT
<213> ORGANISM: Artificial sequence
<220> FEATURE:
<223> OTHER INFORMATION: HBV large surface protein aa 327-358

<400> SEQUENCE: 1468

Pro Ser Ser Trp Ala Phe Ala Lys Tyr Leu Trp Glu Trp Ala Ser Val
1               5                   10                  15
Arg Phe Ser Trp Leu Ser Leu Leu Val Pro Phe Val Gln Trp Phe Val
            20                  25                  30

<210> SEQ ID NO 1469
<211> LENGTH: 31
<212> TYPE: PRT
<213> ORGANISM: Artificial sequence
<220> FEATURE:
<223> OTHER INFORMATION: HBV large surface protein aa 328-358

<400> SEQUENCE: 1469

Ser Ser Trp Ala Phe Ala Lys Tyr Leu Trp Glu Trp Ala Ser Val Arg
1               5                   10                  15
Phe Ser Trp Leu Ser Leu Leu Val Pro Phe Val Gln Trp Phe Val
            20                  25                  30
```

```
<210> SEQ ID NO 1470
<211> LENGTH: 30
<212> TYPE: PRT
<213> ORGANISM: Artificial sequence
<220> FEATURE:
<223> OTHER INFORMATION: HBV large surface protein aa 371-400

<400> SEQUENCE: 1470

Met Met Trp Tyr Trp Gly Pro Ser Leu Tyr Ser Ile Val Ser Pro Phe
1               5                   10                  15

Ile Pro Leu Leu Pro Ile Phe Phe Cys Leu Trp Val Tyr Ile
            20                  25                  30

<210> SEQ ID NO 1471
<211> LENGTH: 31
<212> TYPE: PRT
<213> ORGANISM: Artificial sequence
<220> FEATURE:
<223> OTHER INFORMATION: HBV large surface protein aa 370-400

<400> SEQUENCE: 1471

Trp Met Met Trp Tyr Trp Gly Pro Ser Leu Tyr Ser Ile Val Ser Pro
1               5                   10                  15

Phe Ile Pro Leu Leu Pro Ile Phe Phe Cys Leu Trp Val Tyr Ile
            20                  25                  30
```